(12) United States Patent
Regev et al.

(10) Patent No.: US 12,049,643 B2
(45) Date of Patent: Jul. 30, 2024

(54) METHODS AND COMPOSITIONS FOR MODULATING CYTOTOXIC LYMPHOCYTE ACTIVITY

(71) Applicants: The Broad Institute, Inc., Cambridge, MA (US); Massachusetts Institute of Technology, Cambridge, MA (US); The Brigham and Women's Hospital, Inc., Boston, MA (US)

(72) Inventors: Aviv Regev, Cambridge, MA (US); Ana C. Anderson, Boston, MA (US); Vijay K. Kuchroo, Boston, MA (US); Sema Kurtulus, Boston, MA (US); Asaf Madi, Boston, MA (US)

(73) Assignees: THE BROAD INSTITUTE, INC., Cambridge, MA (US); MASSACHUSETTS INSTITUTE OF TECHNOLOGY, Cambridge, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 777 days.

(21) Appl. No.: 16/630,887

(22) PCT Filed: Jul. 13, 2018

(86) PCT No.: PCT/US2018/042069
§ 371 (c)(1),
(2) Date: Jan. 14, 2020

(87) PCT Pub. No.: WO2019/014581
PCT Pub. Date: Jan. 17, 2019

(65) Prior Publication Data
US 2020/0149009 A1    May 14, 2020

Related U.S. Application Data

(60) Provisional application No. 62/636,637, filed on Feb. 28, 2018, provisional application No. 62/532,556, filed on Jul. 14, 2017.

(51) Int. Cl.
*C12N 5/0787* (2010.01)
*A61K 35/17* (2015.01)
*A61P 35/00* (2006.01)
*C07K 14/705* (2006.01)
*C12N 5/0783* (2010.01)
*G01N 33/569* (2006.01)
*G01N 33/574* (2006.01)

(52) U.S. Cl.
CPC ............ *C12N 5/0638* (2013.01); *A61K 35/17* (2013.01); *C07K 14/70503* (2013.01); *G01N 33/56972* (2013.01); *G01N 33/57492* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,270,163 A | 12/1993 | Gold et al. |
| 5,686,281 A | 11/1997 | Roberts |
| 5,811,097 A | 9/1998 | Allison et al. |
| 5,843,728 A | 12/1998 | Seed et al. |
| 5,851,828 A | 12/1998 | Seed et al. |
| 5,858,358 A | 1/1999 | June et al. |
| 5,869,326 A | 2/1999 | Hofmann |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |

(Continued)

FOREIGN PATENT DOCUMENTS

| | | |
|---|---|---|
| AU | 2015101792 A4 | 1/2016 |
| EP | 2 784 162 A1 | 10/2014 |

(Continued)

OTHER PUBLICATIONS

Jin et al. (2010) PNAS 107(33): 14733-14738.*

(Continued)

*Primary Examiner* — Ilia I Ouspenski
(74) *Attorney, Agent, or Firm* — WENDEROTH, LIND & PONACK, L.L.P.

(57) ABSTRACT

The subject matter disclosed herein is generally directed to novel CD8$^+$ tumor infiltrating lymphocyte (TIL) subtypes associated with response to immunotherapy treatment. Specifically, the subtypes are associated with checkpoint blockade therapy. Moreover, the subject matter disclosed herein is generally directed to methods and compositions for use of the subtypes. Also, disclosed herein are gene signatures and markers associated with the subtypes and use of said signatures and markers. Further disclosed are therapeutic methods of using said gene signatures and immune cell subtypes. Further disclosed are pharmaceutical compositions comprising populations of CD8$^+$ TILs enriched for a specific subtype.

19 Claims, 74 Drawing Sheets
Specification includes a Sequence Listing.

(56) References Cited

U.S. PATENT DOCUMENTS

| | | |
|---|---|---|
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox, III et al. |
| 6,607,882 B1 | 8/2003 | Cox, III et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox, III et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,115,402 B2 | 8/2015 | Hacohen et al. |
| 9,181,527 B2 | 11/2015 | Sentman |
| 9,233,125 B2 | 1/2016 | Davila et al. |
| 2004/0171156 A1 | 9/2004 | Hartley et al. |
| 2004/0224402 A1 | 11/2004 | Bonyhadi et al. |
| 2010/0104509 A1 | 4/2010 | King et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2012/0269833 A1* | 10/2012 | Krackhardt ........ C07K 14/7051 435/325 |
| 2013/0071414 A1 | 3/2013 | Dotti et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2016/0208243 A1 | 7/2016 | Zhang et al. |
| 2016/0355795 A1 | 12/2016 | Ran et al. |
| 2017/0283504 A1 | 10/2017 | Wiltzius et al. |
| 2017/0306335 A1 | 10/2017 | Zhang et al. |
| 2017/0349894 A1 | 12/2017 | Dahlman et al. |
| 2018/0085444 A1 | 3/2018 | Morgan et al. |
| 2018/0163265 A1 | 6/2018 | Zhang et al. |
| 2018/0312824 A1 | 11/2018 | Zhang et al. |
| 2019/0359971 A1 | 11/2019 | Zhang et al. |
| 2021/0263012 A1* | 8/2021 | Anderson ............ C12N 5/0636 |
| 2022/0170097 A1* | 6/2022 | Boroughs .......... G01N 33/5023 |

FOREIGN PATENT DOCUMENTS

| | | |
|---|---|---|
| EP | 2 771 468 B1 | 2/2015 |
| EP | 2 764 103 B1 | 8/2015 |
| EP | 3 009 511 A2 | 4/2016 |
| EP | 3 470 089 A1 | 4/2019 |
| EP | 3 470 519 A1 | 4/2019 |
| WO | 92/15322 A1 | 9/1992 |
| WO | 96/40281 A2 | 12/1996 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |

(56) References Cited

FOREIGN PATENT DOCUMENTS

| | | |
|---|---|---|
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/168874 A2 | 10/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/085233 A1 | 6/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/095811 A2 | 6/2015 |
| WO | 2015/120096 A2 | 8/2015 |
| WO | 2015/130968 A2 | 9/2015 |
| WO | 2015/142675 A2 | 9/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/028682 A1 | 2/2016 |
| WO | 2016/040476 A1 | 3/2016 |
| WO | 2016/049024 A2 | 3/2016 |
| WO | 2016/049258 A2 | 3/2016 |
| WO | 2016/070061 A1 | 5/2016 |
| WO | 2016/094867 A1 | 6/2016 |
| WO | 2016/094872 A1 | 6/2016 |
| WO | 2016/094874 A1 | 6/2016 |
| WO | 2016/094880 A1 | 6/2016 |
| WO | 2016/100977 A1 | 6/2016 |
| WO | 2016/106244 A1 | 6/2016 |
| WO | 2016/108926 A1 | 7/2016 |
| WO | 2016/161516 A1 | 10/2016 |
| WO | 2016/168584 A1 | 10/2016 |
| WO | 2016/187508 A2 | 11/2016 |
| WO | 2016/191756 A1 | 12/2016 |
| WO | 2016/196388 A1 | 12/2016 |
| WO | 2017/004916 A1 | 1/2017 |
| WO | 2017/011804 A1 | 1/2017 |
| WO | 2017/070395 A1 | 4/2017 |
| WO | 2017/070605 A1 | 4/2017 |
| WO | 2017/075478 A2 | 5/2017 |
| WO | 2017/164936 A1 | 9/2017 |
| WO | 2017/211900 A1 | 12/2017 |
| WO | 2018/028647 A1 | 2/2018 |
| WO | 2018/035250 A1 | 2/2018 |
| WO | 2019/005866 A1 | 1/2019 |
| WO | 2019/014581 A1 | 1/2019 |
| WO | 2019/018423 A1 | 1/2019 |

OTHER PUBLICATIONS

Datar et al. (2019) Clin Cancer Res 25: 4663-4673.*
Comte, et al., "SLAMF7 Engagement Restores Defective Effector CD8+ T cells Activity in Response to Foreign Antigens in Systemic Lupus Erythematosus", Arthritis Rheumatol., vol. 69, No. 5, 2017, pp. 1035-1044.
The Broad Institute, Inc., "Notification of Transmittal of the International Search Report and The Written Opinion of the International Searching Authority, or the Declaration", Nov. 1, 2018, 14 pages.
Bottcher, et al., "Functional Classification of Memory CD8(+) T Cells by CxX3CR1 Expression", Nature Communications, vol. 6, No. 8306, Sep. 25, 2015, 17 pages.
Comte, et al., "Signaling Lymphocytic Activation Molecule Family Member 7 Engagement Restores Defective Effector CD8+ T Cell Function in Systemic Lupus Erythematosus", Arthritis and Rheumatology, vol. 69, No. 5, May 2017, 10 pages.
Fraietta, et al., "Determinants of Response and Resistance to CD19 Chimeric Antigen Receptor (CAR) T Cell Therapy of Chronic Lymphocytic Leukemia", Nature Medicine, vol. 24, No. 5, May 2018, 27 pages.
Ganesan, et al., "Tissue-Resident Memory Features are Linked to the Magnitude of Cytotoxic T Cell Responses in Human Lung Cancer", Nature Immunology, vol. 18, No. 8, Aug. 2017, 28 pages.
Gerlach, et al., "The Chemokine Receptor CX3CR1 Defines Three Antigen-Experienced CD8 T Cell Subsets with Distinct Roles in Immune Surveillance and Homeostasis", Immunity, vol. 45, No. 6, Dec. 20, 2016, 25 pages.
Im, et al., "Defining CD8+ T Cells that provide the Proliferative Burst after PD-1 Therapy", Nature, vol. 537, No. 7620, Sep. 15, 2016, 30 pages.
Joshi, et al., "Inflammation Directs Memory Precursor and Short-Lived Effector CD8(+) T Cell Fates via the Graded Expression of T-Bet Transcription Factor", Immunity, vol. 27, No. 2, Aug. 2007, 281-295.
Lefrancois, "Development, Trafficking, and Function of Memory T-Cell Subsets", Immunological Reviews, vol. 211, Issue 1, Jun. 2006, 93-103.
Leong, et al., "CXCR5(+) Follicular Cytotoxic T Cells Control Viral Infection in B Cell Follicles", Nature Immunology, vol. 17, No. 10, Oct. 2016, 1187-1196.
Philip, et al., "Chromatin States Define Tumour-Specific T Cell Dysfunction and Reprogramming", Nature, vol. 545, No. 7655, May 25, 2017, 35 pages.
Singer, et al., "A Distinct Gene Module for Dysfunction Uncoupled from Activation in Tumor-Infiltrating T Cells", Cell, vol. 166, No. 6, Sep. 8, 2016, 32 pages.
Steinke, et al., "TCF-1 and LEF-1 act Upstream of Th-POK to Promote the CD4(+) T Cell Fate and Interact with Runx3 To Silence CD4 in CD8(+) T Cells", Nature Immunology, vol. 15, No. 7, Jul. 2014, 33 pages.
Utzschneider, et al., "T Cell Factor 1-Expressing Memory-like CD8(+) T Cells Sustain the Immune Response to Chronic Viral Infections", Immunity, vol. 45, No. 2, Aug. 16, 2016, 415-427.
Zhou, et al., "Differentiation and Persistence of Memory CD8(+) T Cells Depend on T Cell Factor 1", Immunity, vol. 33, No. 2, Aug. 27, 2010, 20 pages.

* cited by examiner

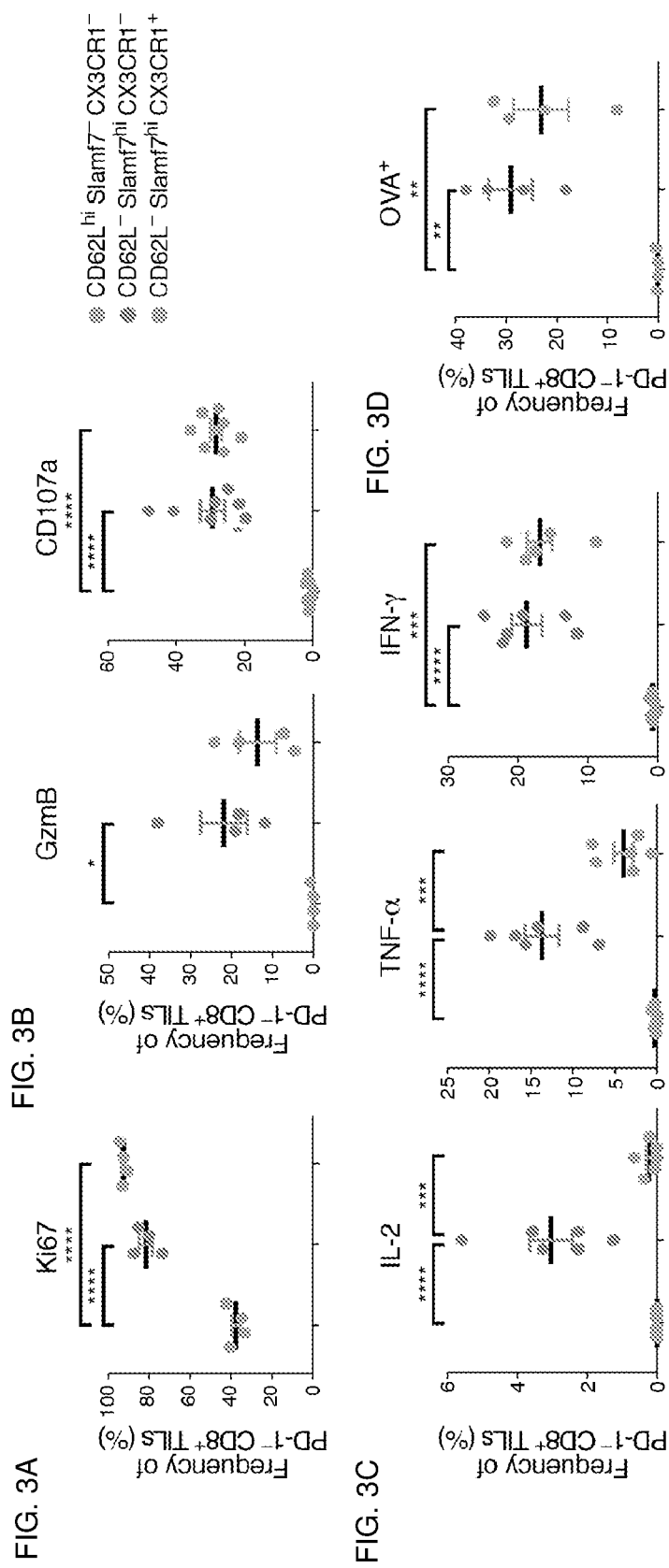

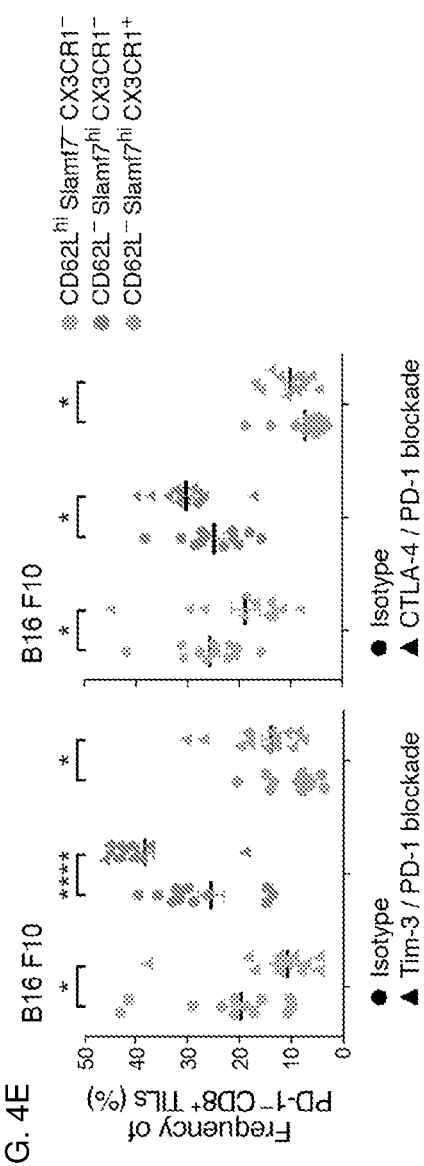
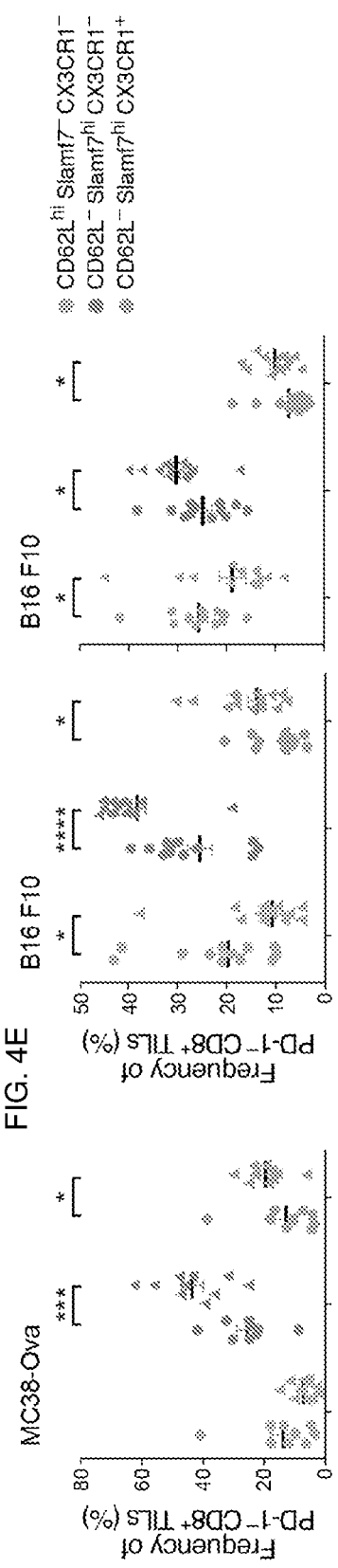
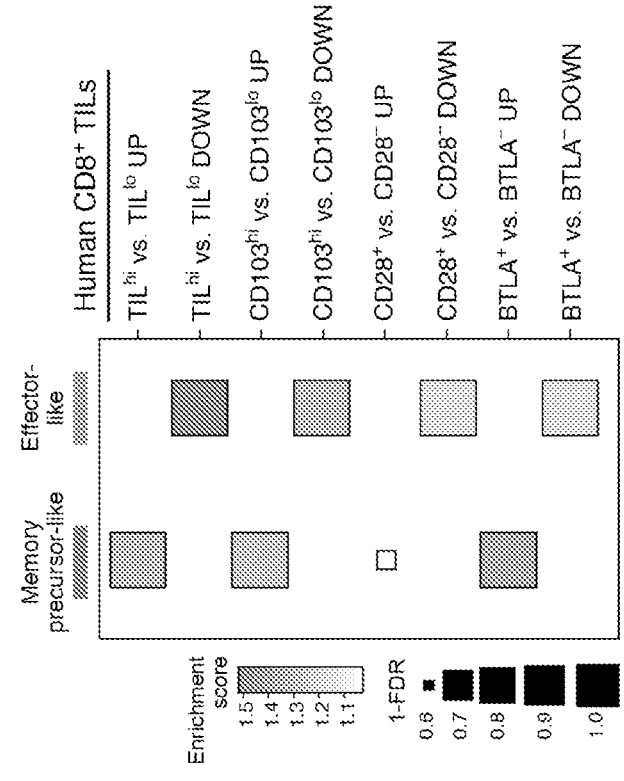
FIG. 4D
FIG. 4E
FIG. 4F

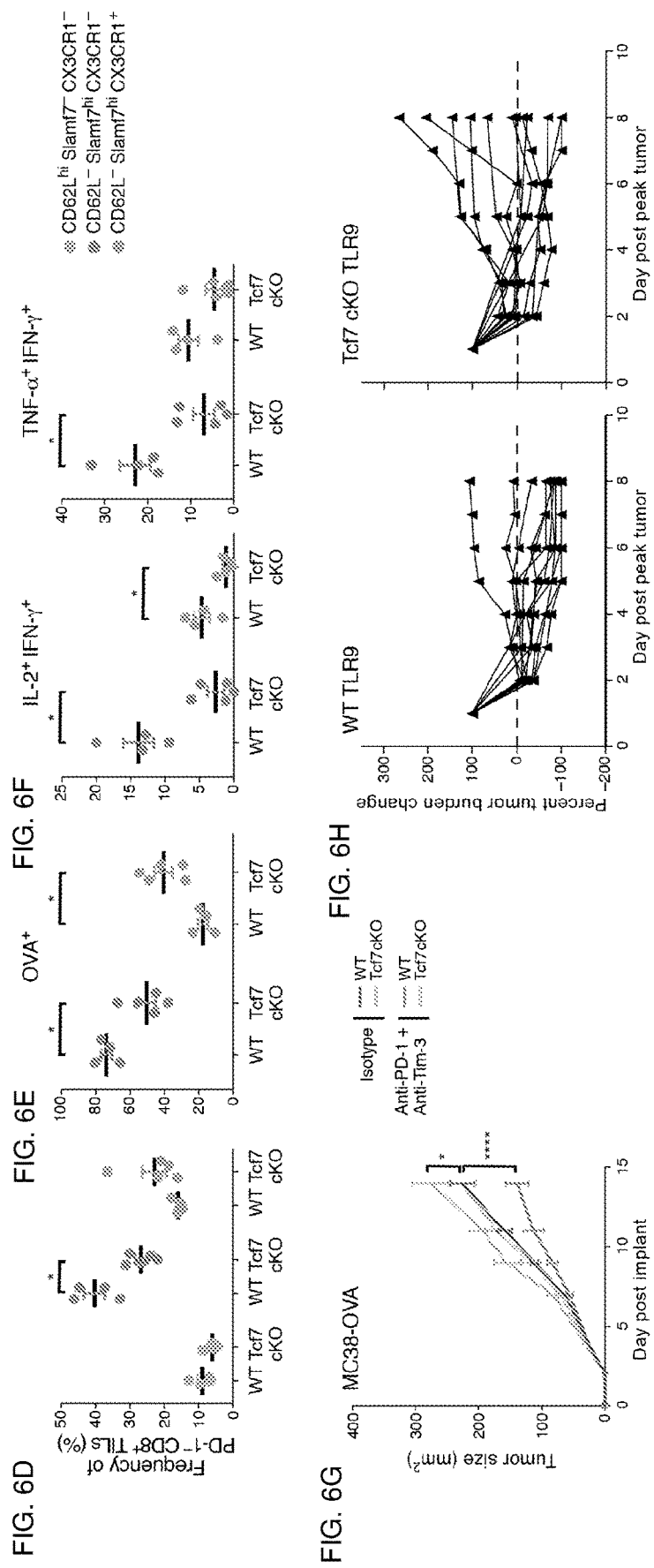

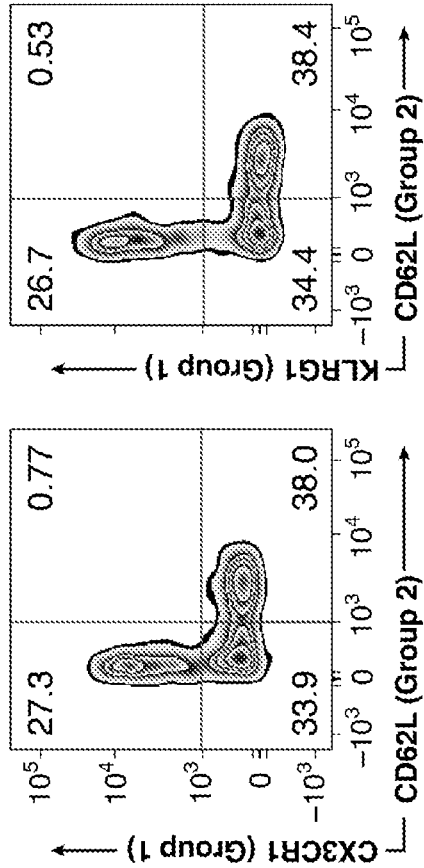
FIG. 7A
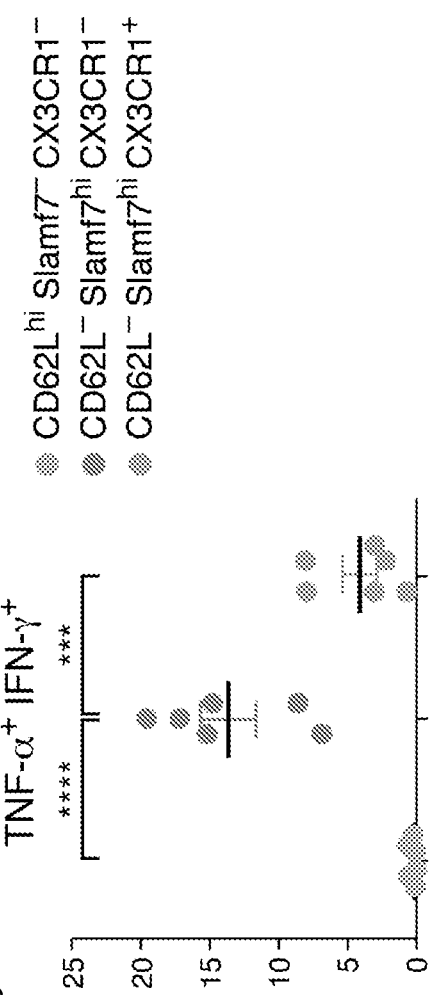
FIG. 7B
FIG. 7C

SEQUENCE LISTING

```
<160> NUMBER OF SEQ ID NOS: 19

<210> SEQ ID NO 1
<211> LENGTH: 107
<212> TYPE: PRT
<213> ORGANISM: Homo sapiens

<400> SEQUENCE: 1

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 2
```

```
<211> LENGTH: 9
<212> TYPE: PRT
<213> ORGANISM: Homo sapiens

<400> SEQUENCE: 2

Ile Glu Val Met Tyr Pro Pro Pro Tyr
1               5

<210> SEQ ID NO 3
<211> LENGTH: 7
<212> TYPE: PRT
<213> ORGANISM: Simian Virus 40

<400> SEQUENCE: 3

Pro Lys Lys Lys Arg Lys Val
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Lys Arg Pro Ala Ala Thr Lys Lys Ala Gly Gln Ala Lys Lys Lys Lys
1               5                   10                  15

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Pro Ala Ala Lys Arg Val Lys Leu Asp
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Arg Gln Arg Arg Asn Glu Leu Lys Arg Ser Pro
1               5                   10

<210> SEQ ID NO 7
<211> LENGTH: 38
<212> TYPE: PRT
<213> ORGANISM: Artificial Sequence
<220> FEATURE:
<223> OTHER INFORMATION: Synthetic

<400> SEQUENCE: 7

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35
```

```
<210> SEQ ID NO 8
<211> LENGTH: 42
<212> TYPE: PRT
<213> ORGANISM: Artificial Sequence
<220> FEATURE:
<223> OTHER INFORMATION: Synthetic

<400> SEQUENCE: 8

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Val Ser Arg Lys Arg Pro Arg Pro
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Pro Pro Lys Lys Ala Arg Glu Asp
1               5

<210> SEQ ID NO 11
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa at position represents "O" for pyrrolysine

<400> SEQUENCE: 11

Pro Xaa Pro Lys Lys Lys Pro Leu
1               5

<210> SEQ ID NO 12
<211> LENGTH: 12
<212> TYPE: PRT
<213> ORGANISM: Mus sp.

<400> SEQUENCE: 12

Ser Ala Leu Ile Lys Lys Lys Lys Lys Met Ala Pro
1               5                   10

<210> SEQ ID NO 13
<211> LENGTH: 7
<212> TYPE: PRT
<213> ORGANISM: Infuenza virus NS1

<400> SEQUENCE: 13

Pro Lys Gln Lys Lys Arg Lys
```

-continued

```
<210> SEQ ID NO 14
<211> LENGTH: 10
<212> TYPE: PRT
<213> ORGANISM: Hepatitis virus

<400> SEQUENCE: 14

Arg Lys Leu Lys Lys Ile Lys Lys Leu
1               5                   10

<210> SEQ ID NO 15
<211> LENGTH: 10
<212> TYPE: PRT
<213> ORGANISM: Mus sp.

<400> SEQUENCE: 15

Arg Glu Lys Lys Lys Phe Leu Lys Arg Arg
1               5                   10

<210> SEQ ID NO 16
<211> LENGTH: 20
<212> TYPE: PRT
<213> ORGANISM: Homo sapiens

<400> SEQUENCE: 16

Lys Arg Lys Gly Asp Glu Val Asp Gly Val Asp Glu Val Ala Lys Lys
1               5                   10                  15

Lys Ser Lys Lys
            20

<210> SEQ ID NO 17
<211> LENGTH: 17
<212> TYPE: PRT
<213> ORGANISM: Homo sapiens

<400> SEQUENCE: 17

Arg Lys Cys Leu Gln Ala Gly Met Asn Leu Glu Ala Arg Lys Thr Lys
1               5                   10                  15

Lys

<210> SEQ ID NO 18
<211> LENGTH: 288
<212> TYPE: PRT
<213> ORGANISM: Artificial Sequence
<220> FEATURE:
<223> OTHER INFORMATION: Sythetic

<400> SEQUENCE: 18

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95
```

```
Thr Glu Ala Ala Thr Gly Glu Trp Asp Glu Val Gln Ser Gly Leu Arg
            100                 105                 110

Ala Ala Asp Ala Pro Pro Thr Met Arg Val Ala Val Thr Ala Ala
        115                 120                 125

Arg Pro Pro Arg Ala Lys Pro Ala Pro Arg Arg Ala Ala Gln Pro
        130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
                180                 185                 190

Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
        210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
                260                 265                 270

Glu Ala Val His Ala Trp Arg Asn Ala Leu Thr Gly Ala Pro Leu Asn
            275                 280                 285

<210> SEQ ID NO 19
<211> LENGTH: 183
<212> TYPE: PRT
<213> ORGANISM: Artificial Sequence
<220> FEATURE:
<223> OTHER INFORMATION: Synthetic

<400> SEQUENCE: 19

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160
```

```
Ala Asp Ser Leu Glu Arg Asp Leu Asp Ala Pro Ser Pro Met His Glu
            165                 170                 175
Gly Asp Gln Thr Arg Ala Ser
            180
```

METHODS AND COMPOSITIONS FOR MODULATING CYTOTOXIC LYMPHOCYTE ACTIVITY

CROSS-REFERENCE TO RELATED APPLICATIONS

This application is a U.S. National Stage of International Application No. PCT/US2018/042069, filed Jul. 13, 2018, which claims the benefit of U.S. Provisional Application Nos. 62/532,556, filed Jul. 14, 2017 and 62/636,637, filed Feb. 28, 2018. The entire contents of the above-identified applications are hereby fully incorporated herein by reference.

STATEMENT REGARDING FEDERALLY SPONSORED RESEARCH

This invention was made with government support under Grant Nos. CA187975, AI073748 and NS045937 awarded by the National Institutes of Health. The government has certain rights in the invention.

REFERENCE TO AN ELECTRONIC SEQUENCE LISTING

The contents of the electronic sequence listing ("BROD_2097WP_ST25.txt", 9,140 bytes, created on Jul. 9, 2018) is herein incorporated by reference in its entirety.

TECHNICAL FIELD

The subject matter disclosed herein is generally directed to $CD8^+$ tumor infiltrating lymphocyte subtypes associated with response to immunotherapy treatment. Moreover, the subject matter disclosed herein is generally directed to detecting, isolating and using said subtypes.

BACKGROUND

The $CD8^+$ T cell response within the tumor microenvironment (TME) is functionally (Sakuishi et al., 2010; Williams et al., 2017; Woo et al., 2012; Xu et al., 2015) and transcriptionally (Singer et al., 2016; Tirosh et al., 2016; Zheng et al., 2017) heterogeneous. At one end of the functional spectrum are $CD8^+$ tumor-infiltrating lymphocytes (TILs) that lack the expression of co-inhibitory or immune checkpoint receptors (eg. CTLA-4 and PD-1) and exhibit effector potential, while at the opposite end are $CD8^+$ TILs that co-express multiple checkpoint receptors and exhibit an "exhausted" or dysfunctional phenotype. Checkpoint blockade immunotherapy, using antibodies against co-inhibitory receptors, unleashes a potent effector $CD8^+$ T cell response resulting in anti-tumor immunity and durable clinical responses. However, it is not clear which $CD8^+$ T cell populations change in response to checkpoint blockade therapy. One possibility is that checkpoint blockade acts directly on dysfunctional T cells that express checkpoint receptors, thereby re-invigorating them. Conversely, checkpoint blockade may indirectly generate an environment that promotes optimal differentiation of T cell precursors into effector cells. Understanding how the functional spectrum of $CD8^+$ TILs changes upon checkpoint blockade immunotherapy could provide information to improve current strategies for harnessing the anti-tumor $CD8^+$ T cell response and could lead to the identification of biomarkers to track responses to therapies.

Antibodies that block the activity of checkpoint receptors, including CTLA-4, PD-1, Tim-3, Lag-3, and TIGIT, either alone or in combination, have been associated with improved effector $CD8^+$ T cell responses in multiple pre-clinical cancer models (Johnston et al., 2014; Ngiow et al., 2011; Sakuishi et al., 2010; Woo et al., 2012). Similarly, blockade of CTLA-4 and PD-1 in patients (Brahmer et al., 2012; Hodi et al., 2010; Schadendorf et al., 2015; Topalian et al., 2012; Wolchok et al., 2017) has shown increased frequencies of proliferating T cells, often with specificity for tumor antigens, as well as increased $CD8^+$ T cell effector function (Ayers et al., 2017; Das et al., 2015; Gubin et al., 2014; Huang et al., 2017; Kamphorst et al., 2017; Kvistborg et al., 2014; van Rooij et al., 2013; Yuan et al., 2008). Accordingly, the success of checkpoint receptor blockade has been attributed to the binding of blocking antibodies to checkpoint receptors expressed on dysfunctional $CD8^+$ T cells and restoring effector function in these cells.

A recent study suggests that PD-1 blockade acts on a distinct subset of $PD-1^+$ precursors in the setting of chronic viral infection (Im et al., 2016; Utzschneider et al., 2016). However, several studies have indicated that although PD-1 pathway blockade can re-invigorate the effector functions of $PD-1^+CD8^+$ T cells, this effect was transient as these cells had limited memory potential due to their acquisition of a stable epigenetic state that cannot be modified by therapy (Ghoneim et al., 2017; Pauken et al., 2016; Philip et al., 2017; Scott-Browne et al., 2016; Sen et al., 2016). These observations raise the important question of the origin and phenotype of the effector T cells that arise after checkpoint blockade therapy and are responsible for the therapeutic effect. Thus, there is a need to better understand tumor immunity and response to immunotherapy.

Citation or identification of any document in this application is not an admission that such document is available as prior art to the present invention.

SUMMARY

The mechanisms underlying how checkpoint blockade therapy alters the functional spectrum of $CD8^+$ tumor-infiltrating lymphocytes (TILs) is poorly understood. Applicants have examined the RNA profiles from bulk and single-cell $CD8^+$ tumor-infiltrating lymphocytes (TILs) following Tim-3/PD-1 blockade. Surprisingly, there were significantly higher transcriptional changes in $Tim-3^-PD-1^-$ compared to $Tim-3^+PD-1^+CD8^+$ TILs, leading to the identification of three novel precursor $PD-1^-$ populations that separately have features of naïve, effector, and memory-precursor-like $CD8^+$ T cells. Following Tim-3/PD-1 blockade, the proportion of memory-precursor-like and effector-like TIL subsets increases relative to the naïve-like subset. Applicants further identified Tcf7 as a regulator of the memory-precursor-like subset and show that different immunotherapies fail in its absence. The memory-precursor- and effector-like subsets contain tumor-antigen specific cells and expand following multiple checkpoint blockade therapies in different cancers. The memory-precursor-like subset shares features with $CD8^+$ T cells that are associated with response to checkpoint blockade in patients and is compromised in the absence of Tcf7, which Applicants show is requisite for the efficacy of diverse immunotherapies. The findings uncover previously unappreciated changes in $PD-1^-$ precursor populations within $CD8^+$ TILs, providing critical insight into development of the effector $CD8^+$ T cell response after immunotherapy.

It is an objective of the present invention to identify CD8+ TIL subtypes responsive to checkpoint blockade therapy. It is another objective of the present invention to detect gene signatures and biomarkers specific to the CD8+ TIL subtypes, whereby cells may be detected and isolated. It is another objective of the present invention to provide for adoptive cell transfer methods for treatment of a cancer by transferring more functional CD8+ TILs. It is another objective of the present invention to provide for treatment of a cancer by modulating CD8+ T cells to be more functional. It is another objective of the present invention to improve immunotherapy treatment.

In one aspect, the present invention provides for an isolated CD8+ T cell characterized in that the CD8+ T cell comprises: expression of SLAMF7 and does not express CD62L, CX3CR1, TIM3 and PD1. The isolated CD8+ T cell may be further characterized in that the CD8+ T cell does not express KLRG1.

In another aspect, the present invention provides for an isolated CD8+ T cell characterized in that the CD8+ T cell comprises: expression of SLAMF7 and CX3CR1 and does not express CD62L, TIM3 and PD1. The isolated CD8+ T cell may be further characterized in that the CD8+ T cell expresses KLRG1. The isolated CD8+ T cell may be further characterized in that the CD8+ T cell does not express KLRG1. Not being bound by a theory the CD62L− Slamf7+ CX3CR1+ CD8+ T cell may be further characterized as a KLRG1+ or KLRG1− cell.

The isolated CD62L− Slamf7+ CX3CR1− CD8+ T cell and isolated CD62L− Slamf7+CX3CR1+CD8+ T cell may be further characterized by a gene signature comprising one or more genes or polypeptides in Table 5. The isolated CD62L− Slamf7+ CX3CR1− CD8+ T cell may be further characterized in that the CD8+ T cell also expresses or does not express one or more genes or polypeptides selected from Table 5. The isolated CD62L− Slamf7+ CX3CR1+ CD8+ T cell may be further characterized in that the CD8+ T cell also expresses or does not express one or more genes or polypeptides selected from Table 5. Table 5 list genes differentially expressed between the two CD62L− Slamf7+ subtypes described herein. Thus, the signature of genes up and down regulated in Table 5 may be used to further distinguish between each subtype. In certain embodiments, the overall signatures or subset of signature genes listed in Table 5 may be used to identify each subtype.

The gene signature in Table 5 comprises one or more transcription factors that may be key regulators or drivers of the phenotype of the two CD62L− Slamf7+ subtypes. Transcription factors may indicate key pathways for modulating activity of the cells and may be therapeutic targets. The CD62L− Slamf7+ CX3CR1− CD8+ T cell may comprise higher expression of one or more transcription factors selected from the group consisting of Tcf7, Egr2, Zfp827, Satb1, Zfp512, Irf8, Relb, Sp140, Myb, Id3, Hes6, Fos, Ikzf2 and Myc relative to the CD62L− Slamf7+ CX3CR1+ CD8+ T cell. The CD62L− Slamf7+ CX3CR1+CD8+ T cell may comprise higher expression of one or more transcription factors selected from the group consisting of Bhlhe40, Klf2, Zeb2, Prdm1, Arnt1, Ets1, Junb, Id2, Hivep2, Rora, Nr1d2, Meis2, Arnt, Nr4a1, Meis3, Zmiz1, Vezf1, Nfe2l1, Mxi1, Rxra and Creb5 relative to the CD62L− Slamf7+ CX3CR1− CD8+ T cell.

In another aspect, the present invention provides for an isolated CD8+ T cell characterized in that the CD8+ T cell comprises: expression of CD62L and does not express SLAMF7, CX3CR1, KLRG1, TIM3 and PD1.

The isolated CD62L− Slamf7+ CX3CR1− CD8+ T cell, isolated CD62L− Slamf7+ CX3CR1+ CD8+ T cell, and isolated CD62Lhi Slamf7− CD8+ T cell may be further characterized by a gene signature comprising one or more genes or polypeptides in Tables 3 or 4. Tables 3 or 4 list genes differentially expressed in one or more of the CD8+ T cell subtypes described herein relative to one or more of another subtype (i.e. genes differentially expressed relative to all three subtypes). Thus, genes up and down regulated in one subtype relative to the other subtypes listed in Tables 3 or 4 may be used to further distinguish between each subtype. In certain embodiments, the overall signatures or subset of signature genes listed in Tables 3 or 4 may be used to identify each subtype.

The isolated CD8+ T cell according to any embodiment herein, may be a human cell. The isolated CD8+ T cell may be a CAR T cell. The CAR T cell may be autologous or allogenic. In preferred embodiments, the isolated CD8+ T cell may be autologous for a subject suffering from cancer. The isolated CD8+ T cell may express an exogenous CAR or TCR. The isolated CD8+ T cell may display tumor specificity.

In another aspect, the present invention provides for a method for detecting or quantifying CD8+ T cells in a biological sample of a subject, or for isolating CD8+ T cells from a biological sample of a subject, the method comprising detecting or quantifying in a biological sample of the subject CD8+ T cells as defined in any embodiment herein, or isolating from the biological sample CD8+ T cells as defined in any embodiment herein. The CD8+ T cells may be detected, quantified or isolated using a set of markers comprising: SLAMF7, CD62L, CX3CR1, and PD1; or SLAMF7, CD62L, CX3CR1, and TIM3; or SLAMF7, CD62L, CX3CR1, KLRG1 and PD1; or SLAMF7, CD62L, CX3CR1, KLRG1 and TIM3; or any of the above markers and one or more genes or polypeptides selected from the group consisting of Tables 3 or 4; or any of the above markers and one or more genes or polypeptides selected from the group consisting of Table 5.

The CD8+ T cells may be detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof. The technique may employ one or more agents capable of specifically binding to one or more gene products expressed or not expressed by the CD8+ T cells, preferably on the cell surface of the CD8+ T cells. The one or more agents may be one or more antibodies.

The biological sample may be a tumor sample obtained from a subject in need thereof and the CD8+ T cells may be CD8+ tumor infiltrating lymphocytes (TIL). The biological sample may comprise ex vivo or in vitro CD8+ T cells. The biological sample may be treated with an antigen. The biological sample may be treated with a differentiation agent. The differentiating agent may be a cytokine. The cytokine may be an agent known to effect T cell differentiation. The biological sample may be treated with an agent capable of increasing the proportion of Slamf7+ CX3CR1− CD62L− cells as defined herein. The agent may be any agent predicted to affect the function or gene expression of any of the cells described herein. The agent may affect the ratio of cells in a population of cells. The agent may be a drug candidate. The agent may be a drug predicted to induce a gene signature described herein. The agent may be a drug predicted to reduce a gene signature described herein. Agents may be those predicted in silico (e.g., CMAP) or screened from a known compound library to affect a gene signature. The agent may also include drugs targeting a specific subtype for reducing said subtype. Not being bound by a theory, targeting a subtype for removal can increase the proportion of another subtype. Drugs targeting a specific subtype may include antibody drug conjugates specific for a subtype specific surface marker. The agent may also maintain a specific subtype, thus increasing the proportion of that subtype in a biological sample. The agent may be selected to activate or maintain expression a transcription factor. In other embodiments, the agent may be selected to repress a transcription factor. In certain example embodiments, the agent may include an agent selected to activate TCF7. In certain example embodiments, the agent may include an agent selected to downregulate expression of Bhlhe40, also known as DEC1, to maintain a basal level.

In another aspect, the present invention provides for a population of CD8+ T cells comprising CD8+ T cells as defined in any embodiment herein or isolated according to a method of any embodiment herein. The population may comprise greater than 5%, 10%, 20%, 30%, 40%, 50%, 60%, 70%, 80%, 90% or 95% of a CD8$^+$ T cell as defined in any embodiment herein. In certain embodiments, the population of cells is less than 5% of any one cell type, such as when cells are directly isolated from a patient. Not being bound by a theory, a population of cells isolated from a patient will include a heterogeneous population of cells, such that specific cell subtypes make up less than a majority of the total cells (e.g., less than 30%, 20%, 10%, 5%). In certain embodiments, a subtype of cells is expanded or enriched ex vivo to obtain a non-naturally occurring cell population enriched for certain cell types. The population of cells may comprise CD8$^+$ T cells as defined in any embodiment herein. In preferred embodiments, the population of cells are characterized in that the population comprises CD8$^+$ T cells that express SLAMF7 and that do not express CD62L, CX3CR1, TIM3 and PD1 (CD62L$^-$ Slamf7$^+$ CX3CR1$^-$). In other preferred embodiments, the population of cells are characterized in that the population comprises CD8$^+$ T cells that express CD62L and that do not express SLAMF7, CX3CR1, KLRG1, TIM3 and PD1 (CD62L$^{hi}$ Slamf7$^-$). Not being bound by a theory, the CD62L$^{hi}$ Slamf7$^-$ CD8$^+$ T cells may be the progenitor population that gives rise to the CD62L$^-$ Slamf7$^+$ CX3CR1$^-$ CD8$^+$ T cells. Not being bound by a theory, a population of progenitor cells may provide for a population of cells capable of differentiating into polyfunctional cells capable of controlling or eliminating cancer in vivo (e.g., for use in adoptive cell transfer).

The population of cells may be enriched for the CD8$^+$ T cells that express SLAMF7 and that do not express CD62L, CX3CR1, TIM3 and PD1 or for the CD8$^+$ T cells that express CD62L and that do not express SLAMF7, CX3CR1, KLRG1, TIM3 and PD1. The enriched population of cells may comprise CAR T cells. The population of enriched cells may comprise CD8$^+$ T cells autologous for a subject suffering from cancer. The population of cells may express an exogenous CAR or TCR. Not being bound by a theory, the enriched cell types may be more effective in targeting a tumor expressing antigens specific for the CAR or TCR than a population of unenriched T cells. Not being bound by a theory, unenriched T cells may include suppressive cell types.

The population of cells may display tumor specificity. The population of cells may comprise expanded cells. The population of cells may comprise activated CD8$^+$ T cells. The population of cells may comprise T cells activated with tumor specific antigens. The tumor specific antigens are subject specific antigens.

The population of CD8$^+$ T cells may comprise cells modified to knockout or downregulate expression of one or more genes selected from the group consisting of Bhlhe40 (DEC1), Klf2, Zeb2, Prdm1, Arnt1, Ets1, Junb, Id2, Hivep2, Rora, Nr1d2, Meis2, Arnt, Nr4a1, Meis3, Zmiz1, Vezf1, Nfe2l1, Mxi1, Rxra and Creb5. The population of cells may comprise cells modified to downregulate expression of Bhlhe40, such that the population of cells maintain at least a basal level of Bhlhe40 expression. As used herein, the term "basal" refers to the minimum expression level of a gene in a cell (e.g., T cell). Not being bound by a theory, at least basal expression of Bhlhe40 is required for proper function of the CD62L$^-$ Slamf7$^+$ CX3CR1$^-$ cells. The population of CD8$^+$ T cells may comprise cells modified to increase expression of one or more genes selected from the group consisting of Tcf7, Egr2, Zfp827, Satb1, Zfp512, Irf8, Relb, Sp140, Myb, Id3, Hes6, Fos, Ikzf2 and Myc. The population of cells may comprise cells modified to increase expression of Tcf7. The cells may be modified by any method known in the art. In preferred embodiments, the cells are modified with a CRISPR system. Not being bound by a theory, modifying the ability of the CD8$^+$ T cells to express one or more genes selected from the group consisting of Bhlhe40 (DEC1), Klf2, Zeb2, Prdm1, Arnt1, Ets1, Junb, Id2, Hivep2, Rora, Nr1d2, Meis2, Arnt, Nr4a1, Meis3, Zmiz1, Vezf1, Nfe2l1, Mxi1, Rxra and Creb5 may prevent the cells from differentiating to nonfunctional cells and/or suppressive cells or from differentiating to CD8$^+$ T cells characterized by expression of SLAMF7 and CX3CR1 and lack of expression of CD62L, TIM3 and PD1 (CD62L$^-$ Slamf7$^+$ CX3CR1$^+$).

In another aspect, the present invention provides for a pharmaceutical composition comprising the CD8$^+$ T cell as defined in any embodiment herein or the CD8$^+$ T cell population as defined in any embodiment herein.

In another aspect, the present invention provides for a method for treating or preventing cancer comprising administering to a subject in need thereof the pharmaceutical composition as described herein. The method may comprise: isolating from a biological sample of the subject a CD8$^+$ T cell or CD8$^+$ T cell population; in vitro expanding the CD8$^+$ T cell or CD8$^+$ T cell population; and administering the in vitro expanded CD8$^+$ T cell or CD8$^+$ T cell population to the subject. The method may further comprise enriching the expanded cells for CD8$^+$ T cells that express SLAMF7 and that do not express CD62L, CX3CR1, TIM3 and PD1 (CD62L$^-$ Slamf7$^+$ CX3CR1$^-$). The method may further comprise enriching the expanded cells for CD8$^+$ T cells that express CD62L and that do not express SLAMF7, CX3CR1, KLRG1, TIM3 and PD1 (CD62L$^{hi}$ Slamf7$^-$). The pharmaceutical composition may be administered after ablation therapy or before surgery. Not being bound by a theory, providing the pharmaceutical composition before surgery may shrink the tumor before it is removed. Not being bound by a theory, providing the pharmaceutical composition after ablation therapy or lymphodepletion may eliminate suppressor cells that can attenuated the activity of the transferred cells.

The method of treatment according to any embodiment, may further comprise administering a checkpoint blockade therapy. The checkpoint blockade therapy may comprise anti-TIM3, anti-CTLA4, anti-PD-L1, anti-PD1, anti-TIGIT, anti-LAG3, or combinations thereof. Not being bound by a theory, a treatment that increases the number or activity of cells that express SLAMF7 and that do not express CD62L, CX3CR1, TIM3 and PD1 (CD62L⁻ Slamf7⁺ CX3CR1⁻) may have an improved response to checkpoint blockade therapy.

In another aspect, the present invention provides for a method for identifying an immunomodulant capable of modulating one or more phenotypic aspects of the CD8⁺ T cell as defined in any embodiment herein or the CD8⁺ T cell population as defined in any embodiment herein, comprising: applying a candidate immunomodulant to the CD8⁺ T cell or CD8⁺ T cell population; and detecting modulation of one or more phenotypic aspects of the CD8⁺ T cell or CD8⁺ T cell population by the candidate immunomodulant, thereby identifying the immunomodulant.

In another aspect, the present invention provides for an immunomodulant capable of modulating one or more phenotypic aspects of the CD8⁺ T cell as defined in any embodiment herein or the CD8⁺ T cell population as defined in any embodiment herein, such as an immunomodulant identified using the method as defined above. The immunomodulant may be capable of modulating the proliferation, differentiation, maturation, migration, cytokine expression, cytotoxicity and/or viability of the CD8⁺ T cell or CD8⁺ T cell population. The immunomodulant may be capable of inducing or repressing the proliferation, differentiation, maturation, migration, cytokine expression, cytotoxicity and/or viability of the CD8⁺ T cell or CD8⁺ T cell population. The immunomodulant may comprise a therapeutic antibody, antibody fragment, antibody-like protein scaffold, aptamer, protein, CRISPR system or small molecule.

In another aspect, the present invention provides for a pharmaceutical composition comprising the immunomodulant as defined in any embodiment herein.

In another aspect, the present invention provides for a method for determining the CD8⁺ T cell status of a subject, or for diagnosing, prognosing or monitoring a disease comprising an immune component in a subject, the method comprising detecting or quantifying in a biological sample of the subject CD8⁺ T cells as defined in any embodiment herein. In certain embodiments, detecting or quantifying the CD8 + T cells in a biological sample of the subject may comprise detecting Tcf7. The disease may be cancer, an autoimmune disease or a chronic infection (e.g., viral infection). The CD8⁺ T cell status of the subject may be determined before and after therapy, whereby the efficacy of the therapy is determined or monitored. The therapy may be, but is not limited to an immunotherapy, innate immune agonists, vaccines, chemotherapies, and small molecules. Not being bound by a theory, determining the CD8⁺ T cell status by detection of the subtypes described herein after a treatment may indicate that the patient requires an increase in a specific subtype (e.g., adoptive cell transfer). The immunotherapy may comprise checkpoint blockade therapy. Not being bound by a theory, determining the CD8+ T cell status of a subject may indicate that the subject will respond to a checkpoint blockade therapy. In certain embodiments, detecting CD62L- Slamf7+ CX3CR1⁻ CD8+ T cells indicates an improved prognosis. In certain embodiments, the proportion of CD8+ subtypes is determined and subjects having a higher proportion of CD62L- Slamf7+ CX3CR1⁻ CD8+ T cells as compared to other subjects have an improved prognosis. In certain embodiments, detecting CD62L- Slamf7+ CX3CR1⁻ CD8+ T cells indicates that a subject can respond to an immunotherapy. In certain embodiments, the proportion of CD8+ subtypes is determined and subjects having a higher proportion of CD62L- Slamf7+CX3CR1- CD8+ T cells as compared to other subjects will respond better to an immunotherapy. In certain embodiments, detecting CD62L- Slamf7⁺CX3CR1- CD8+ T cells may comprise detecting cells positive for Tcf7.

In another aspect, the present invention provides for a method of identifying T cell receptors (TCR) specific for an antigen comprising isolating CD8⁺ T cells that express SLAMF7 and that do not express CD62L, CX3CR1, TIM3 and PD1 (CD62L⁻ Slamf7⁺CX3CR1⁻) and identifying TCRs expressed by the isolated cells. The cells may be isolated from a tumor. The antigen may be a tumor specific antigen. Not being bound by a theory, the CD62L⁻ Slamf7⁺ CX3CR1⁻ CD8⁺ cells isolated from a tumor express tumor specific TCRs. Not being bound by a theory the antigen determining regions of these TCRs may be used to generate tumor specific CARs.

In another aspect, the present invention provides for a method of preparing a CAR T cell specific for a tumor antigen comprising identifying TCRs according to any embodiment herein and generating a CAR T cell comprising the antigen-binding portion of the TCR identified.

In another aspect, the present invention provides for a method of preparing cells for use in adoptive cell transfer comprising: obtaining CD8⁺ T cells; and enriching for CD8⁺ T cells that express SLAMF7 and that do not express CD62L, CX3CR1, TIM3 and PD1 (CD62L⁻ Slamf7⁺ CX3CR1⁻) or for CD8⁺ T cells that express CD62L and that do not express SLAMF7, CX3CR1, KLRG1, TIM3 and PD1 (CD62L^hi Slamf7⁻). The method may further comprise expanding the cells. The method may further comprise activating the cells. The CD8⁺ T cells may further comprise a CAR. The CD8⁺ T cells may be autologous TILs. The method may further comprise treating the CD8⁺ T cells with an agonist of a transcription factor selected from the group consisting of Tcf7, Egr2, Zfp827, Satb1, Zfp512, Irf8, Relb, Sp140, Myb, Id3, Hes6, Fos, Ikzf2 and Myc. In preferred embodiments, the transcription factor is Tcf7. The Tcf7 agonist may comprise an agonist of Wnt/beta-catenin signaling.

In another aspect, the present invention provides for a method of preparing cells for use in adoptive cell transfer comprising: obtaining CD8⁺ T cells; and treating the CD8⁺ T cells with an agonist of a transcription factor selected from the group consisting of Tcf7, Egr2, Zfp827, Satb1, Zfp512, Irf8, Relb, Sp140, Myb, Id3, Hes6, Fos, Ikzf2 and Myc. In preferred embodiments, the transcription factor is Tcf7. The Tcf7 agonist may comprise an agonist of Wnt/beta-catenin signaling. The method may further comprise expanding the cells. The method may further comprise activating the cells. The CD8⁺ T cells may further comprise a CAR. The CD8⁺ T cells may be autologous TILs.

In another aspect, the present invention provides for a method of detecting a CD8⁺ T cell checkpoint blockade (CPB) therapy gene signature in a tumor comprising detecting in CD8⁺ T cells obtained from a subject in need thereof the expression or activity of a signature comprising one or more genes selected from Table 1 or 2.

In another aspect, the present invention provides for a method for determining the CD8⁺ T cell status of a subject suffering from cancer, said method comprising detecting in Tim-3⁺PD-1 CD8⁺ TILs from the subject a Tim-3⁺PD-1⁻ CPB gene signature and/or detecting in Tim-3⁻PD-1⁻CD8⁺ TILs from the subject a Tim-3⁻PD-1⁻ CPB gene signature, said gene signatures comprising one or more genes selected from Table 1. In certain embodiments, the subject is undergoing or has received CPB treatment and an increase in the Tim-3⁺PD-1⁺ and/or Tim-3⁻PD-1⁻ CPB gene signature as compared to a reference level before treatment indicates an enhanced CD8⁺ T cell immune response.

In another aspect, the present invention provides for a method for determining the CD8+ T cell status of a subject suffering from cancer, said method comprising detecting in CD8+ TILs from the subject a gene signature comprising one or more genes selected from Table 2. In certain embodiments, the subject is undergoing or has received CPB treatment and upregulation of the one or more genes as compared to a reference level before treatment indicates an enhanced CD8+ T cell immune response.

In certain embodiments, the CPB treatment comprises anti-PD1, anti-TIM3, anti-CTLA4, anti-PD-L1, anti-TIGIT, anti-LAG3, or combinations thereof.

In another aspect, the present invention provides for a method of preparing cells for use in adoptive cell transfer comprising: increasing expression or activity of one or more genes selected from Table 2 in CD8+ T cells; or modulating expression or activity of one or more genes selected from Table 1 in CD8+ T cells, wherein the genes are modulated in Tim-3+PD-1+CD8+ and/or Tim-3−PD-1−CD8+ T cells according to Table 1. In certain embodiments, the method further comprises expanding the cells. In certain embodiments, the method further comprises activating the cells. In certain embodiments, the method further comprises the CD8+ T cells are CAR T cells. In certain embodiments, the method further comprises the CD8+ T cells are autologous TILs.

In certain embodiments, the expression or activity of the one or more genes is modulated by treating the CD8+ T cells with an agent, said agent comprising a small molecule, genetic modifying agent, therapeutic antibody, antibody fragment, antibody-like protein scaffold, aptamer or protein. The genetic modifying agent may comprise a CRISPR system, a zinc finger nuclease system, a TALEN, or a meganuclease.

In another aspect, the present invention provides for a method of treating cancer in a subject in need thereof comprising administering to the subject cells prepared according to any embodiment herein.

In another aspect, the present invention provides for a method of identifying an immunomodulant capable of enhancing a CD8+ T cell immune response, comprising: applying a candidate immunomodulant to a population of CD8+ T cells; and (a) detecting increased expression or activity of one or more genes selected from Table 2 in the CD8+ T cells; and/or (b) detecting differential expression or activity of one or more genes selected from Table 1 in the CD8+ T cells, wherein the genes are differentially expressed in Tim-3+PD-1+CD8+ and/or Tim-3−PD-1−CD8+ T cells according to Table 1, thereby identifying an immunomodulant.

In another aspect, the present invention provides for a kit comprising reagents to detect at least one gene or polypeptide as defined in any embodiment herein.

An aspect of the invention provides the immune cell or immune cell population as taught herein for use in immunotherapy, such as adoptive immunotherapy, such as adoptive cell transfer. Also provided is a method of treating a subject in need thereof, particularly in need of immunotherapy, such as adoptive immunotherapy, such as adoptive cell transfer, comprising administering to said subject the immune cell or immune cell population as taught herein. Further provided is use of the immune cell or immune cell population as taught herein for the manufacture of a medicament for immunotherapy, such as adoptive immunotherapy, such as adoptive cell transfer. In certain embodiments, the immune cell is a T-cell, such as a CD8+ T-cell. In certain embodiments, the immunotherapy, adoptive immunotherapy or adoptive cell transfer may be for treating a proliferative disease, such as tumor or cancer, or a chronic infection, such as chronic viral infection.

In certain embodiments, an immune cell suitable for immunotherapy, such as a CD8+ T-cell, displays tumor specificity, more particularly displays specificity to a tumor antigen. In certain embodiments, an immune cell suitable for immunotherapy, such as a CD8+ T-cell, displays specificity to an antigen of an infectious agent, for example displays viral antigen specificity. In certain embodiments, an immune cell suitable for immunotherapy, such as a CD8+ T-cell, has been isolated from a tumor of a subject, preferably the cell is a tumor infiltrating lymphocyte (TIL). In certain embodiments, an immune cell suitable for immunotherapy, such as a CD8+ T-cell, comprises a chimeric antigen receptor (CAR). Such cell can also be suitably denoted as having been engineered to comprise or to express the CAR. In certain embodiments, the CAR comprises an extracellular antigen-binding element (or portion or domain) configured to specifically bind to a target antigen, a transmembrane domain, and an intracellular signaling domain. In certain embodiments, the intracellular signaling domain comprises a primary signaling domain and/or a costimulatory signaling domain. In certain embodiments, the CAR comprises the antigen-binding element, costimulatory signaling domain and primary signaling domain (such as CD3 zeta portion) in that order. In certain embodiments, the antigen-binding element comprises, consists of or is derived from an antibody, for example, the antigen-binding element is an antibody fragment. In certain embodiments, the antigen-binding element is derived from, for example is a fragment of, a monoclonal antibody, such as a human monoclonal antibody or a humanized monoclonal antibody. In certain embodiments, the antigen-binding element is a single-chain variable fragment (scFv). In certain preferred embodiments, the target antigen is selected from a group consisting of: CD19, BCMA, CLL-1, MAGE A3, MAGE A6, HPV E6, HPV E7, WT1, CD22, CD171, ROR1, MUC16, and SSX2. In certain preferred embodiments, the target antigen is CD19. In certain embodiments, the transmembrane domain is derived from the most membrane proximal component of the endodomain. In certain embodiments, the transmembrane domain is not CD3 zeta transmembrane domain. In certain embodiments, the transmembrane domain is a CD8α transmembrane domain or a CD28 transmembrane domain, preferably CD28 transmembrane domain. In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain preferred embodiments, the primary signaling domain comprises a functional signaling domain of CD3ζ. In certain embodiments, the one or more costimulatory signaling domains comprise a functional signaling domain of a protein selected, each independently, from the group consisting of: CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD103, ITGAL, CD11a, LFA-1, ITGAM, CD1 Ib, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Lyl08), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D. In certain preferred embodiments, the one or more costimulatory signaling domains comprise a functional signaling domain of a protein selected, each independently, from the group consisting of: 4-1BB, CD27, and CD28. In certain preferred embodiments, the costimulatory signaling domain comprises a functional signaling domain of CD28. In certain embodiments, the CAR comprises an anti-CD19 scFv, an intracellular domain of a CD3ζ chain, and a signaling domain of CD28. In certain preferred embodiments, the CD28 sequence is as set forth in Genbank identifier NM_006139 (sequence version 1, 2 or 3) starting with the amino acid sequence IEVMYPPPY and continuing all the way to the carboxy-terminus of the protein. In certain preferred embodiments, the CAR is as included in KTE-C19 (axicabtagene ciloleucel) anti-CD19 CAR-T therapy product in development by Kite Pharma, Inc. In certain embodiments, an immune cell suitable for immunotherapy, such as a CD8$^+$ T-cell, comprises an exogenous T-cell receptor (TCR). Such cell can also be suitably denoted as having been engineered to comprise or to express the TCR.

In certain embodiments, an immune cell suitable for immunotherapy, such as a CD8$^+$ T-cell, may be further genetically modified, such as gene edited, i.e., a target locus of interest in the cell may be modified by a suitable gene editing tool or technique, such as without limitation CRISPR, TALEN or ZFN. An aspect relates to an immune cell obtainable by or obtained by said gene editing method, or progeny thereof, wherein the cell comprises a modification of the target locus not present in a cell not subjected to the method. Another aspect relates to a cell product from said cell or progeny thereof, wherein the product is modified in nature or quantity with respect to a cell product from a cell not subjected to the gene editing method. A further aspect provides an immune cell comprising a gene editing system, such as a CRISPR-Cas system, configured to carry out the modification of the target locus.

In certain preferred embodiments, the cell may be edited using any CRISPR system and method of use thereof as described herein. In certain preferred embodiments, cells are edited ex vivo and transferred to a subject in need thereof.

Further genetically modifying, such as gene editing, of the cell may be performed for example (1) to insert or knock-in an exogenous gene, such as an exogenous gene encoding a CAR or a TCR, at a preselected locus in the cell; (2) to knock-out or knock-down expression of an endogenous TCR in the cell; (3) to disrupt the target of a chemotherapeutic agent in the cell; (4) to knock-out or knock-down expression of an immune checkpoint protein or receptor in the cell; (5) to knock-out or knock-down expression of other gene or genes in the cell, the reduced expression or lack of expression of which can enhance the efficacy of adoptive therapies using the cell; (6) to knock-out or knock-down expression of an endogenous gene in a cell, said endogenous gene encoding an antigen targeted by an exogenous CAR or TCR; (7) to knock-out or knock-down expression of one or more MHC constituent proteins in the cell; (8) to activate a T cell, and/or increase the differentiation and/or proliferation of functionally exhausted or dysfunctional CD8$^+$ T cells; and/or (9) to modulate CD8$^+$ T cells, such that CD8$^+$ T cells have increased resistance to exhaustion or dysfunction. In certain preferred embodiments, the cell may be edited to produce any one of the following combinations of the modifications set forth above: (1) and (2); (1) and (4); (2) and (4); (1), (2) and (4); (1) and (7); (2) and (7); (4) and (7); (1), (2) and (7); (1), (4) and (7); (1), (2), (4) and (7); optionally adding modification (8) or (9) to any one of the preceding combinations. In certain preferred embodiments, the targeted immune checkpoint protein or receptor is PD-1, PD-L1 and/or CTLA-4. In certain preferred embodiments, the targeted endogenous TCR gene or sequence may be TRBC1, TRBC2 and/or TRAC. In certain preferred embodiments, the targeted MHC constituent protein may be HLA-A, B and/or C, and/or B2M. In certain embodiments, the cell may thus be multiply edited (multiplex genome editing) to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1—Transcriptional changes in CD8$^+$ TILs populations upon checkpoint blockade. FIG. 1C shows mean tumor size. ****p<0.0001, linear regression. FIG. 1D shows principle component analysis (PCA) of Tim-3$^+$PD-1$^+$ and Tim-3-PD-1$^-$CD8$^+$ TILs in mice treated with isotype vs. Tim-3/PD-1 blockade. Tim-3$^+$PD-1$^+$ and Tim-3$^-$PD-1$^-$CD8$^+$ TILs were isolated two days after the last treatment and gene expression analyzed by RNA sequencing. Bar graph shows comparison of the mean delta Euclidean distance between the isotype and anti-Tim-3/anti-PD-1 treated groups for Tim-3$^-$PD-1$^-$ and Tim-3$^+$PD-1$^+$CD8$^+$ TILs (p=0.0002, t-test). FIG. 1E shows wheel graphs showing enrichment of effector signatures (Hervas-Stubbs et al., 2010; Kaech et al., 2002; Kalia et al., 2010; Sarkar et al., 2008) in upregulated (Left) and downregulated (Right) genes in Tim-3$^+$PD-1$^+$ and Tim-3$^-$PD-1$^-$CD8$^+$ TILs after anti-Tim-3/anti-PD-1 blockade, (p=0.008, paired t-test). P values for enrichment of each signature in Tim-3$^-$PD-1$^-$ and Tim-3$^+$PD-1$^+$CD8$^+$ TILs are indicated, hypergeometric test. FIG. 1F shows a bar graph showing fold changes in selected effector T cell genes after Tim-3/PD-1 blockade in Tim-3⁺PD-1⁺ and Tim-3⁻PD-1⁻ CD8⁺ TILs.

FIG. 2—Identification of novel PD-1⁻CD8⁺ TILs subsets that change upon checkpoint blockade. FIG. 2E shows projection of the differentially expressed genes in Tim-3⁻PD-1⁻CD8⁺ TILs (Tim-3/PD-1 blockade vs isotype) and FIG. 2F shows projection of an effector CD8⁺ T cell signature (Kaech et al., 2002) onto the single-cell RNA profiles of Tim-3⁻PD1⁻CD8⁺ TILs (Singer et al., 2016). Single-cells expressing Tim-3 (Havcr2) or PD-1 (Pdcd1) were excluded from the analysis (grey).

FIG. 3—Functional and transcriptional characterization of novel PD-1⁻CD8⁺ TILs subsets. FIG. 3A shows the frequency of Ki67⁺ cells among the indicated PD-1⁻CD8⁺ TILs populations. FIG. 3B shows the frequency of Granzyme B⁺ (left) or CD107a⁺ (right) cells among the indicated PD-1⁻CD8⁺ TILs populations. For CD107a staining, cells were stimulated with 5 µg/ml OVA$_{257-264}$ peptide. FIG. 3C shows the frequency of IL-2, TNF-α, and IFN-γ-producing cells among the indicated PD-1⁻CD8⁺ TILs populations after stimulation with 5 µg/ml OVA$_{257-264}$ peptide. FIG. 3D shows TILs stained with H-2K$^b$/OVA$_{257-264}$ dextramer and antibodies against CD8, PD-1, CD62L, Slamf7, and CX3CR1. The frequency of OVA-specific cells within the indicated subsets of PD-1⁻CD8⁺ TILs populations is shown. All the p values indicated are calculated by One-way ANOVA, Tukey's multiple comparison test. *$p<0.05$, $p<0.01$, *$p<0.001$, ****$p<0.0001$.

FIG. 4—PD-1⁻CD8⁺ TILs in different therapeutic contexts and their relevance in human cancer. FIG. 4D shows the frequency of the indicated PD1⁻CD8⁺ TILs subsets from CTLA-4/PD-L1 blockade- or isotype-treated MC38OVA-bearing mice. ***$p<0.001$, *$p<0.05$, Mann Whitney U test. FIG. 4E shows the frequency of the indicated PD-1⁻CD8⁺ TILs subsets from B16F10-bearing mice treated with isotype vs. Tim-3/PD-1 blockade (left panel) and isotype vs. CTLA-4/PD-1 blockade (right panel). *$p<0.05$, ****$p<0.0001$, Mann-Whitney U test. Data are from two independent experiments. FIG. 4F shows GSEA of signatures from human CD8⁺ TILs (Methods) in the memory-precursor-like CD62L⁻Slamf7$^{hi}$CX3CR1⁻PD-1⁻ and effector-like CD62L⁻Slamf7$^{hi}$CX3CR1⁺PD-1⁻CD8⁺ TIL subsets.

FIG. 5—Single-cell analysis reveals shared transcriptional programs after checkpoint blockade in murine and human cancer.

FIG. 6—Tcf7 is required for effective anti-tumor responses after immunotherapy. FIGS. 6D-F shows E8i-Cre$^-$×Tcf7$^{fl/fl}$ (WT) and E8i-Cre$^+$×Tcf7 conditional knock-out (Tcf7cKO) were implanted with MC38-OVA and TILs analyzed 10-12 days post implantation. FIG. 6D shows the frequency of the indicated subsets within PD-1$^-$CD8$^+$ TILs in WT and Tcf7cKO mice. *p<0.05, Mann-Whitney U test. FIG. 6E shows the frequency of H-2K$^b$/OVA$_{257-264}$+PD-1$^-$CD8$^+$ TILs in WT and Tcf7cKO mice. *p<0.05, Mann-Whitney U test. FIG. 6F shows the frequency of IL-2-, TNF-α-, and IFN-γ-producing cells within Slamf7$^{hi}$CX3CR1$^-$ and Slamf7$^{hi}$ CX3CR1$^+$PD-1$^-$CD8$^+$ TILs from WT and Tcf7cKO after ex vivo stimulation with 5 ug/ml OVA$_{257-264}$ peptide. *p<0.05, Mann-Whitney U test. FIG. 6G shows WT and Tcf7cKO were implanted with MC38-OVA and treated with isotype or Tim-3/PD-1 blockade. Mean tumor growth is shown. Data are pooled from three independent experiments. p<0.01, **p<0.0001, linear regression. FIG. 6H shows WT and Tcf7cKO mice were implanted with MC38-OVA and treated with PBS or TLR9 agonist (IMO-2125). % change in tumor burden in WT vs Tcf7cKO mice is shown. Data are from three independent experiments. p=0.0361, Fisher's exact test.

FIG. 7—Poly-functionality of PD-1$^-$CD8$^+$ TILs subsets. FIG. 7A shows representative flow cytometry data showing expression of CD62L, CX3CR1, and KLRG1 within PD-1$^-$CD8$^+$ TILs. FIGS. 7B-C show the frequency of IL-2$^+$IFN-γ$^+$ (B) and TNF-α$^+$IFN-γ$^+$ (C) cells among the indicated PD-1$^-$CD8$^+$ TILs populations after ex vivo stimulation with 5 µg/ml OVA$_{257-264}$ peptide. *p<0.001 and **p<0.0001, One-way ANOVA, Tukey's multiple comparison test.

FIG. 8 shows plots showing the numbers of the indicated PD1$^-$CD8$^+$ TILs subsets in tumors from Tim3/PD1 blockade– or isotype-treated MC380VA-bearing mice overtime. p<0.01, *p<0.001, Mann-Whitney U test.

FIG. 9—Analysis of single-cell RNA profiles from Tim-3/PD-1 blockade versus isotype treated mice.

FIG. 10 shows projection of several human signatures (Methods) onto the single-cell clusters (5A, panel II). The scale shows the average expression signature score of all the cells that compose the cluster. Circle size indicates the percentage of the cells in each cluster that expresses a signature above the median and the dark borders indicate clusters that were either significantly concentrated or depleted of high scoring cells (FDR– adjusted P value <0.05, t-test). A '+' sign indicates clusters that had a statistically significant score (FDR-adjusted P value <0.05) compared to randomly generated signatures (Methods). Clusters that are Naïve-like, effector-like, and memory-precursor-like (FIG. 5) are indicated by the shaded bars.

FIG. 11—Analysis of Tcf7 expression in PD-1$^-$CD8$^+$ TILs subsets and Thymic development and peripheral homeostasis in Tcf7cKO mice.

FIG. 12—Tumor-antigen specific CD8$^+$ TILs in the absence of Tcf7 and tumor regression in TLR9 agonist treated mice. WT and Tcf7cKO were implanted with MC38-OVA and TILs were analyzed 10-12 days post implantation.

FIG. 13—Naïve, effector, and memory-precursor-like cells in human CD8$^+$ TILs.

Figure 1A:
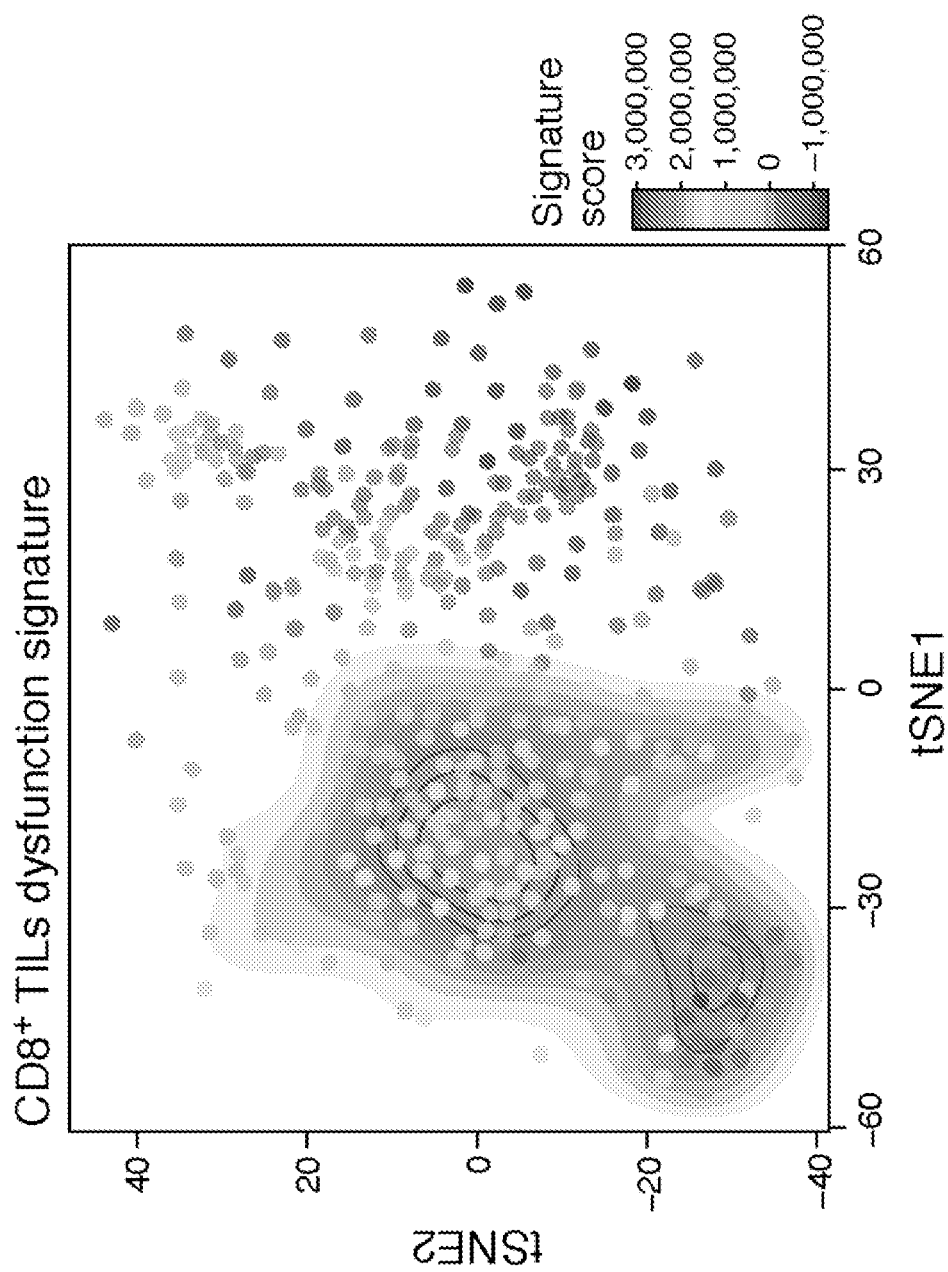
FIG. 1A shows a tSNE plot showing projection of the CD8$^+$ T cell dysfunction signature (genes differentially expressed in Tim-3$^+$PD-1$^+$CD8$^+$ TILs compared to Tim-3$^-$PD-1$^-$CD8$^+$ TILs isolated from MC38-OVA tumor-bearing C57BL/6 mice) onto single-cell CD8$^+$ TILs data (Singer et al., 2016).

The figures herein are for illustrative purposes only and are not necessarily drawn to scale.

DETAILED DESCRIPTION

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes I X, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

The terms "subject", "individual" or "patient" are used interchangeably throughout this specification, and typically and preferably denote humans, but may also encompass reference to non-human animals, preferably warm-blooded animals, even more preferably mammals, such as, e.g., non-human primates, rodents, canines, felines, equines, ovines, porcines, and the like. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is a non-human mammal. In another embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The terms "subtype", "subset" or "subpopulation" are used interchangeably throughout this specification.

All gene name symbols refer to the gene as commonly known in the art. The examples described herein that refer to the mouse gene names are to be understood to also encompasses human genes, as well as genes in any other organism (e.g., homologous, orthologous genes). The term, homolog, may apply to the relationship between genes separated by the event of speciation (e.g., ortholog). Orthologs are genes in different species that evolved from a common ancestral gene by speciation. Normally, orthologs retain the same function in the course of evolution. Gene symbols may be those referred to by the HUGO Gene Nomenclature Committee (HGNC) or National Center for Biotechnology Information (NCBI). Any reference to the gene symbol is a reference made to the entire gene or variants of the gene. The signature as described herein may encompass any of the genes described herein.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide cell products, substances, compositions, markers, marker signatures, molecular targets, kits of parts and methods useful in characterizing, evaluating and modulating the immune system and immune responses. Specifically, Applicants examined changes in RNA profiles in populations and single $CD8^+$ TILs after Tim-3/PD-1 blockade. Applicants discovered greater change in response to Tim-3/PD-1 blockade in Tim-3$^-$PD-1$^-$CD8$^+$ cells than in Tim-3$^+$PD-1$^+$CD8$^+$ cells. Applicants identified three novel CD8$^+$ TILs subsets within Tim-3$^-$PD-1$^-$CD8$^+$ TILs that separately have features of naïve, memory-precursor, and effector CD8$^+$ T cells. Applicants identify changes in the proportions of these subsets in response to different checkpoint blockades across different cancers. Importantly, Applicants find that the memory-precursor-like subset increases upon therapy and shares features with CD8$^+$ T cells that are associated with favorable prognosis and response to checkpoint blockade in cancer patients. Applicants further identify Tcf7 as a critical regulator of the memory-precursor-like subset and show that different immunotherapies fail in its absence. The findings pinpoint previously unappreciated changes within CD8$^+$ TILs and provide increased resolution of the dynamics of the effector CD8$^+$ T cell response within the TME in response to immunotherapy, with implications both for the design of novel T cell-based therapeutic approaches and for the evaluation of responses to immunotherapy in patients.

In one aspect, the CD8$^+$ T cells of the present invention were discovered by analysis of single immune cells obtained from a mouse tumor model treated with checkpoint blockade therapy (anti-TIM3 and anti-PD-1) or isotype control. As used herein, the terms "anti-Tim-3 and anti-PD-1 antibodies" may be referred to as Tim-3/PD-1 blockade. Unexpectedly, checkpoint blockade therapy had a strong preferential effect on gene expression in the population of cells not expressing the targeted coinhibitory receptors (TIM3$^-$, PD1$^-$ T cells). Applicants identified cell surface markers expressed by CD8$^+$ TILs isolated from mice treated with either checkpoint blockade therapy or isotype control. The identified markers could be used to distinguish between PD1$^-$CD8$^+$ T cell subtypes. Applicants unexpectedly identified 3 distinct CD8$^+$ TIL subtypes. Applicants characterized the 3 subtypes by gene expression programs and phenotype (e.g., proliferation, cytolytic activity, antigen specificity, functionality). One subtype may represent the progenitor population that gives rise to the following two subpopulations (CD62L$^{hi}$ Slamf7$^-$), a second subtype is enriched for a memory-precursor signature (CD62L$^-$ Slamf7$^{hi}$CX3CR1$^-$), and a third subtype is enriched for an effector signature (CD62L$^-$ Slamf7$^{hi}$ CX3CR1$^+$). Moreover, Applicants confirmed the presence of the CD8$^+$ TIL subtypes in human samples.

Immune checkpoints are inhibitory pathways that slow down or stop immune reactions and prevent excessive tissue damage from uncontrolled activity of immune cells. Immune checkpoints are described further herein. As used herein, the terms "checkpoint blockade therapy" and "checkpoint inhibitors" refer to agents, drugs, or pharmaceutical compositions capable of blocking or inhibiting the activity of an immune checkpoint.

In certain embodiments, the subtype may be used in adoptive cell transfer (e.g., TIL therapy, CAR T therapy). Not being bound by a theory TILs may be isolated from a tumor and the isolated cells selected for one or more specific subtypes. The one or more specific subtypes may be expanded or may be used to express a CAR. Not being bound by a theory allogenic CAR T cells may be enriched for one or more specific subtypes. Particular advantageous uses include methods for identifying agents capable of inducing or suppressing one or more immune cell subtypes based on the gene signatures, protein signature, and/or other genetic or epigenetic signature as defined herein. In certain example embodiments, detection or quantifying the subtypes may be used to determine responsiveness to various therapeutics (e.g., an increase in one or more of the Slamf7$^{hi}$ subtypes and/or decrease in the CD62L$^{hi}$ subtype for determining responsiveness to e.g., checkpoint blockade therapy).

In one aspect, the invention relates to a signature or set of biomarkers that distinguish between CD8$^+$ tumor infiltrating lymphocytes (TILs). The signature may be a gene signature, protein signature, and/or other genetic or epigenetic signature of particular tumor cell subpopulations, as defined herein. In certain embodiments, CD8$^+$ T cell subtypes may be detected and isolated by subtype specific signature biomarkers. In certain embodiments, pharmaceutical compositions comprising one or more subtypes may be used in treating cancer (e.g., adoptive cell transfer). In certain embodiments, one or more subtypes are used in combination with other therapies (e.g., checkpoint blockade therapy, CAR T cell therapy). In certain embodiments, one or more subtypes are used in controlling inflammatory responses by targeting biomarkers relevant to the cell subpopulation(s). In certain embodiments, antigen specific TCRs are determined by isolating the CD8+ T cell subtype having antigen specificity to a tumor.

The invention further relates to agents capable of inducing or suppressing particular immune cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. Not being bound by a theory, the CD8+ subtypes described herein are effected by other immune cells in the tumor microenvironment. In certain embodiments, checkpoint blockade therapy targets other immune cells expressing coinhibitory receptors and that are not CD8+ TILs (e.g., CD4+ T cells). In related aspects, modulating, such as inducing or repressing, a particular gene signature, protein signature, and/or other genetic or epigenetic signature may modify overall immune cell composition, such as immune cell composition, such as immune cell subpopulation composition or distribution, or functionality.

In further aspects, the invention relates to a signature or set of biomarkers that may be detected in combination. The signature may be a gene signature, protein signature, and/or other genetic or epigenetic signature of particular tumor cell subpopulations, as defined herein (e.g., tumor cells expressing antigens recognized by TCRs expressed on a CD8+ T cell subtype). The invention hereto also further relates to particular tumor cell subpopulations, which may be identified based on the methods according to the invention as discussed herein; as well as methods to target such cell subpopulations, such as in therapeutics (e.g., CD8+ TIL subtypes, CAR T cells); and screening methods to identify agents capable of inducing or suppressing particular tumor cell (sub)populations.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Thαβ, CD4+, CD8+, effector Th, memory Th, regulatory Th, CD4+/CD8+ thymocytes, CD4−/CD8− thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

As used throughout this specification, "immune response" refers to a response by a cell of the immune system, such as a B cell, T cell (CD4+ or CD8+), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

T cell response refers more specifically to an immune response in which T cells directly or indirectly mediate or otherwise contribute to an immune response in a subject. T cell-mediated response may be associated with cell mediated effects, cytokine mediated effects, and even effects associated with B cells if the B cells are stimulated, for example, by cytokines secreted by T cells. By means of an example but without limitation, effector functions of MHC class I restricted Cytotoxic T lymphocytes (CTLs), may include cytokine and/or cytolytic capabilities, such as lysis of target cells presenting an antigen peptide recognised by the T cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for MHC class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

The term "antigen" as used throughout this specification refers to a molecule or a portion of a molecule capable of being bound by an antibody, or by a T cell receptor (TCR) when presented by MHC molecules. At the molecular level, an antigen is characterized by its ability to be bound at the antigen-binding site of an antibody. The specific binding denotes that the antigen will be bound in a highly selective manner by its cognate antibody and not by the multitude of other antibodies which may be evoked by other antigens. An antigen is additionally capable of being recognized by the immune system. In some instances, an antigen is capable of eliciting a humoral immune response in a subject. In some instances, an antigen is capable of eliciting a cellular immune response in a subject, leading to the activation of B- and/or T-lymphocytes. In some instances, an antigen is capable of eliciting a humoral and cellular immune response in a subject. Hence, an antigen may be preferably antigenic and immunogenic. Alternatively, an antigen may be antigenic and not immunogenic. Typically, an antigen may be a peptide, polypeptide, protein, nucleic acid, an oligo- or polysaccharide, or a lipid, or any combination thereof, a glycoprotein, proteoglycan, glycolipid, etc. In certain embodiments, an antigen may be a peptide, polypeptide, or protein. An antigen may have one or more than one epitope. The terms "antigenic determinant" or "epitope" generally refer to the region or part of an antigen that specifically reacts with or is recognized by the immune system, specifically by antibodies, B cells, or T cells.

An antigen as contemplated throughout this specification may be obtained by any means available to a skilled person, e.g., may be isolated from a naturally-occurring material comprising the antigen, or may be produced recombinantly by a suitable host or host cell expression system and optionally isolated therefrom (e.g., a suitable bacterial, yeast, fungal, plant or animal host or host cell expression system), or may be produced recombinantly by cell-free transcription or translation, or non-biological nucleic acid or peptide synthesis.

The term "tumor antigen" as used throughout this specification refers to an antigen that is uniquely or differentially expressed by a tumor cell, whether intracellular or on the tumor cell surface (preferably on the tumor cell surface), compared to a normal or non-neoplastic cell. By means of example, a tumor antigen may be present in or on a tumor cell and not typically in or on normal cells or non-neoplastic cells (e.g., only expressed by a restricted number of normal tissues, such as testis and/or placenta), or a tumor antigen may be present in or on a tumor cell in greater amounts than in or on normal or non-neoplastic cells, or a tumor antigen may be present in or on tumor cells in a different form than that found in or on normal or non-neoplastic cells. The term thus includes tumor-specific antigens (TSA), including tumor-specific membrane antigens, tumor-associated antigens (TAA), including tumor-associated membrane antigens, embryonic antigens on tumors, growth factor receptors, growth factor ligands, etc. The term further includes cancer/testis (CT) antigens. Examples of tumor antigens include, without limitation, β-human chorionic gonadotropin (βHCG), glycoprotein 100 (gp100/Pme117), carcinoembryonic antigen (CEA), tyrosinase, tyrosinase-related protein 1 (gp75/TRP1), tyrosinase-related protein 2 (TRP-2), NY-BR-1, NY-CO-58, NY-ESO-1, MN/gp250, idiotypes, telomerase, synovial sarcoma X breakpoint 2 (SSX2), mucin 1 (MUC-1), antigens of the melanoma-associated antigen (MAGE) family, high molecular weight-melanoma associated antigen (HMW-MAA), melanoma antigen recognized by T cells 1 (MART1), Wilms' tumor gene 1 (WT1), HER2/neu, mesothelin (MSLN), alphafetoprotein (AFP), cancer antigen 125 (CA-125), and abnormal forms of ras or p53 (see also, WO2016187508A2). Tumor antigens may also be subject specific (e.g., subject specific neoantigens; see, e.g., U.S. Pat. No. 9,115,402; and international patent application publication numbers WO2016100977A1, WO2014168874A2, WO2015085233A1, and WO2015095811A2).

The term "in vitro" generally denotes outside, or external to, a body, e.g., an animal or human body. The term encompasses "ex vivo".

Biomarkers and Signatures

The invention further relates to various biomarkers for detecting $CD8^+$ T cell subpopulations. In certain example embodiments, these $CD8^+$ T cell populations are tumor infiltrating lymphocytes (TIL). The methods may comprise detecting a first population of $CD8^+$ T cell population as described further below, a second population of $CD8^+$ T cell population as described further below, a third population of $CD8^+$ T cell population as described further below or any combination of two subtypes or all three subtypes. The first, second and third $CD8^+$ T cell populations may be detected by detecting one or more biomarkers in a sample.

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of $\geq 5$ consecutive amino acids, or $\geq 10$ consecutive amino acids, or $\geq 20$ consecutive amino acids, or $\geq 30$ consecutive amino acids, e.g., $\geq 40$ consecutive amino acids, such as for example $\geq 50$ consecutive amino acids, e.g., $\geq 60$, $\geq 70$, $\geq 80$, $\geq 90$, $\geq 100$, $\geq 200$, $\geq 300$, $\geq 400$, $\geq 500$ or $\geq 600$ consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of $\geq 5$ consecutive nucleotides, or $\geq 10$ consecutive nucleotides, or $\geq 20$ consecutive nucleotides, or $\geq 30$ consecutive nucleotides, e.g., $\geq 40$ consecutive nucleotides, such as for example $\geq 50$ consecutive nucleotides, e.g., $\geq 60$, $\geq 70$, $\geq 80$, $\geq 90$, $\geq 100$, $\geq 200$, $\geq 300$, $\geq 400$, $\geq 500$ or $\geq 600$ consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

The present invention is also directed to signatures and uses thereof. As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., tumor infiltrating lymphocytes). In certain embodiments, the expression of the $CD8^+$ TIL signatures are dependent on epigenetic modification of the genes or regulatory elements associated with the genes. Thus, in certain embodiments, use of signature genes includes epigenetic modifications that may be detected or modulated. For ease of discussion, when discussing gene expression, any gene or genes, protein or proteins, or epigenetic element(s) may be substituted. Reference to a gene name throughout the specification encompasses the human gene, mouse gene and all other orthologues as known in the art in other organisms. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular immune cell or immune cell (sub)population if it is upregulated or only present, detected or detectable in that particular immune cell or immune cell (sub)population, or alternatively is downregulated or only absent, or undetectable in that particular immune cell or immune cell (sub)population. In this context, a signature consists of one or more differentially expressed genes/proteins or differential epigenetic elements when comparing different cells or cell (sub)populations, including comparing different immune cell or immune cell (sub)populations, as well as comparing immune cell or immune cell (sub)populations with non-immune cell or non-immune cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population or subpopulation level, refer to genes that are differentially expressed in all or substantially all cells of the population or subpopulation (such as at least 80%, preferably at least 90%, such as at least 95% of the individual cells). This allows one to define a particular subpopulation of immune cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In certain example embodiments, the signature genes may be used to deconvolute the network of cells present in a tumor based on comparing them to data from bulk analysis of a tumor sample. In certain example embodiments, the presence of specific immune cells and immune cell subtypes may be indicative of tumor growth, invasiveness and/or resistance to treatment. In one example embodiment, detection of one or more signature genes may indicate the presence of a particular cell type or cell types. In certain example embodiments, the presence of immune cell types within a tumor may indicate that the tumor will be sensitive to a treatment (e.g., checkpoint blockade therapy). In one embodiment, the signature genes of the present invention are applied to bulk sequencing data from a tumor sample obtained from a subject, such that information relating to disease outcome and personalized treatments is determined.

Detection of $CD8^+$ TIL Sub-Populations

In one embodiment, the method comprises detecting or quantifying $CD8^+$ T cells in a biological sample. In preferred embodiments, one or more $PD1^-CD8^+$ T cells are detected or quantified in the biological sample. The $CD8^+$ T cells may be detected or quantified using a set of markers comprising: SLAMF7, CD62L, CX3CR1, and PD1; or SLAMF7, CD62L, CX3CR1, and TIM3; or SLAMF7, CD62L, CX3CR1, KLRG1 and PD1; or SLAMF7, CD62L, CX3CR1, KLRG1 and TIM3; or any of the above markers and one or more genes or polypeptides selected from Table 3; or any of the above markers and one or more genes or polypeptides selected from Table 4; or any of the above markers and one or more genes or polypeptides selected from Table 5. Table 3, 4 and 5 list genes differentially expressed in one or more of the $CD8^+$ T cell subtypes described herein relative to one or more of another subtype (Table 3 and 4 relative to all three subtypes and Table 5 relative to $CD62L^-$ $Slamf7^+$ subtypes). Thus, genes up and down regulated in the subtypes listed in Table 3, 4 and 5 may be used to further distinguish between each subtype. Moreover, the overall signatures or subset of the signature genes may be used to identify each subtype. In certain embodiments, detecting or quantifying $CD8^+$ T cell sub-populations comprises detecting one or more markers selected from a first group consisting of PD1 and TIM3, all three markers from a second group consisting of SLAMF7, CD62L and CX3CR1, optionally KLRG1, and optionally one or more genes or polypeptides selected from Table 3, Table 4 or Table 5. In certain embodiments, the method comprises detecting one or more biomarkers selected from SLAMF7, CD62L, CX3CR1, PD1, TIM3 and KLRG1, and at least N additional biomarkers selected from Table 3, Table 4 or Table 5, wherein N equals 1 to 1265.

A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

In certain embodiments, the biological sample may be a tumor sample obtained from a subject in need thereof and the $CD8^+$ T cells may be $CD8^+$ tumor infiltrating lymphocytes (TIL). In certain embodiments, the biological sample may comprise ex vivo or in vitro $CD8^+$ T cells. The biological sample may be treated with an antigen. The biological sample may be treated with a differentiation agent. The differentiating agent may be a cytokine. The biological sample may be treated with a test agent. The test agent may be any agent predicted to affect the function or gene expression of any of the cells described herein. The agent may affect the ratio of cells in a population of cells. The test agent may be a drug candidate.

The terms "sample" or "biological sample" as used throughout this specification include any biological specimen obtained from a subject. Particularly useful samples are those known to comprise, or expected or predicted to comprise immune cells as taught herein. Preferably, a sample may be readily obtainable by minimally invasive methods, such as blood collection or tissue biopsy, allowing the removal/isolation/provision of the sample from the subject. Examples of particularly useful samples include without limitation whole blood or a cell-containing fraction of whole blood, such as serum, white blood cells, or peripheral blood mononuclear cells (PBMC), lymph, lymphatic tissue, inflammation fluid, tissue specimens, or tissue biopsies. The term "tissue" as used throughout this specification refers to any animal tissue types including, but not limited to, bone, bone marrow, neural tissue, fibrous connective tissue, cartilage, muscle, vasculature, skin, adipose tissue, blood and glandular tissue or other non-bone tissue. The tissue may be healthy or affected by pathological alterations, e.g., tumor tissue or tissue affected by a disease comprising an immune component. The tissue may be from a living subject or may be cadaveric tissue. The tissue may be autologous tissue or syngeneic tissue or may be allograft or xenograft tissue. A biological sample may also include cells grown in tissue culture, such as cells used for screening drugs or primary cells grown in culture for expansion.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$ or $\pm 3 \times SD$, or $\pm 1 \times SE$ or $\pm 2 \times SE$ or $\pm 3 \times SE$). Deviation may also refer to a value falling outside of a reference range defined by values in a given population (for example, outside of a range which comprises $\geq 40\%$, $\geq 50\%$, $\geq 60\%$, $\geq 70\%$, $\geq 75\%$ or $\geq 80\%$ or $\geq 85\%$ or $\geq 90\%$ or $\geq 95\%$ or even $\geq 100\%$ of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

In a further embodiment, the present invention provides for a method for determining the CD8$^+$ T cell status of a subject, or for diagnosing, prognosing or monitoring a disease comprising an immune component in a subject by detecting or quantifying CD8$^+$ T cells as defined in any embodiment herein in a biological sample of the subject. The CD8$^+$ T cell status of the subject may be determined before and after therapy, whereby the efficacy of the therapy is determined or monitored. The therapy may be an immunotherapy (e.g., checkpoint blockade therapy). Not being bound by a theory, an immunotherapy is effective if after treatment the CD62L$^-$ Slamf7$^+$CX3CR1$^-$ CD8$^+$ T cells increase. Not being bound by a theory, a subject having CD62L$^-$ Slamf7$^+$CX3CR1$^-$ CD8$^+$ T cells specific for a tumor has a better prognosis than a subject not having CD62L$^-$ Slamf7$^+$CX3CR1$^-$ CD8$^+$ T cells specific for a tumor.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Treatment Selection

In another aspect, detecting or quantifying CD8$^+$ T cells may be used to select a treatment for a subject in need thereof. In certain embodiments, subjects comprising CD62L$^+$Slamf7$^-$ or CD62L$^-$ Slamf7$^+$CX3CR1$^-$ CD8$^+$ TILs as described herein are treated with an immunotherapy (e.g., checkpoint blockade therapy) and subjects not comprising CD62L$^+$Slamf7$^-$ or CD62L$^-$ Slamf7$^+$CX3CR1$^-$ CD8$^+$ TILs are treated with a treatment other than a checkpoint blockade therapy. In certain embodiments, CD62L$^-$ Slamf7$^+$CX3CR1$^-$ cells are responsive to checkpoint blockade therapy and CD62L$^{hi}$ Slamf7$^-$ are the progenitor cells for the CD62L$^-$ Slamf7$^+$CX3CR1$^-$ cells. The treatment may involve modulating CD8$^+$ TIL subtypes or transferring CAR T cells to a patient followed by checkpoint blockade therapy. In certain embodiments, increasing CD62L$^-$ Slamf7$^+$CX3CR1$^-$ cells specific for a tumor in a subject or transferring CAR T cells specific for a tumor to a subject and having a CD62L$^-$ Slamf7$^+$CX3CR1$^-$ gene signature can make the subject more responsive to checkpoint blockade therapy. In certain embodiments, checkpoint blockade therapy can enhance adoptive cell transfer therapy.

Methods of Detection and Isolation of CD8$^+$ Subtypes Using Biomarkers

In certain embodiments, the CD8$^+$ T cell subtypes may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH) and combinations thereof. The technique may employ one or more agents capable of specifically binding to one or more gene products expressed or not expressed by the CD8$^+$ T cells, preferably on the cell surface of the CD8$^+$ T cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

In other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI– (MS)n; atmospheric pressure photoionization mass spectrometry (APPI-MS); APPI-MS/MS; and APPI– (MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p 666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain embodiments, immune cells are stained for immune cell subtype specific signature genes. In one embodiment, the cells are fixed. In another embodiment, the cells are formalin fixed and paraffin embedded. In another example embodiment, the immune cell subtypes may be quantitated in a section of a tumor.

The method may allow to detect or conclude the presence or absence of the specified immune cells in a tested object (e.g., in a cell population, tissue, organ, organism, or in a biological sample of a subject). The method may also allow to quantify the specified immune cells in a tested object (e.g., in a cell population, tissue, organ, organism, or in a biological sample of a subject). The quantity of the specified immune cells in the tested object such as the biological sample may be suitably expressed for example as the number (count) of the specified immune cells per standard unit of volume (e.g., ml, µl or nl) or weight (e.g., g or mg or ng) of the tested object such as the biological sample. The quantity of the specified immune cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified immune cells in the tested object such as the biological sample may also be suitably represented by an absolute or relative quantity of a suitable surrogate analyte, such as a peptide, polypeptide, protein, or nucleic acid expressed or comprised by the specified immune cells.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+", or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Isolated Cells

In one aspect, the present invention provides for isolated $CD8^+$ T cell subtypes as described herein (e.g., $CD62L^-$ $Slamf7^+CX3CR1^-$; $CD62L^-$ $Slamf7^+CX3CR1^+$; and $CD62L^{hi}$ $Slamf7^-$). The isolated $CD8^+$ T cell subtypes may be isolated using any of the markers described herein. The isolated $CD8^+$ T cell subtypes may be isolated from a human subject. The isolated $CD8^+$ T cell may be isolated from an ex vivo sample (e.g., CAR T cell, autologous T cell or allogenic T cell grown in culture). In preferred embodiments, the isolated $CD8^+$ T cell may be autologous for a subject suffering from cancer. The isolated $CD8^+$ T cell may express an exogenous CAR or TCR. The isolated CD8$^+$ T cell may display tumor specificity.

In one aspect, the invention is directed to isolated cell populations having the phenotypes described herein and/or as identified by the signatures defined herein. Accordingly, methods for detecting, quantifying or isolating the specified immune cells may be marker-based or gene or gene product signature-based, i.e., may involve isolation of cells expressing or not expressing marker(s) or combination(s) of markers the expression or lack of expression of which is taught herein as typifying or characterizing the specified immune cells, or may involve detection, quantification or isolation of cells comprising gene or gene product signature(s) taught herein as typifying or characterizing the specified immune cells.

In another aspect, the present invention provides for a population of CD8$^+$ T cells comprising CD8$^+$ T cells as defined in any embodiment herein or isolated according to a method of any embodiment herein. The isolated population may comprise greater than 30%, 40%, 50%, 60%, 70%, 80%, 90% or 95% of a CD8$^+$ T cell as defined in any embodiment herein. In certain embodiments, the population of cells is less than 30% of any one cell type, such as when cells are directly isolated from a patient. Not being bound by a theory, a population of cells isolated from a patient will include a heterogeneous population of cells, such that specific cell subtypes make up less than a majority of the total cells (e.g., less than 30%, 20%, 10%, 5%). In certain embodiments, a subtype of cells is expanded or enriched ex vivo to obtain a non-naturally occurring cell population enriched for certain cell types.

The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc. Isolating or purifying the specified immune cells from the tested object such as the biological sample may increase the abundance of the specified immune cells relative to all other cells comprised in the tested object such as the biological sample, or relative to other cells of a select subset of the cells comprised in the tested object such as the biological sample, e.g., relative to other white blood cells, peripheral blood mononuclear cells, immune cells, antigen presenting cells, or dendritic cells comprised in the tested object such as the biological sample. By means of example, isolating or purifying the specified immune cells from the tested object such as the biological sample may yield a cell population, in which the specified immune cells constitute at least 40% (by number) of all cells of said cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of said cell population.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the specified immune cells in, or to isolate the specified immune cells from, a tested object (e.g., a cell population, tissue, organ, organism, or a biological sample of a subject). Such methods allow to detect, quantify or isolate the specified immune cells in or from the tested object (e.g., a cell population, tissue, organ, organism, or a biological sample of a subject) substantially to the exclusion of other cells comprised in the tested object. Such methods may allow to detect, quantify or isolate the specified immune cells with sensitivity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified immune cells.

The isolated immune cells or immune cell populations as disclosed throughout this specification may be suitably cultured or cultivated in vitro. The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v CO2 and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Typically, the medium will comprise a basal medium formulation as known in the art. Many basal media formulations (available, e.g., from the American Type Culture Collection, ATCC; or from Invitrogen, Carlsbad, California) can be used, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of basal media are generally known in the art and it is within the skill of one in the art to modify or modulate concentrations of media and/or media supplements as necessary for the cells cultured.

Such basal media formulations contain ingredients necessary for mammalian cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g., glucose, sodium pyruvate, sodium acetate), etc.

For use in culture, basal media can be supplied with one or more further components. For example, additional supplements can be used to supply the cells with the necessary trace elements and substances for optimal growth and expansion. Furthermore, antioxidant supplements may be added, e.g., β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

Also contemplated is supplementation of cell culture media with mammalian plasma or sera. Plasma or sera often contain cellular factors and components that facilitate cell viability and expansion. Optionally, plasma or serum may be heat inactivated. Heat inactivation is used in the art mainly to remove the complement. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure. Optionally, plasma or serum may be sterilised prior to storage or use. Usual means of sterilisation may involve, e.g., filtration through one or more filters with pore size smaller than 1 μm, preferably smaller than 0.5 μm, e.g., smaller than 0.45 μm, 0.40 μm, 0.35 μm, 0.30 μm or 0.25 μm, more preferably 0.2 μm or smaller, e.g., 0.15 μm or smaller, 0.10 μm or smaller. Suitable sera or plasmas for use in media as taught herein may include human serum or plasma, or serum or plasma from non-human animals, preferably non-human mammals, such as, e.g., non-human primates (e.g., lemurs, monkeys, apes), foetal or adult bovine, horse, porcine, lamb, goat, dog, rabbit, mouse or rat serum or plasma, etc., or any combination of such. In certain preferred embodiments, a medium as taught herein may comprise bovine serum or plasma, preferably foetal bovine (calf) serum or plasma, more preferably foetal bovine (calf) serum (FCS or FBS). When culturing human cells, media may preferably comprise human serum or plasma, such as autologous or allogeneic human serum or plasma, preferably human serum, such as autologous or allogeneic human serum, more preferably autologous human serum or plasma, even more preferably autologous human serum.

In certain preferred embodiments, serum or plasma can be substituted in media by serum replacements, such as to provide for serum-free media (i.e., chemically defined media). The provision of serum-free media may be advantageous particularly with view to administration of the media or fraction(s) thereof to subjects, especially to human subjects (e.g., improved bio-safety). By the term "serum replacement" it is broadly meant any a composition that may be used to replace the functions (e.g., cell maintenance and growth supportive function) of animal serum in a cell culture medium. A conventional serum replacement may typically comprise vitamins, albumin, lipids, amino acids, transferrin, antioxidants, insulin and trace elements. Many commercialized serum replacement additives, such as KnockOut Serum Replacement (KOSR), N2, B27, Insulin-Transferrin-Selenium Supplement (ITS), and G5 are well known and are readily available to those skilled in the art.

Plasma or serum or serum replacement may be comprised in media as taught herein at a proportion (volume of plasma or serum or serum replacement/volume of medium) between about 0.5% v/v and about 40.0% v/v, preferably between about 5.0% v/v and about 20.0% v/v, e.g., between about 5.0% v/v and about 15.0% v/v, more preferably between about 8.0% v/v and about 12.0% v/v, e.g., about 10.0% v/v.

In certain embodiments, methods for detecting, quantifying or isolating the specified immune cells may be single-cell-based, i.e., may allow to discretely detect, quantify or isolate the specified immune cells as individual cells. In other embodiments, methods for detecting, quantifying or isolating the specified immune cells may be cell population-based, i.e., may only allow to detect, quantify or isolate the specified immune cells as a group or collection of cells, without providing information on or allowing to isolate individual cells.

Methods for detecting, quantifying or isolating the specified immune cells may employ any of the above-described techniques for measuring markers, insofar the separation or the qualitative and/or quantitative measurement of the marker(s) can be correlated with or translated into detection, quantification or isolation of the specified immune cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the specified immune cells.

In certain embodiments, the cells are detected, quantified or isolated using a technique selected from the group consisting of flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analyzed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyze cells by replacing fluorochrome-labelled binding reagents with mass tagged binding reagents, i.e., tagged with an element or isotope having a defined mass. In these methods, labeled particles are introduced into a mass cytometer, where they are individually atomized and ionized. The individual particles are then subjected to elemental analysis, which identifies and measures the abundance of the mass tags used. The identities and the amounts of the isotopic elements associated with each particle are then stored and analyzed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analyzed by their fluorescence properties. Fluorescence microscopy approaches may be manual or preferably automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 µm, more preferably less than 400 µm, more preferably less than 300 µm, more preferably less than 200 µm, e.g., 100 µm or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

Use of Specific Binding Agents

In certain embodiments, the aforementioned methods and techniques may employ agent(s) capable of specifically binding to one or more gene products, e.g., peptides, polypeptides, proteins, or nucleic acids, expressed or not expressed by the immune cells as taught herein. In certain preferred embodiments, such one or more gene products, e.g., peptides, polypeptides, or proteins, may be expressed on the cell surface of the immune cells (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridization probes or amplification or sequencing primers and primer pairs), small molecules, or combinations thereof.

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., KA in the order $1\times10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

Binding agents may be in various forms, e.g., lyophilised, free in solution, or immobilised on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about $10^4$-fold, or at least about $10^5$-fold, or at least about $10^6$-fold or more greater, than its affinity for a non-target molecule, such as for a suitable control molecule (e.g., bovine serum albumin, casein).

Preferably, the specific binding agent may bind to its intended target(s) with affinity constant (KA) of such binding $K_A \geq 1\times10^6$ $M^{-1}$, more preferably $K_A \geq 1\times10^7$ $M^{-1}$, yet more preferably KA≥1×108 M−1, even more preferably KA≥1×109 M−1, and still more preferably KA≥1×1010 M−1 or KA≥1×1011 M−1 or KA≥1×1012 M−1, wherein KA=[SBA_T]/[SBA][T], SBA denotes the specific-binding agent, T denotes the intended target. Determination of KA can be carried out by methods known in the art, such as for example, using equilibrium dialysis and Scatchard plot analysis.

In certain embodiments, the one or more binding agents may be one or more antibodies. As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunization, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo. Antibodies also encompasses chimeric, humanized and fully humanized antibodies.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbor Laboratory, New York, 1988; Harlow and Lane, "Using Antibodies: A Laboratory Manual", Cold Spring Harbor Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-

1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridisation probes or amplification or sequencing primers and primer pairs) may typically be capable of annealing with (hybridizing to) the respective target nucleic acid sequences at high stringency conditions, and capable of hybridizing specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C—U-3'.

The reference to oligonucleotides may in particular but without limitation include hybridization probes and/or amplification primers and/or sequencing primers, etc., as commonly used in nucleic acid detection technologies.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., $Ni2^+$), maltose:maltose binding protein, etc.

The marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof.

Pharmaceutical Compositions Using Isolated Cells

In another aspect, the present invention provides for a pharmaceutical composition comprising the CD8$^+$ T cell or the CD8$^+$ T cell population as defined in any embodiment herein. In certain embodiments, the CD8$^+$ T cell or the CD8$^+$ T cell population may be formulated into a pharmaceutical composition.

In certain embodiments, the immune cell or immune cell population is autologous to said subject, i.e., the immune cell or immune cell population is isolated from the same subject as the subject to which/whom the immune cell or immune cell population is to be administered. In certain further embodiments, the immune cell or immune cell population is syngeneic to said subject, i.e., the immune cell or immune cell population is isolated from an identical twin of the subject to which/whom the immune cell or immune cell population is to be administered. In certain further embodiments, the immune cell or immune cell population is allogeneic to said subject, i.e., the immune cell or immune cell population is isolated from a different subject of the same species as the subject to which/whom the immune cell or immune cell population is to be administered. In certain embodiments, the immune cell or immune cell population may even be xenogeneic to said subject, i.e., the immune cell or immune cell population may be isolated from a subject of a different species than the subject to which/whom the immune cell or immune cell population is to be administered.

Preferably, non-autologous, such as allogeneic cells may be selected such as to maximize the tissue compatibility between the subject and the administered cells, thereby reducing the chance of rejection of the administered cells by patient's immune system or graft-vs.-host reaction. For example, advantageously the cells may be typically selected which have either identical HLA haplotypes (including one or preferably more HLA-A, HLA-B, HLA-C, HLA-D, HLA-DR, HLA-DP and HLA-DQ) to the subject, or which have the most HLA antigen alleles common to the subject and none or the least of HLA antigens to which the subject contains pre-existing anti-HLA antibodies.

A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatizers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infusion. The skilled person will understand that compositions which are to be administered orally or topically will usually not comprise cells, although it may be envisioned for oral compositions to also comprise cells, for example when gastro-intestinal tract indications are treated. Each of the cells or active components (e.g., immunomodulants) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified immune cells and/or other active components (e.g., immunomodulants). The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

Activated T Cell Compositions

A further aspect of the invention relates to a method for preparing a composition comprising activated T cells, the method comprising isolating T cells from a biological sample of a subject and contacting said T cells in vitro with an immune cell or immune cell population, wherein the immune cell or immune cell population has been loaded with an antigen.

"Activation" generally refers to the state of a cell, such as preferably T cell, following sufficient cell surface moiety ligation (e.g., interaction between the T cell receptor on the surface of a T cell (such as naturally-occurring TCR or genetically engineered TCR, e.g., chimeric antigen receptor, CAR) and MIC-bound antigen peptide presented on the surface of an antigen presenting cell (e.g., dendritic cell) to induce a noticeable biochemical or morphological change of the cell, such as preferably T cell. In particular, "activation" may refer to the state of a T cell that has been sufficiently stimulated to induce detectable cellular proliferation of the T cell. Activation can also encompass induced cytokine production, and detectable T cell effector functions, e.g., regulatory or cytolytic effector functions. The T cells and antigen presenting cells may be suitably contacted by admixing the T cells and antigen presenting cells in an aqueous composition, e.g., in a culture medium, in sufficient numbers and for a sufficient duration of time to produce the desired T cell activation.

A further aspect of the invention relates to a method for adoptive immunotherapy in a subject in need thereof comprising administering to said subject a composition comprising activated T cells prepared with the method as taught above.

In certain embodiments, said T cells are $CD8^+$ T cells, i.e., T cells expressing the $CD8^+$ cell surface marker. More preferably, said T cells may be $CD8^+$ T cells and said subject is suffering from proliferative disease.

In certain embodiments, the T cell, preferably a $CD8^+$ T cell, may display specificity to a desired antigen, such as specificity to a tumor antigen (tumor antigen specificity). By means of an example, the T cell, preferably a $CD8^+$ T cell, may have been isolated from a tumor of a subject. More preferably, the immune cell may be a tumor infiltrating lymphocyte (TIL). Generally, "tumor infiltrating lymphocytes" or "TILs" refer to white blood cells that have left the bloodstream and migrated into a tumor. Such T cells typically endogenously express a T cell receptor having specificity to an antigen expressed by the tumor cells (tumor antigen specificity).

In alternative embodiments, a T cell, preferably a $CD8^+$ T cell, may be engineered to express a T cell receptor having specificity to a desired antigen, such as specificity to a tumor antigen (tumor antigen specificity). For example, the T cell, preferably a $CD8^+$ T cell, may comprise a chimeric antigen receptor (CAR) having specificity to a desired antigen, such as a tumor-specific chimeric antigen receptor (CAR).

Adoptive Cell Therapy

The immune cells or immune cell populations as taught herein may be used for adoptive cell transfer (ACT). In certain embodiments, the present invention comprises adoptive cell therapy. As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostate; Prostatic acid phosphatase (PAP); elongation factor 2 mutant (ELF2M); Insulin-like growth factor 1 receptor (IGF-1R); gp1OO; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GMi; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR5IE2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member IA (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cyclin-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicose antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR a and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD16, CD22, CD33, CD37, CD64, CD80, CD86, CD134, CD137, CD154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD103, ITGAL, CD11a, LFA-1, ITGAM, CD1 Ib, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Lyl08), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3): IEVMYPPPYLD-NEKSNGTIIHVKGKHLCPSPLFPGPSKPFWVLVVVGGV-LACYSLLVT VAFIIFWVRSKRSRLLHSDYMNMTPRRPGP-TRKHYQPYAPPRDFAAYRS) (SEQ ID No. 1)). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ ID No. 2) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated to a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular signaling domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY and continuing all the way to the carboxy-terminus of the protein. The sequence is reproduced herein: IEVMYPPPYLD-NEKSNGTIIHVKGKHLCPSPLFPGPSKPFWVLVVVGGV-LACYSLLVT VAFIIFWVRSKRSRLLHSDYMNMT-PRRPGPTRKHYQPYAPPRDFAAYRS. Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3ζ; CD27-CD3ζ; CD28-CD27-CD3ζ; 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkin's lymphoma, Waldenstrom's macroglobulinemia and multiple myeloma, and by HTLV-1– and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1;

US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring $CD4^+$ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of $CD4^+$ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371;

Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 November 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD.

However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, 0-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

In one embodiment, adoptive cell transfer may comprise: isolating from a biological sample of the subject a CD8$^+$ T cell or CD8$^+$ T cell population as described herein; in vitro expanding the CD8$^+$ T cell or CD8$^+$ T cell population; and administering the in vitro expanded CD8$^+$ T cell or CD8$^+$ T cell population to the subject. The method may further comprise enriching the expanded cells for CD62L$^-$ Slamf7$^+$ CX3CR1$^-$ CD8$^+$ T cells. The method may further comprise enriching the expanded cells for CD62L$^{hi}$ Slamf7$^-$ CD8$^+$ T cells. In certain embodiments, the method may further comprise formulating the in vitro expanded immune cell or immune cell population into a pharmaceutical composition.
Cancer In certain example embodiments, the pharmaceutical compositions and adoptive cell transfer strategies may be used to treat various forms of cancer. Examples of cancer include but are not limited to carcinoma, lymphoma, blastoma, sarcoma, and leukemia or lymphoid malignancies. More particular examples of such cancers include without limitation: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulvar cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, or hematological cancer.

Other non-limiting examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumours, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Glioblastoma, Childhood Cerebellar Astrocytoma, Childhood Cerebral Astrocytoma, Childhood Extracranial Germ Cell Tumours, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumours, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumours, Exocrine Pancreatic Cancer, Extracranial Germ Cell Tumour, Extragonadal Germ Cell Tumour, Extrahepatic Bile Duct Cancer, Eye Cancer, Female Breast Cancer, Gaucher's Disease, Gallbladder Cancer, Gastric Cancer, Gastrointestinal Carcinoid Tumour, Gastrointestinal Tumours, Germ Cell Tumours, Gestational Trophoblastic Tumour, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumour, Pancreatic Cancer, Paraproteinemias, Purpura, Parathyroid Cancer, Penile Cancer, Pheochromocytoma, Pituitary Tumour, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumours, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, or Wilms' Tumour.

In further examples, any combinations of methods such as discussed herein may be employed.

Identifying Immunomodulators

A further aspect of the invention relates to a method for identifying an immunomodulant capable of modulating one or more phenotypic aspects of an immune cell or immune cell population as disclosed herein, comprising: a) applying a candidate immunomodulant to the immune cell or immune cell population; b) detecting modulation of one or more phenotypic aspects of the immune cell or immune cell population by the candidate immunomodulant, thereby identifying the immunomodulant.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of an immune cell or immune cell population may be modulated without substantially altering other (unintended, undesired) phenotypic aspect(s).

The term "immunomodulant" broadly encompasses any condition, substance or agent capable of modulating one or more phenotypic aspects of an immune cell or immune cell population as disclosed herein. Such conditions, substances or agents may be of physical, chemical, biochemical and/or biological nature. The term "candidate immunomodulant" refers to any condition, substance or agent that is being examined for the ability to modulate one or more phenotypic aspects of an immune cell or immune cell population as disclosed herein in a method comprising applying the candidate immunomodulant to the immune cell or immune cell population (e.g., exposing the immune cell or immune cell population to the candidate immunomodulant or contacting the immune cell or immune cell population with the candidate immunomodulant) and observing whether the desired modulation takes place.

Immunomodulants may include any potential class of biologically active conditions, substances or agents, such as for instance antibodies, proteins, peptides, nucleic acids, oligonucleotides, small molecules, or combinations thereof.

By means of example but without limitation, immunomodulants can include low molecular weight compounds, but may also be larger compounds, or any organic or inorganic molecule effective in the given situation, including modified and unmodified nucleic acids such as antisense nucleic acids, RNAi, such as siRNA or shRNA, CRISPR/Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide—nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments, the agent is a small molecule having a chemical moiety. Agents can be known to have a desired activity and/or property, or can be selected from a library of diverse compounds.

In certain embodiments, an immunomodulant may be a hormone, a cytokine, a lymphokine, a growth factor, a chemokine, a cell surface receptor ligand such as a cell surface receptor agonist or antagonist, or a mitogen.

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-α, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signalling molecules, such as tumour necrosis factor (TNF) and interferons (e.g., interferon-α, interferon-β, interferon-γ, interferon-λ, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as immunomodulants include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

Treatment of Cancer by Targeting Transcription Factors

In another aspect, the present invention provides for a method for treating or preventing cancer comprising administering to a subject in need thereof. CD8$^+$ T cells treated with an agonist of a transcription factor selected from the group consisting of Tcf7, Egr2, Zfp827, Satb1, Zfp512, Irf8, Relb, Sp140, Myb, Id3, Hes6, Fos, Ikzf2 and Myc. In preferred embodiments, the transcription factor is Tcf7. The Tcf7 agonist may comprise an agonist of Wnt/beta-catenin signaling.

In another aspect, the present invention provides for a method of treating or preventing cancer comprising administering to a subject in need thereof. CD8$^+$ T cells treated with an antagonist of a transcription factor selected from the group consisting of Bhlhe40 (DEC1), Klf2, Zeb2, Prdm1, Arnt1, Ets1, Junb, Id2, Hivep2, Rora, Nr1d2, Meis2, Arnt, Nr4a1, Meis3, Zmiz1, Vezf1, Nfe2l1, Mxi1, Rxra and Creb5. In preferred embodiments, the transcription factor is Bhlhe40 (DEC1).

The isolated CD8$^+$ T cell gene signatures comprise expression of one or more transcription factors that may be key regulators or drivers of the phenotype of the identified CD8$^+$ T cell subtypes. In certain embodiments, the transcription factors described herein may be therapeutic targets. The transcription factors represented in the signature of the SLAMF$^{hi}$, CD62L$^-$, CX3CR1$^-$ subtype include Tcf7, Egr2, Zfp827, Satb1, Zfp512, Irf8, Relb, Sp140, Myb, Id3, Hes6, Fos, Ikzf2 and Myc. The transcription factors represented in the signature of the SLAMF7$^{hi}$, CD62L$^-$, CX3CR1$^+$ subtype include Bhlhe40 (DEC1), Klf2, Zeb2, Prdm1, Arnt1, Ets1, Junb, Id2, Hivep2, Rora, Nr1d2, Meis2, Arnt, Nr4a1, Meis3, Zmiz1, Vezf1, Nfe2l1, Mxi1, Rxra and Creb5. The expression patterns of these transcription factors appear to be mutually exclusive between the two subtypes (see FIG. 5A). A switch in the expression of transcription factors may allow differentiation of the SLAMF7$^{hi}$, CD62L$^-$, CX3CR1$^-$ subtype to the SLAMF7$^{hi}$, CD62L$^-$, CX3CR1$^+$ subtype. Thus, modulation of the expression of transcription factors may prevent a switch to a non-functional subtype or allow maintenance and longevity of a functional subtype. In certain embodiments, agonists of one or more transcription factors selected from the group consisting of Tcf7, Egr2, Zfp827, Satb1, Zfp512, Irf8, Relb, Sp140, Myb, Id3, Hes6, Fos, Ikzf2 and Myc are used to maintain high levels of the SLAMF7$^{hi}$, CD62L$^-$, CX3CR1$^-$ subtype in patients suffering from cancer or in an ex vivo population of cells. In certain embodiments, antagonists of one or more transcription factors selected from the group consisting of Bhlhe40 (DEC1), Klf2, Zeb2, Prdm1, Arnt1, Ets1, Junb, Id2, Hivep2, Rora, Nr1d2, Meis2, Arnt, Nr4a1, Meis3, Zmiz1, Vezf1, Nfe2l1, Mxi1, Rxra and Creb5 are used to maintain high levels of the SLAMF7$^{hi}$, CD62L$^-$, CX3CR1$-$ subtype in patients suffering from cancer or in an ex vivo population of cells by blocking differentiation into the SLAMF7$^{hi}$, CD62L$^-$, CX3CR1$^+$ subtype.

Applicants have determined experimentally that the transcription factor TCF7 is a key regulator required for maintenance and functionality of the SLAMF7$^{hi}$, CD62L$^-$, CX3CR1$^-$ subtype (see examples). In certain embodiments, Tcf7 agonists are used to maintain high levels of the SLAMF7$^{hi}$, CD62L$^-$, CX3CR1$^-$ subtype in patients suffering from cancer or in an ex vivo population of cells. Not being bound by a theory, high levels of the SLAMF7$^{hi}$, CD62L$^-$, CX3CR1$^-$ subtype can inhibit tumor growth by directly targeting tumor cells.

Tcf7 is also known as TCF-1 (encoded by Tcf7), and as used herein Tcf7 refers to the human gene, mouse gene and all other orthologues. Tcf7 may refer to the genes identified by the accession numbers NM_009331.4, NM_001313981.1, NM 003202.4, NM_213648.4, NM_201634.4, NM_001134851.3, NM_201632.4, NM_001346425.1, and NM_001346450.1.

TCF-1 is best known as a signal-dependent transducer of environmental signals from the Wnt pathway via β-catenin (Rothenberg, Curr Opin Immunol. 2012 April; 24(2):132-8). Wnt is a family of secreted glycoproteins that control a variety of biological activities during development (Ma, et al., Neuroimmune Pharmacol. 2012 December; 7(4):750-62). Wnt signaling pathways include the canonical Wnt pathway, which is mediated by β-catenin/T cell factor (TCF). The ultimate effectors of the canonical Wnt pathway are the TCF/lymphocyte-enhancer-binding factor (LEF) transcription factors. In the absence of Wnt signals, TCF or LEF is bound by co-repressors including Groucho/Transducin-like enhancer (GRG/TLE), and target gene expression is suppressed. Following Wnt signaling, translocated β-catenin replaces the GRG/TLE repressor, and binds TCF/LEF as a co-activator, leading to transcriptional activation of the target genes. Prior to the present invention, the β-catenin/TCF pathway was known to regulate multiple basic developmental processes, including cell-fate specification, progenitor cell proliferation, establishment of the dorsal axis, control of asymmetric cell division, hematopoietic stem cell self-renewal, and the proliferation of progenitor cells (Ma, et al., 2012). In a gain-of-function study, constitutive activation of the canonical Wnt pathway favored memory CD8 T cell formation during an initial immune challenge with a pathogen, resulting in an enhanced immunity upon the second encounter with the same pathogen (Zhao et al., Constitutive activation of Wnt signaling favors generation of memory CD8 T cells. Journal of immunology. 2010; 184:1191-1199).

The results presented herein show for the first time that checkpoint blockade therapy targets a previously unidentified subtype of CD8$^+$ TILs having a memory signature that are indispensable for the therapeutic effect of such therapy. Applicants also show for the first time that maintenance and functionality of this specific CD8$^+$ TIL subtype is dependent upon Tcf7 expression. Thus, tumor immunity may be enhanced by activation of the canonical Wnt pathway in T cells. In certain embodiments, tumor immunity is enhanced by treating T cells for adoptive cell transfer with an agonist of Wnt signaling. In certain embodiments, CD8$^+$ TILs are treated with an agonist of Wnt signaling before use in adoptive cell transfer. Not being bound by a theory, treatment with an agonist of Wnt signaling will increase the SLAMF7$^{hi}$, CD62L$^-$, CX3CR1$^-$ subtype. Small molecules that can activate Wnt signaling have been described and are non-limiting examples of Tcf7 agonists applicable to the present invention (see, e.g., Liu et al., Angew Chem Int Ed Engl. 2005 Mar. 18; 44(13):1987-90; Pai et al., Mol Biol Cell. 2004 May; 15(5):2156-63; Sato et al., Nat Med. 2004 January; 10(1):55-63; Coghlan et al., Chem Biol. 2000 October; 7(10):793-803; Zhang et al., Proc Natl Acad Sci USA. 2007 May 1; 104(18):7444-8; Miyabayashi et al., Proc Natl Acad Sci USA. 2007 Mar. 27; 104(13):5668-73; Gilbert et al., Bioorg Med Chem Lett. 2010 Jan. 1; 20(1):366-70; and Bodine et al., Bone. 2009 June; 44(6):1063-8).

Bhlhe40 is also known as BHLHB2, Clast5, DEC1, HLHB2, SHARP-2, SHARP2, STRA13 and Stra14. As used herein Bhlhe40 refers to the human gene, mouse gene and all other orthologues. Bhlhe40 may refer to the gene identified by accession number NM_003670.2. DEC1 is a basic helix-loop-helix transcription factor that is known to be highly induced in a CD28-dependent manner upon T cell activation (Martinez-Llordella et al. "CD28-inducible transcription factor DEC1 is required for efficient autoreactive CD4+ T cell response." J Exp Med. 2013 Jul. 29; 210(8):1603-19. doi: 10.1084/jem.20122387. Epub 2013 July 22). DEC1 is required for the development of experimental autoimmune encephalomyelitis and plays a critical role in the production of the proinflammatory cytokines GM-CSF, IFNγ, and IL-2 (Martinez-Llordella, 2013). Applicants previously demonstrated that DEC1 has a role in promoting pathogenic Th17 differentiation (see, WO2015130968A2). The present invention shows for the first time that differential expression of Bhlhe40 may be involved in the development and/or differentiation of specific PD1-/TIM3-subtypes of CD8$^+$ T cells. Not being bound by a theory, the ratio of the subtypes may determine the response to checkpoint blockade therapy and moreover a tumor immune response. Thus, Bhlhe40 may be targeted to shift the balance of CD8$^+$ T cell subtypes for enhancement of tumor immunity. In preferred embodiments, Bhlhe40 is modulated ex vivo in T cells to be used for adoptive cell transfer. In certain embodiments, Bhlhe40 is downregulated.

Altering Expression Using Immunomodulants

In certain embodiments, an immunomodulant may alter expression and/or activity of one or more endogenous genes of the CD8$^+$ TIL subtypes. The term "altered expression" denotes that the modification of the immune cell alters, i.e., changes or modulates, the expression of the recited gene(s) or polypeptides(s). The term "altered expression" encompasses any direction and any extent of said alteration. Hence, "altered expression" may reflect qualitative and/or quantitative change(s) of expression, and specifically encompasses both increase (e.g., activation or stimulation) or decrease (e.g., inhibition) of expression.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures of the present may be used to screen for drugs that induce or reduce the signature in immune cells as described herein. The signature may be used for GE-HTS. In certain embodiments, pharmacological screens may be used to identify drugs that selectively activate polyfunctional immune cells. In certain embodiments, drugs that selectively activate CD62L$^-$Slamf7$^+$CX3CR1$^-$ cells are used for treatment of a cancer patient.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature of the present invention in silico.

Any one or more of the several successive molecular mechanisms involved in the expression of a given gene or polypeptide may be targeted by the immune cell modification as intended herein. Without limitation, these may include targeting the gene sequence (e.g., targeting the polypeptide-encoding, non-coding and/or regulatory portions of the gene sequence), the transcription of the gene into RNA, the polyadenylation and where applicable splicing and/or other post-transcriptional modifications of the RNA into mRNA, the localization of the mRNA into cell cytoplasm, where applicable other post-transcriptional modifications of the mRNA, the translation of the mRNA into a polypeptide chain, where applicable post-translational modifications of the polypeptide, and/or folding of the polypeptide chain into the mature conformation of the polypeptide. For compartmentalized polypeptides, such as secreted polypeptides and transmembrane polypeptides, this may further include targeting trafficking of the polypeptides, i.e., the cellular mechanism by which polypeptides are transported to the appropriate sub-cellular compartment or organelle, membrane, e.g. the plasma membrane, or outside the cell.

Hence, "altered expression" may particularly denote altered production of the recited gene products by the modified immune cell. As used herein, the term "gene product(s)" includes RNA transcribed from a gene (e.g., mRNA), or a polypeptide encoded by a gene or translated from RNA.

Also, "altered expression" as intended herein may encompass modulating the activity of one or more endogenous gene products. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein, "modulating" or "to modulate" generally means either reducing or inhibiting the activity of a target or antigen, or alternatively increasing the activity of the target or antigen, as measured using a suitable in vitro, cellular or in vivo assay. In particular, "modulating" or "to modulate" can mean either reducing or inhibiting the (relevant or intended) activity of, or alternatively increasing the (relevant or intended) biological activity of the target or antigen, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve effecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

In certain embodiments, an immunomodulant may be or may result in a genetic modification (e.g., mutation, editing, transgenesis, or combinations thereof) of an immune cell, for example, a genetic perturbation, such as a knock-out (i.e., resulting in a complete absence of expression and/or activity) of one or more endogenous genes/gene products, or a knock-down (i.e., resulting in a partial absence of expression and/or activity) of one or more endogenous genes/gene products, or another type of genetic modification modulating the expression and/or activity of one or more endogenous genes/gene products, or for example, introduction of one or more transgenes, such as one or more transgenes encoding one or more gene products. Such transgene may be suitably operably linked to suitable regulatory sequences, e.g., may be comprised in an expression cassette or an expression vector comprising suitable regulatory sequences, or may be configured to become operably linked to suitable regulatory sequences once inserted into the genetic material (e.g., genome) of the immune cell.

Any types of mutations achieving the intended effects are contemplated herein. For example, suitable mutations may include deletions, insertions, and/or substitutions. The term "deletion" refers to a mutation wherein one or more nucleotides, typically consecutive nucleotides, of a nucleic acid are removed, i.e., deleted, from the nucleic acid. The term "insertion" refers to a mutation wherein one or more nucleotides, typically consecutive nucleotides, are added, i.e., inserted, into a nucleic acid. The term "substitution" refers to a mutation wherein one or more nucleotides of a nucleic acid are each independently replaced, i.e., substituted, by another nucleotide.

In certain embodiments, a mutation may introduce a premature in-frame stop codon into the open reading frame (ORF) encoding a gene product. Such premature stop codon may lead to production of a C-terminally truncated form of said polypeptide (this may preferably affect, such as diminish or abolish, some or all biological function(s) of the polypeptide) or, especially when the stop codon is introduced close to (e.g., about 20 or less, or about 10 or less amino acids downstream of) the translation initiation codon of the ORF, the stop codon may effectively abolish the production of the polypeptide. Various ways of introducing a premature in-frame stop codon are apparent to a skilled person. For example but without limitation, a suitable insertion, deletion or substitution of one or more nucleotides in the ORF may introduce the premature in-frame stop codon.

In other embodiments, a mutation may introduce a frame shift (e.g., +1 or +2 frame shift) in the ORF encoding a gene product. Typically, such frame shift may lead to a previously out-of-frame stop codon downstream of the mutation becoming an in-frame stop codon. Hence, such frame shift may lead to production of a form of the polypeptide having an alternative C-terminal portion and/or a C-terminally truncated form of said polypeptide (this may preferably affect, such as diminish or abolish, some or all biological function(s) of the polypeptide) or, especially when the mutation is introduced close to (e.g., about 20 or less, or about 10 or less amino acids downstream of) the translation initiation codon of the ORF, the frame shift may effectively abolish the production of the polypeptide. Various ways of introducing a frame shift are apparent to a skilled person. For example, but without limitation, a suitable insertion or deletion of one or more (not multiple of 3) nucleotides in the ORF may lead to a frame shift.

In further embodiments, a mutation may delete at least a portion of the ORF encoding a gene product. Such deletion may lead to production of an N-terminally truncated form, a C-terminally truncated form and/or an internally deleted form of said polypeptide (this may preferably affect, such as diminish or abolish, some or all biological function(s) of the polypeptide). Preferably, the deletion may remove about 20% or more, or about 50% or more of the ORF's nucleotides. Especially when the deletion removes a sizeable portion of the ORF (e.g., about 50% or more, preferably about 60% or more, more preferably about 70% or more, even more preferably about 80% or more, still more preferably about 90% or more of the ORF's nucleotides) or when the deletion removes the entire ORF, the deletion may effectively abolish the production of the polypeptide. The skilled person can readily introduce such deletions.

In further embodiments, a mutation may delete at least a portion of a gene promoter, leading to impaired transcription of the gene product.

In certain other embodiments, a mutation may be a substitution of one or more nucleotides in the ORF encoding a gene product resulting in substitution of one or more amino acids of the polypeptide. Such mutation may typically preserve the production of the polypeptide, and may preferably affect, such as diminish or abolish, some or all biological function(s) of the polypeptide. The skilled person can readily introduce such substitutions.

In certain preferred embodiments, a mutation may abolish native splicing of a pre-mRNA encoding a gene product. In the absence of native splicing, the pre-mRNA may be degraded, or the pre-mRNA may be alternatively spliced, or the pre-mRNA may be spliced improperly employing latent splice site(s) if available. Hence, such mutation may typically effectively abolish the production of the polypeptide's mRNA and thus the production of the polypeptide. Various ways of interfering with proper splicing are available to a skilled person, such as for example but without limitation, mutations which alter the sequence of one or more sequence elements required for splicing to render them inoperable, or mutations which comprise or consist of a deletion of one or more sequence elements required for splicing. The terms "splicing", "splicing of a gene", "splicing of a pre-mRNA" and similar as used herein are synonymous and have their art-established meaning. By means of additional explanation, splicing denotes the process and means of removing intervening sequences (introns) from pre-mRNA in the process of producing mature mRNA. The reference to splicing particularly aims at native splicing such as occurs under normal physiological conditions. The terms "pre-mRNA" and "transcript" are used herein to denote RNA species that precede mature mRNA, such as in particular a primary RNA transcript and any partially processed forms thereof. Sequence elements required for splicing refer particularly to cis elements in the sequence of pre-mRNA which direct the cellular splicing machinery (spliceosome) towards correct and precise removal of introns from the pre-mRNA. Sequence elements involved in splicing are generally known per se and can be further determined by known techniques including inter alia mutation or deletion analysis. By means of further explanation, "splice donor site" or "5' splice site" generally refer to a conserved sequence immediately adjacent to an exon-intron boundary at the 5' end of an intron. Commonly, a splice donor site may contain a dinucleotide GU, and may involve a consensus sequence of about 8 bases at about positions $^{+}2$ to −6. "Splice acceptor site" or "3' splice site" generally refers to a conserved sequence immediately adjacent to an intron-exon boundary at the 3' end of an intron. Commonly, a splice acceptor site may contain a dinucleotide AG, and may involve a consensus sequence of about 16 bases at about positions −14 to $^{+}2$.

Genetic Modification and Genetic Modifying Agents

In certain embodiments, the one or more modulating agents may be a genetic modifying agent. The genetic modifying agent may comprise a CRISPR system, a zinc finger nuclease system, a TALEN, or a meganuclease.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molce1.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects, the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters—especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the 3-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), CaslO, Csy1, Csy2, Csy3, Cse1, Cse2, Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csxl, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "ortho-logue" (also referred to as "ortholog" herein) and "homo-logue" (also referred to as "homolog" herein) are well known in the art. By means of further guidance, a "homo-logue" of a protein as used herein is a protein of the same species which performs the same or a similar function as the protein it is a homologue of Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 3); the NLS from nucleoplasmin (e.g. the nucleoplasmin bipartite NLS with the sequence KRPAATKKAGQAKKKK) (SEQ ID NO: 4); the c-myc NLS having the amino acid sequence PAAKRVKLD (SEQ ID NO: 5) or RQRRNELKRSP (SEQ ID NO: 6); the hRNPA1 M9 NLS having the sequence NQSSNFGPMKGGNFGGRSSGPYGGGGQYFAK-PRNQGGY(SEQ ID NO: 7); the sequence RMRIZFKNKGKDTAELRRRRVEVSVELRKAKKD- EQILKRRNV (SEQ ID NO: 8) of the IBB domain from importin-alpha; the sequences VSRKRPRP (SEQ ID NO: 9) and PPKKARED (SEQ ID NO: 10) of the myoma T protein; the sequence POPKKKPL (SEQ ID NO: 11) of human p53; the sequence SALIKKKKKMAP (SEQ ID NO: 12) of mouse c-abl IV; the sequences DRLRR (SEQ ID NO: X) and PKQKKRK (SEQ ID NO: 13) of the influenza virus NS1; the sequence RKLKKKIKKL (SEQ ID NO: 14) of the Hepatitis virus delta antigen; the sequence REKKKFLKRR (SEQ ID NO: 15) of the mouse Mxl protein; the sequence KRKGDEVDGVDEVAKKKSKK (SEQ ID NO: 16) of the human poly(ADP-ribose) polymerase; and the sequence RKCLQAGMNLEARKTKK (SEQ ID NO: 17) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such as deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, *PNAS*, E7110-E7111; Allerson et al., *J. Med. Chem.* 2005, 48:901-904; Bramsen et al., *Front. Genet.,* 2012, 3:154; Deng et al., *PNAS,* 2015, 112:11870-11875; Sharma et al., *MedChemComm.,* 2014, 5:1454-1471; Hendel et al., *Nat. Biotechnol.* (2015) 33(9): 985-989; Li et al., *Nature Biomedical Engineering,* 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., *Nature Biomedical Engineering,* 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, *PNAS,* E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5 moU), inosine, 7-methyl-guanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stemloop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013);

155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm$^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100·mu·s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800

V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2.

Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application entitled "Novel Type VI CRISPR Orthologs and Systems," filed on Apr. 12, 2017.

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional entitled "Novel Crispr Enzymes and Systems" filed Dec. 8, 2016 bearing Broad Institute No. 10035.PA4. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: *Leptotrichia, Listeria, Corynebacter, Sutterella, Legionella, Treponema, Filifactor, Eubacterium, Streptococcus, Lactobacillus, Mycoplasma, Bacteroides, Flavivirus, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*, or the C2c2 effector protein is an organism selected from the group consisting of: *Leptotrichia shahii, Leptotrichia wadei, Listeria seeligeri, Clostridium aminophilum, Carnobacterium gallinarum, Paludibacter propionicigenes, Listeria weihenstephanensis*, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/ 058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/ j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and *Ruminococcus*. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with *Ruminococcus*.

In other example embodiments, the Type VI RNA-targeting Cas enzyme is Cas13d. In certain embodiments, Cas13d is *Eubacterium siraeum* DSM 15702 (EsCas13d) or *Ruminococcus* sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/ 10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of: Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013);

RNA-guided editing of bacterial genomes using CRISPR-Cas systems. Jiang W., Bikard D., Cox D., Zhang F, Marraffini L A. Nat Biotechnol Mar; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, PD., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527 (7577):192-7 (Nov. 12, 2015) doi: 10.1038/nature15521. Epub 2015 September 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molce1.2015.10.008 Epub Oct. 22, 2015.

*Rationally engineered Cas9 nucleases with improved specificity*, Slaymaker et al., Science 216 Jan. 1351 (6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. Doi: 10.1126/science.aaq0180. Epub 2017 Oct. 25.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors developed a pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12-F EB-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable diresidues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-($X_{12}X_{13}$)-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as $X^*$, where X represents $X_{12}$ and (*) indicates that $X_{13}$ is absent. The DNA binding domain comprises several repeats of TALE monomers and this may be represented as $(X_{1-11}$-($X_{12}X_{13}$)-$X_{14-33}$ or 34 or 35)$z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

Figure 8:
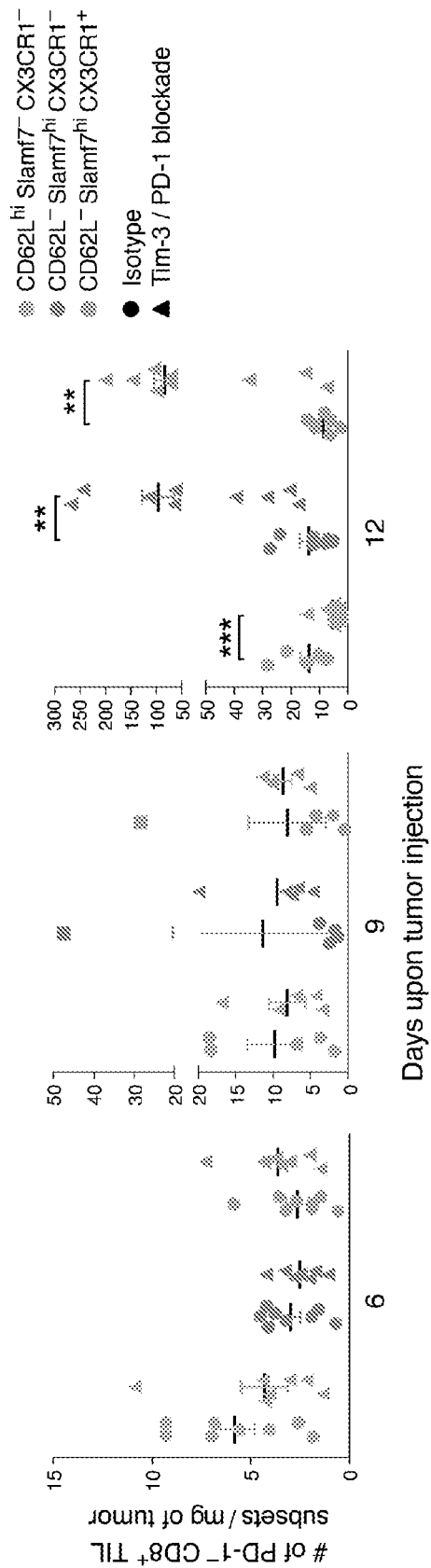
FIG. 8—Changes in PD-1$^-$CD8$^+$ TILs subsets after Tim3/PD-1 blockade.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8). Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                            (SEQ ID NO: 18)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N
```

An exemplary amino acid sequence of a C-terminal capping region is:

```
                                            (SEQ ID NO: 19)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments, the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

Transcriptional Activation/Repression

In certain embodiments, an immunomodulant may comprise (i) a DNA-binding portion configured to specifically bind to the endogenous gene and (ii) an effector domain mediating a biological activity.

In certain embodiments, the DNA-binding portion may comprise a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In some embodiments, the effector domain may be a transcriptional inhibitor (i.e., a repressor domain), such as an mSin interaction domain (SID). SID4X domain or a Kruppel-associated box (KRAB) or fragments of the KRAB domain. In some embodiments, the effector domain may be an enhancer of transcription (i.e. an activation domain), such as the VP16, VP64 or p65 activation domain. In some embodiments, the nucleic acid binding portion may be linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

Antibody Drug Conjugate

In certain embodiments, the agent capable of specifically binding to a gene product expressed on the cell surface of the immune cell is an antibody.

By means of an example, an agent, such as an antibody, capable of specifically binding to a gene product expressed on the cell surface of the immune cells may be conjugated with a therapeutic or effector agent for targeted delivery of the therapeutic or effector agent to the immune cells.

Examples of such therapeutic or effector agents include immunomodulatory classes as discussed herein, such as without limitation a toxin, drug, radionuclide, cytokine, lymphokine, chemokine, growth factor, tumor necrosis factor, hormone, hormone antagonist, enzyme, oligonucleotide, siRNA, RNAi, photoactive therapeutic agent, anti-angiogenic agent and pro-apoptotic agent.

Example toxins include ricin, abrin, alpha toxin, saporin, ribonuclease (RNase), DNase I, Staphylococcal enterotoxin-A, pokeweed antiviral protein, gelonin, diphtheria toxin, Pseudomonas exotoxin, or Pseudomonas endotoxin.

Example radionuclides include $^{103m}$Rh, $^{103}$Ru, $^{105}$Rh, $^{105}$Ru, $^{107}$Hg, $^{109}$Pd, $^{109}$Pt, $^{111}$Ag, $^{111}$In, $^{113m}$In, $^{119}$Sb, $^{11}$C, $^{121m}$Te, $^{121m}$Tem, $^{125}$I, $^{125m}$Te, $^{126}$I, $^{131}$I, $^{133}$I, $^{13}$N, $^{142}$Pr, $^{143}$Pr, $^{149}$Pm, $^{152}$Dy, $^{153}$Sm, $^{15}$O, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$CU, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo or $^{99m}$Tc. Preferably, the radionuclide may be an alpha-particle-emitting radionuclide.

Example enzymes include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase or acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

By means of an example, an agent, such as a bi-specific antibody, capable of specifically binding to a gene product expressed on the cell surface of the immune cells and a tumor cell may be used for targeting polyfunctional immune cells to tumor cells.

Combination Treatment

In certain embodiments, a treatment or pharmaceutical composition that increases the activity or quantity of CD62L$^-$ Slamf7$^+$CX3CR1$^-$ T cells (e.g., CD62L$^-$ Slamf7$^+$ CX3CR1$^-$ cells, CD62L' Slamf7$^-$ cells, immunomodulant, TCF7 agonist) is co-administered with a check point blockade therapy or is administered before administration of a check point blockade therapy to increase an immune response. The check point blockade therapy may be an inhibitor of any check point protein described herein. The checkpoint blockade therapy may comprise anti-TIM3, anti-CTLA4, anti-PD-L1, anti-PD1, anti-TIGIT, anti-LAG3, or combinations thereof. Specific check point inhibitors include, but are not limited to anti-CTLA4 antibodies (e.g., Ipilimumab), anti-PD-1 antibodies (e.g., Nivolumab, Pembrolizumab), and anti-PD-L1 antibodies (e.g., Atezolizumab). In certain embodiments, a treatment that increases the number or activity of CD62L$^-$ Slamf7$^+$CX3CR1$^-$ cells may have an improved response to checkpoint blockade therapy. Not being bound by a theory, a combination therapy may have synergistic effects.

Kits

In another aspect, the invention is directed to kit and kit of parts. The terms "kit of parts" and "kit" as used throughout this specification refer to a product containing components necessary for carrying out the specified methods (e.g., methods for detecting, quantifying or isolating immune cells as taught herein), packed so as to allow their transport and storage. Materials suitable for packing the components comprised in a kit include crystal, plastic (e.g., polyethylene, polypropylene, polycarbonate), bottles, flasks, vials, ampules, paper, envelopes, or other types of containers, carriers or supports. Where a kit comprises a plurality of components, at least a subset of the components (e.g., two or more of the plurality of components) or all of the components may be physically separated, e.g., comprised in or on separate containers, carriers or supports. The components comprised in a kit may be sufficient or may not be sufficient for carrying out the specified methods, such that external reagents or substances may not be necessary or may be necessary for performing the methods, respectively. Typically, kits are employed in conjunction with standard laboratory equipment, such as liquid handling equipment, environment (e.g., temperature) controlling equipment, analytical instruments, etc. In addition to the recited binding agents(s) as taught herein, such as for example, antibodies, hybridization probes, amplification and/or sequencing primers, optionally provided on arrays or microarrays, the present kits may also include some or all of solvents, buffers (such as for example but without limitation histidine-buffers, citrate-buffers, succinate-buffers, acetate-buffers, phosphate-buffers, formate buffers, benzoate buffers, TRIS (Tris (hydroxymethyl)-aminomethane) buffers or maleate buffers, or mixtures thereof), enzymes (such as for example but without limitation thermostable DNA polymerase), detectable labels, detection reagents, and control formulations (positive and/or negative), useful in the specified methods. Typically, the kits may also include instructions for use thereof, such as on a printed insert or on a computer readable medium. The terms may be used interchangeably with the term "article of manufacture", which broadly encompasses any man-made tangible structural product, when used in the present context.

The invention is further described in the following examples, which do not limit the scope of the invention described in the claims.

EXAMPLES

Figure 1B:
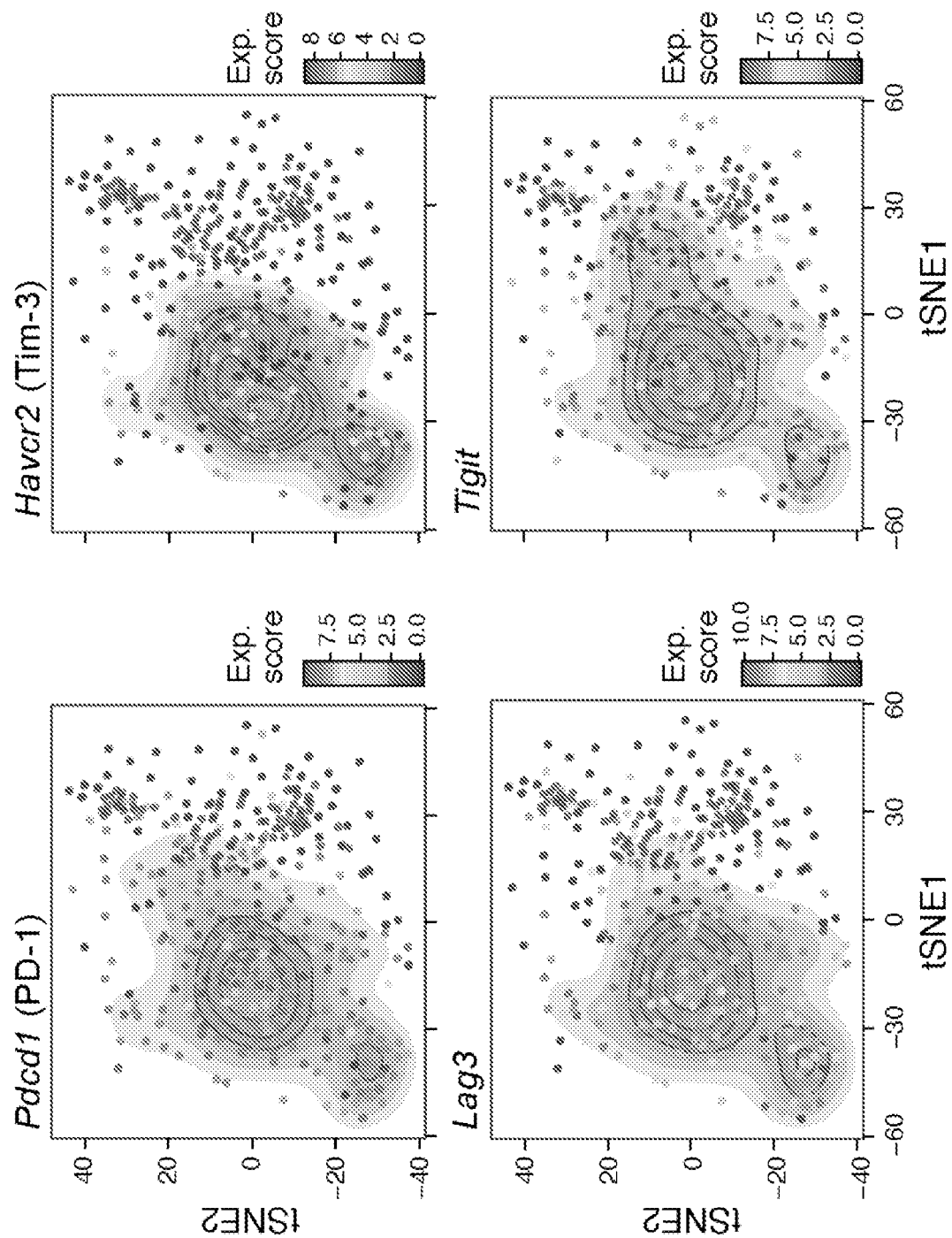
FIG. 1B shows tSNE plots showing expression of Tim-3, Lag-3, TIGIT, PD-1 in single-cell CD8$^+$ TILs data (Singer et al., 2016).

Example 1—Checkpoint Blockade Results in Profound Transcriptional Changes in CD8$^+$ TILs that Lack the Expression of Co-Inhibitory Receptors Applicants have previously demonstrated that Tim-3 and PD-1 can be used to identify CD8$^+$ TILs at opposite ends of the functional spectrum; Tim-3$^+$PD-1$^+$CD8$^+$ TILs (also referred to as PD-1$^-$CD8$^+$ TILs) are severely dysfunctional, whereas Tim-3$^-$PD-1$^-$CD8$^+$ TILs exhibit effector potential (Fourcade et al., 2010; Sakuishi et al., 2010), with each population harboring distinct transcriptional profiles (Singer et al., 2016). To determine the functional and transcriptional heterogeneity present within single CD8$^+$ TILs, Applicants generated a dysfunction signature defined as the differentially expressed genes between Tim-3$^-$PD-1$^-$ and Tim-3$^+$PD-1$^+$CD8$^+$ TILs (Methods) and scored this signature in each of the previously reported scRNA-Seq profiles of CD8$^+$ TILs from B16F10 melanoma (Singer et al., 2016). Applicants observed a gradient of low to high expression of the dysfunction signature across single CD8$^+$ TILs (FIG. 1A). As expected, cells with low expression of the dysfunction signature were negative for checkpoint receptors such as Lag3 and TIGIT in addition to Tim-3 and PD-1 (FIG. 1B).

Figure 1C:
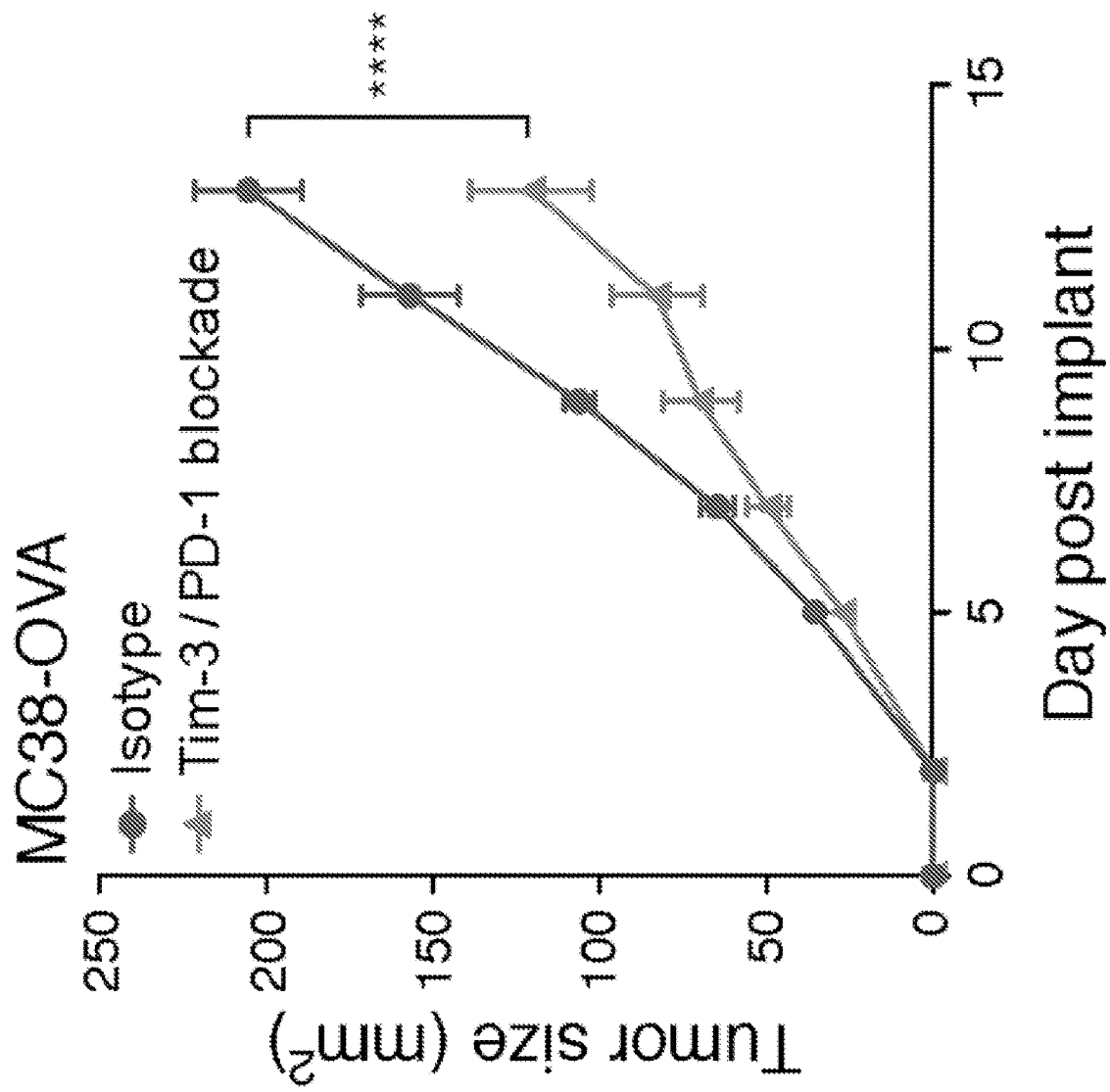
FIGS. 1C-F C57BL/6 mice were implanted subcutaneously with MC38-OVA and treated with either 200 g of rat IgG2a (circles) or anti-Tim-3 (RMT3-23) and 100 μg of anti-PD-1 (RMP1-14) (triangles) on days 4, 7, and 10.
Figure 1D:
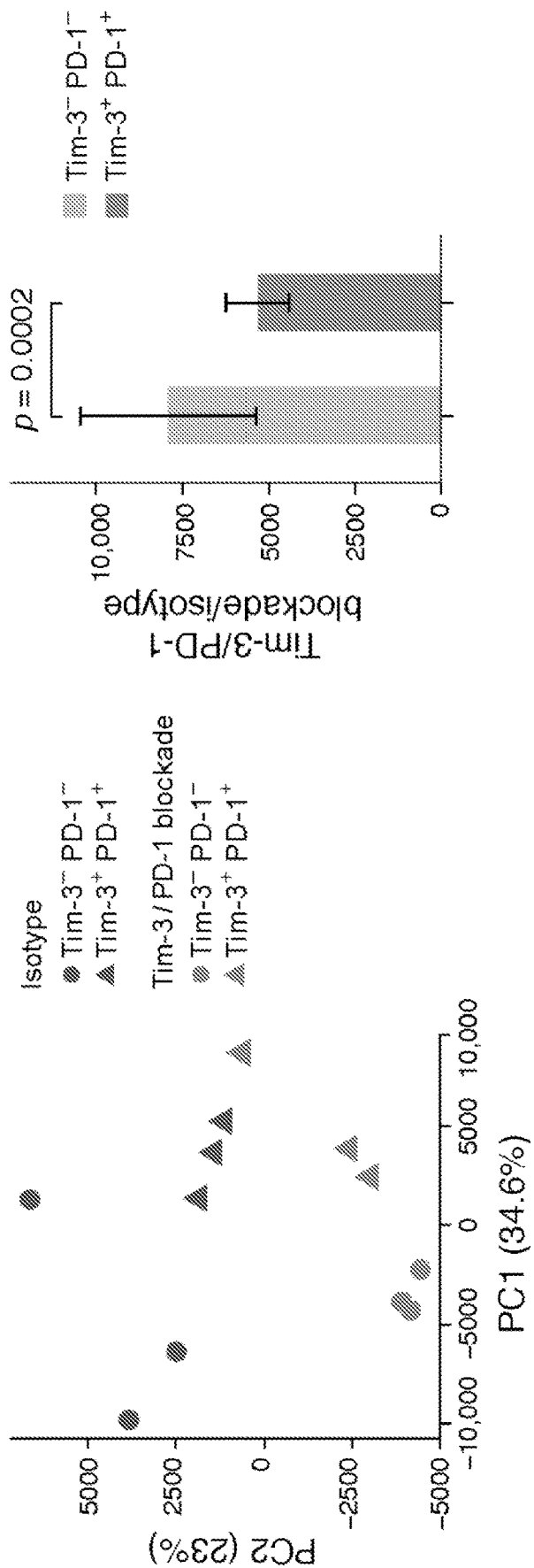

Applicants next determined the effect of checkpoint blockade therapy on these two populations of CD8$^+$ TILs; considering that checkpoint receptor blockade could impact these populations either directly or indirectly due to the expression of checkpoint receptor on additional immune cell populations in the TME (da Silva et al., 2014; Gordon et al., 2017; Jiang et al., 2016; Krempski et al., 2011; Lim et al., 2016; Sakuishi et al., 2013)). Applicants treated MC38-OVA tumor-bearing mice with a combination of anti-Tim-3 and anti-PD-1 antibodies (e.g., Tim-3/PD-1 blockade) (FIG. 1C), given the demonstrated efficacy of this antibody combination in multiple tumor models (Ngiow et al., 2011; Sakuishi et al., 2010; Zhou et al., 2011). Applicants used non-competing anti-Tim-3 and anti-PD-1 antibody clones to isolate low (Tim-3$^-$PD-1$^-$) and high (Tim-3$^+$PD-1$^+$) dysfunction signature-expressing CD8$^+$ TIL populations, and profiled them (in bulk). Principal Component Analysis (PCA) (FIG. 1D) distinguished Tim-3$^+$PD-1$^+$ and Tim-3$^-$PD-1$^-$CD8$^+$ TILs in the first principle component (PC1, 34.6% of variance), irrespective of treatment condition, while PC2 (23% of variance) primarily distinguished between treatment condition, but in a manner that also reflected the CD8$^+$ TILs population. Importantly, the change in profiles between the isotype and the Tim-3/PD-1 blockade groups was more significant for Tim-3$^-$PD-1$^-$ TILs than for Tim-3$^+$PD-1$^+$CD8$^+$ TILs (FIG. 1D, p=0.0002, t-test, and Methods).

Figure 1E:
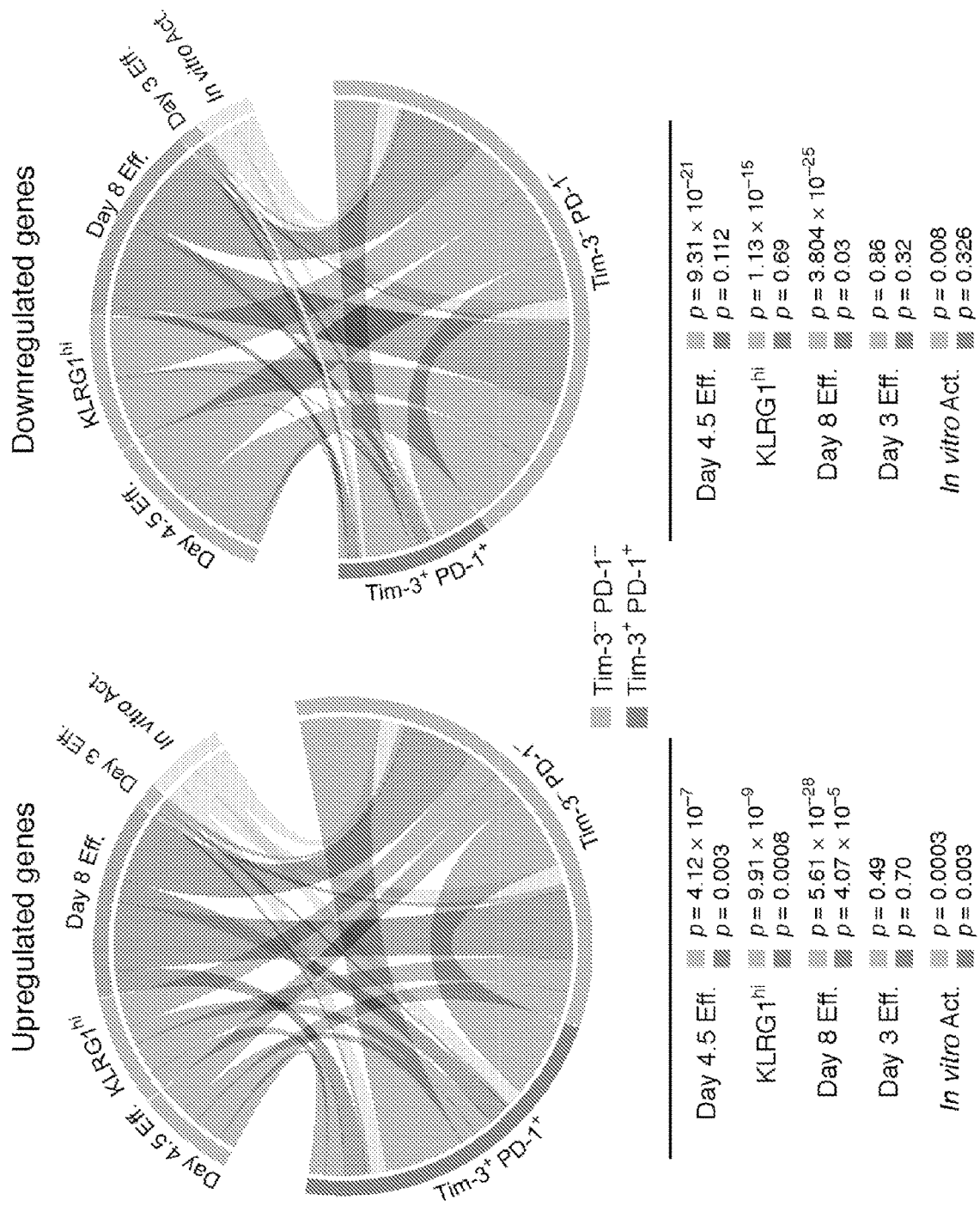
Figure 1F:
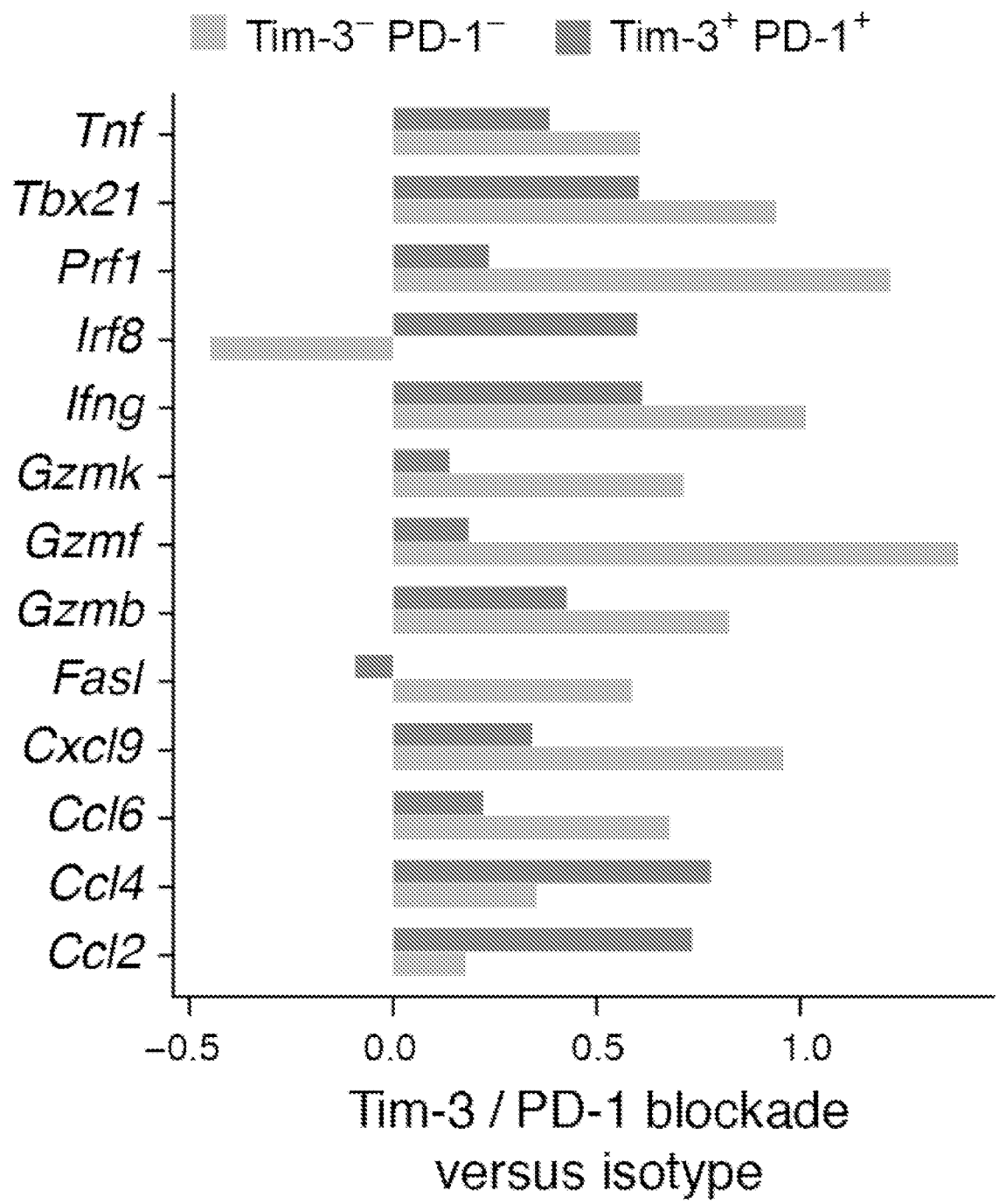

Next, Applicants determined whether the changes observed in the Tim-3$^-$PD-1$^-$ and Tim-3$^+$PD-1$^+$CD8$^+$ TILs populations after Tim-3/PD-1 blockade were associated with the acquisition of effector CD8$^+$ phenotypes. As expected, several effector genes were up-regulated in Tim-3$^+$PD-1$^+$CD8$^+$ TILs after Tim-3/PD-1 blockade (Table 1). However, analysis of multiple effector CD8$^+$ T cell signatures (Hervas-Stubbs et al., 2010; Kaech et al., 2002; Kalia et al., 2010; Sarkar et al., 2008) revealed a more substantial overlap of these signatures with the differentially expressed genes between the isotype and Tim-3/PD-1 blockade groups in the Tim-3$^-$PD-1$^-$CD8$^+$ TILs compared to the Tim-3$^+$PD-1$^+$CD8$^+$ TILs (p-value=0.008, paired t-test, FIG. 1E). Applicants identified 39 genes upregulated in both Tim-3$^-$PD-1$^-$ and Tim-3$^+$PD-1$^+$CD8$^+$ TILs (Table 2), including effector genes such as Ifng, Tnfa, and Gzmb, and transcription factors such as Tbx21. Nevertheless, these genes as well as other well-known effector genes showed greater treatment-induced changes in Tim-3$^-$PD-1$^-$ compared to Tim-3+PD-1$^+$CD8$^+$ TILs (FIG. 1F). Thus, checkpoint blockade-induced transcriptional change in CD8$^+$ TILs resulted in enhanced effector potential, which occurred to a significantly greater extent in CD8$^+$ TILs that lack the expression of co-inhibitory receptors. In other words, the larger transcriptional shift in Tim-3$^-$PD-1$^-$CD8$^+$ TILs following treatment corresponds to induction of gene expression that can lead to enhanced effector potential.

Figure 2A:
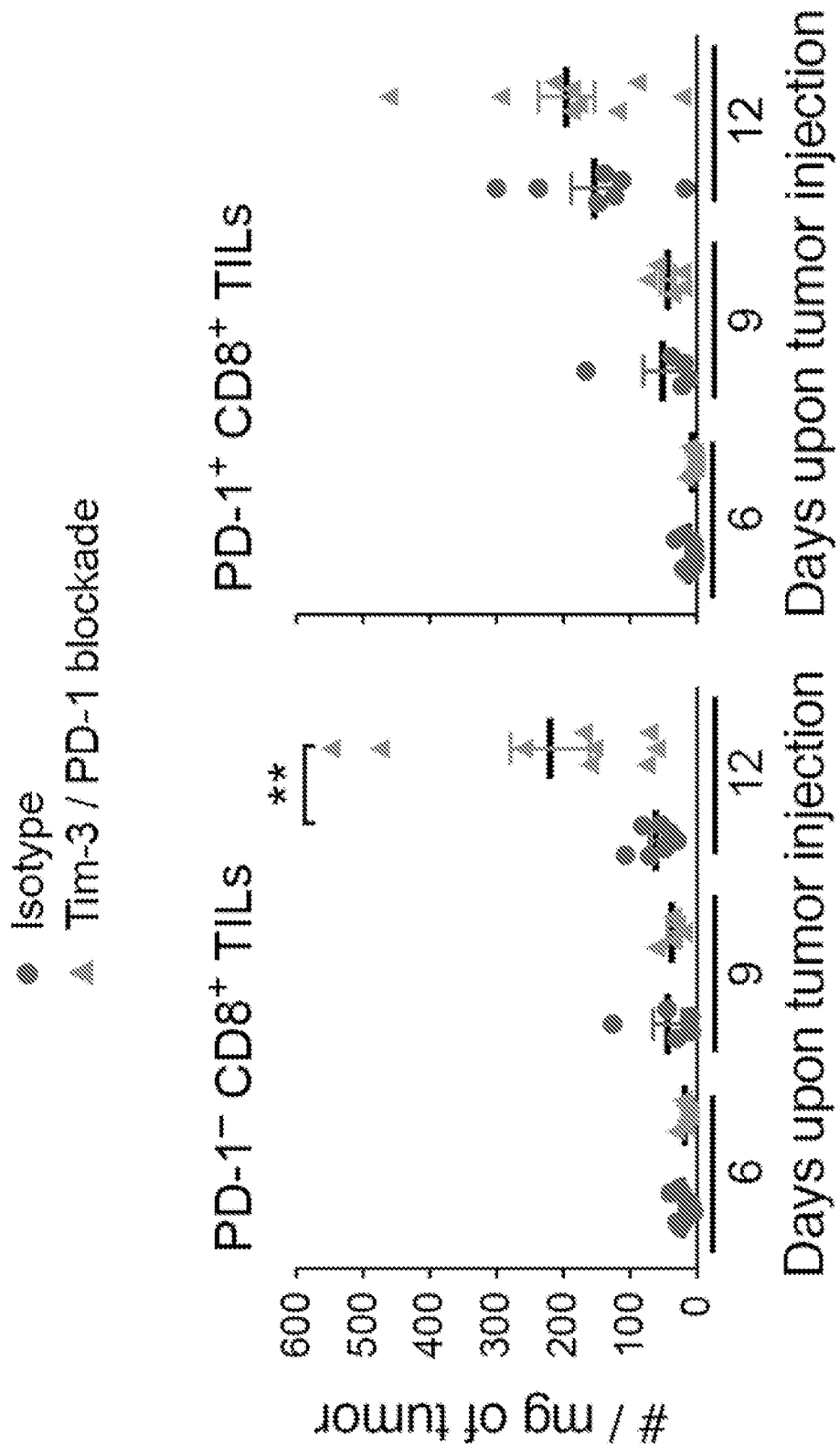
FIG. 2A shows the number of PD1⁻ and PD1⁺CD8⁺ TILs in tumors from Tim3/PD1 blockade- or isotype-treated mice over time. $p<0.01$, Mann Whitney U test.
Figure 2B:
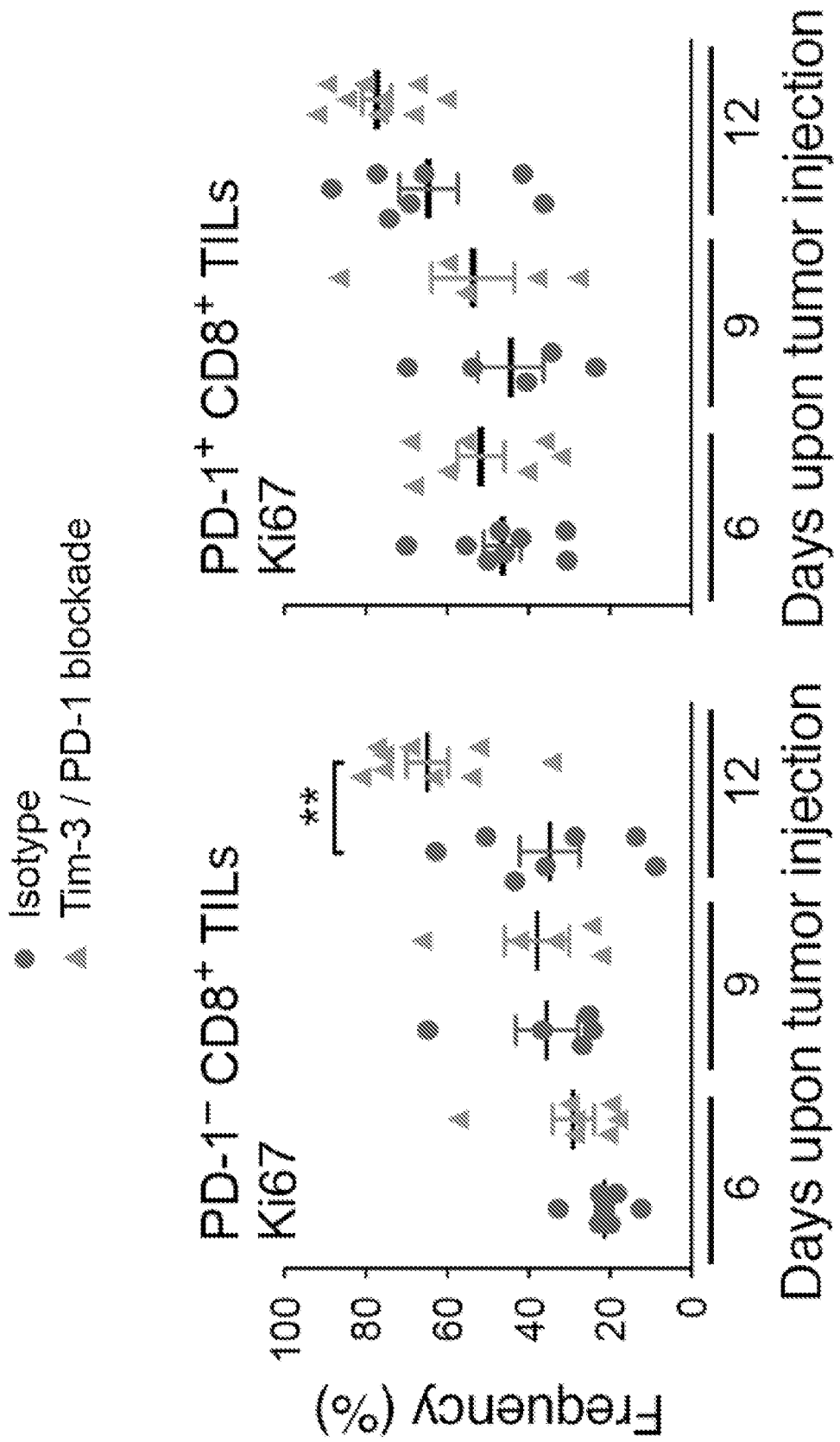
FIG. 2B shows the frequency of Ki67⁺ cells within PD1⁺ and PD1⁻CD8⁺ TILs from Tim3/PD1 blockade- or isotype-treated mice over time. $p<0.01$, Mann Whitney U test.
Figure 2C:
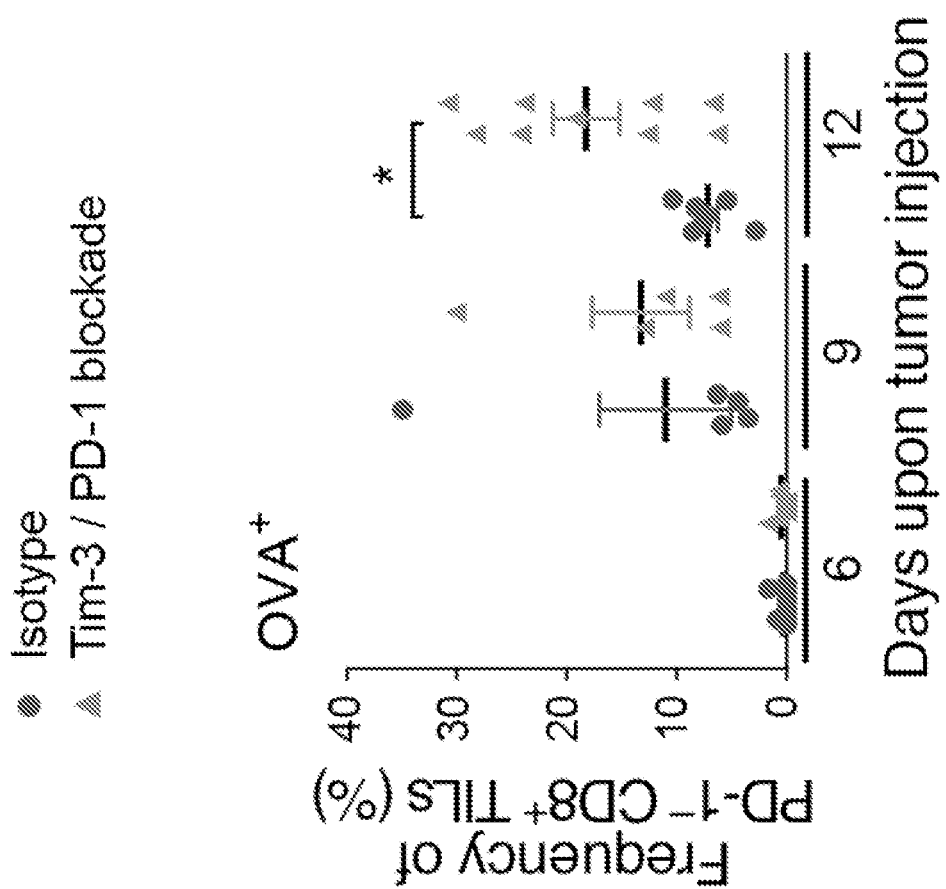
FIG. 2C shows the frequency of OVA-specific PD1⁻CD8⁺ TILs in tumors from Tim3/PD1 blockade- or isotype-treated mice. *$p<0.05$, Mann Whitney U test.

Example 2—PD-1$^-$CD8$^+$ TILs contain tumor-antigen specific precursors that expand in response to checkpoint blockade Given the changes in Tim-3$^-$PD-1$^-$ relative to Tim-3$^+$PD-1$^+$CD8$^+$ TILs (FIG. 1D, E) and recent studies indicating the limited potential of PD-1$^+$ cells to establish long-lasting immunity (Ahn et al., 2016; Ghoneim et al., 2017; Pauken et al., 2016; Utzschneider et al., 2013), Applicants focused on understanding the changes within Tim-3$^-$PD-1$^-$CD8$^+$ TILs and the relationship of these cells to Tim-3$^+$PD-1$^+$CD8$^+$ TILs (e.g., upon Tim3–/PD-1 blockade). Applicants undertook a longitudinal analysis of PD-1$^-$ (cells that are PD-1$^-$ are uniformly negative for Tim-3 as well as other checkpoint receptors; FIG. 1B) and PD-1$^+$CD8$^+$ TILs after checkpoint blockade. Applicants quantified the numbers of PD-1$^-$ and PD-1$^+$CD8$^+$ TIL subsets after each anti-Tim-3/anti-PD-1 treatment and found that blockade led to significantly increased numbers of PD-1$^-$ cells but not PD-1$^+$CD8$^+$ TILs after three treatments (FIG. 2A). This was due to increased proliferation of PD-1$^-$, but not PD-1$^+$CD8$^+$ TILs as determined by Ki67 expression (FIG. 2B). Applicants next determined whether checkpoint blockade-induced proliferation of PD-1$^-$CD8$^+$ TILs was driven by antigen-specificity and found that indeed there were significantly more OVA-specific CD8$^+$ T cells within PD-1$^-$CD8$^+$ TILs (FIG. 2C). Thus, checkpoint blockade induces the expansion of antigen-specific PD-1$^-$CD8$^+$ TILs.

Figure 2D:
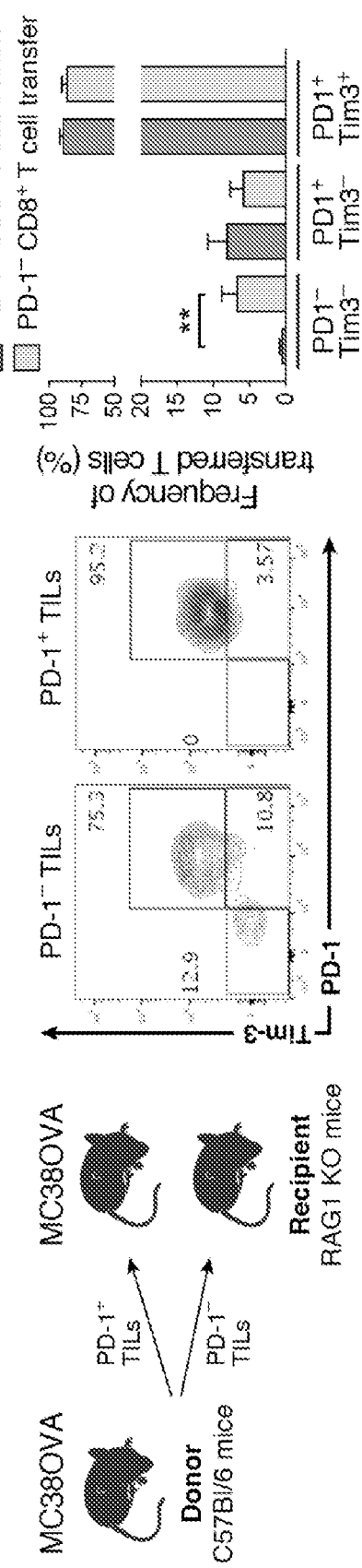
FIG. 2D shows a schematic of the experimental design (left), representative flow cytometry plots (middle) and frequencies (right) of PD1 and Tim3-expressing cells in adoptively transferred mice. **$p<0.01$, Mann Whitney U test.

That checkpoint blockade has significantly greater effects on PD-1$^-$CD8$^+$ TILs compared to PD-1$^+$CD8$^+$ TILs is in line with recent studies showing that PD-1$^+$ cells have impaired clonal expansion and limited potential to establish long-lasting immunity (Ahn et al., 2016; Ghoneim et al., 2017; Pauken et al., 2016; Utzschneider et al., 2013). In contrast, PD-1$^-$ CD8$^+$ TILs are presumably at an earlier phase of effector differentiation and would therefore be predicted to have better potential to give rise to effector cells and sustain a long-lasting immunity. To test whether PD-1$^-$CD8$^+$ TILs contain precursors to PD-1$^+$CD8$^+$ TILs, Applicants performed adoptive transfer studies. As Tim-3/PD-1 blockade induces expansion of antigen-specific cells within PD-1$^-$ subset, Applicants isolated PD-1$^-$ and PD-1$^+$CD8$^+$ TILs from MC38-OVA tumor-bearing mice and adoptively transferred the two subsets into RAG$^{-/-}$mice that were subsequently implanted with MC38-OVA (FIG. 2D). In line with observations made in chronic viral infection models, Applicants found that PD-1 expression remained stable on transferred PD-1$^+$ cells (Ahn et al., 2016; Utzschneider et al., 2013). In contrast, transferred PD-1$^-$CD8$^+$ TILs gave rise to PD-1$^+$ as well as Tim-3+CD8$^+$ TILs but, importantly, also maintained a pool of PD-1$^-$CD8$^+$ TILs (FIG. 2D). Collectively, these data indicate that PD-1$^-$CD8$^+$ TILs contain tumor-antigen specific precursors that are triggered to expand and differentiate in response to checkpoint blockade.

Figure 2E:
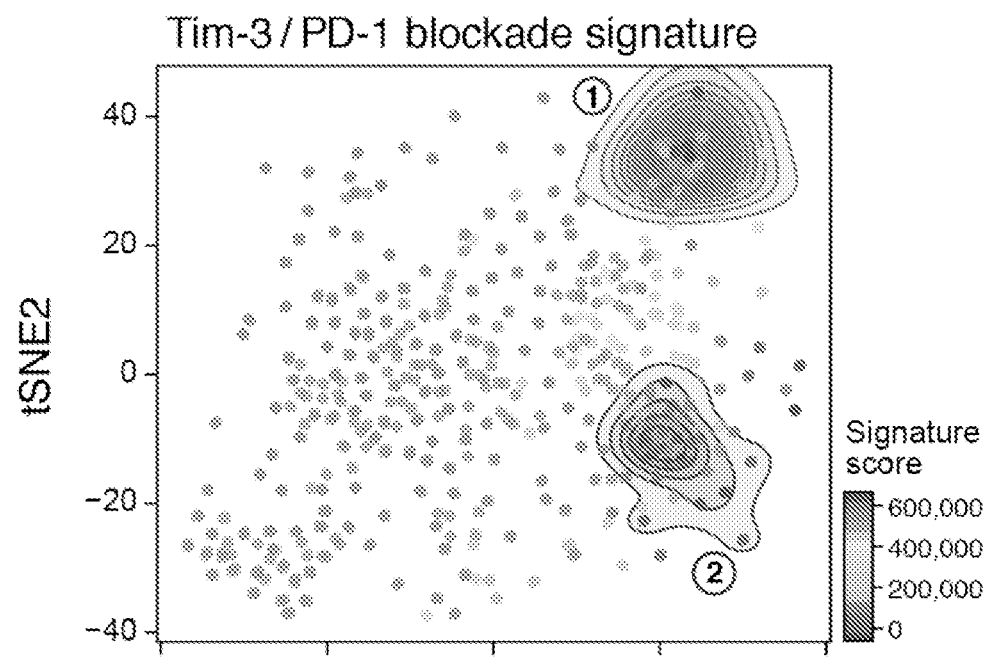
FIGS. 2E-F show tSNE plots.
Figure 2F:
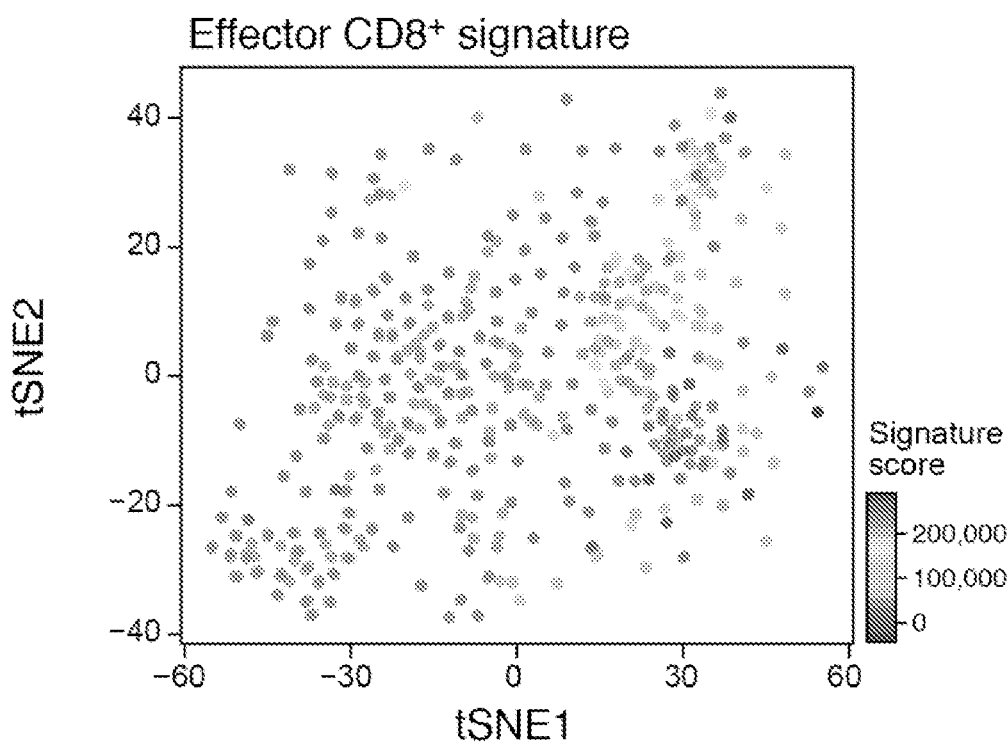
Figure 2G:
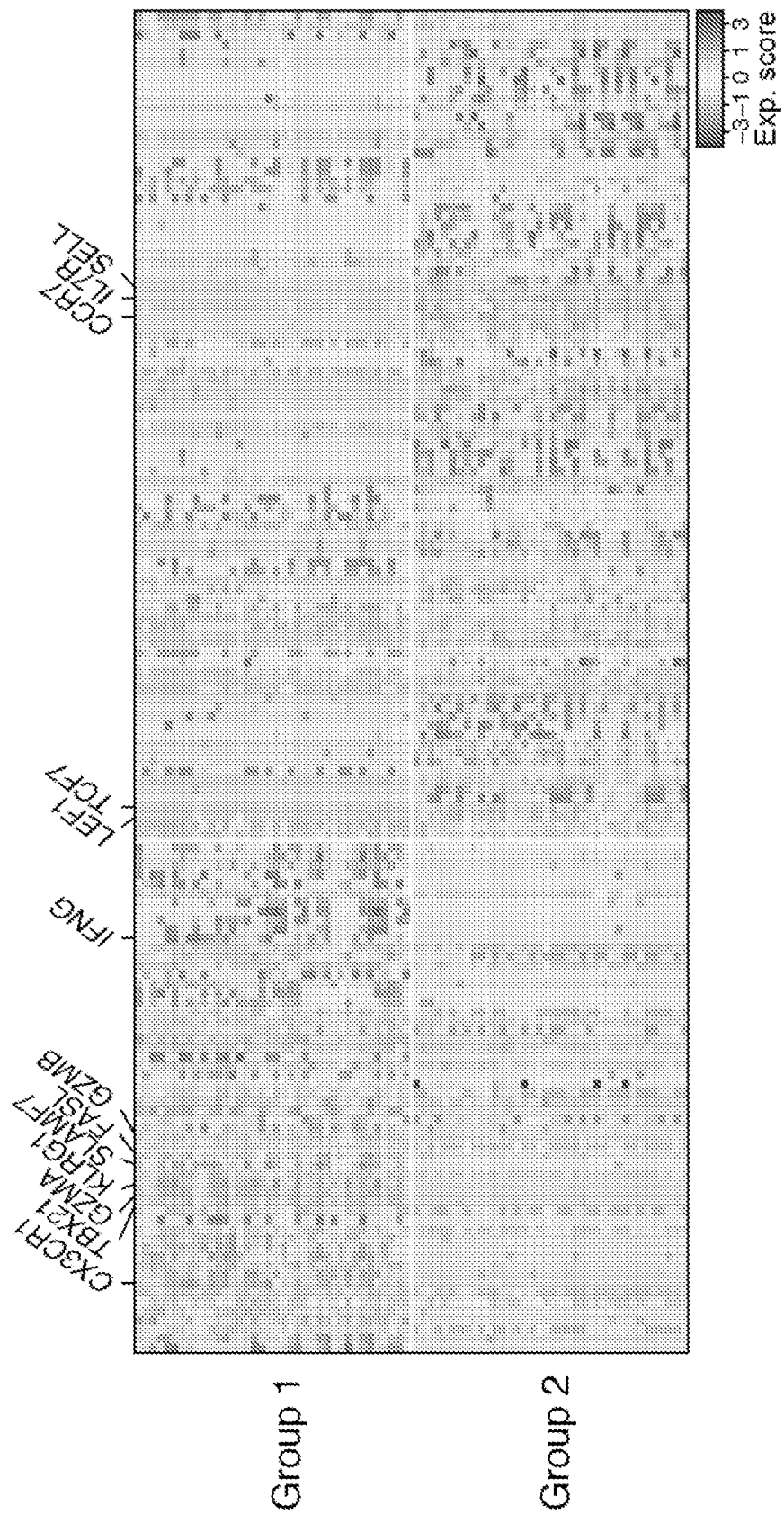
FIG. 2G shows a heatmap showing the differentially expressed genes between Group 1 cells that were enriched in Tim-3/PD-1 blockade and Group 2 cells that were enriched in isotype treated mice.

Example 3—Identification of Distinct PD-1$^-$CD8$^+$ TILs Subsets that Change in Response to Checkpoint Blockade Therapy To determine whether the changes observed in the PD-1$^-$CD8$^+$ TILs were due to cell intrinsic changes or shifts in the proportions of pre-existing sub-populations within PD-1$^-$CD8$^+$ TILs, or both, Applicants scored the differentially expressed gene signature of PD-1$^-$ CD8$^+$ TILs treated with Tim3−/PD-1 blockade vs. isotype within the previously reported scRNA-Seq profiles from untreated mice (Singer et al., 2016). This highlighted two distinct sets of cells within Tim-3$^-$PD-1$^-$CD8$^+$ TILs (FIG. 2E). Group 1 cells (labeled 1) expressed genes that were up-regulated after Tim-3/PD-1 blockade, whereas Group 2 cells (labeled 2) expressed genes that were more highly expressed in the isotype treated group. This suggested that both groups of cells exist even in the absence of checkpoint blockade, and that the differential expression Applicants observed in bulk profiles may reflect proportional differences. Moreover, Group 1 cells also expressed a CD8$^+$ T cell effector signature (Kaech et al., 2002) more highly than Group 2 cells (FIG. 2F), suggesting that Tim-3/PD-1 blockade may induce an increase in CD8$^+$ TIL subsets with higher effector potential within the Tim-3-PD-1$^-$CD8$^+$ TILs population (also referred to as PD-1$^-$CD8$^+$ TILs). Consistent with this interpretation, genes found in effector T cells such as Ifng, Gzma, Gzmb, Tbx21, and Fasl were more highly expressed in Group 1, and genes associated with naïve and memory CD8$^+$ T cells (Sell, Il7r, Ccr7, Tcf7, Lef1) were more highly expressed in Group 2 cells (FIG. 2G). Together, these data indicate that there are distinct subsets within Tim-3$^-$PD-1$^-$CD8$^+$ TILs that differ in their expression of effector (Group 1) and naïve/memory (Group 2) programs.

Figure 2H:
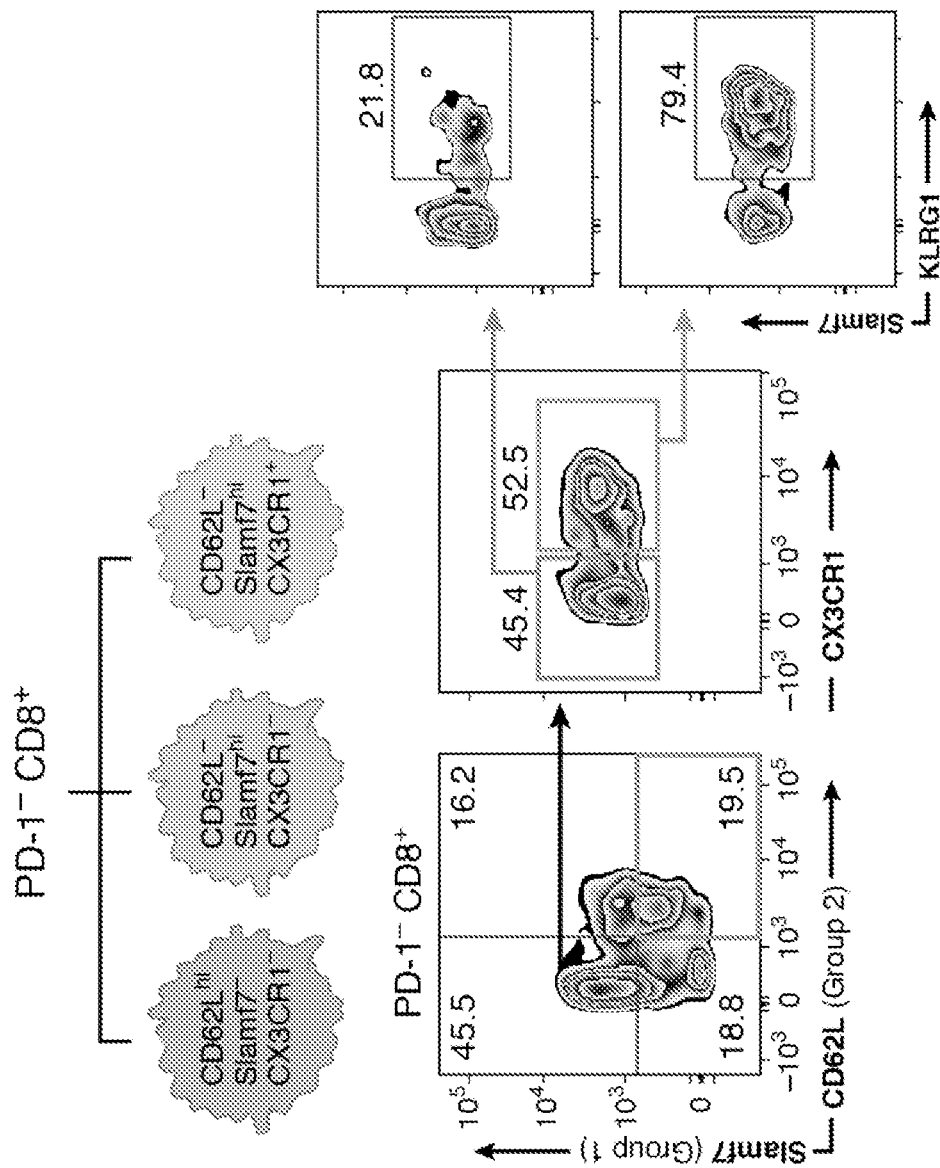
FIG. 2H shows a schematic representation and representative flow cytometry data showing identification of CD62L$^{hi}$Slamf7⁻CX3CR1⁻, CD62L-Slamf7$^{hi}$CX3CR1⁻ and CD62L⁻ Slamf7$^{hi}$CX3CR1⁺ subsets within PD-1⁻CD8⁺ TILs.

To better characterize the cells in Group 1 and Group 2, Applicants sought to identify surface markers that could distinguish them. Applicants identified fractalkine receptor-CX3CR1 and KLRG1 for Group 1 and CD62L for Group 2 based on their differential expression (FIG. 2G) as well as their known associations with effector/effector-memory and naïve/central-memory CD8$^+$ T cell subsets, respectively (Bottcher et al., 2015; Gerlach et al., 2016; Joshi et al., 2007; Lefrancois, 2006). Applicants additionally used Slamf7 for Group 1 as this marker has been associated with effector CD8$^+$ T cell responses (Comte et al., 2017). Applicants examined the expression of these markers within PD-1$^-$CD8$^+$ TILs (cells that are PD-1$^-$ are uniformly negative for Tim-3 and other checkpoint receptors as well; FIG. 1B). Consistent with their differential expression in Group 1 and 2 cells, CD62L expression marks a distinct subset of PD-1$^-$CD8$^+$ TILs from those expressing CX3CR1 and KLRG1 (FIG. 7A). As Slamf7 expression captured a larger proportion of CD62L$^-$ cells (FIG. 2H) than either CX3CR1 or KLRG1, Applicants further examined the expression of these two markers within CD62L$^-$Slamf7$^{hi}$PD-1-CD8$^+$ TILs (FIG. 2H). CX3CR1 expression distinguished two distinct subsets of Slamf7'PD-1$^-$CD8$^+$ TILs that also differ in expression of KLRG1 (FIG. 2H). Two additional small subsets were Slamf7-CD62L$^-$ and CD62L$^{hi}$Slamf7$^{Lo}$; these could not be assigned to either Group 1 or 2 and were not considered further. Applicants subsequently focused on three subsets of PD-1$^-$CD8$^+$ TILs (FIG. 2H): CD62L$^{hi}$Slamf7$^-$CX3CR1$^-$ (also referred to as CD62L$^h$Slamf7$^-$), CD62L$^-$Slamf7$^{hi}$CX3CR1$^-$ (also referred to as Slamf7$^{hi}$CX3CR1$^-$), and CD62L$^-$Slamf7$^{hi}$CX3CR1$^+$ (also referred to as Slamf7$^{hi}$ CX3CR1$^+$).

Figure 3E:
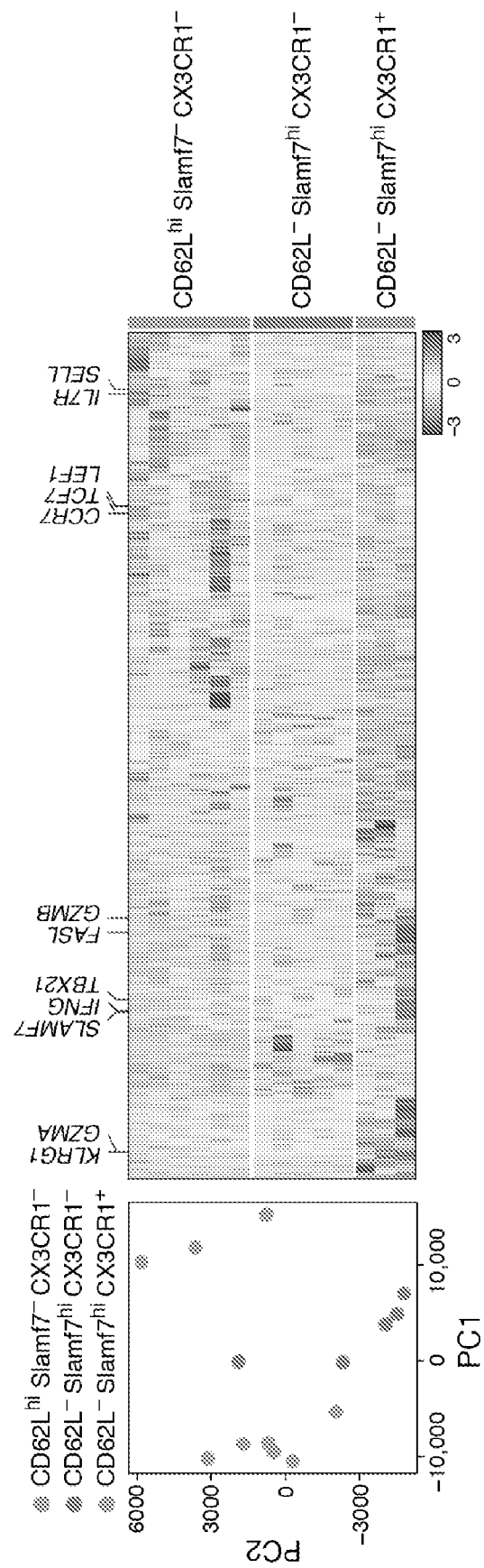
FIG. 3E shows PCA (left) and heatmap (right) of CD62L$^{hi}$Slamf7⁻, CD62L-Slamf7$^{hi}$CX3CR1⁻, and CD62L⁻Slamf7$^{hi}$CX3CR1⁺ populations within PD-1⁻CD8⁺ TILs isolated from MC38-OVA tumors.

Example 4—PD-1$^-$CD8$^+$ TILs subsets exhibit properties of naïve, effector, and memory-precursor T cells Applicants next isolated TILs from MC38-OVA tumor-bearing mice and examined these three newly identified PD-1$^-$CD8$^+$ TILs subsets for their proliferative, cytotoxic, and effector capacities as well as for antigen specificity. Both Slamf7' subsets exhibited higher proliferative capacity compared to the CD62L$^{hi}$Slamf7$^-$CX3CR1$^-$ subset as determined by the proportion of Ki67$^+$ cells (FIG. 3A). The CD62L$^{hi}$SlamF7$^-$CX3CR1$^-$ subset completely lacked Granzyme B and CD107a expression in response to OVA$_{257-264}$ stimulation, while both the CD62L$^-$Slamf7$^{hi}$CX3CR1$^-$ and CX3CR1$^+$ subsets had similar expression of these proteins, indicating similar cytotoxic capacity (FIG. 3B). The CD62L$^-$Slamf7$^{hi}$CX3CR1$^-$ subset had the highest production of IL-2 and TNF-α in response to OVA$_{257-264}$ stimulation, while the both CD62L$^-$Slamf7$^{hi}$CX3CR1$^-$ and CX3CR1$^+$ subsets equally produced IFN-γ (FIG. 3C), and the CD62L$^{hi}$Slamf7$^-$CX3CR1$^-$ subset did not produce any cytokines. Overall, the CD62L$^-$ Slamf7$^{hi}$CX3CR1$^-$ subset exhibited the most poly-functionality in cytokine production (FIG. 7B). Staining with H-2Kb/OVA$_{257-264}$ dextramers further showed that there were OVA-specific CD8$^+$ T cells within both the CD62L$^-$Slamf7$^{hi}$CX3CR1$^-$ and CX3CR1$^+$ subsets, but not in the CD62L$^{hi}$Slamf7$^-$CX3CR1$^-$ subset (FIG. 3D). Thus, the CD62L$^{hi}$Slamf7$^-$CX3CR1$^-$ subset exhibited naïve-like properties while both the CD62L$^-$Slamf7$^{hi}$CX3CR1$^-$ and CX3CR1$^+$ subsets exhibited properties of antigen-specific effector cells with the CD62L$^-$Slamf7$^{hi}$CX3CR1$^-$ subset exhibiting more polyfunctionality.

Figure 3F:
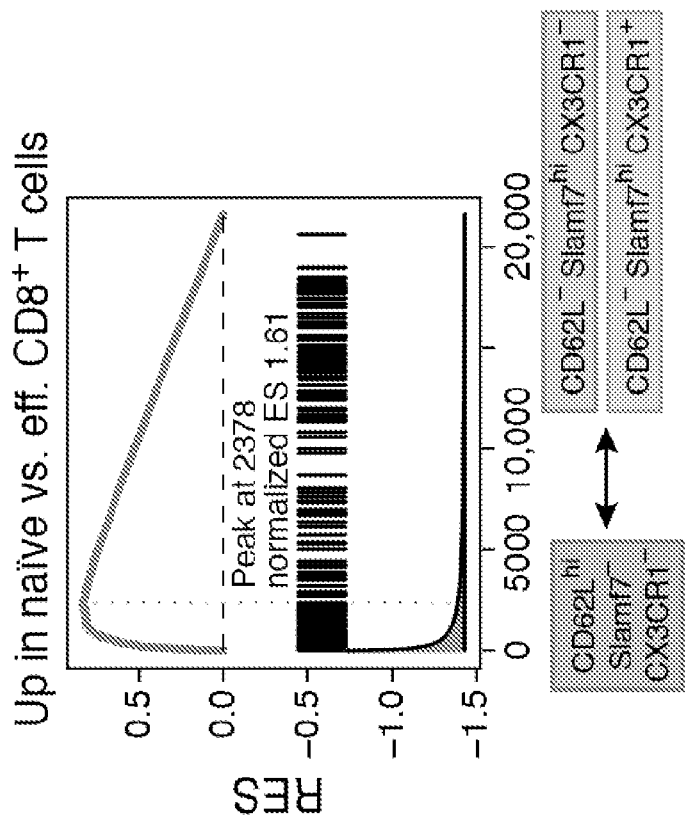
FIG. 3F shows gene-set enrichment analysis (GSEA) plots showing enrichment for a naïve CD8⁺ T cell signature (Kaech et al., 2002) in CD62L$^{hi}$Slamf7⁻ cells, FDR-adjusted P value=0.011, Kolmogorov-Smirnov.
Figure 3G:
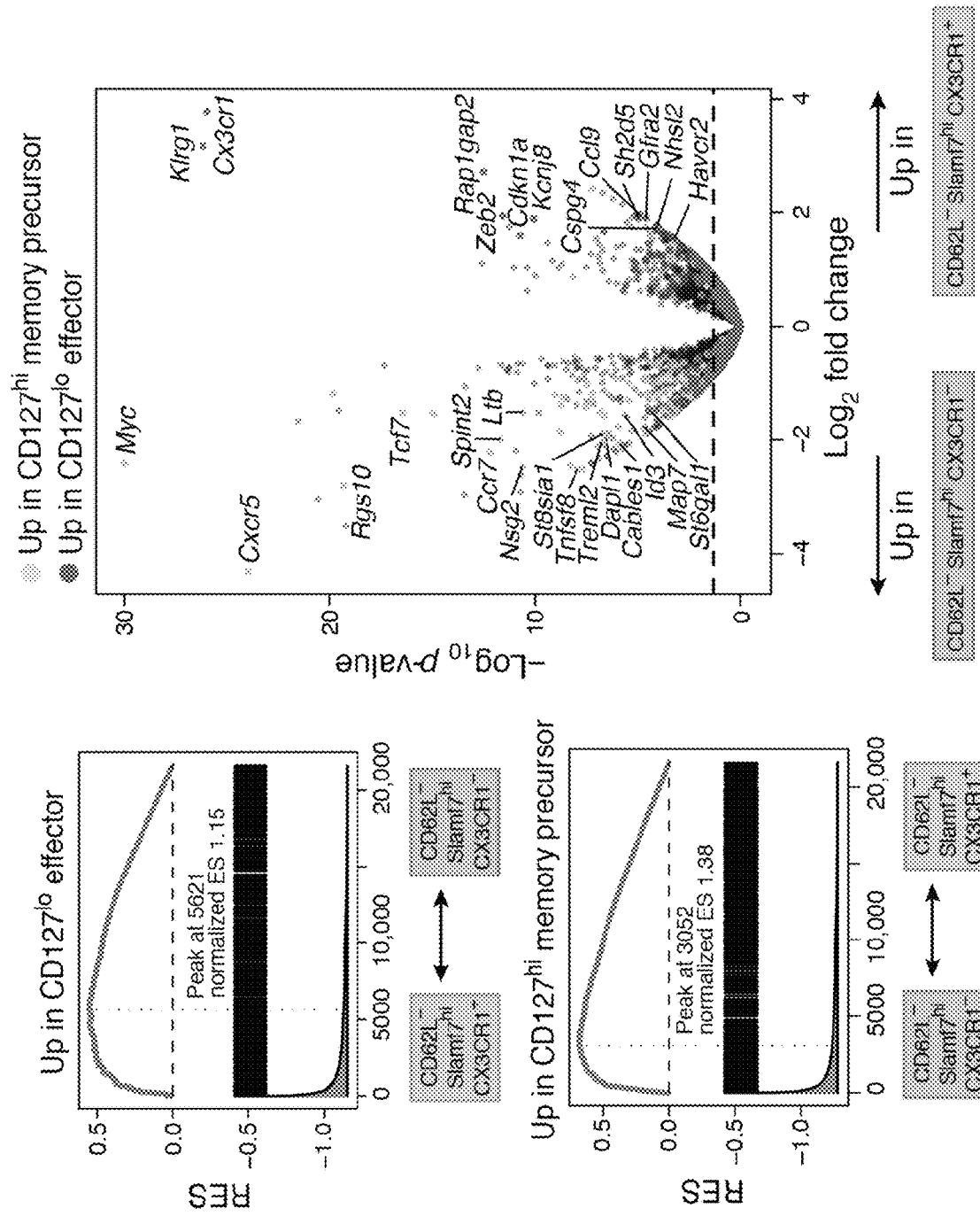
FIG. 3G shows GSEA plots (left) and Volcano plot (right) showing enrichment for CD127$^{lo}$ effector and CD127$^{hi}$ memory-precursor CD8⁺ T cell signatures (Joshi et al., 2007) in CD62L⁻Slamf7$^{hi}$CX3CR1⁻ and CD62L⁻Slamf7$^{hi}$CX3CR1⁺, respectively. FDR- adjusted P value=0.027, Kolmogorov-Smirnov.
Figure 3H:
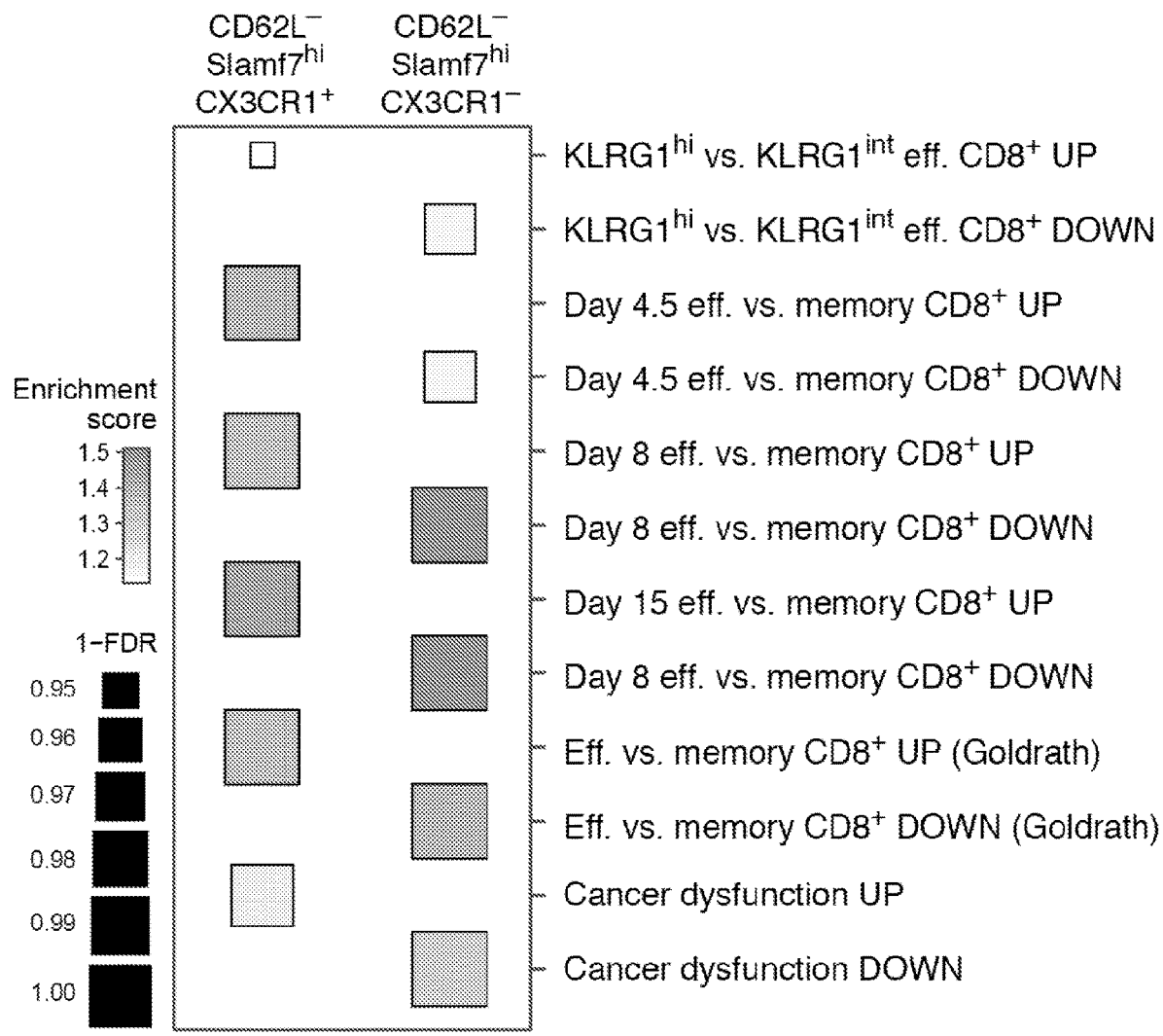
FIG. 3H shows GSEA plot showing enrichment of publicly available memory and effector CD8⁺ T cell signatures (Methods) in CD62L⁻ Slamf7$^{hi}$CX3CR1⁻ vs CX3CR1⁺ subsets. Scale indicates the expression score in the indicated subset and the square size indicates the 1-FDR.

The CD62L$^{hi}$Slamf7$^-$, Slamf7$^{hi}$CX3CR1$^-$, and Slamf7$^{hi}$CX3CR1$^+$PD-1$^-$CD8$^+$ TILs subsets also had distinct RNA expression profiles (FIG. 3E and Table 3 and 4), with the CD62L$^-$Slamf7$^{hi}$CX3CR1$^-$ subset sharing some transcriptional features with both the CD62L$^{hi}$Slamf7$^-$CX3CR1$^-$ and the CD62L$^-$Slamf7$^{hi}$CX3CR1$^+$ subsets. CD62L$^{hi}$Slamf7$^-$CX3CR1$^-$ cells expressed genes associated with naïve T cells, such as IL7r and Ccr7, but not many effector genes (Table 3) and were enriched for a naïve CD8$^+$ T cell signature (FIG. 3F, FDR− adjusted P value=0.011, Kolmogorov-Smirnov) (Kaech et al., 2002), consistent with their naïve-like functional properties (FIG. 3A-D). Within the two Slamf7$^{hi}$ subsets (both of which displayed antigen-specific effector functions), genes higher in CX3CR1$^-$ vs. CX3CR1$^+$ subsets were enriched for a signature of virus-specific CD127$^{hi}$ memory-precursor CD8$^+$ T cells (Joshi et al., 2007) (FDR− adjusted P value=0.012, Kolmogorov-Smirnov) (FIG. 3G) and for other CD8$^+$ T cell memory signatures from acute viral infections (FIG. 3H). Conversely, signatures of virus-specific CD127$^{lo}$ effector CD8$^+$ T cells, and of effector and KLRG1$^{hi}$ terminal effector CD8$^+$ T cells were enriched in the Slamf7$^{hi}$CX3CR1$^+$ subset (FIG. 3G, FDR– adjusted P value=0.027, Kolmogorov-Smirnov), as was a signature of dysfunctional CD8$^+$ TILs (FIG. 3H), suggesting that this subset is further along the trajectory for developing dysfunctional phenotype. Thus, CD62L$^-$ Slamf7$^{hi}$CX3CR1$^-$PD-1$^-$CD8$^+$ TILs maintained polyfunctionality and potentially contained memory precursors, whereas CD62L$^-$ Slamf7$^{hi}$CX3CR1$^+$PD-1$^-$CD8$^+$ TILs more closely resembled terminal KLRG1$^{hi}$ CD127$^{lo}$ effector CD8$^+$ T cells that may eventually develop a dysfunctional phenotype. In light of these data, the CD62L$^{hi}$Slamf7-PD-1$^-$CD8$^+$ subset is hereafter referred to as naïve-like, the CD62L$^-$ Slamf7$^{hi}$CX3CR1$^-$PD-1$^-$CD8$^+$ subset as memory-precursor-like, and the CD62L$^-$ Slamf7$^{hi}$CX3CR1$^+$PD-1$^-$CD8$^+$ subset as effector-like.

Figure 4A:
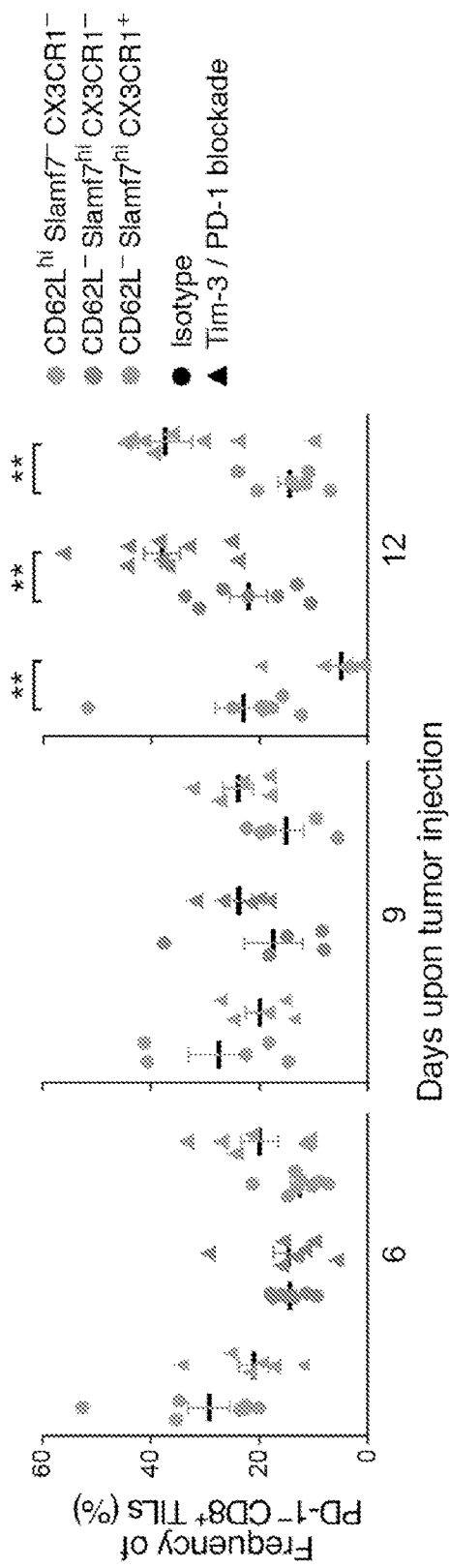
FIG. 4A shows the frequency of the indicated PD1⁻CD8⁺ TILs subsets in tumors from Tim3/PD1 blockade- or isotype-treated MC38OVA-bearing mice over time. **$p<0.01$, Mann Whitney U test.
Figure 4B:
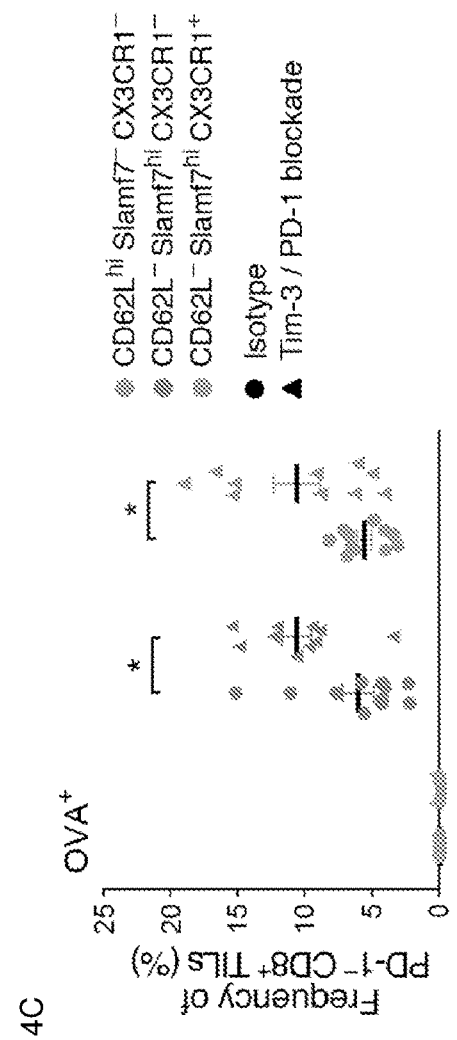
FIG. 4B shows the frequency of Ki67⁺ cells within the indicated PD1⁻CD8⁺ TILs subsets from Tim3/PD1 blockade- or isotype-treated MC38OVA-bearing mice. *$p<0.05$, Mann Whitney U test.
Figure 4C:
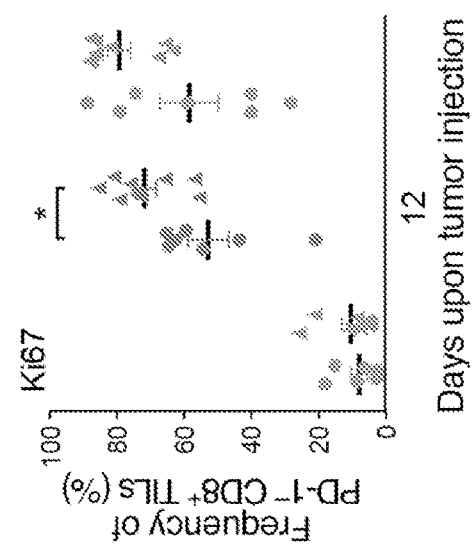
FIG. 4C shows the frequency of OVA-specific cells within the indicated PD1⁻CD8⁺ TILs subsets in tumors from Tim3/PD1 blockade- or isotype-treated MC38OVA-bearing mice. *$p<0.05$, Mann-Whitney U test.

Example 5—Shifts in PD-1$^-$CD8$^+$ TILs Subsets from Naïve-Like to Memory-Precursor- and Effector-Like Cells in Response to Various Immunotherapies in Different Cancers Applicants next determined changes in the naïve-like, memory-precursor-like, and effector-like PD-1$^-$CD8$^+$ TILs subsets upon Tim-3/PD-1 blockade. Applicants treated MC38-OVA tumor-bearing mice with anti-Tim-3/anti-PD-1 or isotype control antibody and analyzed the subsets over the course of the treatment. Applicants found that the naïve-like subset significantly decreased while the memory-precursor and effector-like PD-1$^-$ subsets increased upon Tim-3/PD-1 blockade (FIGS. 4A and 8). Increases in the frequency of memory-precursor-like and effector-like PD-1$^-$ subsets were due to increased proliferation evidenced by the higher frequency of Ki67$^+$ cells within these subsets (FIG. 4B). Moreover, the frequency of OVA-specific CD8$^+$ TILs was significantly increased within these subsets upon blockade (FIG. 4C). In line with the previous data (FIG. 3D), Applicants did not observe OVA-specific CD8$^+$ TILs in the CD62L$^{hi}$Slamf7$^-$ (naïve-like) subset. Together these data indicate that Tim-3/PD-1 blockade increases the expansion of tumor antigen-specific CD8$^+$ T cells within the Slamf7$^{hi}$CX3CR1$^-$PD-1$^-$ (memory-precursor) and Slamf7$^{hi}$CX3CR1$^+$PD-1$^-$ (effector-like) subsets at the expense of the naïve-like CD62L$^{hi}$Slamf7-PD-1$^-$ subset.

Applicants next addressed whether the checkpoint blockade-induced shifts within PD-1$^-$CD8$^+$ TILs subsets are also observed in response to different therapies and in different tumor types. Applicants examined CTLA-4/PD-L1 blockade in MC38-Ova and observed increases in the memory-precursor- and effector-like subsets (FIG. 4D). These data indicate that the observations are generalizable to other checkpoint blockade therapies and, most importantly, show that the changes in PD-1$^-$CD8$^+$ TILs are not due to antibody-induced down-modulation of PD-1 on the surface of CD8$^+$ TILs. Applicants further found decrease in the proportion of naïve-like cells and increase in the memory-precursor- and effector-like cells in B16F10 melanoma-bearing mice upon Tim-3/PD-1 blockade or CTLA-/PD-1 blockade, the latter combination being in clinical use (FIG. 4E). Together these data indicate that the shifts observed within PD-1$^-$CD8$^+$ TILs are neither restricted to the colon carcinoma model nor to Tim-3/PD-1 blockade but can be generalized to other cancer models and immune checkpoint blockade therapies.

Applicants next addressed whether the memory-precursor-like and effector-like subsets that expand after therapy have relevance in human cancer (Slamf7$^{hi}$CX3CR1-PD-1$^-$ memory-precursor-like and Slamf7$^{hi}$CX3CR1$^+$PD-1$^-$ effector-like). Applicants found that the two subset signatures were differentially enriched in human CD8$^+$ TILs signatures associated with better vs. worse prognosis (FIG. 4F). Applicants analyzed TIL signatures from non-small cell lung carcinoma (NSCLC) (Ganesan et al., 2017), where high (TIL$^{hi}$) vs. low (TIL$^{lo}$) CD8$^+$ T cell infiltration has been associated with better survival and found that the TIL$^{hi}$ signature was enriched for the Slamf7$^{hi}$CX3CR1$^-$ memory-precursor-like signature and the TILL® signature was enriched for the Slamf7$^{hi}$CX3CR1$^+$ effector-like signature (FIG. 4F), suggesting that these subsets are present at different proportions in high vs. low infiltration tumors. A T$_{RM}$ signature (CD103$^{hi}$), which has also been correlated with enhanced patient survival (Ganesan et al., 2017), was also enriched for the Slamf7$^{hi}$CX3CR1$^-$ signature. Additional studies have indicated that the expression of CD28 or BTLA may correlate with the persistence of TILs and long-term anti-tumor responses in patients after adoptive cell therapy (Haymaker et al., 2015; Li et al., 2010). The BTLA$^+$CD8$^+$ TIL signature was enriched for the Slamf7$^{hi}$CX3CR1$^-$PD-1$^-$ memory-precursor-like signature. Additional studies have indicated that the expression of CD28 or BTLA may correlate with the persistence of TILs and long-term anti-tumor responses in patients after adoptive cell therapy (Haymaker et al., 2015; Li et al., 2010). Indeed, the BTLA+CD8$^+$ TIL signature was enriched for the memory-precursor-like signature, whereas the BTLA$^-$CD8$^+$ TILs and CD28$^-$CD8$^+$ TILs signatures were enriched for the effector-like signature (FIG. 4F). These data indicate that the CD62L$^-$ Slamf7$^{hi}$CX3CR1$^-$PD-1$^-$ memory-precursor-like subset shares features with human TILs that correlate with better prognosis.

Figure 5A:
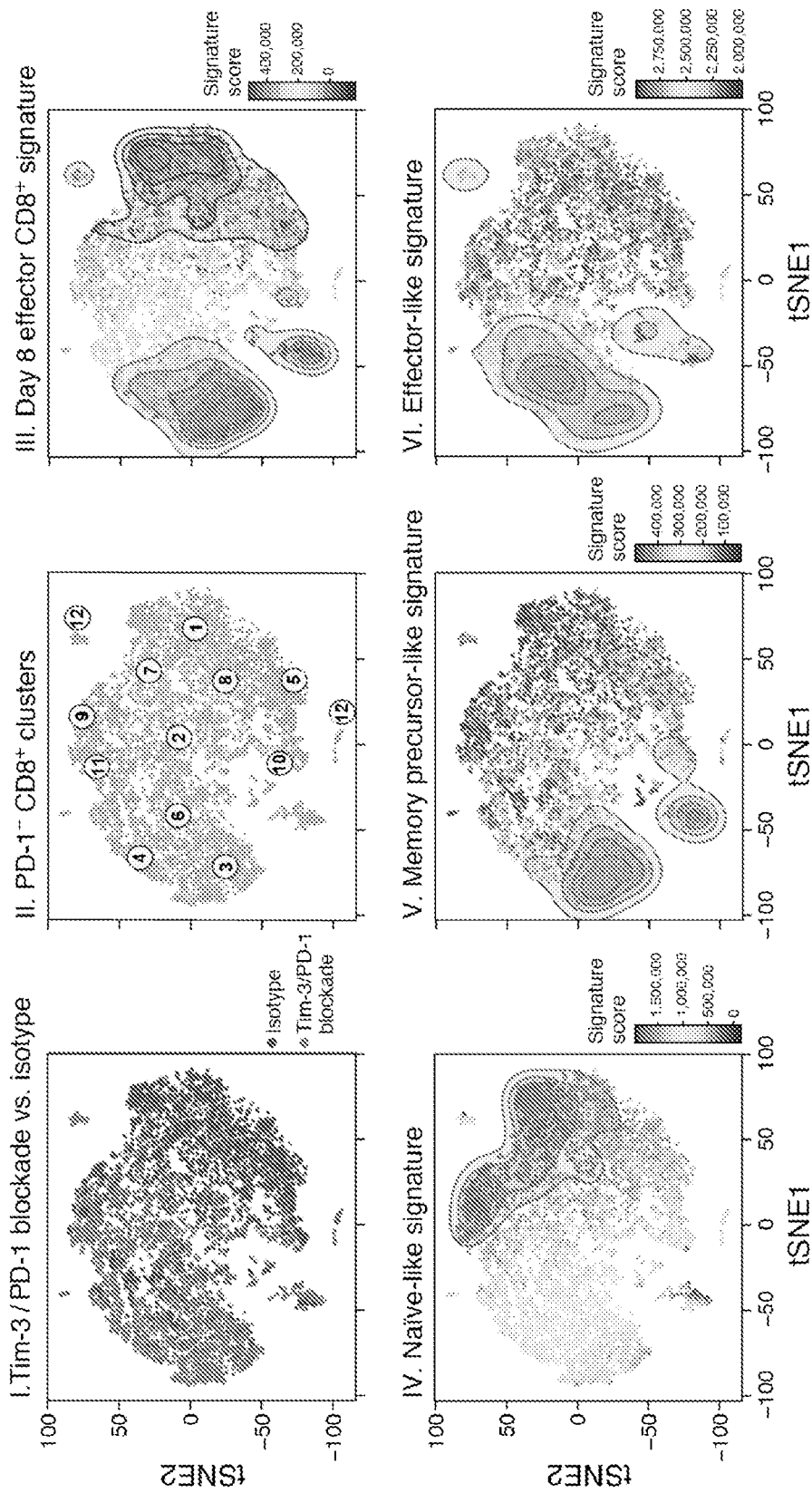
FIG. 5A shows I) tSNE plot of single-cell RNA profiles of PD-1⁻CD8⁺ TILs from isotype and Tim-3/PD-1 blockade-treated mice. II) Unsupervised clustering of the single-cell RNA profiles of PD-1⁻CD8⁺ TILs. (Methods). III) tSNE plot showing projection of an effector CD8⁺ T cell signature (Kaech et al., 2002), IV) the CD62L$^{hi}$Slamf7⁻ naïve-like signature V) the Slamf7$^{hi}$CX3CR1-memory-precursor-like signature, and VI) the Slamf7$^{hi}$CX3CR1⁺ effector-like signature onto the PD-1⁻CD8⁺ TILs single-cell data. The contour plot marks the region of highly scored cells by taking into account only those cells that have a signature score above the 10$^{th}$ percentile.
Figure 9A:
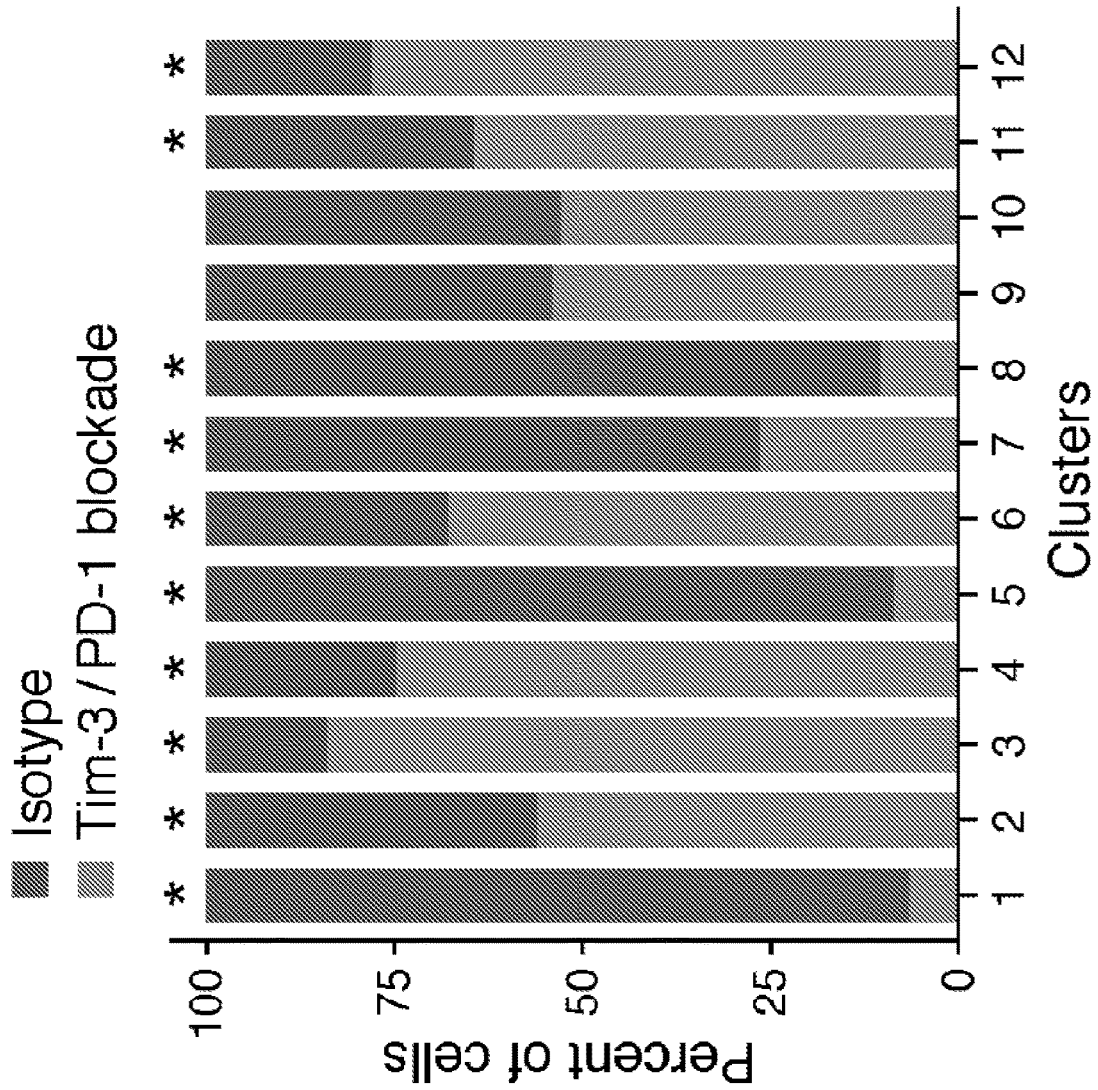
FIG. 9A shows a bar graph showing the frequency of cells present in each cluster from isotype or anti-Tim-3/PD-1-treated groups, *p-values <0.001, Fisher's exact test.
Figure 9B:
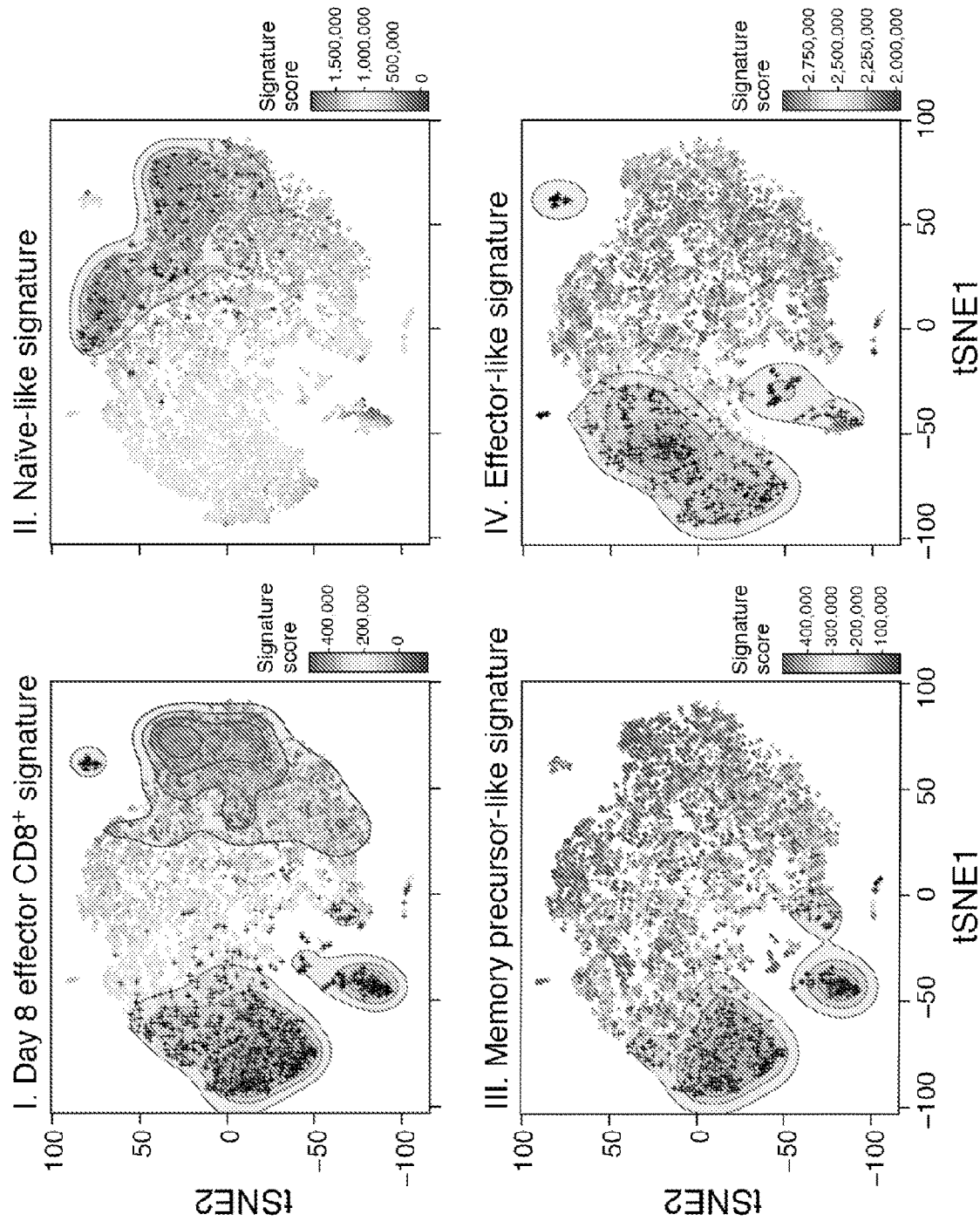
FIG. 9B shows I) tSNE plot showing projection of an effector CD8$^+$ T cell signature (Kaech et al., 2002) onto the PD-1$^-$CD8$^+$ TILs single-cell data. II) tSNE plot showing projection of the CD62L$^{hi}$Slamf7$^-$ signature, III) projection of the Slamf7$^{hi}$CX3CR1$^-$ signature, and IV) projection of the Slamf7$^{hi}$CX3CR1$^+$ signature onto the PD-1$^-$CD8$^+$ TILs single-cell data. The contour plot marks the region of highly scored cells by taking into account only those cells that have a signature score above the 10$^{th}$ percentile. Cells with a statistically significant score are marked with a "+" (Methods).
Figure 9C:
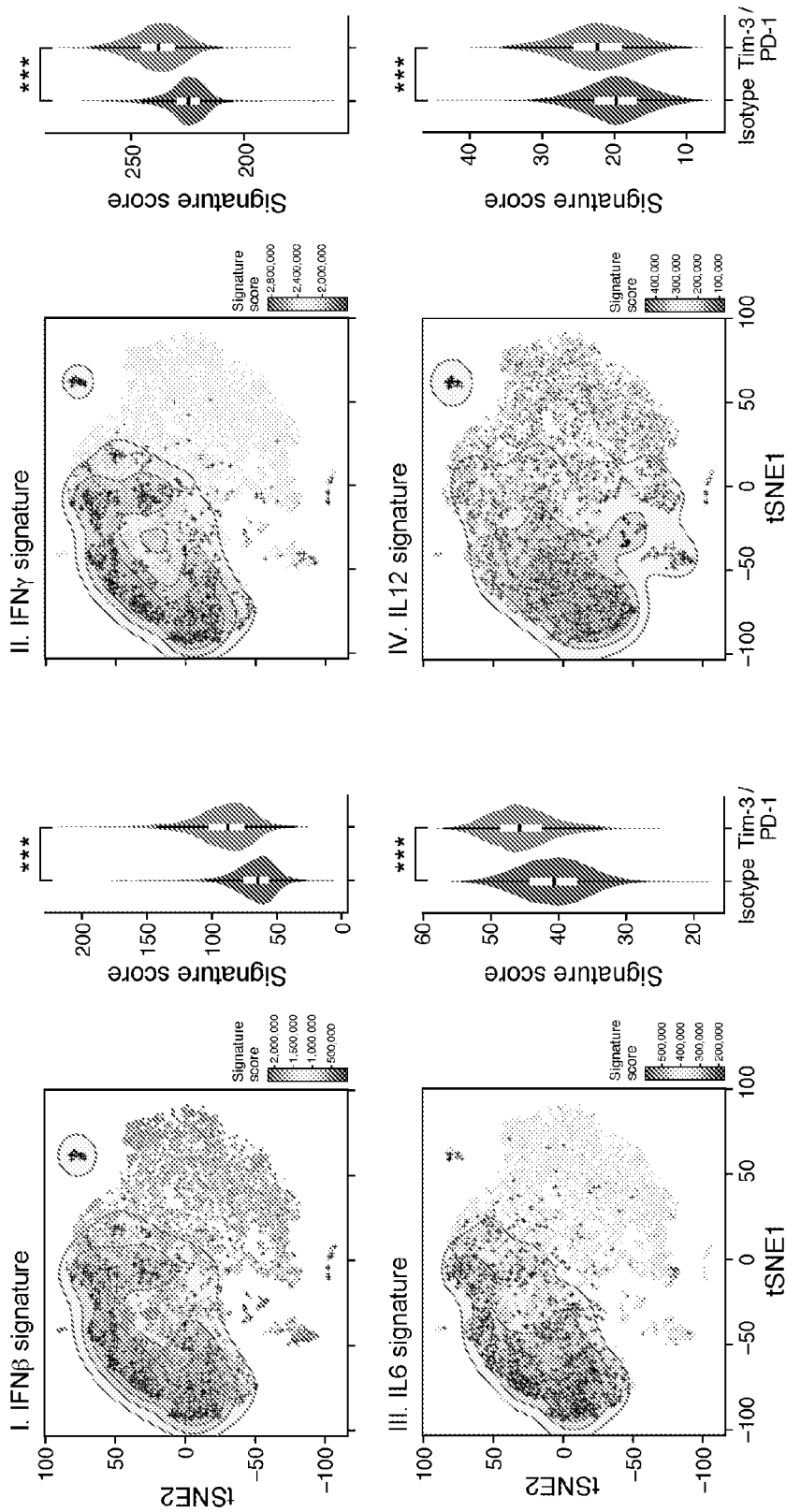
FIG. 9C shows I) tSNE plot showing projection of IFNβ (Iwata et al., 2017), II) IFNγ (Iwata et al., 2017), III) IL-6 (Hirahara et al., 2015), and IV) IL-12 (Agarwal et al., 2009) signatures onto the single-cell RNA profiles of PD-1$^-$CD8$^+$ TILs data (Singer et al., 2016). Scale indicates the signature score. The contour plot marks the region of highly scored cells by taking into account only those cells that have a signature score above the 10$^{th}$ percentile (Methods). Cells with a statistically significant score are marked with a "+". Violin plots show the cytokine signature score from isotype vs Tim-3/PD-1 blockade treated mice. ***p value <0.0001, t-test.

Example 6—Checkpoint Blockade-Induced Memory and Effector-Like Transcriptional Programs in Murine and Human Cancer To get a better resolution of the changes within PD-1$^-$CD8$^+$ TILs after checkpoint blockade, Applicants performed scRNA-Seq of PD-1$^-$CD8$^+$ TILs from MC38-OVA tumor-bearing mice treated with anti-Tim-3/anti-PD-1 or isotype control. Applicants found a major shift in the proportion of cells in different transcriptional clusters (FIG. 5A, panel I). Unsupervised clustering of the cells' profiles showed that all clusters had representation from both treated and control mice, but at dramatically different proportions (FIGS. 5A, panel I and II, 5B and 9A). The clusters enriched for cells from Tim-3/PD-1 blockade treated mice (clusters 3, 4, 6) were also enriched for cells expressing an effector CD8$^+$ T cell signature from acute LCMV infection (Kaech et al., 2002) (FIG. 5A, panel III). Indeed, scoring the single cells with the signatures for the three newly-identified subsets showed that Tim-3/PD-1 blockade changed the proportions within PD-1$^-$CD8$^+$ TILs from more naïve-like cells to more cells expressing memory-precursor-like and effector-like signatures (FIGS. 5A and 9B). Overall, the cells span a spectrum from CD62L$^{hi}$Slamf7$^-$ naïve like (FIG. 5A, panel IV) to Slamf7$^{hi}$CX3CR1$^-$ memory-precursor like (FIG. 5A, panel V) and Slamf7$^{hi}$CX3CR1$^+$effector-like (FIG. 5A, panel VI), and cells from isotype treated or Tim-3/PD-1 blockade treated mice are enriched at the opposite ends of this spectrum, respectively. Importantly, this spectrum is also marked by enrichment of IFNγ, IL-6, and IFN-β signatures and, to a lesser degree, an IL-12 signature (FIG. 9C), suggesting that Tim-3/PD-1 blockade elicits a pro-inflammatory TME that expands effector PD-1$^-$CD8$^+$ TILs.

Figure 5B:
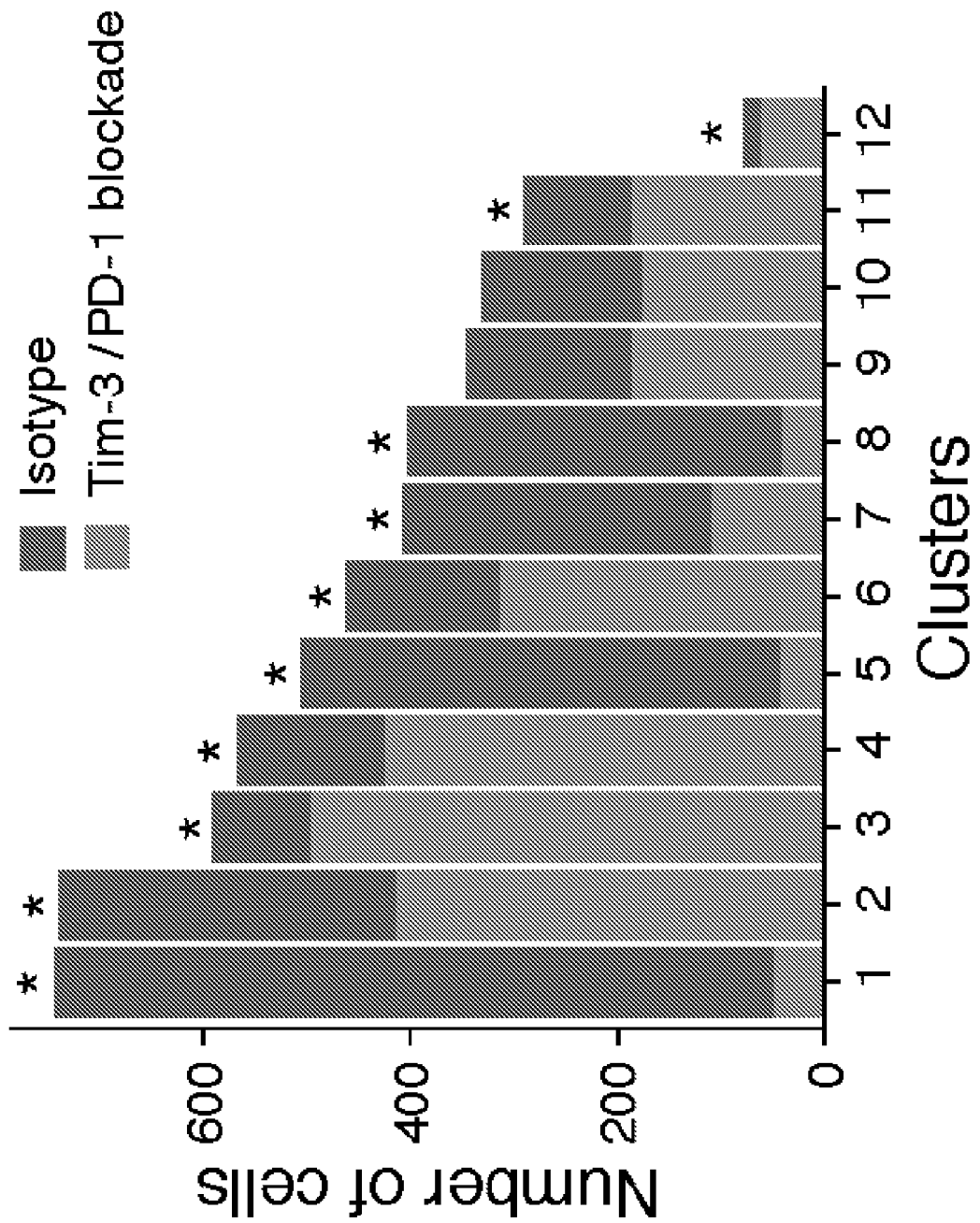
FIG. 5B shows a bar graph showing the number of cells present in each cluster from isotype or anti-Tim-3/PD-1-treated groups, *p-values <0.001, Fisher's exact test.
Figure 5C:
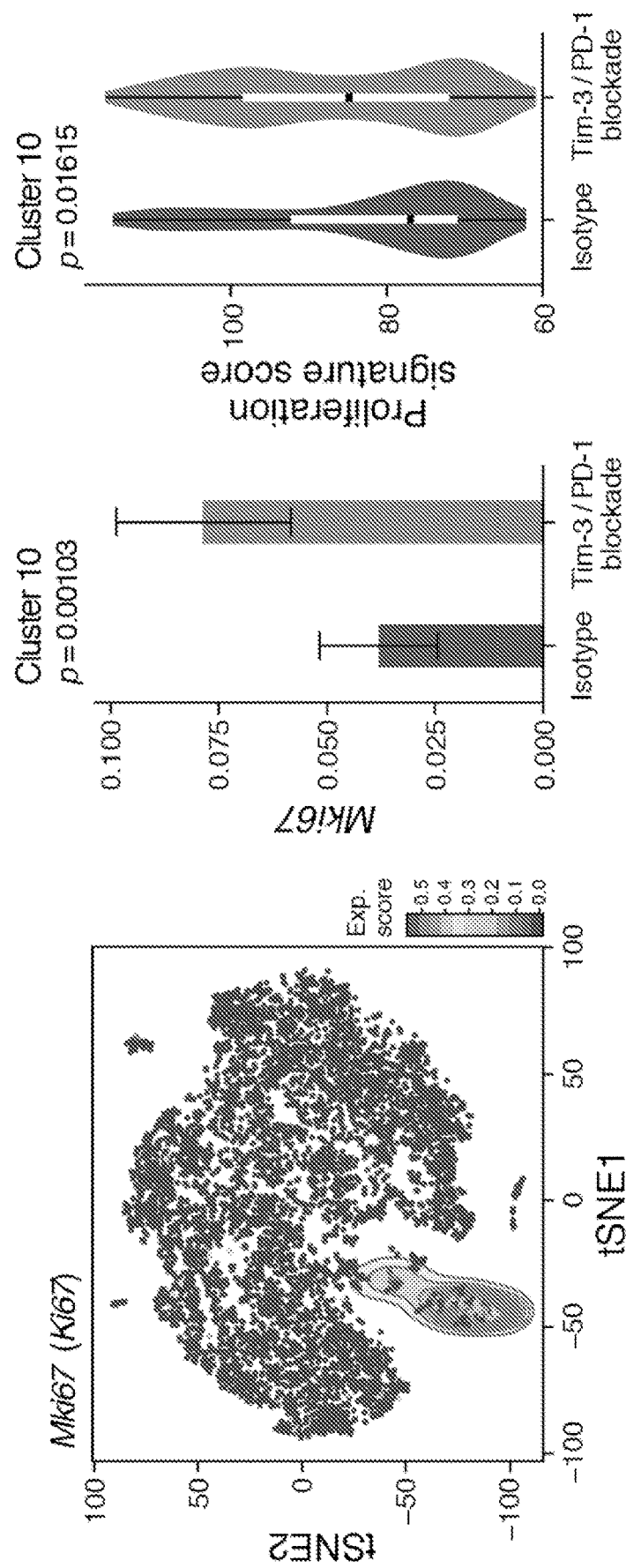
FIG. 5C shows a tSNE plot (left) showing the expression of Ki67 among PD-1⁻CD8⁺ single-cells. Bar plot shows expression of Ki67 and violin plot shows expression of a proliferation signature (Tirosh et al., 2016) in isotype versus Tim-3/PD-1 blockade treated cells in cluster 10.
Figure 5D:
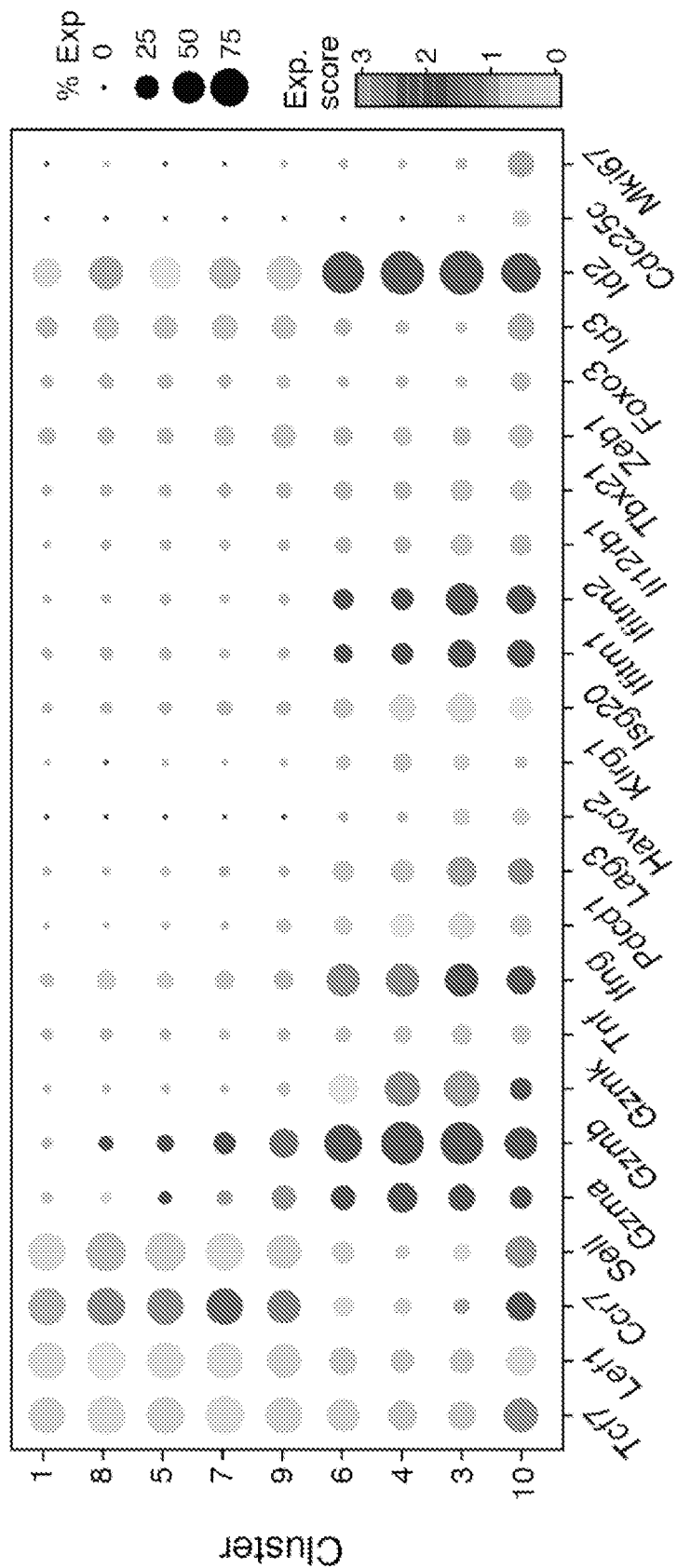
FIG. 5D shows a dot plot showing expression of the indicated genes in selected clusters (5B, panel II). Scale indicates the expression score of each gene in the indicated cluster. Circle size indicates the percentage of cells that expresses the gene within the indicated cluster.
Figure 9D:
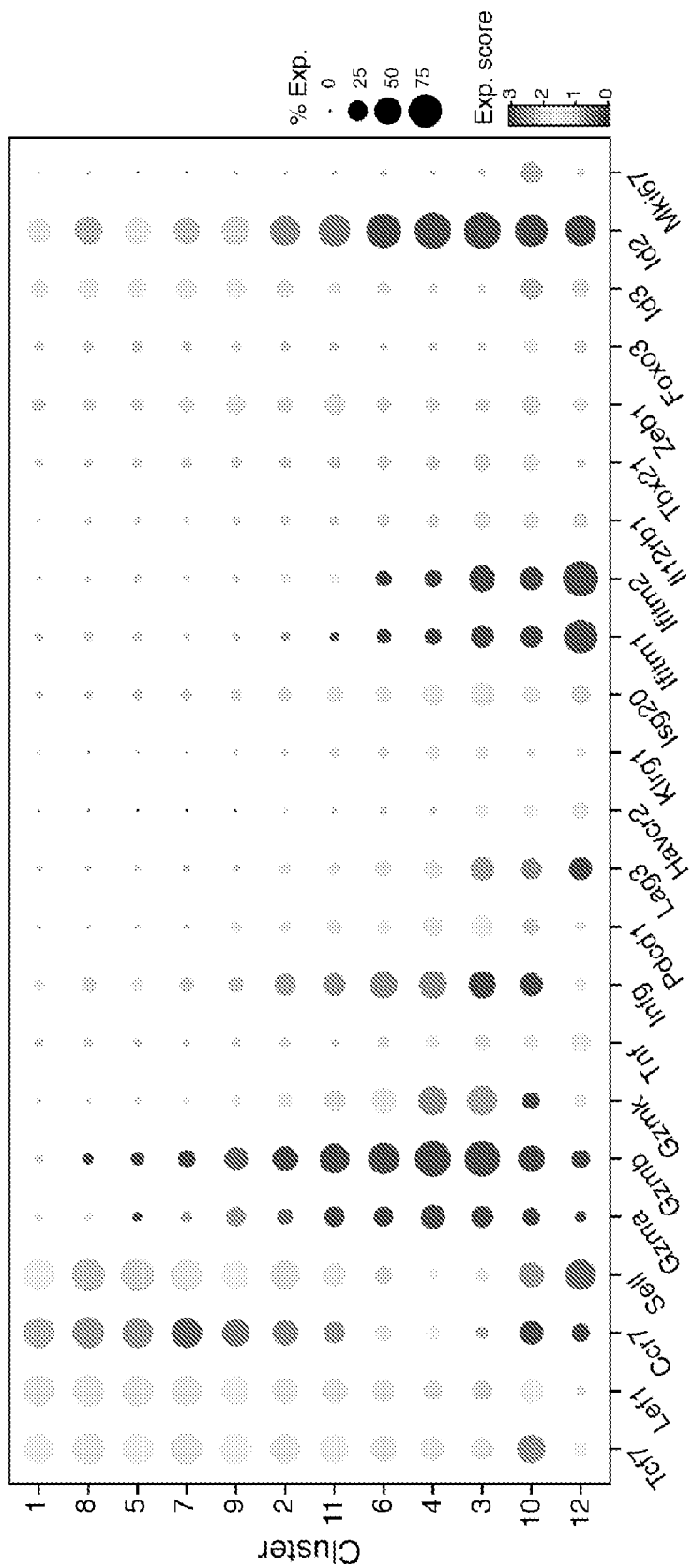
FIG. 9D shows a dot plot showing expression of the indicated genes in each of the single-cell clusters. Scale indicates the expression score of each gene in the indicated cluster. Circle size indicates the percentage of cells that expresses the gene within the indicated cluster.

Clustering highlighted subtler distinctions, including naïve-like cells that begin to adopt features of effector cells and highly proliferative cells that retain features of memory. Specifically, the naïve-like CD62L$^{hi}$Slamf7$^-$ cell signature is expressed in cells from clusters 1, 5, 8, 7 and 9, which show high expression of Tcf7, Lef1, Ccr7, and Sell (FIGS. 5D and 9D), but only the cells in cluster 9, which has equal proportions of isotype and anti-Tim-3/anti-PD-1 treated cells (FIGS. 5B and 9A), also expressed several effector genes including Gzma, Gzmb, and Ifng (FIG. 5D). This indicates that cluster 9 cells retain features of naïve-like cells but have also initiated an effector T cell program. Clusters 3 and 10 cells had the highest expression of the Slamf7$^{hi}$CX3CR1$^-$ memory-precursor-like signature, whereas clusters 4 and 6 cells expressed the Slamf7$^{hi}$CX3CR1+ effector-like signature (FIG. 5A, panels V and VI), with higher levels of many effector genes (FIG. 5D). Cluster 10 was equally comprised of cells from both treatment groups (FIG. 5B and FIG. 9A), but a larger proportion of those from the Tim-3/PD-1 blockade group expressed the proliferation marker Ki67 and a proliferation signature (Tirosh et al., 2016) (FIG. 5C). The cells in cluster 10 also expressed Tcf7, Lef1, Ccr7, and Sell as well as several effector T cell genes (FIG. 5D) and the effector CD8$^+$ T cell signature cell signature from acute LCMV infection (Kaech et al., 2002) (FIG. 5A, panel III). Thus, Tim-3/PD-1 blockade induced cells within cluster 10 that are highly proliferative and exhibit features of effector cells but, importantly, retain features of naïve/memory cells.

Figure 13A:
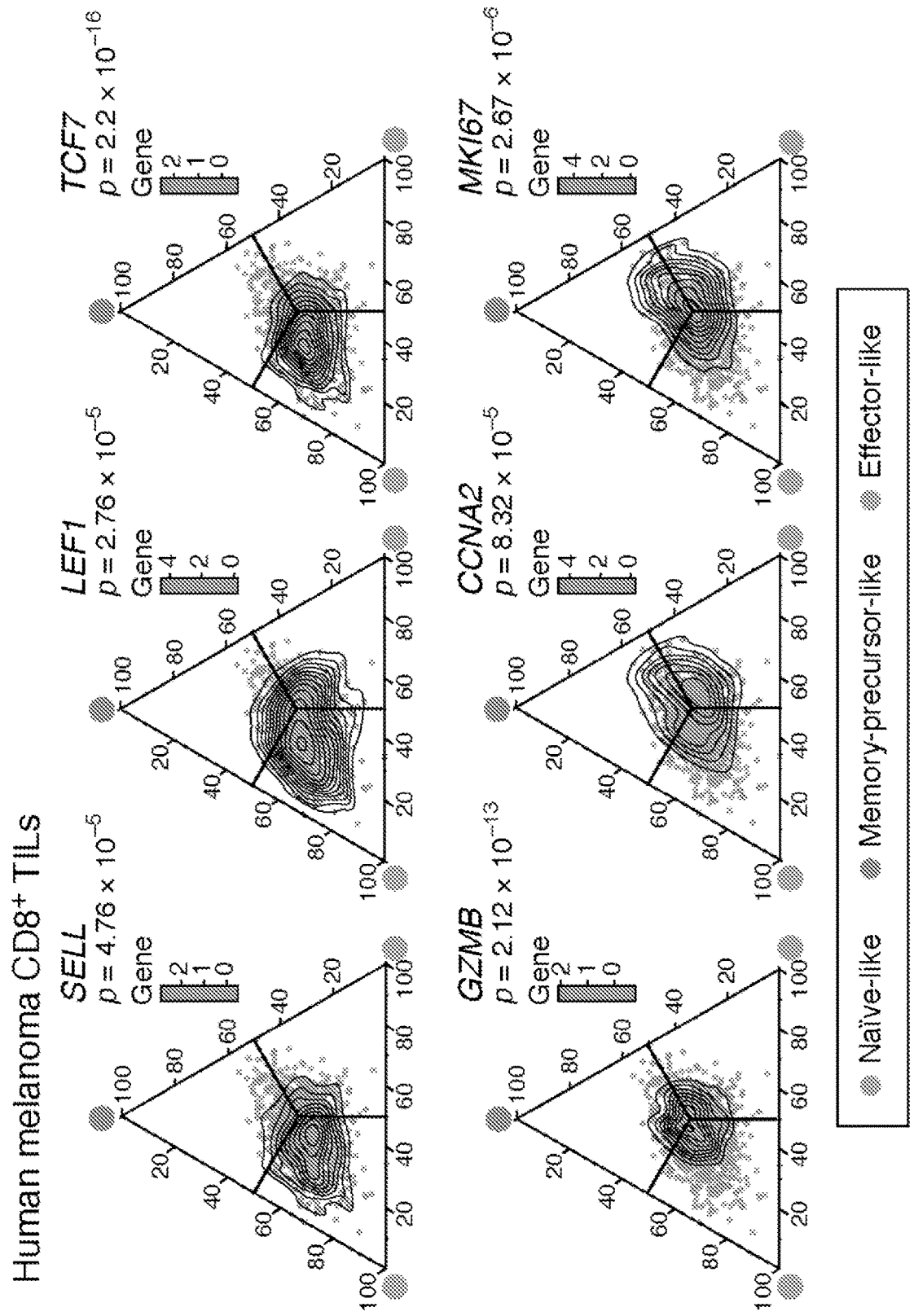
FIG. 13A shows ternary diagrams (Methods) of single-cell profiles from human melanoma (Tirosh et al., 2016) scored based on their similarity to the signatures of the naïve-like CD62L$^{hi}$Slamf7$^-$ (bottom left), the memory-precursor-like Slamf7$^{hi}$CX3CR1$^-$ (top), and the effector-like Slamf7$^{hi}$CX3CR1$^+$ (bottom right) subsets of PD-1$^-$CD8$^+$ TILs. Each single-cell (dots) is positioned on the scale based on its enrichment for the three signatures. Expression of the indicated genes in each triangle is shown (shaded dots).
Figure 13B:
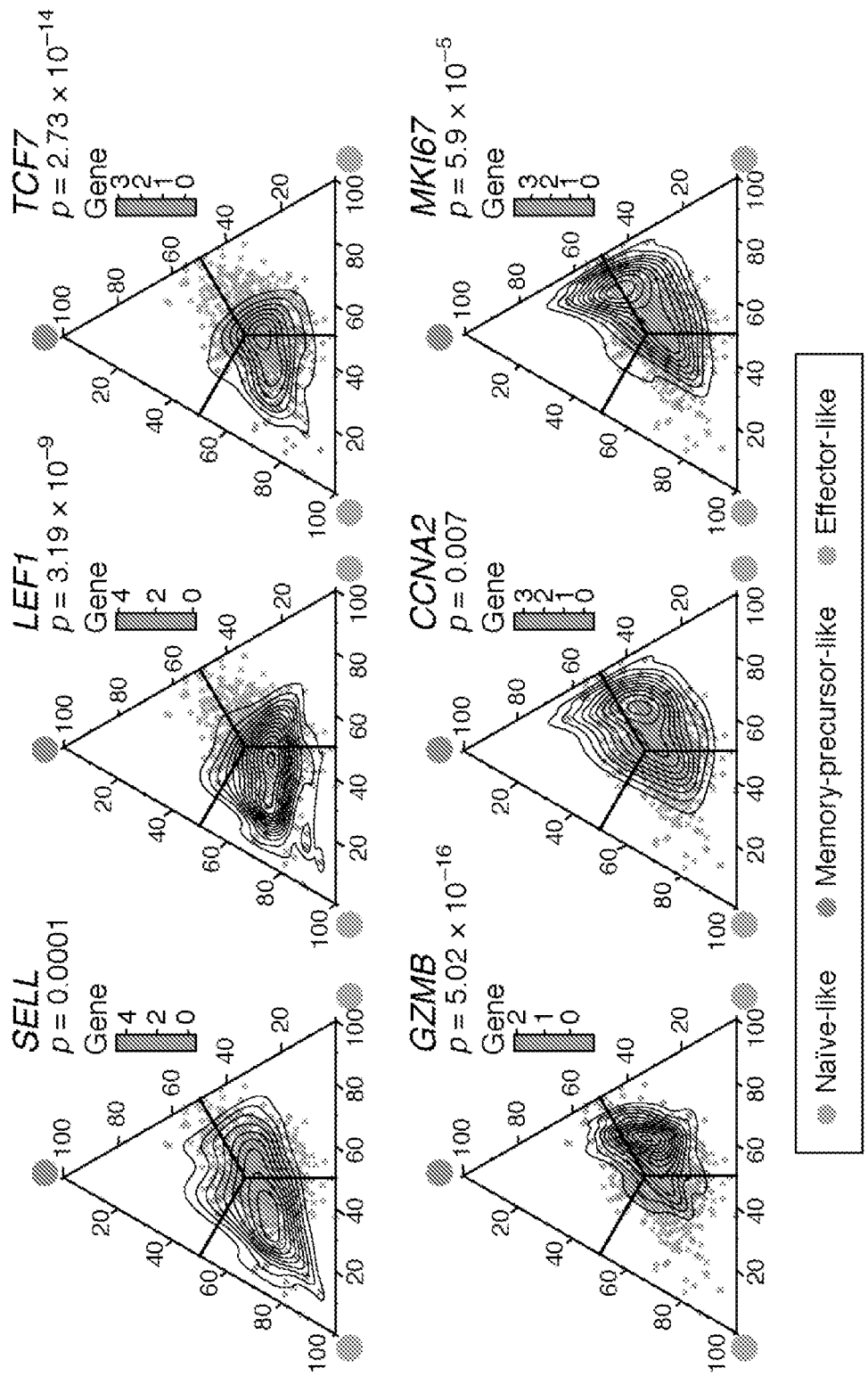
FIG. 13B shows ternary diagrams (Methods) of single-cell profiles from hepatocellular carcinoma (Zheng et al., 2017) scored based on their similarity to the signatures of naïve-like CD62L$^{hi}$Slamf7$^-$ (bottom left), the memory-precursor-like Slamf7$^{hi}$CX3CR1$^-$ (top), and the effector-like Slamf7$^{hi}$CX3CR1$^+$ (bottom right) subsets of PD-1$^-$CD8$^+$ TILs. Each single-cell (dots) is positioned on the scale based on its enrichment for the three signatures. Expression of the indicated genes in each triangle is shown (shaded dots).

Next, Applicants compared the transcriptional signatures of the three PD-1$^-$CD8$^+$ TILs subsets to scRNA-Seq profiles from CD8$^+$ TILs from melanoma (Tirosh et al., 2016) (FIG. 13A and Methods) and hepatocellular carcinoma (FIG. 13B) (Zheng et al., 2017). While many human TILs were not distinguishable by either signature, some cells had high similarity to one of the three subset signatures (FIGS. 13A and 13B). Lef1, and Tcf7 were significantly enriched in TILs that scored highly with the CD62L$^{hi}$Slamf7$^-$ subset signature, whereas effector genes such as Gzmb were enriched in those scoring for either the Slamf7$^{hi}$CX3CR1$^-$ or Slamf7$^{hi}$CX3CR1+ subset signatures. Finally, cell cycle genes, such as cyclin-A2 (Ccna2) and the proliferation marker Mki67, were enriched in cells that were more similar to the memory precursor-like Slamf7$^{hi}$CX3CR1$^-$ cells in both melanoma (FIG. 13A) and hepatocellular carcinoma CD8$^+$ TILs (FIG. 13B).

Figure 5E:
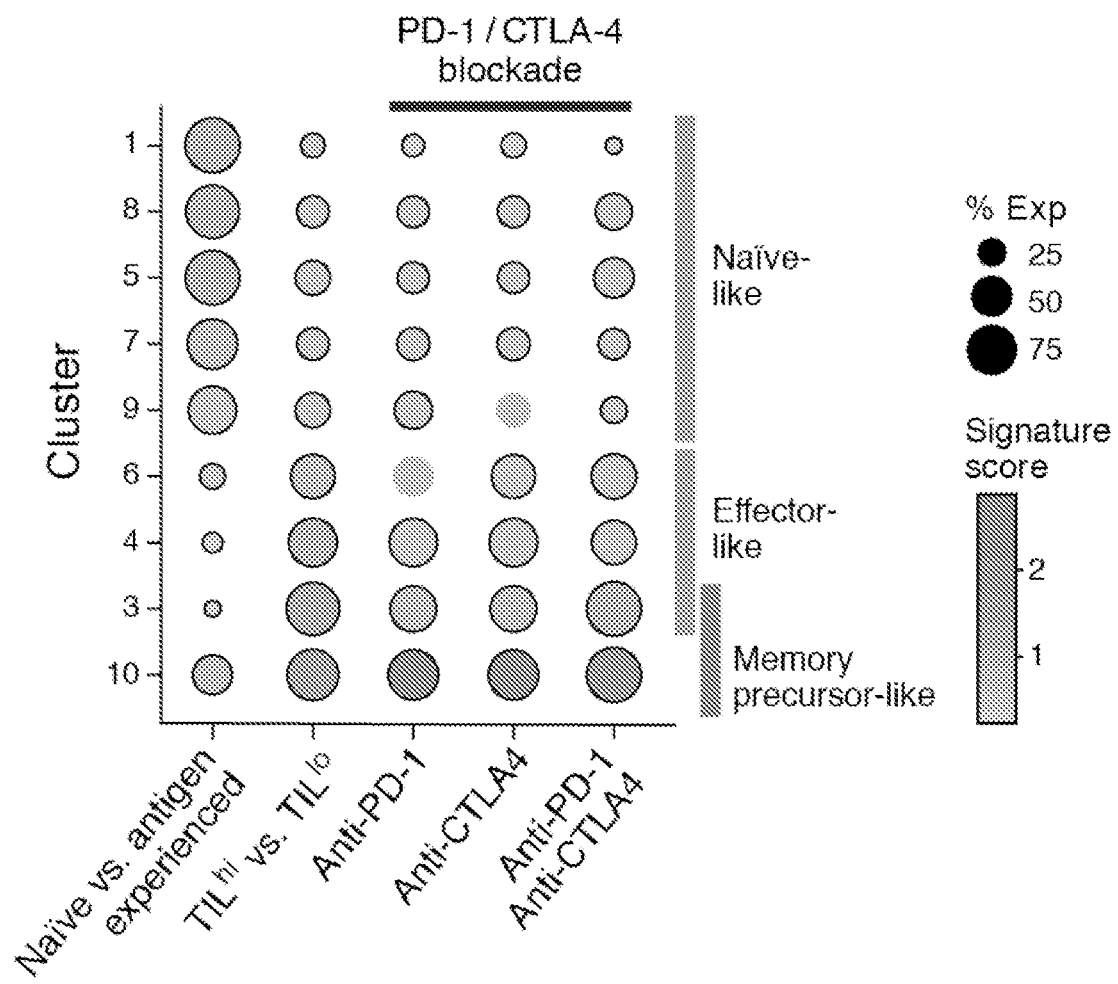
FIG. 5E shows projection of several human signatures (Methods) onto the single-cell clusters (5B, panel II). The scale shows the average expression signature score of all the cells that compose the cluster. Circle size indicates the percentage of the cells in each cluster that expresses a signature above the median and the dark borders indicate clusters that were either significantly concentrated or depleted of high scoring cells (FDR–adjusted P value <0.05, t-test). Clusters that are Naïve-like, effector-like, and memory-precursor-like are indicated by the shaded bars.
Figure 10:
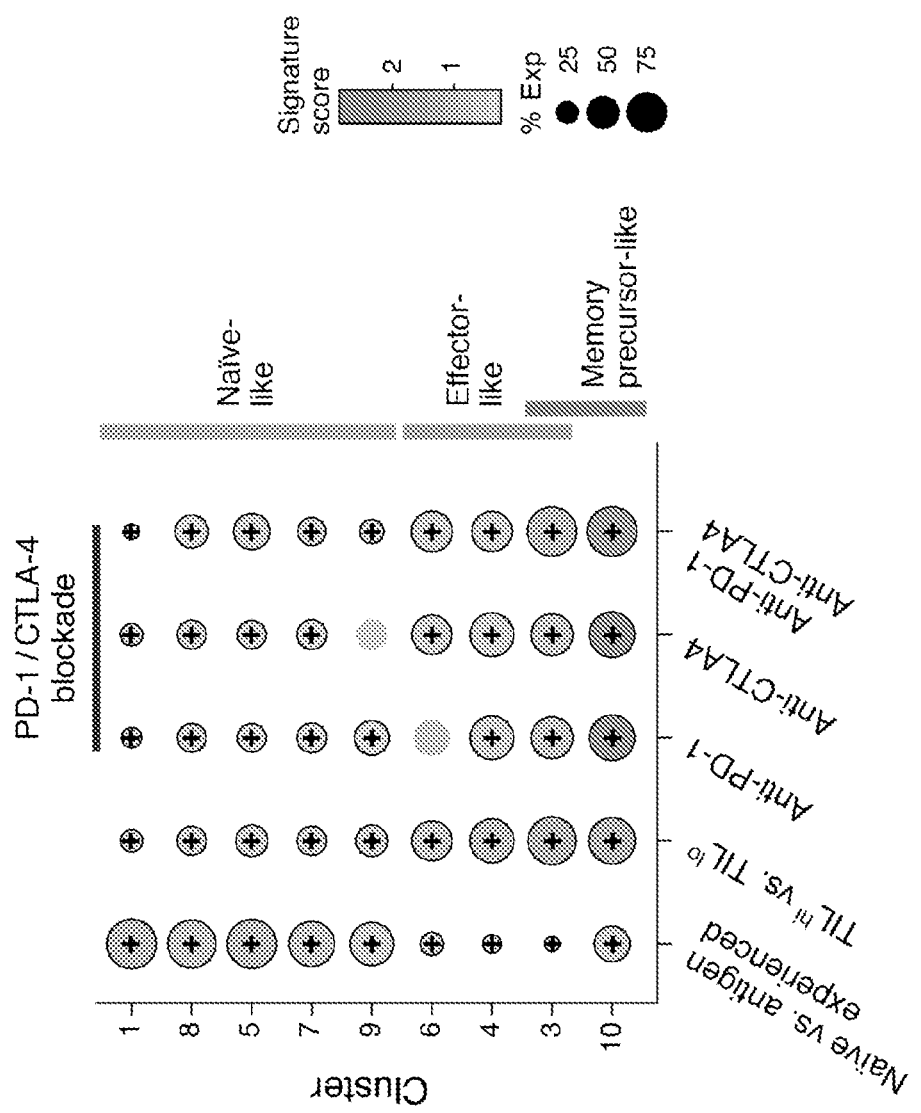
FIG. 10—Naïve, effector, and memory-precursor-like cells in human CD8$^+$ TILs from patients.
Figure 13C:
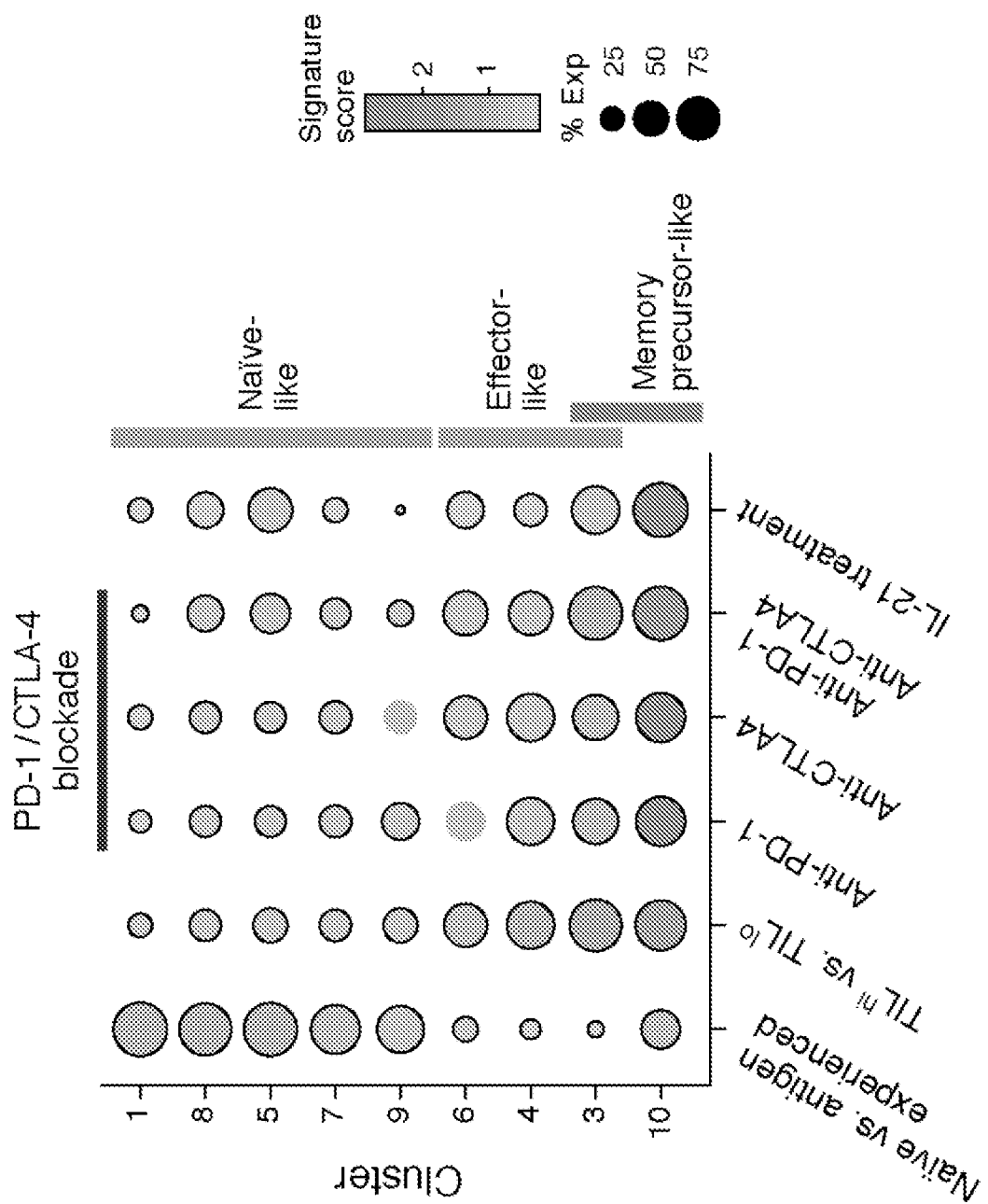
FIG. 13C shows the projection of several human signatures (Methods) onto the single-cell clusters (5A, panel II). The scale shows the average expression signature score of all the cells that compose the cluster. Circle size indicates the percentage of the cells in each cluster that expresses a signature above the median and the dark borders indicate clusters that were either significantly concentrated or depleted of high scoring cells (FDR-adjusted P value <0.05, t-test). Clusters that are Naïve-like, effector-like, and memory-precursor-like are indicated by the shaded bars.
Figure 13D:
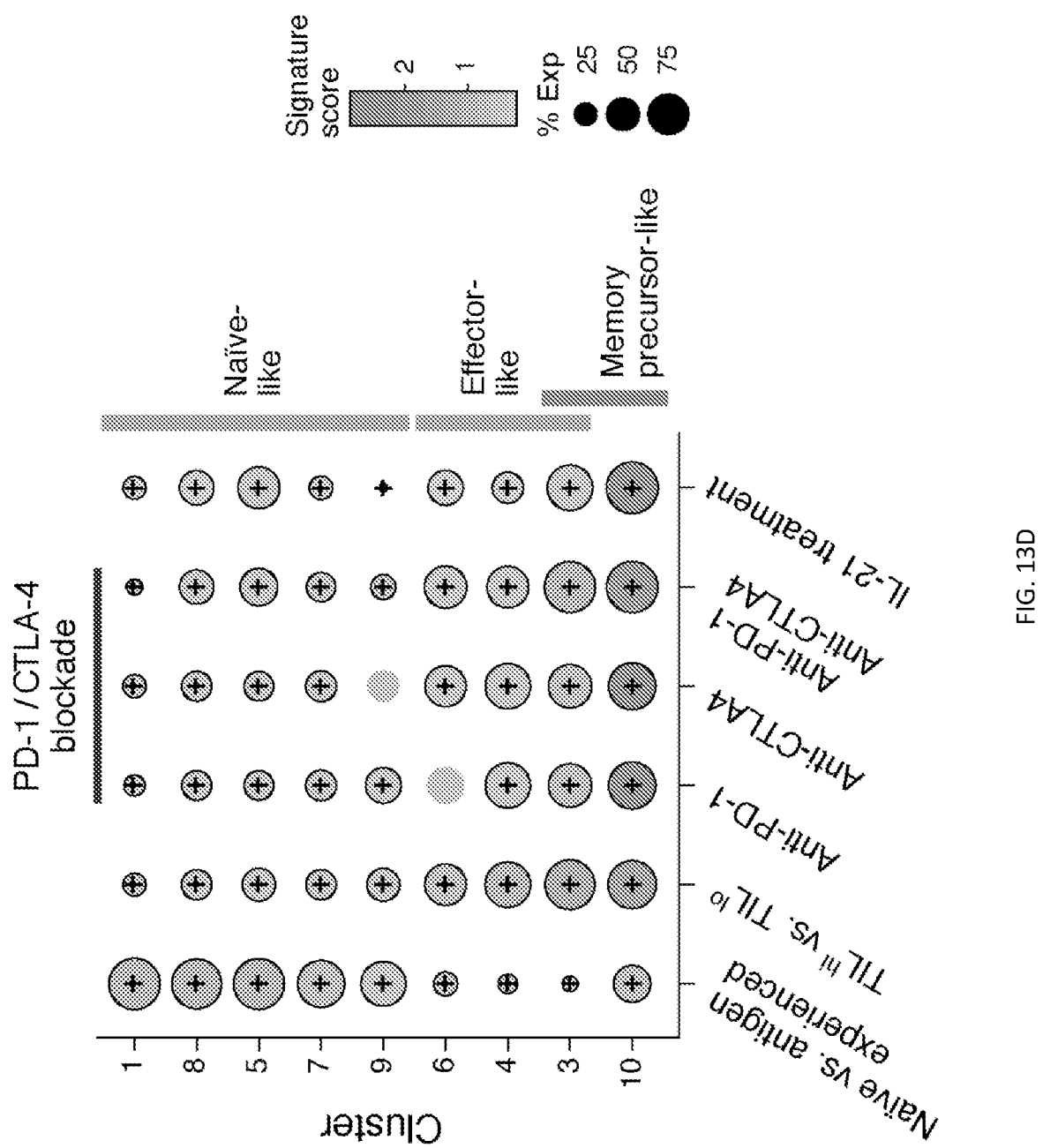
FIG. 13D shows the projection of several human signatures (Methods) onto the single-cell clusters (5A, panel II). The scale shows the average expression signature score of all the cells that compose the cluster. Circle size indicates the percentage of the cells in each cluster that expresses a signature above the median and the dark borders indicate clusters that were either significantly concentrated or depleted of high scoring cells (FDR-adjusted P value <0.05, t-test). A '+' sign indicates clusters that had a statistically significant score (FDR- adjusted P value <0.05) compared to randomly generated signatures (Methods). Clusters that are Naïve-like, effector-like, and memory-precursor-like are indicated by the shaded bars.

Finally, scoring the PD-1$^-$CD8$^+$ TILs scRNA-seq profiles showed that the memory-precursor-like and effector-like clusters (3, 4, 6, and 10) are enriched for the TIL$^{hi}$ vs TIL$^{lo}$ signature associated with better prognosis (Ganesan et al., 2017) (FIGS. 5E, 10, 13C and 13D). In particular, the memory-precursor-like cluster 10 was enriched for the signature from CD8$^+$ T cells from either anti-PD-1 (nivolumab) or anti-CTLA-4 (ipilimumab) or anti-CTLA-4+ anti-PD-1 (combo)-treated cancer patients (Das et al., 2015) (FIGS. 5E and 10). A similar shift was also observed in the RNA profiles of CD8$^+$ T cells from the blood of patients treated with IL-21 (Frederiksen et al., 2008) (FIGS. 13C and 13D). Conversely, a signature of genes differentially expressed between naïve vs. antigen experienced CD8$^+$ T cells from the peripheral blood of melanoma patients (Baitsch et al., 2011) was enriched in the naïve-like clusters (1, 5, 7, 8, and 9). (FIGS. 13C and 13D). Thus, immunotherapy induces either expansion of or conversion into subsets within human CD8$^+$ T cells that share features with the effector- and memory-precursor-like PD-1$^-$CD8$^+$ TILs subsets defined herein.

Figure 6A:
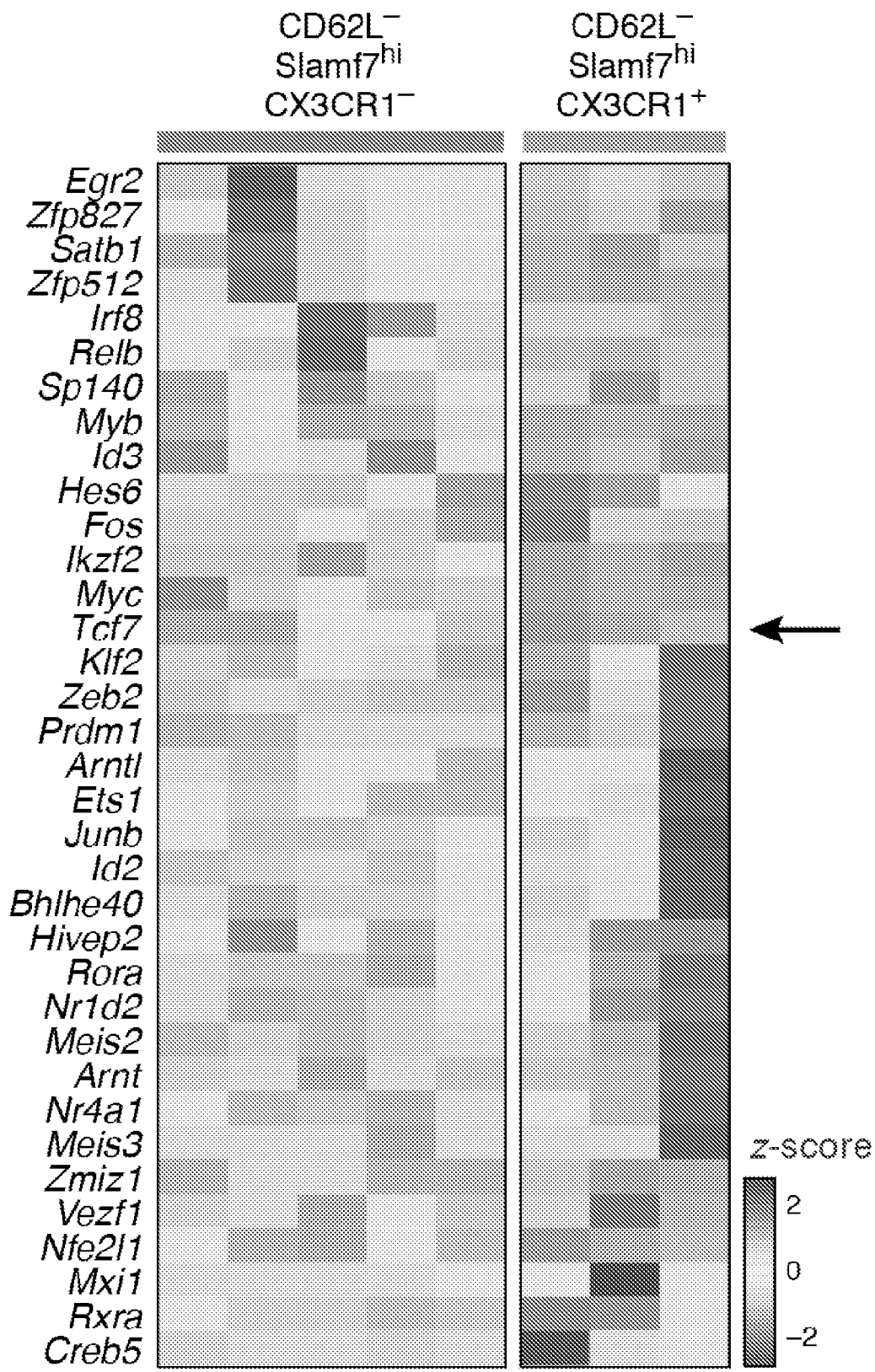
FIG. 6A shows a heatmap showing transcription factors differentially expressed between Slamf7$^{hi}$CX3CR1$^-$ and Slamf7$^{hi}$CX3CR1+PD-1$^-$CD8$^+$ TILs.

Example 7—Tcf7 Plays a Role in the Generation of Sustained Anti-Tumor Responses after Immunotherapy Although both the memory-precursor-like and effector-like PD-1$^-$CD8$^+$ TILs subsets increased following immunotherapy (FIG. 6A), only the memory-precursor-like subset maintained polyfunctionality and retained features of memory-precursor cells. Applicants therefore hypothesized that this subset may be essential to sustain a long-lasting anti-tumor effector CD8$^+$ T cell response. To test this, Applicants identified candidate regulators for the Slamf7$^{hi}$CX3CR1$^-$PD-1$^-$CD8$^+$ TILs subset (memory-precursor-like PD-1$^-$ CD8$^+$ TILs) by focusing on transcription factors that are more highly expressed in Slamf7$^{hi}$CX3CR1$^-$ vs. Slamf7$^{hi}$CX3CR1$^+$PD-1$^-$ cells: Tcf7, Myc, and Id3 (FIG. 6A and Table 5).

Figure 6B:
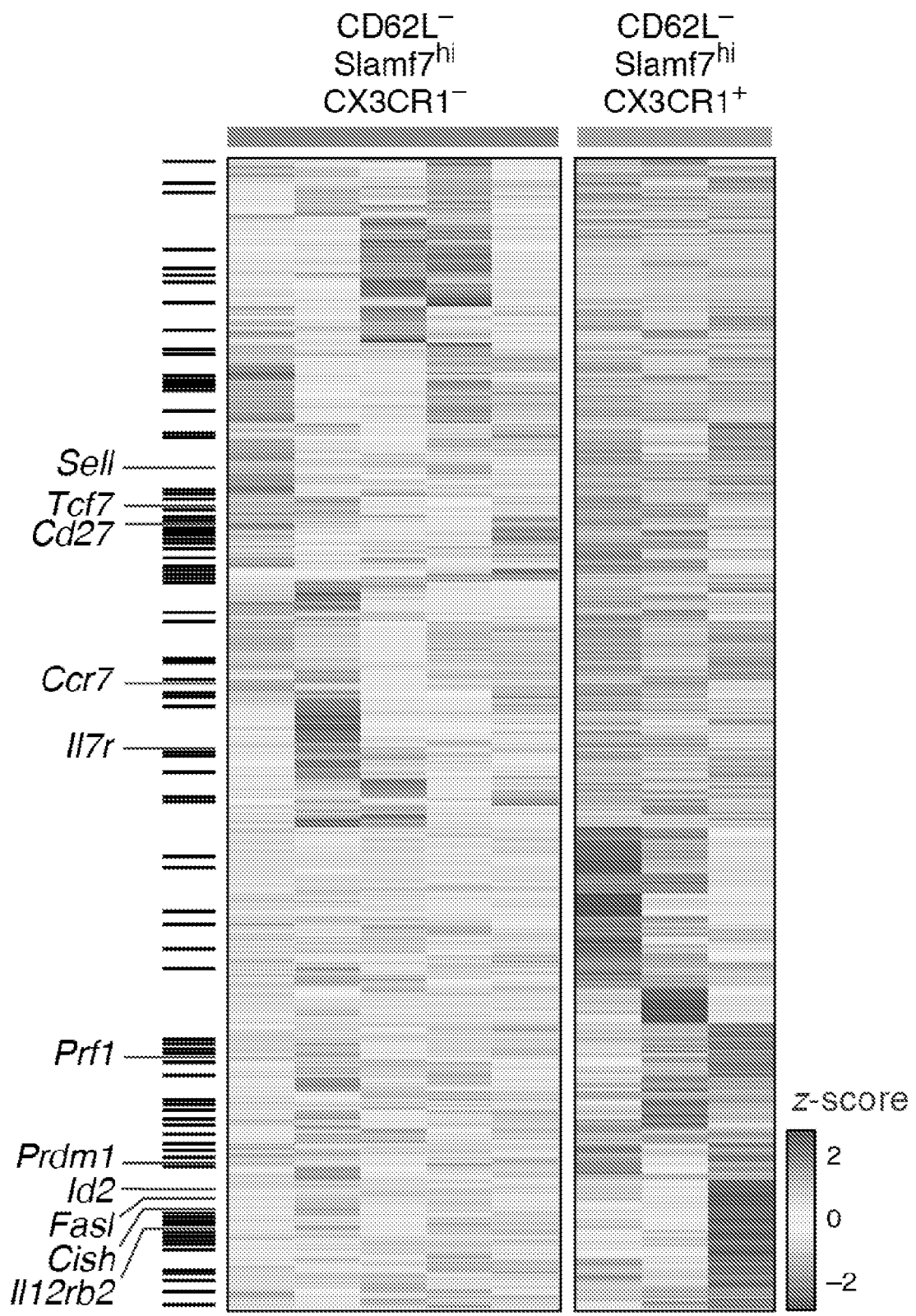
FIG. 6B shows a heatmap showing all differentially expressed genes between Slamf7$^{hi}$CX3CR1$^-$ and Slamf7$^{hi}$ CX3CR1$^+$PD-1$^-$CD8$^+$ TILs. Tick marks indicate the genes that are bound by Tcf7 according to CHIP-Seq of Tcf7 in naïve CD8$^+$ T cells (Steinke et al., 2014) (Methods).
Figure 11A:
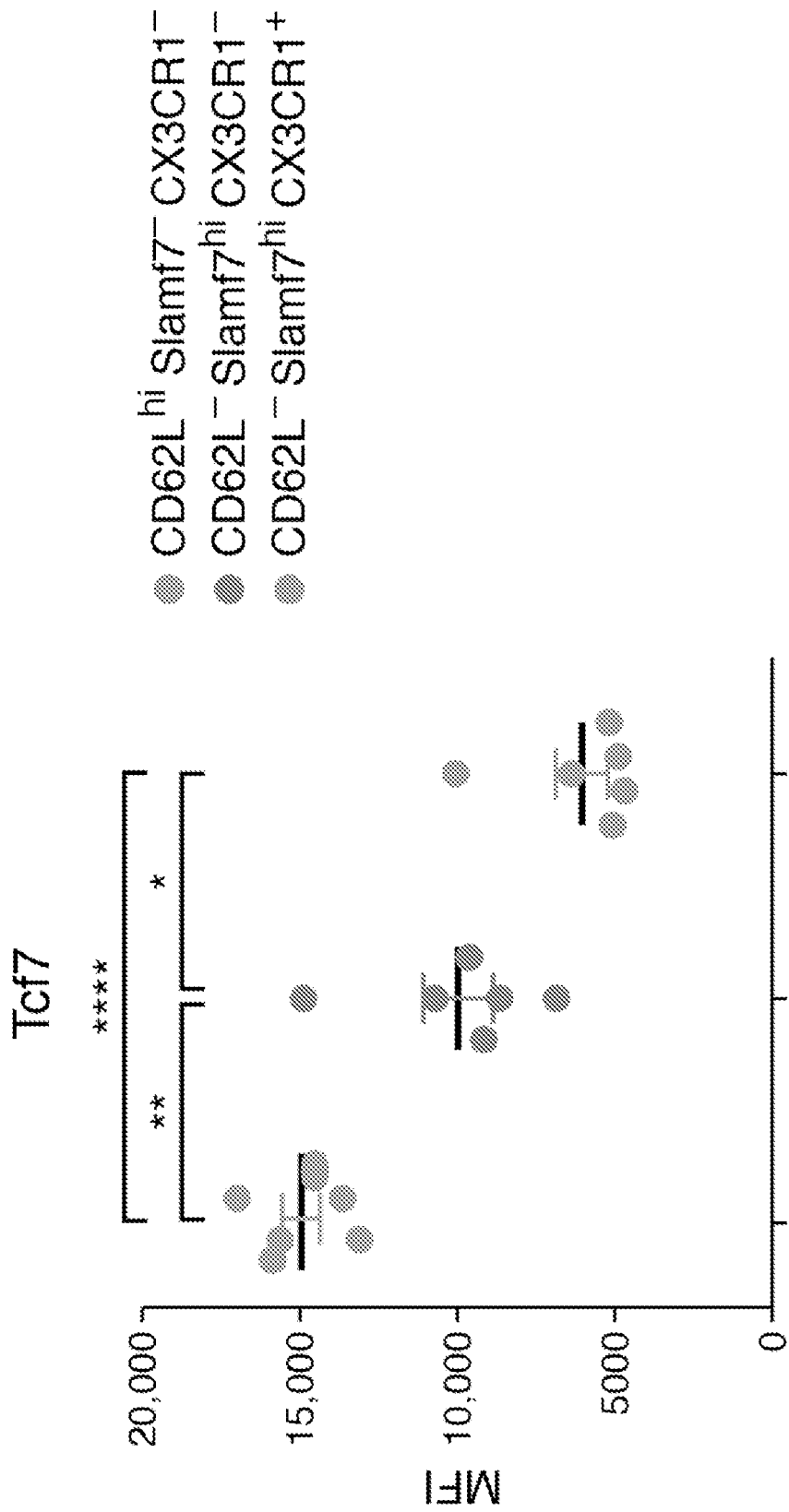
FIG. 11A shows mean fluorescence intensity (MFI) of Tcf7 protein in the indicated populations of PD-1$^-$CD8$^+$ TILs. *p<0.05, p<0.01, **p<0.0001, One-way ANOVA, Tukey's multiple comparison test.)

Tcf7 was of key interest given its role in self-renewal and maintenance of memory CD8$^+$ T cells (Jeannet et al., 2010; Zhou et al., 2010) and from recent studies showing the requirement for Tcf7 in expansion of PD-1$^+$CD8$^+$ T cells after PDL1 blockade (Im et al., 2016; Utzschneider et al., 2016). Tcf7 is indeed more highly expressed in memory-precursor-like vs. effector-like subsets of PD-1$^-$CD8$^+$ TILs at the protein level (FIG. 11A). Moreover, Tcf7 transcriptional targets, either selected from Tcf7 chromatin-immunoprecipitation sequencing (ChIP-Seq) data on naïve CD8$^+$ T cells (Steinke et al., 2014) or from RNA profiling of WT vs. Tcf7-deficient TCR-transgenic memory CD8$^+$ T cells (Zhou et al., 2010), were enriched in genes differentially expressed between the memory and effector-like subsets (FIG. 6B, C).

Figure 11B:
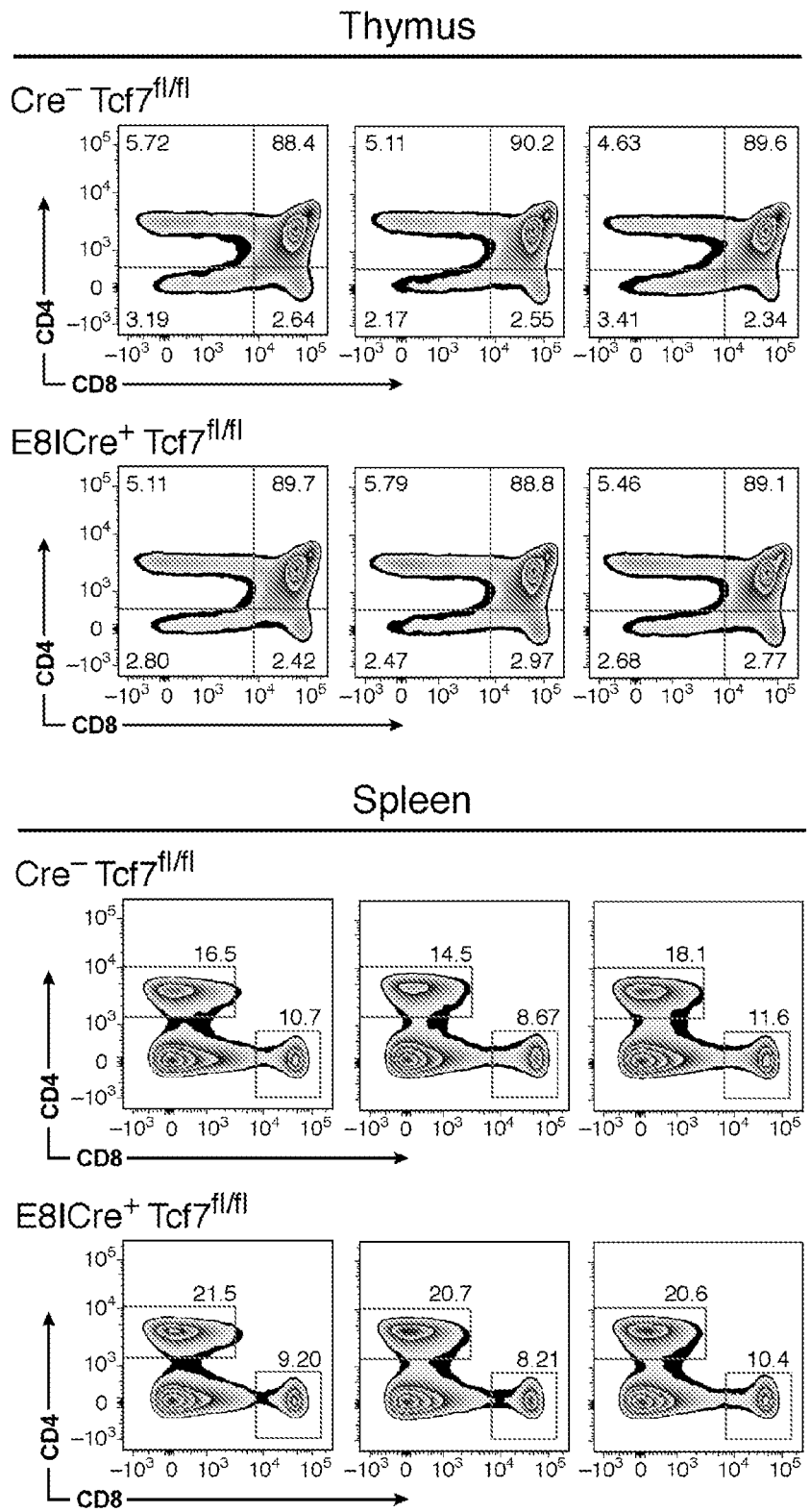
FIG. 11B shows representative FACS plots showing CD4 and CD8 expression in the thymus (top) and spleen (bottom) of WT vs Tcf7cKO mice (n=3 per group).
Figure 12A:
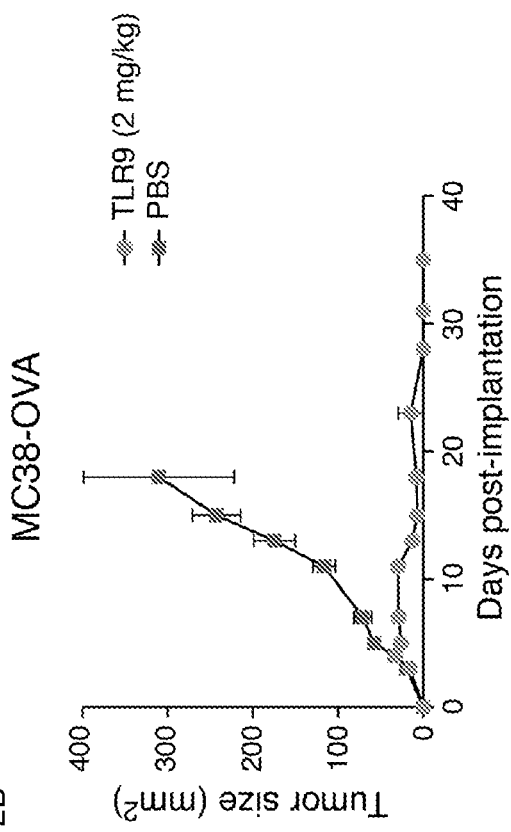
FIG. 12A shows the frequency of H-2K$^b$/OVA$_{257-264}$$^+$ in PD1$^+$ and PD1$^-$CD8$^+$ TILs in WT and Tcf7cKO mice is shown. *p<0.05, *p<0.001, t-test.
Figure 12C:
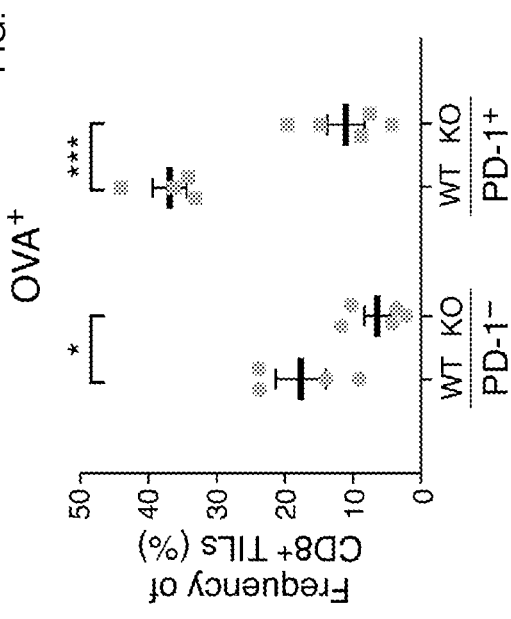
FIG. 12C shows individual tumor size in each group in 12B. **p<0.0001, linear regression. Data is representative of at least three independent experiments.

To determine the role of Tcf7 specifically in CD8$^+$ TILs, Applicants generated mice that harbor deletion of Tcf7 specifically in CD8$^+$ T cells by crossing Tcf7$^{flox/flox}$ mice with mice that expressed Cre recombinase under the E81 promoter (Tcf7cKO) (Maekawa et al., 2008). As these mice do not express Cre until the single positive CD8$^+$ T cell stage in the thymus (Ellmeier et al., 1997), Applicants did not observe any gross defects in T cell development in the thymus or in the peripheral T cell compartment (FIG. 11B). While Applicants did not observe significant changes in the distribution of major subsets (Tim-3$^+$PD-1$^+$ and Tim-3$^-$PD-1$^-$TILs) in wild type vs. Tcf7cKO mice (data not shown), there was a significant decrease in memory-precursor-like subset within PD-1$^-$CD8$^+$ TILs in the absence of Tcf7 (FIG. 6D). This indicates an essential role for Tcf7 in the development and/or maintenance of this subset. Applicants further observed that the frequency of OVA-specific cells was decreased within memory-precursor-like subset, shifting the balance towards the effector-like subset of PD-1$^-$ CD8$^+$ TILs (FIG. 6E). Overall, the frequency of OVA-specific CD8$^+$ TILs was significantly decreased within both PD1$^-$ and PD-1$^+$CD8$^+$ TILs in Tcf7cKO mice (FIG. 12A), suggesting that the defects in the memory-precursor-like subset are propagated to PD-1$^+$CD8$^+$ TILs. Lastly, the polyfunctionality of the memory-precursor-like subset in response to tumor antigen stimulation was reduced in the absence of Tcf7 (FIG. 6F). Together these data indicate that both the maintenance and functionality of tumor antigen-specific memory-precursor-like PD-1$^-$ cells was impaired in the absence of Tcf7 and that defects in these cells have effects that extend to the bulk CD8$^+$ T cell pool.

Figure 12B:
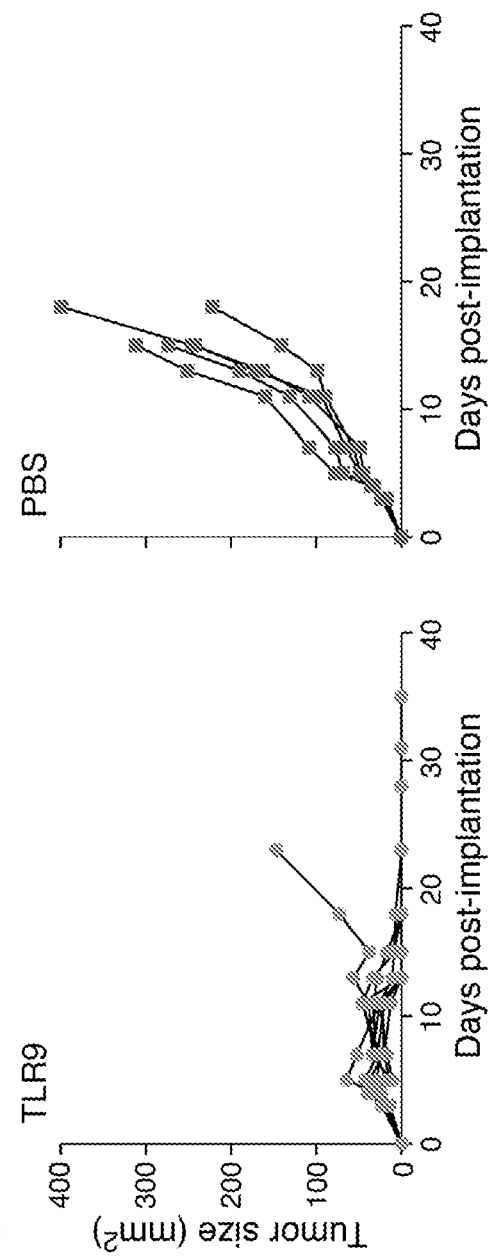
FIG. 12B shows WT mice were implanted with MC38-OVA and treated with PBS (square) or TLR9 agonist (circle; IMO-2125) on days 4 and 7. Mean tumor size is shown

Example 8—Tcf7 is Required for Effective Anti-Tumor Responses Upon Immunotherapy The results indicate that the memory-precursor-like PD-1$^-$CD8$^+$ TILs subset expands upon Tim-3/PD-1 blockade and potentially provides a wave of effector CD8⁺ T cells for an effective anti-tumor response, and that Tcf7 regulates the maintenance of this subset. Thus, Applicants hypothesized that Tcf7 may be essential for effective immunotherapy. To test this, Applicants treated MC38-OVA tumor-bearing WT and Tcf7cKO mice with Tim-3/PD-1 blockade or isotype and followed tumor growth over time. Supporting the hypothesis, the efficacy of Tim-3/PD-1 blockade was lost in the absence of Tcf7 in CD8⁺ T cells (FIG. 6G). Of note, isotype treated Tcf7cKO mice showed accelerated tumor growth compared to controls. Given The data indicating the enrichment of pro-inflammatory cytokine (IFNβ, IL-16, IL-12, and IFNγ) signatures in PD-1⁻CD8⁺ TILs subsets after checkpoint blockade (FIG. 9C), Applicants next examined whether Tcf7 is required for the efficacy of a Toll-like receptor 9 (TLR9) agonist (IMO-2125, currently in clinical development) that induces pro-inflammatory cytokines (IL-12, Type 1 IFN, and IL-6) (Makowska et al., 2013) in the TME and normally results in complete regression of MC38-OVA tumors in WT mice (FIG. 12B, C). Applicants treated MC38-OVA tumor-bearing WT and Tcf7cKO mice with the TLR9 agonist and found that while this therapy induced an effective anti-tumor immune response in WT mice, it failed significantly (p=0.0361) in Tcf7cKO mice (FIG. 6H). Thus, Tcf7 expression in CD8⁺ T cells is required for the generation of effective anti-tumor immunity in response to different immunotherapies.

Example 9—Discussion

Through an integrated experimental and computational approach, Applicants show that Tim-3/PD-1 blockade recruits cells that lack surface expression of PD-1 as well as other known checkpoint receptors. The analysis of the transcriptional changes in PD-1⁻CD8⁺ TILs upon Tim-3/PD-1 blockade led to the identification three distinct subsets of PD-1⁻CD8⁺ TILs that have functional and transcriptional features of naïve, memory-precursor, or effector CD8⁺ T cells. Applicants further show that different checkpoint blockade treatments across different cancers induce expansion of the memory-precursor- and effector-like PD-1⁻CD8⁺ TILs subsets and concomitant decrease in the naïve-like subset. Applicants defined transcriptional signatures for each of these subsets and surface markers (CD62L, Slamf7, CX3CR1) that can be used to track them in vivo. Both flow cytometry and scRNA-seq data show an increase in the proportion of the newly defined Slamf7$^{hi}$CX3CR1⁻PD-1⁻CD8⁺ memory-precursor-like and Slamf7$^{hi}$CX3CR1⁺PD-1⁻CD8⁺ at the expense of the CD62L$^{hi}$Slamf7-PD-1⁻ naïve-like subset after checkpoint blockade. Importantly, the Slamf7$^{hi}$CX3CR1⁻PD-1⁻ subset (memory-precursor-like subset) shares features with CD8⁺ T cells that correlate with better prognosis and also with CD8⁺ T cells that expand after checkpoint blockade in cancer patients, highlighting the clinical relevance of these findings.

The discovery of PD-1⁻CD8⁺ T cell subsets that change in response to immunotherapy is important in light of the recent studies describing a population of PD-1⁺CD8⁺ T cells that expresses CXCR5 and provides the proliferative burst after PD-1 blockade during chronic viral infection (Im et al., 2016). Indeed, several studies have described similar subsets of PD-1⁺CD8⁺ T cells both in the context of chronic viral infection and cancer (Im et al., 2016; Leong et al., 2016; Philip et al., 2017; Utzschneider et al., 2016). These PD-1⁺ cells and the memory-precursor-like subset that Applicants identify share some important features. They both express Tcf7 and are proliferative. However, that the CD62L⁻Slamf7$^{hi}$CX3CR1⁻ memory-precursor-like CD8⁺ TILs subset does not express PD-1 indicates that this subset is much earlier along the T cell activation and differentiation trajectory. This could be critically important as multiple recent studies have shown that PD-1⁺CD8⁺ T cells under chronic stimulation undergo chromatin remodeling, resulting in a fixed epigenetic profile that limits their potential to be reprogrammed in response to interventions such as checkpoint blockade (Ghoneim et al., 2017; Pauken et al., 2016; Philip et al., 2017; Scott-Browne et al., 2016; Sen et al., 2016). Conversely, the CD62L⁻Slamf7$^{hi}$CX3CR1⁻PD-1⁻CD8⁺ TILs subset likely contains precursors that can seed the effector T cell pool and have a better capacity to sustain long-term responses compared to cells that have already up-regulated the PD-1 receptor. This is supported by the data showing that adoptively transferred PD-1⁻CD8⁺ TILs give rise to PD-1⁺ cells and that different immunotherapies fail when this subset is compromised. In accordance with the findings, it was recently reported that in patients treated with chimeric antigen receptor (CAR)-engineered T cells the presence of PD1⁻ CAR-T cells was predictive of complete remission. An analagous population was necessary for tumor control in mice. Notably, this subpopulation of cells had a memory-like transcriptional signature and displayed activation of the IL6/STAT3 pathway (Fraietta et al., 2018). This is in line with the observations of IL-6 pathway induction in PD-1⁻ effector and memory-precursor-like TILs from treated mice.

The data does not exclude that changes in Tim-3⁺PD-1⁺ CD8⁺ TILs contribute to the anti-tumor effect observed after Tim-3/PD-1 blockade. However, Applicants found higher enrichment of effector CD8⁺ T cell signatures and T cell expansion within Tim-3⁻PD-1⁻CD8⁺ TILs as compared to Tim-3⁺PD-1⁺CD8⁺ TILs in response to Tim-3/PD-1 blockade. The findings indicate that Tim-3/PD-1 blockade therapy can also indirectly promote effector programs in Tim-3⁻PD-1⁻CD8⁺ TILs through its action on other Tim-3 and PD-1-expressing cell types in the TME, such as natural killer cells, CD4⁺ effector and Treg, and myeloid cells. Indeed, accumulating evidence indicates that blockade of Tim-3 and PD-1 receptors present on the surface of these cells can significantly contribute to the anti-tumor effect of these immunotherapies. Tim-3 blockade has been shown to improve the function of natural killer cells from melanoma patients (da Silva et al., 2014). PD-1 blockade has been shown to alleviate Treg-mediated suppression of effector CD8⁺ TILs (Duraiswamy et al., 2013) and to induce IFN-γ expression in Treg, which in turn promotes Treg fragility and was shown to be required for the anti-tumor efficacy of anti-PD-1 therapy (Overacre-Delgoffe et al., 2017). Applicants have shown that Tim-3/PD-L1 blockade reduces the expression of Treg effector molecules in intra-tumoral Treg (Sakuishi et al., 2013). In CD4⁺ TILs, PD-1 blockade promotes IFN-γ and TNF-α production ((Duraiswamy et al., 2013; Woo et al., 2012). Both anti-Tim-3 and anti-PD-1 antibodies can affect the phenotype of myeloid cells in the TME. Tim-3 blockade abrogates the acquisition of an M2-like phenotype in tumor-associated macrophages (TAMs) (Jiang et al., 2016) and induces Type 1 IFN, IL-12 and IFN-γ in CD103+ DCs in breast cancer (de Mingo Pulido et al., 2018). Similarly, PD-1 blockade can promote pro-inflammatory cytokine production by DCs in ovarian cancer (Krempski et al., 2011; Lim et al., 2016)). These findings are in line with the observation that Type 1 IFN, IL-12, and IFN-γ signatures were significantly induced in the effector-like and memory-precursor like PD-1⁻CD8⁺ TIL subsets in treated mice. Thus, Tim-3 and PD-1 pathway blockade can act on different immune cell types within the TME to promote anti-tumor CD8+ T cell responses.

The data show that the changes in the proportions of the newly defined naïve-, memory-precursor-, and effector-like PD-1−CD8+ TILs subsets occur in different tumor models (MC38 colon carcinoma and B16F10 melanoma) and in response to different therapies (Tim-3/PD-1, CTLA-4/PD-1, CTLA-4/PD-L1), thus underscoring the robustness of The findings. Moreover, Applicants found enrichment of the memory-precursor-like signature in human CD8+ TIL signatures associated with better prognosis and in the peripheral blood CD8+ T cells from cancer patients treated with anti-CTLA-4/PD-1 therapy. These results support the potential prognostic value of the memory-precursor-like subset and their use as a biomarker for tracking response to therapy in the blood of patients.

The findings identify previously unrecognized changes in CD8+ TILs in response to checkpoint blockade immunotherapy. The identification of PD-1−CD8+ precursor TILs that share features with human CD8+ T cells associated with good prognosis and response to therapy has important clinical implications for the identification of biomarkers of therapeutic response, as well as of targets that can be modulated in T cells used for adoptive cell therapies to ensure sustained and durable effector responses.

TABLE 1

Differentially expressed gene list between isotype and Tim-3/PD-1 blockade treatment in Tim-3−PD-1− and Tim-3+PD-1+ CD8+ TILs.

| Tim-3 + PD-1+ | | | | Tim-3 − PD-1− | | | |
|---|---|---|---|---|---|---|---|
| Gene | UP/DOWN | Gene | UP/DOWN | Gene | UP/DOWN | Gene | UP/DOWN |
| Cfl1 | UP | Hbb-b2 | DOWN | Actg1 | UP | Hba-a2 | DOWN |
| Arpc2 | UP | Alas2 | DOWN | Ncstn | UP | Alas2 | DOWN |
| Mcm7 | UP | Nptx1 | DOWN | Map4 | UP | Snca | DOWN |
| Oaz1-ps | UP | Snca | DOWN | Ctsw | UP | Klk1b27 | DOWN |
| Ctsb | UP | Hbb-b1 | DOWN | Lgals3bp | UP | Apol11b | DOWN |
| Ywhah | UP | Slc4a1 | DOWN | Sept9 | UP | Obscn | DOWN |
| Il2rb | UP | Apol11b | DOWN | Ext2 | UP | Hs3st1 | DOWN |
| Psme2 | UP | Cd24a | DOWN | Pxn | UP | 2610019F03Rik | DOWN |
| Arpc4 | UP | Pdcd4 | DOWN | Tbc1d9b | UP | F630111L10Rik | DOWN |
| Nme1 | UP | Bpgm | DOWN | Ly6a | UP | Lef1 | DOWN |
| Psme1 | UP | Zfp36l2 | DOWN | Baiap3 | UP | Il12a | DOWN |
| Rpn1 | UP | Col7a1 | DOWN | Trafd1 | UP | Gm5086 | DOWN |
| Arsb | UP | Wdfy1 | DOWN | Vmp1 | UP | Slc6a19 | DOWN |
| Klrd1 | UP | Kcnq1ot1 | DOWN | Tm9sf4 | UP | Itgae | DOWN |
| Ctsd | UP | A630089N07Rik | DOWN | Nfkbia | UP | Art2b | DOWN |
| Capg | UP | Gm17821 | DOWN | Psmd3 | UP | Usp28 | DOWN |
| Man2b2 | UP | Grk4 | DOWN | Litaf | UP | Bpgm | DOWN |
| Ctsa | UP | Zfp260 | DOWN | Tpm4 | UP | Pik3ip1 | DOWN |
| Thy1 | UP | Zfp169 | DOWN | Rps6ka4 | UP | Dapl1 | DOWN |
| Tgfbr2 | UP | Prss12 | DOWN | Mlf2 | UP | Klra13-ps | DOWN |
| Mcm2 | UP | Lrrn3 | DOWN | Dusp1 | UP | Bambi-ps1 | DOWN |
| B4galnt1 | UP | Eml5 | DOWN | Nabp1 | UP | Rras2 | DOWN |
| Nkg7 | UP | Nr1d2 | DOWN | Isg20 | UP | Bcl2 | DOWN |
| Prdx5 | UP | Ano1 | DOWN | Zbp1 | UP | Klk1 | DOWN |
| Ptprcap | UP | Fech | DOWN | Incenp | UP | 5830411N06Rik | DOWN |
| Tcerg1 | UP | Pde3b | DOWN | Irf2bpl | UP | Pdcd4 | DOWN |
| Esyt1 | UP | Cxcr4 | DOWN | Sema4a | UP | Ccr7 | DOWN |
| Wbp2 | UP | Sh3gl2 | DOWN | Gadd45b | UP | Siglech | DOWN |
| Me2 | UP | Slc9a9 | DOWN | Bcl2a1b | UP | Slpi | DOWN |
| Lgals3 | UP | 4930467E23Rik | DOWN | Slfn8 | UP | Klra7 | DOWN |
| Tmed2 | UP | Dtx4 | DOWN | Myo1f | UP | Ramp1 | DOWN |
| Ctss | UP | Zfp71-rs1 | DOWN | Stam2 | UP | Als2cl | DOWN |
| Cndp2 | UP | Gm20300 | DOWN | Zfp277 | UP | Cd4 | DOWN |
| Pim3 | UP | Ptprg | DOWN | Gm14446 | UP | Ttc28 | DOWN |
| Vars | UP | Tsc22d3 | DOWN | Nkg7 | UP | Gabrr2 | DOWN |
| Glt25d1 | UP | Atp10d | DOWN | Ctsd | UP | Ints8 | DOWN |
| Cyc1 | UP | Stra6 | DOWN | Desi1 | UP | Fech | DOWN |
| Cotl1 | UP | Epha2 | DOWN | Cln3 | UP | H2-Ob | DOWN |
| Crip1 | UP | Enc1 | DOWN | Soat1 | UP | Nav2 | DOWN |
| Serpine2 | UP | Insr | DOWN | Ttll12 | UP | Tspan32 | DOWN |
| S100a4 | UP | Psrc1 | DOWN | Rbpj | UP | Klra1 | DOWN |
| Chst12 | UP | Cwf19l2 | DOWN | Dok2 | UP | Adamtsl2 | DOWN |
| Lrch1 | UP | Naa30 | DOWN | Agpat4 | UP | Phc1 | DOWN |
| Itgb7 | UP | B230120H23Rik | DOWN | Rac1 | UP | Tmem57 | DOWN |
| Tnfaip3 | UP | Chrnb1 | DOWN | Plec | UP | Acp5 | DOWN |
| Slc25a12 | UP | Zyg11b | DOWN | Crip1 | UP | Tnfsf8 | DOWN |
| Pkp3 | UP | 4931406H21Rik | DOWN | Atp8b4 | UP | D8Ertd82e | DOWN |
| Lmnb1 | UP | Kif18a | DOWN | Nbeal2 | UP | Sesn1 | DOWN |
| Gatad2a | UP | Pign | DOWN | Dynlt1b | UP | Atp1a3 | DOWN |
| Cd244 | UP | Igf1r | DOWN | Slc2a3 | UP | Cox6a2 | DOWN |
| Sh3bp1 | UP | Msc | DOWN | Igsf8 | UP | Myb | DOWN |
| Mxd1 | UP | C030034L19Rik | DOWN | Il18rap | UP | Sh3bp5 | DOWN |
| Prkch | UP | Bcl2 | DOWN | Vim | UP | Mzb1 | DOWN |
| Chaf1b | UP | Rbm26 | DOWN | Triobp | UP | P2rx7 | DOWN |
| Atp6v0c | UP | Olfr613 | DOWN | Ankrd54 | UP | Capn5 | DOWN |
| Tbrg4 | UP | A130077B15Rik | DOWN | Acsbg1 | UP | Sfrp2 | DOWN |

TABLE 1-continued

Differentially expressed gene list between isotype and Tim-3/PD-1 blockade treatment in Tim-3⁻PD-1⁻ and Tim-3⁺PD-1⁺ CD8⁺ TILs.

| Tim-3 + PD-1+ | | | | Tim-3 − PD-1− | | | |
|---|---|---|---|---|---|---|---|
| Gene | UP/DOWN | Gene | UP/DOWN | Gene | UP/DOWN | Gene | UP/DOWN |
| Entpd1 | UP | Tnnt2 | DOWN | Plekho2 | UP | Sell | DOWN |
| Chl1 | UP | Fam212b | DOWN | Tpm1 | UP | Rpgrip1 | DOWN |
| Rgs2 | UP | Gm7102 | DOWN | Ahnak | UP | Peli2 | DOWN |
| Tslp | UP | Zip518a | DOWN | Alad | UP | Ifngr2 | DOWN |
| Letm1 | UP | Zip53 | DOWN | Hif1a | UP | Rnf122 | DOWN |
| Rnaset2a | UP | Actr6 | DOWN | Bcl2l1 | UP | Zfp661 | DOWN |
| Cx3cr1 | UP | Fam175b | DOWN | Tuba1c | UP | Renbp | DOWN |
| Calm3 | UP | Tbrg3 | DOWN | Spsb1 | UP | Klra6 | DOWN |
| Xbp1 | UP | Rin1 | DOWN | B4galt5 | UP | Nsg2 | DOWN |
| Cxcl9 | UP | Txnip | DOWN | S100a10 | UP | Smc4 | DOWN |
| Nans | UP | Zfp871 | DOWN | Rora | UP | Rbm26 | DOWN |
| Gusb | UP | Cdkn1b | DOWN | Icos | UP | Clec12a | DOWN |
| Fam3c | UP | Ikzf5 | DOWN | Cdc42ep3 | UP | Angptl7 | DOWN |
| Fh1 | UP | Synj2 | DOWN | Nfil3 | UP | Whrn | DOWN |
| Rcn1 | UP | Epm2aip1 | DOWN | Swap70 | UP | Kctd7 | DOWN |
| Dusp4 | UP | 2010016I18Rik | DOWN | Endod1 | UP | Dntt | DOWN |
| Ifitm2 | UP | Tmem106b | DOWN | Gem | UP | Kifc3 | DOWN |
| Gltp | UP | Trim44 | DOWN | Tnfrsf9 | UP | Lifr | DOWN |
| Shkbp1 | UP | I830012O16Rik | DOWN | Efhd2 | UP | Folr4 | DOWN |
| Glud1 | UP | Rtn4 | DOWN | Poll | UP | Prl2c2 | DOWN |
| Rp9 | UP | Synj2bp | DOWN | Nr4a2 | UP | Ccr9 | DOWN |
| Glrx | UP | Vmn1r58 | DOWN | Cyth2 | UP | Cd79b | DOWN |
| Cfb | UP | Aebp2 | DOWN | Fasl | UP | Bend4 | DOWN |
| Ermp1 | UP | Sfi1 | DOWN | Egr1 | UP | Dusp10 | DOWN |
| Usp39 | UP | Fam193b | DOWN | Zfp71-rs1 | UP | Ddr1 | DOWN |
| Plek | UP | Chd6 | DOWN | Ctla4 | UP | Lefty1 | DOWN |
| Tmed9 | UP | Gramd3 | DOWN | Casp12 | UP | Trim10 | DOWN |
| Irf1 | UP | Kbtbd2 | DOWN | Il12rb1 | UP | Myc | DOWN |
| Ehd4 | UP | AW549877 | DOWN | Nr4a1 | UP | Spice1 | DOWN |
| Arhgef1 | UP | P2ry10 | DOWN | 1110007C09Rik | UP | Gpr83 | DOWN |
| Vwa9 | UP | Cd6 | DOWN | Col8a1 | UP | Fas | DOWN |
| Nol7 | UP | Mis18bp1 | DOWN | Pacsin2 | UP | Wfs1 | DOWN |
| Plac8 | UP | Kdm3a | DOWN | Bcl2a1d | UP | Herpud1 | DOWN |
| Il1b | UP | Zfp488 | DOWN | Il18r1 | UP | Eng | DOWN |
| Dhx16 | UP | A730017L22Rik | DOWN | Tnf | UP | Gm11346 | DOWN |
| Efha1 | UP | Rptor | DOWN | Synj2bp | UP | Ddc | DOWN |
| Mtus2 | UP | Mob4 | DOWN | S100a11 | UP | Pou2f2 | DOWN |
| Anp32b | UP | Bub1 | DOWN | Flnb | UP | Cd2ap | DOWN |
| Arpc3 | UP | Smad3 | DOWN | Cdkn1a | UP | Per2 | DOWN |
| Ly6a | UP | Arhgef3 | DOWN | Mapkapk3 | UP | Zranb3 | DOWN |
| Lrp10 | UP | Gm17644 | DOWN | Srm | UP | Rnase6 | DOWN |
| Unc119b | UP | Gpr183 | DOWN | Phlda1 | UP | Cdc14b | DOWN |
| Arhgap9 | UP | Arl14ep | DOWN | Casp1 | UP | Klhl24 | DOWN |
| Hibadh | UP | Herc1 | DOWN | Ccr5 | UP | Fggy | DOWN |
| Tnf | UP | Mdm4 | DOWN | Kcnk5 | UP | Smim5 | DOWN |
| Arrdc3 | UP | Fam169b | DOWN | Nfkbid | UP | Epcam | DOWN |
| Zfp36 | UP | Ogt | DOWN | Pdf | UP | H2-Oa | DOWN |
| Rfk | UP | Srsf2 | DOWN | Osbpl3 | UP | Tcp11l2 | DOWN |
| Eea1 | UP | Rbm5 | DOWN | Fosb | UP | Spib | DOWN |
| Fus | UP | Ppil4 | DOWN | Kcnj8 | UP | Adam11 | DOWN |
| Styk1 | UP | Gas5 | DOWN | Ankrd37 | UP | Atp1b1 | DOWN |
| Galnt3 | UP | Zfp277 | DOWN | Tbc1d4 | UP | Cdh5 | DOWN |
| Dusp10 | UP | Nusap1 | DOWN | Sdcbp2 | UP | Tsc22d3 | DOWN |
| Oxsr1 | UP | Eif4a2 | DOWN | Eva1b | UP | Rab3ip | DOWN |
| Gbp2 | UP | Cks2 | DOWN | Gpr68 | UP | Siah1a | DOWN |
| Fosb | UP | 6820431F20Rik | DOWN | Tsen34 | UP | Cybb | DOWN |
| Atf3 | UP | Emb | DOWN | Gpd2 | UP | Mex3c | DOWN |
| Map2k2 | UP | Phip | DOWN | Ncr1 | UP | B3gnt8 | DOWN |
| Slc35d2 | UP | Clk1 | DOWN | BC017158 | UP | Mpeg1 | DOWN |
| Lsm4 | UP | Malat1 | DOWN | Ccl6 | UP | Slc4a1 | DOWN |
| C1qtnf1 | UP | Ptpn22 | DOWN | Gm20300 | UP | Abtb2 | DOWN |
| Eif3f | UP | | | Phex | UP | Satb1 | DOWN |
| Cd209a | UP | | | Fam129a | UP | Cdk19 | DOWN |
| Ltf | UP | | | Dusp4 | UP | Spon1 | DOWN |
| Il10 | UP | | | I830012O16Rik | UP | Piga | DOWN |
| Ptpn13 | UP | | | Plk3 | UP | Abhd15 | DOWN |
| Pskh1 | UP | | | Cxcl16 | UP | Il6ra | DOWN |
| Rbm42 | UP | | | Cish | UP | Ctsh | DOWN |
| Ptpn6 | UP | | | Athl1 | UP | Ggt1 | DOWN |
| Nsun2 | UP | | | Il18bp | UP | Bach2 | DOWN |
| Adcy8 | UP | | | Plbd1 | UP | Zcwpw1 | DOWN |
| Tmod1 | UP | | | Fhl2 | UP | Cpm | DOWN |
| B4galt5 | UP | | | Ms4a6d | UP | Cd33 | DOWN |

TABLE 1-continued

Differentially expressed gene list between isotype and Tim-3/PD-1 blockade treatment in Tim-3⁻PD-1⁻ and Tim-3⁺PD-1⁺ CD8⁺ TILs.

| Tim-3 + PD-1+ | | | | Tim-3 − PD-1− | | | |
|---|---|---|---|---|---|---|---|
| Gene | UP/DOWN | Gene | UP/DOWN | Gene | UP/DOWN | Gene | UP/DOWN |
| Sidt1 | UP | | | Rxra | UP | Irf6 | DOWN |
| Prkcd | UP | | | Fam129b | UP | Serpini1 | DOWN |
| Fam174a | UP | | | C1qc | UP | Sepp1 | DOWN |
| Gzmb | UP | | | Ly6g5b | UP | Acpp | DOWN |
| Abcb10 | UP | | | Ly6i | UP | Gm5547 | DOWN |
| Emilin2 | UP | | | Apod | UP | Klhl6 | DOWN |
| Cd200 | UP | | | Il17rc | UP | Aldh1b1 | DOWN |
| Plbd2 | UP | | | 9930012K11Rik | UP | Dirc2 | DOWN |
| Fam174b | UP | | | Gzmk | UP | Tfrc | DOWN |
| Sipa1 | UP | | | Emilin2 | UP | Pir | DOWN |
| Ubash3b | UP | | | Lipi | UP | Sirpa | DOWN |
| Fos | UP | | | Htr7 | UP | Foxp1 | DOWN |
| Gadd45b | UP | | | Filip1 | UP | Clybl | DOWN |
| C1qb | UP | | | Cd40lg | UP | Sft2d2 | DOWN |
| Gpam | UP | | | Usp46 | UP | St6gal1 | DOWN |
| Nr4a2 | UP | | | Cd40 | UP | Tspan13 | DOWN |
| Heatr2 | UP | | | Tjp1 | UP | Hhex | DOWN |
| Rac1 | UP | | | Prdm1 | UP | Pltp | DOWN |
| Clptm1 | UP | | | Lpcat2 | UP | Slc12a7 | DOWN |
| Lpcat4 | UP | | | Dock5 | UP | Ncf1 | DOWN |
| Rgs16 | UP | | | Ifi205 | UP | Cd72 | DOWN |
| Lysmd2 | UP | | | Entpd1 | UP | Tcf7 | DOWN |
| Tmem30a | UP | | | Ltbp4 | UP | Ikbke | DOWN |
| Csf1r | UP | | | Smug1 | UP | Scimp | DOWN |
| Slc35b2 | UP | | | Pthlh | UP | Rgs10 | DOWN |
| Tmem2 | UP | | | Ppm1n | UP | Spns3 | DOWN |
| Zdhhc3 | UP | | | Ccr8 | UP | Arhgef10 | DOWN |
| Nsmf | UP | | | Efna5 | UP | Fntb | DOWN |
| Syngr3 | UP | | | Gm5934 | UP | Crlf3 | DOWN |
| Egr2 | UP | | | Selenbp1 | UP | Ssbp2 | DOWN |
| Iigp1 | UP | | | Lamp1 | UP | Nt5e | DOWN |
| Ppp4c | UP | | | Rnf43 | UP | Chst15 | DOWN |
| Itih5 | UP | | | Hrh4 | UP | Tmem245 | DOWN |
| Nfil3 | UP | | | Itgb1 | UP | Apoe | DOWN |
| Sdf2l1 | UP | | | Dclk1 | UP | Txnip | DOWN |
| Ifitm1 | UP | | | B230216G23Rik | UP | Fam46c | DOWN |
| Chn2 | UP | | | Arhgef39 | UP | Pld4 | DOWN |
| Fcgr3 | UP | | | Tmem106a | UP | Cyp27a1 | DOWN |
| Pde2a | UP | | | Crmp1 | UP | Lair1 | DOWN |
| St14 | UP | | | Hip1 | UP | Sh3pxd2a | DOWN |
| Get4 | UP | | | Ly6c1 | UP | Slamf6 | DOWN |
| Sdccag3 | UP | | | Lgals3 | UP | Ap1ar | DOWN |
| Desi1 | UP | | | Soga2 | UP | Man2a2 | DOWN |
| Crlf2 | UP | | | Fat1 | UP | Cybasc3 | DOWN |
| Scimp | UP | | | Rab3il1 | UP | Mef2c | DOWN |
| Zdhhc7 | UP | | | Psg28 | UP | Fgfr1op | DOWN |
| Ptpn5 | UP | | | Apobr | UP | Tubb2a | DOWN |
| Galnt2 | UP | | | Farp1 | UP | Fcrla | DOWN |
| Fbn1 | UP | | | Tmem198b | UP | Gtf2i | DOWN |
| Ltb4r1 | UP | | | Slc22a15 | UP | Il7r | DOWN |
| Lyz1 | UP | | | Errfi1 | UP | Dennd1a | DOWN |
| Ier2 | UP | | | Glrx | UP | Gramd4 | DOWN |
| Exoc5 | UP | | | Plscr1 | UP | Ranbp6 | DOWN |
| Arf5 | UP | | | Nav1 | UP | Tns3 | DOWN |
| Polr2m | UP | | | Thbs1 | UP | Kmo | DOWN |
| Msr1 | UP | | | Fgl2 | UP | Poli | DOWN |
| Fcer1g | UP | | | Nrp1 | UP | Trim44 | DOWN |
| Cd74 | UP | | | Stx11 | UP | P2ry10 | DOWN |
| Fcgr4 | UP | | | Lrrk2 | UP | Fam107b | DOWN |
| Fmnl1 | UP | | | Gdpd5 | UP | Nucb2 | DOWN |
| Plod1 | UP | | | Creb5 | UP | Il4ra | DOWN |
| Mpeg1 | UP | | | Il1b | UP | Bcl11a | DOWN |
| Dynlt1b | UP | | | Fgf10 | UP | Zfp53 | DOWN |
| Psmd3 | UP | | | Ifi204 | UP | Lztfl1 | DOWN |
| Eno3 | UP | | | Plod2 | UP | Fnip1 | DOWN |
| Hk3 | UP | | | Rab27b | UP | Rpl22l1 | DOWN |
| Ggt1 | UP | | | Card10 | UP | Timeless | DOWN |
| Gm3435 | UP | | | Mlph | UP | Eepd1 | DOWN |
| Rps2 | UP | | | Gzmb | UP | Plcxd2 | DOWN |
| Ccdc102a | UP | | | Bhlhe40 | UP | Ldhb | DOWN |
| Chaf1a | UP | | | Atf3 | UP | Npc1 | DOWN |
| Ccl1 | UP | | | Unc79 | UP | Bcl2l11 | DOWN |
| Gem | UP | | | Nrn1 | UP | Pecam1 | DOWN |

TABLE 1-continued

Differentially expressed gene list between isotype and Tim-3/PD-1 blockade treatment in Tim-3⁻PD-1⁻ and Tim-3⁺PD-1⁺ CD8⁺ TILs.

| Tim-3 + PD-1+ | | | | Tim-3 − PD-1− | | | |
|---|---|---|---|---|---|---|---|
| Gene | UP/DOWN | Gene | UP/DOWN | Gene | UP/DOWN | Gene | UP/DOWN |
| Emr1 | UP | | | Dixdc1 | UP | Zcchc18 | DOWN |
| Nrp1 | UP | | | Lamc1 | UP | Tnfrsf26 | DOWN |
| Stx6 | UP | | | Syngr3 | UP | Khk | DOWN |
| Clec12a | UP | | | Pcdhgc3 | UP | Zfp281 | DOWN |
| Mmp3 | UP | | | Csf1 | UP | Pde4b | DOWN |
| Hpse | UP | | | Rab11fip4 | UP | Pacsin1 | DOWN |
| Gngt2 | UP | | | Itgam | UP | Slc25a25 | DOWN |
| Nubp1 | UP | | | Serpinb9b | UP | Dnmt3a | DOWN |
| Nfkbid | UP | | | Inppl1 | UP | Rps19 | DOWN |
| Dscc1 | UP | | | H1f0 | UP | Tbxa2r | DOWN |
| Nr4a1 | UP | | | Osgin1 | UP | Rapgef6 | DOWN |
| Tmco6 | UP | | | Dapk3 | UP | 1810026B05Rik | DOWN |
| Cd34 | UP | | | Gzmd | UP | Glce | DOWN |
| Lgmn | UP | | | Capg | UP | Plcb2 | DOWN |
| Klc3 | UP | | | Cxcr6 | UP | Elovl5 | DOWN |
| Lat2 | UP | | | Tmem171 | UP | Pip4k2a | DOWN |
| Ly86 | UP | | | LOC100038947 | UP | Znrf3 | DOWN |
| Nmral1 | UP | | | Adap1 | UP | Rps20 | DOWN |
| Nrgn | UP | | | Ralgds | UP | Rnf138 | DOWN |
| Plbd1 | UP | | | 4931406H21Rik | UP | Rpl31-ps12 | DOWN |
| Xcl1 | UP | | | Ddah1 | UP | Usp24 | DOWN |
| Ung | UP | | | Ptpn13 | UP | Bsdc1 | DOWN |
| Donson | UP | | | Pter | UP | Rictor | DOWN |
| Cd4 | UP | | | Arg1 | UP | Hsdl1 | DOWN |
| Foxp3 | UP | | | Klrc1 | UP | Acss1 | DOWN |
| Coro2a | UP | | | Klrk1 | UP | Slc44a2 | DOWN |
| Irf8 | UP | | | Cd80 | UP | Tubgcp5 | DOWN |
| Tbx21 | UP | | | Agrn | UP | Slc23a2 | DOWN |
| Mrc1 | UP | | | Dkkl1 | UP | Rell1 | DOWN |
| Ccl3 | UP | | | Gm20831 | UP | Zyg11b | DOWN |
| Ifng | UP | | | Tbx21 | UP | Jmjd1c | DOWN |
| Lag3 | UP | | | Gcnt1 | UP | Fam65b | DOWN |
| Xpa | UP | | | Kctd13 | UP | Add3 | DOWN |
| Mafb | UP | | | Cxcl9 | UP | Ppm1h | DOWN |
| Tox | UP | | | Pilra | UP | Rps28 | DOWN |
| Slamf8 | UP | | | Ccr2 | UP | Thada | DOWN |
| C1qc | UP | | | L1cam | UP | Rbm33 | DOWN |
| Rab3il1 | UP | | | Tnfrsf4 | UP | Plaur | DOWN |
| Ccl2 | UP | | | Styk1 | UP | Tcf7l2 | DOWN |
| Dnajb11 | UP | | | Ifng | UP | Tex30 | DOWN |
| Ccl9 | UP | | | Tgfbi | UP | Mdn1 | DOWN |
| Ccl4 | UP | | | Adamts14 | UP | Rps29 | DOWN |
| Col6a2 | UP | | | Ttc39c | UP | Prkcb | DOWN |
| Sell | UP | | | Lyz2 | UP | Irf8 | DOWN |
| Fcgr1 | UP | | | Ifitm2 | UP | Ssh2 | DOWN |
| | | | | Smpdl3b | UP | Dck | DOWN |
| | | | | Plcd1 | UP | Slc29a3 | DOWN |
| | | | | AA467197 | UP | Gab3 | DOWN |
| | | | | Fam20a | UP | Unc93b1 | DOWN |
| | | | | Prf1 | UP | Rpl12 | DOWN |
| | | | | Itgbl1 | UP | Haus3 | DOWN |
| | | | | Dusp2 | UP | Arglu1 | DOWN |
| | | | | Adam8 | UP | 4932438A13Rik | DOWN |
| | | | | Lyz1 | UP | Ivns1abp | DOWN |
| | | | | Pdcd1 | UP | Card6 | DOWN |
| | | | | C3ar1 | UP | Naga | DOWN |
| | | | | Gzmf | UP | Cul3 | DOWN |
| | | | | Itga1 | UP | Rpl5 | DOWN |
| | | | | Fcgr1 | UP | Dgka | DOWN |
| | | | | Havcr2 | UP | Pan3 | DOWN |
| | | | | Snx20 | UP | Rps17 | DOWN |
| | | | | | | Klf13 | DOWN |
| | | | | | | Cdip1 | DOWN |
| | | | | | | Cmah | DOWN |
| | | | | | | Dennd2d | DOWN |
| | | | | | | Rplp1 | DOWN |
| | | | | | | Rpl39 | DOWN |
| | | | | | | Arhgap15 | DOWN |
| | | | | | | Jak1 | DOWN |
| | | | | | | Add1 | DOWN |
| | | | | | | Rps15a | DOWN |
| | | | | | | Sptbn1 | DOWN |
| | | | | | | Srsf2 | DOWN |

TABLE 1-continued

Differentially expressed gene list between isotype and Tim-3/PD-1 blockade treatment in Tim-3⁻PD-1⁻ and Tim-3⁺PD-1⁺ CD8⁺ TILs.

| Tim-3 + PD-1+ | | | | Tim-3 − PD-1− | |
|---|---|---|---|---|---|
| Gene | UP/DOWN | Gene | UP/DOWN | Gene | UP/DOWN |
| | | | | Stk17b | DOWN |
| | | | | Emb | DOWN |
| | | | | Rpl36a | DOWN |
| | | | | Rps5 | DOWN |
| | | | | Rps15a-ps4 | DOWN |
| | | | | Serp1 | DOWN |
| | | | | Cox7a2l | DOWN |
| | | | | Stk38 | DOWN |
| | | | | Rps4x | DOWN |
| | | | | Rps24 | DOWN |
| | | | | Hvcn1 | DOWN |
| | | | | Rplp0 | DOWN |
| | | | | 2410002F23Rik | DOWN |
| | | | | Rnf7 | DOWN |
| | | | | Map3k1 | DOWN |
| | | | | Atp1b3 | DOWN |
| | | | | Thumpd1 | DOWN |
| | | | | Rhoh | DOWN |
| | | | | Rpl31 | DOWN |
| | | | | Rps18 | DOWN |
| | | | | Rps6 | DOWN |
| | | | | Rpl3 | DOWN |
| | | | | Cytip | DOWN |
| | | | | Ets1 | DOWN |
| | | | | Rps25 | DOWN |
| | | | | Tiprl | DOWN |
| | | | | Rps3a1 | DOWN |
| | | | | Gimap6 | DOWN |
| | | | | Grn | DOWN |
| | | | | Snx5 | DOWN |
| | | | | Gas5 | DOWN |
| | | | | Eef1b2 | DOWN |
| | | | | Rpl15 | DOWN |
| | | | | Rps16 | DOWN |
| | | | | Fgfr1op2 | DOWN |
| | | | | Rpl9 | DOWN |
| | | | | Rpl10a | DOWN |
| | | | | Rpl23 | DOWN |
| | | | | Eif4a2 | DOWN |
| | | | | Rpl32 | DOWN |
| | | | | Rpl21 | DOWN |
| | | | | Rpl35a | DOWN |
| | | | | Rps12 | DOWN |
| | | | | Rps3 | DOWN |
| | | | | Tra2b | DOWN |
| | | | | Slbp | DOWN |
| | | | | Rps15a-ps6 | DOWN |
| | | | | Rps27 | DOWN |
| | | | | Rps9 | DOWN |
| | | | | Gm12191 | DOWN |
| | | | | Rpl13 | DOWN |
| | | | | Rpsa | DOWN |
| | | | | Rpl23a | DOWN |
| | | | | Rpl4 | DOWN |
| | | | | Rps8 | DOWN |
| | | | | Rps7 | DOWN |
| | | | | Gm15772 | DOWN |
| | | | | Rps14 | DOWN |
| | | | | Rpl10 | DOWN |
| | | | | Rpl18a | DOWN |
| | | | | Rps23 | DOWN |
| | | | | Rpl17 | DOWN |
| | | | | Rpl8 | DOWN |
| | | | | Rps13 | DOWN |
| | | | | Rplp2 | DOWN |
| | | | | Rps11 | DOWN |
| | | | | Eef1a1 | DOWN |
| | | | | Rps27a | DOWN |
| | | | | Rpl14 | DOWN |
| | | | | Rps10 | DOWN |

TABLE 2

Differentially expressed genes upregulated in both
Tim-3⁻PD-1⁻ and Tim-3⁺PD-1⁺ CD8⁺ TILs
Gene Ly6a
Psmd3
Gadd45b
Nkg7
Ctsd
Desi1
Rac1
Crip1
Dynlt1b
B4galt5
Nfil3
Gem
Nr4a2
Nr4a1
Tnf
Nfkbid
Fosb
Dusp4
Plbd1
C1qc
Emilin2
Entpd1
Lgals3
Rab3il1
Glrx
Nrp1
Il1b
Gzmb
Atf3
Syngr3
Capg
Ptpn13
Tbx21
Cxc19
Styk1
Ifng
Ifitm2
Lyz1
Fcgr1

TABLE 3

Gene signature for: CD62L$^{hi}$Slamf7$^-$, Slamf7$^{hi}$CX3CR1$^+$, and Slamf7$^{hi}$CX3CR1$^-$PD-1$^-$ CD8$^+$ TILs.

| CD62L + SlamF7 − CX3CR1− Down | | CD62L + Slamf7 − CX3CR1− Up | | CD62L − SlamF7hi CX3CR1− Down | CD62L − SlamF7hi CX3CR1− Up | CD62L − SlamF7hi CX3CR1+ Down | | CD62L − SlamF7hi CX3CR1+ Up |
|---|---|---|---|---|---|---|---|---|
| 1-381 | 382-761 | 1-313 | 314-626 | 1-126 | 1-154 | 1-213 | 214-425 | 1-178 |
| Cox4i1 | Ctnna1 | Zscan10 | Klhl24 | Ptk2 | Hmgb1 | Cxcr5 | Dph5 | H3f3b |
| Tpm3 | Plek | Ifngr2 | Foxo1 | Ifngr2 | Cox4i1 | Klra6 | Tigit | Itprip |
| H2-D1 | Pils | Actn1 | Polr3b | Ppargc1b | Rbm3 | Gbpl1 | Pip4k2a | Arhgdia |
| Ssb | Unc93b1 | Abca1 | AB124611 | Peg13 | Ssr1 | Tnfsf8 | Rps19 | Ctsd |
| Mtpn | Gm14446 | Gm14085 | Zyg11b | Cyp2d22 | H2-Q4 | Klra7 | Nudt14 | Gnb1 |
| Ostc | Gnptab | 2610019F03Rik | Addl | Rasgrp2 | Slc25a5 | Klra1 | Cyth3 | Tnfaip3 |
| Capza1 | Irs2 | Irs2 | Tpt1 | Tgfbr3 | Il2rg | Rgs10 | Apol7e | Aph1a |
| Card11 | Rab8b | Ppargc1b | Gm11974 | Ccl9 | Ndfip1 | Myb | Rps26 | Ostf1 |
| Arpc4 | N6amt2 | Usp28 | Smyd3 | Ubtd1 | Ndufa13 | Nsg2 | Rps6 | Itm2c |
| Akr1a1 | Evi2a | Dusp10 | Anks3 | Gm10825 | Tmsb10 | Ikzf2 | Rps4x | Tspo |
| Tmbim6 | Gm6307 | Auts2 | Rsfl | Itga6 | Fkbp8 | Sell | Snhg12 | Nfatc3 |
| Clic1 | Syngr2 | Rab4a | Kreb1 | Il13ra1 | Psmb8 | Klra13-ps | Fasn | Myl12a |
| Acly | Plxnc1 | Bambi-ps1 | Brfl | Acss2 | Tagln2 | Klra23 | Slamf6 | Cers2 |
| Sarnp | Rcc1 | Nsg2 | Grk6 | Mnt | Spcs2 | Ccr7 | Il4ra | Rab14 |
| Spcs2 | Fdft1 | Nipal1 | Rnf145 | Cnnm2 | Cuta | Tmem108 | Rpl22l1 | Vmp1 |
| Calm1 | Tmsb4x | Tmsb4x | Rplp0 | Arhgap31 | Psma1 | 2610019F03Rik | Pglyrp1 | Slc20a1 |
| Erh | Ppil1 | C1qb | Cyb5 | Ica11 | Cldn25 | Treml2 | Vars | Lmbrd1 |
| Atp6v0e | 2010002M12Rik | H2-Ob | Zfp386 | Sipa1l3 | Cst7 | Dapl1 | Rpl5 | Tceb2 |
| Il2rg | Gm17644 | Inadl | Chd6 | Lmbr1l | Lcp1 | Myc | Rps15a-ps4 | Fyn |
| Erp44 | Rdh1 | Bach2 | Mbip | Lsm14b | Stt3a | Id3 | Reck | Tpm4 |
| R3hdm4 | Rasa4 | Pid1 | Gnb2l1 | Rab32 | Edem2 | Klra5 | Rpl10a | Gnptg |
| Psma2 | Phf11b | Il6ra | Rere | Mtmr10 | Padi2 | Aoah | Rps15a | Ankrd44 |
| Ndfip1 | Gm20300 | Fam101b | Mpp1 | Zrsr1 | Arhgap9 | Adck3 | Neurl3 | Strip1 |
| Mrpl4 | Gm20597 | Qrfp | Pde4b | Fam63a | Mrps14 | Xcl1 | Rpusd4 | Pik3r1 |
| Sumo2 | Capg | Pon2af1 | Usp12 | Plk2 | Sub1 | Gm19705 | Hspbp1 | Rab1 |
| Capzb | Zbtb42 | Pde2a | Skil | Arhgef18 | Psme2 | St6gal1 | Rpl28 | Pja1 |
| Pld3 | Tm7sf3 | Tlr13 | Ddx6 | Prss12 | Styx | Atp1b1 | Rapgef6 | Atp2b1 |
| Psmb4 | I830012O16Rik | 5730508B09Rik | Hist3h2a | Pikfyve | Grina | Spint2 | Rpl23 | Actg1 |
| Psmb8 | Cyba | Rapgef4 | Card6 | Trappc10 | Cox5a | Acpp | Rps5 | Adar |
| Atp5j | Als2 | Spon1 | Camk2d | Tab3 | Sp140 | Rpgrip1 | Gm13826 | Prkx |
| Arpc5 | Usp18 | St6gal1 | Cdkn2aip | S1pr1 | Btbd16 | Tcf7 | Rpl18 | Sh2d2a |
| Psma3 | Rrm1 | Vipr1 | Runt | Zfp746 | Jak3 | Slc16a5 | Fastkd3 | Myl6 |
| Minos1 | Rhbdf2 | Pdk2 | Puml | Lrp6 | Ufc1 | Cables1 | Smap2 | Taf12 |
| Ppia | Tbx21 | Lef1 | Evl | Rraga | Nek7 | Folr4 | Samd3 | Cltc |
| Shfm1 | Gm8369 | S1pr1 | Rpl123 | Tprgl | Tram1 | Irs2 | Rps3 | Ube2g2 |
| Ube2n | Serpinb6b | Smad1 | Prrc2c | Med13l | Anapc13 | Qrfp | Rps28 | Ppp1cc |
| Cfl1 | Casp4 | Tct7 | Btg1 | Fech | Rpe | Inadl | Rbfa | Hiatl1 |
| Calm3 | Acad9 | Gm10825 | Rbbp6 | Irf1 | Gpr171 | Actn1 | Mphosph9 | Wdr92 |
| Wvp2 | Pmaip1 | Gm11696 | Ikbkb | Dbf4 | Cd52 | Cldn10 | Rps9 | Ppp1r1l |
| Bnip2 | Ebbp1l1 | Prg4 | Tmem66 | Ercc5 | Ptprcap | Bmp7 | Oasl2 | Park7 |
| Sec11c | E230016K23Rik | Clec4n | Snhg8 | Hdac5 | Ly6c2 | 2010300C02Rik | Fam102a | Cd97 |
| Ndufv2 | Nkg7 | Efhc1 | Rpl8 | Klf2 | Naa20 | Map7 | Clec2i | Smad3 |
| Actb | Gm14005 | Gm11346 | Rpl13 | Sgk1 | Mcm3 | Irs2 | Rpl15 | Lmf2 |
| Cope | 2310003H01Rik | Bend4 | Ssh2 | Kif21b | Ptpn6 | H2-Oa | Limd2 | Lrre8d |

TABLE 3-continued

Gene signature for: CD62L^hi Slamf7-, Slamf7^hi CX3CR1+, and Slamf7^hi CX3CR1-PD-1- CD8+ TILs.

| CD62L + SlamF7 - CX3CR1- Down | | CD62L + Slamf7 - CX3CR1- Up | | CD62L - SlamF7hi CX3CR1- Down | CD62L - SlamF7hi CX3CR1- Up | CD62L - SlamF7hi CX3CR1+ Down | CD62L - SlamF7hi CX3CR1+ Up |
|---|---|---|---|---|---|---|---|
| 1-381 | 382-761 | 1-313 | 314-626 | 1-126 | 1-154 | 1-213 | 214-425 | 1-178 |
| Tmed2 | Lmnb1 | Ccr7 | Dph5 | A430078G23Rik | Psmb9 | Swap70 | Tafld | Prkaa1 |
| Itpripl1 | 9330133O14Rik | Cd55 | Zbtb21 | Prpsap2 | Gng2 | St8sia1 | Rpl29 | Cyth2 |
| Inpp5d | Med12l | Adk | Dcaf17 | Bsdc1 | Rftn1 | Rampl | 2410004N09Rik | Got1 |
| Sdhb | Sytl2 | Frat2 | Rplp1 | Zfp777 | Tnfrsf18 | Vipr1 | Rpl23a | Atg4d |
| Ctsd | Mir22hg | Dbp | Gltscr2 | Klf3 | Nup205 | Figgy | Eif4e3 | Tnrc18 |
| Ldha | Gmnn | Arl5c | Akap9 | Zfp869 | Elof1 | Itm2a | Eef1a1 | Ahnak |
| Psma1 | Isg20 | Sfrp2 | Hipk1 | Pkd1 | Hif1a | Slc37a2 | Rpl21 | Mrpl20 |
| Cox6a1 | A730082K24Rik | Klhdc2 | Rnf125 | Pgrmc1 | Atf6b | Il6ra | Ikbkb | Arhgap26 |
| Atp5h | Whsc1 | Ephx1 | Zfp592 | Plcxd2 | Rell1 | Gm15133 | Gm10548 | Rbms1 |
| Itm2c | Clic4 | Slc6a19 | BC121111 | Tob1 | Chst12 | H2-Ob | Elovl5 | Aplp2 |
| Cd81 | Id2 | Cerk | Usp10 | Sfxn3 | Mcm7 | Pacsin1 | Clec2g | Nfe2l1 |
| Tapl | Cysltr2 | Jag2 | Rps3a1 | Coq10b | Eif2ak2 | Tlr1 | Rpl6 | Tuba1a |
| Ccdc12 | Tmem45b | Ikbke | Trpm7 | Vps37b | H2-Q7 | Acox1 | Spata6 | Suco |
| Mrps14 | Slc2a3 | Sesn1 | Zc3hav1 | Gch1 | St8sia4 | Gpr15 | Rpl31-ps12 | St3gal4 |
| Parp10 | A530064D06Rik | Dyrk2 | Eif4a2 | Glul | Rab19 | Gas7 | Bfar | Ywhaq |
| Laptm5 | Slc39a4 | Slc26a11 | Srsf2 | Dusp5 | Ms4a4c | Ssbp2 | Ipcef1 | Dok2 |
| Atp5d | Mapkapk3 | Itm2a | Ostbpl9 | Il17ra | Foxred1 | Arhgap39 | Apobec3 | Ckb |
| Wnk1 | S100a13 | Accs | Fam169b | Zfp644 | Mcm2 | Cnr2 | Rps15a-ps6 | Pdlim5 |
| Bcap31 | Susd3 | Dapl1 | Kdm3a | Rictor | Al662270 | Ggt1 | Eef1b2 | Meis3 |
| Rin1 | Zwilch | Trim13 | Hsdl1 | Klf7 | Rps6ka1 | Bend4 | Rps3a1 | Plec |
| Srgn | Apaf1 | Pkp4 | Elovl5 | Csrmp1 | Fkbp2 | Pecam1 | Igfr1 | Ttc39b |
| Appl1 | A330050B17Rik | Zrsr1 | Map4k4 | Tpcn1 | Rilpl2 | Cd16311 | Ch6 | Trim35 |
| Rac2 | Pot1b | Thada | Dip2b | Tuba1a | Gpr65 | Dusp10 | Grk6 | Chsy1 |
| Ppp1ca | Prim1 | Klhl1 | Eef1b2 | Cnnm4 | AW112010 | Cd55 | Tapbpl | Baiap3 |
| Cdc42 | Ly6a | Aepp | Ing3 | Zbtb2 | Amical1 | 5730508B09Rik | Utp14a | Itga4 |
| Tspo | Papdc1b | Clqc | Zfp110 | Cbfa2t2 | Glrx | Pdgfb | Rpl8 | Nr4a1 |
| Myl12a | F2rl2 | Ctsf | 6330416G13Rik | Fosl2 | Galns | Aff3 | Rplp2-ps1 | Dusp2 |
| Tmed5 | Atf6 | Lrrc14b | Crebbp | Sun2 | Ppat | Mcc2 | Rplp1 | Rhof |
| Pfn1 | Prim1 | Klhdc1 | Rpl36a | Zfyve19 | Ctla2a | Kctd12 | Eef1g | S100a10 |
| 061003lJ06Rik | Ly6a | Lsm11 | 4833420G17Rik | Hexim1 | Ergic1 | Pdk2 | Trafl1 | Nkg7 |
| Sec61b | Isg15 | Smc4 | Smg1 | Foxn3 | Pqlc3 | Smad1 | Rpl9 | Itgb2 |
| 2010107E04Rik | Icos | Mipol1 | Rps15 | Hivep2 | Mfap3 | Als2cl | Foxo1 | Rnf19b |
| Rtn3 | Ezh2 | Bcl9 | Rabac1 | Cirbp | Gm16938 | Usp28 | Rcsd1 | Rpa2 |
| Myo1g | A730017L22Rik | Rcn3 | Rps3 | Cdk16 | Rdh1 | Ltb | Rpl127a | Antxr2 |
| Rfc2 | Itgal | Ift80 | Cux1 | Mcl1 | Rfc4 | Rnf122 | Rps15 | Tmem109 |
| Ssr4 | Cd48 | Madf | Rpl21 | Smek1 | Bst2 | Gstt2 | Rpl24 | Kpna1 |
| Crep | Slc6a18 | Sacs | Nol6 | 2410004B18Rik | Npc1 | Tspan13 | Odc1 | Tax1bp3 |
| Hprt | Tnf | Slfn4 | Ss18 | Ptg1ip | A730017L22Rik | Zbtb10 | Tmt1 | Cars |
| Nmi | Hist1h2ao | Cables2 | Stk24 | Srst5 | Brip1 | Bach2 | Herc3 | Myo1c |
| Sec61b | Prdx | Pik3ip1 | Rps5 | Ier2 | Spc24 | Ift80 | Rps29 | A830080D01Rik |
| H2-Q9 | Grk1 | Tcp1112 | Kidins220 | Junb | Gm17644 | Cdon | Ptpn6 | Myo18a |
| Ifi35 | Mcm5 | Fam83d | Rps29 | 9430023L20Rik | Fbxl8 | B430306N03Rik | Gbp9 | S100a13 |
| Cox5b | Syce2 | Igf1r | Trappc12 | Stk4 | Gm8234 | Rps4y2 | 1810026B05Rik | Aldh18a1 |
| Pfdn1 | Gins2 | Zfp235 | Stat5b | Zc3hav1 | Zfp937 | N4bp2 | Rplp2 | Id2 |
| Gtpbp2 | Wdr95 | Lmbr1l | Ccnl1 | Btg1 | Gm5547 | Pctp | Eif3e | Ndfip2 |
| Nucb1 | Sh3bp2 | Lrp12 | Kbtbd11 | Mylip | Lig1 | Ttc28 | Mrps2 | |

TABLE 3-continued

Gene signature for: CD62L^hi Slamf7-, Slamf7^hi CX3CR1+, and Slamf7^hi CX3CR1- PD-1- CD8+ TILs.

| CD62L + SlamF7 - CX3CR1- | CD62L + SlamF7 - Down | CD62L + SlamF7 - Up | CD62L + Slamf7 - CX3CR1- Up | CD62L - SlamF7hi CX3CR1- Down | CD62L - SlamF7hi CX3CR1- Up | CD62L - SlamF7hi CX3CR1+ Down | CD62L - SlamF7hi CX3CR1+ Up |
|---|---|---|---|---|---|---|---|
| 1-381 | 382-761 | 1-313 | 314-626 | 1-126 | 1-154 | 1-213 | 214-425 | 1-178 |
| Cox7c | Ntrk2 | Taf4b | Cmah | Arntl | Ifi27l2a | 5830411N06Rik | Ppcdc | Lpin1 |
| Atp5j2 | Fam19a3 | Treml2 | Srsf6 | Chpf2 | Ctla4 | Slc43a2 | Fam189b | Trex1 |
| Tmem258 | Ifi27l2a | Ppm1h | Mns19 | Twf1 | Zfp300 | Thada | Rabgap1l | Ccnd3 |
| Commd3 | Cks1b | Rgs10 | Add3 | Cyth1 | Gjc3 | Adk | Nsmce1 | Runx1 |
| Srp14 | Lgals1 | A930024E05Rik | Chmp2b | Rabac1 | Cxcr3 | Fam101b | Rps16 | Abcb1a |
| Ptprcap | Sord | Ggt1 | Stk11 | Perl | Acad9 | 4930432K21Rik | Sdf39u1 | Notch2 |
| Mrpl18 | Ccl5 | Pnpla7 | Taf1b | Crebbp | Ly6a | Abhd15 | Mfsd11 | Slc4a2 |
| Timm13 | Atp2b4 | C030034I22Rik | Zc3h3 | Jhdm1d | C330024D21Rik | Smc4 | Jak3 | Fam129a |
| Mndal | Sfmbt1 | Ms4a7 | Pcbp2 | Lonp2 | Isg20 | Bambi-ps1 | Rps24 | Snx11 |
| Lcp1 | Cybasc3 | Zbtb10 | Prdx6 | Abtb2 | 4930511M06Rik | Mgst2 | Pgs1 | Xlr4c |
| 2900097C17Rik | Tspan31 | 2810459M11Rik | Rn45s | Ncln | Unc93b1 | Thal | Uba52 | Osbpl3 |
| Ndufa1 | Dtl | Hdc | Hdac2 | Sertad2 | 4933431E20Rik | Elovl6 | Rpl7 | Rundc3b |
| Rab1b | Irf8 | Jmy | Eef1a1 | Neat1 | Uba1y | Rnf144a | Rps11 | Wdr95 |
| Vamp8 | Rassf7 | Zc3h12d | Rplp2-ps1 | Wsb1 | Ncapd2 | Pim2 | Gpr183 | Atp10d |
| Snrpe | Rasal1 | Id3 | Lrrc8a | Fam168b | 1190002F15Rik | Zfp296 | Cnot10 | Emp3 |
| Ube2l3 | Pola1 | Tubb2a | Arap2 | Tax1bp1 | Mcmdc2 | Zfp235 | Qdpr | Prmaip1 |
| Nup54 | Klrb1c | Irf1 | 1810026B05Rik | Ccnl1 | Zfp277 | Klra3 | Pbxip1 | Rap1b |
| Rwdd1 | Vmn1r148 | F2rl1 | Jakmip1 | Tra2a | Prlr | Bbs9 | Use1 | Abhd5 |
| Ms4a6b | Tjp3 | Fbxl20 | Tiprl | Cdk11b | A130077B15Rik | Rapgef4 | Tmem194b | BC030336 |
| Psmd14 | Gm3002 | Mepce | Srrm2 | Ets1 | Fbxo5 | Fam46c | Igbp1 | Flna |
| Ufcl | Nabp1 | Tec | Cirbp | Ndrg3 | Gm9159 | Trim13 | Gramd3 | Spn |
| Surf4 | 6330410L21Rik | Ldlrap1 | Kdsr | Tuba4a | Birc5 | Hdac4 | Kbtbd11 | Gnptab |
| Sub1 | Uba1y | Sell | Rplp2 | Gm13363 | Asf1b | Bphl | Dnajc7 | Insl6 |
| Elf4 | Olfr1258 | Usp53 | Igbp1 | Nisch | Maoa | Il7r | Rnf7 | Lats2 |
| Ndufa3 | Apip | Trib2 | Rps26 | Usp9x | Plac8 | Mcoln2 | Gitscr2 | Nedd4 |
| Atp6v0b | Gpr68 | Acot2 | Fam120b | Mkl1 | Adam11 | Map3k5 | Ccni | Mcu |
| Cox7b | Hnmr | Abcc5 | Slc25a51 | Jak1 | Ly6d | Cd27 | Rpl32 | Zmiz1 |
| Tceb2 | Lgals1 | Prss12 | Rps6 | Eif1 | Ncf1 | Zc3h12d | Arhgap15 | Erol1 |
| H2afz | Gm6602 | Aif3 | Cdk19 | Dnttip2 | Fam185a | Gm12191 | Dnajc7 | Slc4a7 |
| Ndufb7 | Fbxo5 | Scmh1 | Utm | Tob2 | Cd160 | Pik3ip1 | Prps2 | Igst8 |
| Dynlrb1 | Mcmdc2 | A930005H10Rik | Rpl3 | Ddx5 | Olfr856-ps1 | Cul9 | Ablim1 | Scd2 |
| Actg1 | Gjc3 | Rsad1 | Akap8l | Ino80d | 5730577I03Rik | Ephx1 | Hdac7 | Vopp1 |
| Sh3bgrl3 | Casp7 | 4930417O13Rik | Bcas3 | Sptan1 | F630111L10Rik | Mvb12b | Cmah | Capn2 |
| Gabarapl2 | Serpina3i | Ets2 | Gm12191 | Brd2 | Vmn1r58 | 3110057O12Rik | Cox7a21 | Flnb |
| Plekho2 | Cd200r2 | Fchsd2 | Odc1 | Prpsap1 | Tyms | Slc11a2 | Tpt1 | Abcb1b |
| Edf1 | Spc24 | Socs3 | Klhl21 | Sat1 | Ceacam1 | Sh3bp5 | Zfp361 | Itgb1 |
| Lgals3bp | Ugt1a1 | Aven | Use1 | | 4933438K21Rik | Rhobtb2 | Fam169b | Ckb |
| Tceanc2 | A330049N07Rik | Inpp4b | Peli1 | | Ppfia4 | Fahd2a | Clcn3 | Ncald |
| Sec13 | Smpdl3b | Dgka | Stk38 | | Mzb1 | Noa1 | Npm1 | Denmd5a |
| Gpr171 | Cd38 | Arnt2 | Rpl18 | | Kif22 | Wdr4 | Smg1 | Il18rap |
| Cox6c | Gm4297 | Ssbp2 | Thrc6a | | Lag3 | Fchsd2 | Irak2 | Serpinb9 |
| Isy1 | Phf11a | Dos | Stk17b | | Csf2rb2 | Cd2ap | Exosc2 | Ptger4 |
| Spcs1 | 5730409E04Rik | Als2cl | Nfil3 | | Fgl2 | Rnf130 | Rps18 | Il12rb2 |
| Psma6 | Zfp277 | Sidt1 | Fam86 | | Stil | Vwa5a | Rps8 | Ddx28 |
| Nxt1 | Endod1 | Sgk3 | Mat2a | | Olfr613 | Faah | Fbxo7 | Il10ra |
| Psmb9 | Kif22 | | Tmem241 | | Arhgef10 | Aces | Rpl7a | Cst3 |

TABLE 3-continued

Gene signature for: CD62L$^{hi}$Slamf7−, Slamf7$^{hi}$CX3CR1+, and Slamf7$^{hi}$CX3CR1-PD-1- CD8+ TILs.

| CD62L + SlamF7 − CX3CR1− | | CD62L + SlamF7 − CX3CR1− | | CD62L − SlamF7hi CX3CR1− | | CD62L − SlamF7hi CX3CR1− | | CD62L − SlamF7hi CX3CR1+ | | CD62L − SlamF7hi CX3CR1+ | |
|---|---|---|---|---|---|---|---|---|---|---|---|
| Down | | Up | | Down | | Up | | Down | | Up | |
| 1-381 | 382-761 | 1-313 | 314-626 | 1-126 | | 1-154 | | 1-213 | 214-425 | 1-178 | |
| Srrt | Dlg4 | Il7r | Smpdl3a | | | Zfp488 | | Zeb1 | Rpl39 | Nabp1 | |
| Anxa6 | Mira | B430306N03Rik | Ip6k1 | | | Kif15 | | Mdn1 | Naca | Klrb1c | |
| Psmb6 | Dmxl2 | Sh3bp5 | Kpna4 | | | Cdh1 | | Ccdc64 | Rpl10 | 2010012O05Rik | |
| Ndufb6 | Lig1 | Tnrc6c | Atp1b3 | | | Wfs1 | | Tnfrsf26 | Fos | Mxi1 | |
| Nelfcd | Olfr484 | Faah | Mcrs1 | | | Slc18b1 | | Lat2 | Rpl37 | Fcgr2b | |
| F2r | Gm6367 | Cyp4v3 | Taf1d | | | Vmn1r132 | | Ms4a4c | Rps2 | Pogk | |
| Tmc8 | Smyd1 | Abcg1 | Pde4d | | | Tifa | | Rps20 | Cd69 | Bhlhe40 | |
| Ssr2 | Acvr1c | Mnt | Pde3b | | | Tacc3 | | Pou6f1 | Rpl31 | Errfi1 | |
| Myo1f | Cx3cr1 | Guf1 | Tmem71 | | | Lifr | | Pdk1 | Slc38a1 | Hist1h1c | |
| Ywhaq | Cd24a | Ulk2 | Coq9 | | | Xcl1 | | Ganc | Jun | Prdm1 | |
| Sh2d2a | Olfr292 | Sepp1 | Rps7 | | | Pak6 | | Krtcap3 | Rpl19 | Tnfrsf12a | |
| Psma4 | Rab30 | Bcl9l | Dnajc7 | | | Cybasc3 | | Ap1ar | AB124611 | Slamf7 | |
| Vps29 | Vephl | Gramd4 | Rpl7 | | | Ccr9 | | BC021614 | Txlng | Hfe | |
| Ppmel | Wfs1 | Emb | Bptf | | | Pltp | | Inpp4b | Demd2d | Cdkn1a | |
| Mrps18c | Tcf19 | Mrm1 | Rp9 | | | Slco4a1 | | Zfp1 | Srsf6 | Smpdl3b | |
| Smad3 | Gm5797 | Foxo4 | Ndrg3 | | | Cox6a2 | | Tex9 | Paics | Rnf216 | |
| Gba | Vmn2r4 | Ranbp10 | Pan2 | | | Irf8 | | Gm12185 | Rps17 | Alox8 | |
| BC017643 | Ildr1 | Aldh6a1 | Zfp266 | | | Igj | | Ctla2b | 1500012F01Rik | Nav1 | |
| 4930470H14Rik | Olfr617 | Hdac4 | Rpl1 | | | | | Gbp10 | Rpl37a | Plod1 | |
| Al467606 | Cenpe | Zfp955b | Prpf39 | | | | | Apobec1 | Sema4d | Bcl2a1d | |
| Lrp10 | Wnk3 | Eif4ebp2 | Pbxip1 | | | | | Dgka | Dis3l2 | Prf1 | |
| Sptlc2 | Cbfa2t3 | Adi1 | Ing1 | | | | | C1galt1 | Cd3d | Gpd2 | |
| Sra1 | Prf1 | Pdk1 | Sertad1 | | | | | Hvcn1 | Dguok | Tmprss13 | |
| Hist2h3b | Sapcd2 | Mafk | Rgs2 | | | | | Zfp512 | Gnb2l1 | Mt1 | |
| 1190002F15Rik | Galnt3 | Ctf3 | Ifrd1 | | | | | Ppp1r3b | Nsa2 | Dtx1 | |
| Dcc | Ldlr | Vmac | Rpl28 | | | | | Sesn1 | Rpl11 | Dock5 | |
| Commd2 | Fignl1 | Pou6f1 | Junb | | | | | Gm129 | Rpl38 | Cish | |
| Ywhah | Sbf2 | Sesn3 | Abliml | | | | | Btla | Rps23 | Stard10 | |
| Sla | Ska2 | Fam210a | Wdr26 | | | | | Arl5c | Rpl36 | Rora | |
| Rbx1 | Zfp599 | Slc12a7 | Med1 | | | | | Tfdp2 | Relb | Fasl | |
| Cd82 | BC002163 | Slc25a36 | Afl1 | | | | | Ppm1h | Gm15772 | Nhsl2 | |
| Tuba1b | Dcx | Mdn1 | Gramd1a | | | | | Fam78a | Impdh2 | Crabp2 | |
| Psmb3 | Trip13 | Eif2 | Max | | | | | Zfp395 | Rps14 | Trim16 | |
| Cycs | Zfp300 | Rras2 | Rpl119 | | | | | Rgs11 | Wdr43 | Sema3a | |
| Ppp1r11 | Cbfa2t3 | Filip1l | Ubxn7 | | | | | Pde2a | Xist | Hnrpll | |
| Cox5a | Hip1 | Adi1 | Dyrk1a | | | | | Plac8 | Mycbp2 | Kcnj8 | |
| Atg4d | 6330403K07Rik | Pdk1 | 3230401D17Rik | | | | | Tapt1 | Rassf2 | As3mt | |
| Pomp | 9830107B12Rik | Mafk | Lim62 | | | | | Tmem9 | Ru45s | Zeb2 | |
| Cd6 | Cdc20 | Ctf3 | | | | | | Trib2 | Rpl22 | Ccl5 | |
| Gapdh | Il12rb2 | Vmac | | | | | | Cd7 | Unc119b | Gzma | |
| Cd8a | Gm5591 | Pou6f1 | | | | | | A630001G21Rik | Cnp | Rap1gap2 | |
| Tma7 | | Sesn3 | | | | | | Crtam | Rps21 | Ngfr | |
| Taf12 | | Sprr2a2 | | | | | | Fgfr1op | D10Wsu52e | | |
| Park7 | | Sprr2a1 | | | | | | Ptpnm2 | Erap1 | | |
| Pfkp | | | | | | | | Emb | Rnf167 | | |
| Exoc5 | | | | | | | | Klhdc2 | Arhgap27 | | |
| Mrps21 | | | | | | | | | | | |
| Ikzf3 | | | | | | | | | | | |

TABLE 3-continued

Gene signature for: CD62L^hi Slamf7-, Slamf7^hi CX3CR1+, and Slamf7^hi CX3CR1- PD-1- CD8+ TILs.

| CD62L+ SlamF7- CX3CR1- Down | | CD62L+ SlamF7- CX3CR1- Up | | CD62L- SlamF7hi CX3CR1- Down | CD62L- SlamF7hi CX3CR1- Up | CD62L- SlamF7hi CX3CR1+ Down | | CD62L- SlamF7hi CX3CR1+ Up |
|---|---|---|---|---|---|---|---|---|
| 382-761 | 1-313 | 1-313 | 314-626 | 1-126 | 1-154 | 1-213 | 214-425 | 1-178 |
| Fam133b | Sulf2 | Slc11a2 | Elk4 | | | Filip1l | Ctps2 | |
| Synj2bp | Stx11 | Ap1ar | Abhd16a | | | Trim59 | Rpl17 | |
| Hmgn2 | AA792892 | Ugcg | Jak1 | | | P2rx4 | Rnaset2b | |
| Ech1 | Olfr64 | Apobec1 | Sbno2 | | | Plk1s1 | Eef2 | |
| 1110008P14Rik | C130079G13Rik | D15Ertd621e | Rps21 | | | Rpl18a | Atp5g2 | |
| Dpy30 | Mgl2 | Srsf5 | Ass1 | | | Lysmd2 | Rps12 | |
| Ak2 | 4930511M06Rik | Il4ra | Huwe1 | | | Rpl36a | Npc2 | |
| Mrpl20 | Vmn2r42 | Rab3ip | Rpl29 | | | Armcx2 | Rpl14 | |
| Tespa1 | Cd300c | Klf4 | Ccnt1 | | | Fam26f | Rnaset2a | |
| Atp5e | Rasip1 | Cyth3 | Rpl9 | | | Traf4 | Txk | |
| Eif1ax | Cth | Galnt2 | Sidt2 | | | Ldlrad4 | Tubb5 | |
| Anxa2 | Mageb16-ps1 | Socs1 | Uba52 | | | Rpl13 | Cblb | |
| Gm5177 | Gna15 | Tsc1 | Jmjd1c | | | Rpsa | Eif3h | |
| Gimap7 | Pik3r3 | Zfp281 | Sertad2 | | | Sidt1 | Eif3f | |
| Hmgb2 | Iqgap3 | Slmap | Ubr1 | | | Sft2d2 | Gas5 | |
| Ms4a4b | Ni5dc2 | Ubald1 | Setx | | | Rpl4 | Rps13 | |
| Sema4a | Rad51 | Rbfa | Macf1 | | | Rplp0 | Eif3a | |
| Phgdh | Kdr | D230025D16Rik | Gna13 | | | Fam214a | Ccnh | |
| Prr13 | Klrk1 | Cry2 | Hbp1 | | | Ly6e | Vps13a | |
| Ap1s1 | Atp6v1g3 | Tob1 | Lonp2 | | | Sgms1 | Nfkb2 | |
| Dok2 | Cenpf | Vps37b | Nub1 | | | Ddb2 | Psme1 | |
| Ppat | Vmn2r59 | Abl1 | Eif3e | | | Rpl12 | Grcc10 | |
| Etfb | Id1 | Pecam1 | Rps17 | | | Pabpc4 | Ddx21 | |
| Mina | Ckb | Tmem64 | Igf2r | | | Il6st | Rps10 | |
| Lypla2 | Slco4a1 | Rpl18a | 4932438A13Rik | | | Apol7b | Eif3m | |
| Mien1 | Gm10662 | 2410004N09Rik | Fam107b | | | Cyb5 | Eif3k | |
| 9930111J21Rik1 | 2810417H13Rik | Marf1 | Tpr | | | Rps7 | Hspa8 | |
| Atp5l | Sen3a | Pikfyve | Arhgap15 | | | Srpk1 | Ptma | |
| Pmf1 | Gcnt2 | Smad7 | Rps16 | | | Rpl3 | Fau | |
| Dusp2 | Itgb1 | Dtd1 | Dym | | | Mgat5 | | |
| Ran | Paqr4 | Ldlrad4 | Zmynd11 | | | Cd72 | | |
| Ndufa4 | Mdga2 | Satb1 | Ncln | | | | | |
| Ndufa11 | Nlrp4e | Polg2 | Wsb1 | | | | | |
| Cyth4 | 4933431E20Rik | Ube2s | Tmc6 | | | | | |
| 9930111J21Rik2 | Plxdc2 | Nufip1 | Nae1 | | | | | |
| Chsy1 | Vmn2r37 | Zbtb20 | B4galt1 | | | | | |
| Gm14295 | Tnfsf14 | Hspbp1 | Rpl15 | | | | | |
| Abracl | C330024D21Rik | Nin | Adamts10 | | | | | |
| Uqcrq | Cyp7b1 | Zhx2 | Irak1 | | | | | |
| H2-Q7 | A130077B15Rik | Zfp869 | Rpl23a | | | | | |
| Oas3 | Ankle1 | Gramd3 | Tax1bp1 | | | | | |
| Ptplb | Casc5 | Gigyf1 | Rps8 | | | | | |
| Gskip | Vmn2r115 | Insr | Rn7 | | | | | |
| Sdhaf2 | Fcrl6 | Mars2 | Pdcd4 | | | | | |
| Cox6b1 | Chafla | Cebpz | Arid5b | | | | | |
| Timm10b | Adam11 | Socs6 | Tcf20 | | | | | |

TABLE 3-continued

Gene signature for: CD62L$^{hi}$Slamf7-, Slamf7$^{hi}$CX3CR1+/-, and Slamf7$^{hi}$CX3CR1-PD-1- CD8+ TILs.

| CD62L+ Slamf7- CX3CR1- Down | | CD62L+ Slamf7- Up | CD62L+ Slamf7- CX3CR1- Up | CD62L- SlamF7hi CX3CR1- Down | CD62L- SlamF7hi CX3CR1- Up | CD62L- SlamF7hi CX3CR1+ Down | | CD62L- SlamF7hi CX3CR1+ Up |
|---|---|---|---|---|---|---|---|---|
| 1-381 | 382-761 | 1-313 | 314-626 | 1-126 | 1-154 | 1-213 | 214-425 | 1-178 |
| Myl6 | Aqp9 | Sun2 | Nsa2 | | | | | |
| Al662270 | Lilrb4 | Rpsa | Impdh2 | | | | | |
| Nfkbid | Ptchd4 | 9430038I01Rik | Rps9 | | | | | |
| Tipin | Gm9159 | Tle4 | Scaf11 | | | | | |
| Lamtor5 | Denmd5a | Slamf6 | Klhl6 | | | | | |
| Drx4 | Ncapd2 | Spry2 | Ube2h | | | | | |
| Sh2b3 | Gm14327 | Ypel3 | Tars2 | | | | | |
| Elof1 | Pdcd1 | Rgcc | Cblb | | | | | |
| Mcm2 | Rora | Flcn | Zfp36l1 | | | | | |
| Rfwd3 | Maoa | Galnt10 | Rps18 | | | | | |
| Rps6ka4 | Clspn | Rnf19a | Gtf3c2 | | | | | |
| Ttc39b | Asf1b | Kdm5b | Maml2 | | | | | |
| Eno1 | 5730577I03Rik | Dmrta1 | Mysm1 | | | | | |
| Notch2 | Serpinb9 | Trpc4ap | Spk2 | | | | | |
| Arpp19 | Serpinb1b | Klc4 | Srm1 | | | | | |
| Amical | Tacc3 | Ascc1 | Bclaf1 | | | | | |
| Acsbg1 | Fam131a | Rraga | Tra2a | | | | | |
| Grk4 | Uhrf1 | Mgat5 | Elmsan1 | | | | | |
| Lime1 | Rorb | Stk4 | Clk1 | | | | | |
| Lars | Csprs | Rpl5 | Rpl27a | | | | | |
| Tmem1084b | Apitd1 | Dnajb9 | Maf1 | | | | | |
| Uqcr11 | Gdpd5 | Lancl1 | Fam65b | | | | | |
| Necap2 | Gm21119 | Sgms1 | Rbm5 | | | | | |
| Smpd1 | Foxm1 | Cep97 | Rbm38 | | | | | |
| Krtcap2 | Tmem117 | Mcl1 | Rnf167 | | | | | |
| Rpa2 | Olfr856-ps1 | Gigyf2 | Rnf138 | | | | | |
| Agpat3 | Slc18b1 | Pan3 | Ctps2 | | | | | |
| Gm2382 | A530032D15Rik | Smarca5 | Gtf2i | | | | | |
| Slc16a10 | Cish | Srpk1 | Tnrc6b | | | | | |
| BC004004 | Bhlhe40 | Pip4k2a | Eif2c2 | | | | | |
| 1810037I17Rik | Hist1h1b | Zfp777 | Tgtp2 | | | | | |
| Sarlb | Rad51c | Gem | Rbm26 | | | | | |
| Senp1 | Lifr | Zfyve19 | Brd8 | | | | | |
| Cdk6 | Bcl2l1 | Crebrf | Kdm5a | | | | | |
| Pleklb2 | Olfr613 | Rpl12 | D10Wsu52e | | | | | |
| Cd226 | Fam64a | Snx13 | Luc7l2 | | | | | |
| Zmpste24 | Top2a | Fam65a | Ddx5 | | | | | |
| Tram1 | Asb2 | Utp20 | Rabggta | | | | | |
| A630089N07Rik | Cdca8 | Impact | Txnl4a | | | | | |
| Med20 | Vmn1r45 | Hexim1 | Vps39 | | | | | |
| Sept11 | Kif2c | Hsd17b4 | Zbtb11 | | | | | |
| Fam111a | Pik3ap1 | Lrrc61 | Eef2 | | | | | |
| Tor3a | 1700110I01Rik | Dnahc8 | Gm13363 | | | | | |
| Nkap | 4930555G01Rik | Kdm6b | Abi1 | | | | | |
| 8430410A17Rik | Slc5a12 | Prkch | Alkbh5 | | | | | |
| Itgb2 | Olfr295 | Ipcef1 | Rpl22 | | | | | |

TABLE 3-continued

Gene signature for: CD62L^hi Slamf7^-, Slamf7^hi CX3CR1^+, and Slamf7^hi CX3CR1^- PD-1^- CD8^+ TILs.

| CD62L + Slamf7 - CX3CR1- Down | | CD62L + Slamf7 - CX3CR1- Up | | CD62L - SlamF7hi CX3CR1- Down | CD62L - SlamF7hi CX3CR1- Up | CD62L - SlamF7hi CX3CR1+ Down | | CD62L - SlamF7hi CX3CR1+ Up |
|---|---|---|---|---|---|---|---|---|
| 1-381 | 382-761 | 1-313 | 314-626 | 1-126 | 1-154 | 1-213 | 214-425 | 1-178 |
| Dnmt1 | Speer8-ps1 | Acp5 | Klk8 | | | | | |
| Kcnq1ot1 | Ppfia4 | Zfp652 | Pabpc1 | | | | | |
| Mrpl33 | Gp49a | Zmynd8 | Dcaf8 | | | | | |
| Yars | Ube2c | Smap2 | Rps14 | | | | | |
| Furin | Vmn1r58 | Pim3 | Txk | | | | | |
| Cars | Mrgprx2 | Pnrc1 | Gas5 | | | | | |
| Casp3 | Cdh1 | Snhg12 | Cytip | | | | | |
| Acnat1 | Cdca3 | Reck | Nfyc | | | | | |
| Coa3 | Socs2 | Sik1 | Brd2 | | | | | |
| 2010111I01Rik | Ccnb2 | Rpl4 | Vps13a | | | | | |
| Rab19 | Cdca5 | Mdc1 | Pitpnc1 | | | | | |
| Atxn1 | Il10ra | Zbtb2 | Ccpg1 | | | | | |
| Cd52 | Mxd3 | Fam118a | Dnttip2 | | | | | |
| Rpp25l | Vmn1r-ps79 | Plk1s1 | Spop | | | | | |
| AI314180 | Pla2g4c | Cep68 | Tuba4a | | | | | |
| Blvra | Tnfsf9 | Znrf3 | Sdha | | | | | |
| Trex1 | Ccr2 | Abhd11 | Ikbkg | | | | | |
| Runx2 | Gm884 | Tfb2m | Cnppd1 | | | | | |
| Arsb | Bcl11a | Foxp1 | Setd2 | | | | | |
| Mettl21d | Zfp488 | Plekha5 | Map1lc3b | | | | | |
| Eif2ak2 | LOC100861615 | Pim2 | Atf7ip | | | | | |
| Nup205 | E2f2 | Fbxo32 | Dnaja2 | | | | | |
| Mgat1 | Ccr5 | Wdr45 | Eif4b | | | | | |
| St3gal4 | Casp1 | Zfp622 | Eif5 | | | | | |
| 1810009A15Rik | Tmem154 | Bcl10 | Mrpl24 | | | | | |
| 2310039L15Rik | Epas1 | Rars2 | Akap13 | | | | | |
| Rpa3 | Depdc1a | Cox7a2l | Eif1 | | | | | |
| Hif1a | Gm15319 | Fam189b | Hmha1 | | | | | |
| Myo18a | Ly6g5b | Rapgef6 | Slc25a3 | | | | | |
| Armcx3 | Nuf2 | Map3k1 | Slc38a2 | | | | | |
| Ppm1j | Col19a1 | Rps4x | Slc50a1 | | | | | |
| Emp3 | Entpd1 | Il17ra | Nxf1 | | | | | |
| Sigmar1 | Fasl | Acss1 | Rps10 | | | | | |
| Txn1 | Vmn2r117 | 1700094D03Rik | Tspyl1 | | | | | |
| Knstrn | Ncaph | Ttc3 | Paip2 | | | | | |
| Dbi | Pou3f2 | Rps27 | Ist1 | | | | | |
| Cox17 | Dlgap5 | Ppp1r15a | Zfp36 | | | | | |
| Zfp71-rs1 | F730043M19Rik | 2510002D24Rik | Srsf7 | | | | | |
| Mnf1 | Nek2 | Kif21b | Matr3 | | | | | |
| Manea | Hdac9 | | | | | | | |
| F830016B08Rik | B430212C06Rik | | | | | | | |
| Fam162a | Klrg1 | | | | | | | |
| 9030619P08Rik | Lag3 | | | | | | | |
| Soat2 | Gzmm | | | | | | | |
| Il12rb1 | P2rx7 | | | | | | | |
| Capn2 | Kcnk5 | | | | | | | |

TABLE 3-continued

Gene signature for: CD62L^hi Slamf7-, Slamf7^hi CX3CR1+, and Slamf7^hi CX3CR1-PD-1- CD8+ TILs.

| CD62L + Slamf7 - CX3CR1- Down | CD62L + Slamf7 - CX3CR1- Up | CD62L - SlamF7hi CX3CR1- Down | CD62L - SlamF7hi CX3CR1- Up | CD62L - SlamF7hi CX3CR1+ Down | CD62L - SlamF7hi CX3CR1+ Up |
|---|---|---|---|---|---|
| 1-381 | 1-313 | 1-126 | 1-154 | 1-213 | 1-178 |
| 382-761 | 314-626 | | | 214-425 | |

| | |
|---|---|
| Sec61g | Ccl3 |
| Ndufs4 | Prdm1 |
| Cenpw | Cdca2 |
| Mfap3 | 4933438K21Rik |
| Serpina3g | Ifng |
| 4921515E04Rik | Mcam |
| Asah1 | Klrc1 |
| Mthfd2 | Nusap1 |
| Baiap3 | Sgol1 |
| Mtm9 | Bcl2a1c |
| Reep5 | Ccr4 |
| Trerf1 | Cxcr6 |
| Incenp | L1cam |
| Gmppb | Fgl2 |
| Btrip1 | Tyms |
| Cdc102a | Kif15 |
| Timm8b | Neil3 |
| Cdc7 | Spag5 |
| Gpr114 | Wdr31 |
| Txndc5 | 1700091H14Rik |
| Atox1 | Slamf1 |
| S100a10 | Itgax |
| Adam19 | Stmn1 |
| Sc4mol | Kif20a |
| Lsm5 | Ncapg |
| Fkbp2 | Prc1 |
| Prkcd | Birc5 |
| Gm17821 | Slamf7 |
| Dut | Vmn1r132 |
| Pafah1b3 | Bcl2a1b |
| Ifih | Nova1 |
| Dctpp1 | Cd40lg |
| A430107P09Rik | Ska3 |
| Rgs1 | Ryr1 |
| Gypc | BC049352 |
| Snx10 | Tpx2 |
| Il18rap | Gm20139 |
| Flt3l | Apod |
| Zfp937 | Spc25 |
| Lrrk1 | Zfp248 |
| Ccnd3 | Pkib |
| Rfc4 | Ccl4 |
| Gm16938 | Tnfrsf9 |
| Aars | Olfr44 |
| Abcb1a | Stil |
| Mx1 | Il2ra |

TABLE 3-continued

Gene signature for: CD62L^hi Slamf7-, Slamf7^hi CX3CR1+, and Slamf7^hi CX3CR1-PD-1- CD8+ TILs.

| CD62L + SlamF7 - CX3CR1- Down | CD62L + Slamf7 - CX3CR1- Up | CD62L - SlamF7hi CX3CR1- Down | CD62L - SlamF7hi CX3CR1- Up | CD62L - SlamF7hi CX3CR1+ Down | CD62L - SlamF7hi CX3CR1+ Up |
|---|---|---|---|---|---|
| 1-381 | 1-313 | 1-126 | 1-154 | 1-213 | 1-178 |
| 382-761 | 314-626 | | | 214-425 | |
| Espl1 | | | | | |
| Tmprss13 | | | | | |
| Ttc39c | | | | | |
| Slc43a3 | | | | | |
| Mki67 | | | | | |
| Bcl2a1d | | | | | |
| Gzmb | | | | | |
| Gzma | | | | | |
| H2-Q10 | | | | | |
| Gzmk | | | | | |
| B4galt4 | | | | | |
| Kif1l | | | | | |
| Ska1 | | | | | |
| Zbtb32 | | | | | |

Sytl3
Skint4
St8sia4
Rps6ka1
Ddx28
Ccdc50
Aldh18a1
Tmem97
Atf6b
Edaradd
Cnih4
Serpina3f
Dclre1b
Crot
AW112010

Figure 14:
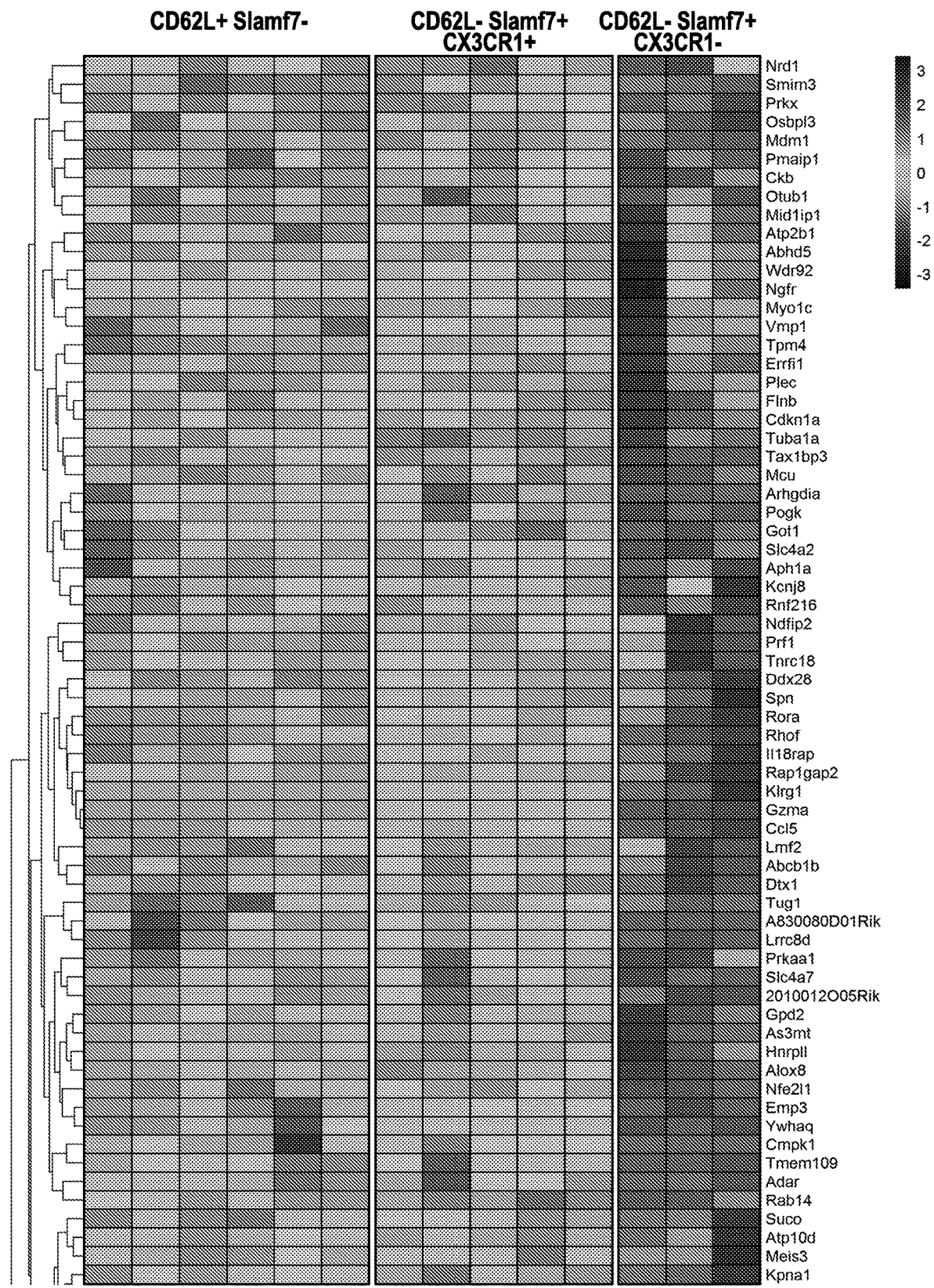
FIG. 14—Heatmap of $CD62L^{hi}$ $Slamf7^-$, $CD62L^-$ $Slamf7^{hi}CX3CR1^-$ and $CD62L^-$ $Slamf7^{hi}$ $CX3CR1^+$ populations within $CD8^+PD-1^-$ TILs isolated from MC38-OVA tumors (see also, Table 4).
Figure 14:
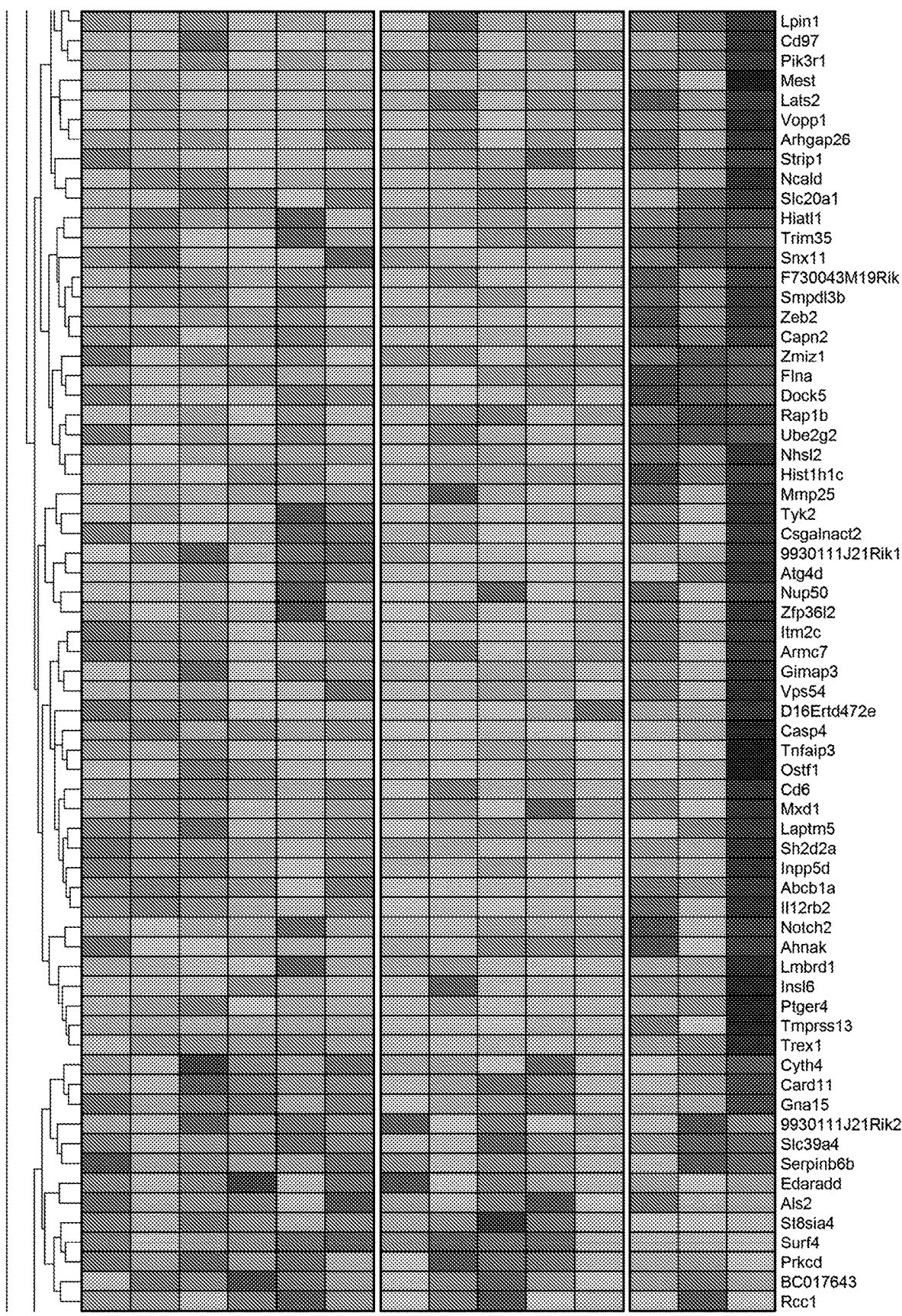
Figure 14:
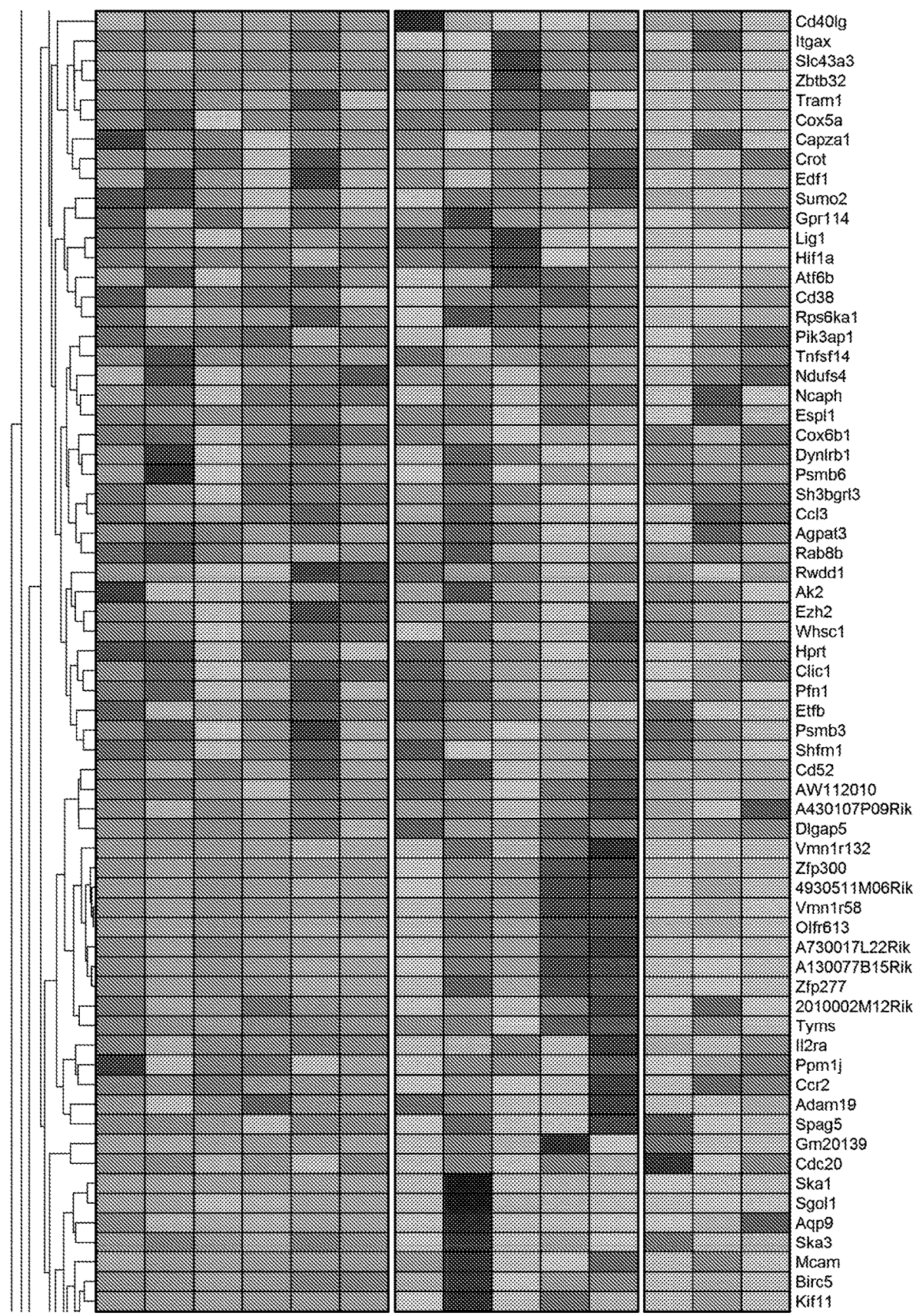
Figure 14:
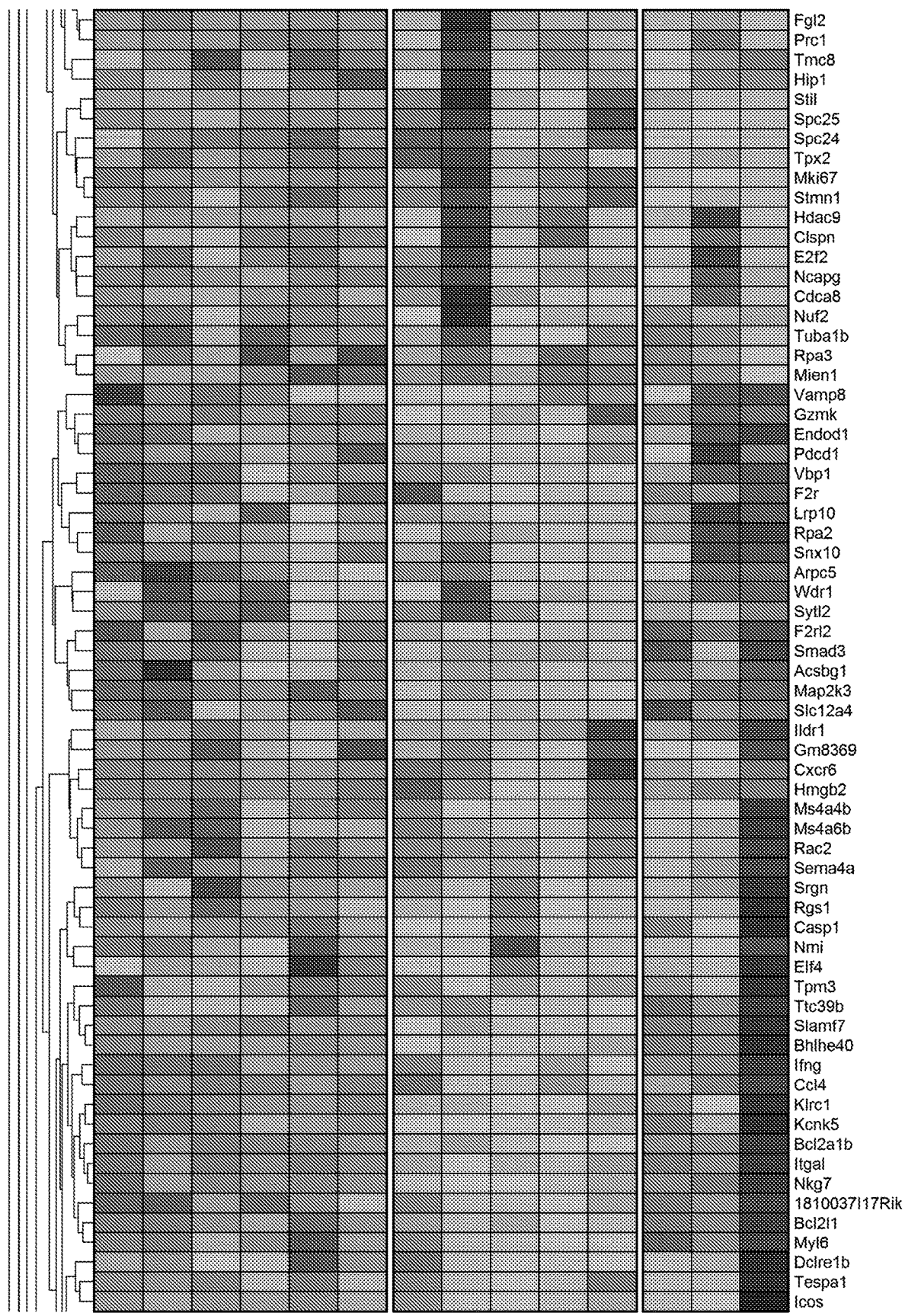
Figure 14:
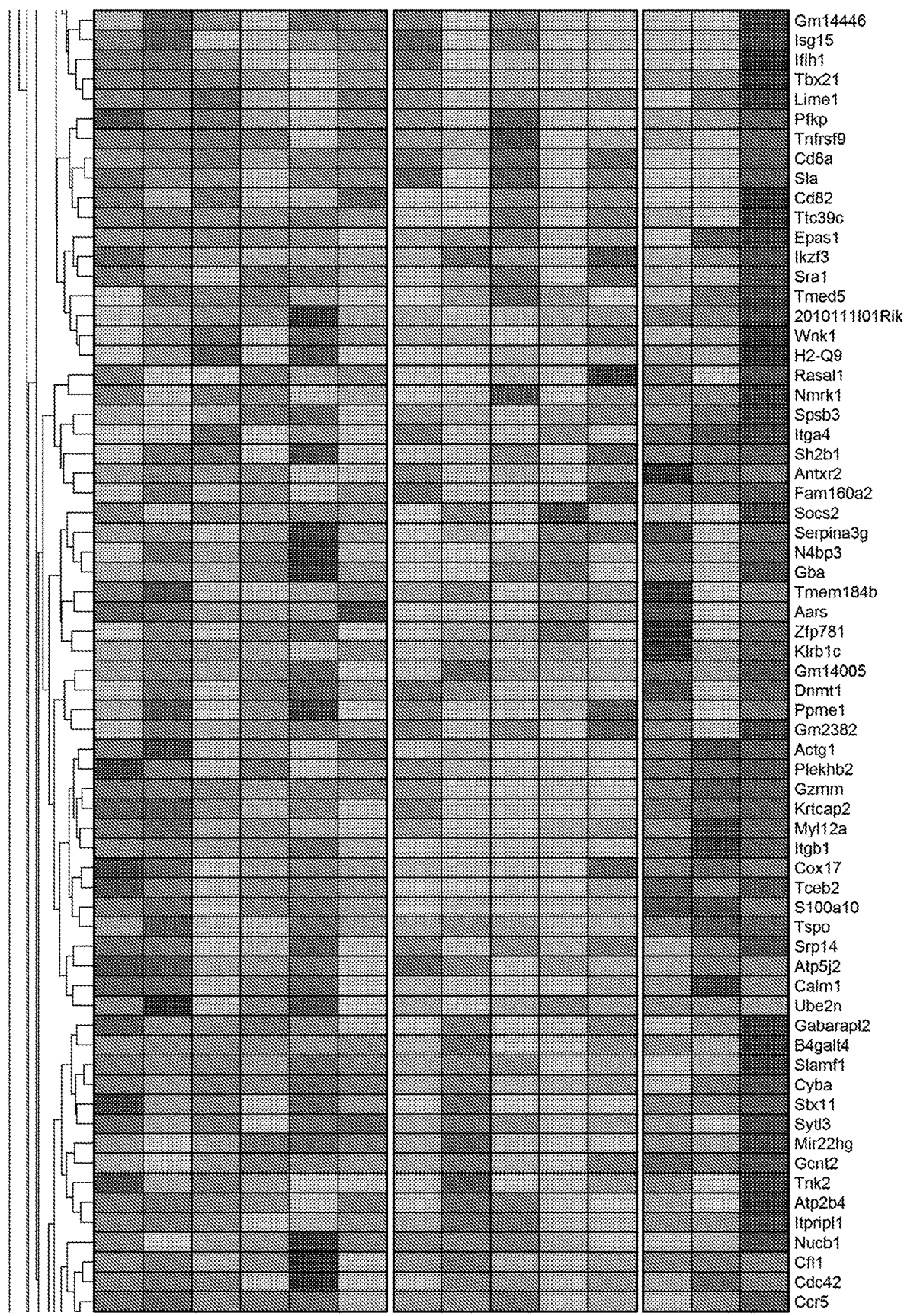
Figure 14:
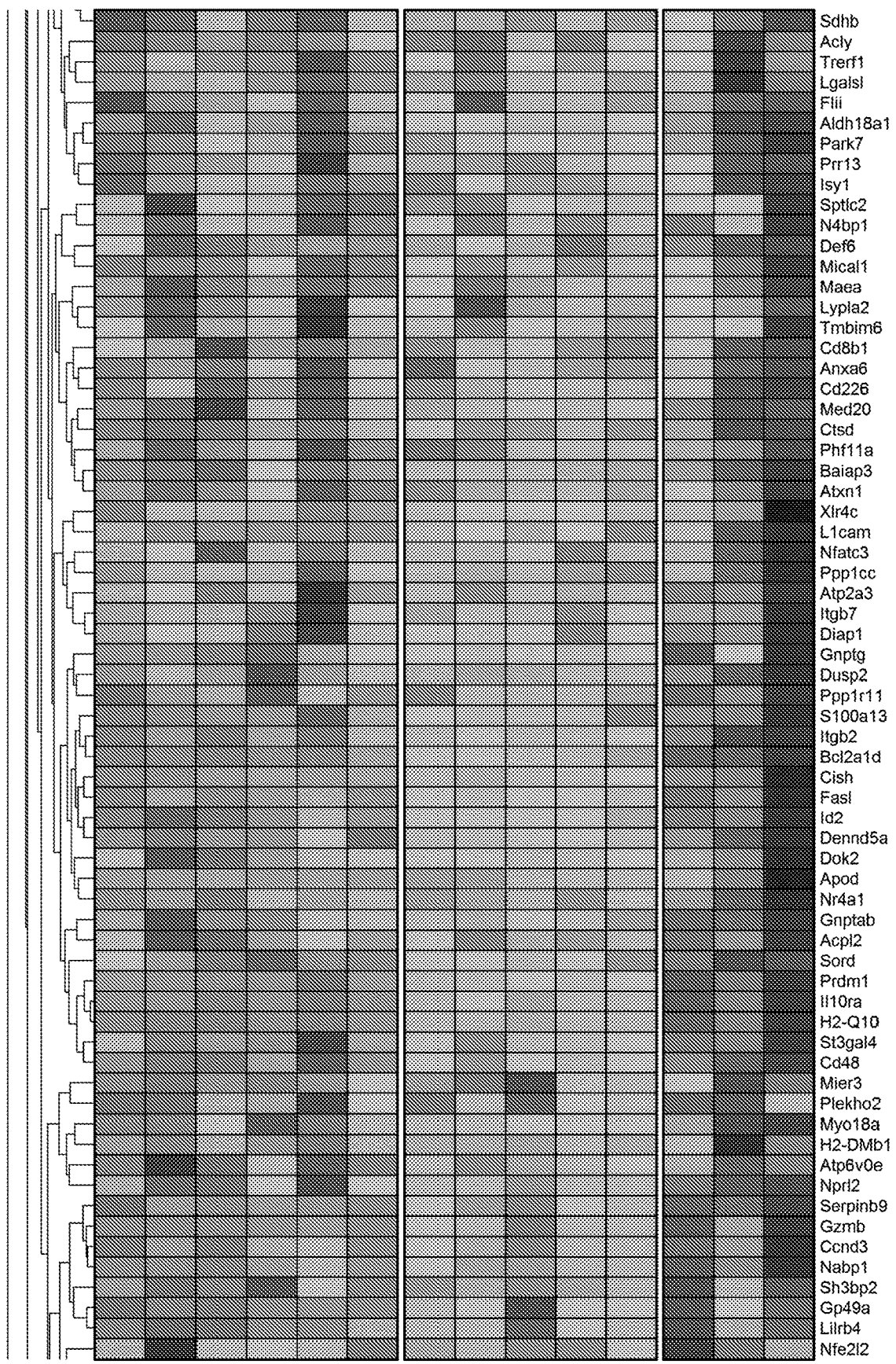
Figure 14:
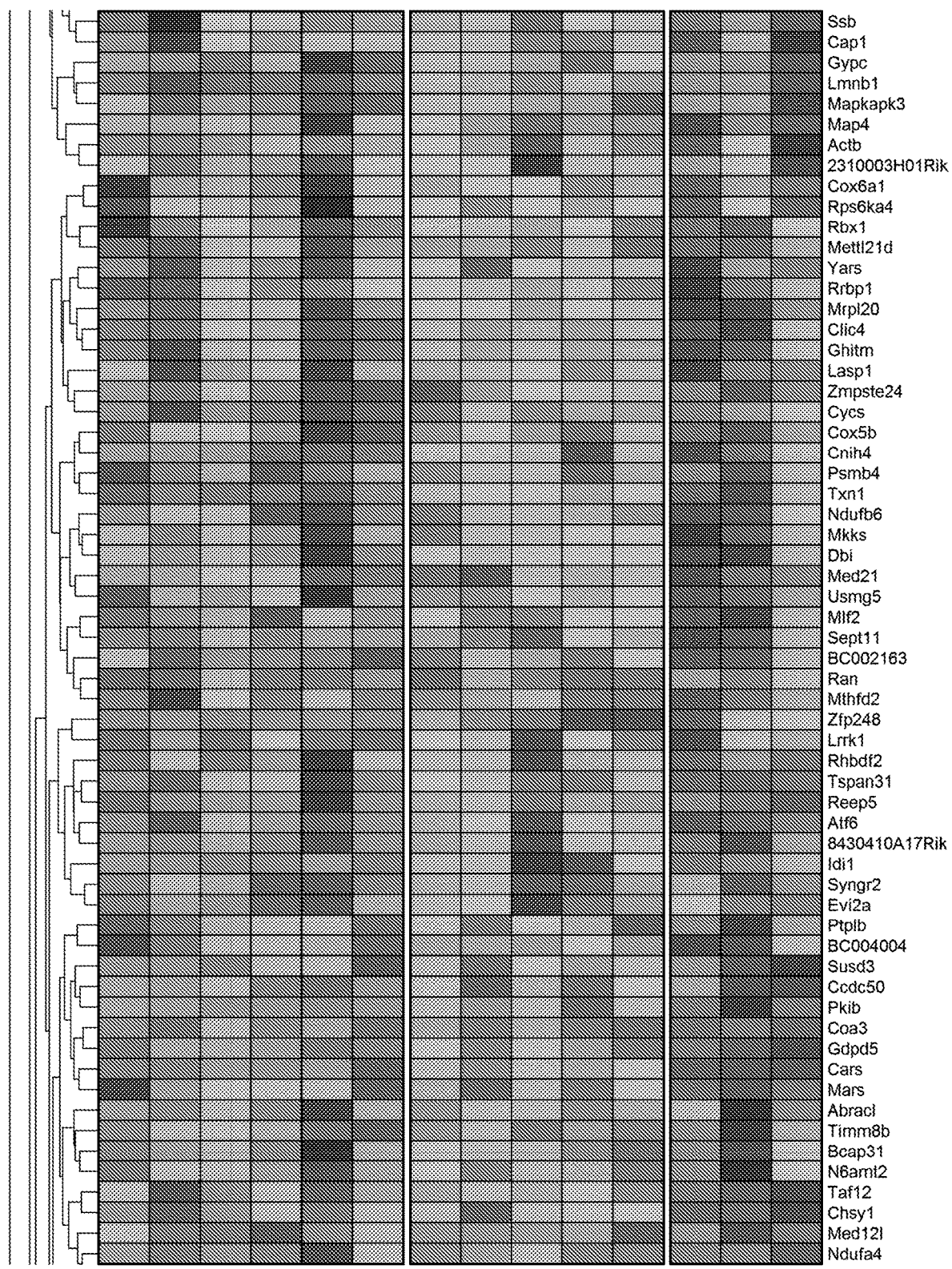
Figure 14:
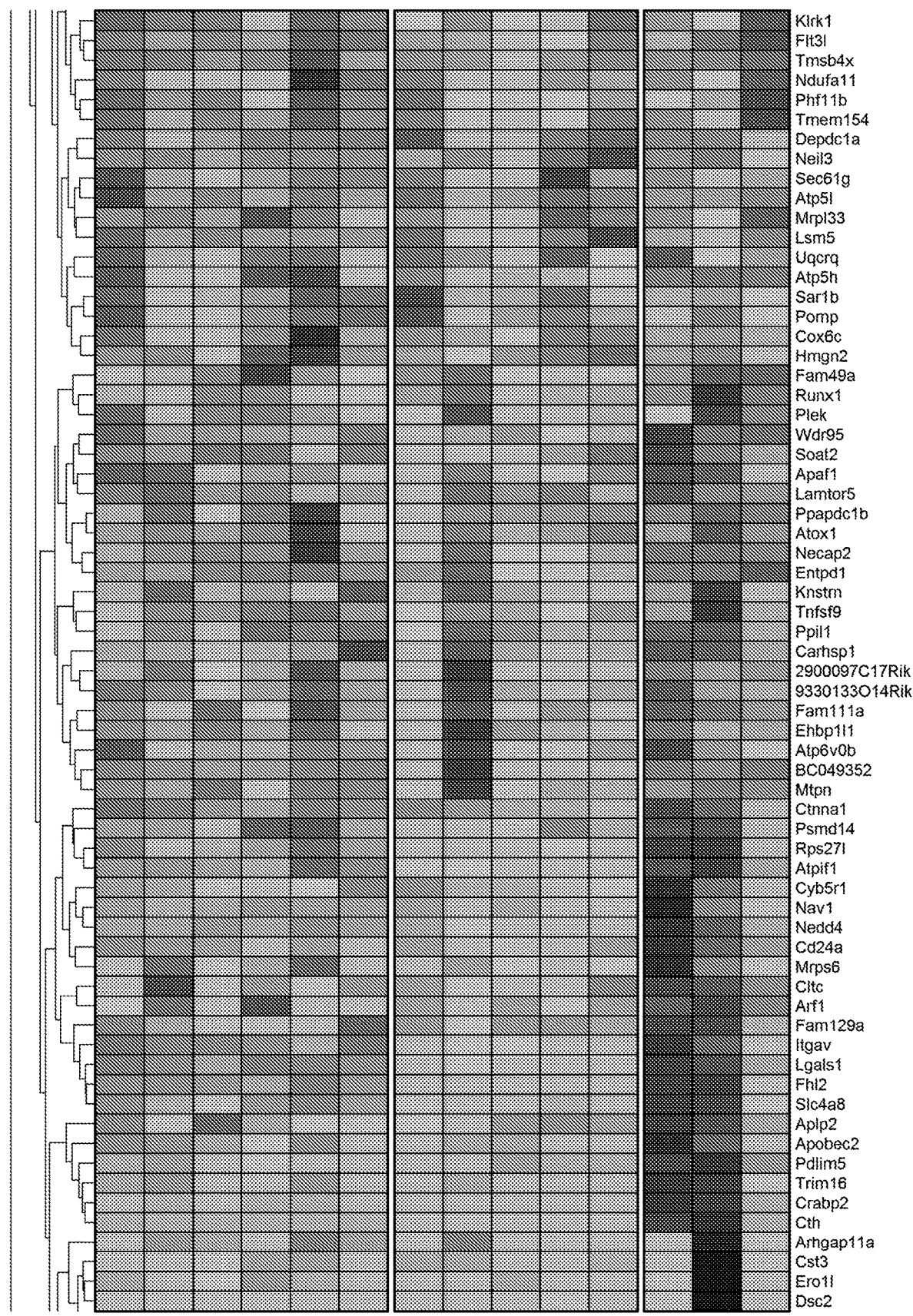
Figure 14:
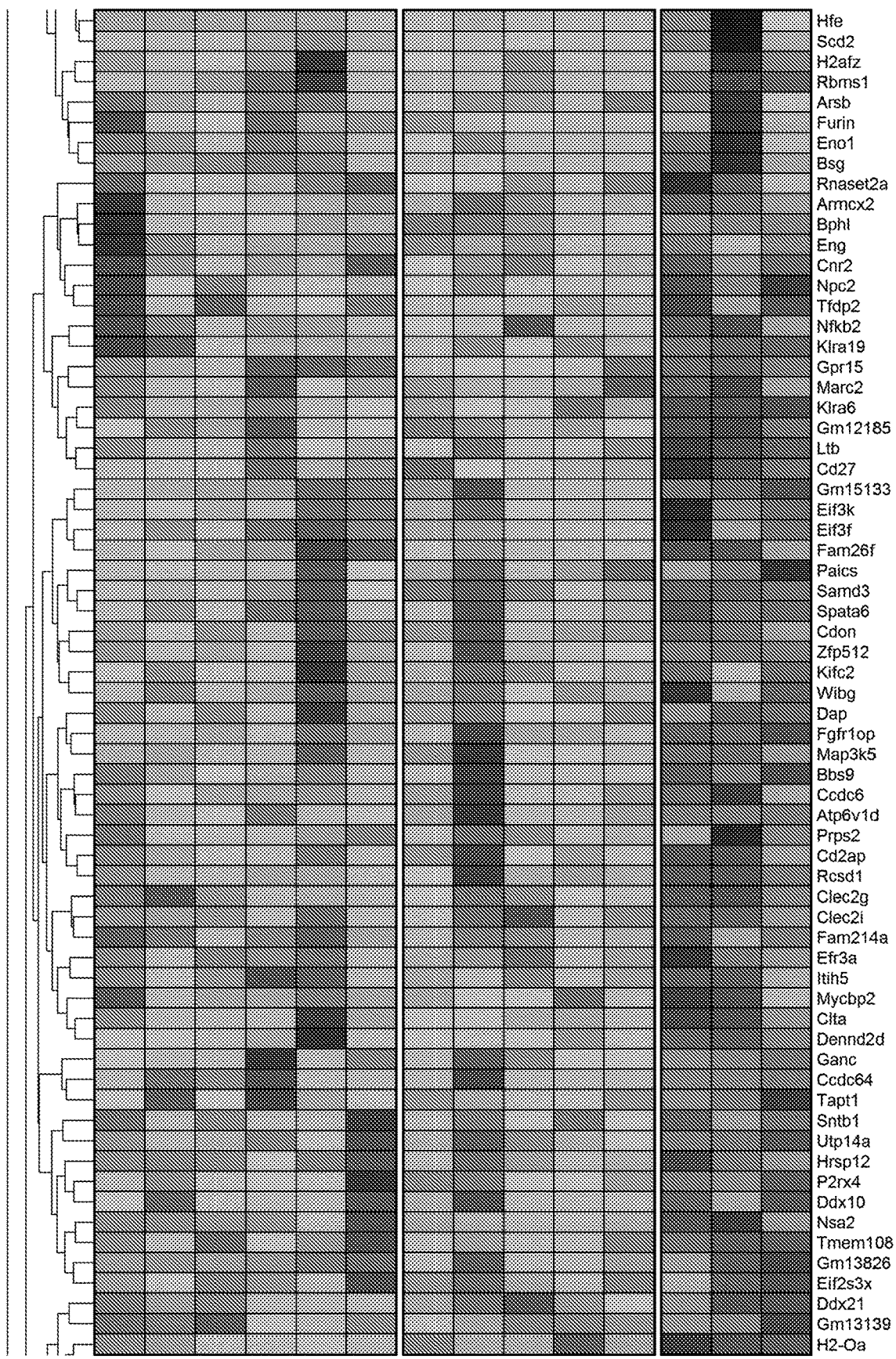
Figure 14:
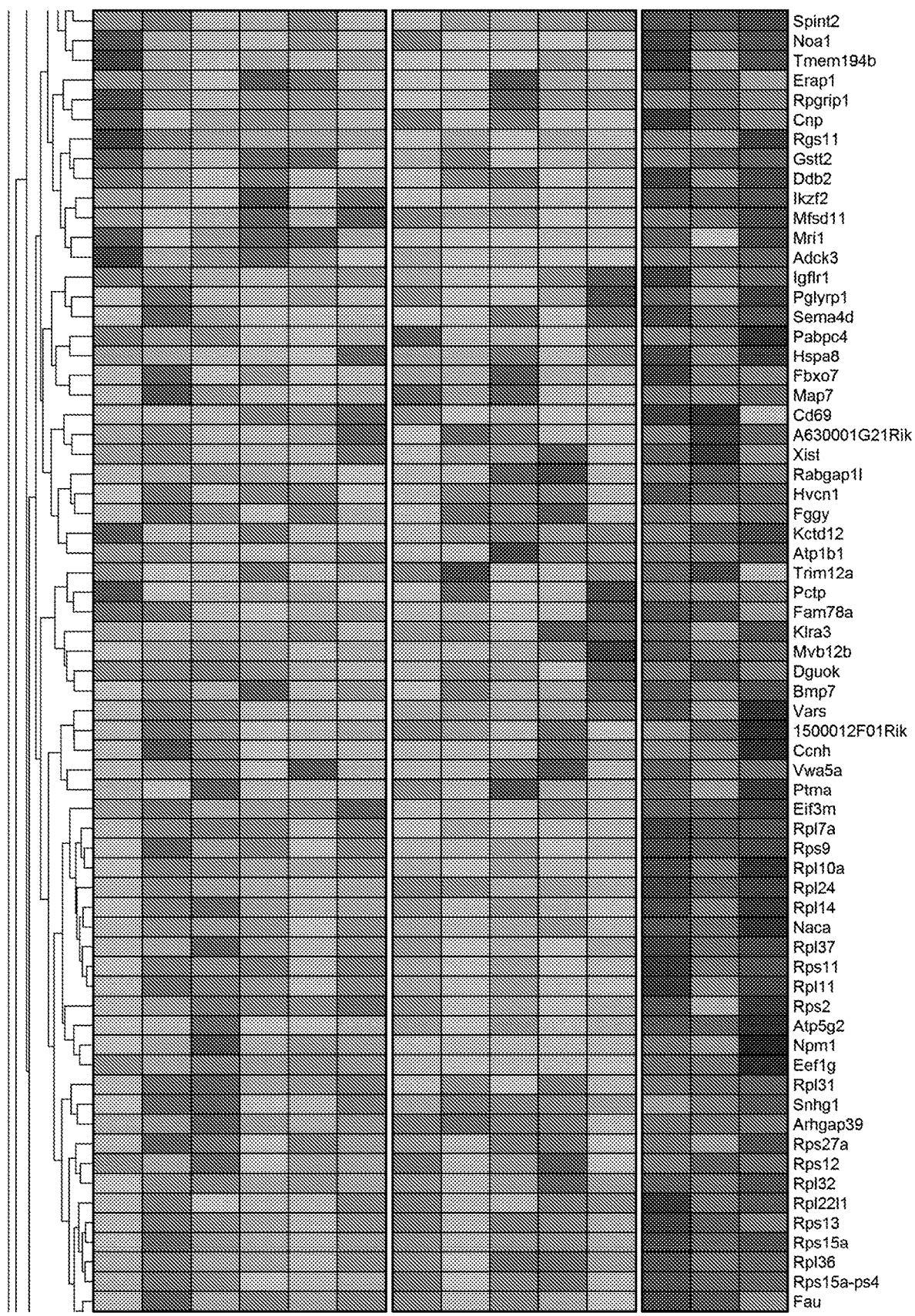
Figure 14:
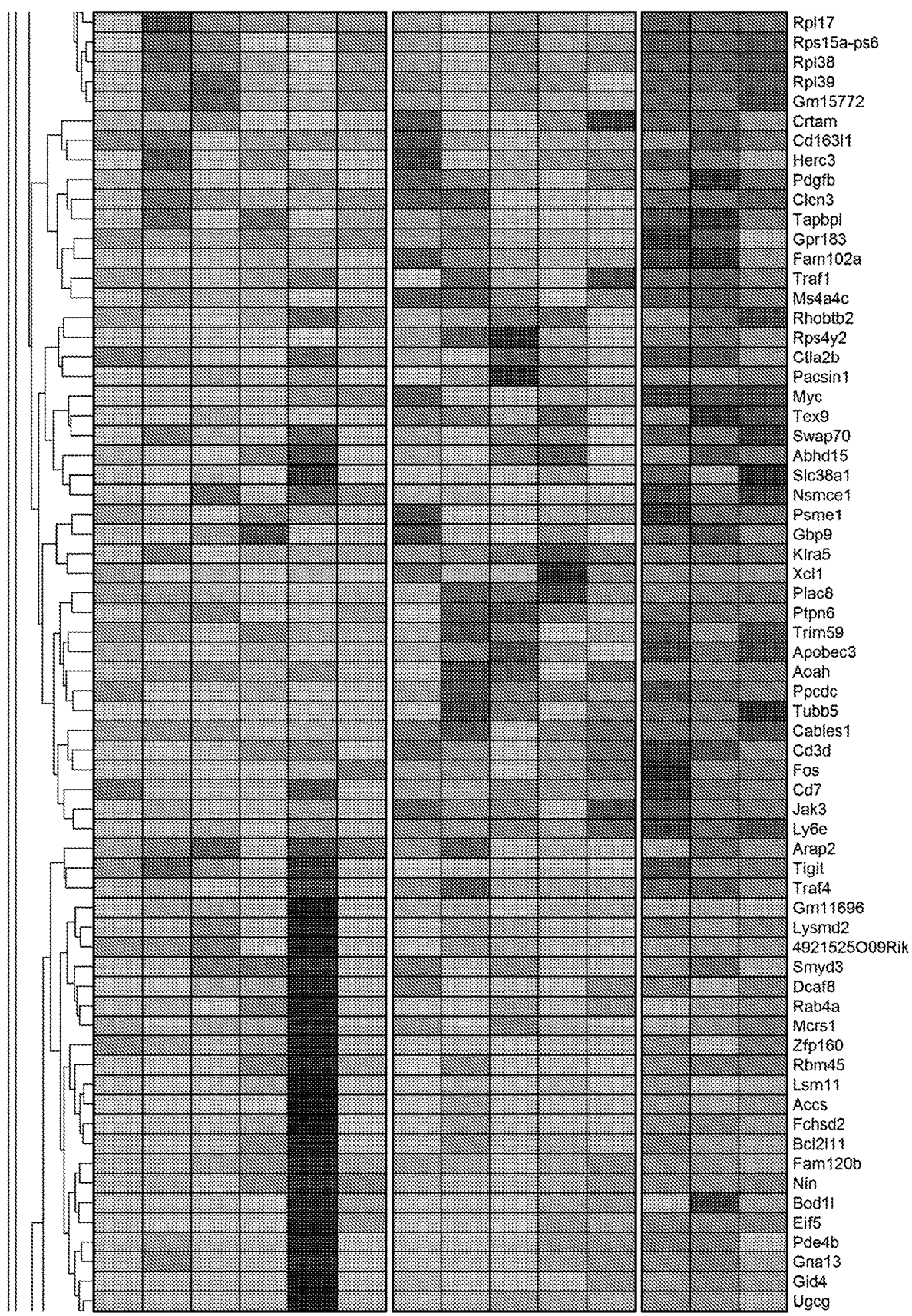
Figure 14:
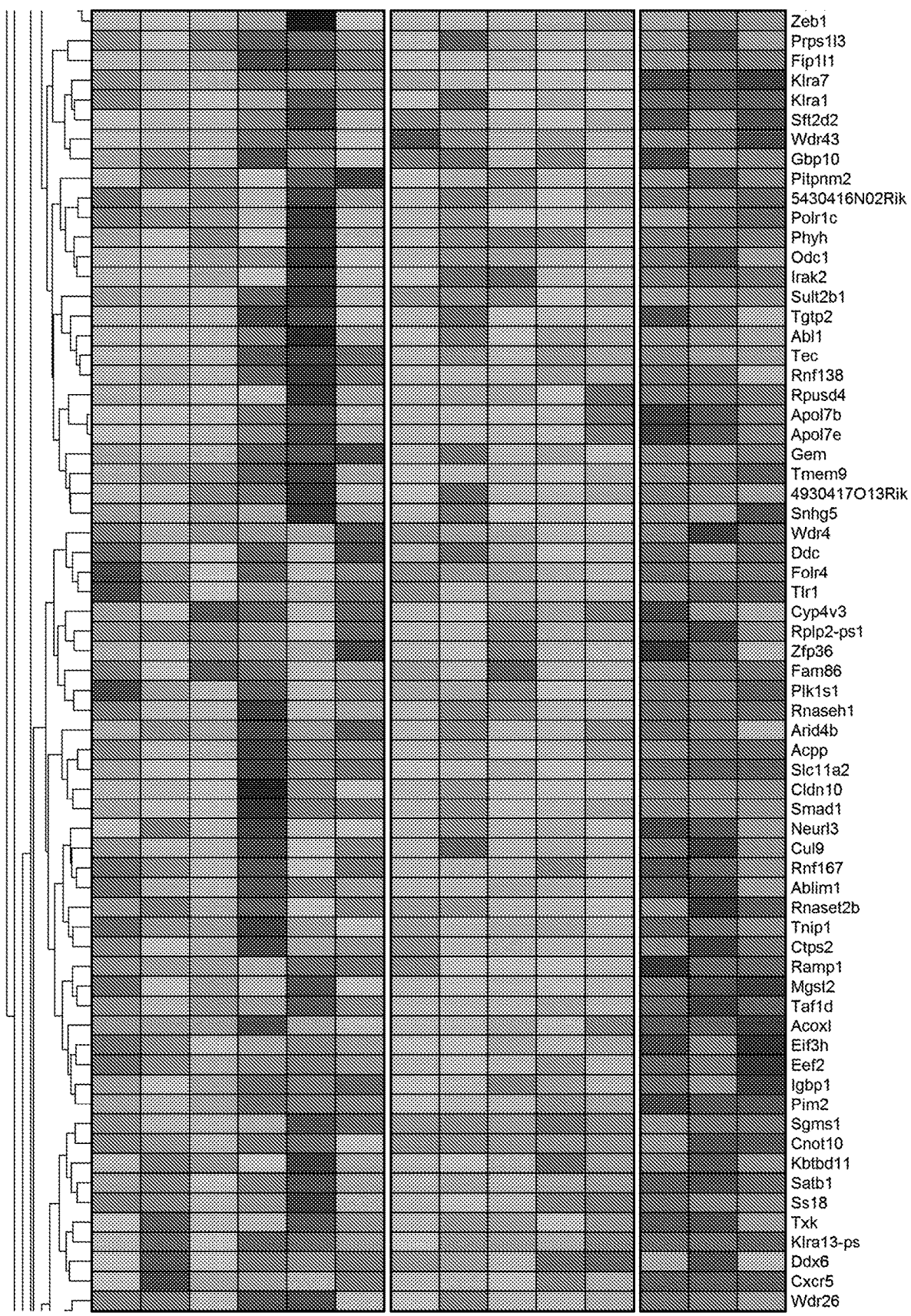
Figure 14:
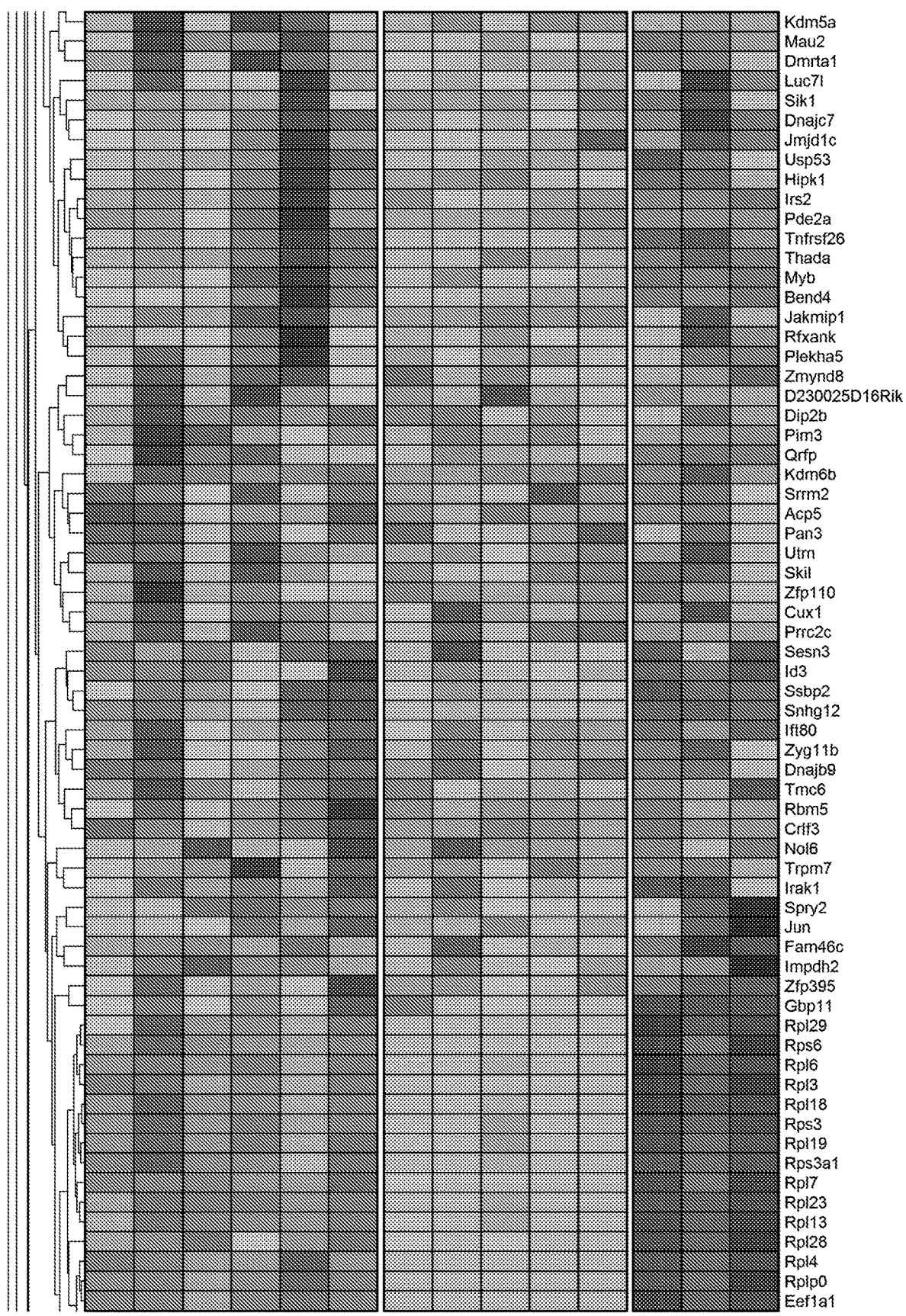
Figure 14:
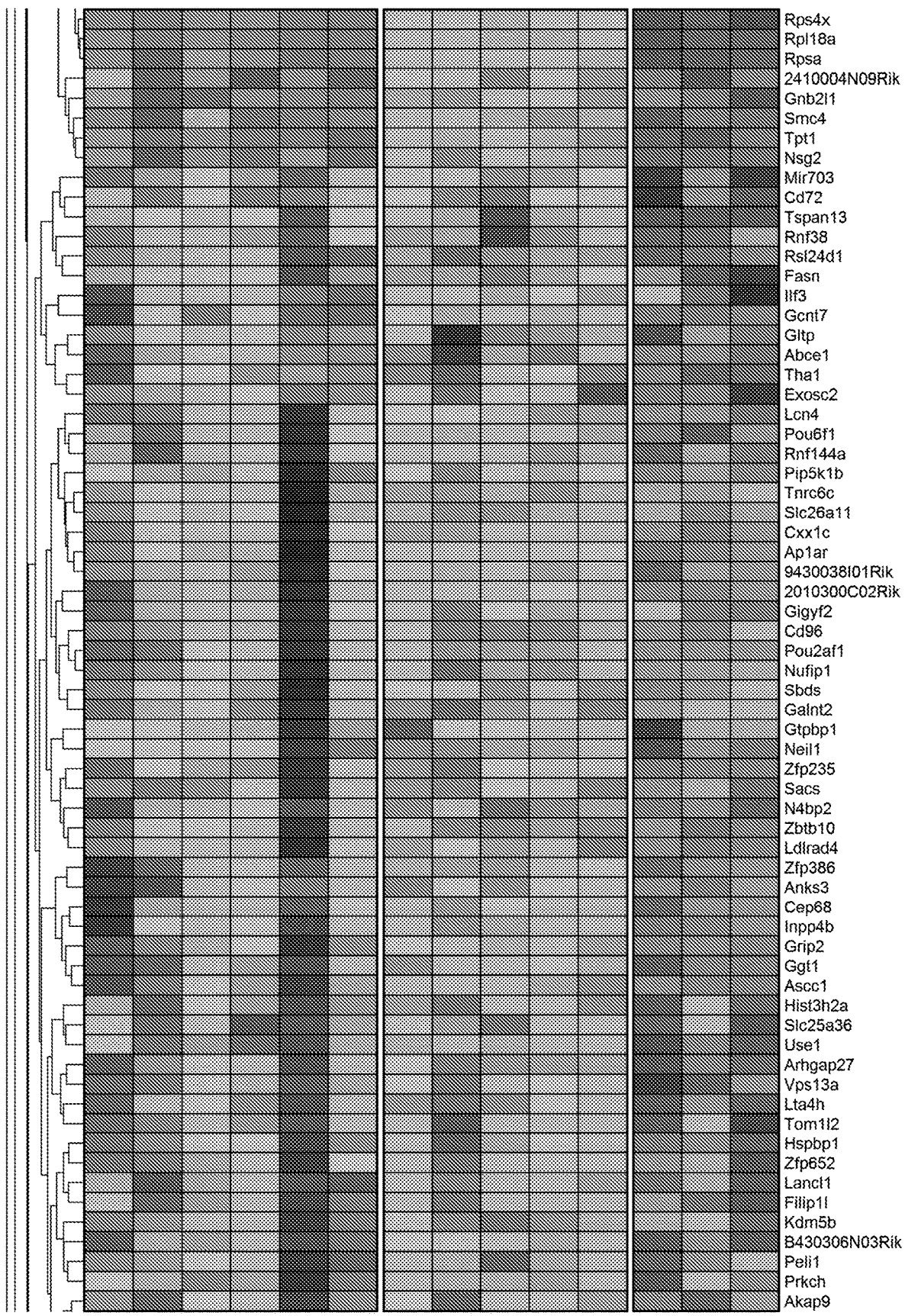
Figure 14:
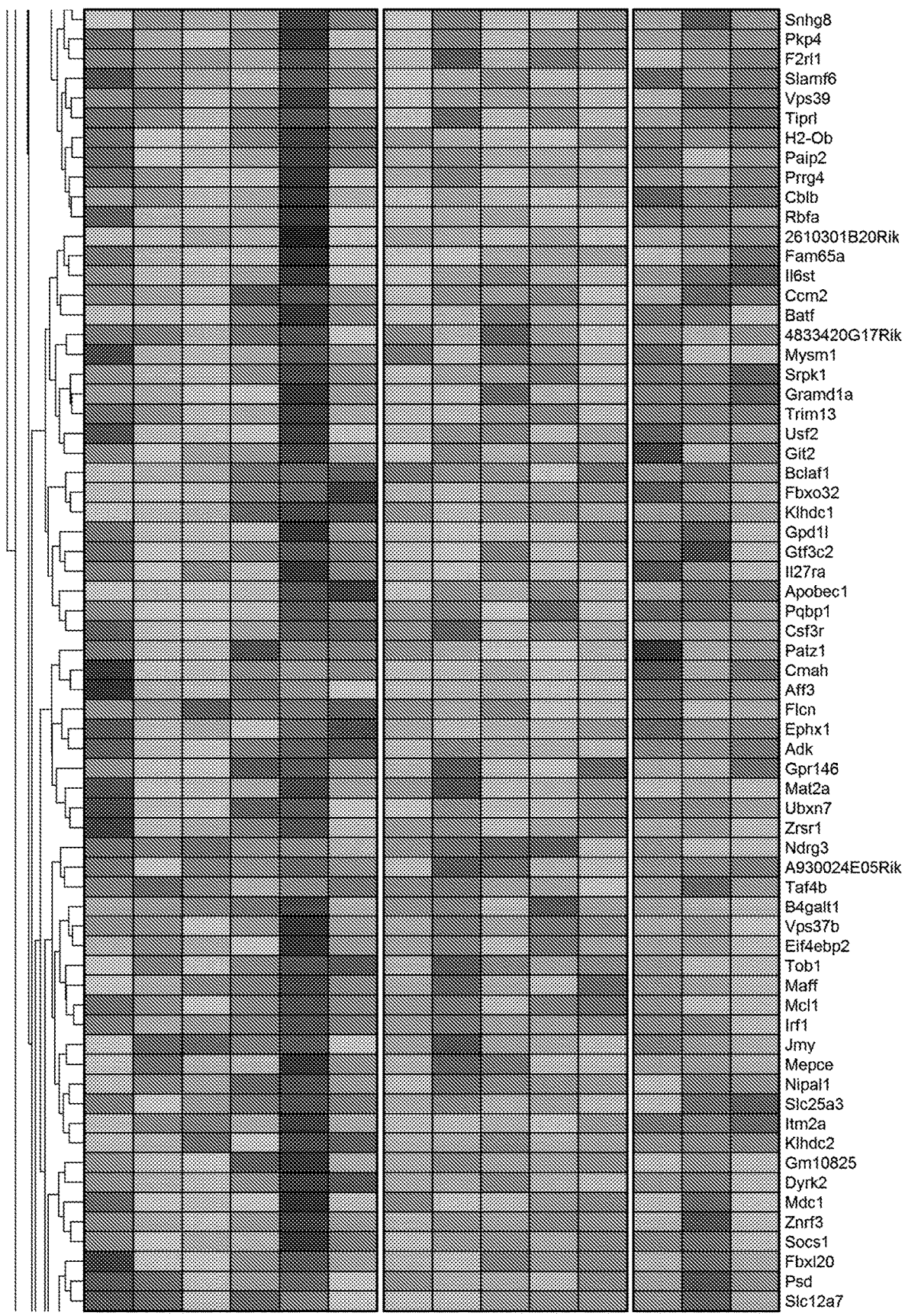
Figure 14:
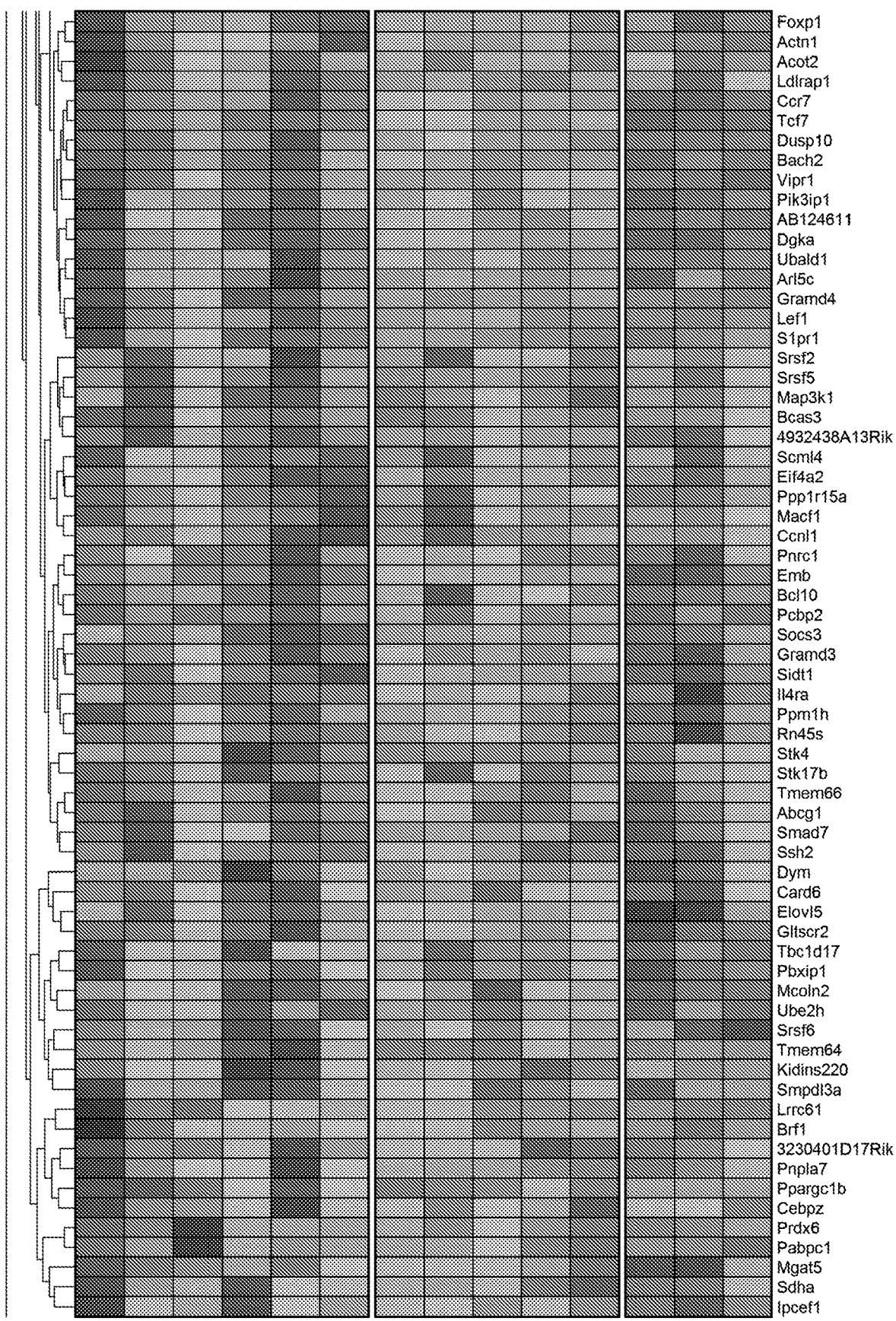
Figure 14:
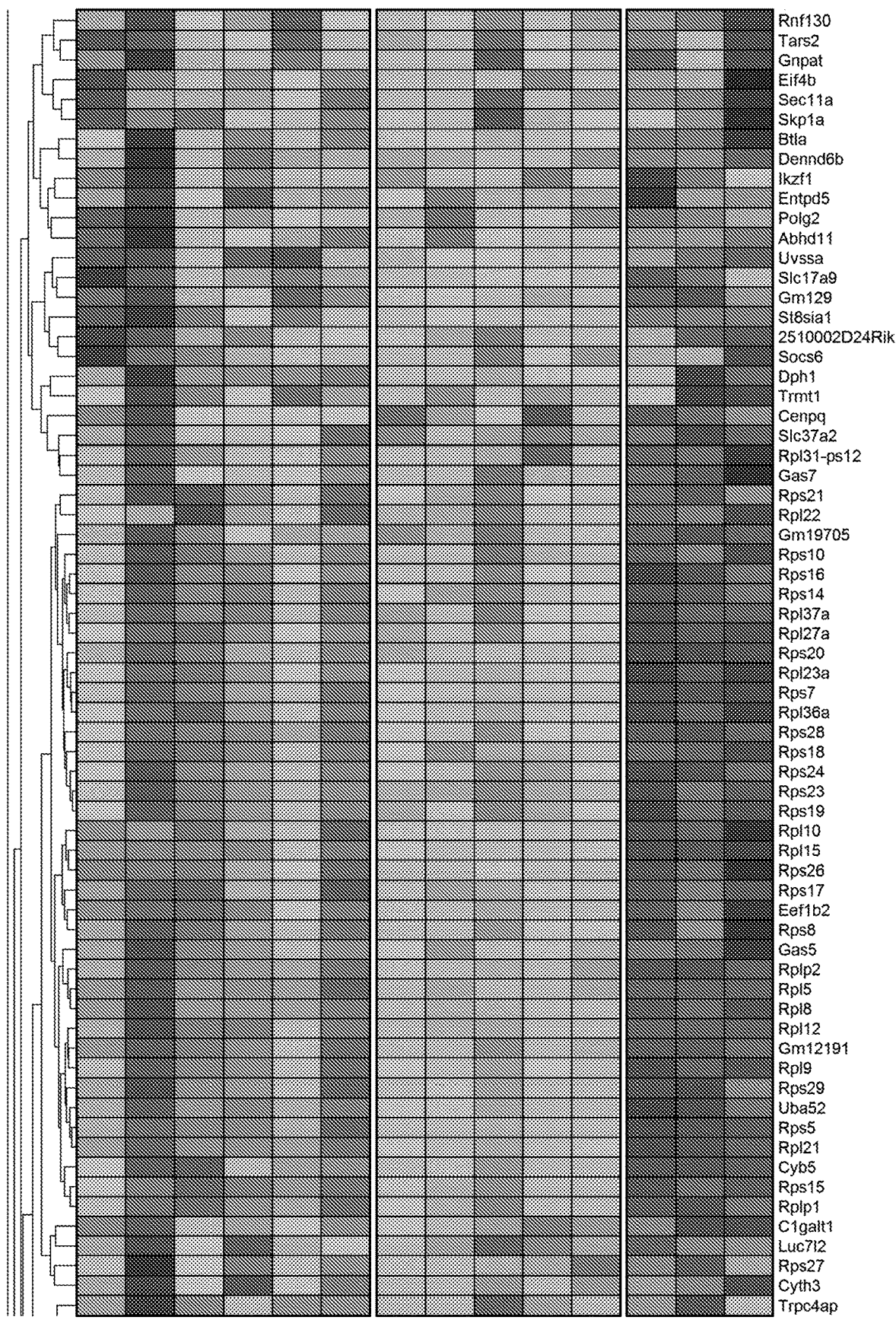
Figure 14:
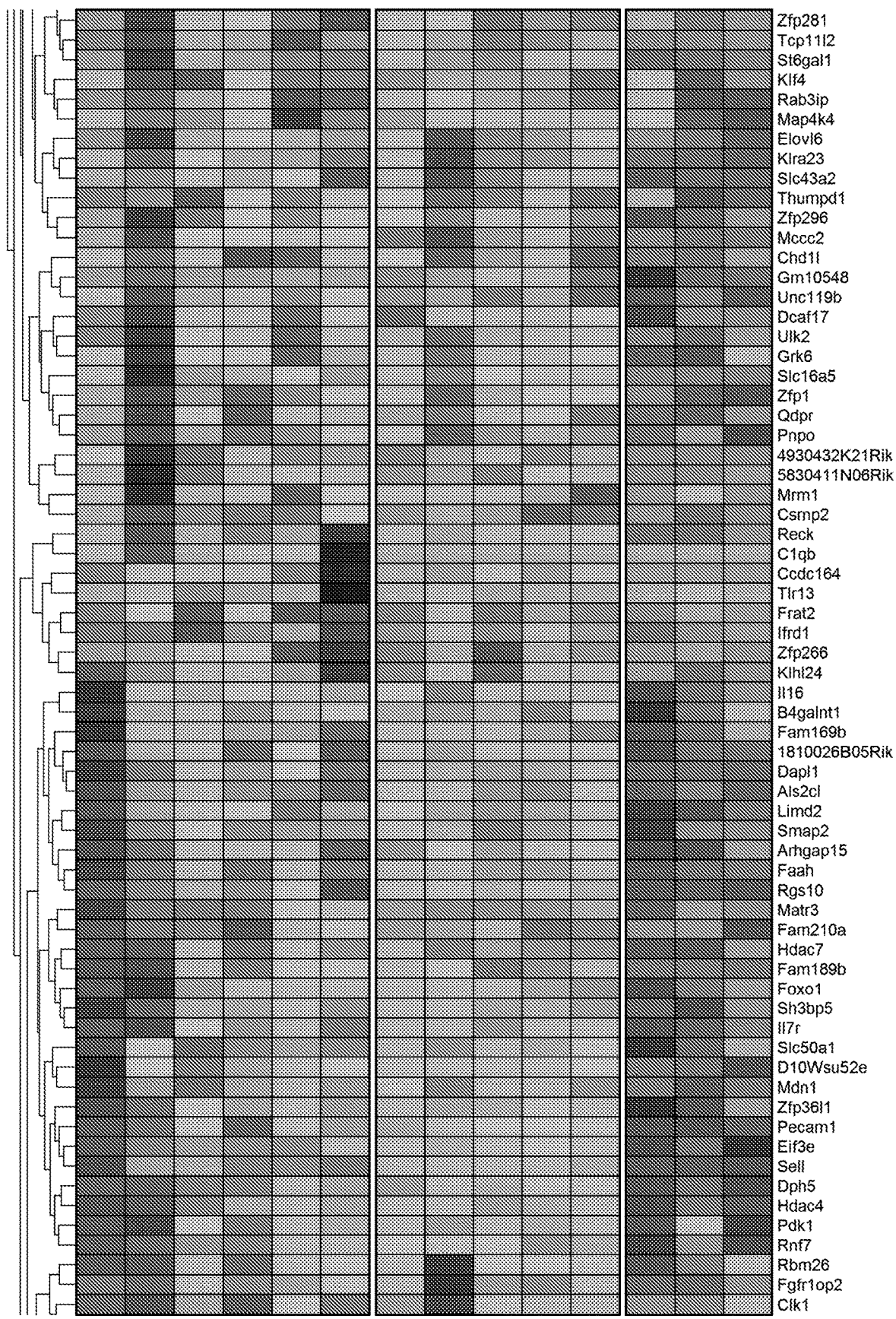
Figure 14:
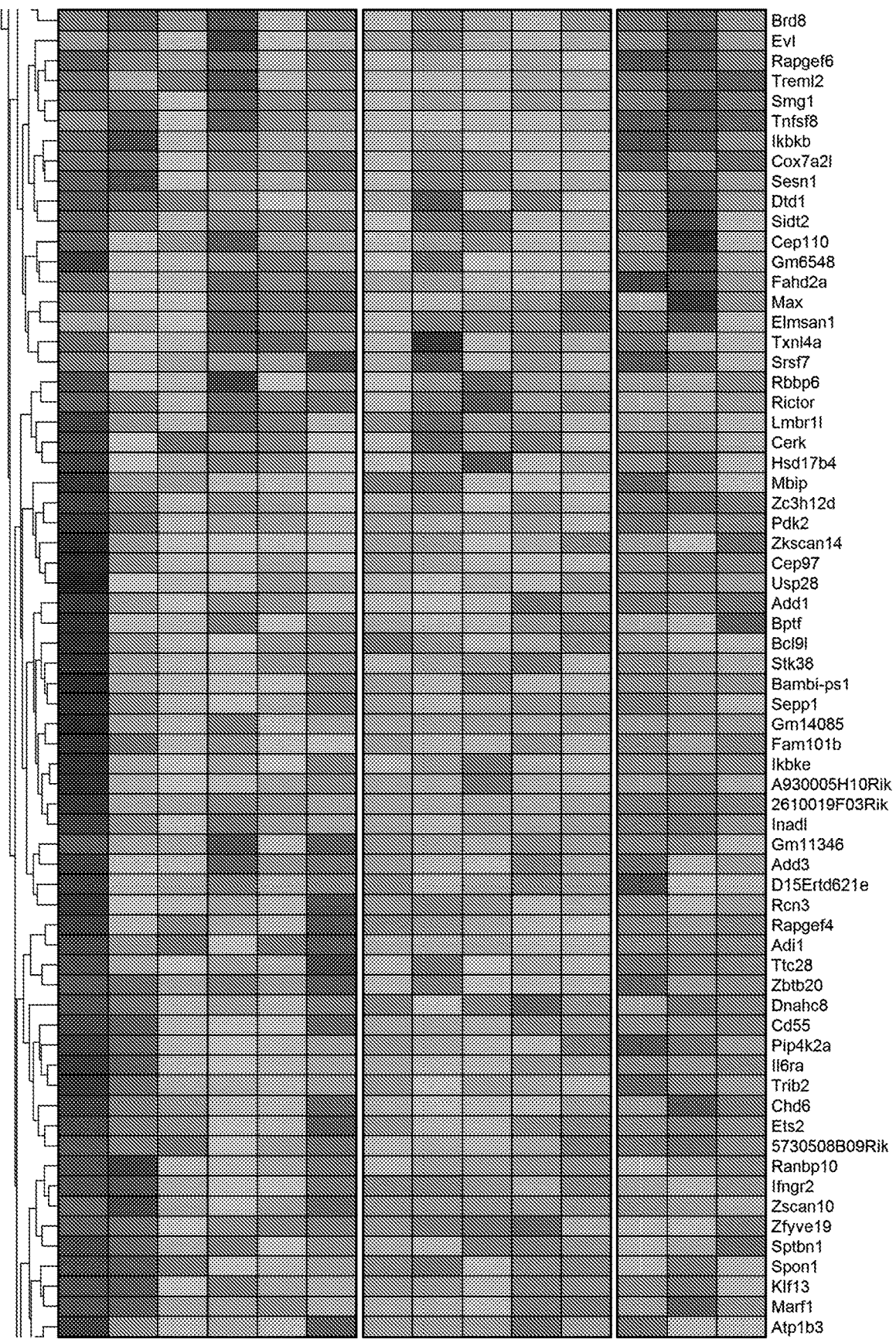
Figure 14:
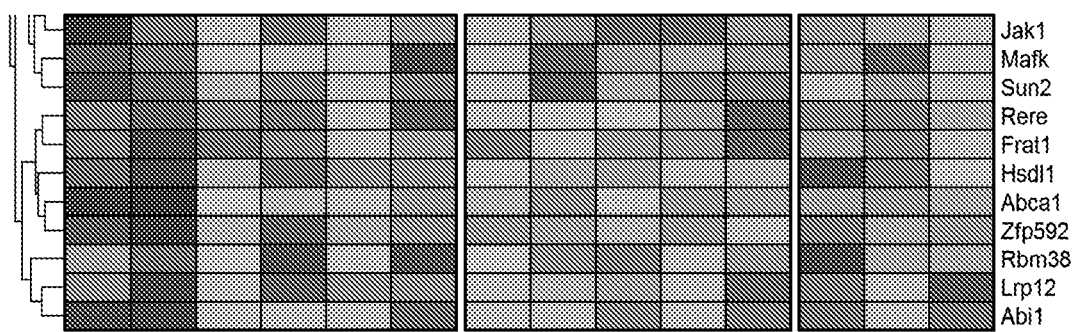

Table 4 shows the expression levels of all genes differentially expressed between the three novel PD-V-CD8 populations (see also FIG. 14).

TABLE 4

Over expressed in CD62L− Slamf7+CX3CR1+ relative to the two other populations

| | CD62L+ Slamf7− | | | | | CD62L− Slamf7+CX3CR1− | | |
|---|---|---|---|---|---|---|---|---|
| Nrd1 | 30.15 | 27.06 | 22.14 | 27.59 | 29.96 | 22.29 | 23.41 | 23.24 |
| Smim3 | 10.54 | 11.34 | 6.93 | 8.08 | 18.98 | 9.19 | 9.15 | 13.68 |
| Prkx | 23.48 | 27.54 | 22.22 | 31.31 | 36.91 | 23.61 | 22.98 | 23 |
| Osbpl3 | 3.88 | 1.6 | 5.26 | 3.33 | 2.54 | 2.06 | 3.81 | 3.26 |
| Mdm1 | 1.63 | 1.38 | 4.43 | 1.59 | 2.91 | 1.92 | 1.46 | 3.4 |
| Pmaip1 | 15.89 | 31.19 | 23.82 | 7.36 | 29.76 | 19.54 | 29.48 | 35.57 |
| Ckb | 4.41 | 5.67 | 2.95 | 1.84 | 1.77 | 3.74 | 4.49 | 5.1 |
| Otub1 | 52.94 | 43.89 | 58.91 | 48.41 | 53.85 | 47.47 | 50.21 | 40.99 |
| Mid1ip1 | 15.53 | 7.25 | 9.39 | 8.4 | 10.68 | 9.77 | 9.56 | 10.08 |
| Atp2b1 | 12.46 | 15.01 | 15.08 | 13.96 | 11.06 | 19.28 | 16.86 | 15.43 |
| Abhd5 | 2.75 | 2.42 | 6.86 | 3.22 | 3.33 | 6.97 | 7.48 | 2.93 |
| Wdr92 | 54.28 | 43.05 | 37.36 | 42.86 | 51.24 | 38.35 | 41.28 | 54.12 |
| Ngfr | 0 | 0 | 0 | 0.04 | 0.05 | 0 | 0.17 | 0.17 |
| Myo1c | 5.94 | 5.75 | 8.98 | 6.97 | 4.83 | 4.95 | 5.84 | 5.98 |
| Vmp1 | 30.97 | 37.41 | 44.01 | 43.25 | 38.92 | 31.92 | 43.81 | 44.49 |
| Tpm4 | 133.45 | 146.71 | 223.34 | 159.93 | 217.03 | 162.31 | 173.31 | 163.21 |
| Errfi1 | 35.29 | 39.36 | 46.58 | 27.66 | 84.66 | 29.68 | 47.74 | 49.55 |
| Plec | 11.27 | 11.16 | 17.68 | 9.23 | 8.91 | 12.41 | 11.26 | 8.94 |
| Flnb | 2.99 | 1.95 | 4.17 | 1.19 | 2.44 | 2.84 | 2.94 | 3.07 |
| Cdkn1a | 25.97 | 16.91 | 37.39 | 15.31 | 16.82 | 30.12 | 17.48 | 26.52 |
| Tuba1a | 197.27 | 230.22 | 279.27 | 211.49 | 212.68 | 229.77 | 146.73 | 128.66 |
| Tax1bp3 | 13.46 | 12.06 | 18.48 | 13.9 | 19.27 | 19.05 | 12.57 | 13.42 |
| Mcu | 4.05 | 3.62 | 8.52 | 3.06 | 4.85 | 3.36 | 4.52 | 2.49 |
| Arhgdia | 136.31 | 162.16 | 163.98 | 155.13 | 158.67 | 162.3 | 169.04 | 133.39 |
| Pogk | 1.2 | 7.03 | 4 | 4 | 4.29 | 4.86 | 5.34 | 0.31 |
| Got1 | 19.07 | 24.08 | 34.59 | 32.99 | 33.22 | 28.93 | 30.56 | 27.92 |
| Slc4a2 | 3.16 | 5.17 | 6.71 | 5.76 | 8.35 | 6.1 | 5.95 | 7.16 |
| Aph1a | 16.41 | 22.52 | 21 | 19.73 | 25.39 | 23.72 | 25.88 | 19.15 |
| Kcnj8 | 8.08 | 3.9 | 11.97 | 11.77 | 34.9 | 15.28 | 18.48 | 13.17 |
| Rnf216 | 1.69 | 2 | 4.73 | 2.09 | 7.03 | 3.82 | 2.23 | 5.06 |
| Ndfip2 | 7.85 | 16.12 | 13.4 | 17.06 | 21.93 | 10.27 | 13.2 | 12.85 |
| Prf1 | 29.97 | 45.36 | 20.04 | 26.92 | 30.8 | 18.52 | 39.91 | 56.13 |
| Tnrc18 | 2.53 | 3.03 | 3.05 | 3.32 | 2.54 | 2.77 | 3.53 | 3.68 |
| Ddx28 | 11.19 | 4.23 | 5.16 | 8.34 | 3.24 | 4.26 | 10.9 | 8.66 |
| Spn | 21.23 | 17.4 | 13.03 | 12.82 | 16.87 | 10.72 | 16.87 | 14.64 |
| Rora | 8.02 | 9.26 | 8.29 | 14.56 | 18.34 | 7.18 | 26.4 | 19.59 |
| Rhof | 20.04 | 23.41 | 21.66 | 24.6 | 29.41 | 28.34 | 29.86 | 25.75 |
| Il18rap | 17.37 | 37.46 | 30.54 | 57.57 | 28.58 | 29.86 | 51.06 | 47.52 |
| Rap1gap2 | 1.16 | 1.94 | 0.47 | 1.09 | 0.05 | 0.22 | 1.1 | 0.32 |
| Klrg1 | 0 | 0.57 | 0.19 | 0 | 0 | 1.58 | 8.86 | 7.34 |
| Gzma | 16.6 | 41.39 | 33.29 | 76.77 | 52.83 | 34.59 | 196.87 | 182.54 |
| Ccl5 | 1586.63 | 1871.59 | 1573.36 | 2569 | 2270.95 | 2573.5 | 2715.86 | 2152.51 |
| Lmf2 | 16.6 | 15.12 | 15.47 | 12.93 | 19.28 | 19.09 | 21.17 | 14.71 |
| Abcb1b | 6.51 | 12.66 | 7.19 | 10.34 | 21.82 | 6.61 | 18.08 | 5.57 |
| Dtx1 | 4.26 | 2.17 | 2.1 | 5.83 | 7.76 | 5 | 5.64 | 1.93 |
| Tug1 | 40.13 | 32.62 | 35.73 | 66.99 | 44.1 | 43.81 | 54.73 | 37.61 |
| A830080D01Rik | 4.84 | 1.57 | 2.71 | 6.14 | 3.9 | 3.74 | 6.07 | 3.75 |
| Lrrc8d | 4.32 | 2.9 | 4.56 | 6.85 | 5.61 | 5.49 | 6.59 | 4.91 |
| Prkaa1 | 5.69 | 4.6 | 7.13 | 8.75 | 6.06 | 6.39 | 6.97 | 4.37 |
| Slc4a7 | 2.31 | 1.68 | 3.17 | 2.87 | 1.66 | 2.06 | 2.76 | 0.25 |
| 2010012O05Rik | 2.31 | 3.4 | 7.02 | 5.41 | 2.24 | 3.1 | 4.27 | 0.79 |
| Gpd2 | 1.41 | 2.51 | 7.27 | 2.45 | 4.61 | 5.4 | 4.88 | 0 |
| As3mt | 4.43 | 6.74 | 6.57 | 5.82 | 4.49 | 9.11 | 9.85 | 4.09 |
| Hnrpll | 0.45 | 1.15 | 1.53 | 1.46 | 0.47 | 1.23 | 0.48 | 0 |
| Alox8 | 0.65 | 0.71 | 0.95 | 0.75 | 0.97 | 0.74 | 0.49 | 0.7 |
| Nfe2l1 | 9.37 | 8.71 | 11.68 | 7.6 | 10.01 | 12.19 | 12.33 | 9.49 |
| Emp3 | 78.7 | 89.53 | 120.3 | 69.74 | 38.49 | 94.3 | 105.7 | 106.59 |
| Ywhaq | 122.63 | 128.91 | 151.8 | 135.68 | 90.33 | 149.54 | 161.03 | 151.51 |
| Cmpk1 | 49.23 | 64.51 | 46.57 | 46.41 | 15.95 | 50.26 | 66.86 | 38.25 |
| Tmem109 | 22.11 | 31.49 | 25.59 | 25.06 | 16.41 | 18.54 | 31.46 | 12.5 |
| Adar | 21.17 | 17.44 | 17.68 | 21.67 | 13.45 | 14.96 | 16.31 | 11.67 |
| Rab14 | 39.7 | 35.33 | 31.03 | 37.17 | 31.02 | 31.42 | 32.69 | 29.58 |
| Suco | 9.27 | 12.23 | 9.02 | 8.45 | 14.68 | 12.04 | 11.67 | 13.11 |
| Atp10d | 7.78 | 9.87 | 5.57 | 7.2 | 10.91 | 8.18 | 6.36 | 7.55 |
| Meis3 | 14.81 | 18.44 | 10.18 | 10.89 | 16.57 | 12.32 | 13.65 | 13.54 |
| Kpna1 | 26.75 | 38.61 | 27.72 | 39.21 | 42.46 | 32.91 | 30.2 | 21.96 |
| Lpin1 | 12.71 | 16 | 12.33 | 15.69 | 22.85 | 17.72 | 18.97 | 9.05 |
| Cd97 | 76.8 | 77.52 | 54.24 | 87.56 | 92.87 | 100.92 | 79.25 | 59.93 |
| Pik3r1 | 17.1 | 18.04 | 15.04 | 19.9 | 21.86 | 21.01 | 15.29 | 14.58 |
| Mest | 0.49 | 0 | 0.05 | 0.06 | 0.39 | 0 | 0.15 | 0 |
| Lats2 | 14.46 | 7.92 | 11.24 | 11.41 | 12.49 | 8.72 | 9.34 | 4.95 |

TABLE 4-continued

| | | | | | | | | |
|---|---|---|---|---|---|---|---|---|
| Vopp1 | 50.77 | 34.17 | 41.61 | 48.55 | 50.76 | 32.45 | 51.22 | 29.63 |
| Arhgap26 | 14.94 | 15.14 | 14.03 | 20.02 | 16.99 | 12.85 | 20.45 | 13.3 |
| Strip1 | 16.41 | 19.03 | 19.73 | 22.78 | 21.3 | 21.36 | 19.17 | 18.13 |
| Ncald | 4.17 | 1.77 | 1.7 | 7.41 | 8 | 2.65 | 5.04 | 3.74 |
| Slc20a1 | 56.24 | 59.23 | 49.39 | 72.95 | 66.98 | 48.83 | 61.88 | 55.97 |
| Hiatl1 | 23.21 | 19.31 | 22.05 | 31.15 | 16.95 | 25.26 | 23 | 30.68 |
| Trim35 | 23.52 | 16.68 | 25.09 | 24.63 | 12.68 | 18.45 | 20.54 | 23.98 |
| Snx11 | 3.92 | 2.82 | 4.78 | 6.58 | 5.18 | 2.24 | 3.88 | 7.37 |
| F730043M19Rik | 0.6 | 0 | 0.17 | 0.68 | 0 | 0.2 | 0.72 | 2.79 |
| Smpdl3b | 3.54 | 1.05 | 1.58 | 5.35 | 0 | 4.78 | 5.78 | 10.17 |
| Zeb2 | 1.16 | 1.99 | 1.34 | 1.32 | 0 | 2.61 | 2.04 | 4.6 |
| Capn2 | 21.61 | 20.38 | 38.79 | 24.59 | 16.88 | 24.51 | 31.1 | 35.77 |
| Zmiz1 | 2.29 | 7 | 4.13 | 4.77 | 3.72 | 7.79 | 4.07 | 10.19 |
| Flna | 32.13 | 40.46 | 35.62 | 29.24 | 34.36 | 38.13 | 39.68 | 48.85 |
| Dock5 | 0.36 | 2.09 | 1.37 | 1.66 | 0.3 | 0.64 | 1.06 | 1.99 |
| Rap1b | 69.23 | 69.75 | 53.59 | 63.96 | 46.01 | 73.88 | 68.93 | 46.18 |
| Ube2g2 | 49.05 | 70.36 | 56.72 | 63.05 | 52.92 | 65.24 | 65.6 | 51.31 |
| Nhsl2 | 0.09 | 0.67 | 0.05 | 0.08 | 0.02 | 0.01 | 0.16 | 0.04 |
| Hist1h1c | 9.6 | 8.73 | 7.7 | 4.85 | 4.62 | 8.25 | 8.16 | 5.89 |
| Mmp25 | 0.46 | 0.23 | 0.24 | 0.04 | 0 | 0 | 0.11 | 2.46 |
| Tyk2 | 17.62 | 14.16 | 16.71 | 17.31 | 7.33 | 11.11 | 15.48 | 22.35 |
| Csgalnact2 | 1.14 | 3.35 | 5.17 | 2.9 | 0.22 | 0.67 | 2.89 | 6.33 |
| 9930111J21Rik1 | 42.92 | 27.45 | 20.34 | 47.27 | 22.82 | 21.37 | 50.12 | 40.52 |
| Atg4d | 17.81 | 16.16 | 11.65 | 19.88 | 10.25 | 11.14 | 17.87 | 19.56 |
| Nup50 | 17.11 | 17.14 | 16.56 | 19.84 | 12.73 | 16 | 20.14 | 17.04 |
| Zfp36l2 | 46.36 | 56.01 | 46.28 | 53.98 | 35.64 | 47.9 | 57.18 | 44.9 |
| Itm2c | 52.24 | 59.23 | 57.43 | 69.23 | 57.65 | 54.34 | 70.83 | 63.09 |
| Armc7 | 23.16 | 28.38 | 26.4 | 42.36 | 34.03 | 30.42 | 42.8 | 24.87 |
| Gimap3 | 523.36 | 470.27 | 401.75 | 603.14 | 449.8 | 474.35 | 631.14 | 581.15 |
| Vps54 | 8.84 | 8.83 | 8.39 | 9.35 | 8.97 | 6.61 | 10.31 | 8.75 |
| D16Ertd472e | 15.77 | 17.68 | 16.32 | 23.69 | 24.06 | 22.39 | 24.69 | 24.9 |
| Casp4 | 4.76 | 2.28 | 6.1 | 3.81 | 15.68 | 3.86 | 13.47 | 11.44 |
| Tnfaip3 | 583.7 | 621.5 | 559.51 | 654.26 | 728.17 | 678.42 | 712.47 | 663.54 |
| Ostf1 | 214.39 | 203.68 | 171.42 | 187.21 | 213.66 | 216.11 | 226.37 | 234.39 |
| Cd6 | 115.93 | 98.67 | 93.9 | 109.78 | 115.75 | 96.73 | 146 | 177.11 |
| Mxd1 | 84.22 | 77.94 | 79.05 | 98.7 | 96.49 | 82.87 | 98.04 | 113.02 |
| Laptm5 | 673.65 | 712.58 | 631.74 | 800.41 | 760.89 | 705.87 | 910.62 | 929.47 |
| Sh2d2a | 89.79 | 104.95 | 103.44 | 116.99 | 129.95 | 109.83 | 159.78 | 160.87 |
| Inpp5d | 29.97 | 32.78 | 30.9 | 34.8 | 43.06 | 31.28 | 43.95 | 38.33 |
| Abcb1a | 17.9 | 15.09 | 19.58 | 19.71 | 36.84 | 14.93 | 35.57 | 35.1 |
| Il12rb2 | 33.46 | 19.92 | 34.33 | 58.74 | 66.3 | 36.69 | 102.56 | 82.18 |
| Notch2 | 7.9 | 9.3 | 8.19 | 8.51 | 4.74 | 8.13 | 9.2 | 10 |
| Ahnak | 19.75 | 36.35 | 29.7 | 27.25 | 27.87 | 29.52 | 27.29 | 30.89 |
| Lmbrd1 | 9.11 | 9.41 | 9.6 | 10.56 | 7.25 | 11.88 | 9.15 | 8.74 |
| Insl6 | 17.62 | 15.53 | 16.43 | 9.41 | 12.91 | 15.11 | 18.27 | 3.14 |
| Ptger4 | 14.56 | 11.55 | 7.37 | 23.22 | 13.12 | 13.96 | 17.69 | 11.11 |
| Tmprss13 | 0 | 0 | 0.08 | 0.14 | 0 | 0 | 0.63 | 0.81 |
| Trex1 | 88.79 | 70.21 | 67.52 | 70.06 | 68.08 | 77.16 | 94.86 | 98.46 |
| Over expressed in CD62L − Slamf7+CX3CR1+ and CD62L − Slamf7+CX3CR1− relative to CD62L+Slamf7− | | | | | | | | |
| Cyth4 | 56.27 | 60.7 | 36.77 | 51.61 | 57.07 | 46.11 | 78.61 | 80.5 |
| Card11 | 27.3 | 29 | 23.58 | 25.6 | 26.94 | 25.93 | 29.63 | 32.7 |
| Gna15 | 7.67 | 14.97 | 8.77 | 8.5 | 14.71 | 9.93 | 24.02 | 29 |
| 9930111J21Rik2 | 10.59 | 12.3 | 7.23 | 9.76 | 8.15 | 9.46 | 18.72 | 14.33 |
| Slc3a4 | 3.83 | 6.91 | 5.05 | 4.63 | 3.24 | 4.27 | 9.58 | 7.42 |
| Serpinb6b | 54.21 | 115.61 | 95.61 | 109.1 | 110.64 | 77.15 | 204.92 | 136.54 |
| Edaradd | 1.15 | 1.57 | 1.14 | 0.58 | 1.82 | 0.97 | 3.23 | 2.18 |
| Als2 | 3.64 | 6.39 | 5.05 | 4.51 | 7.16 | 2.66 | 10.27 | 8.05 |
| St8sia4 | 12.35 | 17.55 | 11.39 | 13.87 | 17.18 | 12.95 | 26.51 | 29.19 |
| Surf4 | 64.04 | 77.72 | 70.99 | 68.57 | 61.55 | 59.8 | 97.13 | 106.33 |
| Prkcd | 20.39 | 26.64 | 18.59 | 24.89 | 19.08 | 27.63 | 36.16 | 53.89 |
| BC017643 | 39.42 | 31.67 | 33.43 | 26.49 | 31.43 | 35.79 | 42.17 | 50.63 |
| Rcc1 | 7.05 | 6.99 | 10.64 | 5.49 | 3.51 | 7.04 | 12.08 | 16.22 |
| Cd40lg | 1.36 | 0 | 0.63 | 0.61 | 0 | 0.37 | 13.06 | 5.12 |
| Itgax | 1.61 | 1.45 | 3.91 | 3.91 | 0 | 5.41 | 12.77 | 14.6 |
| Slc43a3 | 0.24 | 1.07 | 0.24 | 0.12 | 0.05 | 0.41 | 5.06 | 2.39 |
| Zbtb32 | 0 | 0 | 0 | 0.68 | 0 | 0 | 11.49 | 4.35 |
| Tram1 | 34.68 | 33.39 | 38.51 | 41.22 | 28.32 | 45.09 | 64.35 | 61.63 |
| Cox5a | 134.87 | 118.94 | 163.6 | 137.69 | 127.89 | 145.41 | 226.47 | 218.54 |
| Capza1 | 137.72 | 154.9 | 155.57 | 187.48 | 159.54 | 163.31 | 202.46 | 186.32 |
| Crot | 22.01 | 22.94 | 18.19 | 29.4 | 14.21 | 25.61 | 42.22 | 43.61 |
| Edf1 | 100.35 | 79.62 | 99.04 | 116.83 | 73.74 | 106.85 | 140 | 129.21 |
| Sumo2 | 266.9 | 275.86 | 307.17 | 343.8 | 291.66 | 337.89 | 360.35 | 415.36 |
| Gpr114 | 60.61 | 95.25 | 68.55 | 111.13 | 65.87 | 97.19 | 157.91 | 208.11 |
| Lig1 | 3.01 | 5.77 | 8.42 | 5.19 | 6.46 | 5.01 | 19.19 | 18.47 |
| Hif1a | 46.14 | 51.04 | 49.72 | 50.14 | 61.66 | 50.2 | 97.82 | 104.19 |
| Atf6b | 10.51 | 7.2 | 12.42 | 9.13 | 7.66 | 10.46 | 15.9 | 18.13 |
| Cd38 | 3.84 | 10.84 | 7.82 | 5.93 | 7.41 | 11.87 | 16.9 | 22.89 |
| Rps6ka1 | 15.42 | 23.93 | 21.84 | 19.32 | 13.43 | 19.96 | 33.12 | 47.44 |
| Pik3ap1 | 7 | 10.21 | 8.95 | 7.12 | 15.73 | 10.43 | 27.38 | 27.37 |

TABLE 4-continued

| | | | | | | | | |
|---|---|---|---|---|---|---|---|---|
| Tnfsf14 | 9.69 | 3.1 | 9.9 | 8.81 | 10.51 | 11.07 | 30.78 | 24.66 |
| Ndufs4 | 31.53 | 18.32 | 34.57 | 27.55 | 24.44 | 19.7 | 47.41 | 48.7 |
| Ncaph | 1.67 | 0.17 | 4.49 | 0.45 | 0.55 | 0.46 | 5.85 | 7.62 |
| Espl1 | 0 | 0 | 0.14 | 0 | 0 | 0.21 | 1.12 | 1.22 |
| Cox6b1 | 150.74 | 142.68 | 207.41 | 164.07 | 139.22 | 152.46 | 264.06 | 256.58 |
| Dynlrb1 | 108.93 | 83.76 | 123.77 | 106.42 | 101.53 | 113.37 | 141.94 | 169.94 |
| Psmb6 | 108.79 | 72.55 | 140.93 | 98.25 | 99.03 | 110.9 | 140.71 | 169.58 |
| Sh3bgrl3 | 490.33 | 519.91 | 601.4 | 486.56 | 495.53 | 515.28 | 721.12 | 793.95 |
| Ccl3 | 11.19 | 24.77 | 29.97 | 14.76 | 3.73 | 18.64 | 67.38 | 94.64 |
| Agpat3 | 12.44 | 10.93 | 11.77 | 13.48 | 11.39 | 13.92 | 20.39 | 23.38 |
| Rab8b | 23.66 | 19.56 | 28.99 | 36.35 | 35.63 | 31.25 | 61.07 | 71.07 |
| Rwdd1 | 59.26 | 60.42 | 66 | 68.04 | 45.14 | 49.48 | 88.96 | 81.43 |
| Ak2 | 32.02 | 52.09 | 56.08 | 46.98 | 45.72 | 37.42 | 68.4 | 83.65 |
| Ezh2 | 4.21 | 5.33 | 8.03 | 4.91 | 1.98 | 3.3 | 10.35 | 10.87 |
| Whsc1 | 2.35 | 2.57 | 4.58 | 2.51 | 1.62 | 2.13 | 4.88 | 6.87 |
| Hprt | 70.8 | 72.63 | 94.2 | 76.69 | 83.58 | 90.85 | 118.79 | 109.45 |
| Clic1 | 350.72 | 331.48 | 381.66 | 361.64 | 326.78 | 335.58 | 469.66 | 437.11 |
| Pfn1 | 773.39 | 738.14 | 906.76 | 862.18 | 695.11 | 874.35 | 1194.03 | 1176.31 |
| Etfb | 30.18 | 40.71 | 40.09 | 33.34 | 30.28 | 35.97 | 64.22 | 56.67 |
| Psmb3 | 148.46 | 137.66 | 203.17 | 159.35 | 116.58 | 173.33 | 252.95 | 241.66 |
| Shfm1 | 155.04 | 159.08 | 182.08 | 164.12 | 150.2 | 178.07 | 238.69 | 202.52 |
| Cd52 | 545.56 | 641.54 | 539.26 | 640.83 | 433.67 | 644.06 | 1098.05 | 1193.27 |
| AW112010 | 546.93 | 561.36 | 654.26 | 792.14 | 506.29 | 653.94 | 1429.64 | 1263.11 |
| A430107P09Rik | 16.37 | 21.08 | 16.41 | 19.83 | 14.94 | 18.5 | 34.8 | 36.88 |
| Dlgap5 | 0.78 | 0.7 | 0.73 | 0.97 | 0.27 | 1.56 | 5.02 | 3.83 |
| Vmn1r132 | 0.23 | 0.37 | 0.42 | 0.76 | 1.38 | 0.89 | 2.39 | 7.54 |
| Zfp300 | 4.55 | 5.89 | 4.66 | 5.16 | 5.25 | 5.14 | 12.7 | 16.84 |
| 4930511M06Rik | 34.59 | 40.24 | 31.55 | 36.24 | 49.55 | 44.62 | 105.29 | 138.1 |
| Vmn1r58 | 43.19 | 58.63 | 43.02 | 56.79 | 67.58 | 62.78 | 183.53 | 250.98 |
| Olfr613 | 14.58 | 16.39 | 13.56 | 16.27 | 20.82 | 17.91 | 55.01 | 80.53 |
| A730017L22Rik | 27.34 | 37.04 | 27.53 | 36.01 | 37.57 | 43.78 | 66.14 | 96.72 |
| A130077B15Rik | 309.43 | 479.75 | 339.73 | 428.34 | 591.87 | 520.48 | 1208.99 | 1821.4 |
| Zfp277 | 68.04 | 102.53 | 74.49 | 78.32 | 112.64 | 101.87 | 218.87 | 340.77 |
| 2010002M12Rik | 1.04 | 1.51 | 1.35 | 0.97 | 1.31 | 1.35 | 2.06 | 2.66 |
| Tyms | 2.89 | 5.1 | 5.93 | 4.79 | 4.71 | 5.4 | 22.09 | 24.26 |
| Il2ra | 0.11 | 2.18 | 0.47 | 0.74 | 0.07 | 0.49 | 5.55 | 5.71 |
| Ppm1j | 10.73 | 27.63 | 17.99 | 17.17 | 25.16 | 22.03 | 30.62 | 38.87 |
| Ccr2 | 9.03 | 13.43 | 7.81 | 14.07 | 13.93 | 15.7 | 30.43 | 45.44 |
| Adam19 | 7.92 | 9.61 | 7.36 | 5.31 | 7.89 | 7.84 | 16.84 | 15.89 |
| Spag5 | 0 | 0.08 | 0.28 | 0.87 | 0 | 0 | 1.8 | 3.75 |
| Gm20139 | 0.05 | 0.09 | 0.04 | 0 | 0 | 0.03 | 0.29 | 0.72 |
| Cdc20 | 3.04 | 2.26 | 5.04 | 3.23 | 5.97 | 2.49 | 8 | 14.46 |
| Ska1 | 0 | 0.06 | 0.05 | 0 | 0 | 0 | 1.97 | 8.93 |
| Sgol1 | 0.09 | 0.13 | 1.03 | 0.5 | 0.05 | 0.09 | 1.54 | 9.6 |
| Aqp9 | 0.35 | 1.82 | 1.55 | 1.66 | 1.11 | 1.1 | 3.22 | 10.89 |
| Ska3 | 0.69 | 0.15 | 0.73 | 1.03 | 0.15 | 0.55 | 2.71 | 7.62 |
| Mcam | 0.16 | 0 | 0.09 | 0 | 0 | 0 | 0 | 2.74 |
| Birc5 | 2.06 | 2.59 | 3.88 | 3.12 | 1.24 | 1.13 | 11.63 | 23.99 |
| Kif11 | 0 | 0.13 | 0.45 | 0 | 0 | 0.06 | 4.08 | 13 |
| Fgl2 | 11.6 | 3.3 | 11.75 | 12.9 | 9.57 | 12.65 | 43.14 | 94.87 |
| Prc1 | 1.96 | 1.37 | 1.6 | 0.56 | 0.11 | 1.38 | 3.76 | 12.54 |
| Tmc8 | 13.75 | 11.87 | 9.32 | 13.04 | 9.97 | 11.1 | 16.24 | 19.84 |
| Hip1 | 1.18 | 1.84 | 0.84 | 2.66 | 0.65 | 0.06 | 3.35 | 6.67 |
| Stil | 0 | 0.23 | 0.05 | 0 | 0 | 0.03 | 2.92 | 6.05 |
| Spc25 | 0 | 0.68 | 2.21 | 0 | 0.12 | 0 | 12.41 | 18.49 |
| Spc24 | 13.58 | 8.02 | 7.7 | 6.99 | 5.14 | 9.48 | 28.53 | 28.74 |
| Tpx2 | 1.51 | 0.2 | 1.7 | 0.91 | 0.39 | 0.58 | 7.01 | 8.47 |
| Mki67 | 0 | 0.55 | 0.89 | 0.62 | 0.1 | 0.3 | 5.14 | 9.1 |
| Stmn1 | 9.95 | 7.33 | 24.83 | 6.85 | 0.46 | 8.97 | 64.04 | 85.1 |
| Hdac9 | 0.06 | 0 | 0.03 | 0 | 0 | 0.06 | 0.14 | 0.67 |
| Clspn | 0.31 | 0.72 | 0.9 | 0.24 | 0.23 | 0.34 | 1.3 | 3.02 |
| E2f2 | 0.88 | 0.07 | 1.28 | 0.35 | 0.14 | 0.84 | 2.97 | 4.65 |
| Ncapg | 0 | 0.09 | 1.05 | 1.71 | 0 | 0.08 | 7.8 | 10.61 |
| Cdca8 | 0.95 | 3.82 | 4.55 | 1.58 | 0 | 4.34 | 14.71 | 29.88 |
| Nuf2 | 0.57 | 0.47 | 3.5 | 0.62 | 0.63 | 0.98 | 4.26 | 11.08 |
| Tuba1b | 282.85 | 268.04 | 449.2 | 268.05 | 308.08 | 315.73 | 457.04 | 566.02 |
| Rpa3 | 30.13 | 18.99 | 23.84 | 14.01 | 22.09 | 13.46 | 35.17 | 40.74 |
| Mien1 | 40.64 | 43.21 | 42.66 | 38.28 | 31.28 | 33.4 | 60.33 | 65.56 |
| Vamp8 | 52.07 | 68.25 | 65.28 | 68.41 | 93.62 | 86.06 | 81.86 | 95.12 |
| Gzmk | 1.96 | 10.2 | 4.17 | 17.98 | 11.8 | 6.2 | 62.06 | 52.55 |
| Endod1 | 2.25 | 2.85 | 5.62 | 5.25 | 4.22 | 3.91 | 9.83 | 6.7 |
| Pdcd1 | 5.14 | 9.9 | 7.81 | 12.64 | 9.6 | 2.7 | 25.27 | 19.01 |
| Vbp1 | 63.9 | 65.38 | 65.56 | 81.26 | 91.82 | 70.23 | 91.76 | 70.46 |
| F2r | 33.59 | 36.43 | 37.45 | 47.2 | 60.66 | 34.97 | 75.3 | 47.37 |
| Lrp10 | 24.86 | 30.11 | 34.91 | 24.59 | 44.73 | 30.45 | 49.88 | 47.96 |
| Rpa2 | 20.01 | 36.86 | 28.49 | 32.22 | 53.89 | 33.83 | 46.52 | 64.57 |
| Snx10 | 9.55 | 10.83 | 12.49 | 13.39 | 14.82 | 10.2 | 21.92 | 26.8 |
| Arpc5 | 208.61 | 191.39 | 210.95 | 228.21 | 261.9 | 275.09 | 302.3 | 313.83 |
| Wdr1 | 221.99 | 167.86 | 189.86 | 181.74 | 234.67 | 228.06 | 245.02 | 300.48 |
| Sytl2 | 6.75 | 4.1 | 4.87 | 3.88 | 12.19 | 6.56 | 15.56 | 18.58 |

TABLE 4-continued

| | | | | | | | | |
|---|---|---|---|---|---|---|---|---|
| F2rl2 | 1.26 | 7.18 | 1.99 | 6.89 | 13.44 | 3.8 | 14.53 | 11.69 |
| Smad3 | 16.33 | 18.79 | 15.64 | 26.01 | 28.47 | 18.59 | 24.96 | 31.75 |
| Acsbg1 | 13.8 | 7.22 | 17.73 | 23.53 | 23.92 | 14.32 | 26.48 | 28.1 |
| Map2k3 | 34.36 | 34.34 | 38.28 | 42.66 | 90.03 | 39.87 | 60.51 | 76.69 |
| Slc12a4 | 5.46 | 4.13 | 8.9 | 7.63 | 13.69 | 4.24 | 8.81 | 10.17 |
| Ildr1 | 1.29 | 0.76 | 0.14 | 1.32 | 2.11 | 1.33 | 4.25 | 4.19 |
| Gm8369 | 21.22 | 18.34 | 11.75 | 26.45 | 35.75 | 8.87 | 42.27 | 49.49 |
| Cxcr6 | 18.76 | 18.95 | 16.7 | 40.57 | 37.23 | 22.36 | 144.22 | 131.82 |
| Hmgb2 | 57.93 | 57.97 | 56.67 | 62.01 | 61.12 | 55.03 | 106.3 | 93.47 |
| Ms4a4b | 851.98 | 737.51 | 687.28 | 1043.22 | 795.01 | 767.18 | 1344.44 | 1155.06 |
| Ms4a6b | 371.57 | 295.36 | 308.13 | 447.34 | 402.75 | 404.29 | 568.87 | 519.44 |
| Rac2 | 403.64 | 389.36 | 334.68 | 420.63 | 374.79 | 405.61 | 533.86 | 522.63 |
| Sema4a | 62.3 | 45.37 | 53.19 | 60.72 | 51.11 | 51.52 | 92.25 | 82.73 |
| Srgn | 712.22 | 768.66 | 556.41 | 710.82 | 708.6 | 740.15 | 950.95 | 793.6 |
| Rgs1 | 331.97 | 428.51 | 258.43 | 427.41 | 402.88 | 543.31 | 732.46 | 649.77 |
| Casp1 | 4.41 | 9.24 | 5.07 | 4.3 | 0 | 9.33 | 18.14 | 20.29 |
| Nmi | 52.08 | 51.23 | 57.74 | 67.5 | 46.18 | 54.75 | 72.05 | 60.85 |
| Elf4 | 11.72 | 10.49 | 10.71 | 13.08 | 6.12 | 9.5 | 12.88 | 13.66 |
| Tpm3 | 300.94 | 343.55 | 360.65 | 333.49 | 313.87 | 323.08 | 399.68 | 350.72 |
| Ttc39b | 8.11 | 11.68 | 11.86 | 12.12 | 7.07 | 10.42 | 17.69 | 9.28 |
| Slamf7 | 4.99 | 9.14 | 5.22 | 3.35 | 6.47 | 6.48 | 26.35 | 7.53 |
| Bhlhe40 | 33.92 | 66.05 | 67.25 | 62.96 | 41.43 | 52.72 | 128.29 | 87.18 |
| Ifng | 7.06 | 10.81 | 9.86 | 28.24 | 22.4 | 24.91 | 80.52 | 41.82 |
| Ccl4 | 46.71 | 95.76 | 66.13 | 75.28 | 149.96 | 86.5 | 607.03 | 325.74 |
| Klrc1 | 38.66 | 63.11 | 78.48 | 105.68 | 98.91 | 75.84 | 270.34 | 277.83 |
| Kcnk5 | 0 | 0 | 0.43 | 3.06 | 2.18 | 1.23 | 7.33 | 7.28 |
| Bcl2a1b | 28.03 | 68.34 | 42.49 | 49.72 | 56.3 | 69 | 219.21 | 242.4 |
| Itgal | 64.61 | 94.65 | 69.77 | 82.86 | 68.98 | 83.83 | 163.97 | 151.22 |
| Nkg7 | 663.26 | 956.66 | 787.21 | 897.65 | 831.66 | 890.01 | 1608.34 | 1538.02 |
| 1810037I17Rik | 29.23 | 28.48 | 38.62 | 30.73 | 35.26 | 47.93 | 61.76 | 45.73 |
| Bcl2l1 | 12.1 | 12.9 | 17.46 | 22.17 | 9.12 | 19.08 | 49.28 | 30.69 |
| Myl6 | 519.4 | 506.09 | 608.7 | 532.62 | 411.86 | 576.87 | 876.87 | 705.78 |
| Dclre1b | 1.95 | 1.52 | 2.38 | 2.58 | 0.46 | 1.68 | 4.84 | 2.46 |
| Tespa1 | 16.47 | 17.69 | 15.69 | 21.99 | 14.8 | 20.37 | 31.1 | 21.87 |
| Icos | 38.64 | 46.9 | 37.72 | 45.51 | 33.24 | 51.19 | 108.52 | 79.7 |
| Gm14446 | 46.25 | 22.31 | 36.48 | 66.62 | 26.58 | 30.87 | 90.2 | 69.21 |
| Isg15 | 32.61 | 13.56 | 51.96 | 48.49 | 37.07 | 27.59 | 110.15 | 68.51 |
| Ifih1 | 4.7 | 4.56 | 6.66 | 9.11 | 9.83 | 6.53 | 16.6 | 11.43 |
| Tbx21 | 29.46 | 28.35 | 29.38 | 38.94 | 62.76 | 38.59 | 87.68 | 51.95 |
| Lime1 | 86.74 | 82.68 | 74.25 | 106.16 | 120.8 | 81.04 | 156.87 | 125.94 |
| Pfkp | 42.08 | 51.82 | 50.74 | 61.03 | 74.32 | 55.21 | 88.35 | 80.61 |
| Tnfrsf9 | 12.28 | 10.85 | 6.85 | 13.04 | 60.12 | 5.13 | 132 | 117.83 |
| Cd8a | 154.48 | 147.66 | 140.78 | 163.18 | 149.28 | 143.09 | 246.82 | 215.69 |
| Sla | 110.26 | 124.6 | 126.71 | 143.68 | 121.09 | 120.79 | 208.3 | 172.59 |
| Cd82 | 124.76 | 154.18 | 121.73 | 160.3 | 156.01 | 117.3 | 194.69 | 185.63 |
| Ttc39c | 0 | 0 | 0.44 | 0.57 | 0 | 0.77 | 2.8 | 3.4 |
| Epas1 | 0.14 | 0.17 | 0.07 | 0.14 | 0.1 | 1.15 | 0.53 | 0.19 |
| Ikzf3 | 18.84 | 23.53 | 25.3 | 26.58 | 24.88 | 26.05 | 35.98 | 19.85 |
| Sra1 | 57.89 | 66.16 | 76.95 | 56.87 | 57.38 | 67.68 | 81.26 | 67.08 |
| Tmed5 | 45.16 | 32.15 | 34.65 | 32.04 | 36.64 | 39.68 | 47.26 | 36.72 |
| 2010111I01Rik | 11.18 | 9.47 | 8.59 | 8.63 | 4.25 | 9.66 | 14.85 | 11.32 |
| Wnk1 | 22.31 | 18.56 | 16.84 | 21.85 | 16.15 | 19.19 | 25.35 | 20.12 |
| H2-Q9 | 770.58 | 656.46 | 544.64 | 711.9 | 512.75 | 752.51 | 750.32 | 755.2 |
| Rasal1 | 0.24 | 0.92 | 0.91 | 0.19 | 0.61 | 0.43 | 0.98 | 1.35 |
| Nmrk1 | 21.67 | 28.49 | 22.05 | 22.79 | 29.5 | 25.34 | 30.84 | 27.72 |
| Spsb3 | 42.53 | 38.64 | 33.98 | 29.83 | 28.7 | 35.34 | 32.7 | 34.69 |
| Itga4 | 31.56 | 27.76 | 16.29 | 25.91 | 21.17 | 25.34 | 18.06 | 27.97 |
| Sh2b1 | 16.54 | 12.17 | 12.2 | 18.61 | 10.24 | 16.68 | 15.58 | 19.31 |
| Antxr2 | 13.97 | 11.55 | 12.91 | 12.44 | 18.04 | 17.18 | 11.57 | 17.27 |
| Fam160a2 | 4.02 | 2.91 | 3.78 | 3.21 | 3.83 | 3.33 | 2.77 | 4.97 |
| Socs2 | 0 | 4.04 | 1.28 | 2.19 | 0.16 | 1.85 | 7.66 | 0.18 |
| Serpina3g | 69.26 | 62.49 | 79.32 | 65.93 | 31.16 | 68.42 | 97.83 | 71.42 |
| N4bp3 | 6.03 | 2.35 | 4.56 | 2.83 | 0.06 | 5.19 | 6.56 | 8.27 |
| Gba | 35.07 | 32.11 | 35.53 | 30.23 | 23.89 | 32.74 | 42.36 | 42.59 |
| Tmem184b | 12.32 | 8.32 | 18.73 | 18.79 | 14.87 | 12.92 | 24.67 | 13.17 |
| Aars | 6.85 | 7.4 | 20.14 | 10.9 | 10.56 | 4.98 | 17.17 | 15.29 |
| Zfp781 | 6.87 | 3.14 | 5.79 | 3.23 | 2.36 | 6.92 | 5.72 | 4.35 |
| Klrb1c | 12.19 | 5.72 | 11.1 | 11.73 | 14.26 | 8.06 | 21.83 | 9.08 |
| Gm14005 | 5.46 | 4.17 | 5.98 | 4.62 | 2.97 | 7.2 | 10.38 | 14.44 |
| Dnmt1 | 16.23 | 10.04 | 15.77 | 11.17 | 9.43 | 13.52 | 24.94 | 22.87 |
| Ppme1 | 21.75 | 15.26 | 23.81 | 20.33 | 13.88 | 27.44 | 32.91 | 26.8 |
| Gm2382 | 28.95 | 17.06 | 24.93 | 21.62 | 19.15 | 23.28 | 43.32 | 28.46 |
| Actg1 | 2135.15 | 1729.76 | 2589.57 | 2358.61 | 2801.82 | 2171.07 | 3118.49 | 3191.06 |
| Plekhb2 | 17.4 | 25.24 | 33.69 | 23.43 | 32.48 | 28.03 | 46.93 | 42.57 |
| Gzmm | 7.47 | 7.85 | 10.28 | 14.84 | 9.3 | 10.85 | 40.09 | 32.36 |
| Krtcap2 | 94.65 | 91.19 | 117.64 | 134.16 | 114.98 | 140.61 | 207.39 | 152.93 |
| Myl12a | 160.65 | 155.11 | 183.91 | 173.94 | 185.18 | 192.4 | 237.79 | 199.13 |
| Itgb1 | 27.32 | 23.33 | 38.09 | 32.64 | 16.18 | 42.96 | 76.28 | 61.98 |
| Cox17 | 34.49 | 42.74 | 68.86 | 59.76 | 52.62 | 59.1 | 87.63 | 79.49 |
| Tceb2 | 89.12 | 104.44 | 128.35 | 108.84 | 105.17 | 112.33 | 140.92 | 138.28 |

TABLE 4-continued

| | | | | | | | | |
|---|---|---|---|---|---|---|---|---|
| S100a10 | 222.45 | 194.94 | 372.1 | 224.9 | 204.48 | 266.9 | 401.39 | 433.16 |
| Tspo | 258.28 | 209.55 | 283.35 | 279.59 | 226.87 | 259.3 | 333.45 | 350.48 |
| Srp14 | 95.38 | 98.64 | 122.71 | 117.91 | 90.86 | 123.88 | 156.82 | 128.02 |
| Atp5j2 | 76.06 | 78.13 | 95.65 | 91.46 | 83.83 | 103.87 | 132.2 | 124.66 |
| Calm1 | 155.19 | 155.41 | 188.23 | 165.67 | 155.92 | 208.71 | 211.85 | 182.72 |
| Ube2n | 22.85 | 18.07 | 27.58 | 22.89 | 20.09 | 27.92 | 29.86 | 27.78 |
| Gabarapl2 | 105.68 | 125.98 | 126.18 | 115.77 | 122.25 | 148.38 | 162.38 | 187.95 |
| B4galt4 | 0 | 0 | 0 | 0 | 0.14 | 0 | 0.4 | 2.7 |
| Slamf1 | 8.25 | 13 | 10.63 | 16.74 | 4.76 | 10.5 | 44.57 | 52.19 |
| Cyba | 165.86 | 203.78 | 168.68 | 187.4 | 144.02 | 170.37 | 320.11 | 375.92 |
| Stx11 | 1.38 | 11 | 8.42 | 13.76 | 5.11 | 9.83 | 20.31 | 29.77 |
| Sytl3 | 16.42 | 22.99 | 18.01 | 26.29 | 17.28 | 15.69 | 35.12 | 41.79 |
| Mir22hg | 3.77 | 7.12 | 4.27 | 2.32 | 1.86 | 2.95 | 4.52 | 11.73 |
| Gcnt2 | 2.56 | 4.17 | 1.85 | 0.04 | 0.9 | 1.85 | 2.69 | 12.01 |
| Tnk2 | 1.66 | 3.11 | 2.35 | 3 | 3.96 | 3.39 | 4.01 | 6.05 |
| Atp2b4 | 2.35 | 2.07 | 2.71 | 2.86 | 4.55 | 2.31 | 4.46 | 8.25 |
| Itpripl1 | 10.75 | 10.52 | 11.19 | 12.59 | 12.14 | 11.28 | 11.84 | 16.86 |
| Nucb1 | 44.3 | 58.08 | 48.31 | 47.3 | 34.47 | 44.7 | 67.4 | 67.08 |
| Cfl1 | 732.63 | 701.7 | 776.96 | 733.32 | 596.45 | 786.39 | 939.7 | 989.89 |
| Cdc42 | 327.84 | 316.62 | 324.38 | 365.5 | 259.28 | 378.26 | 415.65 | 453.87 |
| Ccr5 | 16.77 | 13 | 26.88 | 20.32 | 15.6 | 38.09 | 73.62 | 75.75 |
| Sdhb | 94.35 | 99.43 | 121.74 | 104.61 | 95.61 | 128.66 | 137.5 | 137.26 |
| Acly | 43.52 | 45.07 | 47.48 | 44.74 | 46.08 | 54.97 | 62.35 | 64.25 |
| Trerf1 | 3.32 | 6.62 | 3.74 | 3.39 | 1.61 | 3.46 | 6.35 | 8.42 |
| Lgalsl | 1.24 | 1.75 | 2.62 | 1.17 | 0 | 1.14 | 4.23 | 4.97 |
| Flii | 28.56 | 35.15 | 37.78 | 44.08 | 29.78 | 43.51 | 45.09 | 57.03 |
| Aldh18a1 | 15.79 | 11.32 | 23.23 | 17.36 | 8.41 | 19.85 | 28.73 | 28.21 |
| Park7 | 95.28 | 104.94 | 139.97 | 117.92 | 79.13 | 105.49 | 166.57 | 139.4 |
| Prr13 | 56.82 | 64.91 | 69.98 | 80.23 | 43.33 | 74.02 | 96.13 | 100.74 |
| Isy1 | 64.06 | 78.17 | 86.2 | 93.51 | 68.63 | 75.61 | 120.63 | 101.09 |
| Sptlc2 | 22.63 | 11.33 | 26.35 | 22.27 | 14.32 | 15.69 | 29.68 | 30.97 |
| N4bp1 | 4.76 | 1.86 | 4.07 | 4.22 | 1.29 | 2.51 | 5.22 | 6.84 |
| Def6 | 64.28 | 46.79 | 49.66 | 67.79 | 53.91 | 52.81 | 66.7 | 64.1 |
| Mical1 | 50.69 | 32.5 | 33.44 | 42.39 | 28.93 | 31.85 | 42.27 | 50.37 |
| Maea | 52.36 | 42.26 | 47.92 | 52.82 | 44.51 | 69.74 | 59.79 | 73.1 |
| Lypla2 | 43.6 | 32.56 | 40.93 | 47.7 | 26.75 | 54.79 | 59.73 | 81.22 |
| Tmbim6 | 189.19 | 156.26 | 180.01 | 193.29 | 137.99 | 190.44 | 195.46 | 227.93 |
| Cd8b1 | 523.26 | 439.68 | 333.27 | 428.78 | 379.11 | 441.21 | 593.15 | 465.69 |
| Anxa6 | 136.47 | 148.93 | 130.55 | 184.99 | 107.89 | 168.14 | 249.15 | 190.77 |
| Cd226 | 29.05 | 41.51 | 23.5 | 32.1 | 20.43 | 35.86 | 54.66 | 49.68 |
| Med20 | 10.87 | 8.91 | 6.81 | 12.33 | 8.03 | 14.14 | 16.64 | 16.06 |
| Ctsd | 295.48 | 284.99 | 289 | 323.97 | 290.96 | 358.12 | 370.55 | 409.63 |
| Phf11a | 29.61 | 13.67 | 25.24 | 35.73 | 6.71 | 24.86 | 71.41 | 66.57 |
| Baiap3 | 15.78 | 14.66 | 12.32 | 26.66 | 13.77 | 17.64 | 28.93 | 25.7 |
| Atxn1 | 3.05 | 2.41 | 2.75 | 4.38 | 2.01 | 2.62 | 5.24 | 4.73 |
| Xlr4c | 5.4 | 10.7 | 10.79 | 11.47 | 5.47 | 7.36 | 12.12 | 10.27 |
| L1cam | 0.97 | 0.5 | 0.43 | 0.52 | 0.31 | 0.41 | 1.82 | 2.2 |
| Nfatc3 | 16.96 | 19.52 | 13.57 | 20.33 | 14.58 | 18.39 | 18.38 | 18.04 |
| Ppp1cc | 19.88 | 24.02 | 24.63 | 27.25 | 15.36 | 28.18 | 24.4 | 30.24 |
| Atp2a3 | 35.67 | 43.23 | 29.15 | 38.13 | 18.67 | 32.8 | 40.36 | 50.74 |
| Itgb7 | 159.77 | 179.68 | 162.53 | 150.58 | 121.92 | 184.02 | 193.65 | 173.7 |
| Diap1 | 5.6 | 8.05 | 6.04 | 4.26 | 2.4 | 6.26 | 8.11 | 7.27 |
| Gnptg | 51.64 | 52.41 | 49.01 | 46.24 | 54.97 | 64.12 | 66.11 | 60.53 |
| Dusp2 | 166.57 | 216.24 | 173.43 | 93.99 | 175.84 | 236.57 | 279 | 187.05 |
| Ppp1r11 | 11.82 | 14.52 | 15.12 | 10.74 | 16.5 | 14.07 | 22.53 | 16.15 |
| S100a13 | 29.92 | 33.01 | 35.33 | 35.17 | 21.09 | 42.48 | 60.7 | 53.73 |
| Itgb2 | 125.87 | 150.31 | 124.06 | 154.12 | 118.72 | 165.13 | 194.59 | 196.23 |
| Bcl2a1d | 8.14 | 12.04 | 5.07 | 15.21 | 8.45 | 28.14 | 76.9 | 47.05 |
| Cish | 23.68 | 24.58 | 33.43 | 39.32 | 35.57 | 42.62 | 103.5 | 44.19 |
| Fasl | 19.67 | 50.5 | 27.6 | 44.95 | 63.46 | 29.06 | 119.58 | 115.87 |
| Id2 | 142.73 | 108.66 | 128.99 | 168.59 | 207.68 | 171.14 | 264.12 | 277.73 |
| Dennd5a | 2.19 | 1.35 | 2.51 | 2.42 | 3.97 | 1.02 | 4.9 | 4.18 |
| Dok2 | 90.39 | 45.85 | 61.31 | 80.19 | 89.91 | 103.81 | 106.18 | 105.41 |
| Apod | 0 | 0 | 0.07 | 0 | 0.09 | 0 | 2.69 | 0 |
| Nr4a1 | 157.04 | 169.73 | 141.27 | 194.53 | 176.53 | 205.38 | 274.2 | 177.74 |
| Gnptab | 5.78 | 1.73 | 4.55 | 4.69 | 7.46 | 7.52 | 7.88 | 10.86 |
| Acpl2 | 12.08 | 3.83 | 5.34 | 8.35 | 13.34 | 8.75 | 13.08 | 17.87 |
| Sord | 5.83 | 2.75 | 1.46 | 0.6 | 2.25 | 2.04 | 6.32 | 6.09 |
| Prdm1 | 1.75 | 1.48 | 1.36 | 1.53 | 0.1 | 1.94 | 2.99 | 3.66 |
| Il10ra | 25.52 | 25.07 | 17.57 | 24.85 | 12 | 22.66 | 49.27 | 61.17 |
| H2-Q10 | 3.25 | 1.77 | 0.79 | 3.58 | 0.58 | 4.9 | 15 | 23.31 |
| St3gal4 | 39.27 | 28.01 | 31.09 | 29.41 | 16.07 | 32.66 | 42.41 | 54.3 |
| Cd48 | 141.31 | 108.41 | 111.88 | 155.3 | 79.94 | 142.39 | 240.03 | 286.05 |
| Mier3 | 1.91 | 1.68 | 2.11 | 1.89 | 2.14 | 3.6 | 4.08 | 1.68 |
| Plekho2 | 12.57 | 12.5 | 15.59 | 14.93 | 10.48 | 19.11 | 22.8 | 15.68 |
| Myo18a | 2.23 | 2.1 | 3.22 | 1.37 | 1.91 | 4.39 | 3.28 | 3.33 |
| H2-DMb1 | 7.85 | 2.77 | 11.68 | 6.1 | 0 | 28.9 | 10.7 | 11.29 |
| Atp6v0e | 130.21 | 109.64 | 125.68 | 146.84 | 120.79 | 179.75 | 148.41 | 176.72 |
| Nprl2 | 19.57 | 14.7 | 15.15 | 25.35 | 12.36 | 24.48 | 21.75 | 20.93 |
| Serpinb9 | 24.14 | 58.01 | 42.21 | 54.49 | 48.72 | 41.45 | 114.98 | 58.05 |

TABLE 4-continued

| | | | | | | | | |
|---|---|---|---|---|---|---|---|---|
| Gzmb | 69.85 | 73.37 | 92.09 | 186.03 | 301.27 | 111.54 | 1153.31 | 533.21 |
| Ccnd3 | 79.04 | 108.29 | 85.08 | 122.65 | 126.79 | 94.69 | 180.8 | 120.92 |
| Nabp1 | 25.18 | 25.89 | 19.99 | 32.45 | 43.25 | 28.48 | 61.93 | 34.26 |
| Sh3bp2 | 2.9 | 1.48 | 2.09 | 0.8 | 5.52 | 2.27 | 6.88 | 3.46 |
| Gp49a | 47.96 | 68.52 | 60 | 81.02 | 89.29 | 76.76 | 201.7 | 173.8 |
| Lilrb4 | 67.58 | 44.17 | 47.86 | 75.86 | 72.77 | 106.51 | 182.14 | 155.74 |
| Nfe2l2 | 30.58 | 16.92 | 31.28 | 38 | 34.45 | 25.29 | 40.5 | 31.2 |
| Ssb | 59.26 | 49.65 | 72.14 | 66.88 | 61.14 | 63.37 | 73.63 | 68.75 |
| Cap1 | 43.54 | 34.78 | 52.22 | 44.81 | 48.21 | 46.83 | 51.38 | 48.79 |
| Gypc | 17.41 | 8.9 | 7.46 | 10.97 | 3.08 | 6.82 | 16.57 | 11.48 |
| Lmnb1 | 16.03 | 2.89 | 4.51 | 5.17 | 3.69 | 5.34 | 10.69 | 13.31 |
| Mapkapk3 | 27.97 | 13.29 | 21.21 | 17.97 | 11.47 | 13.29 | 31.09 | 25.68 |
| Map4 | 33.77 | 26.27 | 27.71 | 26.46 | 17.94 | 27.85 | 31.9 | 25.93 |
| Actb | 2494.06 | 2417.94 | 2577.65 | 2814.33 | 2511.2 | 2726.16 | 3148.15 | 3425.63 |
| 2310003H01Rik | 5.81 | 3.03 | 5.46 | 4.63 | 1.6 | 6.28 | 8.76 | 8.48 |
| Cox6a1 | 139.33 | 179.18 | 185.85 | 173.93 | 143.29 | 204.6 | 221.3 | 212.71 |
| Rps6ka4 | 10.83 | 19.5 | 19.54 | 16.39 | 6.12 | 19.11 | 22.31 | 26.13 |
| Rbx1 | 27.35 | 37.9 | 52.8 | 42.1 | 32.42 | 38.46 | 49.53 | 54.05 |
| Mettl21d | 16.91 | 14.97 | 24.6 | 27.14 | 12.45 | 20.91 | 21.31 | 33.38 |
| Yars | 13.11 | 8.59 | 17.3 | 13.02 | 9.18 | 16.28 | 18.33 | 26.14 |
| Rrbp1 | 5.04 | 4.92 | 7.98 | 6.02 | 5.65 | 8.23 | 8.42 | 8.74 |
| Mrpl20 | 50.59 | 40.86 | 69.01 | 66.06 | 34.5 | 50.92 | 75.35 | 69.38 |
| Clic4 | 13.89 | 12.34 | 30.36 | 20.45 | 9.15 | 11.58 | 27.89 | 36.8 |
| Ghitm | 100.03 | 86.03 | 110.66 | 119.34 | 90.47 | 97.72 | 122.3 | 132.49 |
| Lasp1 | 71.32 | 52.19 | 84.9 | 71.12 | 50.94 | 69.3 | 84.06 | 75.6 |
| Zmpste24 | 12.25 | 10.14 | 15.42 | 11.26 | 8.22 | 8.68 | 22.12 | 18.34 |
| Cycs | 38.73 | 29.36 | 56.1 | 35.23 | 29.84 | 33.09 | 60.63 | 52.62 |
| Cox5b | 153.4 | 190.25 | 212.67 | 168.25 | 127.59 | 143.65 | 232.73 | 207.86 |
| Cnih4 | 5.8 | 5.89 | 12.47 | 3.31 | 3.05 | 3.78 | 10.27 | 7.63 |
| Psmb4 | 94.92 | 105.87 | 139.22 | 97.06 | 103.1 | 116.61 | 145.4 | 118.67 |
| Txn1 | 69.33 | 89.54 | 235.98 | 80.57 | 65.8 | 101.29 | 184.58 | 169.7 |
| Ndufb6 | 63 | 71.83 | 78.26 | 50.21 | 47.26 | 61.76 | 97.94 | 69.48 |
| Mkks | 3.7 | 2.74 | 3.63 | 2.96 | 1.66 | 3.36 | 5.51 | 3.81 |
| Dbi | 54.14 | 40.21 | 56.33 | 40.77 | 11.45 | 38.2 | 68.25 | 50.37 |
| Med21 | 31.73 | 31.64 | 35.61 | 41.17 | 22.69 | 25.17 | 55.39 | 21.01 |
| Usmg5 | 84.57 | 120.62 | 167.93 | 126.16 | 65.36 | 116.51 | 170.78 | 107.14 |
| Mlf2 | 26.06 | 28.55 | 43.42 | 23.07 | 35.08 | 29.71 | 41.04 | 27.82 |
| 11-Sep | 6.66 | 6.26 | 9.4 | 6.68 | 7.98 | 7.96 | 12.85 | 6.69 |
| BC002163 | 30.86 | 11.79 | 22.02 | 20.28 | 18.53 | 9.63 | 59.29 | 36.17 |
| Ran | 94.73 | 96.99 | 145.03 | 101.17 | 103.07 | 116.45 | 194.46 | 125.86 |
| Mthfd2 | 19.77 | 10.13 | 34.95 | 19.76 | 27.24 | 19.49 | 43.45 | 24.56 |
| Zfp248 | 0 | 0.04 | 0 | 0.04 | 0.04 | 0 | 0.2 | 0 |
| Lrrk1 | 2.48 | 3.42 | 2.4 | 4.71 | 2.7 | 2.43 | 5.1 | 3.87 |
| Rhbdf2 | 4.04 | 8.22 | 4.1 | 5.9 | 0.72 | 7.62 | 8.09 | 9.04 |
| Tspan31 | 16.19 | 9.7 | 22.73 | 22.1 | 3.83 | 15.47 | 31.18 | 22.94 |
| Reep5 | 28.85 | 33.02 | 34.97 | 36.29 | 19.12 | 34.36 | 53.01 | 40.05 |
| Atf6 | 4.38 | 2.37 | 6.24 | 4.93 | 2.86 | 4.52 | 5.61 | 8.35 |
| 8430410A17Rik | 15.43 | 14.11 | 16.73 | 14.1 | 10.02 | 15.04 | 23.2 | 16.87 |
| Idi1 | 4.77 | 4.39 | 3.51 | 3.44 | 4.86 | 3.1 | 8.2 | 6.05 |
| Syngr2 | 64.5 | 87.63 | 77.39 | 45.82 | 40 | 61.6 | 79.59 | 90.95 |
| Evi2a | 23.59 | 30.75 | 27.49 | 19.44 | 17.02 | 30.86 | 34.47 | 43.24 |
| Ptplb | 2.71 | 3.4 | 4.15 | 4.29 | 4.91 | 2.98 | 5.15 | 3.19 |
| BC004004 | 9.77 | 13.88 | 19.11 | 17.69 | 17.44 | 12.18 | 24.96 | 16.83 |
| Susd3 | 9.08 | 8.96 | 6.82 | 14.17 | 12.03 | 2.55 | 16.05 | 4.28 |
| Ccdc50 | 3.89 | 3.76 | 4.33 | 3.08 | 2.42 | 3.43 | 5.55 | 2.06 |
| Pkib | 0.53 | 0.32 | 0.2 | 0.14 | 0 | 0.12 | 1.1 | 0.14 |
| Coa3 | 28.29 | 23.36 | 38.13 | 27.85 | 32.41 | 22.86 | 49.34 | 24.39 |
| Gdpd5 | 0.09 | 1.95 | 2.03 | 1.65 | 0 | 0.43 | 4.5 | 0.37 |
| Cars | 8.07 | 7.92 | 18.06 | 9.29 | 9.78 | 5.85 | 13.79 | 8.74 |
| Mars | 11.54 | 19.74 | 27.24 | 23.12 | 25.57 | 14.3 | 29.74 | 15.04 |
| Abracl | 63.24 | 59.51 | 70.13 | 58.04 | 38.69 | 66.74 | 97.43 | 79.15 |
| Timm8b | 15.22 | 20.33 | 21.58 | 19.26 | 11.82 | 10.77 | 33.35 | 23.59 |
| Bcap31 | 82.63 | 87.5 | 99.57 | 83.85 | 63.31 | 90.91 | 101.44 | 100.68 |
| N6amt2 | 8.35 | 16.35 | 13.92 | 11.6 | 4.12 | 12.48 | 20.27 | 8.79 |
| Taf12 | 30.54 | 19.44 | 25.99 | 30.96 | 21.24 | 28.06 | 38.6 | 30.13 |
| Chsy1 | 14.32 | 10.23 | 14.73 | 20.93 | 12.21 | 18.25 | 23.63 | 10.69 |
| Med12l | 0.79 | 0.33 | 0.33 | 0.18 | 0.4 | 0.61 | 1.1 | 0.46 |
| Ndufa4 | 207.98 | 180.01 | 205.85 | 188.1 | 142.24 | 244.43 | 321.55 | 214.74 |
| Gpr68 | 7.81 | 5.4 | 7.03 | 7.49 | 7.61 | 13.96 | 18.75 | 11.39 |
| Ndufb7 | 59.63 | 68.76 | 100.49 | 82.13 | 69.18 | 69.93 | 109.26 | 86.92 |
| Tnf | 20.22 | 15.55 | 18.47 | 12.26 | 8.81 | 24.27 | 47 | 21.42 |
| Tma7 | 82.02 | 81.42 | 92.39 | 102.49 | 63.03 | 107.4 | 133.05 | 99.64 |
| Ndufa1 | 105.35 | 97.96 | 125.01 | 112.76 | 81.45 | 121.66 | 145.96 | 103.14 |
| Klrk1 | 37.65 | 50.87 | 51.93 | 106.67 | 39.95 | 61.07 | 138.7 | 167.96 |
| Flt3l | 19.33 | 23.55 | 20.67 | 24.1 | 16.01 | 18.26 | 37.27 | 36.44 |
| Tmsb4x | 1006.62 | 1045.63 | 1188.49 | 1119.81 | 751.62 | 1244.85 | 2092.36 | 2069.99 |
| Ndufa11 | 9.38 | 12.26 | 13.37 | 12.3 | 4.87 | 9.22 | 18.05 | 13.73 |
| Phf11b | 35.39 | 50.98 | 42.17 | 81.48 | 29.4 | 43.85 | 112.66 | 82.49 |
| Tmem154 | 1.25 | 5.06 | 2.49 | 4.03 | 0.69 | 2.94 | 12.54 | 7.95 |
| Depdc1a | 0 | 0.94 | 0.52 | 0.05 | 0 | 0.05 | 3.35 | 1.14 |

TABLE 4-continued

| | | | | | | | | |
|---|---|---|---|---|---|---|---|---|
| Neil3 | 0 | 0 | 0.76 | 0 | 0 | 0.2 | 3.13 | 0.17 |
| Sec61g | 34.68 | 60.61 | 64.75 | 58.13 | 48.15 | 51.77 | 105.72 | 72.67 |
| Atp5l | 89.46 | 128.96 | 116.71 | 132.58 | 112.13 | 130.37 | 207.52 | 175.86 |
| Mrpl33 | 65.21 | 61.98 | 71.52 | 46.48 | 59.44 | 79.66 | 111.44 | 87.3 |
| Lsm5 | 16.4 | 23.87 | 20.06 | 23.28 | 23.23 | 23.25 | 48.12 | 28.95 |
| Uqcrq | 54.68 | 83.19 | 94.61 | 62.82 | 58.81 | 85.76 | 137.51 | 75.86 |
| Atp5h | 266.58 | 349.54 | 337.53 | 271.81 | 253.83 | 354.83 | 419.72 | 345.82 |
| Sar1b | 27.84 | 39.91 | 39.26 | 34.94 | 26.81 | 29.99 | 69.86 | 51.93 |
| Pomp | 84.28 | 119.54 | 119.64 | 105.45 | 94.22 | 93.97 | 185.21 | 125.47 |
| Cox6c | 162.44 | 203.76 | 210.87 | 178.55 | 111.43 | 195.47 | 258.46 | 246.74 |
| Hmgn2 | 142.43 | 139.94 | 178.49 | 118.9 | 103.89 | 144.34 | 208.81 | 191.64 |
| Fam49a | 11.85 | 11.02 | 8.85 | 4.69 | 9.97 | 15.1 | 9.52 | 19.44 |
| Runx1 | 4.25 | 4.54 | 2.98 | 3.04 | 4.96 | 4.77 | 3.87 | 8.62 |
| Plek | 16.19 | 45.72 | 24.87 | 23 | 31.77 | 36.48 | 39.96 | 88.43 |
| Wdr95 | 2.12 | 4.69 | 4.05 | 4.64 | 5.35 | 3.21 | 7.02 | 9.71 |
| Soat2 | 5.27 | 5.82 | 4.8 | 4.72 | 7.3 | 4.85 | 7.42 | 9.13 |
| Apaf1 | 1.35 | 1.52 | 3.46 | 2.9 | 2.74 | 3.43 | 4.32 | 6.72 |
| Lamtor5 | 50.22 | 44.58 | 55.41 | 50.61 | 61.63 | 56.45 | 68.05 | 97.89 |
| Ppapdc1b | 3.27 | 1.48 | 3.68 | 1.85 | 0.22 | 3.54 | 4.66 | 6.27 |
| Atox1 | 54.87 | 46.09 | 54.35 | 47.03 | 26.19 | 60.24 | 69.87 | 100.62 |
| Necap2 | 35.85 | 31.96 | 30.3 | 31.5 | 19.82 | 33.69 | 39.17 | 55.58 |
| Entpd1 | 4.8 | 4.81 | 2.33 | 0.9 | 0 | 2.85 | 4.2 | 24.01 |
| Knstrn | 4.33 | 2.49 | 4.45 | 3.94 | 5.1 | 2.31 | 6.6 | 8.82 |
| Tnfsf9 | 4.41 | 1.39 | 2.26 | 0.86 | 0.27 | 2.49 | 6.48 | 9.34 |
| Ppil1 | 22.33 | 16.36 | 26.12 | 12.59 | 13.76 | 13.13 | 32.21 | 44.95 |
| Carhsp1 | 12.03 | 12.21 | 16.43 | 12.44 | 11.68 | 4.9 | 14.84 | 25.71 |
| 2900097C17Rik | 40.12 | 32.31 | 48.31 | 39.17 | 26.78 | 38.95 | 44.7 | 74.08 |
| 9330133O14Rik | 1.37 | 1.82 | 4.43 | 2.47 | 0.87 | 2.45 | 2.97 | 8.15 |
| Fam111a | 12.46 | 21.07 | 10.09 | 20.79 | 6.76 | 15.01 | 20.35 | 33.26 |
| Ehbp1l1 | 9.34 | 11.88 | 7.46 | 11.73 | 5.48 | 14.18 | 15.24 | 36.99 |
| Atp6v0b | 36.08 | 53.32 | 48.47 | 49.73 | 42.45 | 45.43 | 55.86 | 84.14 |
| BC049352 | 0 | 0.28 | 0.32 | 0.45 | 0 | 0 | 1.44 | 4.37 |
| Mtpn | 63.17 | 66 | 60.83 | 68.77 | 61.39 | 62.06 | 73.28 | 93.81 |
| Ctnna1 | 3.5 | 5.24 | 19.64 | 8.82 | 5.31 | 6.68 | 6.21 | 19.57 |
| Psmd14 | 76.68 | 76.79 | 88.14 | 61.14 | 59.16 | 77.64 | 82.08 | 99.6 |
| Rps27l | 19.05 | 41.5 | 72.97 | 31.01 | 8.12 | 31.74 | 45.17 | 50.31 |
| Atpif1 | 27.04 | 26.79 | 80.73 | 38.22 | 7.3 | 22.77 | 62.28 | 69.53 |
| Cyb5r1 | 11.4 | 12.74 | 20.51 | 14.91 | 21.07 | 8.97 | 9.93 | 14.02 |
| Nav1 | 0.06 | 0.29 | 1.27 | 0.05 | 0.07 | 0.15 | 0.11 | 0.63 |
| Nedd4 | 9.31 | 9.05 | 25.73 | 9.59 | 5.78 | 8.66 | 9.35 | 20.36 |
| Cd24a | 0.77 | 1.88 | 3.35 | 6.76 | 3.52 | 9.12 | 2.66 | 8.71 |
| Mrps6 | 40.92 | 21.7 | 46.29 | 33.21 | 21.01 | 39.71 | 38.04 | 32.34 |
| Cltc | 21.44 | 12.44 | 23.06 | 18.12 | 24.51 | 18.2 | 18.93 | 23.88 |
| Arf1 | 282.97 | 236.59 | 271.53 | 227.43 | 267.61 | 270.04 | 252.58 | 278.28 |
| Fam129a | 4.61 | 6.82 | 12.03 | 8.5 | 8.86 | 2.84 | 5.84 | 11.81 |
| Itgav | 1.03 | 1.3 | 4.35 | 1.5 | 2.02 | 1 | 2.23 | 2.94 |
| Lgals1 | 117.64 | 178.39 | 744.52 | 113.8 | 147.7 | 174.48 | 460.42 | 659.18 |
| Fhl2 | 1.69 | 1.89 | 22.51 | 5.43 | 0 | 3.34 | 10.68 | 12.53 |
| Slc4a8 | 0.05 | 0.24 | 0.58 | 0.09 | 0 | 0.14 | 0.33 | 0.48 |
| Aplp2 | 10.34 | 15.28 | 8.57 | 11.93 | 15.46 | 15.66 | 16.33 | 13.03 |
| Apobec2 | 0 | 0.13 | 1.19 | 4.6 | 0 | 3.4 | 2.89 | 7.42 |
| Pdlim5 | 9.13 | 8.53 | 10.24 | 12.9 | 9.57 | 9.88 | 10.68 | 11.34 |
| Trim16 | 0.28 | 0 | 0.44 | 0.62 | 0 | 0.67 | 1 | 0.24 |
| Crabp2 | 2.93 | 0 | 6.91 | 0 | 0 | 0.51 | 1.03 | 2.93 |
| Cth | 0 | 0 | 0 | 0 | 0 | 0 | 0.72 | 1.05 |
| Arhgap11a | 1.7 | 0.84 | 1.24 | 3.33 | 0 | 1.07 | 2.4 | 6.04 |
| Cst3 | 161.51 | 188.78 | 249.89 | 80.84 | 76.86 | 167.01 | 95.23 | 101.78 |
| Ero1l | 9.76 | 14.73 | 20.06 | 6.62 | 10.61 | 13.58 | 16.16 | 17.05 |
| Dsc2 | 0 | 0 | 0 | 0 | 0 | 0 | 0 | 0 |
| Hfe | 0 | 0 | 0 | 0 | 0 | 1.16 | 0.97 | 0.22 |
| Scd2 | 3.13 | 3.86 | 4.41 | 2.42 | 1.56 | 2.81 | 3.81 | 4.25 |
| H2afz | 408.7 | 434.99 | 450.61 | 393.44 | 239.71 | 458.25 | 537.74 | 551.34 |
| Rbms1 | 30.65 | 31.92 | 43.73 | 21.29 | 13.55 | 35.95 | 33.96 | 35.65 |
| Arsb | 8.73 | 12.72 | 14.28 | 9.41 | 9.63 | 16.61 | 17.26 | 21.92 |
| Furin | 2.27 | 5.44 | 6.57 | 3.05 | 4.45 | 4.19 | 7.97 | 5.2 |
| Eno1 | 289.91 | 341.11 | 477.53 | 286.25 | 323.96 | 404.37 | 524.9 | 634.34 |
| Bsg | 84.04 | 92.89 | 158.09 | 74.64 | 78.26 | 105.5 | 118.42 | 129.9 |
| Over expressed in CD62L+Slamf7− and CD62L− Slamf7+CX3CR1− relative to CD62L− Slamf7+ CX3CR1+ | | | | | | | | |
| Rnaset2a | 308.4 | 225.39 | 262.59 | 216.16 | 289.86 | 307.28 | 258.27 | 243.74 |
| Armcx2 | 9.71 | 3.6 | 5.22 | 4.43 | 5.61 | 6.22 | 3.39 | 7.22 |
| Bphl | 23.08 | 7.45 | 5.91 | 9.55 | 11.52 | 10.66 | 1.69 | 14.02 |
| Eng | 11.83 | 1.54 | 3.93 | 5.78 | 5.68 | 6.66 | 1.57 | 5.98 |
| Cnr2 | 13.38 | 8.84 | 5.9 | 3.2 | 7.93 | 11.85 | 6.66 | 9.12 |
| Npc2 | 169.57 | 132.84 | 146.2 | 119.76 | 130.53 | 137.12 | 129.65 | 144.11 |
| Tfdp2 | 4.07 | 1.87 | 3.56 | 2.38 | 2.64 | 3.28 | 2.08 | 2.27 |
| Nfkb2 | 65.18 | 39.19 | 47.93 | 55.39 | 55.13 | 45.45 | 50.35 | 49.51 |
| Klra19 | 9.09 | 0 | 4.31 | 5.12 | 4.96 | 2.36 | 3.28 | 6.06 |
| Gpr15 | 9.13 | 3.61 | 7.18 | 11.74 | 0 | 10.58 | 4.31 | 6.86 |
| 2-Mar | 48.74 | 41.07 | 43.98 | 52.68 | 44.65 | 46.76 | 37.43 | 45.81 |

TABLE 4-continued

| | | | | | | | | |
|---|---|---|---|---|---|---|---|---|
| Klra6 | 144.37 | 70.83 | 116.27 | 149.07 | 71.11 | 99.1 | 128.37 | 107.9 |
| Gm12185 | 7.06 | 4.43 | 7.75 | 9.94 | 5.82 | 7.06 | 8.92 | 8.2 |
| Ltb | 359.04 | 273.85 | 274.52 | 402.69 | 307.07 | 339.84 | 294.88 | 401.09 |
| Cd27 | 121.15 | 112.67 | 112.56 | 152.16 | 123.35 | 135 | 152.24 | 116.44 |
| Gm15133 | 2.8 | 2.05 | 4 | 1.64 | 5.12 | 4.79 | 4.24 | 5.89 |
| Eif3k | 315.89 | 334.16 | 346.28 | 321.17 | 378.24 | 370.28 | 345.87 | 378.61 |
| Eif3f | 432.31 | 453.82 | 428.96 | 308.25 | 515.26 | 468.35 | 440.36 | 452.77 |
| Fam26f | 31.38 | 36.17 | 38.89 | 24.08 | 56.04 | 48.62 | 33.94 | 41.08 |
| Paics | 75.4 | 69.77 | 73.66 | 69.28 | 105.74 | 81.31 | 87.16 | 102.12 |
| Samd3 | 48.56 | 42.23 | 48.91 | 62.27 | 76.76 | 52.92 | 67.2 | 74.24 |
| Spata6 | 27.85 | 21.91 | 28.8 | 38.89 | 42.28 | 27.86 | 29.52 | 42.73 |
| Cdon | 0.49 | 1.16 | 0.42 | 1.26 | 2.07 | 1.57 | 1.47 | 2.06 |
| Zfp512 | 7.71 | 12.06 | 9.07 | 15.99 | 27.24 | 9.12 | 15.86 | 24.51 |
| Kifc2 | 3.4 | 4.4 | 2.4 | 2.55 | 7.09 | 4.15 | 2.12 | 5.21 |
| Wibg | 10.8 | 14.94 | 9.87 | 13.13 | 17.12 | 13.48 | 9.23 | 15.46 |
| Dap | 141.01 | 114.92 | 142.47 | 121.71 | 175.84 | 103.37 | 98.56 | 146.4 |
| Fgfr1op | 8.88 | 10.83 | 11.32 | 10.05 | 13.32 | 7.45 | 7.94 | 15.59 |
| Map3k5 | 3.88 | 1.99 | 3.02 | 2.67 | 5.74 | 2.35 | 1.69 | 7.09 |
| Bbs9 | 12.09 | 10.18 | 9.39 | 9.71 | 11.39 | 7.81 | 7.12 | 15.61 |
| Ccdc6 | 8.87 | 7.64 | 8.4 | 8.41 | 8.65 | 7.04 | 6.16 | 10.94 |
| Atp6v1d | 102.48 | 69.83 | 82.1 | 101.41 | 79.54 | 84.21 | 64.32 | 132.5 |
| Prps2 | 35.28 | 27.83 | 26.1 | 25.4 | 31.52 | 33.7 | 26.56 | 35.93 |
| Cd2ap | 4.51 | 2.13 | 3.39 | 3.03 | 4.72 | 2.95 | 4.23 | 6.07 |
| Rcsd1 | 70.21 | 59.34 | 56.32 | 66.87 | 65.61 | 60.63 | 61.05 | 91.17 |
| Clec2g | 9.49 | 10.46 | 5.38 | 6.34 | 8.2 | 6.13 | 7.9 | 9.7 |
| Clec2i | 53.69 | 51.1 | 29.68 | 35.27 | 60.41 | 36.85 | 43.64 | 60.41 |
| Fam214a | 14.54 | 13.2 | 7.9 | 4.72 | 14.43 | 6.35 | 7.95 | 12.91 |
| Efr3a | 58.74 | 50.27 | 40.61 | 58.26 | 61.49 | 45.99 | 44.96 | 57.47 |
| Itih5 | 1.84 | 1.29 | 0.52 | 2.52 | 2.25 | 0.95 | 0.68 | 1.07 |
| Mycbp2 | 15.1 | 11.27 | 9.46 | 12.37 | 13.93 | 12.37 | 12.37 | 11.61 |
| Clta | 227.39 | 202.18 | 218.11 | 201.7 | 257.84 | 220.44 | 216.19 | 213.11 |
| Dennd2d | 59.28 | 56.57 | 49.34 | 62.38 | 89.85 | 54.86 | 57.55 | 57.36 |
| Ganc | 5.55 | 3.75 | 5.74 | 10.69 | 5.78 | 2.11 | 4.02 | 8.51 |
| Ccdc64 | 2.68 | 6.2 | 1.71 | 7.36 | 3.89 | 3.64 | 3 | 7.93 |
| Tapt1 | 10.13 | 14.24 | 9.48 | 15.85 | 11.09 | 7.61 | 5.85 | 11.07 |
| Sntb1 | 12.03 | 9.3 | 4.79 | 8.23 | 7.46 | 15.1 | 7.06 | 11.55 |
| Utp14a | 20.61 | 25.99 | 23.07 | 35.38 | 24.61 | 42.09 | 31.27 | 40.13 |
| Hrsp12 | 7.17 | 12.97 | 12.77 | 10.85 | 12.86 | 14.97 | 9.14 | 14.02 |
| P2rx4 | 10.35 | 14.57 | 11.08 | 11.7 | 8.96 | 21.24 | 6.05 | 15.5 |
| Ddx10 | 23.15 | 28.82 | 22.85 | 20.15 | 19.66 | 30.13 | 18.94 | 31.2 |
| Nsa2 | 72.5 | 71.8 | 71.44 | 71.2 | 64.12 | 84.92 | 53.78 | 68.08 |
| Tmem108 | 4.33 | 2.94 | 5.05 | 2.83 | 4.08 | 5.98 | 2.01 | 3.98 |
| Gm13826 | 68.57 | 69.9 | 68.41 | 71.25 | 34.94 | 80.88 | 52.65 | 84.71 |
| Eif2s3x | 79.83 | 72.82 | 84.14 | 81.12 | 70.86 | 92.11 | 62.92 | 87 |
| Ddx21 | 44.48 | 41.89 | 44.05 | 34.8 | 35.05 | 34.73 | 41.64 | 29.26 |
| Gm13139 | 12.26 | 11.71 | 13.17 | 9.82 | 8.34 | 6.36 | 7.9 | 7.22 |
| H2-Oa | 30.74 | 28.57 | 23.32 | 23.39 | 23.9 | 19.3 | 31.12 | 16.88 |
| Spint2 | 48.24 | 53.23 | 31.64 | 42.92 | 50.36 | 34.82 | 31.93 | 23.85 |
| Noa1 | 19.86 | 14.9 | 12.12 | 12.03 | 15.66 | 10.26 | 17.07 | 12.68 |
| Tmem194b | 18.45 | 13.7 | 11.98 | 13.72 | 11.63 | 10.06 | 12.12 | 12.42 |
| Erap1 | 50.56 | 48.02 | 42.12 | 57.46 | 29.56 | 39.93 | 38.05 | 43.4 |
| Rpgrip1 | 12.64 | 8.23 | 4.07 | 8.32 | 1.5 | 2.67 | 6.49 | 4.06 |
| Cnp | 183.35 | 145.24 | 121.65 | 162.51 | 122.37 | 136.14 | 167.66 | 128.84 |
| Rgs11 | 19.55 | 14.4 | 7.52 | 12.91 | 7.68 | 12.85 | 10.91 | 12.77 |
| Gstt2 | 19.46 | 13.72 | 10.52 | 18.69 | 3.23 | 12.2 | 8.12 | 17.46 |
| Ddb2 | 36.11 | 31.73 | 24.09 | 36.32 | 23.09 | 30.66 | 23.9 | 34.89 |
| Ikzf2 | 11.72 | 7.91 | 10.28 | 17.19 | 8.33 | 14.47 | 9.08 | 9.07 |
| Mfsd11 | 19.74 | 17.16 | 18.59 | 22.87 | 14.45 | 23.02 | 12.11 | 19.05 |
| Mri1 | 29.87 | 21.97 | 24.25 | 28.83 | 12.43 | 23.7 | 22.87 | 22.79 |
| Adck3 | 9.68 | 2.61 | 6.1 | 7.86 | 1.81 | 4.81 | 2.42 | 4.48 |
| Igflr1 | 31.5 | 30.12 | 20.63 | 21.46 | 28.19 | 29.49 | 28.46 | 25.41 |
| Pglyrp1 | 48.04 | 64.99 | 40.98 | 39.82 | 35.14 | 45.05 | 58.01 | 49.78 |
| Sema4d | 69 | 88.61 | 58.75 | 73.12 | 71.24 | 68.49 | 72.42 | 73.83 |
| Pabpc4 | 3.18 | 6.19 | 6.29 | 4.98 | 4.38 | 5.86 | 7.27 | 5.63 |
| Hspa8 | 1916.43 | 2274.63 | 2039.85 | 2051.54 | 2178.14 | 2507.37 | 2311.39 | 2260.12 |
| Fbxo7 | 20.55 | 29.31 | 22.37 | 17.27 | 23.2 | 20.66 | 24.98 | 23.87 |
| Map7 | 1.88 | 5.3 | 3.69 | 2.39 | 1.86 | 1.39 | 4.74 | 1.31 |
| Cd69 | 722.75 | 842.18 | 748.1 | 950.27 | 613.4 | 1009.39 | 914.69 | 807.84 |
| A630001G21Rik | 8.57 | 15.16 | 10.32 | 10.88 | 8.72 | 16.8 | 12.26 | 16.44 |
| Xist | 45.25 | 62.06 | 49.6 | 47.04 | 52.86 | 63.68 | 54.01 | 58.4 |
| Rabgap1l | 39.28 | 45.01 | 30.63 | 44.16 | 33.27 | 42.12 | 33.12 | 42.59 |
| Hvcn1 | 34.72 | 44.85 | 29.62 | 42.62 | 20.26 | 33.36 | 31.38 | 42.95 |
| Fggy | 2.68 | 5.05 | 0.9 | 2.62 | 0.43 | 1.53 | 2.92 | 4.94 |
| Kctd12 | 7.47 | 4.08 | 3.95 | 6.3 | 3.71 | 4.56 | 4.1 | 5.82 |
| Atp1b1 | 32.97 | 33.15 | 23.24 | 20.83 | 14.68 | 34.83 | 21.75 | 19.13 |
| Trim12a | 86.19 | 76.27 | 70.5 | 90.96 | 74.31 | 82.07 | 87.83 | 45.11 |
| Pctp | 8.75 | 4.57 | 3.56 | 5.3 | 2.26 | 4.36 | 4.57 | 0.1 |
| Fam78a | 35.53 | 35.31 | 21.66 | 26.93 | 19.37 | 30.27 | 28.07 | 19.02 |
| Klra3 | 23.73 | 19.31 | 23.42 | 24.47 | 9.83 | 15.7 | 25.86 | 7.87 |
| Mvb12b | 0.59 | 0.34 | 0.71 | 0.67 | 0.56 | 0.64 | 0.41 | 0.41 |

TABLE 4-continued

| | | | | | | | | |
|---|---|---|---|---|---|---|---|---|
| Dguok | 55.6 | 56.12 | 57.96 | 55.71 | 40.04 | 50.66 | 43.78 | 35.67 |
| Bmp7 | 4.89 | 7.11 | 6.26 | 9.09 | 4 | 6.87 | 5.47 | 1.53 |
| Vars | 58.84 | 80.73 | 75.55 | 62.68 | 57.97 | 66 | 70.6 | 49.76 |
| 1500012F01Rik | 108.61 | 143.72 | 130.82 | 120.48 | 106.37 | 126.99 | 136.71 | 96.97 |
| Ccnh | 24.72 | 32.22 | 29.18 | 25.6 | 23.14 | 23.75 | 24.87 | 25.26 |
| Vwa5a | 10.06 | 17.19 | 18.93 | 14.38 | 2.7 | 15.49 | 13.03 | 10.4 |
| Ptma | 631.7 | 685.56 | 835.52 | 675.51 | 640.03 | 681.91 | 767.51 | 650.55 |
| Eif3m | 225.43 | 291.5 | 269.13 | 273.03 | 274.97 | 300.66 | 257.58 | 239.51 |
| Rpl7a | 1025.75 | 1217.24 | 1244.26 | 1214.58 | 1116.37 | 1235.47 | 1097.12 | 1143.09 |
| Rps9 | 1796.5 | 2292.26 | 1968.29 | 2066.57 | 1833.31 | 2066.51 | 1865.21 | 1722.09 |
| Rpl10a | 1358.2 | 1592.53 | 1497.71 | 1444.39 | 1413.97 | 1513.75 | 1402.84 | 1359.38 |
| Rpl24 | 1077.16 | 1381.17 | 1318.63 | 1259.76 | 1135.15 | 1275.18 | 1380.66 | 1352.18 |
| Rpl14 | 887.15 | 980.65 | 1024.9 | 925.54 | 830.66 | 910.43 | 940.73 | 839.94 |
| Naca | 655.67 | 710.61 | 693.43 | 701.74 | 626.78 | 714.37 | 681.06 | 598.05 |
| Rpl37 | 569.12 | 647.67 | 742.23 | 664.51 | 545.07 | 675.84 | 661.6 | 604.85 |
| Rps11 | 2456.07 | 2975.03 | 2897.4 | 3009.58 | 2317.54 | 3007.48 | 2706.98 | 2444.1 |
| Rpl11 | 1631.81 | 1986.07 | 1931.2 | 1832.23 | 1494.86 | 1885.76 | 1765.21 | 1611.72 |
| Rps2 | 1506.18 | 1797.37 | 1978.09 | 1180.62 | 1868.97 | 2020.78 | 1854.52 | 1600.73 |
| Atp5g2 | 395.86 | 378.99 | 455.83 | 383.96 | 394.64 | 400.9 | 411.92 | 387.43 |
| Npm1 | 993.4 | 1063.55 | 1318.67 | 1040.29 | 1089.54 | 1073.11 | 983.99 | 878.12 |
| Eef1g | 905.36 | 856.07 | 946.04 | 874.69 | 895.57 | 886.43 | 740.68 | 768.68 |
| Rpl31 | 406.96 | 555.41 | 571.68 | 483 | 340.74 | 537.23 | 436.83 | 331.11 |
| Snhg1 | 133.53 | 164.54 | 167.26 | 128.8 | 117.06 | 154.36 | 139.88 | 85.87 |
| Arhgap39 | 0.88 | 1.02 | 1.41 | 0.99 | 0.36 | 1.04 | 1.21 | 0 |
| Rps27a | 1550.71 | 2053.05 | 1990.28 | 1709.68 | 1307.7 | 1834.97 | 1859.34 | 1570.63 |
| Rps12 | 1352.84 | 1864.7 | 2136.96 | 1741.95 | 1404.44 | 1871.16 | 2079.01 | 1686.25 |
| Rpl32 | 1518.75 | 1980.54 | 2058.5 | 1893.74 | 1327.19 | 1875.9 | 2008.99 | 1615.08 |
| Rpl22l1 | 364.69 | 512.04 | 436.12 | 445.57 | 346.23 | 509.48 | 516.32 | 372.98 |
| Rps13 | 2381.78 | 2900.11 | 2753.45 | 2648.46 | 2251.62 | 2742.45 | 2827.55 | 2336.34 |
| Rps15a | 199.03 | 268.84 | 236.97 | 225.25 | 186.44 | 234.65 | 242.26 | 197.42 |
| Rpl36 | 547.4 | 761.93 | 691.81 | 682.94 | 597.57 | 721.36 | 723.63 | 621.45 |
| Rps15a-ps4 | 116.5 | 184.57 | 170.22 | 150.91 | 124.86 | 157.24 | 180.02 | 150.26 |
| Fau | 2137.44 | 2602.29 | 2341.29 | 2453.14 | 1982.53 | 2446.4 | 2463.55 | 2094.58 |
| Rpl17 | 1374.06 | 2091.37 | 1738.21 | 1713.13 | 1259.31 | 1710.55 | 1693.64 | 1368.75 |
| Rps15a-ps6 | 238.54 | 320.55 | 296.99 | 257.65 | 215.17 | 296.7 | 277.91 | 218.87 |
| Rpl38 | 692.52 | 911.19 | 856.53 | 809.55 | 727.91 | 825.39 | 817.8 | 679.67 |
| Rpl39 | 1936.7 | 2610.8 | 2811.67 | 2365.89 | 1890.85 | 2507.19 | 2574.87 | 2037.15 |
| Gm15772 | 1609.5 | 2049.82 | 2092.45 | 1778.7 | 1459.94 | 1886.34 | 1881.63 | 1488.93 |
| Crtam | 23.51 | 37.83 | 18.85 | 31.03 | 32.45 | 26.24 | 51.13 | 28.14 |
| Cd163l1 | 4.26 | 21.85 | 15.05 | 17.76 | 5.5 | 7.46 | 26.58 | 17.18 |
| Herc3 | 12.06 | 21.11 | 13.54 | 17.75 | 12.61 | 13.72 | 22.83 | 12.54 |
| Pdgfb | 2.63 | 3.33 | 1.89 | 1.96 | 2.9 | 1.93 | 3.66 | 3.14 |
| Clcn3 | 7.91 | 10.76 | 6.75 | 9.12 | 9.19 | 6.53 | 11.03 | 11.06 |
| Tapbpl | 89.44 | 122.95 | 99 | 121.62 | 94.13 | 79.57 | 108.8 | 114.47 |
| Gpr183 | 71.35 | 104.83 | 76.55 | 110.18 | 104.71 | 108.25 | 103.51 | 112.47 |
| Fam102a | 38.49 | 43.82 | 36.85 | 47.05 | 46.29 | 41.94 | 57.26 | 51.27 |
| Traf1 | 59.92 | 62.05 | 71.03 | 93.09 | 103.31 | 66.23 | 82.8 | 108.48 |
| Ms4a4c | 87.45 | 68.79 | 76.75 | 117.26 | 108.2 | 85.85 | 155 | 155.58 |
| Rhobtb2 | 1.51 | 1.75 | 1.89 | 2.87 | 3.73 | 3.18 | 1.67 | 2.99 |
| Rps4y2 | 5.11 | 6.27 | 6.18 | 7.08 | 8.71 | 6.03 | 3.94 | 14.01 |
| Ctla2b | 65.16 | 155.43 | 98.73 | 139.33 | 185.4 | 92.51 | 153.46 | 129.68 |
| Pacsin1 | 17.16 | 12.8 | 8.39 | 14.13 | 24.53 | 11.48 | 19.51 | 7.05 |
| Myc | 78.99 | 75.48 | 74.76 | 75.65 | 97.29 | 100.65 | 124.15 | 87.54 |
| Tex9 | 2.48 | 1.83 | 2.6 | 2.12 | 2.49 | 2.1 | 2.96 | 2.99 |
| Swap70 | 7.2 | 3.12 | 8.98 | 6.88 | 11.98 | 8.59 | 9.47 | 8.59 |
| Abhd15 | 4.39 | 2.87 | 4.1 | 1.54 | 6.86 | 2.79 | 2.28 | 3.48 |
| Slc38a1 | 17.74 | 18.61 | 19.2 | 17.6 | 25.84 | 18.65 | 17.18 | 17.33 |
| Nsmce1 | 57.16 | 55.06 | 66.99 | 49.59 | 69.95 | 41.87 | 58.28 | 57.95 |
| Psme1 | 445.61 | 490.99 | 523.3 | 575.96 | 557.74 | 474.14 | 635.18 | 517.22 |
| Gbp9 | 74.11 | 70.32 | 62.06 | 116.48 | 78.11 | 69.17 | 117.92 | 79.23 |
| Klra5 | 4.17 | 0.54 | 8.38 | 9.87 | 9.65 | 3.2 | 11.11 | 1.47 |
| Xcl1 | 22.85 | 51.97 | 37.67 | 78.34 | 38.77 | 84.94 | 194.27 | 39.8 |
| Plac8 | 326.67 | 339.21 | 377.89 | 403.06 | 466.69 | 379.73 | 625.42 | 890.76 |
| Ptpn6 | 106.4 | 91.45 | 85.16 | 128.32 | 104.25 | 146.34 | 128.77 | 178.72 |
| Trim59 | 22.41 | 13.03 | 14.49 | 24.07 | 13.53 | 14.08 | 20.9 | 29.41 |
| Apobec3 | 97.6 | 120.17 | 113.53 | 127.78 | 106.78 | 112.37 | 125.8 | 142.44 |
| Aoah | 1.49 | 3.25 | 0.59 | 1.09 | 0.45 | 1.26 | 2.1 | 5.81 |
| Ppcdc | 20.45 | 16.93 | 18.7 | 13.99 | 15.4 | 15.78 | 13.82 | 24.58 |
| Tubb5 | 443.05 | 447.5 | 447.05 | 404.53 | 419.97 | 439.07 | 428.01 | 566.49 |
| Cables1 | 2.69 | 2.37 | 6.61 | 4.94 | 3.14 | 5 | 7.83 | 9.53 |
| Cd3d | 372.67 | 404.62 | 355.58 | 437.45 | 297.43 | 398.01 | 477.04 | 442.62 |
| Fos | 521.78 | 493.41 | 560.86 | 541.12 | 464.02 | 629.32 | 594.94 | 598.56 |
| Cd7 | 213.03 | 152.75 | 149.55 | 151.88 | 67.58 | 165.05 | 183.61 | 174.39 |
| Jak3 | 62.05 | 82.32 | 62 | 73.03 | 56.17 | 63.12 | 97.55 | 88.5 |
| Ly6e | 570.09 | 564.86 | 675.24 | 608.31 | 432.13 | 535.85 | 712.12 | 691.37 |
| Arap2 | 8.86 | 14.51 | 16.44 | 10.04 | 17.54 | 14.69 | 13.83 | 5.91 |
| Over expressed in CD62L+Slamf7− relative to the other two populations | | | | | | | | |
| Tigit | 85.2 | 180.55 | 146.2 | 104.21 | 202.48 | 113.2 | 128.47 | 113.9 |
| Traf4 | 15.99 | 20.08 | 17.76 | 13.61 | 28.75 | 17.24 | 21.15 | 5.93 |

TABLE 4-continued

| | | | | | | | | |
|---|---|---|---|---|---|---|---|---|
| Gm11696 | 1.3 | 0.06 | 1.85 | 0.72 | 6.1 | 1.01 | 0.21 | 0.17 |
| Lysmd2 | 14.73 | 11.52 | 23.25 | 13.76 | 39.88 | 16.23 | 13.6 | 8.6 |
| 4921525O09Rik | 1.28 | 0 | 1.5 | 0.65 | 3.06 | 0.47 | 0.62 | 0 |
| Smyd3 | 9.34 | 9.2 | 12.13 | 12.43 | 16.42 | 9.21 | 5.73 | 7.91 |
| Dcaf8 | 37.07 | 36.8 | 39.54 | 39.29 | 56.31 | 34.83 | 26.56 | 36.07 |
| Rab4a | 6.26 | 10.23 | 9.27 | 13.95 | 28.32 | 5 | 3.68 | 4.27 |
| Mcrs1 | 43.49 | 39.09 | 43.18 | 43.4 | 66.46 | 37.06 | 29.01 | 37.69 |
| Zfp160 | 1.6 | 6.55 | 4.91 | 6.79 | 14.34 | 3.19 | 3.76 | 3.97 |
| Rbm45 | 3.11 | 2.78 | 2.44 | 3.83 | 6.39 | 1.7 | 2.93 | 1.29 |
| Lsm11 | 0.46 | 0.65 | 0.29 | 0.82 | 2.31 | 0.29 | 0.29 | 0.22 |
| Accs | 6.05 | 6.3 | 5.69 | 5.91 | 19.76 | 4.15 | 3.25 | 1.89 |
| Fchsd2 | 10.08 | 7.16 | 7.07 | 11.07 | 25.5 | 8.77 | 6.67 | 3.73 |
| Bcl2l11 | 39.35 | 42.93 | 37.86 | 49.77 | 79.78 | 38.98 | 35.47 | 26.6 |
| Fam120b | 13.82 | 13.89 | 17.83 | 18.86 | 29.38 | 18.17 | 11.58 | 12.34 |
| Nin | 8.24 | 5.41 | 7.96 | 9.64 | 15.09 | 9.74 | 5.46 | 6.16 |
| Bod1l | 3.75 | 3.67 | 3.69 | 3.98 | 7.37 | 4.51 | 3.31 | 3.32 |
| Eif5 | 74.92 | 80.03 | 77.34 | 75.24 | 118.68 | 85.61 | 70.23 | 72.61 |
| Pde4b | 58.1 | 77.49 | 53.88 | 72.17 | 135.35 | 68.4 | 50.96 | 65.01 |
| Gna13 | 33.9 | 43.82 | 33.23 | 38.48 | 61.72 | 34.8 | 31.5 | 38.27 |
| Gid4 | 10.68 | 10.91 | 9.17 | 12.98 | 31.16 | 8.16 | 6.95 | 12.63 |
| Ugcg | 13.8 | 17.04 | 15.48 | 18.94 | 43.24 | 15.92 | 11.27 | 15.85 |
| Zeb1 | 13.62 | 17.81 | 14.1 | 22.8 | 52.24 | 17.06 | 12.27 | 11.64 |
| Prps1l3 | 21.97 | 19.71 | 22.83 | 24.93 | 24.23 | 14.97 | 18.46 | 12.67 |
| Fip1l1 | 32.37 | 34.22 | 38.99 | 52.21 | 53.11 | 22.54 | 33.57 | 33.34 |
| Klra7 | 274.72 | 165.19 | 233.18 | 291.38 | 278.41 | 258.26 | 248.98 | 146.92 |
| Klra1 | 67.99 | 28.32 | 45.63 | 57.57 | 85.58 | 64.85 | 49.98 | 1.97 |
| Sft2d2 | 19.63 | 16.66 | 16.53 | 23.2 | 29.01 | 19.87 | 22.89 | 13.26 |
| Wdr43 | 35.5 | 34.06 | 34.92 | 45 | 46.03 | 36.95 | 50.21 | 28.33 |
| Gbp10 | 30.1 | 13.38 | 22.02 | 45.04 | 34.84 | 28 | 36.32 | 8.02 |
| Pitpnm2 | 2.97 | 1.62 | 4.2 | 3.62 | 5.32 | 6.21 | 3.19 | 2.36 |
| 5430416N02Rik | 35.1 | 25.05 | 32.53 | 24.19 | 42.15 | 30.87 | 21.63 | 16.65 |
| Polr1c | 52.61 | 28.99 | 48.85 | 40.74 | 68.7 | 44.67 | 36.38 | 28.57 |
| Phyh | 35.45 | 28.02 | 38.31 | 33.71 | 48.48 | 34.45 | 30.2 | 22.87 |
| Odc1 | 38.48 | 43.78 | 49.52 | 50.76 | 72.45 | 43.77 | 39.19 | 28.9 |
| Irak2 | 27.6 | 30.58 | 34.11 | 32.04 | 47.73 | 29.48 | 32.32 | 18.77 |
| Sult2b1 | 4.5 | 6.15 | 8.62 | 21.33 | 28.85 | 9.86 | 16 | 1.66 |
| Tgtp2 | 322.34 | 354.51 | 297.59 | 471.49 | 472.89 | 344.84 | 322.89 | 218.47 |
| Abl1 | 8.46 | 10.31 | 7.61 | 13.96 | 21.22 | 11.5 | 9.03 | 4.33 |
| Tec | 6.95 | 9.08 | 5.27 | 14.09 | 16.43 | 12.41 | 6.27 | 3.72 |
| Rnf138 | 117.96 | 134.49 | 108.5 | 157.53 | 186.29 | 149.57 | 111.35 | 116.1 |
| Rpusd4 | 13.29 | 15.64 | 17.52 | 16.01 | 31.56 | 19.63 | 18.99 | 12.47 |
| Apol7b | 40.34 | 40.21 | 36.91 | 50.01 | 57.84 | 42.36 | 33.23 | 34.37 |
| Apol7e | 37.91 | 40.21 | 34.28 | 46.49 | 57.84 | 42.36 | 33.04 | 34.24 |
| Gem | 73.84 | 101.07 | 115.79 | 152.91 | 165.65 | 164.95 | 89.94 | 52 |
| Tmem9 | 15.5 | 13.93 | 26.81 | 33.3 | 38.05 | 24.79 | 21.72 | 18.96 |
| 4930417O13Rik | 2.7 | 3.27 | 5.2 | 5.54 | 7.95 | 3.93 | 3.73 | 0.34 |
| Snhg5 | 56.95 | 63.04 | 78.57 | 76.8 | 110.42 | 79.08 | 69.04 | 47.9 |
| Wdr4 | 10.32 | 5.51 | 9.28 | 9.19 | 5.31 | 11.91 | 9.3 | 4.99 |
| Ddc | 6.66 | 2.38 | 4.19 | 6.74 | 4.36 | 7.78 | 4.55 | 0 |
| Folr4 | 20.25 | 3.32 | 9.7 | 17.21 | 8.14 | 14.88 | 13.88 | 3.74 |
| Tlr1 | 15.68 | 3.39 | 8.44 | 10.3 | 9.14 | 12.72 | 10.95 | 5.62 |
| Cyp4v3 | 6.09 | 5.41 | 8.4 | 7.75 | 4.7 | 7.75 | 4.24 | 5.01 |
| Rplp2-ps1 | 27.85 | 27.95 | 29.16 | 28.29 | 25.17 | 31.6 | 22.39 | 21.51 |
| Zfp36 | 255.15 | 243.36 | 267.21 | 264.76 | 255.16 | 306.7 | 242.31 | 248.73 |
| Fam86 | 16.06 | 13.17 | 17.41 | 16.49 | 13.69 | 14.6 | 10.16 | 11.8 |
| Plk1s1 | 20.05 | 14.52 | 10.27 | 17.9 | 10.75 | 15.12 | 8.63 | 13.93 |
| Rnaseh1 | 20.54 | 16.2 | 17.88 | 24.43 | 14.85 | 18.21 | 14.51 | 19.78 |
| Arid4b | 25.48 | 17.57 | 18.97 | 34.41 | 26.61 | 31.63 | 20.8 | 16.57 |
| Acpp | 6.36 | 3.35 | 4.92 | 9.62 | 5.81 | 6.29 | 2.52 | 1.72 |
| Slc11a2 | 33.09 | 29.1 | 29.65 | 49.52 | 36.05 | 39.56 | 27.67 | 23.56 |
| Cldn10 | 2.46 | 1.31 | 3.63 | 12.01 | 5.37 | 3.24 | 2.35 | 0.4 |
| Smad1 | 0.56 | 1.68 | 1.65 | 4.73 | 2.64 | 2.77 | 0.91 | 0.19 |
| Neurl3 | 58.96 | 76.23 | 49.9 | 95.86 | 64.39 | 61.97 | 51.68 | 71.3 |
| Cul9 | 3.18 | 2.2 | 2.26 | 4.44 | 2.47 | 3.4 | 1.82 | 3.84 |
| Rnf167 | 130.5 | 121.66 | 91.66 | 140.34 | 101.73 | 127.89 | 98.09 | 111.96 |
| Ablim1 | 169.28 | 143.69 | 114.29 | 184.41 | 160.49 | 150.84 | 125.37 | 142.11 |
| Rnaset2b | 131.38 | 138.08 | 103.25 | 148.82 | 117.87 | 136.74 | 99.19 | 131.73 |
| Tnip1 | 25.32 | 23.01 | 16.83 | 28.35 | 22.46 | 20.96 | 16.85 | 18.68 |
| Ctps2 | 20.01 | 17.88 | 18.31 | 23.03 | 18.48 | 19.24 | 13.58 | 16.03 |
| Ramp1 | 8.94 | 8.62 | 8.46 | 7.96 | 10.29 | 10.05 | 3.49 | 7.09 |
| Mgst2 | 47.38 | 35.33 | 39.29 | 36.26 | 52.59 | 35.68 | 27.39 | 34.85 |
| Taf1d | 57.61 | 52.04 | 56.36 | 55.53 | 66.75 | 58.05 | 44.96 | 44.08 |
| Acoxl | 7.32 | 7.22 | 7.17 | 9.74 | 7.05 | 5.42 | 5.12 | 5.33 |
| Eif3h | 507.51 | 483.59 | 427.56 | 463.31 | 487.97 | 472.41 | 440.79 | 447.52 |
| Eef2 | 2116.66 | 1984.78 | 1858.84 | 1978.88 | 2066.96 | 1943.36 | 1690.6 | 1824.14 |
| Igbp1 | 92.33 | 83.58 | 90.43 | 104.88 | 101.92 | 106 | 82.23 | 70.97 |
| Pim2 | 118.35 | 111.62 | 118.45 | 140.42 | 134.82 | 131.82 | 103.05 | 100.49 |
| Sgms1 | 17.5 | 15.03 | 10.47 | 15.63 | 22.92 | 20.01 | 7.88 | 17.6 |
| Cnot10 | 29.93 | 28.53 | 23.05 | 30.72 | 31.81 | 25.86 | 17.72 | 29.11 |
| Kbtbd11 | 17.68 | 24.91 | 22.64 | 20.11 | 30.13 | 21.4 | 16.84 | 20.33 |

TABLE 4-continued

| | | | | | | | | |
|---|---|---|---|---|---|---|---|---|
| Satb1 | 57.02 | 63.41 | 47.97 | 62.68 | 80.69 | 55.6 | 46.46 | 56.04 |
| Ss18 | 79.85 | 78.99 | 61.27 | 75.44 | 101.07 | 70.34 | 57.19 | 63.46 |
| Txk | 93.95 | 116.34 | 87 | 95.28 | 117.95 | 101.59 | 89.7 | 102.36 |
| Klra13-ps | 23.95 | 59 | 37.68 | 60.63 | 57.12 | 44.27 | 38.36 | 46.13 |
| Ddx6 | 16.88 | 25.86 | 17.99 | 22.77 | 21.16 | 22.73 | 12.48 | 20.42 |
| Cxcr5 | 15.3 | 33.55 | 20.18 | 20.45 | 18.68 | 24.81 | 10.85 | 18.58 |
| Wdr26 | 11.53 | 11.93 | 8.31 | 13.11 | 13.55 | 8.32 | 10.07 | 6.93 |
| Kdm5a | 16.78 | 21.23 | 14.08 | 20.38 | 19.48 | 14.78 | 13.71 | 12.59 |
| Mau2 | 29.88 | 45.78 | 25.81 | 38.77 | 45.24 | 36.52 | 31.2 | 31.54 |
| Dmrta1 | 4.22 | 10.33 | 5.36 | 11.42 | 9.36 | 7.7 | 6.45 | 4.96 |
| Luc7l | 22.42 | 33.22 | 24.16 | 24.56 | 38.45 | 28.33 | 24.47 | 19.64 |
| Sik1 | 27.85 | 29.17 | 27.94 | 27.95 | 39.44 | 25.28 | 16.08 | 17.38 |
| Dnajc7 | 78.86 | 87.65 | 74.71 | 92.12 | 106.06 | 97.23 | 60.48 | 66.06 |
| Jmjd1c | 19.73 | 20.21 | 19.01 | 22.44 | 27.73 | 21.32 | 16.95 | 18.65 |
| Usp53 | 2.59 | 4.64 | 4.68 | 5.06 | 7.84 | 6 | 3.14 | 2.86 |
| Hipk1 | 16.98 | 22.78 | 20.14 | 23.2 | 30.05 | 23.76 | 14.86 | 13.88 |
| Irs2 | 13.25 | 15.2 | 12.39 | 16.91 | 24.55 | 15.29 | 2.59 | 6.81 |
| Pde2a | 153.71 | 152.11 | 116.37 | 180.68 | 255.02 | 156.24 | 64.91 | 63.81 |
| Tnfrsf26 | 126.03 | 140.87 | 99.32 | 159.31 | 203.69 | 161.64 | 105.89 | 83.05 |
| Thada | 17.77 | 19.98 | 18.74 | 23.21 | 29.07 | 23.62 | 11.93 | 12.11 |
| Myb | 7.51 | 11.23 | 9.68 | 15.5 | 20.07 | 13.84 | 5.61 | 2.33 |
| Bend4 | 16.61 | 20.18 | 20.45 | 26.97 | 42.85 | 28.61 | 12.89 | 11.33 |
| Jakmip1 | 32.87 | 47.33 | 43.25 | 53.5 | 57.52 | 43.21 | 29.98 | 44.83 |
| Rfxank | 7.24 | 9.31 | 8.73 | 10.9 | 14.32 | 9.21 | 7.21 | 7.69 |
| Plekha5 | 5.53 | 9.36 | 6.42 | 9.04 | 12.2 | 5.87 | 4.62 | 6.35 |
| Zmynd8 | 26.73 | 35.26 | 27.37 | 33.89 | 35.64 | 26.47 | 14.08 | 20.07 |
| D230025D16Rik | 15.34 | 24.16 | 16.77 | 24.56 | 18.15 | 16.28 | 9.65 | 11.47 |
| Dip2b | 4.96 | 9 | 7.42 | 8.01 | 7.23 | 8.02 | 4.31 | 4.01 |
| Pim3 | 45.83 | 66.57 | 56.7 | 48.22 | 43.36 | 49.78 | 34.12 | 27.31 |
| Qrfp | 4.87 | 10.25 | 6.93 | 7.83 | 5.15 | 5.14 | 2.85 | 1.45 |
| Kdm6b | 28.77 | 37 | 33.4 | 31.75 | 31.85 | 35.09 | 20.07 | 19.64 |
| Srrm2 | 47.63 | 46.52 | 37.58 | 49.53 | 40.07 | 46.71 | 29.63 | 31.6 |
| Acp5 | 137.13 | 135.95 | 99.63 | 114.17 | 109.53 | 133.43 | 68.91 | 79.63 |
| Pan3 | 34.5 | 35.93 | 23.43 | 33.22 | 24.97 | 33.31 | 13.1 | 22.33 |
| Utrn | 25.51 | 26.18 | 18.34 | 28.67 | 23.55 | 22.43 | 16.69 | 15.79 |
| Skil | 27.55 | 36.76 | 26.84 | 36.25 | 28.98 | 25.67 | 17.29 | 23.82 |
| Zfp110 | 25.71 | 37.96 | 25.08 | 27.95 | 22.9 | 24.46 | 15.25 | 16.5 |
| Cux1 | 14.85 | 18.68 | 13.99 | 16.51 | 16.36 | 15.13 | 12.36 | 7 |
| Prrc2c | 28.42 | 34.77 | 27.86 | 36.05 | 32.04 | 28.22 | 22.08 | 15.72 |
| Sesn3 | 10.27 | 9.43 | 10.23 | 7.23 | 11.39 | 12.08 | 6.79 | 1.92 |
| Id3 | 75.32 | 79.68 | 82.06 | 55.63 | 59.67 | 108.48 | 52.93 | 21.15 |
| Ssbp2 | 8.34 | 11.26 | 10.37 | 8.51 | 12.83 | 13.37 | 8.79 | 4.24 |
| Snhg12 | 122.47 | 134.53 | 113.92 | 88.99 | 144.67 | 146.3 | 91.2 | 79.25 |
| Ift80 | 10.12 | 14.39 | 8.44 | 9.59 | 12.18 | 13.16 | 8.8 | 2.21 |
| Zyg11b | 12.64 | 16.31 | 11.95 | 11.55 | 13.73 | 16.04 | 9.33 | 6.99 |
| Dnajb9 | 153.79 | 160.17 | 117.58 | 132.77 | 153.51 | 156.24 | 85.12 | 65.41 |
| Tmc6 | 55.07 | 66.29 | 57.31 | 48.47 | 58.95 | 63.56 | 38.7 | 45.56 |
| Rbm5 | 57.13 | 66.1 | 53.8 | 61.19 | 64.24 | 76.71 | 45.54 | 49.05 |
| Crlf3 | 161.75 | 149.55 | 129.26 | 143.01 | 157.33 | 185.81 | 85.31 | 87.2 |
| Nol6 | 10.96 | 14.2 | 18.38 | 13.95 | 13.6 | 19.47 | 9.93 | 6.29 |
| Trpm7 | 16.47 | 18.91 | 19.42 | 25.76 | 16.29 | 22.48 | 13.06 | 12.05 |
| Irak1 | 10.57 | 14.54 | 13.29 | 14.44 | 13.03 | 15.64 | 11.05 | 7.99 |
| Spry2 | 38.94 | 38.9 | 49.27 | 50.46 | 45.55 | 49.54 | 27.04 | 19.76 |
| Jun | 187.61 | 200.17 | 199.66 | 236.27 | 209.51 | 246.62 | 157.59 | 159.67 |
| Fam46c | 43.32 | 48.14 | 48.1 | 44.72 | 53.6 | 43.85 | 41.32 | 14.85 |
| Impdh2 | 114.78 | 143.45 | 155.65 | 138.35 | 139.03 | 129.79 | 118.47 | 88.78 |
| Zfp395 | 1.32 | 1.98 | 1.09 | 1.59 | 1.35 | 2.29 | 1.58 | 0.79 |
| Gbp11 | 8.81 | 13.73 | 9.92 | 8.11 | 12.67 | 15.69 | 13.73 | 6.65 |
| Rpl29 | 1405.74 | 1736.84 | 1524.58 | 1544.46 | 1446.77 | 1617.74 | 1287.65 | 1270.84 |
| Rps6 | 2243.19 | 2658.91 | 2371.24 | 2346.22 | 2244.22 | 2460.71 | 1904.83 | 1910.47 |
| Rpl6 | 1818.75 | 1947.25 | 1810.58 | 1919.04 | 1713.92 | 1931 | 1546.16 | 1454.53 |
| Rpl3 | 3290.13 | 3382.63 | 3020.01 | 3137.37 | 2946.85 | 3307.98 | 2531.17 | 2569.44 |
| Rpl18 | 1433.67 | 1634.55 | 1417.18 | 1472.76 | 1347.31 | 1501.81 | 1222.05 | 1165.76 |
| Rps3 | 1704.51 | 1949.47 | 1729.79 | 1839.27 | 1668.55 | 1797.61 | 1414.49 | 1350.96 |
| Rpl19 | 4179.2 | 4662.65 | 4164.4 | 4392.98 | 3940.06 | 4513.87 | 3588.98 | 3224.91 |
| Rps3a1 | 3632.73 | 4035.29 | 3545.79 | 3550.47 | 3206.59 | 3819.13 | 2801.21 | 2567.66 |
| Rpl7 | 2552.66 | 2595.53 | 2581.66 | 2477.28 | 2439.15 | 2707.59 | 2188.06 | 1958.84 |
| Rpl23 | 1921.27 | 2179.9 | 2155.37 | 2105.58 | 1999.74 | 2105.18 | 1686.38 | 1549.82 |
| Rpl13 | 3160.12 | 3764.67 | 3585.78 | 3426.42 | 3374.21 | 3653.54 | 2869.89 | 2586.27 |
| Rpl28 | 1256.56 | 1315.59 | 1415.34 | 1197.13 | 1305.16 | 1429.99 | 1164.4 | 1063.54 |
| Rpl4 | 3199.54 | 3103.38 | 2900.15 | 2921.19 | 3510.86 | 2983.91 | 2354.57 | 2193.77 |
| Rpop0 | 3715.62 | 3858.63 | 3509.27 | 3730.45 | 4146.38 | 3838.58 | 2957.5 | 2787.72 |
| Eef1a1 | 9343.36 | 9288.28 | 8715.79 | 9254.3 | 9830.37 | 9361.74 | 7350.71 | 7378.29 |
| Rps4x | 6198.84 | 6466.96 | 6070.38 | 6123.81 | 6424.33 | 6412.56 | 4853.22 | 4392.76 |
| Rpl18a | 3529.5 | 3841.45 | 3539.57 | 3698.82 | 3823.63 | 3833.52 | 2576.84 | 2397.43 |
| Rpsa | 2928.61 | 3313.07 | 2816.94 | 2917.93 | 3168.47 | 3073.24 | 2052.46 | 1940.96 |
| 2410004N09Rik | 63.72 | 92.31 | 78.87 | 94.26 | 79.91 | 92.25 | 62.87 | 52.91 |
| Gnb2l1 | 1322.4 | 1535.63 | 1491.69 | 1363.4 | 1386.52 | 1434.1 | 952.69 | 883.43 |
| Smc4 | 131.54 | 154.04 | 106.56 | 140.45 | 132.05 | 131.12 | 66.65 | 68.33 |
| Tpt1 | 6200.82 | 6879.18 | 6336.93 | 6687.12 | 6724.71 | 6986.46 | 4792.1 | 4503.16 |

TABLE 4-continued

| | | | | | | | | |
|---|---|---|---|---|---|---|---|---|
| Nsg2 | 36.84 | 50.13 | 38.33 | 44.87 | 37.34 | 46.91 | 20.51 | 5.54 |
| Mir703 | 49.31 | 43.94 | 37.82 | 43.79 | 50.9 | 34.84 | 36.02 | 34.59 |
| Cd72 | 26.45 | 34.64 | 26.85 | 35.51 | 35.28 | 26.68 | 29.27 | 18.8 |
| Tspan13 | 100.69 | 97.55 | 73.24 | 95.15 | 142.75 | 85.87 | 80.82 | 62.14 |
| Rnf38 | 14.7 | 10.57 | 11.16 | 13.58 | 16.13 | 12.39 | 8.85 | 9.21 |
| Rsl24d1 | 51.44 | 46.42 | 40.58 | 40.61 | 58.47 | 54.74 | 47.26 | 26.85 |
| Fasn | 7.12 | 5.97 | 5.32 | 6.4 | 9.28 | 7.41 | 7.2 | 4.7 |
| Ilf3 | 45.85 | 34.46 | 35.04 | 34.32 | 42.09 | 43.33 | 32.34 | 34.79 |
| Gcnt7 | 1.96 | 0.84 | 0 | 0.89 | 1.48 | 1.52 | 0.5 | 0.34 |
| Gltp | 85.47 | 74.31 | 77.09 | 73.99 | 86.17 | 83.18 | 63.28 | 35.93 |
| Abce1 | 40.38 | 35.07 | 32.44 | 34.13 | 37.05 | 36.93 | 26.02 | 19.86 |
| Tha1 | 11.46 | 6.5 | 6.61 | 8.31 | 8.02 | 8.67 | 1.61 | 0 |
| Exosc2 | 21.17 | 19.59 | 16.54 | 18.81 | 22.08 | 20.96 | 15.15 | 11.81 |
| Lcn4 | 28.24 | 27.69 | 14.87 | 13.31 | 40.02 | 15.66 | 19.89 | 17.76 |
| Pou6f1 | 11.05 | 14.09 | 8.49 | 8.01 | 19.59 | 9.92 | 7.18 | 6.38 |
| Rnf144a | 2.87 | 4.45 | 1.91 | 2.31 | 5.94 | 2.51 | 1.81 | 1.77 |
| Pip5k1b | 1.53 | 1.97 | 0.47 | 1.26 | 4.8 | 2.43 | 1.47 | 0 |
| Tnrc6c | 8.1 | 6.46 | 5.3 | 6.09 | 15.42 | 7.7 | 3.66 | 3.29 |
| Slc26a11 | 35.76 | 25.56 | 20.98 | 25.37 | 67.94 | 29.17 | 13.99 | 7.7 |
| Cxx1c | 10.34 | 6.66 | 4.59 | 5.6 | 16.78 | 7.41 | 3.34 | 3.55 |
| Ap1ar | 14.27 | 10 | 6.2 | 11.41 | 24.48 | 8.79 | 8.46 | 8.04 |
| 9430038I01Rik | 7.26 | 6.42 | 4.28 | 6.88 | 12.24 | 5.36 | 4.08 | 3.95 |
| 2010300C02Rik | 3.31 | 0.64 | 0.76 | 1.91 | 4.55 | 0.74 | 1.06 | 0.82 |
| Gigyf2 | 14.6 | 6.17 | 8.66 | 8.65 | 18.98 | 9.32 | 8.82 | 3.57 |
| Cd96 | 89.2 | 83.69 | 64.72 | 77.58 | 114.22 | 70.16 | 66.67 | 48.01 |
| Pou2af1 | 3.75 | 3.45 | 1.86 | 1.24 | 5.37 | 1.14 | 0.72 | 0 |
| Nufip1 | 13.25 | 11.89 | 9.3 | 8.55 | 18.52 | 8.65 | 7.05 | 3.8 |
| Sbds | 54.82 | 47.04 | 43.64 | 51.11 | 77.35 | 37.23 | 43.64 | 38.07 |
| Galnt2 | 22.22 | 17.87 | 16.6 | 19.79 | 30.11 | 12.76 | 9.88 | 6.64 |
| Gtpbp1 | 29.83 | 28.93 | 28.06 | 30.4 | 43.65 | 31.6 | 17.96 | 27.66 |
| Neil1 | 14.18 | 15.13 | 14.58 | 14.89 | 23.68 | 18.62 | 9.32 | 9.01 |
| Zfp235 | 3.23 | 1.93 | 2.3 | 2.64 | 4.68 | 1.29 | 0.54 | 0 |
| Sacs | 1.95 | 2.18 | 1.94 | 1.31 | 3.24 | 0.92 | 0.5 | 0.34 |
| N4bp2 | 5.8 | 3.54 | 3.35 | 3.25 | 5.6 | 2.33 | 0.97 | 2.22 |
| Zbtb10 | 3.02 | 2.09 | 1.92 | 1.71 | 4.5 | 2.1 | 1.3 | 0.4 |
| Ldlrad4 | 10.32 | 7.23 | 8.38 | 6.56 | 16.11 | 7.57 | 4.17 | 7.4 |
| Zfp386 | 64.25 | 53.62 | 34.93 | 36.78 | 53.31 | 34.67 | 29.55 | 27.32 |
| Anks3 | 33.53 | 30.45 | 17.2 | 21.41 | 25.87 | 17.12 | 12.47 | 21.16 |
| Cep68 | 17.41 | 10.59 | 7.01 | 9.07 | 13.94 | 9.31 | 7.25 | 5.91 |
| Inpp4b | 31.82 | 16.43 | 12.93 | 15.58 | 28.11 | 12.5 | 12.87 | 6.76 |
| Grip2 | 0.9 | 0.69 | 0.15 | 0.44 | 1.18 | 0.03 | 0.22 | 0.18 |
| Ggt1 | 12.62 | 11.75 | 5.76 | 8.76 | 13.7 | 5.84 | 2.48 | 5.31 |
| Ascc1 | 40.64 | 34.54 | 24.89 | 30.95 | 43.95 | 18.56 | 20.94 | 21.52 |
| Hist3h2a | 17.3 | 21.07 | 16.49 | 18.04 | 23.2 | 18.53 | 12.22 | 9.66 |
| Slc25a36 | 15.75 | 24 | 13.44 | 26.8 | 26.47 | 19.34 | 14.97 | 9.6 |
| Use1 | 131.61 | 169.47 | 151.45 | 171.52 | 184.95 | 145.67 | 113.58 | 115.12 |
| Arhgap27 | 43 | 37.79 | 33.91 | 32.91 | 44.99 | 30.63 | 33.44 | 24.14 |
| Vps13a | 8.98 | 8.74 | 7.58 | 7.88 | 9.25 | 8 | 7.71 | 5.7 |
| Lta4h | 98.01 | 78.17 | 83.75 | 91.06 | 102.12 | 79.81 | 89.59 | 63.08 |
| Tom1l2 | 11.28 | 10.38 | 7.04 | 9.9 | 12.32 | 7.71 | 8.88 | 3.29 |
| Hspbp1 | 31.63 | 28.7 | 24.44 | 23.01 | 37.45 | 29.08 | 19.19 | 9.37 |
| Zfp652 | 6.34 | 6.23 | 5.4 | 3.81 | 8 | 4.72 | 4.11 | 2.4 |
| Lancl1 | 14.32 | 18.99 | 14.62 | 10.51 | 19.14 | 18.66 | 10.84 | 7.87 |
| Filip1l | 12.17 | 19.14 | 15.25 | 11.01 | 22.06 | 17.02 | 9.84 | 4.9 |
| Kdm5b | 8.81 | 8.45 | 7.66 | 6.18 | 12.02 | 9.31 | 6.68 | 4.27 |
| B430306N03Rik | 5.75 | 4.02 | 4.32 | 2.35 | 6.22 | 5.2 | 3.52 | 2.6 |
| Peli1 | 79.5 | 77.4 | 70.86 | 60.94 | 102.71 | 89.3 | 61.63 | 56.9 |
| Prkch | 64.31 | 68.19 | 78.71 | 44.54 | 110.5 | 80.92 | 49.18 | 45.6 |
| Akap9 | 6.71 | 7.68 | 6.1 | 5.51 | 8.85 | 6.97 | 6.11 | 3.37 |
| Snhg8 | 139.83 | 154.89 | 145.18 | 149.7 | 199.84 | 164.94 | 132.54 | 86.61 |
| Pkp4 | 19.11 | 14.32 | 12.34 | 15.72 | 25.94 | 10.34 | 11.4 | 3.01 |
| F2rl1 | 6.47 | 6.08 | 5.87 | 5.49 | 7.85 | 5.56 | 5.09 | 0.89 |
| Slamf6 | 69.3 | 55.18 | 29.67 | 47.31 | 65.54 | 53.12 | 45.25 | 29.68 |
| Vps39 | 18.92 | 19.37 | 14.69 | 18.34 | 23.09 | 17.55 | 16.65 | 13.46 |
| Tiprl | 39.58 | 36.17 | 29.46 | 37.22 | 43.15 | 37.47 | 30.34 | 20.35 |
| H2-Ob | 32.45 | 17.04 | 16.69 | 28.36 | 41.78 | 31.15 | 6.95 | 9.17 |
| Paip2 | 232.23 | 205.16 | 184.73 | 213.11 | 253.45 | 225.79 | 180 | 168.63 |
| Prrg4 | 5.45 | 4.6 | 1.72 | 3.4 | 8.2 | 3.5 | 1.11 | 0 |
| Cblb | 43.57 | 44.42 | 37.18 | 41.63 | 56.8 | 41.6 | 37.71 | 31.7 |
| Rbfa | 50.83 | 37.11 | 25.09 | 38.24 | 64.99 | 35.17 | 30.89 | 22.79 |
| 2610301B20Rik | 10.25 | 5.5 | 4.75 | 10.73 | 24.3 | 8.69 | 4.03 | 11.29 |
| Fam65a | 14.77 | 7.03 | 7.78 | 11.14 | 21.61 | 10.84 | 9.51 | 10.11 |
| Il6st | 23.06 | 14.35 | 17.32 | 21.37 | 32.95 | 18.74 | 18.02 | 21.49 |
| Ccm2 | 63.22 | 39.88 | 45.71 | 71.02 | 74.74 | 60.83 | 44.03 | 62.78 |
| Batf | 56.94 | 53.6 | 64.96 | 83.95 | 112.76 | 79.24 | 61.34 | 71.25 |
| 4833420G17Rik | 52.98 | 51.74 | 33.73 | 53.15 | 59.58 | 43.61 | 28.01 | 44.68 |
| Mysm1 | 23.35 | 18.22 | 15.93 | 18.74 | 22.18 | 18.93 | 12.35 | 16.29 |
| Srpk1 | 70.99 | 62.14 | 52.81 | 71.51 | 92.5 | 70.19 | 45.57 | 66.68 |
| Gramd1a | 79.75 | 77.79 | 70.57 | 72.04 | 106.98 | 80.5 | 66.96 | 74.53 |
| Trim13 | 23.5 | 19.89 | 13.93 | 18.25 | 31.6 | 18.38 | 11.88 | 12.54 |

TABLE 4-continued

| | | | | | | | | |
|---|---|---|---|---|---|---|---|---|
| Usf2 | 13.78 | 8.09 | 8.31 | 8.78 | 14.63 | 8.38 | 7.36 | 10.82 |
| Git2 | 34.11 | 29.19 | 22.73 | 32.82 | 41.09 | 31.05 | 29.06 | 33.95 |
| Bclaf1 | 34.96 | 39.86 | 40.69 | 45.03 | 46.45 | 47.48 | 26.42 | 42.99 |
| Fbxo32 | 6.65 | 7.62 | 8.2 | 9.73 | 10.61 | 12.5 | 5.88 | 8.17 |
| Klhdc1 | 8.59 | 9.64 | 14.86 | 21.99 | 26.57 | 24 | 4 | 14.59 |
| Gpd1l | 19.76 | 9.86 | 11.74 | 9.96 | 27.23 | 17.7 | 10.88 | 13.76 |
| Gtf3c2 | 31.92 | 27.02 | 23.51 | 29.72 | 33.71 | 31.13 | 22.5 | 27.07 |
| Il27ra | 64.16 | 56.32 | 41.94 | 56.99 | 77.63 | 63.83 | 48 | 53.14 |
| Apobec1 | 9.29 | 9.75 | 10.22 | 8.62 | 17.9 | 20.14 | 7.37 | 13.44 |
| Pqbp1 | 55.95 | 46.11 | 48.54 | 43.25 | 62.59 | 57.54 | 37.2 | 56.75 |
| Csf3r | 5.4 | 1.7 | 2.37 | 0.86 | 5.38 | 5.05 | 0.49 | 5.25 |
| Patz1 | 10.61 | 6.48 | 7.15 | 12.15 | 10.33 | 10.4 | 4.49 | 5.46 |
| Cmah | 28.32 | 17.19 | 14.73 | 21.5 | 20.46 | 21.1 | 14.25 | 14.41 |
| Aff3 | 9.54 | 1.94 | 3.54 | 6.17 | 5.37 | 4.08 | 2.84 | 1.97 |
| Flcn | 34.42 | 19.19 | 40.29 | 36.82 | 37.03 | 39.77 | 17.42 | 20.4 |
| Ephx1 | 18.06 | 7.65 | 11.6 | 10.05 | 15.75 | 19.35 | 4.79 | 6.22 |
| Adk | 48.65 | 17.58 | 27.65 | 41.05 | 47.28 | 49.25 | 21.62 | 7.25 |
| Gpr146 | 17.31 | 13.37 | 14.58 | 21.54 | 21.93 | 16.98 | 9.9 | 4.26 |
| Mat2a | 115.05 | 81.84 | 81.34 | 91.24 | 119.85 | 93.65 | 62.82 | 46.32 |
| Ubxn7 | 7.84 | 4.98 | 5.36 | 7.17 | 7.38 | 5.55 | 4.87 | 4.07 |
| Zrsr1 | 6.28 | 2.45 | 3.59 | 4.35 | 5.51 | 2.29 | 1.28 | 0.92 |
| Ndrg3 | 70.14 | 68.5 | 69.66 | 65.38 | 66.79 | 60.57 | 45.1 | 40.33 |
| A930024E05Rik | 4.67 | 3.12 | 4.54 | 4 | 4.85 | 4.13 | 2.45 | 0.2 |
| Taf4b | 7.68 | 8.35 | 7.32 | 6.27 | 7.45 | 8.04 | 2.41 | 2.01 |
| B4galt1 | 81.43 | 84.03 | 86.84 | 89.76 | 100.97 | 80.5 | 61.1 | 58.14 |
| Vps37b | 496.32 | 508.16 | 409.18 | 491.21 | 711.96 | 473.89 | 294.15 | 214.2 |
| Eif4ebp2 | 12.07 | 14 | 12.37 | 11.03 | 20.55 | 12.97 | 7.03 | 5.27 |
| Tob1 | 25.92 | 33.78 | 24.02 | 32.3 | 38.87 | 38.41 | 19.56 | 10.3 |
| Maff | 5.25 | 5.69 | 6.83 | 6.9 | 9.29 | 6.73 | 2.99 | 0.94 |
| Mcl1 | 47.09 | 42.53 | 37.28 | 44.05 | 51.93 | 43.74 | 26.01 | 21.12 |
| Irf1 | 758.22 | 651.4 | 697.75 | 771.04 | 924.75 | 783 | 333.27 | 254.87 |
| Jmy | 3.97 | 5.82 | 5.8 | 5.33 | 6.2 | 3.91 | 2.18 | 0.66 |
| Mepce | 6.86 | 10.59 | 8.06 | 7.99 | 14.24 | 9.11 | 4.69 | 1.61 |
| Nipal1 | 3.17 | 4.25 | 3.68 | 4.97 | 5.89 | 3.9 | 2.07 | 0 |
| Slc25a3 | 580.61 | 536.95 | 560.18 | 590.95 | 624.77 | 580.42 | 475.68 | 446.38 |
| Itm2a | 49.87 | 62.99 | 64.59 | 55.33 | 92.29 | 54.42 | 34.55 | 29.96 |
| Klhdc2 | 81.46 | 82.91 | 112.94 | 75.74 | 138.5 | 119.18 | 44.7 | 43.74 |
| Gm10825 | 4.35 | 1.72 | 2.68 | 5.73 | 7.36 | 3.75 | 1.43 | 0.54 |
| Dyrk2 | 16.41 | 6.7 | 9.83 | 17 | 27.23 | 22.1 | 5.9 | 5.99 |
| Mdc1 | 12.39 | 9 | 8.06 | 8.99 | 15.91 | 9.5 | 5.2 | 7.21 |
| Znrf3 | 23.25 | 21.1 | 18.77 | 21.79 | 29.54 | 21.79 | 14.88 | 12.54 |
| Socs1 | 110.53 | 86.39 | 99.36 | 96.38 | 153.47 | 115.99 | 74.13 | 57.3 |
| Fbxl20 | 5.96 | 3.08 | 3.15 | 4.21 | 5.22 | 3.88 | 2.13 | 2.84 |
| Psd | 4.25 | 3.9 | 2.55 | 3.38 | 4.03 | 2.91 | 1.52 | 3.04 |
| Slc12a7 | 44.33 | 42.1 | 24.14 | 41.54 | 38.94 | 29.66 | 21.98 | 27.17 |
| Foxp1 | 45.31 | 36.89 | 35.89 | 34.59 | 41.22 | 41.88 | 25.88 | 25.19 |
| Actn1 | 15.51 | 9.76 | 7.29 | 7.41 | 9.2 | 13.29 | 3.32 | 1.96 |
| Acot2 | 60.98 | 47.35 | 31.42 | 39.8 | 49.22 | 39.91 | 23.69 | 15.28 |
| Ldlrap1 | 41.79 | 34.75 | 20.65 | 27.9 | 38.53 | 33.99 | 15.48 | 15.79 |
| Ccr7 | 665.43 | 570.84 | 478.17 | 507.23 | 725.29 | 590.03 | 276.74 | 317.64 |
| Tcf7 | 373.15 | 325.7 | 276.1 | 347.49 | 347.79 | 328.07 | 160.89 | 160.64 |
| Dusp10 | 105.82 | 105.89 | 75.25 | 88.08 | 118.69 | 80.63 | 34.78 | 43.89 |
| Bach2 | 10.96 | 10.01 | 7.95 | 10.18 | 11.03 | 7.43 | 4.9 | 3.61 |
| Vipr1 | 14.2 | 12.26 | 8.61 | 11.74 | 12.84 | 9.39 | 3.71 | 4 |
| Pik3ip1 | 103.61 | 65.84 | 67.81 | 76.77 | 91.91 | 65.17 | 34.73 | 52.31 |
| AB124611 | 128.25 | 90.22 | 85.62 | 118.17 | 118.24 | 106.05 | 78.86 | 74.7 |
| Dgka | 404.23 | 315.07 | 244.94 | 387.12 | 406.97 | 356.63 | 217.52 | 212.16 |
| Ubald1 | 48.66 | 35.63 | 34.73 | 35.19 | 49.78 | 38.36 | 25.84 | 23.1 |
| Arl5c | 51.15 | 33.43 | 27.55 | 40.46 | 56.13 | 40.18 | 15.56 | 17.98 |
| Gramd4 | 32.89 | 28.31 | 20.74 | 31.91 | 31.61 | 25.8 | 15.89 | 13.94 |
| Lef1 | 199.9 | 145.82 | 95.73 | 131.53 | 172.95 | 135.65 | 54.41 | 58.04 |
| S1pr1 | 204.33 | 140.02 | 117.32 | 174.56 | 174.37 | 157.52 | 65.27 | 61.49 |
| Srsf2 | 253.21 | 288.72 | 198.28 | 229.6 | 314.46 | 240.7 | 166.66 | 121.03 |
| Srsf5 | 365.75 | 451.98 | 327.6 | 385.77 | 449.46 | 349.53 | 201.55 | 210.91 |
| Map3k1 | 22.76 | 29 | 19.02 | 27.64 | 27.99 | 23.6 | 13.27 | 15.04 |
| Bcas3 | 16.74 | 17.27 | 11.53 | 15.93 | 16.13 | 14.62 | 9.15 | 9.24 |
| 4932438A13Rik | 20.93 | 22.97 | 15.34 | 21.13 | 22.39 | 20.42 | 14.64 | 14.03 |
| Scml4 | 30.16 | 22.61 | 22.63 | 27.98 | 27.26 | 29.39 | 14 | 9.11 |
| Eif4a2 | 349.07 | 301.98 | 271.79 | 344.07 | 376.38 | 371.32 | 231.84 | 193.32 |
| Ppp1r15a | 546.13 | 496.58 | 396.04 | 523.61 | 542.92 | 580.91 | 319.97 | 243.41 |
| Macf1 | 26.56 | 23.39 | 18.52 | 23.78 | 25.14 | 28.43 | 16.32 | 13.42 |
| Ccnl1 | 120.92 | 124.84 | 94.58 | 121.67 | 139.14 | 142.74 | 79.37 | 63.22 |
| Pnrc1 | 70.87 | 60.91 | 72.1 | 71.45 | 84.37 | 66.77 | 47.72 | 45.3 |
| Emb | 533.3 | 484.39 | 539.83 | 531.95 | 633.77 | 550.24 | 369.59 | 308.86 |
| Bcl10 | 79.46 | 71.29 | 68.97 | 79.78 | 83.69 | 73.82 | 51.11 | 34.35 |
| Pcbp2 | 71.53 | 65.38 | 69.05 | 67.28 | 72.57 | 65.4 | 49.43 | 40.88 |
| Socs3 | 279.74 | 324.61 | 283.77 | 374.29 | 397.95 | 365.57 | 162.72 | 164.62 |
| Gramd3 | 377.39 | 359.75 | 316.53 | 385.11 | 424.35 | 386.33 | 249.9 | 202.31 |
| Sidt1 | 74.42 | 84.62 | 60.38 | 79.03 | 85.2 | 93.24 | 48.73 | 43.15 |
| Il4ra | 138.6 | 162.7 | 145.11 | 165.82 | 160.49 | 151.26 | 103.58 | 87.44 |

TABLE 4-continued

| | | | | | | | | |
|---|---|---|---|---|---|---|---|---|
| Ppm1h | 61.34 | 54.63 | 40.62 | 54.24 | 58.92 | 44.11 | 23.79 | 25.81 |
| Rn45s | 36829.15 | 37290.97 | 32277.83 | 36341.45 | 38815.26 | 36991 | 24315.24 | 29504.05 |
| Stk4 | 32.56 | 33.92 | 28.21 | 44.86 | 40.9 | 34.82 | 19.44 | 19.64 |
| Stk17b | 471.63 | 460.77 | 341.23 | 498.49 | 461.92 | 436.41 | 326.49 | 241.8 |
| Tmem66 | 627.32 | 609.81 | 455.42 | 582.09 | 691.26 | 579 | 414.76 | 412.74 |
| Abcg1 | 28.5 | 32.15 | 20.03 | 26.92 | 29.29 | 26 | 16.39 | 16.68 |
| Smad7 | 21.99 | 24.87 | 17.66 | 17.67 | 23.32 | 21.57 | 12.03 | 12.34 |
| Ssh2 | 63.41 | 74.89 | 54.56 | 64.03 | 66.04 | 66.97 | 52.9 | 47.66 |
| Dym | 38.71 | 39.53 | 40.04 | 52.04 | 43.97 | 31.91 | 28.45 | 34.68 |
| Card6 | 28.3 | 30.95 | 20.14 | 32.32 | 34.29 | 24.45 | 17.49 | 18.29 |
| Elovl5 | 106.92 | 129.8 | 103.92 | 126.27 | 131.1 | 110.64 | 97.9 | 92.69 |
| Gltscr2 | 399.5 | 403.04 | 315.15 | 407.63 | 450.79 | 349.68 | 285.41 | 274.22 |
| Tbc1d17 | 25.45 | 20.24 | 17.44 | 27.26 | 20.23 | 18.75 | 15.54 | 24.98 |
| Pbxip1 | 54.87 | 39.02 | 35.18 | 48.95 | 51.33 | 39.85 | 30.86 | 49.98 |
| Mcoln2 | 15.52 | 11.78 | 11.24 | 21.6 | 20.96 | 16.51 | 12.6 | 15.71 |
| Ube2h | 49.04 | 41.92 | 37.75 | 51.29 | 44.19 | 49.95 | 33.49 | 44.7 |
| Srsf6 | 60.25 | 54.13 | 56.09 | 69.99 | 66.83 | 51.35 | 40.8 | 51.91 |
| Tmem64 | 5.51 | 3.02 | 4.89 | 6.7 | 7.75 | 2.79 | 1.78 | 5.67 |
| Kidins220 | 15.88 | 13.49 | 12.88 | 19.4 | 18.28 | 13.08 | 10.72 | 12.42 |
| Smpdl3a | 138.68 | 78.12 | 108.85 | 135.21 | 131.5 | 92.15 | 97.75 | 94.53 |
| Lrrc61 | 16.42 | 11.66 | 12.54 | 9.03 | 9.79 | 6.7 | 9.91 | 8.79 |
| Brf1 | 27.63 | 19.16 | 14.02 | 12.32 | 17.43 | 15.59 | 14 | 14.22 |
| 3230401D17Rik | 105.71 | 92.46 | 94.57 | 76.61 | 107.78 | 90.15 | 70.53 | 70.41 |
| Pnpla7 | 35.42 | 23.38 | 18.4 | 19.01 | 34.46 | 20.12 | 12.45 | 11.49 |
| Ppargc1b | 3.77 | 3.57 | 3 | 1.95 | 3.54 | 1.72 | 0.2 | 0.41 |
| Cebpz | 26.31 | 20.75 | 20.05 | 15.85 | 27.52 | 15.38 | 13.12 | 9.65 |
| Prdx6 | 214.38 | 200.28 | 246.82 | 183.48 | 186.76 | 187.98 | 143.24 | 129.34 |
| Pabpc1 | 396.98 | 370.47 | 445.59 | 357.22 | 373.03 | 364.15 | 296.82 | 298.79 |
| Mgat5 | 15.03 | 13.31 | 12.65 | 11.76 | 13.57 | 9.68 | 11.11 | 9.1 |
| Sdha | 141.82 | 121.49 | 116.94 | 139.07 | 110.52 | 116.33 | 117.74 | 96.64 |
| Ipcef1 | 40.87 | 22.76 | 29.37 | 38.34 | 27.07 | 30.22 | 23.55 | 25.98 |
| Rnf130 | 5.36 | 8.18 | 4.68 | 2.42 | 7.54 | 4.71 | 3.71 | 4.52 |
| Tars2 | 29.62 | 28.61 | 23.28 | 21.98 | 27.95 | 19.35 | 18.24 | 21.03 |
| Gnpat | 36 | 46.84 | 32.71 | 29.59 | 37.95 | 26.73 | 27.78 | 27.33 |
| Eif4b | 167.19 | 149.33 | 137.3 | 144.87 | 136.89 | 147.42 | 120.62 | 123.1 |
| Sec11a | 149.3 | 132.22 | 129.99 | 132.75 | 126.37 | 142.39 | 129.81 | 117.43 |
| Skp1a | 125.18 | 118 | 121.16 | 105.53 | 99.64 | 117.1 | 104.34 | 100.89 |
| Btla | 13.86 | 25.41 | 12.76 | 18.6 | 13.48 | 18.52 | 14.34 | 15.61 |
| Dennd6b | 3.63 | 8.69 | 3.84 | 6.5 | 3.45 | 5.39 | 3.45 | 5.35 |
| Ikzf1 | 62.5 | 74.46 | 47.68 | 62.46 | 48.35 | 56.7 | 60.22 | 51.62 |
| Entpd5 | 13.67 | 17.93 | 12.25 | 17.03 | 8.93 | 13.77 | 12.23 | 6.68 |
| Polg2 | 19.61 | 23.74 | 10.11 | 15.47 | 12.74 | 9.4 | 8.19 | 3.97 |
| Abhd11 | 26.48 | 34.58 | 15.41 | 18.62 | 12.56 | 24.61 | 17.17 | 8.42 |
| Uvssa | 9.23 | 9.39 | 5.89 | 9.03 | 2.6 | 6.95 | 4.91 | 6.31 |
| Slc17a9 | 19.55 | 16.26 | 8.97 | 12.89 | 5.3 | 12.78 | 8.86 | 10.46 |
| Gm129 | 12.45 | 14.58 | 9.58 | 7.93 | 2.94 | 11.11 | 8.38 | 8.51 |
| St8sia1 | 2.6 | 3.3 | 2.23 | 0.92 | 0.24 | 0.96 | 1.14 | 1.58 |
| 2510002D24Rik | 47.34 | 43.11 | 33.74 | 37.32 | 25.7 | 31.26 | 28.61 | 22.4 |
| Socs6 | 20.43 | 16.06 | 14.76 | 12.46 | 8.58 | 9.89 | 7.97 | 10.44 |
| Dph1 | 10.73 | 17.52 | 11.52 | 4.42 | 4.67 | 13.05 | 8.11 | 6.67 |
| Trmt1 | 34.64 | 50.76 | 43.36 | 34.84 | 20.35 | 39.97 | 29.05 | 42.43 |
| Cenpq | 20.43 | 23.37 | 17.98 | 17.86 | 16.59 | 17.34 | 10.93 | 13.45 |
| Slc37a2 | 4.89 | 6.67 | 4.59 | 3.46 | 4.08 | 6.38 | 1.78 | 4 |
| Rpl31-ps12 | 56.21 | 83.2 | 72.66 | 57.79 | 62.61 | 75.5 | 58.29 | 60.58 |
| Gas7 | 9.11 | 12.97 | 8.96 | 7.52 | 8.94 | 10.74 | 6.79 | 7.44 |
| Rps21 | 893.35 | 1235.18 | 1213.79 | 1079.24 | 891.54 | 1176.93 | 959.58 | 772.11 |
| Rpl22 | 127.53 | 137.44 | 169.48 | 140.59 | 123.31 | 158.14 | 135.15 | 108.01 |
| Gm19705 | 19.1 | 29.63 | 23.26 | 20.19 | 21.12 | 22.4 | 10.46 | |
| Rps10 | 1940.58 | 2464.34 | 2328.29 | 2188.07 | 1975.24 | 2248.5 | 2082.51 | 1908.28 |
| Rps16 | 2525.03 | 3359.28 | 2939.09 | 2977.2 | 2550.57 | 2886.31 | 2649.05 | 2230.3 |
| Rps14 | 2721.63 | 3463.75 | 3186.72 | 3234.72 | 2614.53 | 3206.31 | 2854.99 | 2289.32 |
| Rpl37a | 950.27 | 1272.17 | 1199.72 | 1221.58 | 973.29 | 1210.69 | 1136.13 | 930.71 |
| Rpl27a | 941.91 | 1215.5 | 1200.08 | 1120.17 | 965.88 | 1109.71 | 1047.07 | 885.26 |
| Rps20 | 1829.57 | 2285.5 | 2094.06 | 1841.55 | 1548.91 | 2069.53 | 1879.78 | 1427.86 |
| Rpl23a | 2956.5 | 3647.92 | 3574.87 | 3306.72 | 2965.48 | 3376.47 | 2987.55 | 2600.92 |
| Rps7 | 1351.14 | 1666.01 | 1568.17 | 1439.65 | 1207.25 | 1611.83 | 1333.19 | 1140.77 |
| Rpl36a | 1097.52 | 1357.52 | 1390.66 | 1216.09 | 985.24 | 1327.59 | 1090.25 | 860.39 |
| Rps28 | 1613.6 | 2066.04 | 1981.21 | 1937.65 | 1253.1 | 2010.02 | 1667.33 | 1453.44 |
| Rps18 | 2119.94 | 2684.01 | 2580.69 | 2447.27 | 1966.24 | 2551.74 | 2203.29 | 1626.69 |
| Rps24 | 1851.93 | 2495.91 | 2180.71 | 2087.45 | 1700.07 | 2209.58 | 1934.09 | 1616.33 |
| Rps23 | 2195.28 | 2902.56 | 2675.48 | 2523.16 | 2122.57 | 2600.18 | 2427.14 | 1912.49 |
| Rps19 | 1820.31 | 2476.26 | 2267.14 | 2114.61 | 1650.81 | 2201.86 | 2024.78 | 1565.88 |
| Rpl10 | 2807.69 | 2770.7 | 2966.31 | 2692.92 | 2209.51 | 3038.96 | 2404.97 | 2410.41 |
| Rpl15 | 800.76 | 825.91 | 830.6 | 827.95 | 675.14 | 855.28 | 716.04 | 651.22 |
| Rps26 | 1928.46 | 1955.54 | 2004.64 | 1764.21 | 1642.87 | 2051.49 | 1564.2 | 1438.69 |
| Rps17 | 1793.42 | 2043.34 | 2039.22 | 1729.02 | 1395.45 | 2078.25 | 1565.73 | 1288.51 |
| Eef1b2 | 701.78 | 769.01 | 776.28 | 730.61 | 606.88 | 744.17 | 579.67 | 508.72 |
| Rps8 | 2374.89 | 2838.89 | 2664.69 | 2430.76 | 2085.74 | 2668.85 | 2095.53 | 2019.5 |
| Gas5 | 207.01 | 251.66 | 219.82 | 213.53 | 202.47 | 217.03 | 198.28 | 160.56 |
| Rplp2 | 2023.04 | 2523.04 | 2228.37 | 2149.66 | 2092.3 | 2332.45 | 1907.76 | 1620.69 |

TABLE 4-continued

| | | | | | | | | |
|---|---|---|---|---|---|---|---|---|
| Rpl5 | 2598.15 | 3120.72 | 2592.5 | 2686.37 | 2544.63 | 2972.25 | 1905.51 | 1703.82 |
| Rpl8 | 2610.67 | 3145.11 | 2604.58 | 2615.1 | 2566.82 | 2785.59 | 2157.2 | 1838.06 |
| Rpl12 | 3000.39 | 4106.63 | 3450.1 | 3481.08 | 2550.97 | 3527.18 | 2512.77 | 2102.35 |
| Gm12191 | 2160.81 | 2509.31 | 2343.64 | 2195.32 | 1837.57 | 2392.35 | 1816.79 | 1733.56 |
| Rpl9 | 2849.43 | 3470.17 | 3192.06 | 3117.86 | 2581.53 | 3394.57 | 2675.57 | 2425.95 |
| Rps29 | 1837.8 | 2317.5 | 1940.03 | 1890.4 | 1615.27 | 2139.78 | 1571.78 | 1436.23 |
| Uba52 | 3004.18 | 3582.99 | 3134.24 | 3311.29 | 3001.47 | 3372.05 | 2859.32 | 2499.78 |
| Rps5 | 3046.86 | 3629.17 | 3402.7 | 3366.21 | 3046.3 | 3642.57 | 2679.72 | 2589.81 |
| Rpl21 | 1152.74 | 1328.03 | 1194.05 | 1207.3 | 1152.7 | 1286.26 | 994.21 | 891.16 |
| Cyb5 | 112.81 | 151.77 | 149.73 | 115.27 | 124.28 | 130.86 | 102.51 | 103.09 |
| Rps15 | 2080.84 | 2413.7 | 2555.66 | 2418.82 | 2290.99 | 2476.3 | 1966.93 | 1653.13 |
| Rplp1 | 3330.69 | 3969.88 | 4019.6 | 3679.86 | 3425.9 | 4022.82 | 3122.14 | 2537.65 |
| C1galt1 | 8.33 | 9.55 | 5.84 | 7.63 | 6.75 | 7.87 | 6.74 | 5.47 |
| Luc7l2 | 10.71 | 13 | 10.05 | 12.4 | 10.49 | 10.21 | 9.27 | 8.14 |
| Rps27 | 1842.54 | 4413.46 | 2601.71 | 3277.85 | 2205.06 | 3036.72 | 2211.78 | 2041.46 |
| Cyth3 | 18.82 | 27.34 | 17.6 | 25.82 | 12.94 | 21.7 | 13.41 | 14.57 |
| Trpc4ap | 20.08 | 29.01 | 22.17 | 15.21 | 21.33 | 21.64 | 15.49 | 15.73 |
| Zfp281 | 21.37 | 28.22 | 17.32 | 18.71 | 23.54 | 26.48 | 14.49 | 14.72 |
| Tcp11l2 | 110.19 | 137.82 | 93.41 | 98.22 | 134.91 | 101.98 | 58.71 | 51.97 |
| St6gal1 | 27.16 | 46.03 | 24.32 | 26.29 | 30.85 | 31.1 | 16.99 | 9.75 |
| Klf4 | 6.82 | 13.16 | 13.07 | 8.36 | 11.74 | 11.24 | 4.87 | 9.53 |
| Rab3ip | 24.03 | 27.48 | 21.73 | 18.58 | 29.98 | 28.11 | 16.75 | 18.69 |
| Map4k4 | 6.36 | 9.6 | 8.62 | 6.13 | 12.16 | 9.25 | 5.18 | 7.9 |
| Elovl6 | 11.68 | 18.09 | 10.42 | 9.62 | 5.45 | 11.42 | 6.83 | 15.89 |
| Klra23 | 21.23 | 48.36 | 28.06 | 34.45 | 36.49 | 44.06 | 28.94 | 59.29 |
| Slc43a2 | 3.76 | 4.33 | 2.95 | 3.71 | 3.39 | 5.3 | 2.33 | 5.63 |
| Thumpd1 | 37.92 | 36.73 | 42.64 | 32.92 | 38.15 | 27.27 | 31.09 | 40.86 |
| Zfp296 | 3.24 | 10.35 | 7.87 | 5.25 | 7.18 | 4.91 | 5.21 | 7.51 |
| Mccc2 | 2.77 | 9.07 | 5.11 | 5.06 | 5.4 | 4.62 | 7.25 | 8.96 |
| Chd1l | 13.28 | 18.81 | 11.19 | 20.58 | 19.52 | 11.57 | 12.97 | 6.11 |
| Gm10548 | 4.9 | 5.63 | 3.34 | 4.95 | 4.84 | 4.77 | 5.16 | 3.35 |
| Unc119b | 49.45 | 65.18 | 42.55 | 52.52 | 56.49 | 51.37 | 56.05 | 41.93 |
| Dcaf17 | 8.85 | 11.39 | 7.71 | 6.42 | 9.76 | 7.56 | 3.88 | 5.9 |
| Ulk2 | 3.25 | 4.86 | 1.59 | 2.16 | 3.69 | 2.16 | 1.37 | 0.39 |
| Grk6 | 19.24 | 32.05 | 20.79 | 19.4 | 27.46 | 21.65 | 18.3 | 10.58 |
| Slc16a5 | 2.05 | 7.35 | 3.33 | 3.01 | 2.12 | 0.61 | 2.15 | 0 |
| Zfp1 | 13.84 | 20.15 | 7.78 | 18.33 | 15.33 | 11.48 | 11.28 | 4.36 |
| Qdpr | 31.36 | 60.49 | 40.98 | 56.39 | 42.32 | 32.1 | 30.43 | 24.05 |
| Pnpo | 10.74 | 19.75 | 15.59 | 18.08 | 16.66 | 12.05 | 12.21 | 7.77 |
| 4930432K21Rik | 1.38 | 3.76 | 2.45 | 1.59 | 0.07 | 1.92 | 2.24 | 0.38 |
| 5830411N06Rik | 6.26 | 26.99 | 14.62 | 6.32 | 7.22 | 5.23 | 12.52 | 2.81 |
| Mrm1 | 6.95 | 20.75 | 11 | 10.58 | 15.02 | 10.02 | 6.67 | 7.6 |
| Csrnp2 | 1.01 | 2.9 | 2.28 | 2.53 | 2.46 | 1.78 | 2.2 | 0.96 |
| Reck | 5.24 | 10.86 | 7.64 | 9.19 | 4.7 | 12.6 | 5.4 | 4.8 |
| C1qb | 4.82 | 42.74 | 0 | 10.71 | 8.03 | 73.14 | 0 | 0.18 |
| Ccdc164 | 2.18 | 0.44 | 0.96 | 0.55 | 2.24 | 4.81 | 0.3 | 0 |
| Tlr13 | 1.39 | 0.89 | 1.94 | 0 | 0.04 | 4.89 | 0.09 | 0.47 |
| Frat2 | 2.66 | 1.94 | 3.13 | 1.19 | 3.19 | 3.34 | 0.43 | 1.49 |
| Ifrd1 | 126.65 | 126.33 | 138.18 | 82.48 | 114.85 | 142.48 | 83.06 | 100.26 |
| Zfp266 | 11.89 | 11.71 | 10.85 | 11.15 | 13.94 | 15.39 | 7.83 | 11.48 |
| Klhl24 | 15.78 | 13.01 | 9.6 | 11.21 | 12.78 | 17.85 | 7.38 | 10.91 |
| Il16 | 62.97 | 40 | 36.66 | 44.02 | 40.83 | 46.03 | 42.45 | 49.53 |
| B4galnt1 | 295.27 | 223.02 | 186.49 | 237.14 | 193.96 | 216.9 | 224.27 | 231.38 |
| Fam169b | 80.16 | 47.32 | 43.28 | 53.34 | 54.53 | 64.77 | 44.01 | 42.75 |
| 1810026B05Rik | 19.97 | 15.67 | 13.16 | 18.69 | 15.14 | 19.71 | 13.68 | 11.32 |
| Dapl1 | 72.39 | 50.86 | 30.64 | 43.28 | 35.98 | 54.25 | 27.79 | 18.37 |
| Als2cl | 23.56 | 15.85 | 10.21 | 16.71 | 16.96 | 20.32 | 12.58 | 10.02 |
| Limd2 | 304.73 | 246.78 | 223.39 | 231.79 | 275.22 | 241.16 | 221.36 | 240.74 |
| Smap2 | 65.7 | 51.26 | 39.38 | 50.53 | 48.46 | 48.59 | 34.96 | 45.08 |
| Arhgap15 | 126.43 | 114.3 | 86.13 | 97.94 | 85.4 | 120.03 | 69.2 | 96.16 |
| Faah | 40.75 | 32.52 | 22.53 | 33.82 | 22.47 | 32.91 | 16.82 | 22.51 |
| Rgs10 | 146 | 124.76 | 100.66 | 119.62 | 90.84 | 159.53 | 57.65 | 83.3 |
| Matr3 | 69.93 | 63.59 | 63.85 | 64.08 | 57.13 | 52.64 | 50.58 | 61.92 |
| Fam210a | 5.65 | 4.99 | 4.82 | 5.85 | 3.19 | 3.97 | 2.23 | 4.33 |
| Hdac7 | 17.66 | 17.95 | 11.28 | 16.81 | 12.78 | 14.96 | 11.15 | 15.74 |
| Fam189b | 64.7 | 67.62 | 42.53 | 58.31 | 46.72 | 47.36 | 38.62 | 47.04 |
| Foxo1 | 16.39 | 19.3 | 13.43 | 12.58 | 10.57 | 12.52 | 10.02 | 10.96 |
| Sh3bp5 | 128.27 | 105.35 | 78.02 | 81.53 | 62.03 | 86.84 | 60.45 | 62.52 |
| Il7r | 224.01 | 239.96 | 144.87 | 175.1 | 134.09 | 197.59 | 102.2 | 122.87 |
| Slc50a1 | 94.66 | 79.22 | 90.95 | 86.56 | 83.54 | 85.82 | 73.32 | 68.75 |
| D10Wsu52e | 145.48 | 101.37 | 115.35 | 106.62 | 90.18 | 97.58 | 91 | 87.36 |
| Mdn1 | 6.17 | 4.05 | 4.87 | 3.97 | 2.82 | 4.04 | 3.18 | 1.65 |
| Zfp36l1 | 100.54 | 91.91 | 77.14 | 81.17 | 71.84 | 82.82 | 78.68 | 60.6 |
| Pecam1 | 29.88 | 27.23 | 19.32 | 28.78 | 16.94 | 23.39 | 13.06 | 14.13 |
| Eif3e | 441.75 | 402.99 | 379.28 | 393.13 | 395 | 360.73 | 315.93 | 293.3 |
| Sell | 714.58 | 484.62 | 452.12 | 546.81 | 533.17 | 587.16 | 314.69 | 269.59 |
| Dph5 | 37.55 | 38.07 | 34.91 | 34.56 | 26.23 | 31.71 | 20.87 | 28.49 |
| Hdac4 | 23.03 | 22.47 | 19.27 | 16.23 | 15.74 | 16.67 | 12.76 | 13.05 |
| Pdk1 | 39.2 | 44.05 | 25.64 | 35.57 | 20.09 | 28.76 | 20.22 | 14.95 |
| Rnf7 | 149.75 | 144.04 | 129.8 | 134.68 | 98.52 | 119.49 | 113.54 | 112.3 |

TABLE 4-continued

| | | | | | | | | |
|---|---|---|---|---|---|---|---|---|
| Rbm26 | 19.98 | 20.3 | 15.19 | 19.48 | 15.29 | 16.42 | 13.73 | 9.08 |
| Fgfr1op2 | 74.67 | 76.87 | 59.39 | 72.36 | 69.31 | 65.69 | 60.92 | 40.7 |
| Clk1 | 242.34 | 256.99 | 168.33 | 250.55 | 205.32 | 237.3 | 165.17 | 124.93 |
| Brd8 | 19.72 | 20.65 | 12.86 | 21.98 | 16.06 | 19.65 | 15.75 | 12.01 |
| Evl | 19.64 | 21.08 | 15.58 | 27.29 | 16.36 | 17.91 | 19.17 | 10.03 |
| Rapgef6 | 52.58 | 46.74 | 43.23 | 51.63 | 35.36 | 47.15 | 35.34 | 29.32 |
| Treml2 | 18.88 | 13.67 | 17.8 | 22.95 | 11.01 | 16.09 | 10.37 | 7.73 |
| Smg1 | 13.2 | 12.6 | 10.09 | 13.97 | 12.19 | 12.47 | 9.5 | 8.27 |
| Tnfsf8 | 23.8 | 30.73 | 17.1 | 32.56 | 23.83 | 21.27 | 14.48 | 12.09 |
| Ikbkb | 70.57 | 79.78 | 49.94 | 66.23 | 58.99 | 58.17 | 50.54 | 40.03 |
| Cox7a2l | 572.06 | 586.48 | 446.42 | 547.27 | 499.17 | 555.62 | 414.72 | 299.94 |
| Sesn1 | 37.29 | 42.24 | 22.22 | 29.17 | 26.04 | 32.73 | 19.72 | 7.05 |
| Dtd1 | 29 | 27.11 | 24.22 | 22.43 | 18.91 | 21.16 | 21.54 | 6.61 |
| Sidt2 | 55.28 | 50.96 | 45.99 | 50.42 | 50.09 | 50.66 | 43.72 | 30.21 |
| Cep110 | 20.68 | 16.4 | 13 | 21 | 18.04 | 17.51 | 16.18 | 13.32 |
| Gm6548 | 11.71 | 5.06 | 5.65 | 8.42 | 8.91 | 7.77 | 6.52 | 2.82 |
| Fahd2a | 12.65 | 8.36 | 6.58 | 12.6 | 11.23 | 11.39 | 9.68 | 5.38 |
| Max | 20.91 | 16.73 | 17.2 | 21.73 | 21.28 | 21.7 | 16.24 | 14.98 |
| Elmsan1 | 19.87 | 19.47 | 18.8 | 23.21 | 21.94 | 21.16 | 17.02 | 13.51 |
| Txnl4a | 127.59 | 106.78 | 111.42 | 128.92 | 128.85 | 119.64 | 99.32 | 66.46 |
| Srsf7 | 80.75 | 75.64 | 77.13 | 78.69 | 78.05 | 86.95 | 76.38 | 58.03 |
| Rbbp6 | 15.37 | 10.46 | 9.18 | 16.42 | 11.05 | 12.66 | 10.43 | 7.23 |
| Rictor | 12.63 | 11.09 | 7.11 | 12.23 | 11.47 | 11.64 | 7.41 | 4.31 |
| Lmbr1l | 25.97 | 16.63 | 9.89 | 20.27 | 18.46 | 12.03 | 4.96 | 2.26 |
| Cerk | 13.1 | 7.17 | 10.3 | 9.46 | 9.41 | 6.88 | 5.64 | 0.95 |
| Hsd17b4 | 26.27 | 16.71 | 17.98 | 20.25 | 19.29 | 16.85 | 15.13 | 10.32 |
| Mbip | 26.01 | 16.99 | 16.84 | 15.47 | 14.13 | 14.44 | 8.12 | 7.62 |
| Zc3h12d | 21.8 | 16.55 | 12.64 | 15.07 | 14.26 | 12.26 | 7.16 | 5.3 |
| Pdk2 | 16.75 | 10.91 | 7.54 | 8.57 | 8.84 | 5.35 | 2.54 | 3.5 |
| Zkscan14 | 28.8 | 16.7 | 13.62 | 13.84 | 12.24 | 13.94 | 7.86 | 7.42 |
| Cep97 | 21.52 | 13.36 | 9.51 | 9.81 | 12.01 | 11.21 | 6.5 | 7.16 |
| Usp28 | 38.65 | 14.06 | 11.38 | 12.56 | 17.76 | 15.7 | 5.67 | 7.41 |
| Add1 | 84.08 | 57.88 | 48.22 | 61.05 | 58.5 | 53.55 | 40.87 | 51.88 |
| Bptf | 12.34 | 6.56 | 6.64 | 9.14 | 7.73 | 8.49 | 5.67 | 7.03 |
| Bcl9l | 8.15 | 4.95 | 3.47 | 4.09 | 4.95 | 5.18 | 1.57 | 2.19 |
| Stk38 | 88.51 | 59.37 | 43.98 | 56.43 | 60.66 | 61.25 | 46.82 | 41.64 |
| Bambi-ps1 | 53.95 | 22.66 | 11.78 | 14.62 | 18.96 | 27.32 | 4.02 | 11.32 |
| Sepp1 | 208.42 | 127.97 | 70.88 | 103.27 | 112.68 | 138.05 | 57.74 | 84.61 |
| Gm14085 | 79.7 | 32.05 | 11.11 | 40.67 | 19.48 | 30.04 | 3.02 | 2.07 |
| Fam101b | 11.92 | 7.25 | 3.73 | 6.08 | 2.43 | 4.5 | 1.16 | 2.24 |
| Ikbke | 84.17 | 42.18 | 37.65 | 45.52 | 34.54 | 50.32 | 23.62 | 17.93 |
| A930005H10Rik | 61.69 | 32.36 | 29.34 | 31.36 | 33.93 | 37.74 | 17.7 | 18.99 |
| 2610019F03Rik | 74.96 | 36.38 | 37.64 | 45.11 | 40.66 | 36.37 | 11.67 | 12.69 |
| Inadl | 15.77 | 9.36 | 5.63 | 10.93 | 8.59 | 8.13 | 2.86 | 5.3 |
| Gm11346 | 34.07 | 23.12 | 23.25 | 37.22 | 12.79 | 34.12 | 8.48 | 10.3 |
| Add3 | 51.19 | 31.5 | 29.45 | 43.67 | 21.4 | 41.21 | 22.8 | 26.97 |
| D15Ertd621e | 9.74 | 5.22 | 6.19 | 7.37 | 6.04 | 7.18 | 3.13 | 4.22 |
| Rcn3 | 35.21 | 15.18 | 10.83 | 19.29 | 12.18 | 28.19 | 6 | 4.02 |
| Rapgef4 | 11.21 | 5.57 | 7.53 | 6.14 | 2.72 | 9.87 | 1.01 | 1.43 |
| Adi1 | 64.71 | 44.66 | 51.35 | 36.44 | 13.24 | 58.35 | 24.14 | 24.04 |
| Ttc28 | 1.71 | 1.06 | 0.87 | 1.08 | 0.41 | 1.88 | 0.62 | 0 |
| Zbtb20 | 15.62 | 14.13 | 5.88 | 13.12 | 5.36 | 15.71 | 8.85 | 3.84 |
| Dnahc8 | 2.67 | 2.3 | 1.46 | 1.98 | 1.49 | 2.25 | 0.86 | 1.72 |
| Cd55 | 38.18 | 32.03 | 13.87 | 15.53 | 17.26 | 31.76 | 7.34 | 22.16 |
| Pip4k2a | 16.35 | 13.6 | 10.17 | 9.6 | 8.4 | 11.22 | 5.91 | 10.85 |
| Il6ra | 28.75 | 20.95 | 9.1 | 11.87 | 7.3 | 13.58 | 3.99 | 8.62 |
| Trib2 | 25.74 | 18.79 | 14.21 | 14.33 | 11.17 | 15.41 | 6.8 | 11.62 |
| Chd6 | 7.24 | 5.59 | 5.14 | 3.53 | 3.76 | 6.08 | 3.29 | 4.16 |
| Ets2 | 40.41 | 32.58 | 29.57 | 24.49 | 21.2 | 37.69 | 13.3 | 19.81 |
| 5730508B09Rik | 25.15 | 20.83 | 22.02 | 15.31 | 17.59 | 22.97 | 9.02 | 7.99 |
| Ranbp10 | 7.92 | 8.63 | 3.99 | 4.62 | 5.65 | 6.85 | 3.77 | 3.09 |
| Ifngr2 | 50.88 | 49.99 | 27.78 | 22.12 | 25.26 | 39.3 | 2.6 | 2.32 |
| Zscan10 | 2.69 | 3.33 | 1.66 | 1.23 | 1.82 | 2.61 | 0 | 0 |
| Zfyve19 | 18.43 | 17.85 | 13.89 | 16.23 | 16.79 | 17.15 | 9.36 | 8.42 |
| Sptbn1 | 22.65 | 19.76 | 15.85 | 18.43 | 15.18 | 17.27 | 10.63 | 11.02 |
| Spon1 | 7.22 | 6.65 | 5.3 | 3.49 | 3.16 | 4.55 | 0.72 | 0.24 |
| Klf13 | 116.84 | 111.86 | 72.56 | 95.28 | 83.33 | 80.32 | 46.07 | 45.6 |
| Marf1 | 7.77 | 7.14 | 5.72 | 5.89 | 6.1 | 5.61 | 3.85 | 3.9 |
| Atp1b3 | 366.66 | 289.14 | 236.72 | 271.3 | 251.19 | 328.47 | 198.17 | 199.75 |
| Jak1 | 270.61 | 229.72 | 189.8 | 231.37 | 189.08 | 216.28 | 171.52 | 151.19 |
| Mafk | 67.19 | 62.28 | 48.08 | 48.95 | 47.69 | 71.29 | 41.49 | 19.35 |
| Sun2 | 57.24 | 52.25 | 41.26 | 49.33 | 33.41 | 48.22 | 33.88 | 16.84 |
| Rere | 11.79 | 12.6 | 11.51 | 12.13 | 8.02 | 12.66 | 8.13 | 7.88 |
| Frat1 | 20.17 | 24.18 | 20.79 | 19.3 | 12.79 | 18.3 | 8.09 | 12.9 |
| Hsdl1 | 41.6 | 46.06 | 34.26 | 40.96 | 21.41 | 37.32 | 26.39 | 24.19 |
| Abca1 | 4.11 | 4.5 | 1.85 | 2.07 | 0.67 | 2.38 | 0.56 | 0 |
| Zfp592 | 25.79 | 28.17 | 21.07 | 25.38 | 15.14 | 22.92 | 13.99 | 15.01 |
| Rbm38 | 84.69 | 93.23 | 77.67 | 98.02 | 77.32 | 99.52 | 79.14 | 62.21 |
| Lrp12 | 4.31 | 5.92 | 2.44 | 5.11 | 4.19 | 4.34 | 2.69 | 1.85 |
| Abi1 | 80.78 | 81.42 | 57.76 | 66.03 | 65.98 | 75.92 | 59.84 | 60.26 |

TABLE 4-continued

| | CD62L − Slamf7+CX3CR1− | | | CD62L − Slamf7+CXSCR1+ | | |
|---|---|---|---|---|---|---|
| Over expressed in CD62L − Slamf7+CX3CR1+ relative to the two other populations | | | | | | |
| Nrd1 | 39.35 | 26.93 | 24.93 | 41.31 | 43.54 | 31.16 |
| Smim3 | 18.08 | 13.36 | 12.39 | 19.09 | 20.04 | 20.87 |
| Prkx | 30.59 | 28.3 | 31.95 | 41.25 | 39.27 | 44.37 |
| Osbpl3 | 6.4 | 3.12 | 4.72 | 6.74 | 8 | 9.25 |
| Mdm1 | 4.93 | 1.91 | 2.32 | 5.43 | 5.78 | 5.93 |
| Pmaip1 | 57.72 | 29.2 | 29.79 | 73.25 | 55.61 | 66.49 |
| Ckb | 12.2 | 7.97 | 9.67 | 17.97 | 17.24 | 12.21 |
| Otub1 | 63.96 | 55.85 | 56.53 | 70.61 | 62.17 | 72.36 |
| Mid1ip1 | 20.88 | 12.31 | 14.08 | 27.72 | 14.18 | 21.89 |
| Atp2b1 | 15.92 | 12.82 | 12.18 | 24.9 | 17.81 | 21.44 |
| Abhd5 | 4.16 | 4.3 | 3.33 | 16.36 | 5.67 | 8.82 |
| Wdr92 | 50.25 | 37.14 | 36 | 94.77 | 46.94 | 65.24 |
| Ngfr | 0.05 | 0 | 0.05 | 5.05 | 1.09 | 2.46 |
| Myo1c | 8.86 | 10.17 | 4.15 | 17.65 | 10.24 | 10.09 |
| Vmp1 | 48.58 | 44.04 | 39.8 | 68.64 | 51.3 | 50.05 |
| Tpm4 | 165.6 | 172 | 183.26 | 287.74 | 214.04 | 227.26 |
| Errfi1 | 38.81 | 24.75 | 40.4 | 149.7 | 94.25 | 111.22 |
| Plec | 8.88 | 10.26 | 9.12 | 25.1 | 17.01 | 15.68 |
| Flnb | 2.78 | 1.61 | 1.36 | 7.86 | 6.5 | 4.51 |
| Cdkn1a | 18.22 | 14.9 | 19.61 | 78.36 | 60.86 | 49.41 |
| Tuba1a | 164.26 | 143.45 | 175.61 | 375.76 | 292.4 | 311.07 |
| Tax1bp3 | 17.12 | 13.39 | 11.88 | 30.07 | 27.03 | 27.42 |
| Mcu | 5.45 | 2.26 | 3.91 | 11.34 | 10.3 | 8.63 |
| Arhgdia | 187.95 | 155.46 | 153.3 | 202.48 | 200.08 | 196.59 |
| Pogk | 6.61 | 2.73 | 3.88 | 14.56 | 12.19 | 13.12 |
| Got1 | 41.31 | 20.42 | 27.97 | 47.72 | 49.42 | 45.01 |
| Slc4a2 | 8.85 | 7.82 | 6.97 | 13.81 | 14.6 | 11.78 |
| Aph1a | 21.45 | 22.19 | 20.78 | 29.54 | 27.06 | 31.21 |
| Kcnj8 | 17.8 | 14.46 | 9.59 | 67.52 | 34.01 | 90.34 |
| Rnf216 | 5.21 | 3.87 | 4.14 | 12.02 | 9.78 | 14.38 |
| Ndfip2 | 10.96 | 20.16 | 18.22 | 16.27 | 40.05 | 32.2 |
| Prf1 | 88.98 | 45.94 | 39.81 | 84.94 | 171.64 | 138.81 |
| Tnrc18 | 2.76 | 2.62 | 2.55 | 3.35 | 6.13 | 5.11 |
| Ddx28 | 9.81 | 6.48 | 5.9 | 15.67 | 19.52 | 23.84 |
| Spn | 19.29 | 12.94 | 11.16 | 23.96 | 32.13 | 45.12 |
| Rora | 20.29 | 12.08 | 35.43 | 42.66 | 62.01 | 75.5 |
| Rhof | 27.56 | 25.26 | 31.07 | 43.84 | 47.44 | 50.42 |
| Il18rap | 34.95 | 45.61 | 46.37 | 83.23 | 90.43 | 122.06 |
| Rap1gap2 | 1.57 | 0.74 | 0.48 | 5.89 | 9.67 | 11.48 |
| Klrg1 | 15.96 | 6.85 | 6.25 | 85.88 | 95.1 | 144.12 |
| Gzma | 304.5 | 297.87 | 214.28 | 1501.05 | 1661.43 | 1762.14 |
| Ccl5 | 2904.52 | 2943.94 | 3207.63 | 8603.34 | 9549.31 | 10317.16 |
| Lmf2 | 18.84 | 16.45 | 23.28 | 22.35 | 32.57 | 29.27 |
| Abcb1b | 17.51 | 11.87 | 13.74 | 24.71 | 36.63 | 32.42 |
| Dtx1 | 9.15 | 2.98 | 1.41 | 14.08 | 18.56 | 15.69 |
| Tug1 | 39.58 | 45.86 | 49.34 | 60.33 | 66.01 | 63.35 |
| A830080D01Rik | 5.6 | 5.27 | 4.64 | 8.57 | 8.66 | 8.48 |
| Lrrc8d | 5.82 | 5.84 | 6.15 | 8.4 | 9.02 | 8.56 |
| Prkaa1 | 7.72 | 7.55 | 6.26 | 11.34 | 11.55 | 8.5 |
| Slc4a7 | 2.57 | 3.92 | 4.58 | 7.23 | 6.28 | 6.52 |
| 2010012O05Rik | 2.93 | 5.32 | 4.66 | 9.7 | 12.63 | 11.69 |
| Gpd2 | 4.06 | 3.41 | 3.41 | 19.41 | 16.34 | 12.38 |
| As3mt | 8.66 | 7.23 | 4.03 | 31.55 | 23.5 | 21.74 |
| Hnrpll | 0.82 | 0.73 | 1.45 | 6.5 | 4.77 | 3.17 |
| Alox8 | 0.74 | 0.82 | 1.35 | 2.71 | 2.46 | 2.12 |
| Nfe2l1 | 8.74 | 13.05 | 9.86 | 17.92 | 17.36 | 16.34 |
| Emp3 | 123.4 | 118.92 | 102.39 | 198.08 | 223.12 | 199.58 |
| Ywhaq | 162.89 | 153.25 | 164.45 | 244.45 | 235.46 | 245.53 |
| Cmpk1 | 62.47 | 63.18 | 60.05 | 85.13 | 85.8 | 85.42 |
| Tmem109 | 25.97 | 24.61 | 27.21 | 43.77 | 43.47 | 45.66 |
| Adar | 20.27 | 20.69 | 15.51 | 25.87 | 25.45 | 27.25 |
| Rab14 | 32.16 | 46.94 | 29.83 | 48.54 | 48.39 | 44.34 |
| Suco | 12.78 | 9.53 | 10.79 | 17.76 | 17.11 | 22.38 |
| Atp10d | 6.92 | 4.95 | 7.04 | 14.94 | 12.25 | 21.27 |
| Meis3 | 13.72 | 8.79 | 13.92 | 19.84 | 20.06 | 31.41 |
| Kpna1 | 34.29 | 30.28 | 28.21 | 54.33 | 56.44 | 69.06 |
| Lpin1 | 14.07 | 13.58 | 16.24 | 26.64 | 28.11 | 34.88 |
| Cd97 | 86.86 | 72.61 | 76.73 | 103.57 | 113.35 | 160.16 |
| Pik3r1 | 18.82 | 16.85 | 14.63 | 22.51 | 23.58 | 28.69 |
| Mest | 0 | 0 | 0.43 | 2.3 | 0.27 | 5.31 |
| Lats2 | 10.7 | 7.04 | 8.48 | 22.38 | 16.92 | 26.7 |
| Vopp1 | 60.45 | 37.63 | 33.23 | 86.34 | 77.21 | 140.28 |
| Arhgap26 | 20.17 | 14.37 | 16.65 | 25.84 | 21.63 | 33.31 |
| Strip1 | 18.53 | 15.77 | 25.05 | 27.27 | 25.69 | 31.05 |
| Ncald | 2.66 | 4.16 | 4.44 | 8.62 | 8.65 | 17.57 |

TABLE 4-continued

| | | | | | | |
|---|---|---|---|---|---|---|
| Slc20a1 | 50.16 | 51.84 | 62.41 | 69.53 | 79.75 | 93.3 |
| Hiatl1 | 22.02 | 23.64 | 27.27 | 34.3 | 37.29 | 40.25 |
| Trim35 | 17.2 | 15.69 | 22.25 | 34.08 | 35.66 | 37.08 |
| Snx11 | 5.55 | 5.35 | 5.22 | 9.28 | 9.96 | 11.52 |
| F730043M19Rik | 0.82 | 1.36 | 0.82 | 3.86 | 2.99 | 4.86 |
| Smpdl3b | 1.99 | 5.84 | 4.32 | 17.41 | 13.94 | 23.07 |
| Zeb2 | 3.18 | 2.57 | 2.59 | 13.99 | 9.28 | 16.52 |
| Capn2 | 27.64 | 32.49 | 32.43 | 65.05 | 57.28 | 76 |
| Zmiz1 | 6.28 | 4.18 | 4.06 | 11.86 | 13.4 | 13.09 |
| Flna | 30.55 | 29.2 | 31.32 | 78.5 | 76.45 | 72.99 |
| Dock5 | 1.51 | 0.88 | 1.23 | 4.87 | 4.25 | 4.03 |
| Rap1b | 40.62 | 62.87 | 54.64 | 114.49 | 129.88 | 130.51 |
| Ube2g2 | 59.51 | 64.9 | 60.52 | 90.31 | 92.27 | 93.33 |
| Nhsl2 | 0 | 0.26 | 0.28 | 1.25 | 1.03 | 2.07 |
| Hist1h1c | 6.02 | 5.45 | 5.59 | 19.55 | 15 | 21.41 |
| Mmp25 | 0.09 | 0.63 | 0.33 | 2.38 | 0.16 | 3.29 |
| Tyk2 | 16.25 | 16.75 | 21.88 | 25.36 | 17.93 | 36.36 |
| Csgalnact2 | 4.93 | 4.75 | 3.31 | 7.13 | 5.14 | 10.89 |
| 9930111J21Rik1 | 35.1 | 41.25 | 43.09 | 49.64 | 49.71 | 74.36 |
| Atg4d | 17.72 | 19.93 | 18.14 | 19.68 | 26.06 | 35.99 |
| Nup50 | 13.56 | 19.72 | 20.56 | 23.98 | 19.11 | 27.28 |
| Zfp36l2 | 50.62 | 55.52 | 47.89 | 64.76 | 52.44 | 81.16 |
| Itm2c | 73.34 | 69.8 | 75.17 | 84.03 | 76.15 | 100.51 |
| Armc7 | 40.37 | 35.39 | 47.38 | 53.37 | 39.14 | 69.47 |
| Gimap3 | 644.21 | 492.15 | 582.36 | 662.36 | 516.66 | 895.22 |
| Vps54 | 12.33 | 8.87 | 10.75 | 13.33 | 9.52 | 18.64 |
| D16Ertd472e | 24.31 | 19.88 | 15.71 | 26.5 | 25.76 | 37.92 |
| Casp4 | 9.7 | 8.47 | 12.63 | 10.29 | 15.32 | 34.34 |
| Tnfaip3 | 593.9 | 593.52 | 702.75 | 745.62 | 715.44 | 1152.46 |
| Ostf1 | 219.12 | 190.04 | 218.59 | 233.15 | 248.64 | 367.83 |
| Cd6 | 153.3 | 110.47 | 140.48 | 166.95 | 129.62 | 238.04 |
| Mxd1 | 105.68 | 65.06 | 87.03 | 116.25 | 101.78 | 159.81 |
| Laptm5 | 962.56 | 748.32 | 831.37 | 901.96 | 999.43 | 1259.03 |
| Sh2d2a | 136.48 | 120.24 | 131.93 | 167.2 | 157.32 | 244.21 |
| Inpp5d | 46.05 | 37.42 | 40.53 | 44.91 | 40.63 | 63.66 |
| Abcb1a | 38.16 | 25.51 | 27.38 | 49.72 | 43.3 | 67.43 |
| Il12rb2 | 106.1 | 73.7 | 69.37 | 167.78 | 112.32 | 244.02 |
| Notch2 | 13.89 | 8.55 | 8.14 | 19.18 | 12.71 | 20.97 |
| Ahnak | 43.71 | 22.77 | 24.84 | 52.27 | 35.33 | 57.16 |
| Lmbrd1 | 10.27 | 10.6 | 9.57 | 11.82 | 11.78 | 16.99 |
| Insl6 | 19.35 | 20.77 | 15.62 | 28.23 | 27.46 | 53.77 |
| Ptger4 | 21.09 | 17.53 | 17.58 | 28.12 | 31.85 | 58.75 |
| Tmprss13 | 2.61 | 0.27 | 0.45 | 4.7 | 2.53 | 10.42 |
| Trex1 | 124.64 | 102.62 | 89.81 | 133.36 | 144.42 | 226.54 |
| Over expressed in CD62L − Slamf7+CX3CR1+ and CD62L − Slamf7+CX3CR1− relative to CD62L+Slamf7− | | | | | | |
| Cyth4 | 71.09 | 92.8 | 68.13 | 74.52 | 84.38 | 97.89 |
| Card11 | 35.17 | 34.27 | 28.47 | 29.66 | 33.18 | 37.66 |
| Gna15 | 31.91 | 35.22 | 19.56 | 27.26 | 29.13 | 44.69 |
| 9930111J21Rik2 | 17.01 | 13.53 | 10.71 | 11.45 | 19.41 | 16.42 |
| Slc3a4 | 13.41 | 11.37 | 9.75 | 5.02 | 13.59 | 13.09 |
| Serpinb6b | 208.49 | 194.69 | 157.06 | 177.76 | 244.38 | 230.14 |
| Edaradd | 2.65 | 2.39 | 1.85 | 2.42 | 2.14 | 2.37 |
| Als2 | 11.6 | 13.67 | 6.96 | 12.08 | 9.51 | 10.01 |
| St8sia4 | 42.24 | 32.05 | 19.82 | 23.43 | 24.49 | 20.58 |
| Surf4 | 103.71 | 105.37 | 76.21 | 89.78 | 90.1 | 85.53 |
| Prkcd | 48.92 | 48 | 31.36 | 39.4 | 42.09 | 36.15 |
| BC017643 | 54.5 | 48.29 | 44.27 | 48.01 | 51.99 | 46.76 |
| Rcc1 | 19.67 | 12.29 | 8.7 | 11.97 | 18.52 | 11.7 |
| Cd40lg | 4.6 | 3.37 | 4.92 | 0.91 | 6.43 | 3.01 |
| Itgax | 26.55 | 19.41 | 24.81 | 11.59 | 25.51 | 9.21 |
| Slc43a3 | 9.27 | 6.35 | 6.19 | 1.18 | 6.08 | 2.29 |
| Zbtb32 | 14.12 | 8.61 | 8.87 | 4.2 | 7.14 | 6.14 |
| Tram1 | 72.38 | 74.78 | 53.68 | 47.68 | 65.21 | 49.83 |
| Cox5a | 238.96 | 217.37 | 210.19 | 161.05 | 196.15 | 176.49 |
| Capza1 | 196.63 | 205.05 | 205.21 | 176.17 | 210.75 | 185.89 |
| Crot | 44.53 | 45.95 | 51.96 | 27.1 | 39.62 | 48.95 |
| Edf1 | 142.67 | 133.43 | 161.17 | 119.92 | 131.8 | 132.18 |
| Sumo2 | 406.39 | 388.98 | 421.44 | 384.7 | 340.85 | 393.72 |
| Gpr114 | 160.02 | 150.36 | 143.24 | 133.22 | 94.13 | 169.09 |
| Lig1 | 23.69 | 10.96 | 12.58 | 9.95 | 12.16 | 11.99 |
| Hif1a | 119.46 | 78.31 | 93.4 | 68.32 | 78 | 77.6 |
| Atf6b | 24.88 | 22.19 | 19.11 | 16.22 | 13.97 | 17.93 |
| Cd38 | 23.7 | 25.84 | 21.98 | 14.37 | 17.33 | 20.52 |
| Rps6ka1 | 43.31 | 39.9 | 39.51 | 25.83 | 25.99 | 35.78 |
| Pik3ap1 | 33.26 | 34.88 | 33.28 | 26.46 | 32.1 | 36.7 |
| Tnfsf14 | 26.05 | 29.92 | 24.86 | 15.62 | 26.07 | 28.42 |
| Ndufs4 | 37.98 | 51.55 | 45.72 | 35.81 | 50.26 | 54.28 |
| Ncaph | 4.21 | 8.22 | 8.33 | 4.57 | 10.12 | 5.52 |
| Espl1 | 0.72 | 1.25 | 0.96 | 0.42 | 1.42 | 0.84 |

TABLE 4-continued

| | | | | | | |
|---|---|---|---|---|---|---|
| Cox6b1 | 229.46 | 243.57 | 241.81 | 268.44 | 239.37 | 273.65 |
| Dynlrb1 | 153.56 | 132.43 | 141.35 | 156.79 | 148.99 | 156.94 |
| Psmb6 | 136.35 | 150.96 | 149.65 | 160.13 | 152.85 | 150.23 |
| Sh3bgrl3 | 764.45 | 618.13 | 673.23 | 740.74 | 786.26 | 769.51 |
| Ccl3 | 70.69 | 42.92 | 54.27 | 61.92 | 98.5 | 86.84 |
| Agpat3 | 20.89 | 17.47 | 17.31 | 17.38 | 23.38 | 20.75 |
| Rab8b | 55.45 | 44.59 | 56.43 | 54.22 | 60.24 | 55.31 |
| Rwdd1 | 85.71 | 69.51 | 86.94 | 81.59 | 74.82 | 80.63 |
| Ak2 | 69.7 | 55.3 | 67.45 | 72.97 | 71.2 | 62.74 |
| Ezh2 | 11.31 | 8.55 | 13.3 | 11.12 | 10.12 | 9.5 |
| Whsc1 | 5.33 | 4.65 | 7.78 | 6.67 | 5.77 | 4.24 |
| Hprt | 111.92 | 101.32 | 117.37 | 101.19 | 101.02 | 110.67 |
| Clic1 | 430.64 | 387.53 | 460.78 | 410.35 | 425.27 | 442.2 |
| Pfn1 | 1049.21 | 926.7 | 1138.48 | 1014.33 | 1079.56 | 1016.52 |
| Etfb | 57.21 | 50.93 | 51.03 | 60.57 | 48.84 | 46.72 |
| Psmb3 | 207.43 | 231.01 | 235.59 | 261.04 | 237.51 | 193.93 |
| Shfm1 | 192.45 | 209.82 | 228.07 | 229.29 | 208.89 | 194.23 |
| Cd52 | 801.24 | 943.93 | 1175.38 | 659.54 | 942.31 | 955.86 |
| AW112010 | 1060.28 | 1413.14 | 1619.84 | 724.66 | 960.46 | 1168.32 |
| A430107P09Rik | 22.34 | 36.9 | 45.57 | 19.43 | 27.56 | 44.45 |
| Dlgap5 | 1.14 | 4.9 | 4.64 | 1.44 | 3.77 | 4.13 |
| Vmn1r132 | 1.45 | 7.74 | 12.38 | 2.15 | 3.36 | 2.26 |
| Zfp300 | 5.37 | 22.62 | 24.08 | 8.56 | 13.89 | 9.57 |
| 4930511M06Rik | 35.55 | 203.24 | 208.25 | 59.43 | 124.45 | 58.58 |
| Vmn1r58 | 56.83 | 347.26 | 339.68 | 98.77 | 188.41 | 103.67 |
| Olfr613 | 16.42 | 100.77 | 102.37 | 22.74 | 57.92 | 27.65 |
| A730017L22Rik | 38.36 | 120.42 | 134.86 | 56.78 | 68.24 | 60.48 |
| A130077B15Rik | 461.31 | 2327.84 | 2267.5 | 784.07 | 1188 | 821.39 |
| Zfp277 | 108.85 | 377.82 | 365.3 | 134.3 | 191.06 | 149.78 |
| 2010002M12Rik | 1.7 | 2.97 | 3.66 | 2.05 | 3.16 | 2.25 |
| Tyms | 16.42 | 28.81 | 30.42 | 11.02 | 23.9 | 9.54 |
| Il2ra | 8.07 | 3.88 | 11.5 | 6.29 | 4.46 | 7.29 |
| Ppm1j | 38.6 | 28.09 | 44.91 | 29.76 | 35.65 | 39.65 |
| Ccr2 | 36.47 | 26.19 | 67.67 | 27.72 | 54.45 | 48.67 |
| Adam19 | 10.72 | 10.62 | 20.66 | 13.2 | 11.5 | 13.89 |
| Spag5 | 1.5 | 1.61 | 4.73 | 3.86 | 2.14 | 0.93 |
| Gm20139 | 0.11 | 1.31 | 0.43 | 0.79 | 0.23 | 0.2 |
| Cdc20 | 8.23 | 14.68 | 10.95 | 22.06 | 9.47 | 2.67 |
| Ska1 | 1.57 | 2.8 | 1.23 | 2.58 | 2.22 | 1.88 |
| Sgol1 | 0.44 | 2.87 | 1.4 | 1.97 | 2.57 | 1.81 |
| Aqp9 | 3.02 | 2.86 | 3.28 | 3.98 | 1.7 | 7.27 |
| Ska3 | 2.37 | 3.81 | 3.06 | 4.83 | 1.39 | 3.33 |
| Mcam | 0.5 | 0.97 | 1.81 | 0.67 | 1.46 | 0.69 |
| Birc5 | 8.34 | 12.57 | 13.78 | 8.68 | 11.52 | 5.8 |
| Kif11 | 2 | 7.99 | 5.04 | 1.79 | 5.94 | 2.45 |
| Fgl2 | 47.18 | 43.92 | 46.72 | 18.95 | 48.23 | 26.51 |
| Prc1 | 6.52 | 7.56 | 6 | 4.04 | 8.75 | 4.82 |
| Tmc8 | 14.33 | 17.41 | 16.44 | 14.66 | 16.84 | 17.95 |
| Hip1 | 3.41 | 2.13 | 4.1 | 3.49 | 4.41 | 4.34 |
| Stil | 0.33 | 1.81 | 3.74 | 0.21 | 0.59 | 1.23 |
| Spc25 | 3.83 | 8.31 | 17.24 | 3.77 | 6.94 | 4.47 |
| Spc24 | 17.14 | 19.95 | 27.31 | 17.94 | 17.71 | 15.87 |
| Tpx2 | 4.73 | 5.52 | 3.92 | 3.55 | 4.76 | 3.4 |
| Mki67 | 4.4 | 5.62 | 6.75 | 2.48 | 3.72 | 2.24 |
| Stmn1 | 49.39 | 61.17 | 74.41 | 42.01 | 51.56 | 32.73 |
| Hdac9 | 0.06 | 0.48 | 0.29 | 0.08 | 0.63 | 0.19 |
| Clspn | 0.96 | 2.33 | 1.16 | 1.37 | 2.24 | 0.84 |
| E2f2 | 1.62 | 2.74 | 1.57 | 2.02 | 4.8 | 2.01 |
| Ncapg | 2.85 | 6.21 | 6.54 | 4.65 | 9.17 | 1.93 |
| Cdca8 | 2.55 | 9.62 | 11.13 | 7.57 | 20.03 | 7.8 |
| Nuf2 | 3.98 | 5.02 | 5.01 | 6 | 5.2 | 1.86 |
| Tuba1b | 435.59 | 420.13 | 496.37 | 512.52 | 484.83 | 382.42 |
| Rpa3 | 27.27 | 41.31 | 38 | 38.34 | 36.1 | 32.01 |
| Mien1 | 42.69 | 65.42 | 64.92 | 62.92 | 61.91 | 53.83 |
| Vamp8 | 86.91 | 108.88 | 105.42 | 91.83 | 118.77 | 120.83 |
| Gzmk | 81.82 | 75.88 | 122.21 | 101.45 | 119.76 | 112.4 |
| Endod1 | 7.53 | 9.16 | 10.56 | 9.75 | 14.45 | 15.52 |
| Pdcd1 | 17.12 | 22.12 | 25.68 | 20.48 | 40.53 | 29.59 |
| Vbp1 | 77.89 | 80.95 | 83.41 | 87.72 | 98.74 | 100.16 |
| F2r | 57.57 | 49.12 | 54.49 | 65.94 | 64.25 | 73.17 |
| Lrp10 | 42.61 | 35.35 | 45.65 | 32.48 | 64.38 | 58.51 |
| Rpa2 | 36.9 | 42.99 | 42.54 | 60.18 | 81.48 | 85.23 |
| Snx10 | 15.98 | 17.95 | 15.92 | 20.62 | 30.23 | 29.02 |
| Arpc5 | 286.5 | 277.94 | 266.84 | 272.89 | 321.34 | 321.93 |
| Wdr1 | 237.74 | 209.36 | 222.21 | 260.15 | 282.08 | 286.17 |
| Sytl2 | 14.78 | 10.94 | 10.41 | 13.72 | 12.88 | 15.59 |
| F2rl2 | 11.79 | 9.56 | 10.16 | 19.55 | 17.42 | 21.61 |
| Smad3 | 31.11 | 20.64 | 23.21 | 39.59 | 29.74 | 43.16 |
| Acsbg1 | 27.61 | 19.95 | 26.6 | 30.53 | 27.31 | 34.11 |
| Map2k3 | 60.94 | 56.06 | 66.98 | 75.61 | 84 | 87.87 |

TABLE 4-continued

| | | | | | | |
|---|---|---|---|---|---|---|
| Slc12a4 | 11.62 | 10.13 | 8.88 | 16.06 | 12.52 | 13.97 |
| Ildr1 | 1.61 | 0.92 | 7.73 | 1.29 | 5.16 | 7.65 |
| Gm8369 | 32.64 | 34.42 | 56.64 | 36.55 | 36.4 | 61.77 |
| Cxcr6 | 84.91 | 76.02 | 200.98 | 39.71 | 88.7 | 139.15 |
| Hmgb2 | 80.68 | 81.53 | 101.01 | 62.88 | 96.08 | 97.66 |
| Ms4a4b | 1178.42 | 1006.29 | 1406.5 | 1063.82 | 1169.84 | 1709.99 |
| Ms4a6b | 443.95 | 431.36 | 563.35 | 455.08 | 505.92 | 685.81 |
| Rac2 | 516.14 | 456.38 | 539.14 | 425.5 | 499.79 | 614.3 |
| Sema4a | 83.46 | 64.38 | 86.96 | 67.86 | 82.5 | 105.9 |
| Srgn | 984.4 | 855.75 | 843.65 | 850.54 | 936.63 | 1201.63 |
| Rgs1 | 894.47 | 664.57 | 533.47 | 714.65 | 527.16 | 1283.74 |
| Casp1 | 31.54 | 21.18 | 11.12 | 31.16 | 22.43 | 54.25 |
| Nmi | 89.36 | 71.83 | 71.51 | 64.3 | 69.33 | 89.26 |
| Elf4 | 16.46 | 13.01 | 12.69 | 14.27 | 12.98 | 20.35 |
| Tpm3 | 392.31 | 358.66 | 390.36 | 394.47 | 362.58 | 460.78 |
| Ttc39b | 13.35 | 13.12 | 15.9 | 20.54 | 17.88 | 25.4 |
| Slamf7 | 27.4 | 20.02 | 26.88 | 38.89 | 36.15 | 63.46 |
| Bhlhe40 | 120.95 | 116.44 | 171.67 | 221.18 | 194.72 | 345.78 |
| Ifng | 49.19 | 69.44 | 59.95 | 75.69 | 74.07 | 114.28 |
| Ccl4 | 419.03 | 505.58 | 267.54 | 451.87 | 540.48 | 777.54 |
| Klrc1 | 225.48 | 251.91 | 301.9 | 330.08 | 231.74 | 527.57 |
| Kcnk5 | 5.55 | 5.17 | 8.28 | 11.31 | 8.1 | 19.04 |
| Bcl2a1b | 175.82 | 179.78 | 186.8 | 263.49 | 259.89 | 416.21 |
| Itgal | 159.02 | 122.72 | 172.39 | 189.81 | 177.56 | 247.01 |
| Nkg7 | 1497.81 | 1207.55 | 1666.74 | 1838.1 | 1991.88 | 2609.04 |
| 1810037I17Rik | 54.46 | 49.15 | 57.09 | 63.4 | 59.06 | 74.96 |
| Bcl2l1 | 45.86 | 39.87 | 36.55 | 56.98 | 51.73 | 81.03 |
| Myl6 | 693.3 | 768.67 | 727.95 | 961.9 | 856.52 | 1076.26 |
| Dclre1b | 2.94 | 2.92 | 3.17 | 2.26 | 3.69 | 7.22 |
| Tespa1 | 24.87 | 24.26 | 32.15 | 21.52 | 21.26 | 43.42 |
| Icos | 81.48 | 57.43 | 100.07 | 56.79 | 90.26 | 197.66 |
| Gm14446 | 86.69 | 56.13 | 63.77 | 60.12 | 65.06 | 120.59 |
| Isg15 | 98.81 | 63.22 | 57.43 | 65.57 | 64.53 | 125.62 |
| Ifih1 | 12.93 | 9.36 | 11.77 | 9.1 | 10.57 | 22.78 |
| Tbx21 | 76.74 | 52.36 | 73.65 | 82.01 | 83.25 | 130.29 |
| Lime1 | 154.24 | 106.17 | 153.64 | 132.55 | 161.8 | 207.48 |
| Pfkp | 100.18 | 64.63 | 76.36 | 82.5 | 84.18 | 100.17 |
| Tnfrsf9 | 192.73 | 107.43 | 119.06 | 129.71 | 77.19 | 173.03 |
| Cd8a | 252.88 | 192.24 | 248.82 | 197.49 | 182.33 | 258.22 |
| Sla | 213.74 | 167.35 | 198.82 | 146.44 | 148.95 | 215.59 |
| Cd82 | 223.33 | 165.81 | 216.7 | 191.3 | 183.25 | 291.19 |
| Ttc39c | 5.42 | 2.58 | 5.05 | 4.01 | 2.8 | 7.32 |
| Epas1 | 2.71 | 1.44 | 2.28 | 1.72 | 3.14 | 3.97 |
| Ikzf3 | 38.75 | 30.91 | 46.31 | 36.09 | 39.74 | 47.66 |
| Sra1 | 108.22 | 86.77 | 107.1 | 92.62 | 91.98 | 119.78 |
| Tmed5 | 57.69 | 35.81 | 47.65 | 48.8 | 56.1 | 62.91 |
| 2010111I01Rik | 14.1 | 9.81 | 15.35 | 16.48 | 16.33 | 20.32 |
| Wnk1 | 24.03 | 20.48 | 28.02 | 24.89 | 25.94 | 34.01 |
| H2-Q9 | 891.53 | 755.18 | 893.61 | 921.1 | 891.5 | 1234.78 |
| Rasal1 | 0.7 | 0.93 | 3.1 | 2.12 | 1.32 | 2.78 |
| Nmrk1 | 19.05 | 29.35 | 34.83 | 35.06 | 34.63 | 43.15 |
| Spsb3 | 37.03 | 33.43 | 45.64 | 44.72 | 46.79 | 53.7 |
| Itga4 | 26.11 | 20.66 | 30.07 | 40.96 | 43.93 | 47.77 |
| Sh2b1 | 13.26 | 17.09 | 23.3 | 22.24 | 22.89 | 23.95 |
| Antxr2 | 14.43 | 16.68 | 24.21 | 34.16 | 26.27 | 25.95 |
| Fam160a2 | 4.01 | 3.85 | 6.24 | 5.99 | 6.04 | 6.4 |
| Socs2 | 10.08 | 20 | 11.33 | 11.17 | 9.2 | 20.55 |
| Serpina3g | 105.08 | 128.18 | 134.54 | 148.49 | 83.41 | 138.85 |
| N4bp3 | 9.06 | 11.07 | 8.79 | 11.71 | 8.74 | 12.72 |
| Gba | 49.11 | 51.04 | 40.43 | 50.02 | 39.51 | 55.5 |
| Tmem184b | 20.75 | 24.21 | 24.6 | 35.18 | 20.15 | 26.25 |
| Aars | 16.61 | 22.17 | 20.01 | 27.65 | 17.03 | 22.82 |
| Zfp781 | 4.76 | 11.28 | 7.03 | 15.02 | 6.63 | 11.6 |
| Klrb1c | 19.82 | 29.77 | 14.85 | 53.21 | 29.79 | 41.14 |
| Gm14005 | 5.7 | 6.11 | 10.64 | 14.35 | 11.4 | 15.75 |
| Dnmt1 | 15.55 | 17.61 | 17.86 | 27.64 | 17.64 | 26.44 |
| Ppme1 | 25.2 | 22.63 | 35.71 | 34.17 | 28.63 | 34.18 |
| Gm2382 | 20.41 | 34.74 | 49.19 | 43.13 | 29.01 | 53.37 |
| Actg1 | 3023.68 | 2559.35 | 2775.85 | 3578.51 | 3974.47 | 3875.1 |
| Plekhb2 | 35.29 | 34.99 | 38.88 | 50.66 | 52.65 | 55.03 |
| Gzmm | 32.71 | 23.23 | 28.98 | 43.21 | 53.52 | 51.96 |
| Krtcap2 | 176.32 | 164.82 | 161.98 | 209.71 | 218.68 | 221.71 |
| Myl12a | 210.03 | 183.79 | 240 | 244.41 | 287.81 | 262.48 |
| Itgb1 | 66.3 | 57.44 | 67.68 | 103.6 | 143.7 | 116.96 |
| Cox17 | 73.56 | 84.23 | 108.71 | 101.8 | 110.28 | 104.14 |
| Tceb2 | 131.95 | 141.82 | 151.35 | 176.02 | 163.91 | 177.57 |
| S100a10 | 311.86 | 330.08 | 443.65 | 603.09 | 603.83 | 527.07 |
| Tspo | 258.07 | 275.49 | 329.06 | 363.32 | 392.28 | 387.27 |
| Srp14 | 105.87 | 145.23 | 161.21 | 145.37 | 161.98 | 180.86 |
| Atp5j2 | 99.72 | 121.94 | 116.44 | 117.16 | 127.89 | 123.82 |

TABLE 4-continued

| | | | | | | |
|---|---|---|---|---|---|---|
| Calm1 | 204.13 | 204.31 | 217.49 | 220.87 | 258.8 | 223.46 |
| Ube2n | 29.55 | 31.12 | 30.11 | 31.04 | 30.82 | 30.14 |
| Gabarapl2 | 159.29 | 141.65 | 187.56 | 167.77 | 178.69 | 223.56 |
| B4galt4 | 0.69 | 0.99 | 2.2 | 2.25 | 1.9 | 3.97 |
| Slamf1 | 49.42 | 35.3 | 45.03 | 36.04 | 42.19 | 74.98 |
| Cyba | 317.9 | 319.49 | 347.28 | 282.14 | 375.08 | 437.29 |
| Stx11 | 20.18 | 21.1 | 18.2 | 26.83 | 26.64 | 32.22 |
| Sytl3 | 38.07 | 25.86 | 36.32 | 37.44 | 32.87 | 48.17 |
| Mir22hg | 6.87 | 6.67 | 7.17 | 9.63 | 8.64 | 13.25 |
| Gcnt2 | 8.53 | 6.05 | 0.36 | 13.08 | 11.72 | 15.17 |
| Tnk2 | 4.15 | 3.56 | 2.84 | 5.28 | 4.38 | 6.64 |
| Atp2b4 | 7.72 | 4.82 | 5.58 | 6.8 | 6.04 | 10.48 |
| Itpripl1 | 16.66 | 12.29 | 12.28 | 15.57 | 15.49 | 18.56 |
| Nucb1 | 68.65 | 49.41 | 58.75 | 54.38 | 61.76 | 76.11 |
| Cfl1 | 907.34 | 792.5 | 927.32 | 960.54 | 981.6 | 967.01 |
| Cdc42 | 439.07 | 374.1 | 438.83 | 428.95 | 476.73 | 453.78 |
| Ccr5 | 87.98 | 53.27 | 69.87 | 64.86 | 77.58 | 94.48 |
| Sdhb | 142.51 | 122.5 | 140.61 | 130.28 | 150.44 | 163.53 |
| Acly | 54.41 | 44.19 | 55.33 | 55.41 | 69.97 | 62.34 |
| Trerf1 | 6.3 | 3.97 | 5.74 | 6.39 | 10.88 | 7.42 |
| Lgalsl | 3.03 | 2.37 | 1.54 | 2.58 | 8.26 | 5.07 |
| Flii | 42.81 | 39.24 | 36.16 | 47.44 | 54.79 | 55.78 |
| Aldh18a1 | 23.01 | 23.53 | 25.41 | 32.13 | 43.81 | 45.12 |
| Park7 | 146.71 | 122.21 | 140.44 | 160.91 | 198.02 | 223.92 |
| Prr13 | 103.9 | 80.65 | 92.03 | 89.51 | 119.27 | 120.19 |
| Isy1 | 113.96 | 81.62 | 92.38 | 98.25 | 136.67 | 147.17 |
| Sptlc2 | 26.32 | 22.14 | 22.51 | 25.29 | 26.57 | 39.61 |
| N4bp1 | 4.37 | 2.52 | 3.72 | 6.91 | 5.41 | 9.26 |
| Def6 | 55.31 | 48.46 | 55.46 | 69.29 | 75.23 | 79.15 |
| Mical1 | 39.51 | 34.28 | 37.78 | 43.69 | 52.86 | 62.93 |
| Maea | 52.45 | 55.57 | 64.53 | 63.71 | 70.05 | 81.9 |
| Lypla2 | 63.73 | 47.43 | 61.67 | 59.39 | 62.54 | 76.71 |
| Tmbim6 | 207.96 | 193.57 | 220.01 | 206.75 | 210.09 | 266.6 |
| Cd8b1 | 525.25 | 422.81 | 596.98 | 508.56 | 662.79 | 691.59 |
| Anxa6 | 178.63 | 153.02 | 218.28 | 181.41 | 246.8 | 265.97 |
| Cd226 | 41.97 | 40.1 | 48.96 | 38.37 | 64.93 | 69.11 |
| Med20 | 15.1 | 13.7 | 15.7 | 17.95 | 20.84 | 20.31 |
| Ctsd | 315.31 | 358.37 | 410.24 | 397.43 | 473.14 | 480.35 |
| Phf11a | 42.37 | 39.91 | 53.23 | 55.52 | 62.83 | 86.04 |
| Baiap3 | 23.74 | 20.14 | 30.88 | 31.14 | 38.46 | 45.44 |
| Atxn1 | 3.71 | 3.55 | 4.91 | 4.4 | 5.41 | 7.23 |
| Xlr4c | 10.37 | 15.34 | 12.39 | 11.64 | 17.83 | 37.24 |
| L1cam | 0.91 | 2.2 | 3.18 | 1.1 | 4.31 | 6.11 |
| Nfatc3 | 18.87 | 14.96 | 17.24 | 19.07 | 24.04 | 28.32 |
| Ppp1cc | 24.69 | 20.53 | 19 | 26.35 | 36.03 | 47.75 |
| Atp2a3 | 40.63 | 35.01 | 39.6 | 52.13 | 51.05 | 66.92 |
| Itgb7 | 174.66 | 151.8 | 180.84 | 192.56 | 196.62 | 249.83 |
| Diap1 | 7.99 | 4.66 | 8.31 | 9.77 | 9.47 | 14.5 |
| Gnptg | 62.2 | 56.07 | 62.25 | 81.69 | 64.89 | 93.81 |
| Dusp2 | 193.94 | 238.27 | 244.64 | 310.56 | 362.52 | 439.46 |
| Ppp1r11 | 16.35 | 15.8 | 20.69 | 24.34 | 22.16 | 28.22 |
| S100a13 | 52.68 | 58.49 | 79.95 | 77.48 | 79.29 | 113.97 |
| Itgb2 | 189.12 | 168.84 | 218.06 | 257.29 | 312.21 | 333.76 |
| Bcl2a1d | 66.8 | 58.66 | 102.89 | 152.42 | 156.55 | 203.09 |
| Cish | 69.43 | 53.42 | 88.07 | 128.63 | 137.48 | 255.79 |
| Fasl | 76.71 | 76.72 | 100.73 | 213.68 | 184.07 | 359.65 |
| Id2 | 285.46 | 265.93 | 316.88 | 376.81 | 365.45 | 518.68 |
| Dennd5a | 5.21 | 5.53 | 6.54 | 7.72 | 9.63 | 13.52 |
| Dok2 | 97.89 | 91.55 | 118.22 | 124.34 | 136.27 | 207.85 |
| Apod | 0.6 | 0.94 | 2.14 | 1.22 | 3.29 | 7.12 |
| Nr4a1 | 186.53 | 159.96 | 219.41 | 272.75 | 325.87 | 413.71 |
| Gnptab | 9.23 | 7.63 | 5.39 | 14.38 | 14.09 | 18.67 |
| Acpl2 | 9.67 | 8.5 | 11.31 | 18.69 | 16.25 | 24.15 |
| Sord | 4.17 | 6.22 | 2.4 | 8.46 | 10.98 | 10.36 |
| Prdm1 | 5.03 | 4.65 | 5.14 | 9.6 | 8.24 | 12.07 |
| Il10ra | 69.91 | 40.75 | 45.47 | 99.75 | 85.29 | 127.43 |
| H2-Q10 | 24.61 | 13.11 | 18.05 | 37.67 | 31.65 | 50.32 |
| St3gal4 | 40.83 | 37.07 | 47.52 | 57.64 | 56.42 | 75.05 |
| Cd48 | 228.38 | 185.41 | 247.75 | 297.88 | 342.82 | 399.92 |
| Mier3 | 5.41 | 3.1 | 2.59 | 3.38 | 5.45 | 4.62 |
| Plekho2 | 23.64 | 17.8 | 16.67 | 23.45 | 24.24 | 17.51 |
| Myo18a | 4.11 | 4.07 | 3.76 | 4.7 | 6.53 | 6.89 |
| H2-DMb1 | 30.71 | 27.73 | 11.16 | 28.4 | 67.58 | 38.03 |
| Atp6v0e | 170.24 | 166.67 | 163.9 | 168.58 | 191.62 | 181.08 |
| Nprl2 | 28.13 | 21.93 | 21.47 | 30.22 | 32.81 | 35.35 |
| Serpinb9 | 160.35 | 109.25 | 82.65 | 188.11 | 179.31 | 227.24 |
| Gzmb | 1953.95 | 869.3 | 750.39 | 2345.72 | 1521 | 2963.57 |
| Ccnd3 | 222.29 | 144.51 | 139.32 | 241.4 | 202.62 | 323.33 |
| Nabp1 | 79.1 | 41.29 | 48.25 | 110.39 | 85.7 | 139.39 |
| Sh3bp2 | 7.23 | 6.46 | 4.46 | 9.42 | 5.01 | 8.73 |

TABLE 4-continued

| | | | | | | |
|---|---|---|---|---|---|---|
| Gp49a | 320.5 | 178.8 | 166.79 | 312.94 | 188.29 | 276.48 |
| Lilrb4 | 260.7 | 165.63 | 131.18 | 292.85 | 185.31 | 246.77 |
| Nfe2l2 | 43.38 | 26.59 | 32.17 | 54.5 | 44.87 | 39.67 |
| Ssb | 79.94 | 70.89 | 67.35 | 78.46 | 75.02 | 81.37 |
| Cap1 | 59.24 | 42.15 | 47.48 | 64.05 | 54.79 | 69.93 |
| Gypc | 17.78 | 20.86 | 15.01 | 18.41 | 18.42 | 22.72 |
| Lmnb1 | 15.55 | 10.69 | 14.63 | 14.98 | 14.47 | 18.68 |
| Mapkapk3 | 37.58 | 36.82 | 46.71 | 39 | 37.31 | 54.08 |
| Map4 | 38.77 | 25.38 | 25.1 | 42.28 | 36.29 | 39.56 |
| Actb | 4028.37 | 2750.01 | 2507.57 | 3923.77 | 2841.68 | 4426.66 |
| 2310003H01Rik | 17.14 | 7.31 | 6.44 | 10.66 | 6.31 | 14.67 |
| Cox6a1 | 208.43 | 229.79 | 218.93 | 245.21 | 220.15 | 236.95 |
| Rps6ka4 | 21.94 | 24.33 | 22.49 | 29.73 | 23.17 | 28.85 |
| Rbx1 | 56.56 | 53.29 | 60.98 | 63.23 | 65.54 | 52.95 |
| Mettl21d | 36.68 | 27.89 | 39.46 | 39.75 | 40.07 | 32.82 |
| Yars | 19.94 | 18.04 | 16.49 | 29.65 | 22.23 | 23.59 |
| Rrbp1 | 9.19 | 8.19 | 5.91 | 12.68 | 10.18 | 8.73 |
| Mrpl20 | 54.96 | 76.37 | 66.38 | 108.09 | 103.49 | 84.99 |
| Clic4 | 34.05 | 37.27 | 24.04 | 48.23 | 52.61 | 28 |
| Ghitm | 128.04 | 131.49 | 129.2 | 155.58 | 148.71 | 122.74 |
| Lasp1 | 78.9 | 63.68 | 82.84 | 104.93 | 91.02 | 88.32 |
| Zmpste24 | 16.43 | 14.45 | 14.08 | 19.93 | 22.49 | 19.25 |
| Cycs | 58.02 | 54.08 | 53.96 | 58.14 | 55.78 | 49.49 |
| Cox5b | 173.62 | 249.53 | 199.03 | 248.25 | 260.35 | 224.4 |
| Cnih4 | 7.41 | 17.07 | 9 | 17.92 | 14.86 | 10.31 |
| Psmb4 | 122.28 | 155.54 | 138.97 | 148.67 | 161.27 | 136.64 |
| Txn1 | 160.68 | 193.94 | 175.57 | 246.76 | 278.78 | 141.11 |
| Ndufb6 | 74.73 | 86.87 | 92.83 | 108.6 | 107.19 | 82.8 |
| Mkks | 3.44 | 4.24 | 4.25 | 6.98 | 5.83 | 3.82 |
| Dbi | 60.64 | 68.85 | 69.04 | 103.67 | 108.88 | 57.76 |
| Med21 | 37.86 | 46.41 | 36.88 | 63.52 | 55.03 | 51.35 |
| Usmg5 | 146.98 | 161.29 | 148.55 | 199.04 | 189.43 | 165.13 |
| Mlf2 | 48.63 | 39.81 | 40.15 | 53.29 | 59.15 | 37.36 |
| 11-Sep | 15.96 | 12.07 | 8.34 | 17.98 | 16.76 | 10.85 |
| BC002163 | 49.68 | 59.12 | 40.94 | 67.76 | 64.16 | 35.03 |
| Ran | 182.84 | 192.18 | 187.63 | 172.12 | 184.73 | 132.67 |
| Mthfd2 | 37.93 | 46.09 | 47.02 | 52.21 | 46.81 | 25.67 |
| Zfp248 | 1.26 | 1.55 | 1.58 | 1.4 | 0.52 | 0.7 |
| Lrrk1 | 7.64 | 5.12 | 6.38 | 7.71 | 4.68 | 5.53 |
| Rhbdf2 | 16.33 | 10.7 | 7.94 | 14.18 | 11.44 | 13.05 |
| Tspan31 | 43.12 | 44.43 | 24.99 | 46.7 | 46.32 | 44.51 |
| Reep5 | 61.38 | 54.23 | 55.32 | 58.43 | 60.97 | 65.43 |
| Atf6 | 13.04 | 7.49 | 7.32 | 12.26 | 11.78 | 10.49 |
| 8430410A17Rik | 30.86 | 19.36 | 19.93 | 26.83 | 30.41 | 23.39 |
| Idi1 | 20.21 | 17.19 | 9.67 | 14.3 | 13.19 | 6.23 |
| Syngr2 | 159.69 | 151.39 | 121.79 | 118.62 | 158.63 | 131.79 |
| Evi2a | 67.64 | 54.89 | 48.82 | 39.86 | 52.81 | 53.47 |
| Ptplb | 5.18 | 6 | 7.43 | 6.65 | 8.62 | 6.16 |
| BC004004 | 25.17 | 23.02 | 25.05 | 32.12 | 31.07 | 21.32 |
| Susd3 | 19.95 | 23.04 | 20.72 | 23.79 | 31.21 | 36.05 |
| Ccdc50 | 6.67 | 8.66 | 6.32 | 7.05 | 9.59 | 9.75 |
| Pkib | 1.36 | 4.05 | 1.14 | 3.67 | 5.82 | 3.78 |
| Coa3 | 32.68 | 56.29 | 58.2 | 58.43 | 58.08 | 59.92 |
| Gdpd5 | 2.76 | 6.18 | 7.67 | 7.82 | 8.63 | 10.13 |
| Cars | 14.28 | 17.64 | 14.45 | 21.9 | 23.12 | 22.86 |
| Mars | 22.95 | 34.76 | 27.36 | 35.65 | 38.54 | 34.97 |
| Abracl | 79.71 | 98.82 | 91.91 | 73.47 | 134.6 | 98.81 |
| Timm8b | 13.33 | 32.01 | 34.97 | 34.12 | 47.84 | 30.47 |
| Bcap31 | 100.36 | 115.07 | 121.6 | 115.82 | 133.47 | 106.78 |
| N6amt2 | 19.47 | 22.7 | 29 | 26.35 | 41.08 | 20.87 |
| Taf12 | 28.73 | 36.32 | 41.01 | 44.16 | 45.73 | 49.64 |
| Chsy1 | 20.14 | 21.97 | 23.22 | 30.06 | 30.06 | 33.61 |
| Med12l | 0.5 | 1.01 | 1.36 | 1.09 | 1.45 | 1.26 |
| Ndufa4 | 250.76 | 328.94 | 324.68 | 324.63 | 327.9 | 350.92 |
| Gpr68 | 17.04 | 18.43 | 22.33 | 25.4 | 26.59 | 23.78 |
| Ndufb7 | 111.4 | 109.12 | 117.44 | 92.09 | 110.71 | 114.94 |
| Tnf | 40.45 | 35.18 | 41.15 | 33.74 | 43.04 | 46.69 |
| Tma7 | 121.28 | 136 | 145.41 | 134.01 | 132.46 | 157.8 |
| Ndufa1 | 148.49 | 142.57 | 171.37 | 150.82 | 150.93 | 179.37 |
| Klrk1 | 131.77 | 142.03 | 194.45 | 164.08 | 137.1 | 216.51 |
| Flt3l | 29.84 | 33.72 | 41.23 | 35.71 | 42.34 | 47.75 |
| Tmsb4x | 1632.43 | 2068.16 | 2182.52 | 2099.5 | 2161.82 | 2351.92 |
| Ndufa11 | 14.1 | 16.57 | 15.91 | 17.09 | 14.65 | 19.74 |
| Phf11b | 81.61 | 86.3 | 95.05 | 80.49 | 92.71 | 132.12 |
| Tmem154 | 6.54 | 8.99 | 12.49 | 11.63 | 9.3 | 16.14 |
| Depdc1a | 1.01 | 2.7 | 3.05 | 2.59 | 2.55 | 1.02 |
| Neil3 | 1.63 | 4.52 | 5.62 | 3.67 | 4.17 | 2.55 |
| Sec61g | 70.76 | 133.25 | 95.76 | 98.83 | 88.91 | 93.15 |
| Atp5l | 131.69 | 207.24 | 192.9 | 185.72 | 183.83 | 192.47 |
| Mrpl33 | 76.86 | 129.72 | 117.32 | 112.97 | 99.14 | 128.07 |

TABLE 4-continued

| | | | | | | |
|---|---|---|---|---|---|---|
| Lsm5 | 27.72 | 45.95 | 55.25 | 39.12 | 33.73 | 44.72 |
| Uqcrq | 97.59 | 144.38 | 105.86 | 148.91 | 107.34 | 118.4 |
| Atp5h | 388.19 | 388.18 | 381.99 | 430.65 | 431.16 | 424.51 |
| Sarl b | 53.5 | 61.53 | 46.92 | 52.1 | 54.06 | 47.94 |
| Pomp | 153.09 | 166.66 | 150.35 | 144.55 | 166.54 | 138.3 |
| Cox6c | 234.18 | 270.39 | 267.59 | 249.91 | 255.76 | 244.78 |
| Hmgn2 | 209.64 | 227.15 | 232.85 | 206.3 | 217.94 | 183.25 |
| Fam49a | 15.12 | 13.91 | 12.08 | 17.16 | 20.38 | 19.64 |
| Runx1 | 4.46 | 4.2 | 4.05 | 7.66 | 11.42 | 8.28 |
| Plek | 49.74 | 45.03 | 35.42 | 56.02 | 94.85 | 70.26 |
| Wdr95 | 4.44 | 8.07 | 9.11 | 15.21 | 11.81 | 12.22 |
| Soat2 | 6.96 | 9.83 | 11.3 | 13.09 | 10.99 | 9.46 |
| Apaf1 | 3.5 | 5.27 | 6.29 | 8.29 | 7.72 | 4.17 |
| Lamtor5 | 54.41 | 94.53 | 82.36 | 104.38 | 91.21 | 86.9 |
| Ppapdc1b | 2.93 | 6.21 | 6.39 | 6.49 | 7.5 | 6.87 |
| Atox1 | 59.76 | 88.26 | 99.13 | 89.87 | 113.26 | 91.44 |
| Necap2 | 45.59 | 45.74 | 48.62 | 54.99 | 55.29 | 52.34 |
| Entpd1 | 14.22 | 13.61 | 15.95 | 22.39 | 22.89 | 26.17 |
| Knstrn | 6.91 | 5.13 | 4.87 | 7.01 | 10.66 | 4.51 |
| Tnfsf9 | 8.18 | 6.43 | 8.97 | 8.69 | 15.95 | 3.39 |
| Ppil1 | 38.23 | 21.4 | 34.67 | 45.33 | 46.74 | 21.38 |
| Carhsp1 | 11.82 | 13.88 | 12.7 | 25.81 | 25.07 | 19.21 |
| 2900097C17Rik | 41.98 | 42.88 | 44.9 | 59.15 | 53.98 | 55.4 |
| 9330133O14Rik | 2.6 | 4.2 | 5.26 | 7.62 | 5.51 | 5.11 |
| Fam111a | 23.65 | 13.46 | 16.85 | 32.31 | 30.2 | 26.43 |
| Ehbp1l1 | 22.77 | 12.27 | 14.87 | 26.79 | 20.98 | 21.99 |
| Atp6v0b | 58.81 | 60.16 | 47.95 | 84.41 | 68 | 60.71 |
| BC049352 | 1.05 | 0.84 | 1.19 | 2.8 | 2.35 | 2.72 |
| Mtpn | 68.92 | 78.1 | 67.28 | 79.63 | 82 | 80.73 |
| Ctnna1 | 17.28 | 17.5 | 12.55 | 27.98 | 23.95 | 13.43 |
| Psmd14 | 93.43 | 110.15 | 100.26 | 124.94 | 126.69 | 86.46 |
| Rps27l | 47.47 | 70.44 | 48.74 | 135.46 | 135.41 | 41.88 |
| Atpif1 | 43.83 | 60.64 | 60.08 | 121.12 | 136.54 | 35.31 |
| Cyb5r1 | 13.59 | 23.36 | 19.61 | 49.21 | 32.1 | 14.51 |
| Nav1 | 0.21 | 0.56 | 0.88 | 3.53 | 1.7 | 0.8 |
| Nedd4 | 11.48 | 15.67 | 12.02 | 48.53 | 33.78 | 10.07 |
| Cd24a | 12.04 | 9.39 | 18.23 | 39.87 | 25.59 | 2.94 |
| Mrps6 | 48.7 | 43.01 | 46.85 | 88.66 | 59.38 | 37.62 |
| Cltc | 21.87 | 25.23 | 17.08 | 34.49 | 32.14 | 28.07 |
| Arf1 | 252.22 | 277.02 | 252.58 | 314.9 | 326.19 | 298.59 |
| Fam129a | 5.75 | 5.98 | 12.72 | 19.62 | 19.44 | 12.14 |
| Itgav | 3.12 | 2.77 | 2.72 | 6.59 | 5.01 | 3.22 |
| Lgals1 | 506.19 | 466.76 | 422.88 | 1356.25 | 1235.85 | 762.34 |
| Fhl2 | 10.52 | 8.54 | 11.81 | 38.76 | 38.63 | 15.86 |
| Slc4a8 | 0.51 | 0.25 | 0.34 | 1.54 | 1.43 | 0.61 |
| Aplp2 | 11.12 | 10.76 | 11.42 | 24.37 | 22.76 | 17.13 |
| Apobec2 | 1.57 | 2.02 | 2.53 | 17.95 | 11.08 | 4.88 |
| Pdlim5 | 8.27 | 9.01 | 9.14 | 20.69 | 23.45 | 7.83 |
| Trim16 | 0.45 | 0.45 | 0.6 | 3.74 | 3.67 | 1.17 |
| Crabp2 | 1.6 | 0.59 | 0.6 | 43.92 | 40.28 | 0 |
| Cth | 0.44 | 0.39 | 0.7 | 6.39 | 8.1 | 0 |
| Arhgap11a | 1.81 | 2.89 | 2.74 | 2.55 | 11.57 | 3.4 |
| Cst3 | 178.54 | 195.38 | 109.96 | 204.34 | 834.18 | 234.6 |
| Ero1l | 8.96 | 16.74 | 11.38 | 20.6 | 64.56 | 14.09 |
| Dsc2 | 0 | 0.04 | 0.25 | 0.59 | 3.98 | 0.13 |
| Hfe | 1.3 | 0.51 | 0.42 | 3.57 | 8.71 | 1.74 |
| Scd2 | 3.43 | 3.3 | 4.58 | 7.83 | 15.48 | 2.72 |
| H2afz | 379.44 | 499.43 | 546.7 | 576.01 | 804.72 | 619.04 |
| Rbms1 | 26.64 | 34.38 | 36.34 | 49.35 | 58.19 | 52.1 |
| Arsb | 12.4 | 16.22 | 24 | 22.94 | 33.65 | 17.43 |
| Furin | 6.59 | 6.41 | 6.42 | 7.66 | 12.2 | 7.23 |
| Eno1 | 465.46 | 441.97 | 446.48 | 683.78 | 927.53 | 470.44 |
| Bsg | 109.19 | 120.98 | 102.65 | 175.83 | 234.86 | 94.91 |
| Over expressed in CD62L+Slamf7− and CD62L − Slamf7+CX3CR1− relative to CD62L − SlamF7+ CX3CR1+ | | | | | | |
| Rnaset2a | 204.87 | 240.9 | 287.63 | 134.64 | 176.08 | 221.12 |
| Armcx2 | 2.6 | 4.65 | 3.44 | 1.56 | 1.92 | 3.01 |
| Bphl | 3.56 | 6.98 | 8.23 | 2.68 | 2.03 | 2.3 |
| Eng | 1.95 | 4.56 | 3.37 | 0.9 | 2.86 | 1.39 |
| Cnr2 | 1.72 | 6.18 | 4.08 | 0.45 | 2.87 | 0.78 |
| Npc2 | 130.63 | 123.74 | 115.63 | 89.98 | 102.9 | 83.51 |
| Tfdp2 | 2.09 | 2.93 | 1.84 | 0.7 | 1.66 | 0.83 |
| Nfkb2 | 63.74 | 47.18 | 49.53 | 35.49 | 33.05 | 42.07 |
| Klra19 | 4.55 | 5.95 | 5.12 | 0.44 | 0 | 0 |
| Gpr15 | 6.56 | 5.45 | 10.38 | 0.25 | 0 | 1.08 |
| 2-Mar | 39.84 | 38.63 | 51.88 | 33.71 | 31.41 | 38.01 |
| Klra6 | 93 | 152.63 | 121.02 | 0 | 3.05 | 0 |
| Gm12185 | 6.16 | 7.79 | 6.45 | 2.72 | 2.52 | 3.65 |
| Ltb | 227.69 | 251.46 | 367.93 | 72.78 | 99.57 | 124.94 |
| Cd27 | 91.61 | 83.99 | 126.65 | 24.77 | 45.75 | 57.63 |

TABLE 4-continued

| | | | | | | |
|---|---|---|---|---|---|---|
| Gm15133 | 3.65 | 2.32 | 2.83 | 0.78 | 0.66 | 0 |
| Eif3k | 330.17 | 316.89 | 314.55 | 221.29 | 279.08 | 268.03 |
| Eif3f | 377.06 | 385.14 | 415 | 232.99 | 350.69 | 309.16 |
| Fam26f | 26.85 | 33.94 | 28.42 | 12.13 | 13.6 | 23.45 |
| Paics | 76.41 | 61.75 | 100.3 | 63.26 | 54.99 | 36.17 |
| Samd3 | 34.12 | 44.34 | 60.88 | 27.68 | 28.43 | 31.15 |
| Spata6 | 27.82 | 25.66 | 33.66 | 15.68 | 18.45 | 17.57 |
| Cdon | 1.24 | 0.51 | 0.43 | 0.07 | 0.15 | 0.47 |
| Zfp512 | 16.61 | 12.47 | 14.76 | 6.04 | 5.37 | 6.25 |
| Kifc2 | 1.42 | 2.74 | 2.01 | 0.67 | 2.47 | 0.69 |
| Wibg | 12.31 | 8.6 | 13.05 | 4.3 | 9.38 | 6.41 |
| Dap | 125.02 | 129.09 | 93.33 | 94.83 | 81.62 | 85.01 |
| Fgfr1op | 11.4 | 11.19 | 8.67 | 4.79 | 5.19 | 3.9 |
| Map3k5 | 3.58 | 3.49 | 3.79 | 0.78 | 0.83 | 1.65 |
| Bbs9 | 6.36 | 6.75 | 6.31 | 2.73 | 4.16 | 2.13 |
| Ccdc6 | 7.41 | 7.4 | 6.07 | 5.29 | 4.28 | 6.33 |
| Atp6v1d | 70.91 | 73.9 | 63.25 | 53.42 | 53.93 | 53.01 |
| Prps2 | 32.56 | 24.5 | 23.38 | 22.57 | 9.96 | 19.92 |
| Cd2ap | 3.34 | 2.1 | 2.45 | 0.85 | 0.78 | 2.03 |
| Rcsd1 | 65.54 | 47.28 | 49.64 | 33.66 | 34.39 | 40.37 |
| Clec2g | 8.84 | 7.43 | 6.61 | 3.9 | 3.76 | 5.04 |
| Clec2i | 67.37 | 38.62 | 28.03 | 20.8 | 21.58 | 29.4 |
| Fam214a | 12.31 | 6.78 | 6.5 | 2.39 | 6.16 | 4.44 |
| Efr3a | 62.04 | 49.21 | 56.29 | 30.59 | 39.22 | 42.55 |
| Itih5 | 1.89 | 1.2 | 0.62 | 0.04 | 0 | 0.73 |
| Mycbp2 | 11.76 | 7.65 | 12.14 | 6.16 | 6.91 | 10.35 |
| Clta | 219.19 | 193.59 | 209.74 | 165.9 | 168.22 | 189.28 |
| Dennd2d | 59.39 | 43.63 | 57.19 | 36.16 | 34.62 | 40.99 |
| Ganc | 2.26 | 5.17 | 5.33 | 2.26 | 1.96 | 1.49 |
| Ccdc64 | 2.76 | 3.79 | 3.12 | 1.4 | 1.54 | 1.18 |
| Tapt1 | 9.33 | 9.27 | 5.96 | 5.43 | 4.8 | 2.05 |
| Sntb1 | 9.19 | 4 | 8.82 | 3.16 | 5.51 | 3.68 |
| Utp14a | 34.89 | 22.93 | 29.31 | 18.3 | 17.65 | 14.03 |
| Hrsp12 | 7.72 | 9.72 | 8.37 | 4.4 | 6.58 | 7.38 |
| P2rx4 | 12.09 | 11.81 | 7.44 | 5.12 | 6.22 | 3.68 |
| Ddx10 | 20.28 | 20.19 | 20.52 | 14.62 | 18.73 | 13.78 |
| Nsa2 | 56.51 | 57.24 | 54.21 | 41.37 | 36.63 | 50.27 |
| Tmem108 | 2.81 | 2.43 | 0.93 | 0.48 | 0.07 | 0.05 |
| Gm13826 | 57.53 | 54.37 | 43.59 | 43 | 28.87 | 23.45 |
| Eif2s3x | 65.28 | 77.5 | 60.37 | 66.53 | 55.96 | 53.17 |
| Ddx21 | 48.23 | 42.27 | 39.67 | 31.69 | 27.09 | 27.21 |
| Gm13139 | 11.59 | 11.43 | 6.68 | 6.49 | 6 | 3.76 |
| H2-Oa | 27.24 | 36.85 | 27.42 | 4.01 | 6.76 | 7.56 |
| Spint2 | 43.87 | 47.75 | 50.42 | 7.38 | 10.31 | 6.89 |
| Noa1 | 14 | 12.82 | 11.78 | 3.87 | 6.63 | 4.91 |
| Tmem194b | 12.84 | 13.88 | 12.68 | 5.92 | 10 | 7.12 |
| Erap1 | 59.06 | 35.24 | 46.78 | 24.62 | 29.3 | 34.8 |
| Rpgrip1 | 10.8 | 8.26 | 2 | 0.66 | 0.48 | 1.28 |
| Cnp | 169.54 | 148.45 | 145.16 | 82.83 | 102.63 | 111.34 |
| Rgs11 | 11.86 | 7.62 | 10.37 | 5.25 | 6.59 | 2.27 |
| Gstt2 | 12.7 | 11.29 | 14 | 4.37 | 2.88 | 2.75 |
| Ddb2 | 35.02 | 27.02 | 25.97 | 11.7 | 18.85 | 12.23 |
| Ikzf2 | 10.89 | 8.61 | 7.21 | 0.84 | 1.49 | 0.86 |
| Mfsd11 | 19.62 | 16.78 | 15.97 | 11.28 | 11.37 | 8.97 |
| Mri1 | 22.06 | 18.32 | 18.1 | 12.14 | 18.64 | 10.15 |
| Adck3 | 5.24 | 4.67 | 4.48 | 0.69 | 1.06 | 0.15 |
| Igflr1 | 26.65 | 18.52 | 35.69 | 11.06 | 18.39 | 15.05 |
| Pglyrp1 | 49.47 | 54.19 | 74.12 | 23.55 | 35.82 | 16.3 |
| Sema4d | 84.1 | 69.32 | 87.17 | 45.41 | 52.25 | 46.02 |
| Pabpc4 | 5.76 | 5.3 | 6.1 | 3.12 | 3.19 | 1.23 |
| Hspa8 | 2443.53 | 2086.42 | 2380.81 | 1625.73 | 1848.08 | 1594.09 |
| Fbxo7 | 29.87 | 18.73 | 23.69 | 11.25 | 15.32 | 15.98 |
| Map7 | 4.91 | 1.73 | 2.62 | 0.42 | 0.67 | 0.31 |
| Cd69 | 868.25 | 832.45 | 803.52 | 415.37 | 364.5 | 768.11 |
| A630001G21Rik | 15.25 | 11.53 | 12.52 | 6.78 | 3.66 | 5.84 |
| Xist | 59.33 | 66.62 | 54.35 | 36.9 | 31.35 | 42.68 |
| Rabgap1l | 54.6 | 59.87 | 34.99 | 25.21 | 20.99 | 26.44 |
| Hvcn1 | 43.28 | 43.93 | 28.46 | 13.06 | 15.4 | 16.63 |
| Fggy | 4.6 | 5.71 | 2.47 | 0.25 | 0.57 | 0 |
| Kctd12 | 6.51 | 5.72 | 2.06 | 2.03 | 1.22 | 0.65 |
| Atp1b1 | 51.01 | 36.06 | 9.11 | 4.61 | 5.01 | 0.16 |
| Trim12a | 79.08 | 69.18 | 86.87 | 51.15 | 44.98 | 65.09 |
| Pctp | 4.94 | 3.03 | 9.45 | 0.58 | 0.99 | 0.99 |
| Fam78a | 24.39 | 19.94 | 39.2 | 8.48 | 9.72 | 16.46 |
| Klra3 | 17.1 | 33.85 | 33.5 | 3.93 | 11.67 | 2.3 |
| Mvb12b | 0.38 | 0.74 | 1.09 | 0.1 | 0.22 | 0.16 |
| Dguok | 38.22 | 47.75 | 63.56 | 32.75 | 28.68 | 33.92 |
| Bmp7 | 3.25 | 6.43 | 8.83 | 0.33 | 1.8 | 0 |
| Vars | 69.53 | 72.3 | 80.04 | 33.94 | 47.52 | 22.06 |
| 1500012F01Rik | 107.06 | 144.05 | 120.61 | 94.3 | 82.36 | 55.34 |

TABLE 4-continued

| | | | | | | |
|---|---|---|---|---|---|---|
| Ccnh | 24.8 | 30.58 | 27.56 | 20.49 | 20.55 | 14.75 |
| Vwa5a | 19.4 | 23.11 | 15.16 | 3.49 | 6.77 | 4.42 |
| Ptma | 853.01 | 742.1 | 722.97 | 546.9 | 610.51 | 476.41 |
| Eif3m | 236.24 | 275.95 | 253.82 | 200.62 | 202.39 | 186.49 |
| Rpl7a | 976.11 | 1030.08 | 1018.47 | 648.09 | 730.26 | 711.43 |
| Rps9 | 1412.68 | 1821.2 | 1685.33 | 963.4 | 1098.12 | 951.57 |
| Rpl10a | 1047.39 | 1274.72 | 1345.93 | 714.74 | 869.66 | 587.05 |
| Rpl24 | 1010.57 | 1306.36 | 1269.85 | 688.98 | 797.21 | 690.58 |
| Rpl14 | 730.47 | 900.39 | 876.94 | 599.76 | 678.26 | 565.11 |
| Naca | 537.94 | 693.77 | 658.93 | 412.52 | 459.03 | 360.59 |
| Rpl37 | 516.25 | 620.41 | 648.92 | 365.01 | 432.35 | 378.5 |
| Rps11 | 2061.15 | 2574.81 | 2648 | 1367.21 | 1785.57 | 1553.81 |
| Rpl11 | 1393.2 | 1661.91 | 1684.04 | 982 | 1314.89 | 1048.66 |
| Rps2 | 1346.03 | 1613.06 | 1737.46 | 965.35 | 1353.04 | 817.25 |
| Atp5g2 | 415.36 | 375.07 | 401.82 | 284.42 | 293.2 | 242.7 |
| Npm1 | 906.37 | 942.53 | 907.53 | 684.37 | 774.84 | 393.59 |
| Eef1g | 731.67 | 761.16 | 783.39 | 538.22 | 547.61 | 334.46 |
| Rpl31 | 446.57 | 532.83 | 382.3 | 295.59 | 286.55 | 276.79 |
| Snhg1 | 90.2 | 152.21 | 101.1 | 101.41 | 87.26 | 74.14 |
| Arhgap39 | 0.1 | 1.19 | 0.63 | 0.04 | 0.03 | 0.04 |
| Rps27a | 1281.28 | 1971.36 | 1706.28 | 1262.62 | 1399.15 | 1104.33 |
| Rps12 | 1369 | 2220.76 | 1723.89 | 1251.79 | 1152.85 | 1202.62 |
| Rpl32 | 1387.27 | 2242.09 | 1919.97 | 1066.67 | 1189.97 | 991.72 |
| Rpl22l1 | 347.39 | 510.84 | 494.22 | 181.83 | 266.46 | 232.51 |
| Rps13 | 1973.5 | 2785.26 | 2615.01 | 1659.66 | 1816.83 | 1944.8 |
| Rps15a | 157.47 | 245.51 | 225.58 | 106.49 | 126.7 | 112.19 |
| Rpl36 | 441.98 | 780.6 | 699.64 | 398.4 | 454.04 | 441.35 |
| Rps15a-ps4 | 95.88 | 183.19 | 152.47 | 69.89 | 82.36 | 81.69 |
| Fau | 1884.43 | 2346.04 | 2260.34 | 1642.43 | 1714.09 | 1907.54 |
| Rpl17 | 1226.63 | 1655.33 | 1506.87 | 1020.93 | 1067.61 | 1107.75 |
| Rps15a-ps6 | 172.48 | 274.69 | 282.77 | 143.97 | 149.76 | 139.83 |
| Rpl38 | 589.05 | 814.07 | 844.23 | 517.62 | 515.21 | 485.19 |
| Rpl39 | 1664.93 | 2522.97 | 2285.72 | 1428.97 | 1446.23 | 1372.77 |
| Gm15772 | 1328.46 | 1818.11 | 1767.47 | 1164.5 | 1211.44 | 1044.89 |
| Crtam | 28.91 | 42.31 | 57.59 | 11.72 | 12.74 | 19.57 |
| Cd163l1 | 10.95 | 16.43 | 17.28 | 4.88 | 0.2 | 2.87 |
| Herc3 | 10.7 | 9.66 | 18.13 | 6.54 | 7.9 | 10.94 |
| Pdgfb | 1.46 | 1.73 | 3.14 | 0.83 | 0 | 0.74 |
| Clcn3 | 8.89 | 7.89 | 8.16 | 5.4 | 5.46 | 5.16 |
| Tapbpl | 93.87 | 98.27 | 102.91 | 55.93 | 49.47 | 68.69 |
| Gpr183 | 100.25 | 77.59 | 98.85 | 38.1 | 53.83 | 79.46 |
| Fam102a | 47.99 | 34.55 | 48.31 | 21.59 | 18.59 | 31.92 |
| Trai1 | 90.96 | 72.25 | 118.04 | 46.06 | 43.79 | 52.87 |
| Ms4a4c | 134.71 | 108.09 | 133.16 | 40.16 | 36.54 | 56.27 |
| Rhobtb2 | 3.48 | 3.63 | 1.94 | 1.39 | 0.78 | 0.34 |
| Rps4y2 | 18.15 | 9.9 | 4.81 | 1.72 | 1.01 | 3.16 |
| Ctla2b | 199.53 | 168.24 | 148.64 | 39.71 | 42.63 | 83.83 |
| Pacsin1 | 47.7 | 28.59 | 9.71 | 3.51 | 4.73 | 2.47 |
| Myc | 70.6 | 95.01 | 91.26 | 12.16 | 19.03 | 15.7 |
| Tex9 | 2.59 | 3.23 | 1.98 | 1.4 | 0.65 | 0.9 |
| Swap70 | 10.4 | 10.63 | 8.03 | 1.89 | 2.8 | 0.44 |
| Abhd15 | 5.55 | 6.11 | 3.91 | 1.6 | 0.5 | 1.16 |
| Slc38a1 | 16.5 | 20.46 | 18.08 | 12.24 | 14.72 | 8.42 |
| Nsmce1 | 54.5 | 57.04 | 57.36 | 30.73 | 38.86 | 29.76 |
| Psme1 | 533.4 | 551.08 | 554.58 | 341.95 | 401.31 | 409.11 |
| Gbp9 | 85.43 | 96.3 | 82.26 | 47.85 | 41.26 | 56.97 |
| Klra5 | 13.17 | 16.3 | 12.88 | 0.42 | 0 | 0.34 |
| Xcl1 | 131.33 | 317.22 | 163.97 | 6.78 | 5.7 | 15.8 |
| Plac8 | 824.69 | 988.88 | 705.45 | 262.07 | 240.45 | 211.37 |
| Ptpn6 | 182.65 | 160.35 | 137.38 | 73.87 | 74.79 | 77.08 |
| Trim59 | 25.58 | 17.81 | 21.19 | 7.15 | 11.95 | 6.59 |
| Apobec3 | 160.48 | 130.44 | 122.71 | 64.47 | 79.77 | 63.06 |
| Aoah | 4.82 | 2.35 | 4.22 | 0 | 0.19 | 0 |
| Ppcdc | 21.41 | 20.89 | 19.99 | 9.3 | 10.94 | 11.68 |
| Tubb5 | 503.41 | 437.21 | 495.59 | 334.88 | 346.99 | 270.28 |
| Cables1 | 4.25 | 7.63 | 8.61 | 0.73 | 1.47 | 0 |
| Cd3d | 345.28 | 432.49 | 475.86 | 230.37 | 250.61 | 300.18 |
| Fos | 522.07 | 598.45 | 658.72 | 245.26 | 408.24 | 398.15 |
| Cd7 | 202.43 | 189.58 | 196.39 | 38.32 | 83.86 | 93.41 |
| Jak3 | 90.13 | 69.64 | 105.09 | 38.01 | 48.15 | 49.14 |
| Ly6e | 737.45 | 678.46 | 804.25 | 265.73 | 359.9 | 297.5 |
| Arap2 | 9.58 | 9.21 | 9.9 | 8.71 | 6.39 | 8.24 |
| Over expressed in CD62L+Slamf7− relative to the other two populations | | | | | | |
| Tigit | 107.52 | 115.54 | 132.63 | 48.17 | 75.34 | 69.04 |
| Traf4 | 19.53 | 19.58 | 19.73 | 7.09 | 6.64 | 10.39 |
| Gm11696 | 1.05 | 0.2 | 0.21 | 0.18 | 0.07 | 0.37 |
| Lysmd2 | 9.58 | 14.64 | 16.58 | 5.4 | 8.74 | 6.11 |
| 4921525O09Rik | 0.15 | 0.38 | 0.61 | 0.05 | 0 | 0 |
| Smyd3 | 6.21 | 8.27 | 8.6 | 6.69 | 5.23 | 7.49 |

TABLE 4-continued

| | | | | | | |
|---|---|---|---|---|---|---|
| Dcaf8 | 31.6 | 35.26 | 28.71 | 27.26 | 31.2 | 27.54 |
| Rab4a | 1.47 | 3.36 | 1.02 | 4.13 | 1.54 | 0.14 |
| Mcrs1 | 26.73 | 31.56 | 33.16 | 31.99 | 29.43 | 25.79 |
| Zfp160 | 3.5 | 5.97 | 3.15 | 1.75 | 3.23 | 0.84 |
| Rbm45 | 2.36 | 2.32 | 2.86 | 1.28 | 1.01 | 1.05 |
| Lsm11 | 0.35 | 0.19 | 0.31 | 0.06 | 0.25 | 0.19 |
| Accs | 4.15 | 2.9 | 3.71 | 1.38 | 2.25 | 1.19 |
| Fchsd2 | 6.73 | 7.25 | 6.17 | 2.84 | 2.29 | 3.75 |
| Bcl2l11 | 35.68 | 29.91 | 34.46 | 23.53 | 28.14 | 30.87 |
| Fam120b | 17.02 | 12.31 | 10.89 | 11.01 | 11.08 | 12.76 |
| Nin | 6.41 | 5.34 | 4.6 | 4.22 | 4.39 | 4.1 |
| Bod1l | 3.76 | 2.78 | 2.56 | 3.29 | 1.24 | 2.6 |
| Eif5 | 79.96 | 62.76 | 66.05 | 59.75 | 60.31 | 59.89 |
| Pde4b | 50.81 | 40.45 | 40.73 | 33.91 | 33.75 | 65.99 |
| Gna13 | 29.84 | 27.96 | 25.88 | 25.58 | 23.33 | 28.03 |
| Gid4 | 12.05 | 8.21 | 5.43 | 5.79 | 4.09 | 5.5 |
| Ugcg | 9.23 | 9.88 | 10.29 | 8.1 | 8.18 | 12.37 |
| Zeb1 | 11.71 | 9.05 | 6.92 | 7.64 | 3.36 | 5.67 |
| Prps1l3 | 21.2 | 17.69 | 17.77 | 14.99 | 11.54 | 15.63 |
| Fip1l1 | 37.82 | 30.12 | 28.37 | 25.14 | 21.33 | 22.77 |
| Klra7 | 224.46 | 199.62 | 219.05 | 12.92 | 30.84 | 6.44 |
| Klra1 | 44.29 | 53.67 | 49.19 | 2.63 | 1.01 | 0.71 |
| Sft2d2 | 16.12 | 19.43 | 20.33 | 8.09 | 11.59 | 8.29 |
| Wdr43 | 35.02 | 41.17 | 31.72 | 27.14 | 26.35 | 21.37 |
| Gbp10 | 23.85 | 34.98 | 23.35 | 3.11 | 14.44 | 12.19 |
| Pitpnm2 | 4.41 | 2.55 | 2.51 | 1.81 | 0.95 | 1.59 |
| 5430416N02Rik | 30.34 | 28.63 | 20.51 | 16.04 | 16.76 | 14.57 |
| Polr1c | 43.18 | 43.76 | 36.6 | 30.66 | 25.69 | 23.4 |
| Phyh | 39.11 | 23.01 | 30.19 | 21.87 | 21.36 | 21.79 |
| Odc1 | 49.4 | 34.92 | 37.17 | 24.52 | 19.86 | 31.49 |
| Irak2 | 40.85 | 28.57 | 28.3 | 20.14 | 18.27 | 19.43 |
| Sult2b1 | 17.98 | 7.27 | 5.73 | 3.42 | 2.88 | 2.97 |
| Tgtp2 | 346.61 | 298.46 | 287.07 | 191.42 | 233.55 | 329.75 |
| Abl1 | 9.23 | 5.76 | 6.41 | 5.09 | 5.32 | 6.44 |
| Tec | 6.18 | 3.87 | 4.58 | 3.08 | 4.09 | 4.22 |
| Rnf138 | 115.19 | 101.17 | 104.13 | 88.08 | 89.25 | 113.7 |
| Rpusd4 | 12.61 | 17.21 | 23.96 | 8.74 | 8.95 | 9.82 |
| Apol7b | 33.35 | 37.96 | 50.43 | 15.86 | 19.24 | 25.86 |
| Apol7e | 33.35 | 35.89 | 48.02 | 15.86 | 19.24 | 25.86 |
| Gem | 89.7 | 75.52 | 107.09 | 59.5 | 64.22 | 55.69 |
| Tmem9 | 15.96 | 21.78 | 15.12 | 11.43 | 9.15 | 7.33 |
| 4930417O13Rik | 2.77 | 2.25 | 1.82 | 0.89 | 1.25 | 1.63 |
| Snhg5 | 68.11 | 74.98 | 70.39 | 53.11 | 56.59 | 40.79 |
| Wdr4 | 8.62 | 7.32 | 7.26 | 4 | 1.65 | 3.01 |
| Ddc | 1.71 | 3.41 | 2.13 | 0 | 1.32 | 0 |
| Folr4 | 4.39 | 11.81 | 6.77 | 0.74 | 2.5 | 0.91 |
| Tlr1 | 4.8 | 7.61 | 5.21 | 2.83 | 1.31 | 1.48 |
| Cyp4v3 | 2.56 | 3.12 | 1.91 | 0.28 | 2.51 | 3.32 |
| Rplp2-ps1 | 16.07 | 19.86 | 26.6 | 13.25 | 12.21 | 17.18 |
| Zfp36 | 199.13 | 225.4 | 237.29 | 168.3 | 191.34 | 226.01 |
| Fam86 | 7.63 | 13.8 | 12.71 | 8.55 | 8.47 | 8.43 |
| Plk1s1 | 6.83 | 11.52 | 10.77 | 5.88 | 6.02 | 4.61 |
| Rnaseh1 | 12.82 | 16.58 | 15.89 | 11.45 | 11.6 | 11.29 |
| Arid4b | 23.07 | 20.74 | 27.61 | 14.77 | 15.7 | 20.01 |
| Acpp | 3.8 | 3.13 | 1.73 | 1.15 | 0.24 | 0.18 |
| Slc11a2 | 20.25 | 22.77 | 21.79 | 12.08 | 9.76 | 10.77 |
| Cldn10 | 1.69 | 1.67 | 3.25 | 0 | 0 | 0 |
| Smad1 | 0.89 | 1.1 | 0.48 | 0.05 | 0.09 | 0.33 |
| Neurl3 | 51.56 | 47.28 | 62.93 | 24.99 | 28.87 | 43.6 |
| Cul9 | 2.01 | 1.75 | 2.21 | 0.91 | 0.27 | 1.39 |
| Rnf167 | 91.29 | 79.56 | 100.18 | 62.71 | 70.91 | 83.91 |
| Ablim1 | 106.82 | 110.6 | 117.93 | 75.85 | 69.45 | 104.82 |
| Rnaset2b | 124.99 | 117.47 | 107.96 | 94.89 | 72.23 | 83.6 |
| Tnip1 | 21.7 | 17.36 | 19.11 | 14.37 | 14.45 | 16.23 |
| Ctps2 | 18.16 | 15.15 | 15.89 | 13.16 | 10.2 | 12.58 |
| Ramp1 | 6.51 | 7.65 | 5.61 | 0.38 | 2.25 | 2.26 |
| Mgst2 | 26.83 | 31.62 | 32.25 | 15.4 | 11.34 | 8.75 |
| Taf1d | 42.21 | 53.81 | 41.66 | 30.53 | 23.92 | 30.13 |
| Acox1 | 4.07 | 5.4 | 7.78 | 1.7 | 2.19 | 0.97 |
| Eif3h | 383.83 | 420.41 | 461.87 | 304.98 | 361.79 | 282.55 |
| Eef2 | 1567.36 | 1451.99 | 1640.22 | 1284.48 | 1349.66 | 1094.44 |
| Igbp1 | 56.57 | 63.09 | 87.24 | 50.68 | 61.5 | 38.92 |
| Pim2 | 89.86 | 66.29 | 116.56 | 33.09 | 40.73 | 42.55 |
| Sgms1 | 16.51 | 5.75 | 7.57 | 7.67 | 5.59 | 5.78 |
| Cnot10 | 28.68 | 17.85 | 18.13 | 18.41 | 12.75 | 13.49 |
| Kbtbd11 | 20.94 | 10.98 | 14.15 | 12.44 | 9.34 | 13.52 |
| Satb1 | 41.34 | 32.87 | 31.23 | 17.1 | 14.13 | 20.21 |
| Ss18 | 61.66 | 44.63 | 43.97 | 40.87 | 44.96 | 47.28 |
| Txk | 74.68 | 82.18 | 72.98 | 60.97 | 57.33 | 76.12 |
| Klra13-ps | 15.62 | 18.13 | 8.52 | 2.4 | 2.78 | 0 |

TABLE 4-continued

| | | | | | | |
|---|---|---|---|---|---|---|
| Ddx6 | 16.21 | 9.72 | 9.17 | 13.53 | 7.88 | 15.28 |
| Cxcr5 | 17.4 | 4.23 | 8.58 | 0 | 0 | 0 |
| Wdr26 | 8.19 | 8.39 | 8.01 | 6.35 | 6.58 | 7.45 |
| Kdm5a | 14.03 | 12.51 | 12.78 | 13.75 | 12.76 | 13.39 |
| Mau2 | 27.11 | 33.38 | 29.5 | 23.71 | 24.79 | 27.67 |
| Dmrta1 | 4.35 | 4.52 | 3.91 | 3.22 | 3.01 | 5.21 |
| Luc7l | 25.27 | 20.83 | 19.21 | 22.97 | 11.52 | 17.02 |
| Sik1 | 28.89 | 21.28 | 13.84 | 12.97 | 8.92 | 19.7 |
| Dnajc7 | 84.2 | 74.64 | 58.84 | 54.34 | 37.77 | 51.02 |
| Jmjd1c | 20.08 | 15.26 | 11.72 | 14.79 | 11.28 | 13.12 |
| Usp53 | 1.95 | 2.14 | 2.3 | 0.32 | 0.95 | 2.72 |
| Hipk1 | 12.97 | 16.77 | 19.61 | 11.19 | 11.43 | 15.49 |
| Irs2 | 6.52 | 4.16 | 3.61 | 2.02 | 1.9 | 0.69 |
| Pde2a | 63.12 | 50.37 | 45.35 | 42 | 46.76 | 47.43 |
| Tnfrsf26 | 93.56 | 85.1 | 72.74 | 42.15 | 31.82 | 65.88 |
| Thada | 6.67 | 9.53 | 10.31 | 5.71 | 3.23 | 5.57 |
| Myb | 5.8 | 5.42 | 4.33 | 0.28 | 0.63 | 0.17 |
| Bend4 | 10.56 | 9.26 | 9.85 | 4.73 | 5.77 | 3.3 |
| Jakmip1 | 26.67 | 29.14 | 27.42 | 32.51 | 20.88 | 31.71 |
| Rfxank | 6.55 | 8.9 | 7.77 | 7.52 | 4.65 | 6.21 |
| Plekha5 | 4.5 | 4.45 | 6.14 | 5.38 | 3.32 | 3.48 |
| Zmynd8 | 16.42 | 21.88 | 22.55 | 19.85 | 17.71 | 13.6 |
| D230025D16Rik | 5.12 | 10.8 | 14 | 9.53 | 10.55 | 10.98 |
| Dip2b | 5.7 | 4.4 | 5.52 | 5.66 | 3.85 | 4.69 |
| Pim3 | 31.41 | 28.62 | 35.52 | 31.58 | 29.63 | 28.85 |
| Qrfp | 2.23 | 2.33 | 3.1 | 0.85 | 0.38 | 0.83 |
| Kdm6b | 18.64 | 18.49 | 16.25 | 17.8 | 13.48 | 30.8 |
| Srrm2 | 34.16 | 22.2 | 28.66 | 27.06 | 25.45 | 38.48 |
| Acp5 | 63.62 | 70.95 | 72.38 | 67.78 | 63.02 | 90.66 |
| Pan3 | 20.22 | 16.69 | 11.96 | 19.71 | 13.03 | 24.29 |
| Utrn | 20.96 | 15.64 | 14.49 | 15.71 | 11.18 | 18.51 |
| Skil | 26.02 | 16.22 | 15.54 | 14.54 | 13.5 | 23.64 |
| Zfp110 | 25.49 | 17.23 | 15.75 | 13.73 | 16.03 | 20.87 |
| Cux1 | 15.06 | 10.8 | 9.36 | 9.91 | 6.78 | 10.89 |
| Prrc2c | 27.62 | 16.94 | 15.71 | 19.51 | 19.64 | 20.22 |
| Sesn3 | 7.32 | 7 | 6.12 | 2.4 | 5.62 | 2.3 |
| Id3 | 38.35 | 55.5 | 32.84 | 7.48 | 13.73 | 3.33 |
| Ssbp2 | 5.28 | 6.53 | 6.09 | 1.54 | 2.61 | 2.43 |
| Snhg12 | 83.23 | 94.24 | 82.1 | 54.53 | 51.95 | 55.29 |
| Ift80 | 7.3 | 3.39 | 3.89 | 1.43 | 3.5 | 1.21 |
| Zyg11b | 11.52 | 8.03 | 8.69 | 7.24 | 6.03 | 9.71 |
| Dnajb9 | 124.04 | 88.48 | 70.23 | 72 | 67.26 | 95.57 |
| Tmc6 | 43.59 | 42.94 | 44.44 | 39.99 | 43.44 | 33.87 |
| Rbm5 | 45.91 | 46.34 | 46.82 | 43.34 | 48.87 | 46.63 |
| Crlf3 | 73.64 | 78.45 | 89.3 | 66.75 | 81.63 | 81.11 |
| Nol6 | 14.53 | 9.45 | 10.05 | 8.17 | 11.49 | 7.74 |
| Trpm7 | 17.42 | 10.45 | 13.03 | 11.36 | 10.67 | 13.38 |
| Irak1 | 12.03 | 9.72 | 11.67 | 7.46 | 7.05 | 10.62 |
| Spry2 | 34.49 | 28.54 | 32.77 | 31.5 | 16 | 5.13 |
| Jun | 220.61 | 202.19 | 154.46 | 169.71 | 120.96 | 78.14 |
| Fam46c | 37.49 | 42.52 | 35.39 | 19.4 | 8.4 | 13.09 |
| Impdh2 | 117.1 | 124.57 | 95.74 | 97.5 | 91.66 | 52.83 |
| Zfp395 | 1.43 | 1.23 | 0.77 | 0.66 | 0.52 | 0.47 |
| Gbp11 | 9.06 | 6.86 | 7.01 | 0.06 | 0.31 | 0.55 |
| Rpl29 | 1192.96 | 1262.23 | 1307.07 | 720.69 | 831.56 | 770.29 |
| Rps6 | 1709.69 | 1951.47 | 1931.67 | 1041.89 | 1305.26 | 948.46 |
| Rpl6 | 1348.75 | 1532.84 | 1578.04 | 859.83 | 1038.78 | 921.9 |
| Rpl3 | 2378.96 | 2508.25 | 2647.06 | 1353.75 | 1653.1 | 1314.74 |
| Rpl18 | 1025.04 | 1188.11 | 1159.12 | 659.87 | 758.04 | 693.21 |
| Rps3 | 1183.41 | 1417.56 | 1327.93 | 791.05 | 926.91 | 816.06 |
| Rpl19 | 3030.83 | 3517.22 | 3373.55 | 2328.08 | 2612.49 | 2401.62 |
| Rps3a1 | 2501.2 | 2740.51 | 2618.5 | 1700.88 | 1924.93 | 1718.21 |
| Rpl7 | 1975.16 | 1912.79 | 1902.67 | 1285.77 | 1508.24 | 1281.95 |
| Rpl23 | 1385.62 | 1514.75 | 1443.68 | 936.78 | 1027.74 | 911.64 |
| Rpl13 | 2304.29 | 2727.63 | 2673.76 | 1402.65 | 1645.87 | 1345.31 |
| Rpl28 | 1156.55 | 1013.59 | 996.83 | 632.93 | 718.83 | 565.62 |
| Rpl4 | 2119.14 | 2064.5 | 2176.07 | 1237.43 | 1426.75 | 1195.69 |
| Rpop0 | 2612.32 | 2774.28 | 2790.53 | 1586.28 | 1888.07 | 1355.36 |
| Eef1a1 | 6786.69 | 6688.31 | 7195.22 | 4270.83 | 5008.33 | 4352.54 |
| Rps4x | 4152.45 | 4492.87 | 4479.02 | 2737.59 | 2959.42 | 2630.75 |
| Rpl18a | 2308.12 | 2285.8 | 2359.89 | 1283.54 | 1473.3 | 1471.56 |
| Rpsa | 2006.19 | 2017.16 | 1911.3 | 1152.96 | 1226.05 | 1238.08 |
| 2410004N09Rik | 40.45 | 53.51 | 44.53 | 38.74 | 29.11 | 40.48 |
| Gnb2l1 | 1046.4 | 1009.62 | 884.5 | 851.4 | 801.16 | 676.86 |
| Smc4 | 64.28 | 52.09 | 62.62 | 24.77 | 36.26 | 34 |
| Tpt1 | 4697.91 | 4503.34 | 4121.53 | 3397.98 | 3190.75 | 3655.53 |
| Nsg2 | 14.94 | 14.49 | 11.78 | 0.94 | 2.19 | 1.15 |
| Mir703 | 45.38 | 27.36 | 39.48 | 14.13 | 25.97 | 14.3 |
| Cd72 | 36.25 | 27.79 | 26.54 | 9.86 | 18.85 | 14.78 |
| Tspan13 | 145.42 | 103.26 | 87.33 | 27.21 | 30.97 | 31.96 |

TABLE 4-continued

| | | | | | | |
|---|---|---|---|---|---|---|
| Rnf38 | 18.04 | 8.03 | 10.55 | 6.56 | 6.97 | 9.14 |
| Rsl24d1 | 50.37 | 34.67 | 33.51 | 25.86 | 28.29 | 30.74 |
| Fasn | 8 | 4.72 | 6.53 | 4.4 | 3.2 | 2.29 |
| Ilf3 | 39.15 | 36.82 | 31.03 | 33.52 | 27.65 | 21.32 |
| Gcnt7 | 0.65 | 1.03 | 0.49 | 0 | 0 | 0.09 |
| Gltp | 86.4 | 82.36 | 78.14 | 42.89 | 59.54 | 52.49 |
| Abce1 | 35.21 | 38.07 | 30.18 | 25.66 | 26.2 | 24.33 |
| Tha1 | 4.86 | 6.69 | 9.14 | 1.5 | 0 | 0.32 |
| Exosc2 | 15.61 | 18.97 | 24.3 | 12.32 | 12.67 | 8.72 |
| Lcn4 | 14.44 | 10.22 | 11.22 | 9.63 | 10.04 | 6.66 |
| Pou6f1 | 7.99 | 8.53 | 5.93 | 3.65 | 2.32 | 5.07 |
| Rnf144a | 1.93 | 0.83 | 1.31 | 0 | 1.12 | 0.33 |
| Pip5k1b | 1.26 | 0.49 | 0.79 | 0 | 0.27 | 0 |
| Tnrc6c | 4.15 | 2.88 | 4.17 | 3.82 | 3.36 | 5.25 |
| Slc26a11 | 8.6 | 13.9 | 20.16 | 13.3 | 6.94 | 11.71 |
| Cxx1c | 7.71 | 5.17 | 5.87 | 2.96 | 1.8 | 3.14 |
| Ap1ar | 7.61 | 7.06 | 7.34 | 2.78 | 3.82 | 4.81 |
| 9430038I01Rik | 5.04 | 3.44 | 5.03 | 1.8 | 3.58 | 3.36 |
| 2010300C02Rik | 0.81 | 1.73 | 0.95 | 0.07 | 0 | 0.27 |
| Gigyf2 | 9.87 | 5.69 | 6.62 | 7.05 | 3.87 | 3.73 |
| Cd96 | 50.12 | 51 | 78.64 | 52.51 | 49.73 | 63 |
| Pou2af1 | 0.31 | 0.21 | 1.34 | 0 | 0 | 0.08 |
| Nufip1 | 6.59 | 5.5 | 9.05 | 5.83 | 6.27 | 6.66 |
| Sbds | 32.59 | 37.78 | 32.41 | 30.34 | 33.63 | 37.4 |
| Galnt2 | 10.5 | 13.72 | 8.14 | 10.21 | 11.87 | 12.98 |
| Gtpbp1 | 29.64 | 24.62 | 26.35 | 15.45 | 23.94 | 23.92 |
| Neil1 | 16.1 | 16.37 | 11.29 | 5.81 | 9.78 | 8.13 |
| Zfp235 | 1.81 | 1.43 | 1.39 | 0.19 | 0.32 | 0.34 |
| Sacs | 1.53 | 0.95 | 0.32 | 0.44 | 0.73 | 0.12 |
| N4bp2 | 4.93 | 0.92 | 1.56 | 0.59 | 1.05 | 0 |
| Zbtb10 | 2.79 | 0.76 | 0.53 | 0.63 | 0.09 | 0.32 |
| Ldlrad4 | 9.28 | 5.15 | 3.05 | 3.57 | 2.95 | 3.26 |
| Zfp386 | 26.1 | 35.43 | 38.13 | 20.29 | 25.39 | 26.04 |
| Anks3 | 13.18 | 16.77 | 15.81 | 12.98 | 11.47 | 14.37 |
| Cep68 | 9.69 | 7.05 | 7.15 | 4 | 6.01 | 6.02 |
| Inpp4b | 8.83 | 11.12 | 12.44 | 4.56 | 5.32 | 7.26 |
| Grip2 | 0.53 | 0.27 | 0.11 | 0 | 0.03 | 0 |
| Ggt1 | 5.13 | 4.61 | 3.94 | 0 | 1.89 | 1.67 |
| Ascc1 | 22.85 | 18.78 | 15.68 | 15.63 | 15.2 | 14.39 |
| Hist3h2a | 13.73 | 15.56 | 11.38 | 8.64 | 14.65 | 9.38 |
| Slc25a36 | 6.1 | 15.5 | 12.11 | 5.03 | 13.42 | 3.5 |
| Use1 | 113.08 | 132.3 | 128.16 | 73.79 | 96.39 | 81.26 |
| Arhgap27 | 26.71 | 37.38 | 36.33 | 21.22 | 24.89 | 23.22 |
| Vps13a | 6.66 | 7.65 | 6.95 | 4.86 | 5.43 | 6.23 |
| Lta4h | 67.06 | 83.62 | 76.27 | 60.02 | 68.73 | 60.27 |
| Tom1l2 | 7.18 | 7.17 | 7.92 | 3.64 | 7.66 | 2.87 |
| Hspbp1 | 16.84 | 23.85 | 20.67 | 12.19 | 13.76 | 9.86 |
| Zfp652 | 3.95 | 3.89 | 3.94 | 3.04 | 3.48 | 1.79 |
| Lancl1 | 10.2 | 12.15 | 9.34 | 6.96 | 9.73 | 5.91 |
| Filip1l | 10.96 | 10.51 | 11.04 | 8.05 | 4.97 | 3.1 |
| Kdm5b | 3.65 | 4.57 | 5.43 | 5.4 | 5.73 | 3.59 |
| B430306N03Rik | 2.52 | 2.06 | 2.48 | 0.62 | 1.68 | 0.67 |
| Peli1 | 42.84 | 55.72 | 63.09 | 41.69 | 51.26 | 58.15 |
| Prkch | 45.8 | 43.02 | 56.52 | 22.87 | 47.53 | 37.67 |
| Akap9 | 4.88 | 4.95 | 4.47 | 3.88 | 3.28 | 4.47 |
| Snhg8 | 109.63 | 111.51 | 95.18 | 102.11 | 70.48 | 96.32 |
| Pkp4 | 8 | 5.26 | 5.33 | 6.18 | 3.63 | 4.31 |
| F2rl1 | 3.13 | 1.59 | 2.3 | 3.23 | 2.42 | 1.87 |
| Slamf6 | 26 | 36.61 | 32.8 | 18.5 | 26.06 | 21.26 |
| Vps39 | 13.97 | 13.89 | 14.8 | 14.44 | 12.01 | 12.22 |
| Tiprl | 27.2 | 23.78 | 28.5 | 24.95 | 22.02 | 20.51 |
| H2-Ob | 11.6 | 12.44 | 8.4 | 2.73 | 5.92 | 2.67 |
| Paip2 | 179.44 | 179.91 | 182.05 | 163.01 | 189.99 | 172.51 |
| Prrg4 | 2.64 | 0.86 | 1.15 | 0.45 | 1 | 0 |
| Cblb | 36.23 | 34.69 | 33.45 | 25.65 | 29.23 | 28.07 |
| Rbfa | 21.93 | 25.2 | 25.13 | 15.36 | 17.2 | 19.84 |
| 2610301B20Rik | 6.93 | 4.15 | 9.14 | 4.59 | 3.41 | 2.53 |
| Fam65a | 6.37 | 6.16 | 5.91 | 7.49 | 6.03 | 3.5 |
| Il6st | 9.83 | 12.59 | 16.23 | 11.41 | 8.05 | 6.8 |
| Ccm2 | 38.58 | 36.63 | 53.03 | 41.84 | 30.67 | 34.85 |
| Batf | 36.37 | 46.46 | 58.44 | 36.38 | 39.8 | 55.27 |
| 4833420G17Rik | 22.49 | 30.09 | 35.69 | 29.06 | 33.64 | 29.36 |
| Mysm1 | 12.57 | 13.47 | 16.3 | 12.02 | 15.28 | 15.37 |
| Srpk1 | 36.68 | 30.14 | 54.41 | 29.5 | 31.99 | 23.43 |
| Gramd1a | 44.23 | 58.2 | 63.09 | 48.16 | 50.32 | 43.11 |
| Trim13 | 5.97 | 5.13 | 9.87 | 4.21 | 5.19 | 4.02 |
| Usf2 | 5.15 | 7.77 | 6.13 | 3.75 | 5.86 | 6.07 |
| Git2 | 24.03 | 22.35 | 22.65 | 15.51 | 24.01 | 21.16 |
| Bclaf1 | 28.8 | 36.99 | 26.3 | 28.45 | 26.76 | 30.22 |
| Fbxo32 | 5.67 | 5.46 | 4.94 | 3.63 | 4.77 | 5.8 |

TABLE 4-continued

| | | | | | | |
|---|---|---|---|---|---|---|
| Klhdc1 | 5.16 | 4.6 | 6.13 | 4.74 | 3.43 | 6.21 |
| Gpd1l | 11.77 | 13.16 | 6.51 | 5.86 | 4.03 | 10.92 |
| Gtf3c2 | 18.55 | 24.44 | 19.92 | 17.87 | 15.03 | 25.32 |
| Il27ra | 42.94 | 53.68 | 48.66 | 35.25 | 42.38 | 47.44 |
| Apobec1 | 6.35 | 4.05 | 7.11 | 5.34 | 2.84 | 3.14 |
| Pqbp1 | 48.09 | 31.4 | 46.59 | 31.36 | 32.23 | 38.45 |
| Csf3r | 1.38 | 0.34 | 1.01 | 0.44 | 0.83 | 0.83 |
| Patz1 | 7.78 | 7.66 | 5.64 | 1.08 | 5.29 | 4.67 |
| Cmah | 13.51 | 16.79 | 15.87 | 8.32 | 13.46 | 10.46 |
| Aff3 | 1.83 | 3.8 | 2.2 | 0.05 | 1.13 | 1.02 |
| Flcn | 16.98 | 22.89 | 21.99 | 13.81 | 21.76 | 20.15 |
| Ephx1 | 5.27 | 5.7 | 3.59 | 0.1 | 4.26 | 2.38 |
| Adk | 15.36 | 15.46 | 17.71 | 7.48 | 9.37 | 5.23 |
| Gpr146 | 12.09 | 14.43 | 5.12 | 9.48 | 9.79 | 5.66 |
| Mat2a | 74.18 | 69.24 | 61.61 | 71.17 | 67.4 | 71.67 |
| Ubxn7 | 5.3 | 4.73 | 4.16 | 4 | 4.07 | 4.34 |
| Zrsr1 | 1.95 | 1.37 | 1.13 | 1.66 | 1.21 | 2.16 |
| Ndrg3 | 39.41 | 38.6 | 53.26 | 45.31 | 52.71 | 52.7 |
| A930024E05Rik | 0.59 | 1.86 | 3.35 | 1.28 | 1.08 | 0.84 |
| Taf4b | 3.16 | 3.17 | 5.66 | 2.99 | 1.48 | 2.93 |
| B4galt1 | 69.47 | 51.03 | 62.91 | 62.77 | 66.26 | 67.56 |
| Vps37b | 280.71 | 218.39 | 251.27 | 295.65 | 275.16 | 405.93 |
| Eif4ebp2 | 8.76 | 4.92 | 6.79 | 7.17 | 6.56 | 8.1 |
| Tob1 | 14.67 | 18 | 14.88 | 16.73 | 21.06 | 23.43 |
| Maff | 3.01 | 3.71 | 1.11 | 2.34 | 2.65 | 3.3 |
| Mcl1 | 29.16 | 22.22 | 20.73 | 24.16 | 29.47 | 32.58 |
| Irf1 | 358.6 | 349.33 | 288.31 | 304.38 | 296.21 | 489.69 |
| Jmy | 2.22 | 2.4 | 3.44 | 1.64 | 2.14 | 2.51 |
| Mepce | 2.47 | 5 | 6 | 3.89 | 3.74 | 4.57 |
| Nipal1 | 0.49 | 0.79 | 0.9 | 1.96 | 0.29 | 0.66 |
| Slc25a3 | 478.33 | 471.71 | 482.89 | 493.44 | 431.59 | 420.24 |
| Itm2a | 27.29 | 31.98 | 22.05 | 10.72 | 12.78 | 8.14 |
| Klhdc2 | 29.86 | 45.33 | 39.72 | 32.05 | 28.56 | 29.44 |
| Gm10825 | 1.26 | 1.16 | 0.68 | 2.35 | 0.74 | 1.83 |
| Dyrk2 | 2.84 | 6.58 | 9.31 | 4.47 | 2.61 | 6.87 |
| Mdc1 | 7.93 | 5.69 | 5.34 | 7.56 | 4.13 | 7.24 |
| Znrf3 | 13.36 | 12.14 | 12.73 | 14.83 | 8.31 | 19.88 |
| Socs1 | 54.42 | 62.92 | 50.47 | 50.08 | 41.13 | 80.22 |
| Fbxl20 | 1.22 | 1.71 | 1.39 | 2.09 | 0.98 | 1.98 |
| Psd | 1.88 | 2.12 | 1.48 | 1.79 | 0.73 | 1.53 |
| Slc12a7 | 17.39 | 16.58 | 16.36 | 16.48 | 10.71 | 19.63 |
| Foxp1 | 25.81 | 25.18 | 22.42 | 24.61 | 18.89 | 22.38 |
| Actn1 | 2.18 | 2.96 | 1.84 | 1.3 | 0.69 | 0.32 |
| Acot2 | 22.88 | 23.19 | 16.45 | 24.28 | 14.87 | 19.13 |
| Ldlrap1 | 13.57 | 11.51 | 16.46 | 15.22 | 8.58 | 18.93 |
| Ccr7 | 146.86 | 198.1 | 179.43 | 25.42 | 21.39 | 64.93 |
| Tcf7 | 117.67 | 119.46 | 142.68 | 38.09 | 44.06 | 55.54 |
| Dusp10 | 29.37 | 30.65 | 23.41 | 14.57 | 15.23 | 17.55 |
| Bach2 | 2.32 | 2.97 | 3.2 | 1.08 | 2.37 | 1.66 |
| Vipr1 | 3.06 | 6.09 | 5.94 | 1.92 | 1.81 | 1.25 |
| Pik3ip1 | 23.06 | 40.74 | 35 | 13.87 | 18.41 | 25.99 |
| AB124611 | 65.28 | 63.46 | 77.76 | 54.99 | 59.51 | 56.76 |
| Dgka | 177.03 | 167.72 | 180.17 | 96.85 | 98.24 | 141.46 |
| Ubald1 | 25.25 | 20.79 | 22.45 | 18.23 | 18.68 | 20.71 |
| Arl5c | 16.46 | 13.17 | 16.8 | 4.98 | 16.59 | 10.92 |
| Gramd4 | 15.38 | 14.16 | 15.63 | 13.33 | 12.5 | 12.8 |
| Lef1 | 63.64 | 44.42 | 40.45 | 40.14 | 38.23 | 50.33 |
| S1pr1 | 56.17 | 49.44 | 44.32 | 38.61 | 47.56 | 67.81 |
| Srsf2 | 189.72 | 176.95 | 141.46 | 169.48 | 153.46 | 187.03 |
| Srsf5 | 224.74 | 197.12 | 173.57 | 212.93 | 163.05 | 273.13 |
| Map3k1 | 19.6 | 14.21 | 11.83 | 15.45 | 13.67 | 18.9 |
| Bcas3 | 12.06 | 10.6 | 9.59 | 10.14 | 10.21 | 11.57 |
| 4932438A13Rik | 16.02 | 14.76 | 14.59 | 12.85 | 12.09 | 17.36 |
| Scml4 | 18.33 | 15.74 | 13.76 | 15.25 | 9.59 | 16.42 |
| Eif4a2 | 233.18 | 233.46 | 211.2 | 212.02 | 181.09 | 230.65 |
| Ppp1r15a | 391.5 | 328.63 | 358.35 | 280.28 | 274.77 | 337.81 |
| Macf1 | 19.01 | 16.99 | 16.72 | 16.93 | 16.07 | 21.54 |
| Ccnl1 | 81.01 | 80.45 | 86.4 | 82.31 | 79.42 | 99.27 |
| Pnrc1 | 49.84 | 39.07 | 39.75 | 36.77 | 31.36 | 49.42 |
| Emb | 321.35 | 277.7 | 294.83 | 164.53 | 163.99 | 249.31 |
| Bcl10 | 59.49 | 53.81 | 45.54 | 40.08 | 40.55 | 46.53 |
| Pcbp2 | 54.39 | 44.09 | 48.13 | 39.26 | 45.49 | 41.32 |
| Socs3 | 180.65 | 155.59 | 168.82 | 118.69 | 122.17 | 176.58 |
| Gramd3 | 230.8 | 203.05 | 245.35 | 167.56 | 145.75 | 228.46 |
| Sidt1 | 41.53 | 38.79 | 39.54 | 25.49 | 22.38 | 37.97 |
| Il4ra | 116.3 | 87.96 | 66.13 | 71.94 | 37.3 | 77.97 |
| Ppm1h | 33.02 | 19.95 | 18.18 | 13.35 | 9.78 | 23.92 |
| Rn45s | 31024.73 | 23368.46 | 21338.8 | 21607.43 | 16991.84 | 24150.48 |
| Stk4 | 19.38 | 19.37 | 20.15 | 17.83 | 22.47 | 26.27 |
| Stk17b | 340.02 | 261.22 | 305.53 | 266.57 | 313.82 | 345.42 |

TABLE 4-continued

| | | | | | | |
|---|---|---|---|---|---|---|
| Tmem66 | 369.01 | 316.37 | 404.46 | 292.5 | 367.85 | 416.16 |
| Abcg1 | 9.19 | 9.79 | 14.43 | 8.13 | 10.8 | 17.65 |
| Smad7 | 11.86 | 11.83 | 8.72 | 7.88 | 10.4 | 17.38 |
| Ssh2 | 41.34 | 34.23 | 37.68 | 33.53 | 32.67 | 49.37 |
| Dym | 29.71 | 27.59 | 30.09 | 21.77 | 23.66 | 37 |
| Card6 | 13.25 | 19.43 | 22.12 | 14.05 | 11.87 | 25.04 |
| Elovl5 | 77.68 | 79.11 | 86.71 | 43.26 | 48.07 | 78.75 |
| Gltscr2 | 256.32 | 241.29 | 312.06 | 169.48 | 210.59 | 221.83 |
| Tbc1d17 | 14.11 | 14.32 | 16 | 12.02 | 14.2 | 13.11 |
| Pbxip1 | 28.5 | 26.36 | 37.99 | 19.77 | 24.37 | 26.68 |
| Mcoln2 | 2.09 | 9.91 | 8.19 | 2.64 | 4.49 | 4.57 |
| Ube2h | 28.52 | 33.75 | 34.53 | 27.12 | 33.19 | 28.63 |
| Srsf6 | 35.1 | 46.68 | 40.2 | 40.43 | 30.24 | 27.37 |
| Tmem64 | 1.5 | 3 | 2.47 | 2.03 | 2.34 | 2.08 |
| Kidins220 | 9.36 | 7.93 | 9.29 | 10.83 | 9.87 | 10.12 |
| Smpdl3a | 57.48 | 68.38 | 85.35 | 55.35 | 77.08 | 75.94 |
| Lrrc61 | 5.37 | 5.58 | 5.24 | 5.73 | 4.96 | 5.14 |
| Brf1 | 9.04 | 10.21 | 11.1 | 9.88 | 7.57 | 10.58 |
| 3230401D17Rik | 74.29 | 53.77 | 57.91 | 59.42 | 63.87 | 79.46 |
| Pnpla7 | 11.03 | 9.27 | 8.2 | 6.99 | 8.52 | 14.91 |
| Ppargc1b | 0.48 | 1.15 | 0.35 | 0.93 | 0.93 | 0.87 |
| Cebpz | 13.78 | 11.9 | 7.32 | 13.31 | 13.68 | 9.89 |
| Prdx6 | 151.67 | 133.18 | 123.85 | 125.94 | 128.99 | 141.26 |
| Pabpc1 | 344.81 | 279.03 | 262.75 | 285.36 | 283.48 | 266.32 |
| Mgat5 | 8.59 | 7.3 | 5.25 | 4.17 | 3.42 | 7.6 |
| Sdha | 103.34 | 86.75 | 81.69 | 86.96 | 88.17 | 103.05 |
| Ipcef1 | 17.58 | 20.05 | 16.36 | 14.75 | 12.13 | 16.49 |
| Rnf130 | 2.02 | 3.52 | 5.55 | 2.27 | 1.45 | 0 |
| Tars2 | 14.61 | 19.55 | 23.7 | 15.93 | 19.32 | 12.71 |
| Gnpat | 17.12 | 30.33 | 29.59 | 17.48 | 28.77 | 15.41 |
| Eif4b | 124.74 | 107.7 | 126.98 | 113.48 | 117.64 | 78.4 |
| Sec11a | 99.81 | 114.94 | 133.45 | 106.97 | 105.55 | 90.81 |
| Skp1a | 78.27 | 94.26 | 108.25 | 96.81 | 88.45 | 68.46 |
| Btla | 10.86 | 12.28 | 14.66 | 7.77 | 7.75 | 3.43 |
| Dennd6b | 4.02 | 4.69 | 5.77 | 2.92 | 2.99 | 2.19 |
| Ikzf1 | 49.22 | 40.55 | 52.04 | 34.1 | 41.33 | 48.84 |
| Entpd5 | 8.96 | 8.87 | 13.12 | 3.47 | 8.25 | 7.63 |
| Polg2 | 8.41 | 9.15 | 15.73 | 4.16 | 5.66 | 7.84 |
| Abhd11 | 14.52 | 15.15 | 15.74 | 11.51 | 11.42 | 9.18 |
| Uvssa | 6.36 | 5.94 | 5.73 | 4.47 | 3.31 | 3.11 |
| Slc17a9 | 8.79 | 10.4 | 9.14 | 4.13 | 5.02 | 8.57 |
| Gm129 | 6.87 | 10.08 | 6.87 | 3.02 | 2.34 | 4.97 |
| St8sia1 | 0.81 | 1.26 | 1.3 | 0.21 | 0.23 | 0.24 |
| 2510002D24Rik | 18.06 | 26.52 | 27.6 | 23.67 | 15.38 | 14.7 |
| Socs6 | 4.87 | 10.78 | 6.48 | 7.57 | 7.73 | 2.22 |
| Dph1 | 11.08 | 8.48 | 9.59 | 6.61 | 1.05 | 3.02 |
| Trmt1 | 31.05 | 40.5 | 33.18 | 29.87 | 15.58 | 15.95 |
| Cenpq | 17.16 | 23.03 | 15.81 | 10.33 | 10.87 | 12.65 |
| Slc37a2 | 5.14 | 6.06 | 2.48 | 1.41 | 0.37 | 1.04 |
| Rpl31-ps12 | 69.44 | 82.62 | 55.67 | 39.32 | 40.28 | 30.49 |
| Gas7 | 11.87 | 9.28 | 7.33 | 3.3 | 2.72 | 0.32 |
| Rps21 | 664.17 | 939.26 | 798.12 | 633.45 | 590.31 | 699.26 |
| Rpl22 | 95.02 | 134.02 | 120.33 | 89.45 | 93.8 | 79.08 |
| Gm19705 | 4.63 | 18.68 | 15.29 | 3.13 | 0.99 | 2.87 |
| Rps10 | 1566.61 | 2112.32 | 1860.65 | 1508.21 | 1599.93 | 1441.84 |
| Rps16 | 1855.01 | 2588.66 | 2349.37 | 1412.64 | 1486.94 | 1718.78 |
| Rps14 | 2104.9 | 2888.94 | 2732.97 | 1781.84 | 1844.69 | 1996.69 |
| Rpl37a | 764.2 | 1019.68 | 1042.08 | 644.37 | 707.36 | 706.08 |
| Rpl27a | 730.46 | 1009.8 | 956.49 | 560.55 | 615.59 | 584.85 |
| Rps20 | 1341.13 | 1767.02 | 1507.45 | 703.13 | 739.23 | 765.41 |
| Rpl23a | 2424.94 | 2912.25 | 2877.11 | 1621.49 | 1802.26 | 1609.82 |
| Rps7 | 1032.92 | 1248.51 | 1237.2 | 647.06 | 708.16 | 650.51 |
| Rpl36a | 795.77 | 974.49 | 1045.04 | 493.19 | 574.31 | 461 |
| Rps28 | 1133.25 | 1656.98 | 1618.98 | 884.63 | 864.62 | 923.46 |
| Rps18 | 1723.4 | 2247.83 | 2000.76 | 1413.96 | 1377.31 | 1252.03 |
| Rps24 | 1408.44 | 2084.61 | 1834.21 | 1076.22 | 1143.31 | 1217.77 |
| Rps23 | 1737.47 | 2467.5 | 2369.91 | 1448.85 | 1642.72 | 1529.86 |
| Rps19 | 1255.96 | 2027.35 | 1883.64 | 863.51 | 1088.27 | 971.45 |
| Rpl10 | 2312.94 | 2582.1 | 2345.01 | 1654.24 | 1737.36 | 1449.75 |
| Rpl15 | 605.07 | 687.02 | 694.85 | 400.37 | 424.53 | 383.75 |
| Rps26 | 1399.1 | 1486.56 | 1535.54 | 903.05 | 996.72 | 698.44 |
| Rps17 | 1330.42 | 1551.6 | 1519.23 | 1029.34 | 1130.3 | 1011.47 |
| Eef1b2 | 481.43 | 569.6 | 508.76 | 346.26 | 419.03 | 293.2 |
| Rps8 | 1746.01 | 2137.9 | 2129.15 | 1379.48 | 1679.55 | 1172.19 |
| Gas5 | 182.04 | 189.23 | 170.42 | 151.6 | 148.77 | 122.89 |
| Rplp2 | 1573.01 | 1800.05 | 1495.4 | 1130.38 | 1111.23 | 1202.79 |
| Rpl5 | 1834.15 | 1919.39 | 1678.39 | 1176.66 | 1209.57 | 1191.1 |
| Rpl8 | 1876.37 | 1924.32 | 1949.24 | 1325.57 | 1436.09 | 1265.85 |
| Rpl12 | 2071.94 | 2564.74 | 2229.34 | 1392.89 | 1389.29 | 1359.9 |
| Gm12191 | 1424.58 | 1855.25 | 1598.14 | 1158.12 | 1174.96 | 1254.06 |

TABLE 4-continued

| | | | | | | |
|---|---|---|---|---|---|---|
| Rpl9 | 2169.2 | 2741.73 | 2468.37 | 1546.38 | 1709.42 | 1613.49 |
| Rps29 | 1298.77 | 1446.84 | 1451.05 | 928.66 | 887.19 | 1168.73 |
| Uba52 | 2332.78 | 2645.11 | 2615.14 | 1586.43 | 1695.79 | 1939.72 |
| Rps5 | 2291.33 | 2572.16 | 2554.8 | 1485.03 | 1599.64 | 1642.4 |
| Rpl21 | 821.76 | 951.97 | 893.95 | 556.93 | 599.32 | 623.66 |
| Cyb5 | 77.54 | 97.36 | 95.89 | 54.93 | 55.49 | 57.44 |
| Rps15 | 1443.86 | 1858.89 | 1788.66 | 1137.83 | 1271.44 | 1186.95 |
| Rplp1 | 2163.24 | 2858.09 | 2765.85 | 1814.95 | 1706.16 | 2028.65 |
| C1galt1 | 4.41 | 8.59 | 4.12 | 3.77 | 2.18 | 2.11 |
| Luc7l2 | 6.78 | 11.43 | 8.32 | 6.8 | 7.58 | 7.8 |
| Rps27 | 1760.18 | 2738.27 | 1162.25 | 1382.73 | 960.5 | 1669.04 |
| Cyth3 | 9.82 | 13.92 | 10.18 | 10.72 | 8.69 | 4.65 |
| Trpc4ap | 7.84 | 12.26 | 13.64 | 11.3 | 6.91 | 13.46 |
| Zfp281 | 9.48 | 12.1 | 10.78 | 13.52 | 10.32 | 12.07 |
| Tcp11l2 | 33.51 | 42.18 | 55.82 | 40.87 | 40.37 | 44.25 |
| StGgal1 | 7.46 | 12.51 | 13.7 | 1.65 | 3.3 | 5.08 |
| Klf4 | 5.77 | 5.83 | 3.74 | 6.71 | 2.73 | 4.89 |
| Rab3ip | 14.36 | 13.26 | 10.22 | 15.6 | 7.5 | 7.96 |
| Map4k4 | 6 | 5.86 | 5.9 | 6.15 | 3.76 | 3.3 |
| Elovl6 | 3.25 | 4.67 | 6.36 | 4.17 | 2.45 | 1.24 |
| Klra23 | 8.43 | 9.5 | 19.64 | 3.39 | 0.83 | 0.39 |
| Slc43a2 | 1.55 | 2.9 | 2.38 | 0.85 | 1.1 | 1.12 |
| Thumpd1 | 21.14 | 26.41 | 19.35 | 25.19 | 16.44 | 18.45 |
| Zfp296 | 3.65 | 4.36 | 2.36 | 0.74 | 1.34 | 2.59 |
| Mccc2 | 2.25 | 2.98 | 1.02 | 1.3 | 0.71 | 1.03 |
| Chd1l | 9.18 | 11.7 | 19.31 | 6.94 | 6.61 | 9.15 |
| Gm10548 | 4.01 | 4.11 | 5.52 | 1.92 | 2.69 | 2.79 |
| Unc119b | 37.07 | 53.29 | 61.18 | 32.28 | 37.26 | 33.1 |
| Dcaf17 | 6.1 | 7.06 | 7.68 | 2.87 | 4.81 | 4.73 |
| Ulk2 | 2.66 | 1.78 | 1.68 | 0.75 | 0.4 | 1.19 |
| Grk6 | 16.44 | 15.75 | 20.49 | 9.48 | 8.43 | 15.32 |
| Slc16a5 | 2.64 | 2.79 | 1.74 | 0 | 0 | 0 |
| Zfp1 | 13.74 | 12.59 | 12.62 | 6.75 | 4.15 | 3.5 |
| Qdpr | 39.96 | 41.85 | 50.35 | 22.31 | 20.73 | 28.02 |
| Pnpo | 16.31 | 15.28 | 16.44 | 8.59 | 10.37 | 6.62 |
| 4930432K21Rik | 0.58 | 0.07 | 0.51 | 0 | 0 | 0 |
| 5830411N06Rik | 0.11 | 4.71 | 7.67 | 1.02 | 0.72 | 1.9 |
| Mrm1 | 7.47 | 5.96 | 1.9 | 4.84 | 6.88 | 5.12 |
| Csrnp2 | 2.09 | 0.17 | 0.31 | 0.67 | 0.33 | 0.62 |
| Reck | 5.26 | 6.26 | 6.45 | 3.11 | 3.17 | 4.25 |
| C1qb | 0 | 0 | 0 | 0 | 0.13 | 0 |
| Ccdc164 | 1.16 | 0 | 0.58 | 0 | 0 | 0 |
| Tlr13 | 0 | 0.04 | 0.05 | 0.08 | 0.14 | 0.08 |
| Frat2 | 0.3 | 0.9 | 0.59 | 0.6 | 0.95 | 0.83 |
| Ifrd1 | 79.78 | 90.98 | 85.18 | 72.14 | 80.8 | 85.43 |
| Zfp266 | 6.58 | 9.04 | 8.33 | 8.23 | 8.83 | 8.21 |
| Klhl24 | 5.78 | 10.44 | 8.87 | 7.92 | 6.34 | 7.59 |
| Il16 | 37.21 | 39.34 | 41.56 | 26.75 | 30.57 | 33.94 |
| B4galnt1 | 181.01 | 163.83 | 218.83 | 119.63 | 159.67 | 197.27 |
| Fam169b | 46.79 | 36.73 | 32.06 | 23.75 | 27.56 | 37.94 |
| 1810026B05Rik | 12.7 | 12.22 | 13.9 | 7.49 | 9.23 | 9.4 |
| Dapl1 | 13.63 | 16.53 | 29.31 | 2.28 | 4.51 | 3.45 |
| Als2cl | 6.9 | 6.26 | 13.24 | 2.99 | 5.17 | 3.17 |
| Limd2 | 162.21 | 175.29 | 234.75 | 106.09 | 124.54 | 145.64 |
| Smap2 | 23.57 | 29.88 | 36.74 | 13.38 | 26.74 | 26.48 |
| Arhgap15 | 71.58 | 88.49 | 94.42 | 50.13 | 51.06 | 70.6 |
| Faah | 14.69 | 14.74 | 18.35 | 6.83 | 9.61 | 10.76 |
| Rgs10 | 51.99 | 54.62 | 52.1 | 5.92 | 9.34 | 3.17 |
| Matr3 | 49.14 | 49.92 | 51.94 | 45.75 | 51.11 | 49.26 |
| Fam210a | 3.04 | 1.49 | 1.95 | 2.05 | 2.23 | 0.84 |
| Hdac7 | 10.15 | 9.36 | 9.34 | 7.01 | 7 | 9.84 |
| Fam189b | 26.61 | 30.85 | 40.81 | 26.32 | 27.04 | 26.44 |
| Foxo1 | 10.64 | 8.7 | 8.21 | 5.16 | 6.95 | 8.32 |
| Sh3bp5 | 44.15 | 47.11 | 39.65 | 22.4 | 12.45 | 38.56 |
| Il7r | 82.24 | 117.66 | 105.57 | 36.23 | 44.86 | 70.05 |
| Slc50a1 | 72.94 | 71.68 | 79.13 | 55.47 | 63.74 | 71.73 |
| D10Wsu52e | 84.69 | 84.66 | 100.1 | 71.29 | 68.93 | 60.11 |
| Mdn1 | 3 | 3.24 | 1.92 | 1.5 | 0.99 | 1.5 |
| Zfp36l1 | 62.5 | 76.14 | 68.39 | 35.66 | 45.81 | 59.6 |
| Pecam1 | 19.91 | 20.42 | 15.06 | 5.19 | 5.57 | 6.65 |
| Eif3e | 317.98 | 344.37 | 325.54 | 208.79 | 240.25 | 183.28 |
| Sell | 312.39 | 327.96 | 237.34 | 54.67 | 49.5 | 30.08 |
| Dph5 | 22.59 | 29.08 | 24.05 | 14.42 | 16.74 | 13.19 |
| Hdac4 | 9 | 10.35 | 11.9 | 3.7 | 6.95 | 4.88 |
| Pdk1 | 20.41 | 17 | 23.07 | 5.8 | 19.1 | 3.28 |
| Rnf7 | 117.45 | 88.3 | 94.45 | 61.71 | 87.28 | 62.88 |
| Rbm26 | 15.96 | 15.82 | 14.08 | 10.15 | 11.89 | 14.38 |
| Fgfr1op2 | 70.15 | 72.3 | 64.36 | 48.92 | 48.81 | 53.7 |
| Clk1 | 180.26 | 176.38 | 181.45 | 161.75 | 157.54 | 184.33 |
| Brd8 | 17.94 | 15.65 | 12.9 | 11.3 | 10.6 | 12.96 |

TABLE 4-continued

| | | | | | | |
|---|---|---|---|---|---|---|
| Evl | 12.95 | 13.06 | 12.67 | 10.44 | 7.34 | 12.06 |
| Rapgef6 | 35.5 | 28.96 | 32.35 | 18.23 | 19.15 | 24.96 |
| Treml2 | 8.42 | 6.08 | 6.66 | 2.01 | 1.16 | 0.18 |
| Smg1 | 10.21 | 7.98 | 8.67 | 7.22 | 5.67 | 6.86 |
| Tnfsf8 | 14.11 | 13.72 | 10.07 | 0 | 0 | 1.25 |
| Ikbkb | 45.61 | 47.09 | 47.44 | 26.16 | 28.43 | 36.72 |
| Cox7a2l | 310.21 | 389.35 | 380.48 | 244.18 | 304.91 | 266.56 |
| Sesn1 | 9.48 | 13.76 | 14.03 | 9.19 | 3.61 | 12 |
| Dtd1 | 15.8 | 9.31 | 18.47 | 10.48 | 6.27 | 12.21 |
| Sidt2 | 31.31 | 37.88 | 40.97 | 32.77 | 25.93 | 41.98 |
| Cep110 | 18.65 | 14.12 | 14.34 | 13.16 | 8.46 | 14.23 |
| Gm6548 | 6.63 | 5.67 | 5.93 | 3.62 | 2.01 | 4.67 |
| Fahd2a | 7.94 | 6.74 | 7.23 | 1.59 | 2.11 | 5.5 |
| Max | 18.72 | 13 | 11.56 | 14.52 | 8.03 | 13.37 |
| Elmsan1 | 21.42 | 14.15 | 13.1 | 13.3 | 11.8 | 17.14 |
| Txnl4a | 105.09 | 87.09 | 93.07 | 80.68 | 93.44 | 95.62 |
| Srsf7 | 71.29 | 64.63 | 69.18 | 58.08 | 61.42 | 67.76 |
| Rbbp6 | 5.68 | 7.76 | 8.19 | 7.89 | 8.37 | 7.14 |
| Rictor | 3.14 | 5.64 | 5.38 | 6.28 | 6.28 | 5.71 |
| Lmbr1l | 5.97 | 5.92 | 8.26 | 7.03 | 6.48 | 11.71 |
| Cerk | 2.88 | 2.01 | 4.26 | 2.85 | 3.03 | 4.19 |
| Hsd17b4 | 7.6 | 13.81 | 11.86 | 10.32 | 9.69 | 12.77 |
| Mbip | 11.75 | 15.03 | 13.8 | 6.76 | 9.58 | 11.96 |
| Zc3h12d | 12.31 | 5.96 | 8.75 | 3.8 | 3.46 | 4.36 |
| Pdk2 | 3.53 | 2.87 | 5.12 | 0.43 | 2.11 | 1.58 |
| Zkscan14 | 14.18 | 8.69 | 6.12 | 7.93 | 9.91 | 4.2 |
| Cep97 | 9.79 | 9.22 | 8.63 | 6.16 | 5.47 | 5.7 |
| Usp28 | 5.9 | 6.12 | 3.13 | 2.11 | 1.91 | 4.04 |
| Add1 | 45.76 | 28.72 | 36.34 | 30.48 | 33.73 | 28.52 |
| Bptf | 6.88 | 5.32 | 4.99 | 5.9 | 6.17 | 4.07 |
| Bcl9l | 3.09 | 2.54 | 2 | 2.37 | 2.81 | 3.09 |
| Stk38 | 39.9 | 35.49 | 46.16 | 38.08 | 40.12 | 43.36 |
| Bambi-ps1 | 0.94 | 8.02 | 9.62 | 1.32 | 4.77 | 2.39 |
| Sepp1 | 62.4 | 55.14 | 57.57 | 42.29 | 55.28 | 73.73 |
| Gm14085 | 0.21 | 3.01 | 2.74 | 0 | 0.16 | 0.04 |
| Fam101b | 2 | 0.81 | 2.99 | 0.37 | 1.51 | 0.34 |
| Ikbke | 8.32 | 21.83 | 25.19 | 13.15 | 16.34 | 13.8 |
| A930005H10Rik | 10.3 | 19.13 | 20.43 | 16.11 | 12.46 | 18.66 |
| 2610019F03Rik | 11.36 | 13.98 | 11.38 | 0.92 | 1.88 | 3.3 |
| Inadl | 2.21 | 2.77 | 2.47 | 0.39 | 0.26 | 1.91 |
| Gm11346 | 10.88 | 7.41 | 8.92 | 6.1 | 6.6 | 13.16 |
| Add3 | 30.62 | 18.97 | 23.31 | 16.74 | 27.27 | 22.31 |
| D15Ertd621e | 3.78 | 3.06 | 3.48 | 1.53 | 5.43 | 4.06 |
| Rcn3 | 5.27 | 11.66 | 8.47 | 3.9 | 12.01 | 6.41 |
| Rapgef4 | 2.24 | 2.98 | 4.4 | 0.8 | 1.74 | 0.91 |
| Adi1 | 22.05 | 29.04 | 27.44 | 16.4 | 17.17 | 16.57 |
| Ttc28 | 0.81 | 0.33 | 0.59 | 0 | 0.1 | 0.13 |
| Zbtb20 | 8.72 | 7.17 | 7.27 | 2.4 | 5.61 | 4.37 |
| Dnahc8 | 2.17 | 0.63 | 0.98 | 1.14 | 0.75 | 0.88 |
| Cd55 | 8.68 | 3.62 | 5.16 | 3.91 | 3.78 | 2.83 |
| Pip4k2a | 7.45 | 8.86 | 5.06 | 3.22 | 4.47 | 6.34 |
| Il6ra | 6.78 | 2.63 | 3.25 | 1.16 | 2.49 | 1.25 |
| Trib2 | 7.11 | 7.58 | 8.62 | 3.16 | 5.49 | 6.94 |
| Chd6 | 3.84 | 3.78 | 3.1 | 3.01 | 1.87 | 2.48 |
| Ets2 | 20.38 | 12.11 | 11.11 | 12.39 | 10.08 | 12.15 |
| 5730508B09Rik | 9.76 | 7.56 | 2.93 | 2.93 | 1.79 | 4.7 |
| Ranbp10 | 3.16 | 2.78 | 2.69 | 3.54 | 2.93 | 2.54 |
| Ifngr2 | 5.28 | 10.7 | 2.45 | 9.1 | 11.19 | 4.79 |
| Zscan10 | 0 | 0.06 | 0 | 0 | 0.25 | 0.37 |
| Zfyve19 | 8.13 | 7.22 | 10.82 | 11.88 | 12.83 | 8.66 |
| Sptbn1 | 7.89 | 8.22 | 9.62 | 11.06 | 10.4 | 7.18 |
| Spon1 | 3 | 0.71 | 0.59 | 2 | 0.38 | 2.32 |
| Klf13 | 55.38 | 39.71 | 44.27 | 43.99 | 36.24 | 63.95 |
| Marf1 | 4.97 | 2.81 | 2.88 | 3.61 | 2.35 | 3.32 |
| Atp1b3 | 194.07 | 161.32 | 196.23 | 167.17 | 211.56 | 246.64 |
| Jak1 | 132.78 | 132.29 | 149.47 | 152.81 | 159.49 | 188.99 |
| Mafk | 30.45 | 32.03 | 27.53 | 28.5 | 18.86 | 37.69 |
| Sun2 | 27.28 | 21.45 | 21.18 | 30.67 | 25.12 | 32 |
| Rere | 8.2 | 7.19 | 5.31 | 6.47 | 6.25 | 7.47 |
| Frat1 | 9.71 | 9.55 | 6.3 | 10.41 | 8.5 | 14.23 |
| Hsdl1 | 22.97 | 25.06 | 24.66 | 14.72 | 19.13 | 30.97 |
| Abca1 | 0.84 | 0.17 | 0.26 | 0.24 | 0.17 | 0.5 |
| Zfp592 | 15.69 | 14.29 | 16.52 | 12.42 | 15.19 | 14.38 |
| Rbm38 | 59.29 | 71.48 | 63.84 | 51.87 | 66.37 | 66.83 |
| Lrp12 | 1.53 | 2.21 | 0.4 | 0.76 | 2.05 | 0.1 |
| Abi1 | 49.46 | 55.91 | 48.25 | 47.49 | 58.43 | 47.58 |

Figure 15:
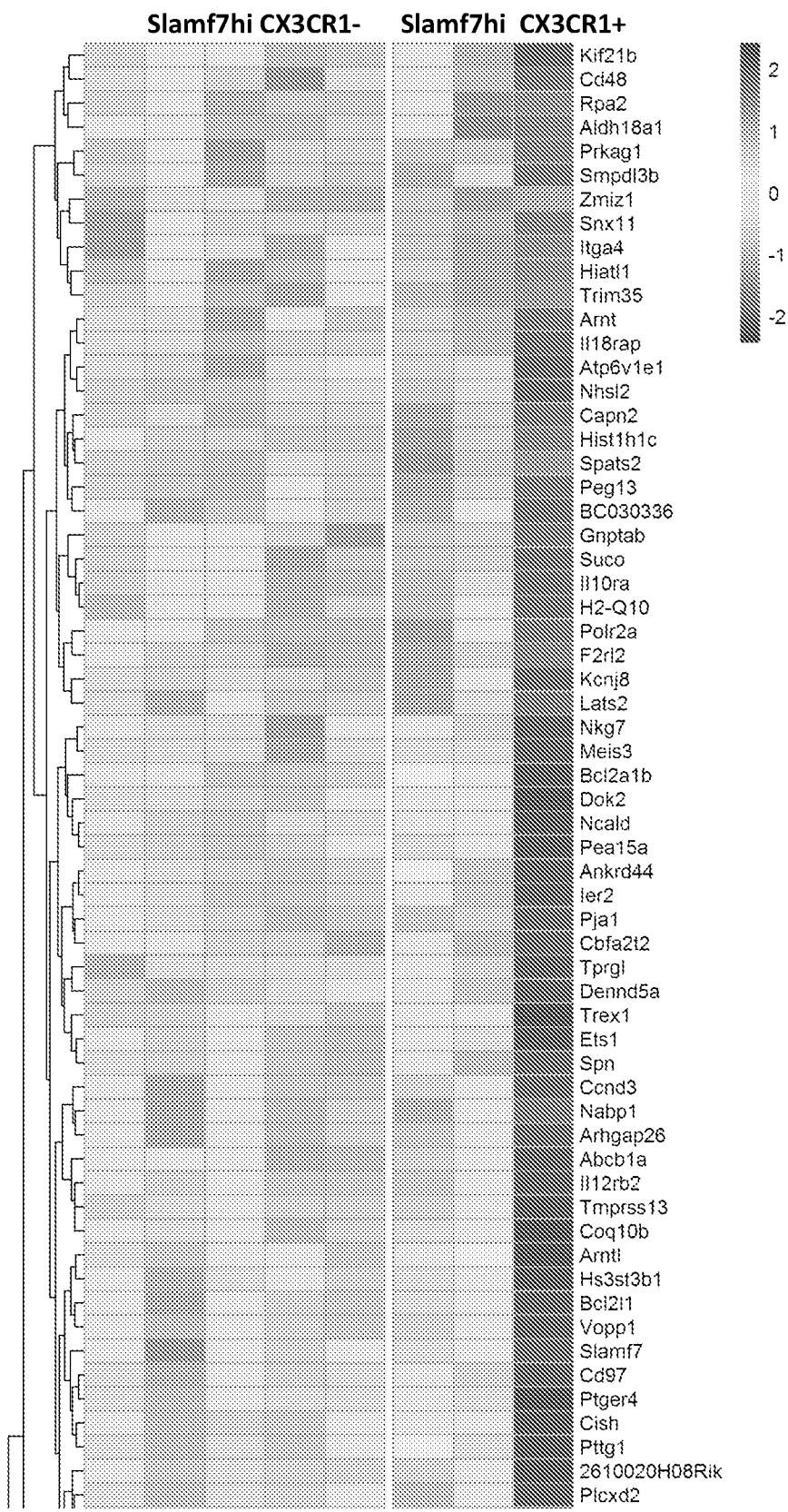
FIG. 15—Heatmap of $CD62L^-$ $Slamf7^{hi}CX3CR1^-$ and $CD62L^-$ $Slamf7^{hi}CX3CR1^+$ populations within $CD8^+PD-1^-$ TILs isolated from MC38-OVA tumors (see also, Table 5).
Figure 15:
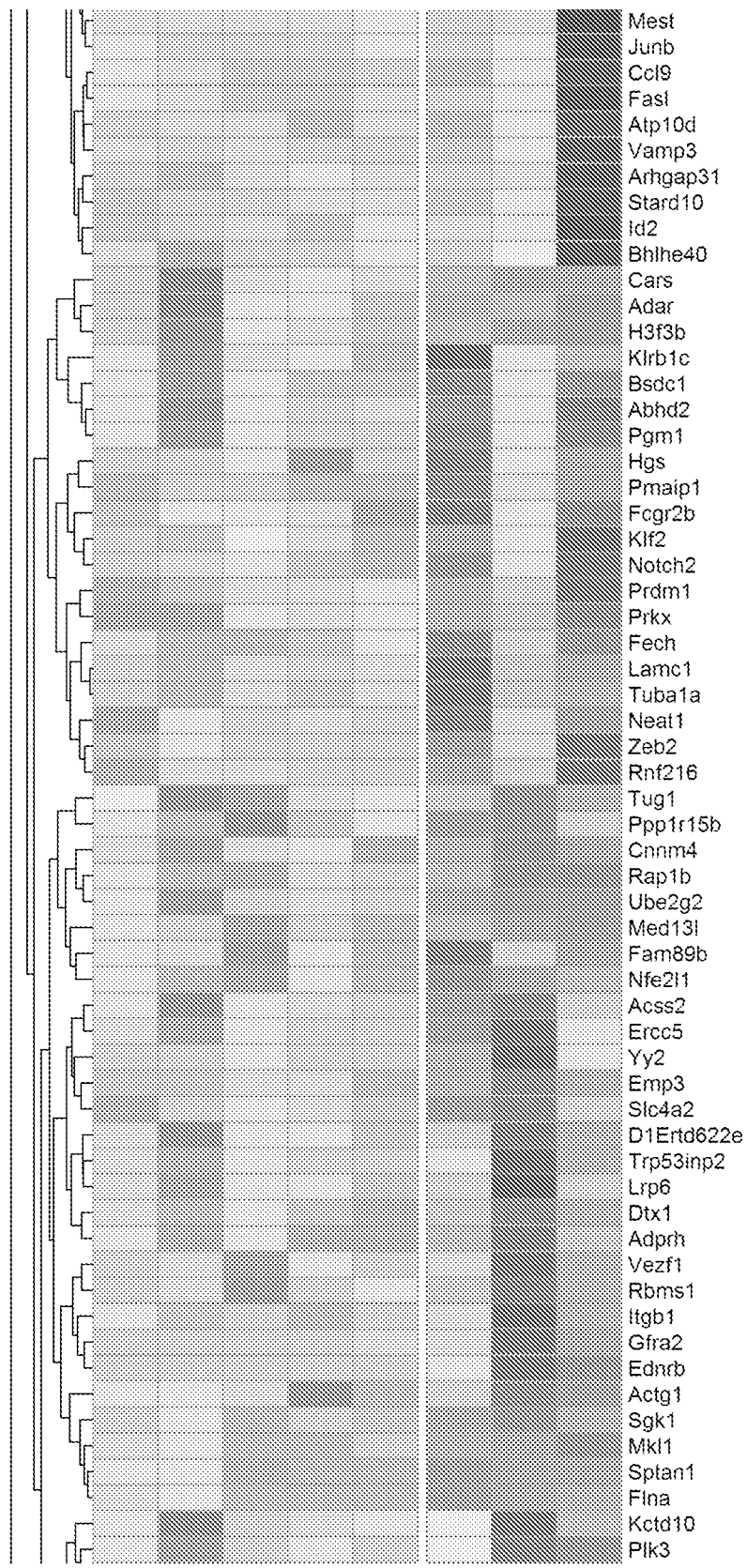
Figure 15:
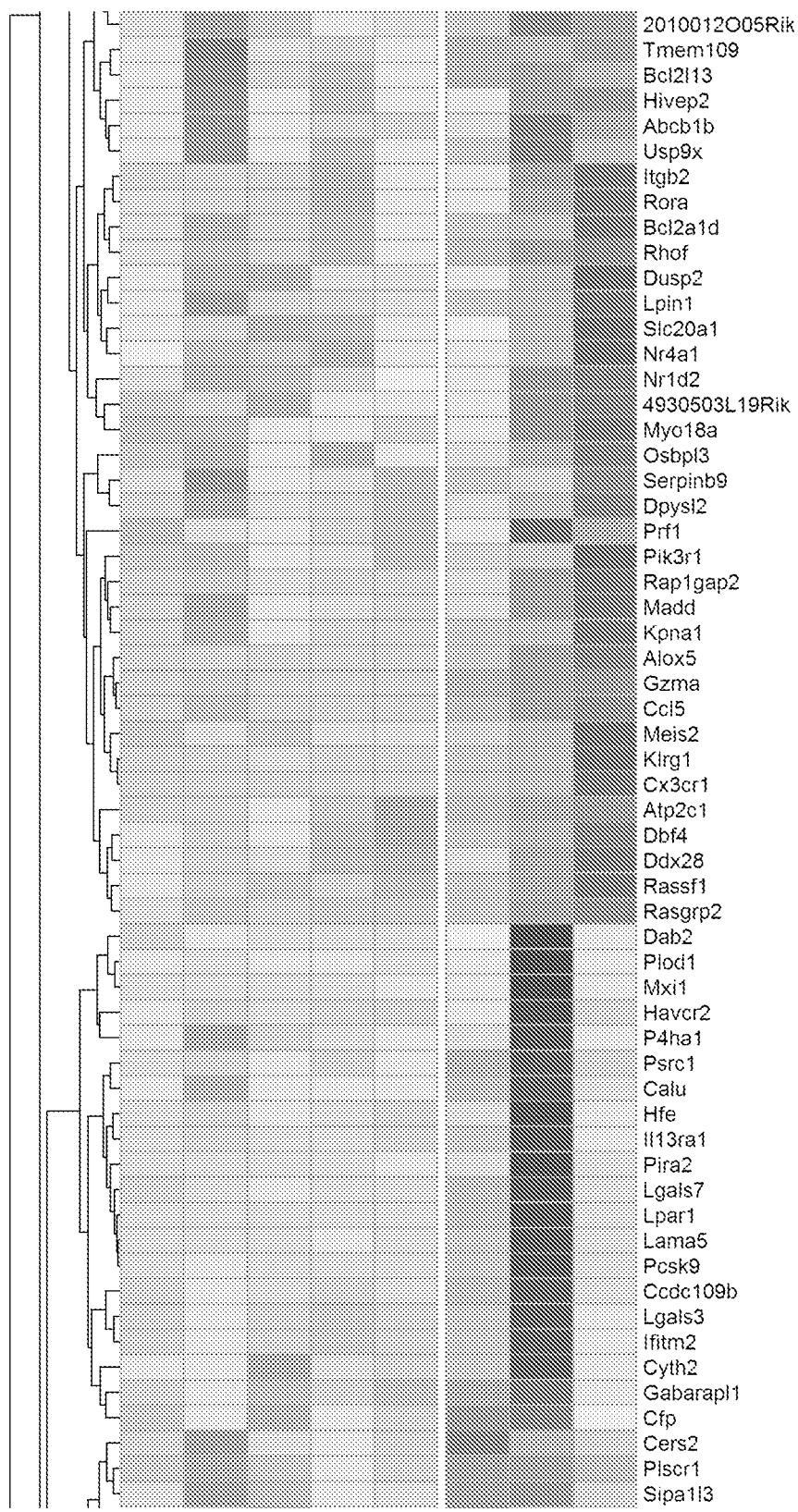
Figure 15:
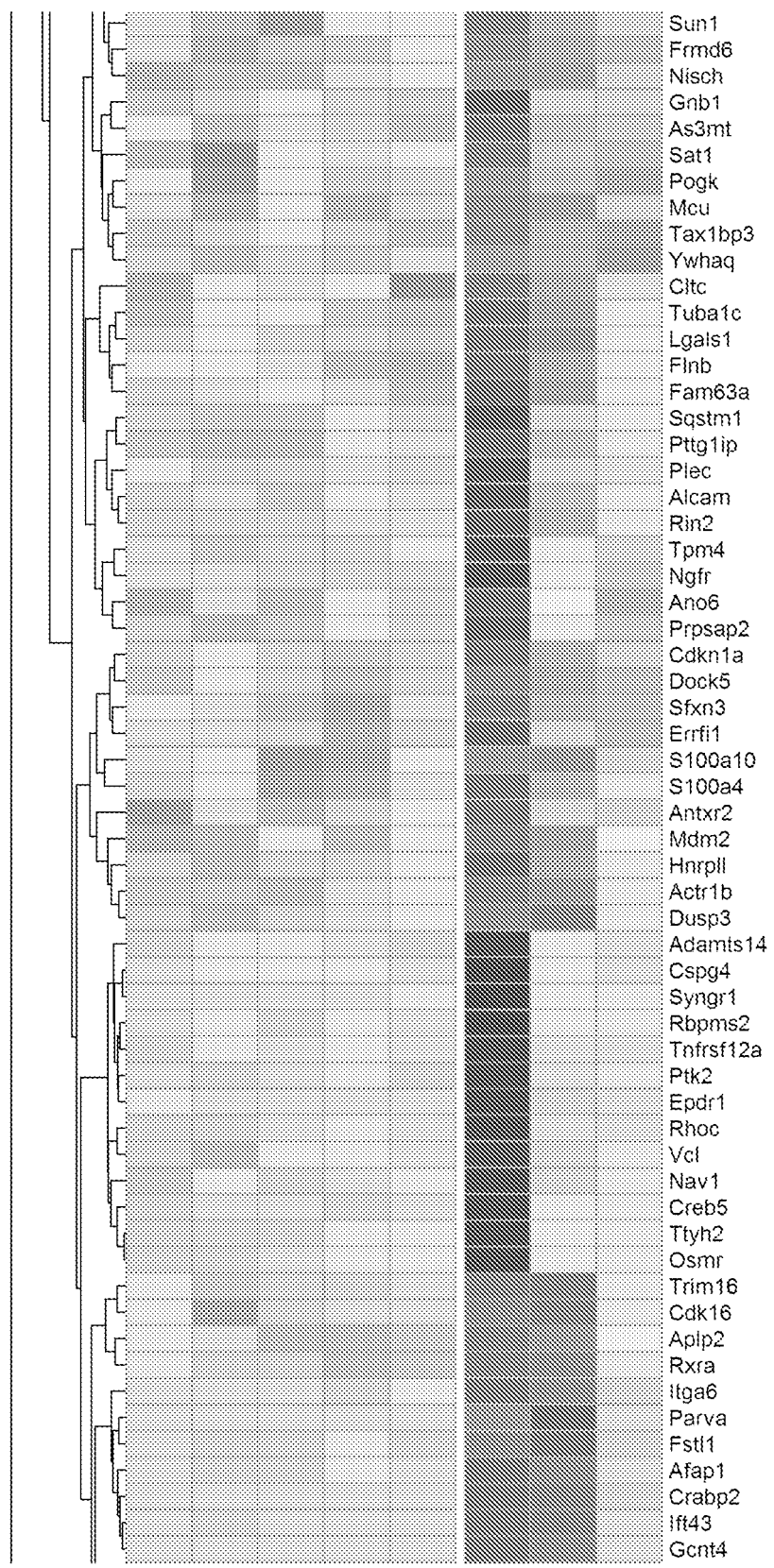
Figure 15:
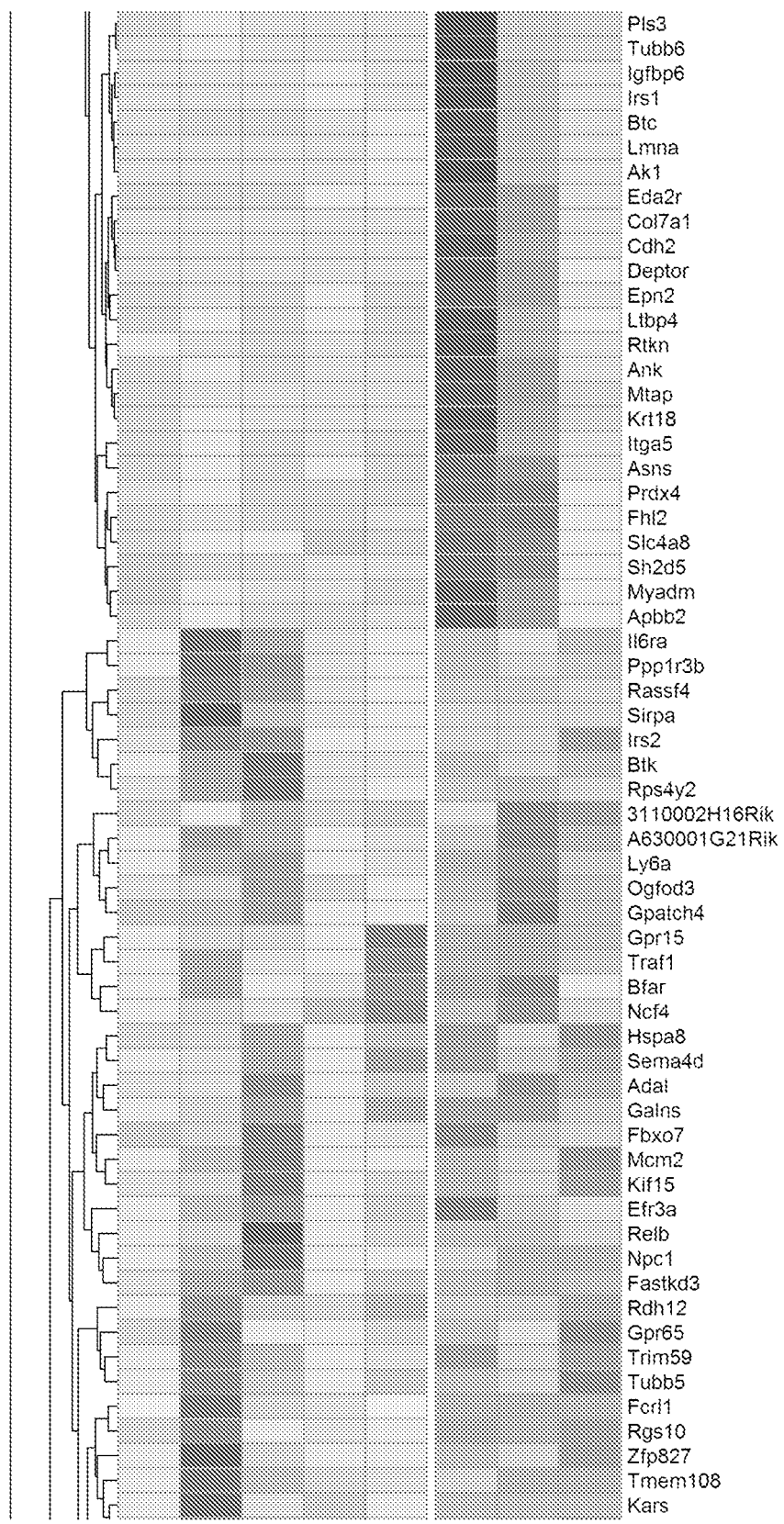
Figure 15:
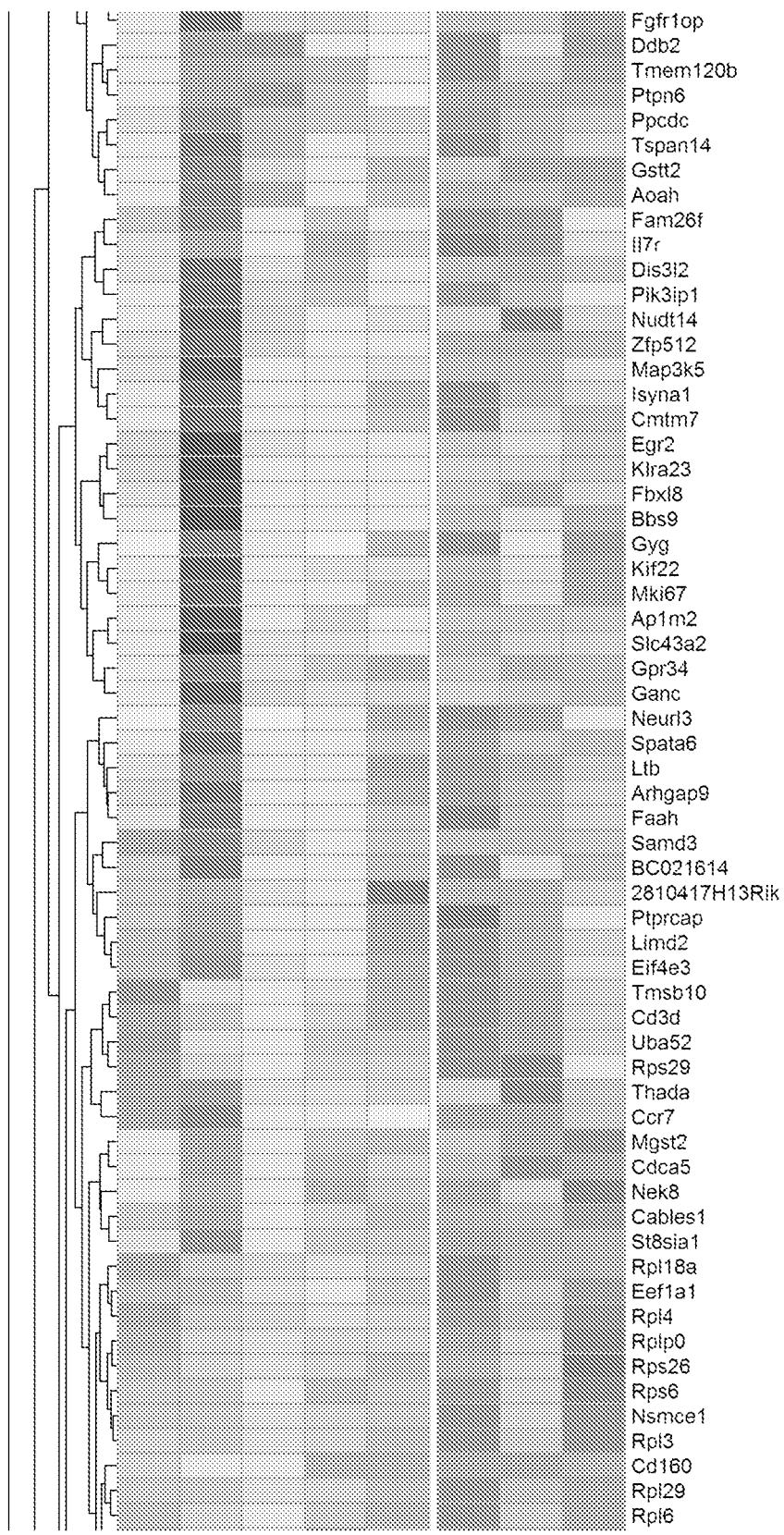
Figure 15:
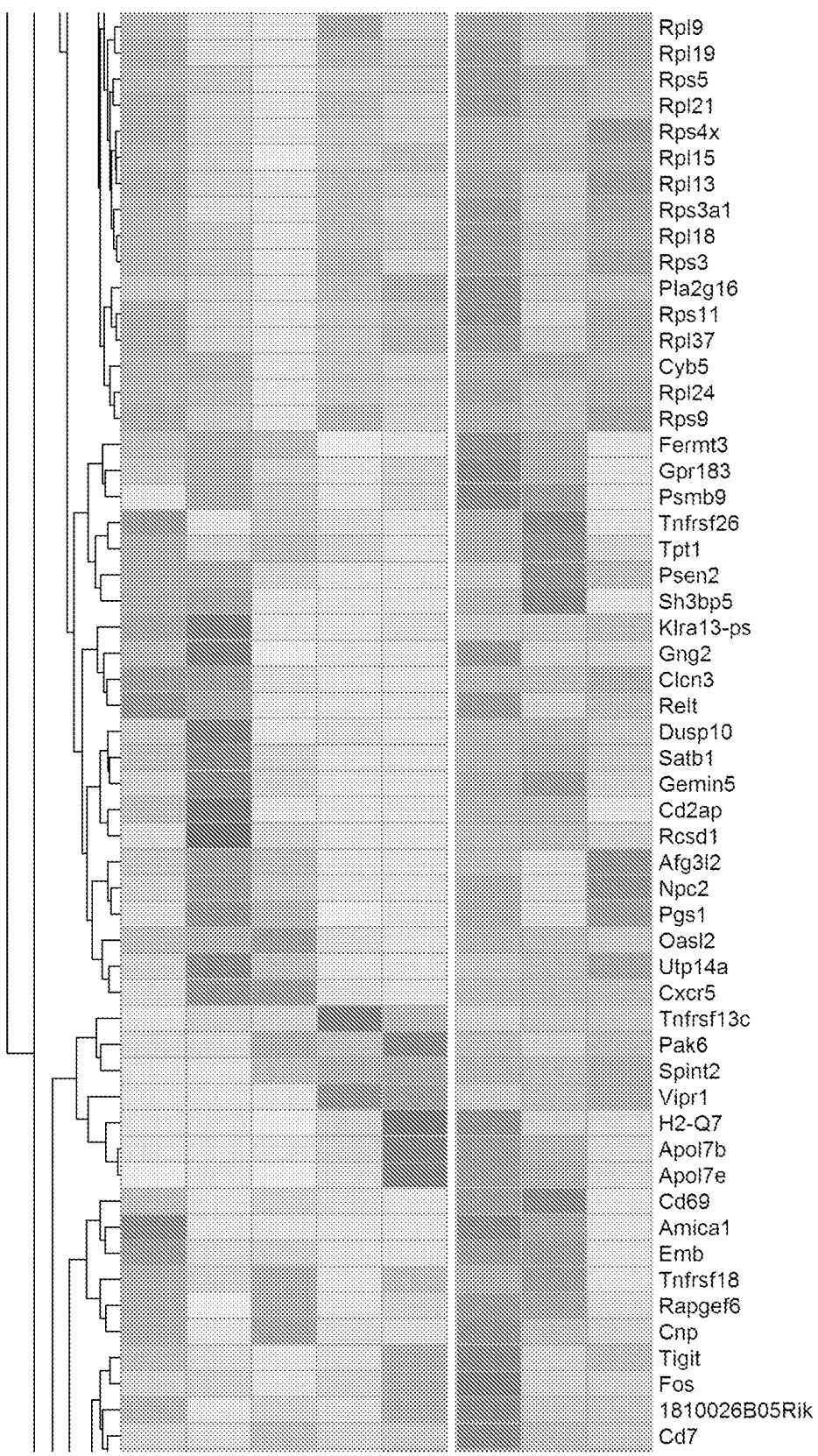
Figure 15:
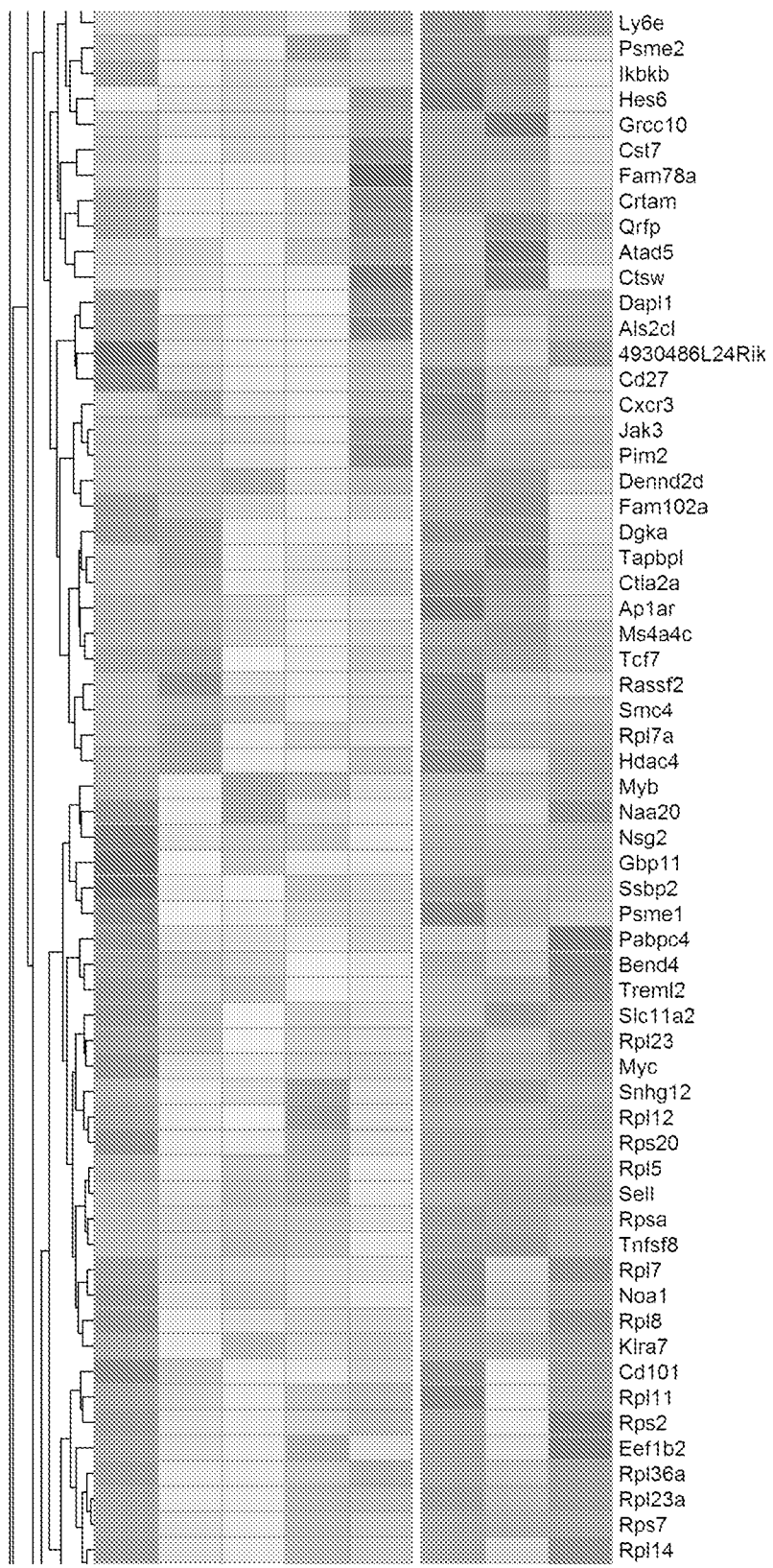
Figure 15:
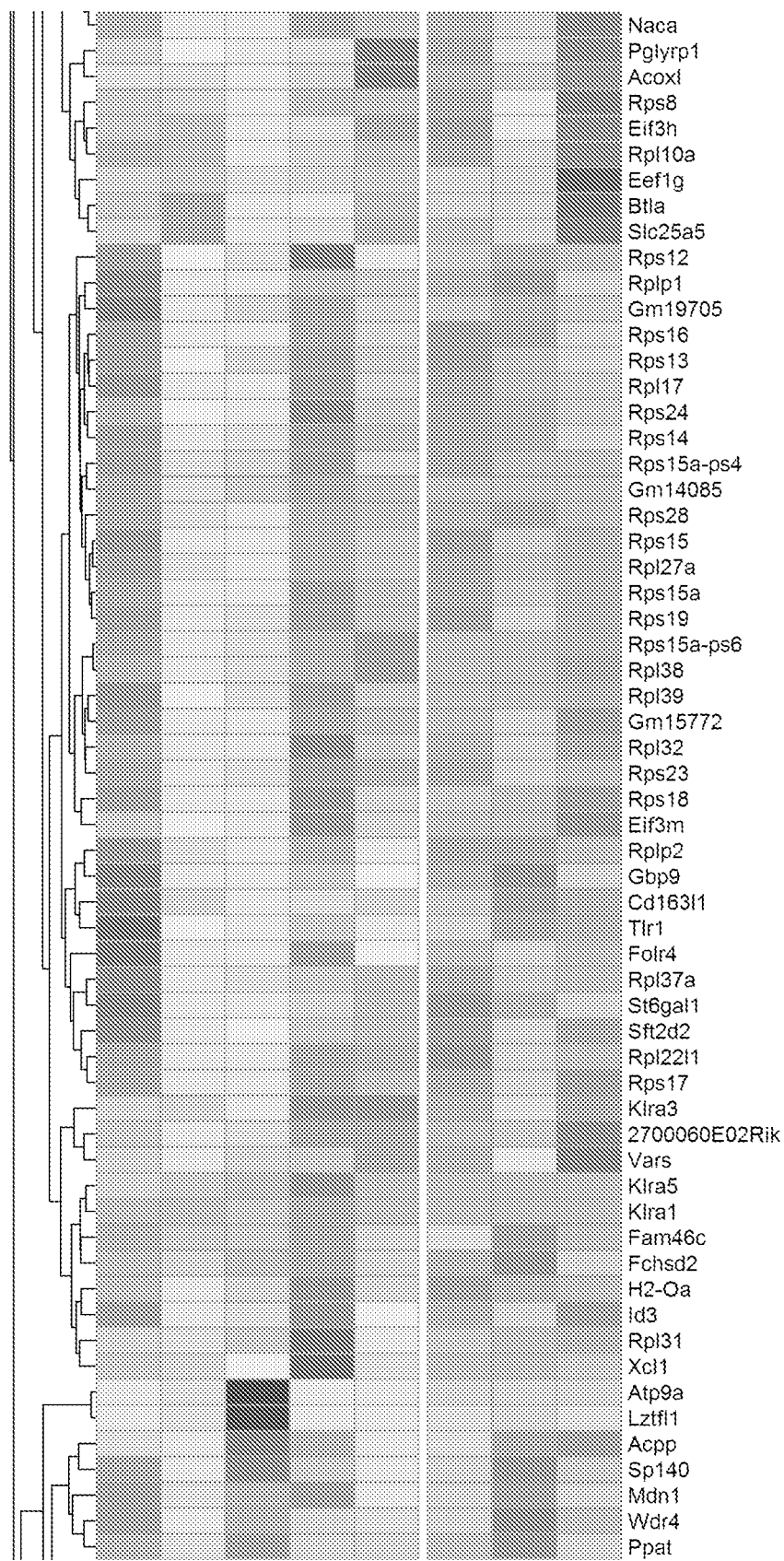
Figure 15:
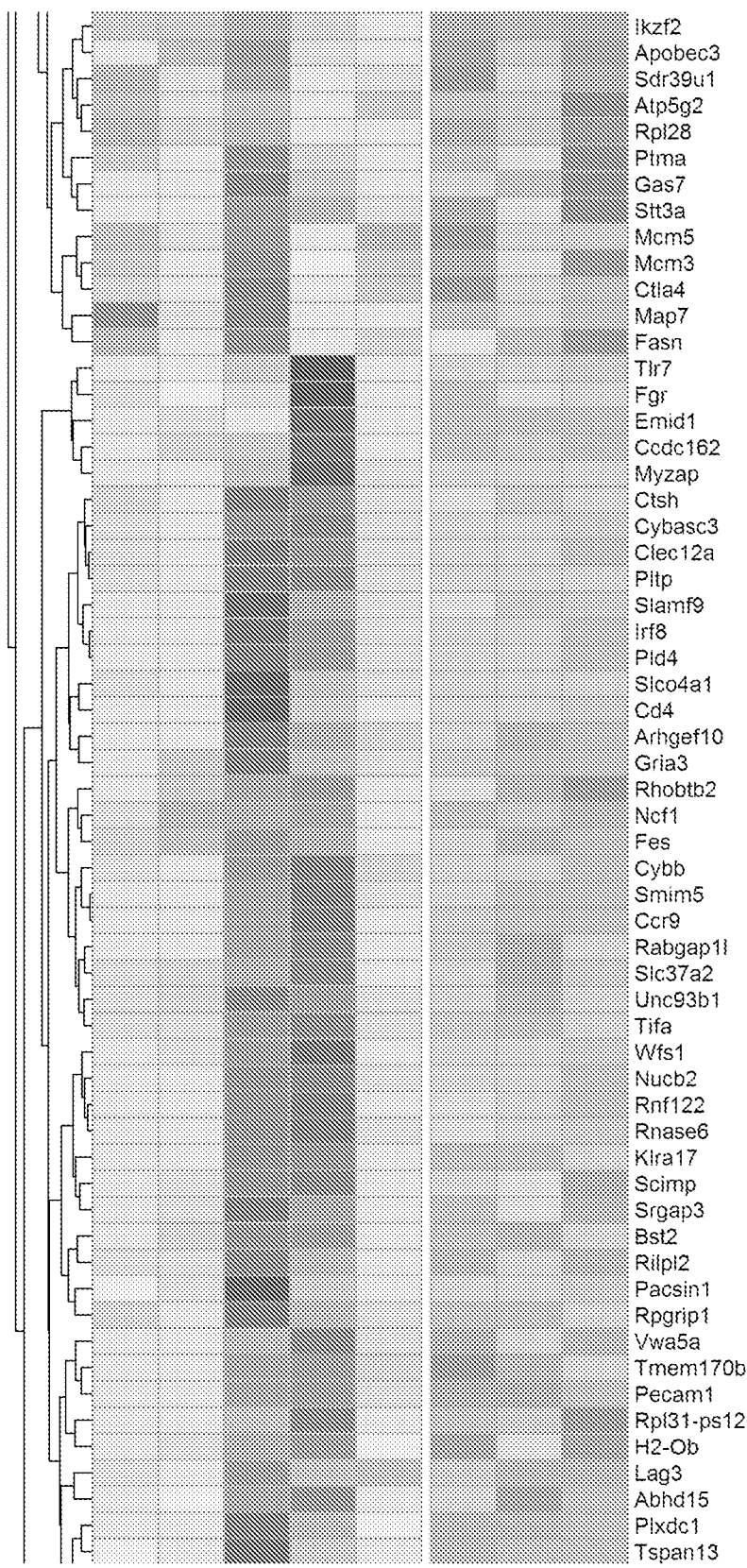
Figure 15:
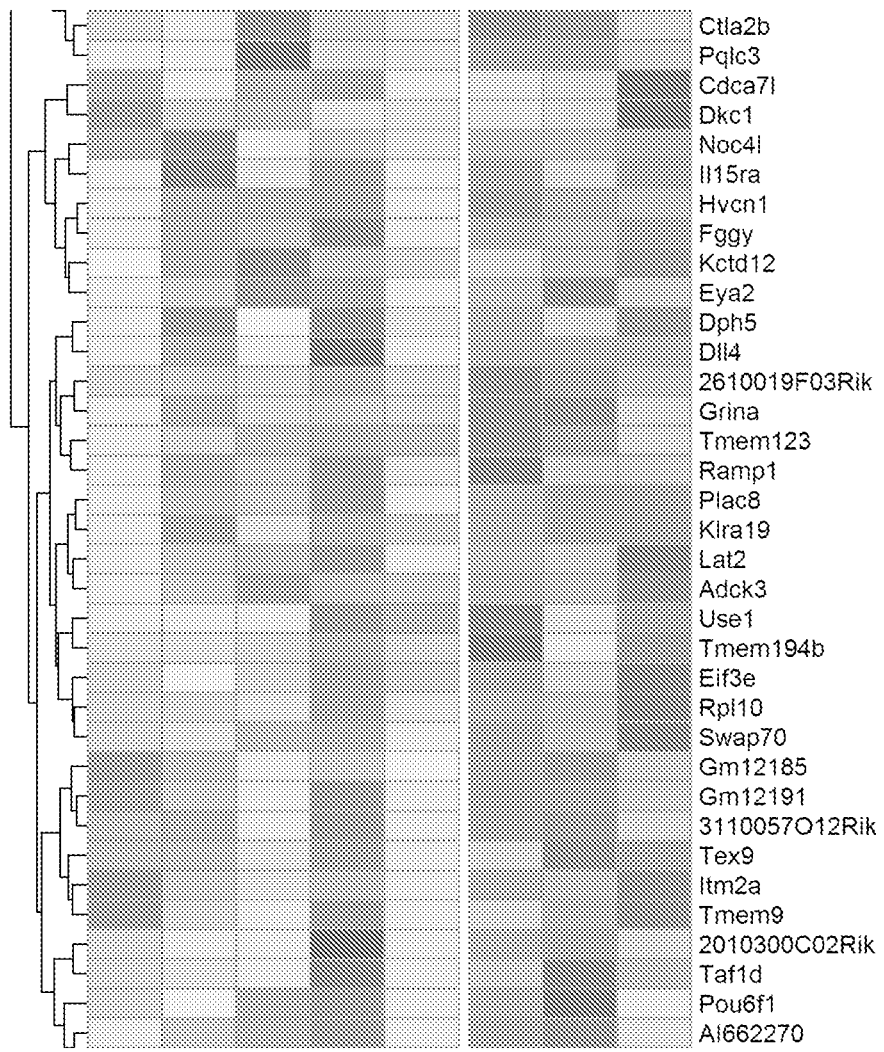

Table 5 shows the expression levels of all genes differentially expressed between Slamf7$^{hi}$ CX3CR1$^-$ and Slamf7$^{hi}$ CX3CR1$^+$ cells (see also FIG. 15).

TABLE 5

| | CD62L-Slamf7$^+$CX3CR1- | | | | | CD62L-Slamf7$^+$CX3CR1$^+$ | | |
|---|---|---|---|---|---|---|---|---|
| | Over expressed in CD62L-Slamf7$^+$Cx3cr1$^+$ relative to CD62L-Slamf7$^+$Cx3cr1- | | | | | | | |
| Kif21b | 10.92 | 14.21 | 12.64 | 9.62 | 10.55 | 13.59 | 18.71 | 23.13 |
| Cd48 | 240.03 | 286.05 | 228.38 | 185.41 | 247.75 | 297.88 | 342.82 | 399.92 |
| Rpa2 | 46.52 | 64.57 | 36.9 | 42.99 | 42.54 | 60.18 | 81.48 | 85.23 |
| Aldh18a1 | 28.73 | 28.21 | 23.01 | 23.53 | 25.41 | 32.13 | 43.81 | 45.12 |
| Prkag1 | 55.22 | 73.65 | 46.45 | 57.57 | 57.18 | 80.94 | 80.82 | 95.08 |
| Smpdl3b | 5.78 | 10.17 | 1.99 | 5.84 | 4.32 | 17.41 | 13.94 | 23.07 |
| Zmiz1 | 4.07 | 10.19 | 6.28 | 4.18 | 4.06 | 11.86 | 13.4 | 13.09 |
| Snx11 | 3.88 | 7.37 | 5.55 | 5.35 | 5.22 | 9.28 | 9.96 | 11.52 |
| Itga4 | 18.06 | 27.97 | 26.11 | 20.66 | 30.07 | 40.96 | 43.93 | 47.77 |
| Hiat11 | 23 | 30.68 | 22.02 | 23.64 | 27.27 | 34.3 | 37.29 | 40.25 |
| Trim35 | 20.54 | 23.98 | 17.2 | 15.69 | 22.25 | 34.08 | 35.66 | 37.08 |
| Arnt | 10.13 | 10.44 | 8.79 | 10.6 | 9.57 | 13.17 | 13.71 | 15.74 |
| Il18rap | 51.06 | 47.52 | 34.95 | 45.61 | 46.37 | 83.23 | 90.43 | 122.06 |
| Atp6v1e1 | 57.46 | 54.75 | 47.46 | 56.92 | 58.45 | 73.59 | 71.08 | 90.24 |
| Nhsl2 | 0.16 | 0.04 | 0 | 0.26 | 0.28 | 1.25 | 1.03 | 2.07 |
| Capn2 | 31.1 | 35.77 | 27.64 | 32.49 | 32.43 | 65.05 | 57.28 | 76 |
| Hist1h1c | 8.16 | 5.89 | 6.02 | 5.45 | 5.59 | 19.55 | 15 | 21.41 |
| Spats2 | 1.17 | 0.73 | 0.62 | 1.28 | 1.14 | 4.8 | 3.64 | 4.72 |
| Peg13 | 1.02 | 0.84 | 0.61 | 2.19 | 1.19 | 4.35 | 3.4 | 5.45 |
| BC030336 | 1.3 | 0.54 | 0.76 | 1.16 | 0.86 | 2.59 | 1.99 | 3.47 |
| Gnptab | 7.88 | 10.86 | 9.23 | 7.63 | 5.39 | 14.38 | 14.09 | 18.67 |
| Suco | 11.67 | 13.11 | 12.78 | 9.53 | 10.79 | 17.76 | 17.11 | 22.38 |
| Il10ra | 49.27 | 61.17 | 69.91 | 40.75 | 45.47 | 99.75 | 85.29 | 127.43 |
| H2-Q10 | 15 | 23.31 | 24.61 | 13.11 | 18.05 | 37.67 | 31.65 | 50.32 |
| Polr2a | 15.61 | 15.56 | 13.05 | 12.79 | 12.54 | 21.98 | 17.79 | 23.59 |
| F2rl2 | 14.53 | 11.69 | 11.79 | 9.56 | 10.16 | 19.55 | 17.42 | 21.61 |
| Kcnj8 | 18.48 | 13.17 | 17.8 | 14.46 | 9.59 | 67.52 | 34.01 | 90.34 |
| Lats2 | 9.34 | 4.95 | 10.7 | 7.04 | 8.48 | 22.38 | 16.92 | 26.7 |
| Nkg7 | 1608.34 | 1538.02 | 1497.81 | 1207.55 | 1666.74 | 1838.1 | 1991.88 | 2609.04 |
| Meis3 | 13.65 | 13.54 | 13.72 | 8.79 | 13.92 | 19.84 | 20.06 | 31.41 |
| Bcl2a1b | 219.21 | 242.4 | 175.82 | 179.78 | 186.8 | 263.49 | 259.89 | 416.21 |
| Dok2 | 106.18 | 105.41 | 97.89 | 91.55 | 118.22 | 124.34 | 136.27 | 207.85 |
| Ncald | 5.04 | 3.74 | 2.66 | 4.16 | 4.44 | 8.62 | 8.65 | 17.57 |
| Pea15a | 47.02 | 43.34 | 41.5 | 43.77 | 49.59 | 59.64 | 56.23 | 84.06 |
| Ankrd44 | 33.28 | 30.95 | 30.23 | 28 | 29.7 | 38.52 | 44.78 | 56.93 |
| Ier2 | 337.39 | 321.91 | 274.76 | 278.01 | 301.44 | 441.79 | 489.24 | 657.59 |
| Pja1 | 54.93 | 52.87 | 47.58 | 45.48 | 46.69 | 74.98 | 73.84 | 96.49 |
| Cbfa2t2 | 7.24 | 6.99 | 6.05 | 6.22 | 4.81 | 9.54 | 10.91 | 14.24 |
| Tprgl | 6.92 | 10.17 | 10.45 | 10.09 | 10.39 | 14.89 | 17.38 | 25.85 |
| Dennd5a | 4.9 | 4.18 | 5.21 | 5.53 | 6.54 | 7.72 | 9.63 | 13.52 |
| Trex1 | 94.86 | 98.46 | 124.64 | 102.62 | 89.81 | 133.36 | 144.42 | 226.54 |
| Ets1 | 259.85 | 236.17 | 266.72 | 222.31 | 221.39 | 300.93 | 314.46 | 423.7 |
| Spn | 16.87 | 14.64 | 19.29 | 12.94 | 11.16 | 23.96 | 32.13 | 45.12 |
| Ccnd3 | 180.8 | 120.92 | 222.29 | 144.51 | 139.32 | 241.4 | 202.62 | 323.33 |
| Nabp1 | 61.93 | 34.26 | 79.1 | 41.29 | 48.25 | 110.39 | 85.7 | 139.39 |
| Arhgap26 | 20.45 | 13.3 | 20.17 | 14.37 | 16.65 | 25.84 | 21.63 | 33.31 |
| Abcb1a | 35.57 | 35.1 | 38.16 | 25.51 | 27.38 | 49.72 | 43.3 | 67.43 |
| Il12rb2 | 102.56 | 82.18 | 106.1 | 73.7 | 69.37 | 167.78 | 112.32 | 244.02 |
| Tmprss13 | 0.63 | 0.81 | 2.61 | 0.27 | 0.45 | 4.7 | 2.53 | 10.42 |
| Coq10b | 29.62 | 26.38 | 29 | 18.41 | 24.39 | 42.51 | 32.49 | 73.55 |
| Arntl | 6.58 | 4.23 | 7.53 | 7.28 | 3.69 | 12.41 | 11.25 | 26.05 |
| Hs3st3b1 | 7.23 | 4.36 | 6.6 | 6.88 | 5.9 | 9.68 | 8.85 | 15.48 |
| Bcl2l1 | 49.28 | 30.69 | 45.86 | 39.87 | 36.55 | 56.98 | 51.73 | 81.03 |
| Vopp1 | 51.22 | 29.63 | 60.45 | 37.63 | 33.23 | 86.34 | 77.21 | 140.28 |
| Slamf7 | 26.35 | 7.53 | 27.4 | 20.02 | 26.88 | 38.89 | 36.15 | 63.46 |
| Cd97 | 79.25 | 59.93 | 86.86 | 72.61 | 76.73 | 103.57 | 113.35 | 160.16 |
| Ptger4 | 17.69 | 11.11 | 21.09 | 17.53 | 17.58 | 28.12 | 31.85 | 58.75 |
| Cish | 103.5 | 44.19 | 69.43 | 53.42 | 88.07 | 128.63 | 137.48 | 255.79 |
| Pttg1 | 61.13 | 48.28 | 60.18 | 50.79 | 69.34 | 78.34 | 84.76 | 124.68 |
| 2610020H08Rik | 10.97 | 6.45 | 7.87 | 7.66 | 7.51 | 16.14 | 11.03 | 25.72 |
| Plcxd2 | 13.95 | 9.83 | 14.55 | 12.64 | 15.75 | 27.33 | 15.98 | 38.05 |
| Mest | 0.15 | 0 | 0 | 0 | 0.43 | 2.3 | 0.27 | 5.31 |
| Junb | 1454.29 | 1269.15 | 1269.42 | 1329.89 | 1522.49 | 1876.6 | 1465.45 | 2530.6 |
| Ccl9 | 1.64 | 1.08 | 0.14 | 0.15 | 0.52 | 6.38 | 4.26 | 10.82 |
| Fasl | 119.58 | 115.87 | 76.71 | 76.72 | 100.73 | 213.68 | 184.07 | 359.65 |
| Atp10d | 6.36 | 7.55 | 6.92 | 4.95 | 7.04 | 14.94 | 12.25 | 21.27 |
| Vamp3 | 39.52 | 36.95 | 38.67 | 37.4 | 36.29 | 54.02 | 49.61 | 69.74 |
| Arhgap31 | 1.13 | 0.73 | 1.61 | 1.62 | 1.41 | 3.17 | 2.93 | 5.42 |
| Stard10 | 0.15 | 0.63 | 0.67 | 1.03 | 1.06 | 4.19 | 2.84 | 7.61 |
| Id2 | 264.12 | 277.73 | 285.46 | 265.93 | 316.88 | 376.81 | 365.45 | 518.68 |
| Bhlhe40 | 128.29 | 87.18 | 120.95 | 116.44 | 171.67 | 221.18 | 194.72 | 345.78 |

TABLE 5-continued

| | CD62L-Slamf7+CX3CR1- | | | | | CD62L-Slamf7+CX3CR1+ | | |
|---|---|---|---|---|---|---|---|---|
| Cars | 13.79 | 8.74 | 14.28 | 17.64 | 14.45 | 21.9 | 23.12 | 22.86 |
| Adar | 16.31 | 11.67 | 20.27 | 20.69 | 15.51 | 25.87 | 25.45 | 27.25 |
| H3f3b | 522.07 | 472.38 | 590.06 | 549.58 | 518.79 | 673.14 | 691.98 | 698.17 |
| Klrb1c | 21.83 | 9.08 | 19.82 | 29.77 | 14.85 | 53.21 | 29.79 | 41.14 |
| Bsdc1 | 14.51 | 6.59 | 13.09 | 9.38 | 9.39 | 23.39 | 15.27 | 22.29 |
| Abhd2 | 42.73 | 31.23 | 41.4 | 38.68 | 39.94 | 58.14 | 45.47 | 60.17 |
| Pgm1 | 14.49 | 9.35 | 15.77 | 13.08 | 12.47 | 24.63 | 17.41 | 25.15 |
| Hgs | 15.45 | 16.07 | 20.11 | 12.46 | 15.94 | 28.38 | 21.34 | 25.93 |
| Pmaip1 | 29.48 | 35.57 | 57.72 | 29.2 | 29.79 | 73.25 | 55.61 | 66.49 |
| Fcgr2b | 6.66 | 11.29 | 12.04 | 9.31 | 2.39 | 32.2 | 17.07 | 31.4 |
| Klf2 | 16.44 | 14.21 | 28.65 | 18.58 | 12.45 | 41.75 | 25.29 | 50.66 |
| Notch2 | 9.2 | 10 | 13.89 | 8.55 | 8.14 | 19.18 | 12.71 | 20.97 |
| Prdm1 | 2.99 | 3.66 | 5.03 | 4.65 | 5.14 | 9.6 | 8.24 | 12.07 |
| Prkx | 22.98 | 23 | 30.59 | 28.3 | 31.95 | 41.25 | 39.27 | 44.37 |
| Fech | 4.67 | 3.38 | 3.52 | 3.64 | 5.74 | 11.27 | 8.69 | 10.73 |
| Lamc1 | 0.49 | 0 | 0.67 | 0.35 | 0.71 | 4.53 | 2.99 | 3.59 |
| Tuba1a | 146.73 | 128.66 | 164.26 | 143.45 | 175.61 | 375.76 | 292.4 | 311.07 |
| Neat1 | 35.73 | 48.08 | 44.11 | 44.75 | 42.54 | 78.93 | 62.2 | 74.01 |
| Zeb2 | 2.04 | 4.6 | 3.18 | 2.57 | 2.59 | 13.99 | 9.28 | 16.52 |
| Rnf216 | 2.23 | 5.06 | 5.21 | 3.87 | 4.14 | 12.02 | 9.78 | 14.38 |
| Tug1 | 54.73 | 37.61 | 39.58 | 45.86 | 49.34 | 60.33 | 66.01 | 63.35 |
| Ppp1r15b | 19.81 | 14.33 | 12.02 | 14.78 | 17.86 | 25.79 | 26.02 | 22.39 |
| Cnnm4 | 8.9 | 6.17 | 8.92 | 9.89 | 6.48 | 15.24 | 16.3 | 15.49 |
| Rap1b | 68.93 | 46.18 | 40.62 | 62.87 | 54.64 | 114.49 | 129.88 | 130.51 |
| Ube2g2 | 65.6 | 51.31 | 59.51 | 64.9 | 60.52 | 90.31 | 92.27 | 93.33 |
| Med13I | 3.57 | 2.11 | 1.51 | 2.38 | 1.81 | 4.72 | 5.09 | 5.33 |
| Fam89b | 35.95 | 35.45 | 26.87 | 37.3 | 30 | 56.81 | 47.69 | 51.84 |
| Nfe2l1 | 12.33 | 9.49 | 8.74 | 13.05 | 9.86 | 17.92 | 17.36 | 16.34 |
| Acss2 | 12.11 | 3.86 | 11.72 | 11.29 | 8.68 | 25.1 | 26.55 | 19.32 |
| Ercc5 | 6.06 | 4.09 | 6.73 | 5.7 | 5.68 | 11.19 | 12.4 | 8.45 |
| Yy2 | 1.62 | 1.71 | 2.28 | 1.59 | 1.83 | 4.79 | 6.27 | 3.46 |
| Emp3 | 105.7 | 106.59 | 123.4 | 118.92 | 102.39 | 198.08 | 223.12 | 199.58 |
| Slc4a2 | 5.95 | 7.16 | 8.85 | 7.82 | 6.97 | 13.81 | 14.6 | 11.78 |
| D1Ertd622e | 9.48 | 3.85 | 11.43 | 10.53 | 7.73 | 17.63 | 23.66 | 19.42 |
| Trp53inp2 | 4.34 | 1.96 | 5.64 | 4.02 | 3.4 | 8.11 | 13.89 | 10.43 |
| Lrp6 | 1.19 | 0.64 | 1.35 | 1.33 | 0.93 | 2.06 | 3.13 | 2.12 |
| Dtx1 | 5.64 | 1.93 | 9.15 | 2.98 | 1.41 | 14.08 | 18.56 | 15.69 |
| Adrph | 60.69 | 48.9 | 60.49 | 48.95 | 48.91 | 72.65 | 79.81 | 70.51 |
| Vezf1 | 13.64 | 14.22 | 11.84 | 14.84 | 13.18 | 17.67 | 21.79 | 19.25 |
| Rbms1 | 33.96 | 35.65 | 26.64 | 34.38 | 36.34 | 49.35 | 58.19 | 52.1 |
| Itgb1 | 76.28 | 61.98 | 66.3 | 57.44 | 67.68 | 103.6 | 143.7 | 116.96 |
| Gfra2 | 0.08 | 0.12 | 0.06 | 0.12 | 0.28 | 0.98 | 1.99 | 1.51 |
| Ednrb | 0 | 0.05 | 0 | 0.05 | 0 | 0.61 | 1.69 | 1.47 |
| Actg1 | 3118.49 | 3191.06 | 3023.68 | 2559.35 | 2775.85 | 3578.51 | 3974.47 | 3875.1 |
| Sgk1 | 65.97 | 84.16 | 59.7 | 67.94 | 61.7 | 140.03 | 145.82 | 135.88 |
| Mkl1 | 17.82 | 18.73 | 15.11 | 15.16 | 16.22 | 25.27 | 25.56 | 26.61 |
| Sptan1 | 8.68 | 9.04 | 7.25 | 7.41 | 7.54 | 11.54 | 11.27 | 11.23 |
| Flna | 39.68 | 48.85 | 30.55 | 29.2 | 31.32 | 78.5 | 76.45 | 72.99 |
| Kctd10 | 42.13 | 28.42 | 37.58 | 40.53 | 45.85 | 48.56 | 66.87 | 56.89 |
| Plk3 | 7.52 | 3.9 | 5.93 | 7.79 | 6.33 | 9.79 | 15.03 | 13.99 |
| 2010012O05Rik | 4.27 | 0.79 | 2.93 | 5.32 | 4.66 | 9.7 | 12.63 | 11.69 |
| Tmem109 | 31.46 | 12.5 | 25.97 | 24.61 | 27.21 | 43.77 | 43.47 | 45.66 |
| Bcl2l13 | 8.48 | 3.94 | 6.57 | 5.65 | 7.51 | 11.07 | 11.83 | 11.18 |
| Hivep2 | 5.66 | 2.68 | 6.25 | 3.92 | 6.19 | 7.78 | 10.16 | 10.5 |
| Abcb1b | 18.08 | 5.57 | 17.51 | 11.87 | 13.74 | 24.71 | 36.63 | 32.42 |
| Usp9x | 8.27 | 5.71 | 7.76 | 6.67 | 8.09 | 9.99 | 11.6 | 10.41 |
| Itgb2 | 194.59 | 196.23 | 189.12 | 168.84 | 218.06 | 257.29 | 312.21 | 333.76 |
| Rora | 26.4 | 19.59 | 20.29 | 12.08 | 35.43 | 42.66 | 62.01 | 75.5 |
| Bcl2a1d | 76.9 | 47.05 | 66.8 | 58.66 | 102.89 | 152.42 | 156.55 | 203.09 |
| Rhof | 29.86 | 25.75 | 27.56 | 25.26 | 31.07 | 43.84 | 47.44 | 50.42 |
| Dusp2 | 279 | 187.05 | 193.94 | 238.22 | 244.64 | 310.56 | 362.52 | 439.46 |
| Lpin1 | 18.97 | 9.05 | 14.07 | 13.58 | 16.24 | 26.64 | 28.11 | 34.88 |
| Slc20a1 | 61.88 | 55.97 | 50.16 | 51.84 | 62.41 | 69.53 | 79.75 | 93.3 |
| Nr4a1 | 274.2 | 177.74 | 186.53 | 159.96 | 219.41 | 272.75 | 325.87 | 413.71 |
| Nr1d2 | 6.84 | 4.36 | 4.68 | 5.83 | 10.06 | 8.97 | 14.89 | 16.37 |
| 4930503L19Rik | 4.45 | 4.77 | 3.76 | 6.6 | 6.48 | 8.63 | 12.67 | 13.67 |
| Myo18a | 3.28 | 3.33 | 4.11 | 4.07 | 3.76 | 4.7 | 6.53 | 6.89 |
| Osbpl3 | 3.81 | 3.26 | 6.4 | 3.12 | 4.72 | 6.74 | 8 | 9.25 |
| Serpinb9 | 114.98 | 58.05 | 160.35 | 109.18 | 82.65 | 188.11 | 179.31 | 227.24 |
| Dpysl2 | 27.7 | 23.29 | 37.24 | 27.43 | 25.45 | 37.84 | 41.2 | 46.29 |
| Prf1 | 39.91 | 56.13 | 88.98 | 45.94 | 39.81 | 84.94 | 171.64 | 138.81 |
| Pik3r1 | 15.29 | 14.58 | 18.82 | 16.85 | 14.63 | 22.51 | 23.58 | 28.69 |
| Rap1gap2 | 1.1 | 0.32 | 1.57 | 0.74 | 0.48 | 5.89 | 9.67 | 11.48 |
| Madd | 25.15 | 21.08 | 27.62 | 26.85 | 24.66 | 33.65 | 39.29 | 42.62 |
| Kpna1 | 30.2 | 21.96 | 34.29 | 30.28 | 28.21 | 54.33 | 56.44 | 69.06 |
| Alox5 | 0 | 0 | 0 | 0 | 0 | 1.09 | 1.45 | 1.68 |
| Gzma | 196.87 | 182.54 | 304.5 | 297.87 | 214.28 | 1501.05 | 1661.43 | 1762.14 |
| Ccl5 | 2715.86 | 2152.51 | 2904.52 | 2943.94 | 3207.63 | 8603.34 | 9549.31 | 10317.16 |

TABLE 5-continued

| | CD62L-Slamf7+CX3CR1- | | | | | CD62L-Slamf7+CX3CR1+ | | |
|---|---|---|---|---|---|---|---|---|
| Meis2 | 0 | 0.12 | 0 | 0.12 | 0.15 | 0.62 | 0.76 | 1.12 |
| Klrg1 | 8.86 | 7.34 | 15.96 | 6.85 | 6.25 | 85.88 | 95.1 | 144.12 |
| Cx3cr1 | 2.1 | 5.51 | 5.43 | 3.49 | 0.95 | 68.51 | 74.63 | 109.8 |
| Atp2c1 | 7.97 | 7.7 | 11.06 | 7.04 | 5.13 | 15.25 | 16.18 | 17.71 |
| Dbf4 | 6.68 | 4.39 | 6.14 | 3.95 | 2.89 | 10.01 | 10.87 | 13.22 |
| Ddx28 | 10.9 | 8.66 | 9.81 | 6.48 | 5.9 | 15.67 | 19.52 | 23.84 |
| Rassf1 | 48.58 | 44.86 | 43.07 | 44.04 | 41.86 | 58.93 | 62.45 | 68.2 |
| Rasgrp2 | 10.49 | 6.61 | 8.52 | 5.69 | 6.1 | 24.01 | 28.71 | 30.74 |
| Dab2 | 0.22 | 1.94 | 0.9 | 1.15 | 0.85 | 3.19 | 9.43 | 2.15 |
| Plod1 | 2.57 | 0.58 | 2.26 | 2.27 | 1.39 | 7.37 | 28.08 | 3.05 |
| Mxi1 | 1.03 | 0.82 | 0.59 | 1.05 | 1.31 | 2.64 | 10.41 | 1.68 |
| Havcr2 | 2.11 | 0.07 | 0.82 | 0.39 | 0.46 | 2.38 | 11.51 | 5.11 |
| P4ha1 | 14.77 | 4.84 | 11.45 | 13.39 | 16.56 | 24.02 | 46.28 | 19.22 |
| Psrc1 | 2.24 | 0.54 | 3.03 | 1.11 | 3.12 | 14.89 | 23.17 | 0.57 |
| Calu | 34.6 | 15.46 | 36.45 | 37.15 | 34.77 | 77.37 | 112.93 | 31.44 |
| Hfe | 0.97 | 0.22 | 1.3 | 0.51 | 0.42 | 3.57 | 8.71 | 1.74 |
| Il13ra1 | 0.65 | 0 | 1.08 | 0.81 | 0.34 | 8.88 | 17.68 | 3.07 |
| Pira2 | 0 | 0 | 0 | 0 | 0.28 | 2.66 | 7.66 | 0.18 |
| Lgals7 | 0 | 0.63 | 2.94 | 0.29 | 0.91 | 16.01 | 30.13 | 1 |
| Lpar1 | 0 | 0 | 0.14 | 0.15 | 0 | 2.71 | 5.24 | 0.06 |
| Lama5 | 0.05 | 0.2 | 0.07 | 0.29 | 0 | 2.1 | 4.2 | 0.05 |
| Pcsk9 | 0.26 | 4.61 | 2.82 | 2.85 | 1.65 | 32.05 | 65.81 | 1.02 |
| Ccdc109b | 1.83 | 8.29 | 4.24 | 2.27 | 5.08 | 19.85 | 33.69 | 3.16 |
| Lgals3 | 45.74 | 87.48 | 51.41 | 37.4 | 50.47 | 157.71 | 255.57 | 92.24 |
| Ifitm2 | 30.89 | 89.3 | 19.09 | 16.25 | 21.43 | 138.73 | 242.45 | 69.25 |
| Cyth2 | 13.51 | 14.04 | 9.1 | 12.94 | 11.25 | 19.56 | 27.09 | 16.25 |
| Gabarapl1 | 21.23 | 27.41 | 17.91 | 20.91 | 17.24 | 40.29 | 47.12 | 30.19 |
| Cfp | 4.87 | 11.62 | 1.47 | 14.3 | 5.82 | 36.46 | 39.97 | 20.43 |
| Cers2 | 67.4 | 58.08 | 71.79 | 78.06 | 69.42 | 111.05 | 101.23 | 94.56 |
| Plscr1 | 9.79 | 8 | 9.77 | 14.45 | 10.98 | 20.66 | 20.94 | 18.61 |
| Sipa1l3 | 1.06 | 0.37 | 0.74 | 1.57 | 1.03 | 2.77 | 2.9 | 2.26 |
| Sun1 | 10.77 | 8.56 | 7.1 | 12.37 | 13.19 | 21.82 | 18.99 | 16.8 |
| Frmd6 | 1.55 | 0 | 0.89 | 0.87 | 2.52 | 7.05 | 6.26 | 5.36 |
| Nisch | 25.32 | 25.56 | 26.17 | 28.72 | 32.68 | 41.41 | 40.74 | 36.56 |
| Gnb1 | 56.82 | 59.53 | 65.07 | 58.55 | 57.36 | 97.15 | 78.98 | 78.48 |
| As3mt | 9.85 | 4.09 | 8.66 | 7.23 | 4.03 | 31.55 | 23.5 | 21.74 |
| Sat1 | 149.8 | 131.24 | 177.63 | 160.91 | 168.26 | 229.4 | 202.4 | 208.01 |
| Pogk | 5.34 | 0.31 | 6.61 | 2.73 | 3.88 | 14.56 | 12.19 | 13.12 |
| Mcu | 4.52 | 2.49 | 5.45 | 2.26 | 3.91 | 11.34 | 10.3 | 8.63 |
| Tax1bp3 | 12.57 | 13.42 | 17.12 | 13.39 | 11.88 | 30.07 | 27.03 | 27.42 |
| Ywhaq | 161.03 | 151.51 | 162.89 | 153.25 | 164.45 | 244.45 | 235.46 | 245.53 |
| Cltc | 18.93 | 23.88 | 21.87 | 25.23 | 17.08 | 34.49 | 32.14 | 28.07 |
| Tuba1c | 48.84 | 70.3 | 62.55 | 51.22 | 50.29 | 106.92 | 95.45 | 69.93 |
| Lgals1 | 460.42 | 659.18 | 506.19 | 466.76 | 422.88 | 1356.25 | 1235.85 | 762.3 |
| Flnb | 2.94 | 3.07 | 2.78 | 1.61 | 1.36 | 7.86 | 6.5 | 4.51 |
| Fam63a | 6.29 | 7.05 | 7.61 | 6.83 | 3.84 | 22.1 | 18.25 | 9.74 |
| Sqstm1 | 320.46 | 306.79 | 304.7 | 355.31 | 316.48 | 496.26 | 408 | 381.5 |
| Pttg1ip | 36.56 | 34.62 | 35.66 | 51.77 | 42.6 | 83.63 | 68.28 | 56.82 |
| Plec | 11.26 | 8.94 | 8.88 | 10.26 | 9.12 | 25.1 | 17.01 | 15.68 |
| Alcam | 0.3 | 0.68 | 0.23 | 1.13 | 0.66 | 6.04 | 3.8 | 2.04 |
| Rin2 | 0 | 0 | 0 | 0.26 | 0.27 | 5.6 | 3.57 | 2.17 |
| Tpm4 | 173.31 | 163.21 | 165.6 | 172 | 183.26 | 287.74 | 214.04 | 227.26 |
| Ngfr | 0.17 | 0.17 | 0.05 | 0 | 0.05 | 5.05 | 1.09 | 2.46 |
| Ano6 | 9.25 | 11.99 | 9.94 | 14.89 | 11.14 | 23.05 | 15.6 | 19.36 |
| Prpsap2 | 6.63 | 5.71 | 6.01 | 9.92 | 6.78 | 19.26 | 11.77 | 13.67 |
| Cdkn1a | 17.48 | 26.52 | 18.22 | 14.9 | 19.61 | 78.36 | 60.86 | 49.41 |
| Dock5 | 1.06 | 1.99 | 1.51 | 0.88 | 1.23 | 4.87 | 4.25 | 4.03 |
| Sfxn3 | 30.51 | 29.1 | 23.73 | 21.86 | 29.24 | 52.18 | 46.16 | 44.61 |
| Errfi1 | 47.74 | 49.55 | 38.81 | 24.75 | 40.4 | 149.7 | 94.25 | 111.22 |
| S100a10 | 401.39 | 433.16 | 311.86 | 330.08 | 443.65 | 603.09 | 603.83 | 527.07 |
| S100a4 | 107.04 | 180.41 | 68.45 | 75.71 | 118.19 | 278.85 | 227.22 | 160.92 |
| Antxr2 | 11.57 | 17.27 | 14.43 | 16.68 | 24.21 | 34.16 | 26.27 | 25.95 |
| Mdm2 | 27.75 | 28.73 | 34.37 | 28.8 | 40.44 | 56.04 | 51.57 | 41.17 |
| Hnrpll | 0.48 | 0 | 0.82 | 0.73 | 1.45 | 6.5 | 4.77 | 3.17 |
| Actr1b | 28.4 | 28.02 | 26.97 | 31.13 | 33.97 | 46.01 | 44.77 | 35.99 |
| Dusp3 | 0.75 | 0.27 | 0.72 | 1.54 | 2.05 | 6.95 | 6.96 | 3.33 |
| Adamts14 | 0.43 | 1.78 | 2.31 | 0.85 | 0.39 | 12.3 | 4.67 | 1.26 |
| Cspg4 | 0 | 0.09 | 0.08 | 0.15 | 0 | 5.86 | 1.15 | 0.05 |
| Syngr1 | 0.07 | 0 | 0 | 0.07 | 0.22 | 4.92 | 1.09 | 0.24 |
| Rbpms2 | 0.47 | 1.44 | 0 | 1.62 | 0.83 | 18.14 | 5.64 | 1.32 |
| Tnfrsf12a | 4.69 | 11.72 | 8.8 | 11.61 | 8.58 | 76.69 | 33.77 | 9.62 |
| Ptk2 | 0.42 | 0.09 | 0.33 | 1.07 | 0.12 | 7.82 | 2.86 | 1.03 |
| Epdr1 | 0.23 | 0 | 0 | 0.15 | 0 | 6.18 | 2.45 | 0.08 |
| Rhoc | 8.78 | 8.92 | 13.6 | 21.63 | 12.51 | 68.24 | 33.04 | 12.77 |
| Vcl | 1.1 | 0.58 | 2.56 | 2.72 | 2.01 | 10.56 | 5.55 | 2.58 |
| Nav1 | 0.11 | 0.63 | 0.21 | 0.56 | 0.88 | 3.53 | 1.7 | 0.8 |
| Creb5 | 0 | 0.07 | 0.17 | 0 | 0.06 | 2.93 | 1.04 | 0.7 |
| Ttyh2 | 0.11 | 0.11 | 0.18 | 0.51 | 0.58 | 4.22 | 1.42 | 1.03 |

TABLE 5-continued

| | CD62L-Slamf7+CX3CR1- | | | | | CD62L-Slamf7+CX3CR1+ | | |
|---|---|---|---|---|---|---|---|---|
| Osmr | 0 | 0 | 0.07 | 0.18 | 0.19 | 2.04 | 0.68 | 0.49 |
| Trim16 | 1 | 0.24 | 0.45 | 0.45 | 0.6 | 3.74 | 3.67 | 1.17 |
| Cdk16 | 6.22 | 3.9 | 5.3 | 5.37 | 5.35 | 10.7 | 10.93 | 6.97 |
| Aplp2 | 16.33 | 13.03 | 11.12 | 10.76 | 11.42 | 24.37 | 22.76 | 17.13 |
| Rxra | 1.8 | 1.32 | 1.39 | 1 | 1.1 | 4.12 | 3.98 | 2.6 |
| Itga6 | 1.15 | 1.34 | 1.52 | 0.75 | 2.5 | 8.9 | 8.07 | 0.71 |
| Parva | 0.08 | 0.04 | 0 | 0.08 | 0.28 | 5.02 | 6.49 | 0 |
| Fstl1 | 0.87 | 0.16 | 0.18 | 1.31 | 0.15 | 9.92 | 11.06 | 0.05 |
| Afap1 | 0.37 | 0 | 0.12 | 0.96 | 0.33 | 6.08 | 5.52 | 0.45 |
| Crabp2 | 1.03 | 2.93 | 1.6 | 0.59 | 0.6 | 43.92 | 40.28 | 0 |
| Ift43 | 0.7 | 0 | 0.6 | 0.44 | 0.68 | 8.18 | 7.57 | 0.75 |
| Gcnt4 | 0.07 | 0 | 0 | 0.03 | 0.11 | 2.79 | 2.41 | 0.06 |
| Pls3 | 1.01 | 4.75 | 2.5 | 2.24 | 2.66 | 32.94 | 16.93 | 1.39 |
| Tubb6 | 6.38 | 13.93 | 7.5 | 7.76 | 6.43 | 75.43 | 41.02 | 3.98 |
| Igfbo6 | 0.29 | 0.73 | 1.61 | 3 | 1.26 | 32.8 | 17.87 | 0.46 |
| Irs1 | 0 | 0.02 | 0 | 0.06 | 0 | 1.04 | 0.55 | 0.04 |
| Btc | 0.35 | 0.07 | 0 | 0.49 | 0.5 | 6.31 | 3.6 | 0.28 |
| Lmna | 22.79 | 27.09 | 22.46 | 23.63 | 33.54 | 143.01 | 91.82 | 22.94 |
| Ak1 | 0.09 | 0.09 | 0 | 0.26 | 1.67 | 16.39 | 8.42 | 0.58 |
| Eda2r | 0.34 | 0 | 0.66 | 2.21 | 1.76 | 15.99 | 11.53 | 1.28 |
| Col7a1 | 0 | 0 | 0 | 0.02 | 0.02 | 1.87 | 1.39 | 0 |
| Cdh2 | 0 | 0 | 0 | 0.11 | 0.08 | 4.88 | 3.2 | 0.13 |
| Deptor | 0 | 0 | 0 | 0 | 0 | 3.18 | 2.21 | 0.23 |
| Epn2 | 0.35 | 0.84 | 0.23 | 1.61 | 0 | 7.1 | 5.52 | 0.89 |
| Ltbp4 | 0.32 | 1.01 | 0 | 0.91 | 0.28 | 7.51 | 4.79 | 0.91 |
| Rtkn | 1.44 | 0.26 | 0 | 0.4 | 0 | 10.85 | 6.77 | 0.63 |
| Ank | 5.57 | 14.81 | 4.47 | 7.59 | 7.76 | 66.44 | 50.98 | 9.64 |
| Mtap | 22.48 | 28.93 | 24.83 | 25.07 | 29.28 | 114.18 | 87 | 21.7 |
| Krt18 | 0.93 | 7.4 | 4.1 | 2.76 | 3.49 | 53.46 | 35.34 | 1.84 |
| Itga5 | 0.89 | 5.69 | 1.02 | 1.85 | 0.7 | 16.96 | 11.33 | 1.95 |
| Asns | 5.87 | 17.01 | 4.56 | 15.14 | 4.6 | 51.95 | 45.26 | 8.13 |
| Prdx4 | 17.31 | 21.05 | 14.24 | 15.32 | 12.06 | 56.99 | 55.21 | 19.52 |
| Fhl2 | 10.68 | 12.53 | 10.52 | 8.54 | 11.81 | 38.76 | 38.63 | 15.86 |
| Slc4a8 | 0.33 | 0.48 | 0.51 | 0.25 | 0.34 | 1.54 | 1.43 | 0.61 |
| Sh2d5 | 0.18 | 0.66 | 0.61 | 1.4 | 1.38 | 8.87 | 8.2 | 2.21 |
| Myadm | 2.78 | 9.46 | 8.35 | 8.71 | 5.69 | 49.79 | 38.5 | 9.95 |
| Apbb2 | 0 | 0.59 | 0.09 | 0.15 | 0.26 | 4.22 | 3.04 | 0.96 |
| Over expressed in CD62L-Slamf7+Cx3cr1- relative to CD62L-Slamf7+Cx3cr1+ | | | | | | | | |
| Il6ra | 3.99 | 8.62 | 6.78 | 2.63 | 3.25 | 1.16 | 2.49 | 1.25 |
| Ppp1r3b | 3.5 | 9.44 | 8.4 | 2.64 | 4.33 | 1.38 | 2.2 | 1.83 |
| Rassf4 | 1.46 | 8.61 | 7.57 | 5.01 | 3.31 | 1.2 | 1.42 | 1.53 |
| Sirpa | 2.38 | 19.57 | 13.12 | 10.49 | 5.16 | 2.5 | 2.85 | 2.8 |
| Irs2 | 2.59 | 6.81 | 6.52 | 4.16 | 3.61 | 2.02 | 1.9 | 0.69 |
| Btk | 1.17 | 4.46 | 5.92 | 3.12 | 1.14 | 0.13 | 0.48 | 0.16 |
| Rps4y2 | 3.94 | 14.01 | 18.15 | 9.9 | 4.81 | 1.72 | 1.01 | 3.16 |
| 3110002H16Rik | 32.55 | 30.94 | 35.27 | 33.38 | 33.48 | 25.84 | 19.06 | 20.62 |
| A630001G21Rik | 12.26 | 16.44 | 15.25 | 11.53 | 12.52 | 6.78 | 3.66 | 5.84 |
| Ly6a | 614.02 | 732 | 760.8 | 611.72 | 648.78 | 376.84 | 318.75 | 425.16 |
| Ogfod3 | 8.95 | 9.09 | 11.78 | 9.47 | 8.44 | 3.39 | 1.32 | 3.67 |
| Gpatch4 | 8.52 | 8.89 | 9.98 | 7.32 | 6.87 | 4.37 | 2.09 | 4.13 |
| Gpr15 | 4.31 | 6.86 | 6.56 | 5.45 | 10.38 | 0.25 | 0 | 1.08 |
| Traf1 | 82.8 | 108.48 | 90.96 | 72.25 | 118.04 | 46.06 | 43.79 | 52.87 |
| Bfar | 16.45 | 25.57 | 19.33 | 21.57 | 26.94 | 9.51 | 7.68 | 15.81 |
| Ncf4 | 37.37 | 44.69 | 43.47 | 48.22 | 52.76 | 29.75 | 26.06 | 32.04 |
| Hspa8 | 2311.39 | 2260.12 | 2443.53 | 2086.42 | 2380.81 | 1625.73 | 1848.08 | 1594.09 |
| Sema4d | 72.42 | 73.83 | 84.1 | 69.32 | 87.17 | 45.41 | 52.25 | 46.02 |
| Adal | 4 | 4.15 | 5.86 | 3.41 | 4.68 | 1.75 | 0.82 | 1.29 |
| Galns | 10.85 | 12.65 | 14.98 | 11.11 | 14.5 | 5.47 | 5.62 | 7.24 |
| Fbxo7 | 24.98 | 23.87 | 29.87 | 18.73 | 23.69 | 11.25 | 15.32 | 15.98 |
| Mcm2 | 46 | 52.86 | 59.56 | 43.21 | 46.05 | 31.28 | 35.15 | 27.23 |
| Kif15 | 3.24 | 3.56 | 4.84 | 2.05 | 3.5 | 1.12 | 1.77 | 0.77 |
| Efr3a | 44.96 | 57.47 | 62.04 | 49.21 | 56.29 | 30.59 | 39.22 | 42.55 |
| Relb | 50.5 | 65.74 | 86.67 | 50.82 | 65.04 | 38.73 | 38.34 | 41.91 |
| Npc1 | 4.93 | 8.5 | 11.23 | 7.17 | 6.84 | 3.84 | 3.02 | 2.86 |
| Fastkd3 | 4.63 | 9.01 | 9.66 | 6.77 | 8.04 | 3.5 | 3.12 | 3.53 |
| Rdh12 | 3.1 | 5.74 | 4.48 | 1.26 | 4.97 | 0.68 | 0.73 | 0 |
| Gpr65 | 51.31 | 64.99 | 47.58 | 39.37 | 52.07 | 28.29 | 35.93 | 19.76 |
| Trim59 | 20.9 | 29.41 | 25.58 | 17.81 | 21.19 | 7.15 | 11.95 | 6.59 |
| Tubb5 | 428.01 | 566.49 | 503.41 | 437.21 | 495.59 | 334.88 | 346.99 | 270.28 |
| Fcrl1 | 1.99 | 4.13 | 2.53 | 2.42 | 2.03 | 0 | 0 | 0 |
| Rgs10 | 57.65 | 83.3 | 51.99 | 54.62 | 52.1 | 5.92 | 9.34 | 3.17 |
| Zfp827 | 1.37 | 2.87 | 1.84 | 1.45 | 1.48 | 0.68 | 0.89 | 0.43 |
| Tmem108 | 2.01 | 3.98 | 2.81 | 2.43 | 0.93 | 0.48 | 0.07 | 0.05 |
| Kars | 65.23 | 95.56 | 74.63 | 77.75 | 62.46 | 50.06 | 49.35 | 50.81 |
| Fgfr1op | 7.94 | 15.59 | 11.4 | 11.19 | 8.67 | 4.79 | 5.19 | 3.9 |
| Ddb2 | 23.9 | 34.89 | 35.02 | 27.02 | 25.97 | 11.7 | 18.85 | 12.23 |
| Tmem120b | 2.19 | 3.54 | 3.35 | 3.21 | 2.63 | 0.44 | 1.1 | 0.75 |

TABLE 5-continued

| | CD62L-Slamf7+CX3CR1- | | | | | CD62L-Slamf7+CX3CR1+ | | |
|---|---|---|---|---|---|---|---|---|
| Ptpn6 | 128.77 | 178.72 | 182.65 | 160.35 | 137.38 | 73.87 | 74.79 | 77.08 |
| Ppcdc | 13.82 | 24.58 | 24.41 | 20.89 | 19.99 | 9.3 | 10.84 | 11.68 |
| Tspan14 | 43.56 | 62.52 | 55.34 | 50.1 | 51.95 | 31.8 | 36.88 | 38.84 |
| Gstt2 | 8.12 | 17.46 | 12.7 | 11.29 | 14 | 4.37 | 2.88 | 2.75 |
| Aoah | 2.1 | 5.81 | 4.82 | 2.35 | 4.22 | 0 | 0.19 | 0 |
| Fam26f | 33.94 | 41.08 | 26.85 | 33.94 | 28.42 | 12.13 | 13.6 | 23.45 |
| Il17r | 102.2 | 122.87 | 82.24 | 117.66 | 105.57 | 36.23 | 44.86 | 70.05 |
| Dis3l2 | 17.11 | 23.01 | 11.88 | 18.73 | 16 | 10.25 | 9.37 | 10.53 |
| Pik3ip1 | 34.73 | 52.31 | 23.06 | 40.74 | 35 | 13.87 | 18.41 | 25.99 |
| Nudt14 | 23.39 | 42.27 | 28.38 | 20.61 | 27.83 | 14.09 | 5.5 | 15.18 |
| Zfp512 | 15.86 | 24.51 | 16.61 | 12.47 | 14.76 | 6.04 | 5.37 | 6.25 |
| Map3k5 | 1.69 | 7.09 | 3.58 | 3.49 | 3.79 | 0.78 | 0.83 | 1.65 |
| Isyna1 | 41.57 | 64.45 | 41.41 | 46.46 | 53.35 | 22.74 | 29.95 | 33.01 |
| Cmtm7 | 75.74 | 111.73 | 83.85 | 83 | 92.32 | 50.48 | 63.17 | 58.64 |
| Egr2 | 12.7 | 22.42 | 4.9 | 7.53 | 6.96 | 2.84 | 4.41 | 2.88 |
| Klra23 | 28.94 | 59.29 | 8.43 | 9.5 | 19.64 | 3.39 | 0.83 | 0.39 |
| Fbxl8 | 23.61 | 40.92 | 18.56 | 16.66 | 19.22 | 8.61 | 6.88 | 9.7 |
| Bbs9 | 7.12 | 15.61 | 6.36 | 6.75 | 6.31 | 2.73 | 4.16 | 2.13 |
| Gyg | 66.44 | 96.14 | 57.74 | 66.93 | 82.12 | 31.66 | 56.77 | 32.16 |
| Kif22 | 6.56 | 17.61 | 5.99 | 9.7 | 9.55 | 2.43 | 4.56 | 0.67 |
| Mki67 | 5.14 | 9.1 | 4.4 | 5.62 | 6.75 | 2.48 | 3.72 | 2.24 |
| Ap1m2 | 2.35 | 9.12 | 2.3 | 4.46 | 2.82 | 0.19 | 0 | 0 |
| Slc43a2 | 2.33 | 5.63 | 1.55 | 2.9 | 2.38 | 0.85 | 1.1 | 1.12 |
| Gpr34 | 4.59 | 12.2 | 2.61 | 8.15 | 9.44 | 1.11 | 0 | 0.1 |
| Ganc | 4.02 | 8.51 | 2.26 | 5.17 | 5.33 | 2.26 | 1.96 | 1.49 |
| Neurl3 | 51.68 | 71.3 | 51.56 | 47.28 | 62.93 | 24.99 | 28.87 | 43.6 |
| Spata6 | 29.52 | 42.73 | 27.82 | 25.66 | 33.66 | 15.68 | 18.45 | 17.57 |
| Ltb | 294.88 | 401.09 | 227.69 | 251.46 | 367.93 | 72.78 | 99.57 | 124.94 |
| Arhgap9 | 117.66 | 151.1 | 95.27 | 95.57 | 130.26 | 62.88 | 71.56 | 79.51 |
| Faah | 16.82 | 22.51 | 14.69 | 14.74 | 18.35 | 6.83 | 9.61 | 10.76 |
| Samd3 | 67.2 | 74.24 | 34.12 | 44.34 | 60.88 | 27.68 | 28.43 | 31.15 |
| BC021614 | 62.65 | 82.87 | 32.63 | 39.83 | 63.79 | 5.04 | 26.65 | 15.86 |
| 2810417H13Rik | 26.34 | 28.33 | 15.26 | 17.97 | 32.69 | 11 | 10.77 | 14.64 |
| Ptprcap | 315.03 | 332.58 | 258.1 | 272.1 | 331.67 | 161.41 | 195.24 | 247.01 |
| Limd2 | 221.36 | 240.74 | 162.21 | 175.29 | 234.75 | 106.09 | 124.54 | 145.64 |
| Eif4e3 | 19.93 | 22.41 | 10.8 | 14.96 | 20.23 | 5.29 | 7.32 | 10.42 |
| Tmsb10 | 1244.01 | 1073.58 | 897.18 | 1053.2 | 1176.32 | 665.95 | 718.14 | 827.9 |
| Cd3d | 477.04 | 442.62 | 345.28 | 432.49 | 475.86 | 230.37 | 250.61 | 300.18 |
| Uba52 | 2859.32 | 2499.78 | 2332.78 | 2645.11 | 2615.14 | 1586.43 | 1695.79 | 1939.72 |
| Rps29 | 1571.78 | 1436.23 | 1298.77 | 1446.84 | 1451.05 | 928.66 | 887.19 | 1168.73 |
| Thada | 11.93 | 12.11 | 6.67 | 9.53 | 10.31 | 5.71 | 3.23 | 5.57 |
| Ccr7 | 276.74 | 317.64 | 146.86 | 198.1 | 179.43 | 25.42 | 21.39 | 64.93 |
| Mgst2 | 27.39 | 34.85 | 26.83 | 31.62 | 32.25 | 15.4 | 11.34 | 8.75 |
| Cdca5 | 6.81 | 8.5 | 6.53 | 7.93 | 7.4 | 3.82 | 2.72 | 3.33 |
| Nek8 | 6.49 | 8 | 6.5 | 7.91 | 7.62 | 3.51 | 4.41 | 2.83 |
| Cables1 | 7.83 | 9.53 | 4.25 | 7.63 | 8.61 | 0.73 | 1.47 | 0 |
| St8sia1 | 1.14 | 1.58 | 0.81 | 1.26 | 1.3 | 0.21 | 0.23 | 0.24 |
| Rpl18a | 2576.84 | 2397.63 | 2308.12 | 2285.8 | 2359.89 | 1283.54 | 1473.3 | 1471.56 |
| Eef1a1 | 7350.71 | 7378.29 | 6786.69 | 6688.31 | 7195.22 | 4270.83 | 5008.33 | 4352.54 |
| Rpl4 | 2354.57 | 2193.77 | 2119.14 | 2064.5 | 2176.91 | 1237.43 | 1426.75 | 1195.69 |
| Rplp0 | 2957.5 | 2787.72 | 2612.32 | 2774.28 | 2790.53 | 1586.28 | 1888.07 | 1355.36 |
| Rps26 | 1564.2 | 1438.69 | 1399.1 | 1486.56 | 1535.54 | 903.05 | 996.72 | 694.44 |
| Rps6 | 1904.83 | 1910.47 | 1709.69 | 1951.47 | 1931.67 | 1041.89 | 1305.26 | 948.46 |
| Nsmce1 | 58.28 | 57.95 | 54.5 | 57.04 | 57.36 | 30.73 | 38.86 | 29.76 |
| Rpl3 | 2531.17 | 2569.44 | 2378.96 | 2508.25 | 2647.06 | 1353.75 | 1653.1 | 1314.74 |
| Cd160 | 48.36 | 42.96 | 41.43 | 54.14 | 53.37 | 15.61 | 16 | 17.36 |
| Rpl29 | 1287.65 | 1270.84 | 1192.96 | 1262.23 | 1307.07 | 720.69 | 831.56 | 770.29 |
| Rpl6 | 1546.16 | 1454.53 | 1348.75 | 1532.84 | 1578.04 | 859.83 | 1038.78 | 921.9 |
| Rpl9 | 2675.57 | 2425.95 | 2169.2 | 2741.73 | 2468.37 | 1546.38 | 1709.42 | 1613.49 |
| Rpl19 | 3588.98 | 3224.91 | 3030.83 | 3517.22 | 3373.55 | 2328.08 | 2612.49 | 2401.62 |
| Rps5 | 2679.72 | 2589.81 | 2291.33 | 2572.16 | 2554.8 | 1485.03 | 1599.64 | 1642.4 |
| Rpl21 | 994.21 | 891.16 | 821.76 | 951.97 | 893.95 | 556.93 | 599.32 | 623.66 |
| Rps4x | 4853.22 | 4392.76 | 4152.45 | 4492.87 | 4479.02 | 2737.59 | 2959.42 | 2630.75 |
| Rpl15 | 716.04 | 651.22 | 605.07 | 687.02 | 694.85 | 400.37 | 424.53 | 383.75 |
| Rpl13 | 2869.89 | 2586.27 | 2304.29 | 2727.63 | 2673.76 | 1402.65 | 1645.87 | 1345.31 |
| Rps3a1 | 2801.21 | 2567.66 | 2501.2 | 2740.51 | 2618.5 | 1700.88 | 1924.93 | 1718.21 |
| Rpl18 | 1222.05 | 1165.76 | 1025.04 | 1188.11 | 1159.12 | 659.87 | 758.04 | 693.21 |
| Rps3 | 1414.49 | 1350.96 | 1183.41 | 1417.56 | 1327.93 | 791.05 | 926.91 | 816.06 |
| Pla2g16 | 24.64 | 23.82 | 20.16 | 25.05 | 26.14 | 12.09 | 16.01 | 15.03 |
| Rps11 | 2706.98 | 2444.1 | 2061.15 | 2574.81 | 2648 | 1367.21 | 1787.57 | 1553.81 |
| Rpl37 | 661.6 | 604.85 | 516.25 | 620.41 | 648.92 | 365.01 | 432.35 | 378.5 |
| Cyb5 | 102.51 | 103.09 | 77.54 | 97.36 | 95.89 | 54.93 | 55.49 | 57.44 |
| Rpl24 | 1380.66 | 1352.18 | 1010.57 | 1306.57 | 1269.85 | 688.98 | 797.21 | 690.58 |
| Rps9 | 1865.21 | 1722.09 | 1412.68 | 1821.2 | 1685.33 | 963.4 | 1098.12 | 951.57 |
| Fermt3 | 140.66 | 148.44 | 141.35 | 125.52 | 120.42 | 79.89 | 89.95 | 109.24 |
| Gpr183 | 103.51 | 112.47 | 100.25 | 77.59 | 98.85 | 38.1 | 53.83 | 79.46 |
| Psmb9 | 219.98 | 253.33 | 240.81 | 217.36 | 235.23 | 131.04 | 144.06 | 194.33 |
| Tnfrsf26 | 105.89 | 83.05 | 93.56 | 85.1 | 72.74 | 42.15 | 31.82 | 65.88 |

TABLE 5-continued

| | CD62L-Slamf7+CX3CR1- | | | | | CD62L-Slamf7+CX3CR1+ | | |
|---|---|---|---|---|---|---|---|---|
| Tpt1 | 4792.1 | 4503.16 | 4697.91 | 4503.34 | 4121.53 | 3397.98 | 3190.75 | 3655.53 |
| Psen2 | 19.32 | 19.43 | 17.02 | 15.84 | 14.59 | 10.06 | 6.28 | 9.53 |
| Sh3bp5 | 60.45 | 62.52 | 44.15 | 47.11 | 39.65 | 22.4 | 12.45 | 38.56 |
| Klra13-ps | 38.36 | 46.13 | 15.62 | 18.13 | 8.52 | 2.4 | 2.78 | 0 |
| Gng2 | 33.22 | 38.47 | 26.42 | 22.84 | 25.82 | 11.87 | 17.64 | 18.51 |
| Clcn3 | 11.03 | 11.06 | 8.89 | 7.89 | 8.16 | 5.4 | 5.46 | 5.16 |
| Relt | 27.72 | 25.87 | 19.21 | 18.84 | 20.74 | 11.21 | 14.71 | 13.44 |
| Dusp10 | 34.78 | 43.89 | 29.37 | 30.65 | 23.41 | 14.57 | 15.23 | 17.55 |
| Satb1 | 46.46 | 56.04 | 41.34 | 32.87 | 31.23 | 17.1 | 14.13 | 20.21 |
| Gemin5 | 7.02 | 8.7 | 7.12 | 6.48 | 5.59 | 3.55 | 3.25 | 4.6 |
| Cd2ap | 4.23 | 6.07 | 3.34 | 2.1 | 2.45 | 0.85 | 0.78 | 2.03 |
| Rcsd1 | 61.05 | 91.17 | 65.54 | 47.28 | 49.64 | 33.66 | 34.39 | 40.37 |
| Afg3l2 | 30.02 | 34.06 | 31.12 | 24.42 | 25.68 | 19.12 | 21.17 | 14.52 |
| Npc2 | 129.65 | 144.11 | 130.63 | 123.74 | 115.63 | 89.98 | 102.9 | 83.51 |
| Pgs1 | 23.81 | 31.55 | 27.92 | 22.18 | 20.39 | 12.23 | 16.96 | 10.7 |
| Oasl2 | 29.04 | 30.73 | 32.37 | 16.64 | 21.52 | 11.05 | 12.34 | 13.28 |
| Utp14a | 31.27 | 40.13 | 34.89 | 22.93 | 29.31 | 18.3 | 17.65 | 14.03 |
| Cxcr5 | 10.85 | 18.58 | 17.4 | 4.23 | 8.58 | 0 | 0 | 0 |
| Tnfrsf13c | 1.36 | 0.31 | 3.29 | 5.36 | 4.02 | 0.41 | 0.19 | 0.2 |
| Pak6 | 0.94 | 0.78 | 4.01 | 3.46 | 4.76 | 0 | 0.48 | 0.05 |
| Spint2 | 31.93 | 23.85 | 43.87 | 47.75 | 50.42 | 7.38 | 10.31 | 6.89 |
| Vipr1 | 3.71 | 4 | 3.06 | 6.09 | 5.94 | 1.92 | 1.81 | 1.25 |
| H2-Q7 | 312.14 | 281.93 | 316.73 | 353.38 | 443.6 | 174.22 | 240.15 | 263.99 |
| Apol7b | 33.23 | 34.37 | 33.35 | 37.96 | 50.43 | 15.86 | 19.24 | 25.86 |
| Apol7e | 33.04 | 34.24 | 33.35 | 35.89 | 48.02 | 15.86 | 19.24 | 25.86 |
| Cd69 | 914.69 | 807.84 | 868.25 | 832.45 | 803.52 | 415.37 | 364.5 | 768.11 |
| Amica1 | 162.6 | 118.91 | 114.77 | 116.54 | 119.79 | 48.25 | 61.86 | 110.18 |
| Emb | 369.59 | 308.86 | 321.35 | 277.7 | 294.83 | 164.53 | 163.99 | 249.31 |
| Tnfrsf18 | 242.38 | 117.64 | 241.72 | 190.9 | 224.39 | 79.3 | 64.92 | 139.79 |
| Rapgef6 | 35.34 | 29.32 | 35.5 | 28.96 | 32.35 | 18.23 | 19.15 | 24.96 |
| Cnp | 167.66 | 128.84 | 169.54 | 148.45 | 145.16 | 82.83 | 102.63 | 111.34 |
| Tigit | 128.47 | 113.9 | 107.52 | 115.54 | 132.63 | 48.17 | 75.34 | 69.04 |
| Fos | 594.94 | 598.56 | 522.07 | 598.45 | 658.72 | 245.26 | 408.24 | 398.15 |
| 1810026B05Rik | 13.68 | 11.32 | 12.7 | 12.22 | 13.9 | 7.49 | 9.23 | 9.4 |
| Cd7 | 183.61 | 174.39 | 202.43 | 189.58 | 196.39 | 38.32 | 83.86 | 93.41 |
| Ly6e | 712.12 | 691.37 | 737.45 | 678.46 | 804.25 | 265.73 | 359.9 | 297.5 |
| Psme2 | 460.67 | 418.8 | 419.64 | 475.58 | 455.4 | 298.73 | 303.05 | 365.17 |
| Ikbkb | 50.54 | 40.03 | 45.61 | 47.09 | 47.44 | 26.16 | 28.43 | 36.72 |
| Hes6 | 21.39 | 22.29 | 23.31 | 20.93 | 26.7 | 7.89 | 11.13 | 16.93 |
| Grcc10 | 272.47 | 259.41 | 268.56 | 259.71 | 289.41 | 179.7 | 154.31 | 209.81 |
| Cst7 | 226.47 | 200.56 | 215.3 | 160.57 | 253.75 | 124.37 | 125.08 | 155.44 |
| Fam78a | 28.07 | 19.02 | 24.39 | 19.94 | 39.2 | 8.48 | 9.72 | 16.46 |
| Crtam | 51.13 | 28.14 | 28.91 | 42.31 | 57.59 | 11.72 | 12.74 | 19.57 |
| QrfP | 2.85 | 1.45 | 2.23 | 2.33 | 3.1 | 0.85 | 0.38 | 0.83 |
| Atad5 | 1.84 | 1.74 | 1.25 | 1.88 | 2.19 | 0.74 | 0.22 | 0.9 |
| Ctsw | 472.23 | 453.8 | 404.6 | 415.48 | 566.82 | 297.02 | 243.8 | 388.94 |
| Dapl1 | 27.79 | 18.37 | 13.63 | 16.53 | 29.31 | 2.28 | 4.51 | 3.45 |
| Als2cl | 12.58 | 10.02 | 6.9 | 6.26 | 13.24 | 2.99 | 5.17 | 3.17 |
| 4930486L24Rik | 15.8 | 10.7 | 7.56 | 8.83 | 12.12 | 3.89 | 5.34 | 2.89 |
| Cd27 | 152.24 | 116.44 | 91.61 | 83.99 | 126.65 | 24.77 | 45.75 | 57.63 |
| Cxcr3 | 152.26 | 161.86 | 134.7 | 117.91 | 164.03 | 35.36 | 61.28 | 70.77 |
| Jak3 | 97.55 | 88.5 | 90.13 | 69.64 | 105.09 | 38.01 | 48.15 | 49.14 |
| Pim2 | 103.05 | 100.49 | 89.86 | 66.29 | 116.56 | 33.09 | 40.73 | 42.55 |
| Dennd2d | 57.55 | 57.36 | 59.39 | 43.63 | 57.19 | 36.16 | 34.62 | 40.99 |
| Fam102a | 57.26 | 51.27 | 47.99 | 34.55 | 48.31 | 21.59 | 18.59 | 31.92 |
| Dgka | 217.52 | 212.16 | 177.03 | 167.72 | 180.17 | 96.85 | 98.24 | 141.46 |
| Tapbpl | 108.8 | 114.47 | 93.87 | 98.27 | 102.91 | 55.93 | 49.47 | 68.69 |
| Ctla2a | 480.5 | 495.65 | 394.16 | 413.93 | 472.46 | 138.55 | 162.99 | 271.55 |
| Ap1ar | 8.46 | 8.04 | 7.61 | 7.06 | 7.34 | 2.78 | 3.82 | 4.81 |
| Ms4a4c | 155 | 155.58 | 134.71 | 108.09 | 133.16 | 40.16 | 36.54 | 56.27 |
| Tcf7 | 160.89 | 160.64 | 117.67 | 119.46 | 142.68 | 38.09 | 44.06 | 55.54 |
| Rassf2 | 23.06 | 25.07 | 21.28 | 17.82 | 22.04 | 11.1 | 14.84 | 15.16 |
| Smc4 | 66.65 | 68.33 | 64.28 | 52.09 | 62.62 | 24.77 | 36.26 | 34 |
| Rpl7a | 1097.12 | 1143.09 | 976.11 | 1030.08 | 1018.47 | 648.09 | 730.26 | 711.43 |
| Hdac4 | 12.76 | 13.05 | 9 | 10.35 | 11.9 | 3.7 | 6.95 | 4.88 |
| Myb | 5.61 | 2.33 | 5.8 | 5.42 | 4.33 | 0.28 | 0.63 | 0.17 |
| Naa20 | 101.14 | 75.02 | 95.75 | 87.11 | 83.55 | 62.55 | 66.61 | 54.84 |
| Nsg2 | 20.51 | 5.54 | 14.94 | 14.49 | 11.78 | 0.94 | 2.19 | 1.15 |
| Gbp11 | 13.73 | 6.65 | 9.06 | 6.86 | 7.01 | 0.06 | 0.31 | 0.55 |
| Ssbp2 | 8.79 | 4.24 | 5.28 | 6.53 | 6.09 | 1.54 | 2.61 | 2.43 |
| Psme1 | 635.18 | 517.22 | 533.4 | 551.08 | 554.48 | 341.95 | 401.31 | 409.11 |
| Pabpc4 | 7.27 | 5.63 | 5.76 | 5.3 | 6.1 | 3.12 | 3.19 | 1.23 |
| Bend4 | 12.89 | 11.33 | 10.56 | 9.26 | 9.85 | 4.73 | 5.77 | 3.3 |
| Treml2 | 10.37 | 7.73 | 8.42 | 6.08 | 6.66 | 2.01 | 1.16 | 0.18 |
| Slc11a2 | 27.67 | 23.56 | 20.25 | 22.77 | 21.79 | 12.08 | 9.76 | 10.77 |
| Rpl23 | 1686.38 | 1549.82 | 1385.62 | 1514.75 | 1443.68 | 936.78 | 1027.74 | 911.64 |
| Myc | 124.15 | 87.54 | 70.6 | 95.01 | 91.26 | 12.16 | 19.03 | 15.7 |
| Snhg12 | 91.2 | 79.25 | 83.23 | 94.24 | 82.1 | 54.53 | 51.95 | 55.29 |

TABLE 5-continued

| | CD62L-Slamf7+CX3CR1- | | | | | CD62L-Slamf7+CX3CR1+ | | |
|---|---|---|---|---|---|---|---|---|
| Rpl12 | 2512.77 | 2102.35 | 2071.94 | 2564.74 | 2229.34 | 1392.89 | 1389.29 | 1359.9 |
| Rps20 | 1879.78 | 1427.86 | 1341.13 | 1767.02 | 1507.41 | 703.13 | 739.23 | 765.41 |
| Rpl5 | 1905.51 | 1703.82 | 1834.15 | 1919.39 | 1678.39 | 1176.66 | 1209.57 | 1191.1 |
| Sell | 314.69 | 269.59 | 312.39 | 327.96 | 237.34 | 54.67 | 49.5 | 30.08 |
| Rpsa | 2052.46 | 1940.96 | 2006.19 | 2017.16 | 1911.3 | 1152.96 | 1226.05 | 1238.08 |
| Tnfsf8 | 14.48 | 12.09 | 14.11 | 13.72 | 10.07 | 0 | 0 | 1.25 |
| Rpl7 | 2188.06 | 1958.84 | 1975.16 | 1912.79 | 1902.07 | 1285.77 | 1508.24 | 1281.95 |
| Noa1 | 17.07 | 12.68 | 14 | 12.82 | 11.78 | 3.87 | 6.63 | 4.91 |
| Rpl8 | 2157.2 | 1838.06 | 1876.37 | 1924.32 | 1949.24 | 1325.57 | 1436.09 | 1265.85 |
| Klra7 | 248.98 | 146.92 | 224.46 | 199.62 | 219.61 | 12.92 | 30.84 | 6.44 |
| Cd101 | 10.75 | 8.64 | 6.38 | 7.53 | 8.3 | 2.61 | 5.66 | 3.01 |
| Rpl11 | 1765.21 | 1611.72 | 1393.2 | 1661.91 | 1684.04 | 982 | 1314.89 | 1048.66 |
| Rps2 | 1854.52 | 1600.73 | 1346.03 | 1613.06 | 1737.46 | 965.35 | 1353.04 | 817.25 |
| Eef1b2 | 579.67 | 508.72 | 481.43 | 569.6 | 508.76 | 346.26 | 419.03 | 293.2 |
| Rpl36a | 1090.25 | 860.39 | 795.77 | 974.49 | 1045.45 | 493.19 | 574.31 | 461 |
| Rpl23a | 2987.55 | 2600.92 | 2424.94 | 2912.25 | 2877.11 | 1621.49 | 1802.26 | 1609.82 |
| Rps7 | 1333.19 | 1140.77 | 1032.92 | 1248.51 | 1237.2 | 647.06 | 708.16 | 650.51 |
| Rpl14 | 940.73 | 839.94 | 730.47 | 900.39 | 876.94 | 599.76 | 678.26 | 565.11 |
| Naca | 681.06 | 598.05 | 537.94 | 693.77 | 658.93 | 412.52 | 459.03 | 360.59 |
| Pglyrp1 | 58.01 | 49.78 | 49.47 | 54.19 | 74.12 | 23.55 | 35.82 | 16.3 |
| Acoxl | 5.12 | 5.33 | 4.07 | 5.4 | 7.78 | 1.7 | 2.19 | 0.97 |
| Rps8 | 2095.53 | 2019.5 | 1746.01 | 2137.9 | 2129.15 | 1379.48 | 1679.55 | 1172.19 |
| Eif3h | 440.79 | 447.52 | 383.83 | 420.41 | 461.87 | 304.98 | 361.79 | 282.55 |
| Rpl10a | 1402.84 | 1359.38 | 1047.39 | 1274.72 | 1345.93 | 714.74 | 869.66 | 587.05 |
| Eef1g | 740.68 | 768.68 | 731.67 | 761.16 | 783.39 | 538.22 | 547.61 | 334.46 |
| Btla | 14.34 | 15.61 | 10.86 | 12.28 | 14.66 | 7.77 | 7.75 | 3.43 |
| Slc25a5 | 644.66 | 700.22 | 601.06 | 629.33 | 688.96 | 473.23 | 498.67 | 377.51 |
| Rps12 | 2079.01 | 1686.25 | 1369 | 2220.76 | 1723.89 | 1251.79 | 1152.85 | 1202.62 |
| Rplp1 | 3122.14 | 2537.65 | 2163.24 | 2858.09 | 2765.85 | 1814.95 | 1706.16 | 2028.65 |
| Gm19705 | 22.4 | 10.46 | 4.63 | 18.68 | 15.29 | 3.13 | 0.99 | 2.87 |
| Rps16 | 2649.05 | 2230.3 | 1855.01 | 2588.66 | 2349.37 | 1412.64 | 1486.94 | 1718.78 |
| Rps13 | 2827.55 | 2336.34 | 1973.5 | 2785.26 | 2615.12 | 1659.66 | 1816.83 | 1944.8 |
| Rpl17 | 1693.64 | 1368.75 | 1226.63 | 1655.33 | 1506.87 | 1020.93 | 1067.61 | 1107.75 |
| Rps24 | 1934.09 | 1616.33 | 1408.44 | 2084.61 | 1834.21 | 1076.22 | 1143.31 | 1217.77 |
| Rps14 | 2854.99 | 2289.32 | 2104.9 | 2888.94 | 2732.97 | 1781.84 | 1844.69 | 1996.69 |
| Rps15a-ps4 | 180.02 | 150.26 | 95.88 | 183.19 | 152.47 | 69.89 | 82.36 | 81.69 |
| Gm14085 | 3.02 | 2.07 | 0.21 | 3.01 | 2.74 | 0 | 0.16 | 0.04 |
| Rps28 | 1667.33 | 1453.44 | 1133.25 | 1656.98 | 1618.98 | 884.63 | 864.62 | 923.46 |
| Rps15 | 1966.93 | 1653.13 | 1443.86 | 1858.89 | 1788.66 | 1137.83 | 1271.44 | 1186.95 |
| Rpl27a | 1047.07 | 885.26 | 730.46 | 1009.8 | 956.49 | 560.55 | 615.59 | 584.85 |
| Rps15a | 242.26 | 197.42 | 157.47 | 245.51 | 225.58 | 106.49 | 126.7 | 112.19 |
| Rps19 | 2024.78 | 1565.88 | 1255.96 | 2027.35 | 1883.64 | 863.51 | 1088.27 | 971.45 |
| Rps15a-ps6 | 277.91 | 218.87 | 172.48 | 274.69 | 282.77 | 143.97 | 149.76 | 139.83 |
| Rpl38 | 817.8 | 679.67 | 589.05 | 814.07 | 844.23 | 517.62 | 515.21 | 485.19 |
| Rpl39 | 2574.87 | 2037.15 | 1664.93 | 2522.97 | 2285.72 | 1428.75 | 1446.23 | 1372.77 |
| Gm15772 | 1881.63 | 1488.93 | 1328.46 | 1818.11 | 1767.47 | 1164.5 | 1211.44 | 1044.89 |
| Rpl32 | 2008.99 | 1615.08 | 1387.27 | 2242.09 | 1919.97 | 1066.67 | 1189.97 | 991.72 |
| Rps23 | 2427.14 | 1912.49 | 1737.47 | 2467.5 | 2369.91 | 1448.85 | 1642.72 | 1529.86 |
| Rps18 | 2203.29 | 1626.69 | 1723.4 | 2247.83 | 2000.76 | 1413.96 | 1377.31 | 1252.03 |
| Eif3m | 257.58 | 239.51 | 236.24 | 275.95 | 253.82 | 200.62 | 202.39 | 186.49 |
| Rplp2 | 1907.76 | 1620.69 | 1573.01 | 1800.05 | 1495.4 | 1130.38 | 1111.23 | 1202.79 |
| Gbp9 | 117.92 | 79.23 | 85.43 | 96.3 | 82.26 | 47.85 | 41.26 | 56.97 |
| Cd163l1 | 26.58 | 17.18 | 10.95 | 16.43 | 17.28 | 4.88 | 0.2 | 2.87 |
| Tlr1 | 10.95 | 5.62 | 4.8 | 7.61 | 5.21 | 2.83 | 1.31 | 1.48 |
| Folr4 | 13.88 | 3.74 | 4.39 | 11.81 | 6.77 | 0.74 | 2.5 | 0.91 |
| Rpl37a | 1136.13 | 930.71 | 764.2 | 1019.68 | 1042.08 | 644.37 | 707.36 | 706.08 |
| St6gal1 | 16.99 | 9.75 | 7.46 | 12.51 | 13.7 | 1.65 | 3.3 | 5.08 |
| Sft2d2 | 22.89 | 13.26 | 16.12 | 19.43 | 20.33 | 8.09 | 11.59 | 8.29 |
| Rpl22l1 | 516.32 | 372.98 | 347.39 | 510.84 | 494.22 | 181.83 | 266.46 | 232.51 |
| Rps17 | 1565.73 | 1288.51 | 1330.42 | 1551.6 | 1519.23 | 1029.34 | 1130.3 | 1011.47 |
| Klra3 | 25.86 | 7.87 | 17.1 | 33.85 | 33.5 | 3.93 | 11.67 | 2.3 |
| 2700060E02Rik | 110.55 | 94.04 | 105.75 | 115.21 | 115.14 | 81.52 | 82.94 | 71.63 |
| Vars | 70.6 | 49.76 | 69.53 | 72.3 | 80.04 | 33.94 | 47.52 | 22.06 |
| Klra5 | 11.11 | 1.47 | 13.17 | 16.3 | 12.88 | 0.42 | 0 | 0.34 |
| Klra1 | 49.98 | 1.97 | 44.29 | 53.67 | 49.19 | 2.63 | 1.01 | 0.71 |
| Fam46c | 41.32 | 14.85 | 37.49 | 42.52 | 35.39 | 19.4 | 8.4 | 13.09 |
| Fchsd2 | 6.67 | 3.73 | 6.73 | 7.25 | 6.17 | 2.84 | 2.29 | 3.75 |
| H2-Oa | 31.12 | 16.88 | 27.24 | 36.85 | 27.42 | 4.01 | 6.76 | 7.56 |
| Id3 | 52.93 | 21.15 | 38.35 | 55.5 | 32.84 | 7.48 | 13.73 | 3.33 |
| Rpl31 | 436.83 | 331.11 | 446.57 | 532.83 | 382.3 | 295.59 | 286.55 | 276.79 |
| Xcl1 | 194.27 | 39.8 | 131.33 | 317.22 | 163.97 | 6.78 | 5.7 | 15.8 |
| Atp9a | 0.74 | 0.16 | 4.93 | 0.85 | 1.38 | 0 | 0 | 0 |
| Lztfl1 | 5.2 | 4.07 | 21.6 | 7.24 | 8.73 | 3.22 | 2.11 | 3.29 |
| Acpp | 2.52 | 1.72 | 3.8 | 3.13 | 1.73 | 1.15 | 0.24 | 0.18 |
| Sp140 | 73.99 | 55.64 | 79.14 | 68.26 | 51.58 | 45.19 | 34.02 | 43.19 |
| Mdn1 | 3.18 | 1.65 | 3 | 3.24 | 1.92 | 1.5 | 0.99 | 1.5 |
| Wdr4 | 9.3 | 4.99 | 8.62 | 7.32 | 7.26 | 4 | 1.65 | 3.01 |
| Ppat | 14.25 | 8.6 | 14.77 | 12.98 | 12.59 | 7.23 | 5.47 | 8.06 |

TABLE 5-continued

| | CD62L-Slamf7+CX3CR1- | | | | | CD62L-Slamf7+CX3CR1+ | | |
|---|---|---|---|---|---|---|---|---|
| Ikzf2 | 9.08 | 9.07 | 10.89 | 8.61 | 7.21 | 0.84 | 1.49 | 0.86 |
| Apobec3 | 125.8 | 142.44 | 160.48 | 130.44 | 122.71 | 64.47 | 79.77 | 63.06 |
| Sdr39u1 | 32.05 | 27.17 | 33.56 | 24.49 | 27.72 | 12.67 | 17.39 | 13.73 |
| Atp5g2 | 411.92 | 387.43 | 415.36 | 375.07 | 401.82 | 284.42 | 293.2 | 242.7 |
| Rpl28 | 1164.4 | 1063.54 | 1156.55 | 1013.59 | 996.83 | 632.93 | 718.83 | 565.62 |
| Ptma | 767.51 | 650.55 | 853.01 | 742.1 | 722.97 | 546.9 | 610.51 | 476.41 |
| Gas7 | 6.79 | 7.44 | 11.87 | 9.28 | 7.33 | 3.3 | 2.72 | 0.32 |
| Stt3a | 76.49 | 73.88 | 92.31 | 87.83 | 79.89 | 54.54 | 63.97 | 50.43 |
| Mcm5 | 43.58 | 29.45 | 48.56 | 36.26 | 44.47 | 20.31 | 27.81 | 26.49 |
| Mcm3 | 52.89 | 41.31 | 60.23 | 46.46 | 52.59 | 30.37 | 36.79 | 27.82 |
| Ctla4 | 73.01 | 51.69 | 99.1 | 57.06 | 75.47 | 15.21 | 31.24 | 24.95 |
| Map7 | 4.74 | 1.31 | 4.91 | 1.73 | 2.62 | 0.42 | 0.67 | 0.31 |
| Fasn | 7.2 | 4.7 | 8 | 4.72 | 6.53 | 4.4 | 3.2 | 2.29 |
| Tlr7 | 3.07 | 3.22 | 9.46 | 17.73 | 4.25 | 0.99 | 1.09 | 0 |
| Fgr | 7.27 | 13.13 | 15.19 | 28.24 | 9.2 | 3.78 | 7.3 | 5.58 |
| Emid1 | 4.95 | 7.79 | 7.52 | 14.53 | 6.25 | 1.53 | 1.64 | 1.25 |
| Ccdc162 | 1.28 | 2.53 | 2.9 | 4.79 | 0.99 | 0 | 0.15 | 0 |
| Myzap | 0.73 | 1.48 | 2.66 | 4.39 | 0.48 | 0 | 0 | 0 |
| Ctsh | 24.8 | 52.57 | 125 | 115.09 | 30.99 | 32.64 | 15.45 | 18.45 |
| Cybasc3 | 48.4 | 80.95 | 157.08 | 161.81 | 47.19 | 37.61 | 32.91 | 29.74 |
| Clec12a | 2.34 | 4.49 | 14.29 | 13.05 | 2.36 | 1.46 | 1.17 | 0 |
| Pltp | 26.26 | 49.95 | 179.49 | 171.09 | 22.41 | 7.78 | 3.04 | 1.22 |
| Slamf9 | 7.61 | 13.16 | 44.48 | 31.77 | 4.58 | 6.79 | 1.19 | 1.39 |
| Irf8 | 62.16 | 83.54 | 252.15 | 210.01 | 55.55 | 31.97 | 37.7 | 12.48 |
| Pld4 | 47.44 | 60.56 | 200.85 | 171.28 | 36.86 | 20.56 | 13.02 | 2.51 |
| Slco4a1 | 4.33 | 11.84 | 32.73 | 19.58 | 4.4 | 1.73 | 3.09 | 3.6 |
| Cd4 | 4.49 | 4.94 | 22.49 | 12.72 | 5.32 | 0.64 | 0.84 | 0 |
| Arhgef10 | 3.08 | 3.52 | 6.11 | 4.99 | 1.62 | 1.63 | 0.89 | 1.04 |
| Gria3 | 0.5 | 1.27 | 2.09 | 1.39 | 0.31 | 0.06 | 0 | 0 |
| Rhobtb2 | 1.67 | 2.99 | 3.48 | 3.63 | 1.94 | 1.39 | 0.78 | 0.34 |
| Ncf1 | 19.76 | 50.28 | 52.27 | 54.37 | 26.26 | 10.89 | 13.92 | 9.4 |
| Fes | 2.95 | 10.09 | 11.79 | 11.2 | 6.29 | 2.99 | 1.43 | 1.79 |
| Cybb | 15.06 | 29.29 | 46.72 | 52.45 | 12.18 | 12.37 | 11.82 | 5.59 |
| Smim5 | 8.48 | 13.42 | 22.41 | 27.29 | 5.39 | 2.58 | 0 | 0 |
| Ccr9 | 26.68 | 44.2 | 72.28 | 86.72 | 19.06 | 5.67 | 1.76 | 2.65 |
| Rabgap1l | 33.12 | 42.59 | 54.6 | 59.87 | 34.99 | 25.21 | 20.99 | 26.44 |
| Slc37a2 | 1.78 | 4 | 5.14 | 6.06 | 2.48 | 1.41 | 0.37 | 1.04 |
| Unc93b1 | 42.97 | 83.36 | 116.29 | 108.95 | 47.1 | 37.74 | 26.52 | 40.78 |
| Tifa | 7.29 | 20.8 | 32.34 | 35.52 | 6.77 | 2.8 | 1.21 | 3.15 |
| Wfs1 | 2.92 | 2.06 | 6.99 | 8.24 | 2.26 | 1.14 | 1.23 | 1.06 |
| Nucb2 | 12.74 | 12.27 | 34.21 | 36 | 6.21 | 5.85 | 3.55 | 1.41 |
| Rnf122 | 4.24 | 4.25 | 13.6 | 14.86 | 3.21 | 2.33 | 1.11 | 0 |
| Rnase6 | 25.46 | 25.84 | 104.88 | 116.65 | 20.95 | 14.22 | 9.54 | 1.85 |
| Klra17 | 10.71 | 10.24 | 26.02 | 25.68 | 13.84 | 3.99 | 4.52 | 5.9 |
| Scimp | 14.59 | 7.5 | 30.11 | 31.65 | 12 | 5.83 | 7.36 | 0.94 |
| Srgap3 | 1.77 | 1.15 | 5.11 | 4.17 | 1.94 | 0.35 | 1.12 | 0.17 |
| Bst2 | 265.37 | 159.32 | 380.28 | 368.65 | 241.37 | 138.09 | 127.56 | 164.36 |
| Rilpl2 | 102.3 | 70.24 | 139.18 | 119.38 | 98.93 | 56.18 | 64.03 | 54.13 |
| Pacsin1 | 19.51 | 7.05 | 47.7 | 28.59 | 9.71 | 3.51 | 4.73 | 2.47 |
| Rpgrip1 | 6.49 | 4.06 | 10.8 | 8.26 | 2 | 0.66 | 0.48 | 1.28 |
| Vwa5A | 13.03 | 10.4 | 19.4 | 23.11 | 15.16 | 3.49 | 6.77 | 4.42 |
| Tmem170b | 5.9 | 6.3 | 8.48 | 8.77 | 7.27 | 3.52 | 4.07 | 4.99 |
| Pecam1 | 13.06 | 14.13 | 19.91 | 20.42 | 15.06 | 5.19 | 5.57 | 6.65 |
| Rpl31-ps12 | 58.29 | 60.58 | 69.44 | 82.62 | 5.67 | 39.32 | 40.28 | 30.49 |
| H2-Ob | 6.95 | 9.17 | 11.6 | 12.44 | 8.4 | 2.73 | 5.92 | 2.67 |
| Lag3 | 26.13 | 40.53 | 57.54 | 50.55 | 50.68 | 21.72 | 18.5 | 17.42 |
| Abhd15 | 2.28 | 3.48 | 5.55 | 6.11 | 3.91 | 1.6 | 0.5 | 1.16 |
| Plxdc1 | 2.5 | 2.73 | 5.18 | 4.13 | 2.94 | 0.9 | 0.85 | 0.96 |
| Tspan13 | 80.82 | 62.14 | 145.42 | 103.26 | 87.33 | 27.21 | 30.97 | 31.96 |
| Ctla2b | 153.46 | 129.68 | 199.53 | 168.24 | 148.64 | 39.71 | 42.63 | 83.83 |
| Pqlc3 | 45.31 | 47.47 | 67.78 | 53.28 | 49.07 | 23.53 | 23.61 | 29.1 |
| Cdca7I | 27.83 | 20.85 | 27.39 | 28.13 | 16.62 | 14.89 | 13.67 | 6.37 |
| Dkc1 | 49.81 | 43.59 | 44.99 | 41.11 | 29.73 | 28.49 | 27.62 | 14.78 |
| Noc4l | 41.26 | 44.52 | 36.24 | 39.73 | 29.1 | 24.93 | 25.06 | 24.37 |
| Il15ra | 23.76 | 34.41 | 25.05 | 31.24 | 16.97 | 8.94 | 12.95 | 8.63 |
| Hvcn1 | 31.38 | 42.95 | 43.28 | 43.93 | 28.46 | 13.06 | 15.4 | 16.63 |
| Fggy | 2.92 | 4.94 | 4.6 | 5.71 | 2.47 | 0.25 | 0.57 | 0 |
| Kctd12 | 4.1 | 5.82 | 6.51 | 5.72 | 2.06 | 2.03 | 1.22 | 0.65 |
| Eya2 | 15.07 | 17.84 | 20.11 | 19.57 | 11.1 | 7.57 | 4.27 | 7.9 |
| Dph5 | 20.87 | 28.49 | 22.59 | 29.08 | 24.05 | 14.42 | 16.74 | 13.19 |
| Dll4 | 0.91 | 1.53 | 0.88 | 1.93 | 0.94 | 0 | 0 | 0 |
| 2610019F03Rik | 11.67 | 12.69 | 11.36 | 13.98 | 11.38 | 0.92 | 1.88 | 3.3 |
| Grina | 130.47 | 146.73 | 138.4 | 140.43 | 138.59 | 82.86 | 83.31 | 102.82 |
| Tmem123 | 114.52 | 130.61 | 133.71 | 136.1 | 133.55 | 91.06 | 95.44 | 103.21 |
| Ramp1 | 3.49 | 7.09 | 6.51 | 7.65 | 5.61 | 0.38 | 2.25 | 2.26 |
| Plac8 | 625.42 | 890.76 | 824.69 | 988.88 | 705.45 | 262.07 | 240.45 | 211.37 |
| Klra19 | 3.28 | 6.06 | 4.55 | 5.95 | 5.12 | 0.44 | 0 | 0 |
| Lat2 | 20.56 | 30.62 | 32.49 | 35.46 | 26.13 | 10.12 | 10.99 | 2 |

TABLE 5-continued

| | CD62L-Slamf7+CX3CR1- | | | | | CD62L-Slamf7+CX3CR1+ | | |
|---|---|---|---|---|---|---|---|---|
| Adck3 | 2.42 | 4.48 | 5.24 | 4.67 | 4.48 | 0.69 | 1.06 | 0.15 |
| Use1 | 113.58 | 115.12 | 113.08 | 132.3 | 128.16 | 73.79 | 96.39 | 81.26 |
| Tmem194b | 12.12 | 12.42 | 12.84 | 13.88 | 12.68 | 5.92 | 10 | 7.12 |
| Eif3e | 315.93 | 293.3 | 317.98 | 344.37 | 325.54 | 208.79 | 240.25 | 183.28 |
| Rpl10 | 2404.97 | 2410.41 | 2312.94 | 2582.1 | 2345.01 | 1654.24 | 1737.36 | 1449.75 |
| Swap70 | 9.47 | 8.59 | 10.4 | 10.63 | 8.03 | 1.89 | 2.8 | 0.44 |
| Gm12185 | 8.92 | 8.2 | 6.16 | 7.79 | 6.45 | 2.72 | 2.52 | 3.65 |
| Gm12191 | 1816.79 | 1733.56 | 1424.58 | 1855.25 | 1598.14 | 1158.12 | 1174.96 | 1254.06 |
| 3110057O12Rik | 5.43 | 5.74 | 3.46 | 6.44 | 3.95 | 0.85 | 0.71 | 1.92 |
| Tex9 | 2.96 | 2.99 | 2.59 | 3.23 | 1.98 | 1.4 | 0.65 | 0.9 |
| Itm2a | 34.55 | 29.96 | 27.29 | 31.98 | 22.05 | 10.72 | 12.78 | 8.14 |
| Tmem9 | 21.72 | 18.96 | 15.96 | 21.78 | 15.12 | 11.43 | 9.15 | 7.33 |
| 2010300C02Rik | 1.06 | 0.82 | 0.81 | 1.73 | 0.95 | 0.07 | 0 | 0.27 |
| Taf1d | 44.96 | 44.08 | 42.21 | 53.81 | 41.66 | 30.53 | 23.92 | 30.13 |
| Pou6f1 | 7.18 | 6.38 | 7.99 | 8.53 | 5.93 | 3.65 | 2.32 | 5.07 |
| Al662270 | 52.56 | 64.74 | 68.33 | 71.89 | 56.53 | 37.97 | 34.75 | 46.19 |
| Xist | 54.01 | 58.4 | 59.33 | 66.62 | 54.35 | 36.9 | 31.35 | 42.68 |

Example 10—Experimental Model and Subject Details Mice 6-8 week old C57BL/6 and Rag$^{-/-}$ mice were purchased from the Jackson Laboratories. Embryonic stem cells with a targeted Tcf7 gene were obtained from Eucomm. Embryonic stem cells were injected into blastocysts to obtain chimeras. Presence of the targeted Tcf7 locus was confirmed by Southern Blot. Chimeras were bred to mice that transgenically express flpO recombinase (MINMRC, UC Davis) to remove the neomycin cassette and then bred with mice that express Cre recombinase under the CD8 Enhancer I (E81-Cre) that was previously described (Maekawa et al., 2008). All experiments were approved and conducted according to the guidelines set forth by the Harvard Medical Area Standing Committee on Animals.

Tumor Experiments

MC38-OVA cell line was derived from MC38 as previously described (Gilfillan et al., 2008). MC38-OVA (0.5× $10^6$) cells were implanted subcutaneously into the right flank. Tumor size was measured in two dimensions by caliper and is expressed as the product of two perpendicular diameters. In some experiments, mice were treated with 200 μg of anti-Tim-3 (RMT3-23) and 100 μg of anti-PD-1 (RMP1-14) antibodies or 200 μg of control immunoglobulin (Rat IgG2a) i.p. on days 4, 7 and 10 post tumor implant. Mice were either monitored for tumor growth or sacrificed on day 12 for functional and transcriptional analysis. The B16F10 cell line was purchased from ATCC. B16F10 (0.2× $10^6$) cells were implanted subcutaneously into the right flank. Tumor size was measured as described above. For Tim-3/PD-1 blockade, mice were treated with 200 μg of anti-Tim-3 (RMT3-23) and 200 μg of anti-PD-1 (RMP1-14) antibodies or control immunoglobulin (Rat IgG2a) i.p. on days 4, 7, and 10 post tumor implant. For CTLA-4/PD-1 blockade, mice were treated with 200 μg of anti-CTLA4 (9H10) and 200 μg of anti-PD-1 (RMP1-14) or 200 μg of each control immunoglobulin (Syrian hamster IgG and Rat IgG2a, respectively) i.p. on days 4, 7, and 10 post tumor implant. For CTLA-4 and PD-L1 blockade experiments, mice were injected with 100 ug (MC38-OVA model) or 200 ug (B16 model) of anti-CTLA-4 (9H10) and 200 ug of PD-L1 (29E.2A3) or 200 g of control immunoglobulin (Syrian hamster polyclonal IgG), i.p. on days 4, 7 and 10 post tumor implant. Mice were sacrificed on day 11 for analysis by flow cytometry. In some experiments, mice were treated with either PBS or 2 mg/kg of a TLR9 agonist (IMO-2125 provided by Sudhir Agrawal of Idera Pharmaceuticals under MTA) by intra-tumoral injection on days 4, 7, 10, and 13 post tumor implantation. % Tumor burden change is calculated as % change in tumor size compared to the peak tumor size (day 8-10). For response to treatment, a threshold of ≥30% decrease in reference to baseline is considered (Nishino et al., 2016). For adoptive cell transfer experiments, PD1+ or PD1− TILs were sorted from Tim-3/PD-1-treated C57Bl/6 mice bearing MC38-OVA tumors at 12 days upon tumor injection. A total of $10^5$ sorted cells were transferred intravenously into RAG KO donor mice that were injected subcutaneously with MC38-OVA tumors the same day.

Example 11—Method Details

Isolation of Tumor Infiltrating Lymphocytes (TILs). TILs were isolated by dissociating tumor tissue in the presence of collagenase D (2.5 mg/ml) for 20 min prior to centrifugation on a discontinuous Percoll gradient (GE Healthcare). Isolated cells were then used in various assays of T cell function (below).

Flow cytometry. Single cell suspensions were stained with antibodies against TCRβ (H57-597), CD8 (53-6.7), PD-1 (RMP1-30), Tim-3 (5D12), CX3CR1 (SAO11F11), CD319 (4G2), KLRG1 (MAFA) and CD62L (MEL-14). Fixable viability dye eF506 (ebioscience) or Zombie UV fixable viability dye (Biolegend) was used to exclude dead cells. All data were collected on a BD Fortessa (BD Biosciences) and analyzed with FlowJo software (Tree Star). To assess OVA-specific CD8+ cells, TILs were stained with H-2Kb/OVA$_{257-264}$ dextramers (Immudex) and then stained with surface antibodies. To determine Tcf7 protein levels, TILs were stained with surface antibodies then fixed and permeabilized with eBioscience Transcription Factor Staining Buffer Set. Cells were then stained with anti-Tcf7 antibody (C63D9) followed by fluorescently tagged anti-Rabbit IgG (Cell Signaling). For intra-cytoplasmic cytokine staining, cells were stimulated in vitro with 5 μg/ml OVA$_{257-264}$ peptide for 3.5 hrs in the presence of Golgi stop (BD Biosciences). Cells were then harvested and stained with antibodies against surface proteins prior to fixation and permeabilization. Permeabilized cells were then stained with antibodies against IL-2 (JES6-5H4), TNF-α (MP6-XT22) and IFN-γ (XMG1.2). For Granzyme B staining, TILs were stained with antibodies against surface proteins prior to fixation and permeabilization. Permeabilized cells were then stained with antibody against Granzyme B (2C5/F5). For CD107a staining, TILs were stimulated in vitro with 5 µg/ml OVA$_{257-264}$ peptide for 3.5 hrs in the presence of Golgi stop and an antibody against CD107a (1D4B). Cells were then harvested and stained with antibodies against surface proteins. To assess cell proliferation, TILs were stained with surface antibodies and fixed/permeabilized with eBioscience Transcription Factor Staining Buffer Set and stained with the antibody against Ki67 (SolA15).

Population RNA-seq. On day 12 post tumor implantation, Tim-3$^+$PD-1$^+$ and Tim-3-PD-1$^-$CD8$^+$ TILs were isolated by cell sorting (BD FACS Aria II) from MC38-OVA tumor-bearing mice that were treated with anti-PD-1 and anti-Tim-3 antibodies or isotype controls. Isolated cells were immediately lysed in RLT Plus lysis buffer (Qiagen). In another set of experiments, TILs were isolated from MC38-OVA bearing mice. CD62L$^{hi}$ CD319$^-$, CD62L$^-$ CD319+ CX3CR1$^-$ and CD62L$^-$CD319+CX3CR1-CD8$^+$ T cells from TILs were sorted by BD FACS Aria II and were immediately lysed in RLT buffer (Qiagen). In all cases, full-length RNA-seq libraries were prepared as previously described (Picelli et al., 2013) using the SMART-seq2 protocol with reduced PCR cycle number (12-15 cycles) and one-fourth of the standard Illumina Nextera XT reaction volume, followed by paired-end Illumina sequencing (38 bp×2) with a 75 cycle Nextseq 500 high output V2 kit.

Population RNA-Seq data pre-processing. RNA-seq reads were aligned using Tophat (Trapnell et al., 2009) (to mouse genome version mm9), and expression levels were calculated using RSEM (Li and Dewey, 2011) using known transcripts (mm9), followed by further processing using the Bioconductor package DESeq in R (Anders and Huber, 2010). The data was normalized using TMM normalization, and differentially expressed genes were defined using the differential expression pipeline on the raw counts with a single call to the function DESeq (FDR− adjusted P value <0.05). Heatmap figures were generated using pheatmap package (Kolde and Vilo, 2015).

To quantify the global genomic changes in Tim-3$^-$PD-1$^-$ and Tim-3$^+$PD-1$^+$ sub-populations CD8$^+$ TILs following treatment, Applicants calculated the Euclidean distance between each pair of profiles, Applicants then compared the difference in Euclidean distance between the isotype and anti-Tim-3/anti-PD-1 treated groups for the Tim-3$^-$PD-1$^-$ and Tim-3+PD-1$^+$ cells.

Plate-based CD8$^+$ TILs single-cell RNA-Seq. CD8$^+$ TILs data was obtained from (Singer et al., 2016), where it was collected in 96 well plates.

Plate-based single-cell RNA-seq data processing. Initial preprocessing was performed as described in (Singer et al., 2016). Briefly, paired reads were mapped to mouse annotation mm10 using Bowtie (Langmead et al., 2009) (allowing a maximum of one mismatch in seed alignment, and suppressing reads that had more than 10 valid alignments) and TPMs were computed using RSEM (Li and Dewey, 2011), and log$_2$ (TPM+1) values were used for subsequent analyses. Next, Applicants filtered out low quality cells and cell doublets, maintaining for subsequent analysis the 588 cells that had (1) 1,000-4,000 detected genes (defined by at least one mapped read), (2) at least 200,000 reads mapped to the transcriptome, and (3) at least 50% of the reads mapped to the transcriptome. Here, Applicants restricted the genes considered in subsequent analyses to be the 7,790 genes expressed at log$_2$(TPM+1)≥2 in at least ten percent of the cells. After removal of low quality cells/genes, the data were normalized using quantile normalization followed by PCA. PCs 1-8 were chosen for subsequent analysis due to a drop in the proportion of variance explained following PC8. Applicants used tSNE (Maaten L, 2008) to visualize single cells in a two-dimensional non-linear embedding.

Gene Signatures

Mouse: CD8$^+$ TILs dysfunction signature (FIGS. 1 and 3H) was generated by using the differentially expressed genes between Tim-3$^-$PD-1$^-$ and Tim-3$^+$PD-1$^+$CD8$^+$ TILs from MC38-OVA (FDR− adjusted P value <0.05 3,382 DE genes; Bioconductor package DESeq2 (Love et al., 2014)).

CD8$^+$ TILs treatment signature for Tim-3$^-$PD-1$^-$ (DN) and Tim-3$^+$PD-1$^+$ (DP) CD8$^+$ TILs (FIGS. 1 and 2) was generated by using the differentially expressed genes between MC38-OVA treated with anti-PD1/anti-Tim-3 and isotype control (FDR− adjusted P value <0.2, 608 and 364 DE genes respectively).

Cytokine signatures (FIG. 9): IFN-γ and IFN-β signatures were from (Iwata et al., 2017)-table S2, which lists DE genes between naïve CD4$^+$ T cells after 6 h, 24 h and 72 h with or without cytokine treatment. IL-6 signature was defined by differentially expressed genes between cytokine treated and non-treated naïve CD4$^+$ T cells for 72 h using RNAseq data from (Hirahara et al., 2015) (FDR− adjusted P value <0.05, 116 DE genes; bioconductor package DESeq2 (Love et al., 2014)). IL-12 signature was defined by differentially expressed genes between CD8$^+$ T cells stimulated with or without IL-12 for 48 h using microarray data from (Agarwal et al., 2009) (P value <0.05 and log$_2$ (fold change)>0.7, 527 DE genes, Limma package).

For the analyses in FIG. 1, CD8$^+$ T cell effector signatures were downloaded from MSigDB: Day 4.5 effector CD8$^+$ T cell and KLRG1$^{hi}$CD8$^+$ T cell signatures (Sarkar et al., 2008), Day 3 effector CD8$^+$ T cell (Kalia et al., 2010), for day 8 effector CD8$^+$ T cell, (Kaech et al., 2002), and for in vitro activated CD8$^+$ T cells (Hervas-Stubbs et al., 2010) (FIG. 1).

Proliferation signature is taken from (Tirosh et al., 2016) (FIG. 5C).

Gene sets for naïve cells (FIG. 3F) were downloaded from MSigDB (Kaech et al., 2002). Microarray dataset of memory-precursor and effector CD8$^+$ T cell data was downloaded from (Joshi et al., 2007) (FIG. 3G). Limma package was used to estimate the fold changes and standard errors by fitting a linear model for each gene for the assessment of differential expression (p.value <0.05 and log$_2$ (fold change) >2, 2,036 DE genes).

Figure 6C:
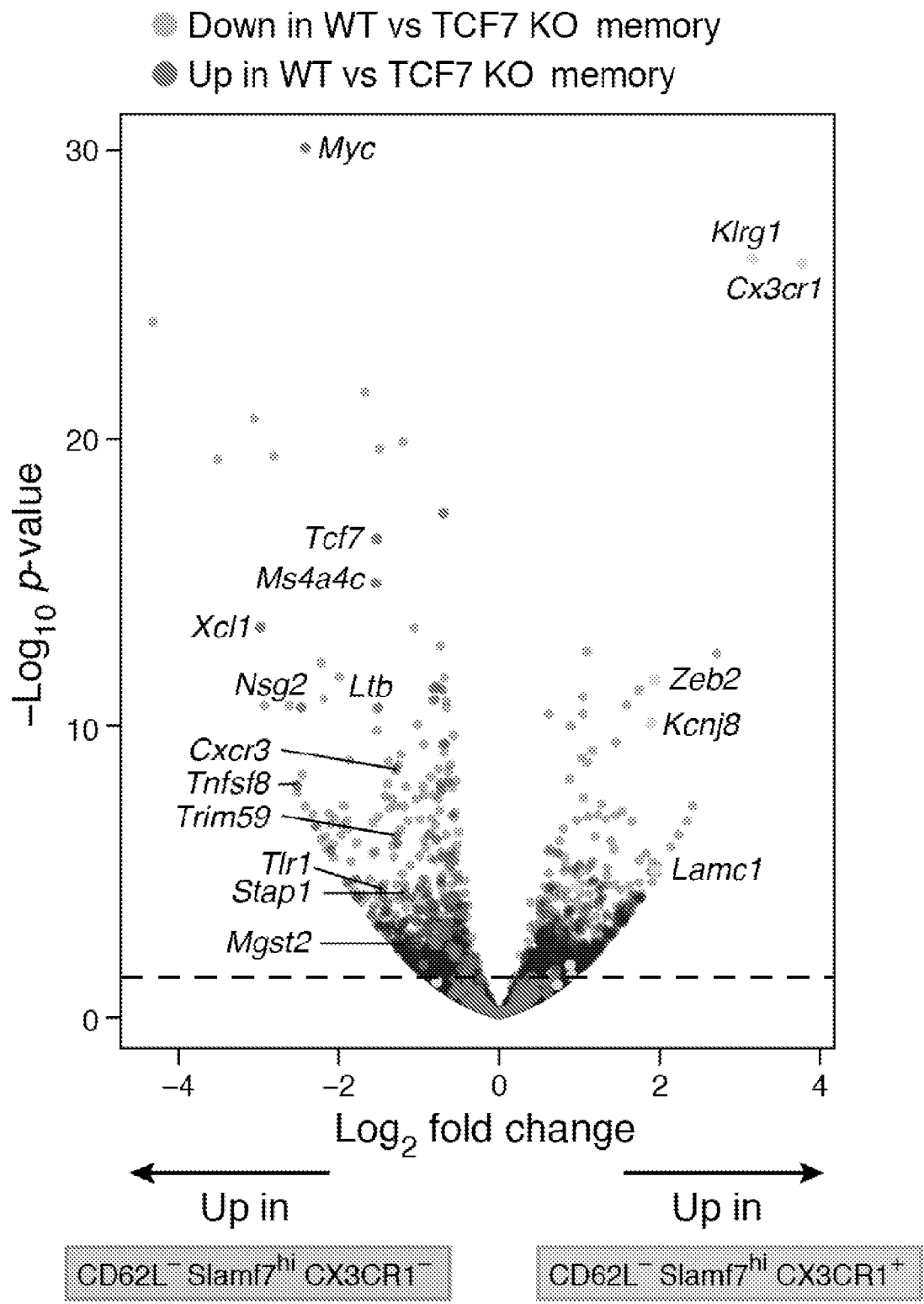
FIG. 6C shows a volcano plot showing the enrichment for differentially expressed genes in Tcf7-deficient TCR transgenic memory CD8$^+$ T cells (Zhou et al., 2010) in Slamf7$^{hi}$CX3CR1$^-$ and Slamf7$^{hi}$CX3CR1$^+$PD-1$^-$CD8$^+$ TILs.

Tcf7 ChIP-Seq data (FIG. 6B) for naïve CD8$^+$ T cells was downloaded from (Steinke et al., 2014). ChIPpeakAnno R package (Zhu et al., 2010) was used to annotate CHIP-Seq peaks to gene promoter regions based on the following thresholds (upstream=1000, downstream=500 of TSS). Microarray gene expression data from Tcf7$^{-/-}$ memory CD8$^+$ T cells (FIG. 6C) was downloaded from (Zhou et al., 2010). Limma package was used for the assessment of differential expression (p-value <0.05 and log$_2$ (fold-change >0.7), 253 DE genes).

CD8$^+$ T cells signatures were downloaded from MSigDB. For KLRG1$^{hi}$ versus KLRG1$^{int}$ and memory versus day 4.5 effector (Sarkar et al., 2008), day 8 and day 15 effector versus memory CD8$^+$ T cells is from (Kaech et al., 2002) and another effector versus memory CD8$^+$ T cell signature is from (Luckey et al., 2006) (FIG. 3H).

for the assessment of differential expression (p value <0.05 and $\log_2$ (fold change) >0.7, 1146 and 124 DE genes respectively).

Gene sets for naïve vs antigen-specific CD8+ T cells are from (Baitsch et al., 2011). Microarray data of blood CD8+ T cells after anti-CTLA-4, anti-PD-1 or combination treatments was downloaded from (Das et al., 2015) (FIGS. 5E and 10). Limma package was used for the assessment of differential expression (p value <0.05, 548, 244 and 800 DE genes respectively). IL-21 therapy data was downloaded from (Frederiksen et al., 2008) (FIG. 13C).

Single-cell gene signature scoring. As an initial step, the data was scaled (z-score across each gene) to remove bias towards highly expressed genes. Given a gene signature (list of genes), a cell-specific signature score was computed by first sorting the normalized scaled gene expression values for each cell followed by summing up the indices (ranks) of the signature genes. For gene-signatures consisting of an upregulated and downregulated set of genes, two ranking scores were obtained separately, and the down-regulated associated signature score was subtracted from the up-regulated generated signature score. A contour plot was added on top of the tSNE space, which takes into account only those cells that have a signature score above the indicated threshold to further emphasis the region of highly scored cells.

As background to assess significance, Applicants used a scheme that controls for expression of the signature using expression-level-matched subsets of genes. The p-value for each cell is calculated by generating random sets of signatures that are composed of genes with a similar average and variance expression levels as the original signature. This was followed by comparing the generated scores to the score obtained from the original signature. Cells that had a statistically significant score (FDR– adjusted P value <0.05) were marked by '+' (FIG. 10). Statistical significance for the human signatures for each of the clusters in FIG. 5E was calculated by averaging the human signature scores across the cells that compose each cluster and comparing them to random sets of signatures as described above. Clusters that had a statistically significant score (FDR– adjusted P value <0.05) were marked by '-' (FIGS. 10 and 13D).

Droplet-based single-cell RNA-Seq of Tim-3−PD-1− CD8+ TILs. Tim-3−PD-1− CD8+ TILs were sorted from MC38-OVA tumor-bearing mice that were treated with anti-PD-1 and anti-Tim-3 antibodies or isotype controls and were encapsulated into droplets, and libraries were prepared using Chromium Single Cell 3' Reagent Kits v2 according to manufacturer's protocol (10× Genomics). The generated single cell RNA-seq libraries were sequenced using a 75 cycle Nextseq 500 high output $V^2$ kit.

Droplet-based single-cell RNA-Seq data processing. Gene counts were obtained by aligning reads to the mm10 genome using CellRanger software (v1.3 10× Genomics). To remove doublets and poor-quality cells, Applicants removed cells that contained more than 10% mitochondrially derived transcripts, or where less than 500 genes were detected. Among the retained cells, Applicants considered only genes that are present in >30 cells and have >60 transcripts summed across all the selected cells, yielding 5,457 cells and 9,505 genes. Transcript count for each library was normalized to the median of the transcript counts across all cells. For PCA and clustering, Applicants used a log-transformed expression matrix. The top 13 PCs were included for subsequent tSNE analysis, determined by a drop in the proportion of variance explained by subsequent PCs. Applicants confirmed that the resulting analyses were not particularly sensitive to this choice.

Single cell RNA-seq clustering. Cells were clustered based on their top 13 PCs scores using the Louvain-Jaccard graph clustering algorithm (Blondel et al., 2008) as previously described (Levine et al., 2015; Shekhar et al., 2016). Shifts in the distribution of Tim-3−PD-1−CD8+ TILs from mice treated with anti-PD-1 and anti-Tim-3 antibodies or isotype controls for each of the clusters were calculated using Fisher's exact test.

Differentially expressed genes between clusters. Applicants used a binomial test to find genes differentially expressed (DE) between clusters, as previously described (Shekhar et al., 2016). To find marker genes for subpopulation A against all the other cell types in the data, Applicants pooled the cells from all the subpopulations except A, and regarded this pool as subpopulation B. Applicants corrected for multiple hypothesis testing with a Benjamini-Hochberg FDR. A gene was considered statistically significant if it satisfied FDR<0.01.

Visualization of single cell data. To generate tSNE plots (Maaten L, 2008) of single cell profiles, the scores along the 13 significant PCs estimated above were used as input to the R implementation of tSNE (Maaten, 2009; Maaten L, 2008) for 1000 steps and setting the perplexity parameter to 50.

Expression patterns of selected genes across cell clusters are shown in dot plots, which depict the fraction of cells in a cluster (row) that express a particular gene (column) based on the size of the dot, and the average number of transcripts in the expressing cells indicated by the scale. Applicants plotted the expression of selected cell surface, cytokines and transcription factor markers.

Gene Set Enrichment Analysis. Gene Set Enrichment Analysis (GSEA) (Mootha et al., 2003; Subramanian et al., 2005) was run for each cell subset in pre-ranked list mode with 1,000 permutations (nominal P-value cutoff <0.01). Enrichment scores were visualized using the SeqGSEA package in R (Wang and Cairns, 2014).

Ternary diagrams. Ternary diagrams (FIG. 13A, B) were generated using a Bioconductor 'ggtern' package in R. Ternary diagrams are Baycentric plots that depict the ratios of three variables as positions in an equilateral triangle. Every point on a ternary plot represents a different composition of the three components. In this case, a parallel to a side of the triangle is the locus of points representing a gene expression composition with lower signature score to the component situated in the vertex opposed to the side (Ponsen et al., 2009). In other words, the closer a single cell is to a specific corner the higher its similarity to a specific subset signature. Signature score per cell was calculated as described above in Single-cell gene signature scoring. Statistical significance for the distribution of key genes was calculated by comparing the single cell expression of the specific gene of interest in one-third sector versus the other two using t-test.

Two human single cell datasets were used in this analysis: CD8+ TILs from hepatocellular carcinoma patients (Zheng et al., 2017) and CD8+ from melanoma patients (Tirosh et al., 2016). For the latter, T cells were sorted based on index provided by the authors following additional sorting of CD8 cells based on reads count data aligned to CD8α and CD8b (CD8a>2 or CD8b>2). Counts data each library were normalized to the median of the transcript counts across all cells following, log transform expression values.

REFERENCES

Agarwal, P., Raghavan, A., Nandiwada, S. L., Curtsinger, J. M., Bohjanen, P. R., Mueller, D. L., and Mescher, M.

F. (2009). Gene regulation and chromatin remodeling by IL-12 and type I IFN in programming for CD8 T cell effector function and memory. Journal of immunology 183, 1695-1704.

Ahn, E., Youngblood, B., Lee, J., Lee, J., Sarkar, S., and Ahmed, R. (2016). Demethylation of the PD-1 Promoter Is Imprinted during the Effector Phase of CD8 T Cell Exhaustion. Journal of virology 90, 8934-8946.

Anders, S., and Huber, W. (2010). Differential expression analysis for sequence count data. Genome biology 11, R106.

Ayers, M., Lunceford, J., Nebozhyn, M., Murphy, E., Loboda, A., Kaufman, D. R., Albright, A., Cheng, J. D., Kang, S. P., Shankaran, V., et al. (2017). IFN-gamma-related mRNA profile predicts clinical response to PD-1 blockade. The Journal of clinical investigation 127, 2930-2940.

Baitsch, L., Baumgaertner, P., Devevre, E., Raghav, S. K., Legat, A., Barba, L., Wieckowski, S., Bouzourene, H., Deplancke, B., Romero, P., et al. (2011). Exhaustion of tumor-specific CD8(+) T cells in metastases from melanoma patients. The Journal of clinical investigation 121, 2350-2360.

Blondel, V., D., Guillaume, J., Lambiotte, R., and Lefebvre, E. (2008). Fast unfolding of communities in large networks. Journal of Statistical Mechanics: Theory and Experiment 2008, P10008.

Bottcher, J. P., Beyer, M., Meissner, F., Abdullah, Z., Sander, J., Hochst, B., Eickhoff, S., Rieckmann, J. C., Russo, C., Bauer, T., et al. (2015). Functional classification of memory CD8(+) T cells by CX3CR1 expression. Nature communications 6, 8306.

Brahmer, J. R., Tykodi, S. S., Chow, L. Q., Hwu, W. J., Topalian, S. L., Hwu, P., Drake, C. G., Camacho, L. H., Kauh, J., Odunsi, K., et al. (2012). Safety and activity of anti-PD-L1 antibody in patients with advanced cancer. The New England journal of medicine 366, 2455-2465.

Comte, D., Karampetsou, M. P., Yoshida, N., Kis-Toth, K., Kyttaris, V. C., and Tsokos, G. C. (2017). Signaling Lymphocytic Activation Molecule Family Member 7 Engagement Restores Defective Effector CD8+ T Cell Function in Systemic Lupus Erythematosus. Arthritis & rheumatology 69, 1035-1044.

da Silva, I. P., Gallois, A., Jimenez-Baranda, S., Khan, S., Anderson, A. C., Kuchroo, V. K., Osman, I., and Bhardwaj, N. (2014). Reversal of NK-cell exhaustion in advanced melanoma by Tim-3 blockade. Cancer immunology research 2, 410-422.

Das, R., Verma, R., Sznol, M., Boddupalli, C. S., Gettinger, S. N., Kluger, H., Callahan, M., Wolchok, J. D., Halaban, R., Dhodapkar, M. V., et al. (2015). Combination therapy with anti-CTLA-4 and anti-PD-1 leads to distinct immunologic changes in vivo. Journal of immunology 194, 950-959.

de Mingo Pulido, A., Gardner, A., Hiebler, S., Soliman, H., Rugo, H. S., Krummel, M. F., Coussens, L. M., and Ruffell, B. (2018). TIM-3 Regulates CD103(+) Dendritic Cell Function and Response to Chemotherapy in Breast Cancer. Cancer cell 33, 60-74 e66.

Duraiswamy, J., Kaluza, K. M., Freeman, G. J., and Coukos, G. (2013). Dual blockade of PD-1 and CTLA-4 combined with tumor vaccine effectively restores T-cell rejection function in tumors. Cancer research 73, 3591-3603.

Ellmeier, W., Sunshine, M. J., Losos, K., Hatam, F., and Littman, D. R. (1997). An enhancer that directs lineage-specific expression of CD8 in positively selected thymocytes and mature T cells. Immunity 7, 537-547.

Fourcade, J., Sun, Z., Benallaoua, M., Guillaume, P., Luescher, I. F., Sander, C., Kirkwood, J. M., Kuchroo, V., and Zarour, H. M. (2010). Upregulation of Tim-3 and PD-1 expression is associated with tumor antigen-specific CD8+ T cell dysfunction in melanoma patients. The Journal of experimental medicine 207, 2175-2186.

Fraietta, J. A., Lacey, S. F., Orlando, E. J., Pruteanu-Malinici, I., Gohil, M., Lundh, S., Boesteanu, A. C., Wang, Y., O'Connor, R. S., Hwang, W. T., et al. (2018). Determinants of response and resistance to CD19 chimeric antigen receptor (CAR) T cell therapy of chronic lymphocytic leukemia. Nat Med 24, 563-571.

Frederiksen, K. S., Lundsgaard, D., Freeman, J. A., Hughes, S. D., Holm, T. L., Skrumsager, B. K., Petri, A., Hansen, L. T., McArthur, G. A., Davis, I. D., et al. (2008). IL-21 induces in vivo immune activation of NK cells and CD8(+) T cells in patients with metastatic melanoma and renal cell carcinoma. Cancer immunology, immunotherapy: CII 57, 1439-1449.

Ganesan, A. P., Clarke, J., Wood, O., Garrido-Martin, E. M., Chee, S. J., Mellows, T., Samaniego-Castruita, D., Singh, D., Seumois, G., Alzetani, A., et al. (2017). Tissue-resident memory features are linked to the magnitude of cytotoxic T cell responses in human lung cancer. Nature immunology 18, 940-950.

Gerlach, C., Moseman, E. A., Loughhead, S. M., Alvarez, D., Zwijnenburg, A. J., Waanders, L., Garg, R., de la Torre, J. C., and von Andrian, U. H. (2016). The Chemokine Receptor CX3CR1 Defines Three Antigen-Experienced CD8 T Cell Subsets with Distinct Roles in Immune Surveillance and Homeostasis. Immunity 45, 1270-1284.

Ghoneim, H. E., Fan, Y., Moustaki, A., Abdelsamed, H. A., Dash, P., Dogra, P., Carter, R., Awad, W., Neale, G., Thomas, P. G., et al. (2017). De Novo Epigenetic Programs Inhibit PD-1 Blockade-Mediated T Cell Rejuvenation. Cell 170, 142-157 el 19.

Gilfillan, S., Chan, C. J., Cella, M., Haynes, N. M., Rapaport, A. S., Boles, K. S., Andrews, D. M., Smyth, M. J., and Colonna, M. (2008). DNAM-1 promotes activation of cytotoxic lymphocytes by nonprofessional antigen-presenting cells and tumors. The Journal of experimental medicine 205, 2965-2973.

Gordon, S. R., Maute, R. L., Dulken, B. W., Hutter, G., George, B. M., McCracken, M. N., Gupta, R., Tsai, J. M., Sinha, R., Corey, D., et al. (2017). PD-1 expression by tumour-associated macrophages inhibits phagocytosis and tumour immunity. Nature 545, 495-499.

Gubin, M. M., Zhang, X., Schuster, H., Caron, E., Ward, J. P., Noguchi, T., Ivanova, Y., Hundal, J., Arthur, C. D., Krebber, W. J., et al. (2014). Checkpoint blockade cancer immunotherapy targets tumour-specific mutant antigens. Nature 515, 577-581.

Haymaker, C. L., Wu, R. C., Ritthipichai, K., Bernatchez, C., Forget, M. A., Chen, J. Q., Liu, H., Wang, E., Marincola, F., Hwu, P., et al. (2015). BTLA marks a less-differentiated tumor-infiltrating lymphocyte subset in melanoma with enhanced survival properties. Oncoimmunology 4, e1014246.

Hervas-Stubbs, S., Riezu-Boj, J. I., Gonzalez, I., Mancheno, U., Dubrot, J., Azpilicueta, A., Gabari, I., Palazon, A., Aranguren, A., Ruiz, J., et al. (2010). Effects of IFN-alpha as a signal-3 cytokine on human naïve and antigen-experienced CD8(+) T cells. European journal of immunology 40, 3389-3402.

Hirahara, K., Onodera, A., Villarino, A. V., Bonelli, M., Sciume, G., Laurence, A., Sun, H. W., Brooks, S. R., Vahedi, G., Shih, H. Y., et al. (2015). Asymmetric Action of STAT Transcription Factors Drives Transcriptional Outputs and Cytokine Specificity. Immunity 42, 877-889.

Hodi, F. S., O'Day, S. J., McDermott, D. F., Weber, R. W., Sosman, J. A., Haanen, J. B., Gonzalez, R., Robert, C., Schadendorf, D., Hassel, J. C., et al. (2010). Improved survival with ipilimumab in patients with metastatic melanoma. The New England journal of medicine 363, 711-723.

Huang, A. C., Postow, M. A., Orlowski, R. J., Mick, R., Bengsch, B., Manne, S., Xu, W., Harmon, S., Giles, J. R., Wenz, B., et al. (2017). T-cell invigoration to tumour burden ratio associated with anti-PD-1 response. Nature 545, 60-65.

Im, S. J., Hashimoto, M., Gerner, M. Y., Lee, J., Kissick, H. T., Burger, M. C., Shan, Q., Hale, J. S., Lee, J., Nasti, T. H., et al. (2016). Defining CD8+ T cells that provide the proliferative burst after PD-1 therapy. Nature 537, 417-421.

Iwata, S., Mikami, Y., Sun, H. W., Brooks, S. R., Jankovic, D., Hirahara, K., Onodera, A., Shih, H. Y., Kawabe, T., Jiang, K., et al. (2017). The Transcription Factor T-bet Limits Amplification of Type I IFN Transcriptome and Circuitry in T Helper 1 Cells. Immunity 46, 983-991 e984.

Jeannet, G., Boudousquie, C., Gardiol, N., Kang, J., Huelsken, J., and Held, W. (2010). Essential role of the Wnt pathway effector Tcf-1 for the establishment of functional CD8 T cell memory. Proceedings of the National Academy of Sciences of the United States of America 107, 9777-9782.

Jiang, X., Zhou, T., Xiao, Y., Yu, J., Dou, S., Chen, G., Wang, R., Xiao, H., Hou, C., Wang, W., et al. (2016). Tim-3 promotes tumor-promoting M2 macrophage polarization by binding to STAT1 and suppressing the STAT1-miR-155 signaling axis. Oncoimmunology 5, e1211219.

Johnston, R. J., Comps-Agrar, L., Hackney, J., Yu, X., Huseni, M., Yang, Y., Park, S., Javinal, V., Chiu, H., Irving, B., et al. (2014). The immunoreceptor TIGIT regulates antitumor and antiviral CD8(+) T cell effector function. Cancer cell 26, 923-937.

Joshi, N. S., Cui, W., Chandele, A., Lee, H. K., Urso, D. R., Hagman, J., Gapin, L., and Kaech, S. M. (2007). Inflammation directs memory precursor and short-lived effector CD8(+) T cell fates via the graded expression of T-bet transcription factor. Immunity 27, 281-295.

Kaech, S. M., Hemby, S., Kersh, E., and Ahmed, R. (2002). Molecular and functional profiling of memory CD8 T cell differentiation. Cell 111, 837-851.

Kalia, V., Sarkar, S., Subramaniam, S., Haining, W. N., Smith, K. A., and Ahmed, R. (2010). Prolonged interleukin-2Ralpha expression on virus-specific CD8+ T cells favors terminal-effector differentiation in vivo. Immunity 32, 91-103.

Kamphorst, A. O., Pillai, R. N., Yang, S., Nasti, T. H., Akondy, R. S., Wieland, A., Sica, G. L., Yu, K., Koenig, L., Patel, N. T., et al. (2017). Proliferation of PD-1+ CD8 T cells in peripheral blood after PD-1-targeted therapy in lung cancer patients. Proceedings of the National Academy of Sciences of the United States of America 114, 4993-4998.

Kolde, R., and Vilo, J. (2015). GOsummaries: an R Package for Visual Functional Annotation of Experimental Data. F1000Research 4, 574.

Krempski, J., Karyampudi, L., Behrens, M. D., Erskine, C. L., Hartmann, L., Dong, H., Goode, E. L., Kalli, K. R., and Knutson, K. L. (2011). Tumor-infiltrating programmed death receptor-1+ dendritic cells mediate immune suppression in ovarian cancer. Journal of immunology 186, 6905-6913.

Kvistborg, P., Philips, D., Kelderman, S., Hageman, L., Ottensmeier, C., Joseph-Pietras, D., Welters, M. J., van der Burg, S., Kapiteijn, E., Michielin, O., et al. (2014). Anti-CTLA-4 therapy broadens the melanoma-reactive CD8+ T cell response. Science translational medicine 6, 254ra128.

Langmead, B., Trapnell, C., Pop, M., and Salzberg, S. L. (2009). Ultrafast and memory-efficient alignment of short DNA sequences to the human genome. Genome biology 10, R25.

Lefrancois, L. (2006). Development, trafficking, and function of memory T-cell subsets. Immunological reviews 211, 93-103.

Leong, Y. A., Chen, Y., Ong, H. S., Wu, D., Man, K., Deleage, C., Minnich, M., Meckiff, B. J., Wei, Y., Hou, Z., et al. (2016). CXCR5(+) follicular cytotoxic T cells control viral infection in B cell follicles. Nature immunology 17, 1187-1196.

Levine, J. H., Simonds, E. F., Bendall, S. C., Davis, K. L., Amir el, A. D., Tadmor, M. D., Litvin, O., Fienberg, H. G., Jager, A., Zunder, E. R., et al. (2015). Data-Driven Phenotypic Dissection of AML Reveals Progenitor-like Cells that Correlate with Prognosis. Cell 162, 184-197.

Li, B., and Dewey, C. N. (2011). RSEM: accurate transcript quantification from RNA-Seq data with or without a reference genome. BMC bioinformatics 12, 323.

Li, Y., Liu, S., Hernandez, J., Vence, L., Hwu, P., and Radvanyi, L. (2010). MART-1-specific melanoma tumor-infiltrating lymphocytes maintaining CD28 expression have improved survival and expansion capability following antigenic restimulation in vitro. Journal of immunology 184, 452-465.

Lim, T. S., Chew, V., Sieow, J. L., Goh, S., Yeong, J. P., Soon, A. L., and Ricciardi-Castagnoli, P. (2016). PD-1 expression on dendritic cells suppresses CD8+ T cell function and antitumor immunity. Oncoimmunology 5, e1085146.

Love, M. I., Huber, W., and Anders, S. (2014). Moderated estimation of fold change and dispersion for RNA-seq data with DESeq2. Genome biology 15, 550.

Luckey, C. J., Bhattacharya, D., Goldrath, A. W., Weissman, I. L., Benoist, C., and Mathis, D. (2006). Memory T and memory B cells share a transcriptional program of self-renewal with long-term hematopoietic stem cells. Proceedings of the National Academy of Sciences of the United States of America 103, 3304-3309.

Maaten, L. (2009). Learning a Parametric Embedding by Preserving Local Structure. In Proceedings of the Twelfth International Conference on Artificial Intelligence and Statistics, D. David van, and W. Max, eds. (Proceedings of Machine Learning Research: PMLR), pp. 384-391.

Maaten L, H. G. (2008). Visualizing Data using t-SNE. Journal of Machine Learning Research, 2579-2605.

Maekawa, Y., Minato, Y., Ishifune, C., Kurihara, T., Kitamura, A., Kojima, H., Yagita, H., Sakata-Yanagimoto, M., Saito, T., Taniuchi, I., et al. (2008). Notch2 integrates signaling by the transcription factors RBP-J and CREB1 to promote T cell cytotoxicity. Nature immunology 9, 1140-1147.

Makowska, Z., Blumer, T., Duong, F. H., La Monica, N., Kandimalla, E. R., and Heim, M. H. (2013). Sequential induction of type I and II interferons mediates a long-lasting gene induction in the liver in response to a novel toll-like receptor 9 agonist. J Hepatol 58, 743-749.

Mootha, V. K., Lindgren, C. M., Eriksson, K. F., Subramanian, A., Sihag, S., Lehar, J., Puigserver, P., Carlsson, E., Ridderstrale, M., Laurila, E., et al. (2003). PGC-1alpha-responsive genes involved in oxidative phosphorylation are coordinately downregulated in human diabetes. Nature genetics 34, 267-273.

Ngiow, S. F., von Scheidt, B., Akiba, H., Yagita, H., Teng, M. W., and Smyth, M. J. (2011). Anti-TIM3 antibody promotes T cell IFN-gamma-mediated antitumor immunity and suppresses established tumors. Cancer research 71, 3540-3551.

Nishino, M., Ramaiya, N. H., Chambers, E. S., Adeni, A. E., Hatabu, H., Janne, P. A., Hodi, F. S., and Awad, M. M. (2016). Immune-related response assessment during PD-1 inhibitor therapy in advanced non-small-cell lung cancer patients. Journal for immunotherapy of cancer 4, 84.

Overacre-Delgoffe, A. E., Chikina, M., Dadey, R. E., Yano, H., Brunazzi, E. A., Shayan, G., Horne, W., Moskovitz, J. M., Kolls, J. K., Sander, C., et al. (2017). Interferon-gamma Drives Treg Fragility to Promote Anti-tumor Immunity. Cell 169, 1130-1141 e1111.

Pauken, K. E., Sammons, M. A., Odorizzi, P. M., Manne, S., Godec, J., Khan, O., Drake, A. M., Chen, Z., Sen, D. R., Kurachi, M., et al. (2016). Epigenetic stability of exhausted T cells limits durability of reinvigoration by PD-1 blockade. Science 354, 1160-1165.

Philip, M., Fairchild, L., Sun, L., Horste, E. L., Camara, S., Shakiba, M., Scott, A. C., Viale, A., Lauer, P., Merghoub, T., et al. (2017). Chromatin states define tumour-specific T cell dysfunction and reprogramming. Nature 545, 452-456.

Picelli, S., Bjorklund, A. K., Faridani, O. R., Sagasser, S., Winberg, G., and Sandberg, R. (2013). Smart-seq2 for sensitive full-length transcriptome profiling in single cells. Nature methods 10, 1096-1098.

Sakuishi, K., Apetoh, L., Sullivan, J. M., Blazar, B. R., Kuchroo, V. K., and Anderson, A. C. (2010). Targeting Tim-3 and PD-1 pathways to reverse T cell exhaustion and restore anti-tumor immunity. The Journal of experimental medicine 207, 2187-2194.

Sakuishi, K., Ngiow, S. F., Sullivan, J. M., Teng, M. W., Kuchroo, V. K., Smyth, M. J., and Anderson, A. C. (2013). TIM3+FOXP3+ regulatory T cells are tissue-specific promoters of T-cell dysfunction in cancer. Oncoimmunology 2, e23849.

Sarkar, S., Kalia, V., Haining, W. N., Konieczny, B. T., Subramaniam, S., and Ahmed, R. (2008). Functional and genomic profiling of effector CD8 T cell subsets with distinct memory fates. The Journal of experimental medicine 205, 625-640.

Schadendorf, D., Hodi, F. S., Robert, C., Weber, J. S., Margolin, K., Hamid, O., Patt, D., Chen, T. T., Berman, D. M., and Wolchok, J. D. (2015). Pooled Analysis of Long-Term Survival Data From Phase II and Phase III Trials of Ipilimumab in Unresectable or Metastatic Melanoma. Journal of clinical oncology: official journal of the American Society of Clinical Oncology 33, 1889-1894.

Scott-Browne, J. P., Lopez-Moyado, I. F., Trifari, S., Wong, V., Chavez, L., Rao, A., and Pereira, R. M. (2016). Dynamic Changes in Chromatin Accessibility Occur in CD8+ T Cells Responding to Viral Infection. Immunity 45, 1327-1340.

Sen, D. R., Kaminski, J., Barnitz, R. A., Kurachi, M., Gerdemann, U., Yates, K. B., Tsao, H. W., Godec, J., LaFleur, M. W., Brown, F. D., et al. (2016). The epigenetic landscape of T cell exhaustion. Science 354, 1165-1169.

Shekhar, K., Lapan, S. W., Whitney, I. E., Tran, N. M., Macosko, E. Z., Kowalczyk, M., Adiconis, X., Levin, J. Z., Nemesh, J., Goldman, M., et al. (2016). Comprehensive Classification of Retinal BipolarNeurons by Single-Cell Transcriptomics. Cell 166, 1308-1323 e1330.

Singer, M., Wang, C., Cong, L., Marjanovic, N. D., Kowalczyk, M. S., Zhang, H., Nyman, J., Sakuishi, K., Kurtulus, S., Gennert, D., et al. (2016). A Distinct Gene Module for Dysfunction Uncoupled from Activation in Tumor-Infiltrating T Cells. Cell 166, 1500-1511 e1509.

Steinke, F. C., Yu, S., Zhou, X., He, B., Yang, W., Zhou, B., Kawamoto, H., Zhu, J., Tan, K., and Xue, H. H. (2014). TCF-1 and LEF-1 act upstream of Th-POK to promote the CD4(+) T cell fate and interact with Runx3 to silence Cd4 in CD8(+) T cells. Nature immunology 15, 646-656.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Tirosh, I., Izar, B., Prakadan, S. M., Wadsworth, M. H., 2nd, Treacy, D., Trombetta, J. J., Rotem, A., Rodman, C., Lian, C., Murphy, G., et al. (2016). Dissecting the multicellular ecosystem of metastatic melanoma by single-cell RNA-seq. Science 352, 189-196.

Topalian, S. L., Hodi, F. S., Brahmer, J. R., Gettinger, S. N., Smith, D. C., McDermott, D. F., Powderly, J. D., Carvajal, R. D., Sosman, J. A., Atkins, M. B., et al. (2012). Safety, activity, and immune correlates of anti-PD-1 antibody in cancer. The New England journal of medicine 366, 2443-2454.

Trapnell, C., Pachter, L., and Salzberg, S. L. (2009). TopHat: discovering splice junctions with RNA-Seq. Bioinformatics 25, 1105-1111.

Utzschneider, D. T., Charmoy, M., Chennupati, V., Pousse, L., Ferreira, D. P., Calderon-Copete, S., Danilo, M., Alfei, F., Hofmann, M., Wieland, D., et al. (2016). T Cell Factor 1-Expressing Memory-like CD8(+) T Cells Sustain the Immune Response to Chronic Viral Infections. Immunity 45, 415-427.

Utzschneider, D. T., Legat, A., Fuertes Marraco, S. A., Carrie, L., Luescher, I., Speiser, D. E., and Zehn, D. (2013). T cells maintain an exhausted phenotype after antigen withdrawal and population reexpansion. Nature immunology 14, 603-610.

van Rooij, N., van Buuren, M. M., Philips, D., Velds, A., Toebes, M., Heemskerk, B., van Dijk, L. J., Behjati, S., Hilkmann, H., El Atmioui, D., et al. (2013). Tumor exome analysis reveals neoantigen-specific T-cell reactivity in an ipilimumab-responsive melanoma. Journal of clinical oncology: official journal of the American Society of Clinical Oncology 31, e439-442.

Wang, X., and Cairns, M. J. (2014). SeqGSEA: a Bioconductor package for gene set enrichment analysis of RNA-Seq data integrating differential expression and splicing. Bioinformatics 30, 1777-1779.

Williams, J. B., Horton, B. L., Zheng, Y., Duan, Y., Powell, J. D., and Gajewski, T. F. (2017). The EGR2 targets LAG-3 and 4-1BB describe and regulate dysfunctional antigen-specific CD8+ T cells in the tumor microenvironment. The Journal of experimental medicine 214, 381-400.

Wolchok, J. D., Chiarion-Sileni, V., Gonzalez, R., Rutkowski, P., Grob, J. J., Cowey, C. L., Lao, C. D., Wagstaff, J., Schadendorf, D., Ferrucci, P. F., et al. (2017). Overall Survival with Combined Nivolumab and Ipilimumab in Advanced Melanoma. The New England journal of medicine 377, 1345-1356.

Woo, S. R., Turnis, M. E., Goldberg, M. V., Bankoti, J., Selby, M., Nirschl, C. J., Bettini, M. L., Gravano, D. M., Vogel, P., Liu, C. L., et al. (2012). Immune inhibitory molecules LAG-3 and PD-1 synergistically regulate T-cell function to promote tumoral immune escape. Cancer research 72, 917-927.

Xu, B., Yuan, L., Gao, Q., Yuan, P., Zhao, P., Yuan, H., Fan, H., Li, T., Qin, P., Han, L., et al. (2015). Circulating and tumor-infiltrating Tim-3 in patients with colorectal cancer. Oncotarget 6, 20592-20603.

Yuan, J., Gnjatic, S., Li, H., Powel, S., Gallardo, H. F., Ritter, E., Ku, G. Y., Jungbluth, A. A., Segal, N. H., Rasalan, T. S., et al. (2008). CTLA-4 blockade enhances polyfunctional NY-ESO-1 specific T cell responses in metastatic melanoma patients with clinical benefit. Proceedings of the National Academy of Sciences of the United States of America 105, 20410-20415.

Zheng, C., Zheng, L., Yoo, J. K., Guo, H., Zhang, Y., Guo, X., Kang, B., Hu, R., Huang, J. Y., Zhang, Q., et al. (2017). Landscape of Infiltrating T Cells in Liver Cancer Revealed by Single-Cell Sequencing. Cell 169, 1342-1356 e1316.

Zhou, Q., Munger, M. E., Veenstra, R. G., Weigel, B. J., Hirashima, M., Munn, D. H., Murphy, W. J., Azuma, M., Anderson, A. C., Kuchroo, V. K., et al. (2011). Coexpression of Tim-3 and PD-1 identifies a CD8+ T-cell exhaustion phenotype in mice with disseminated acute myelogenous leukemia. Blood 117, 4501-4510.

Zhou, X., Yu, S., Zhao, D. M., Harty, J. T., Badovinac, V. P., and Xue, H. H. (2010). Differentiation and persistence of memory CD8(+) T cells depend on T cell factor 1. Immunity 33, 229-240.

Zhu, L. J., Gazin, C., Lawson, N. D., Pages, H., Lin, S. M., Lapointe, D. S., and Green, M. R. (2010). ChIP-peakAnno: a Bioconductor package to annotate ChIP-seq and ChIP-chip data. BMC bioinformatics 11, 237.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. An isolated CD8⁺ T cell obtained by sorting CD8⁺ T cells for TIM3⁻PD1⁻CD62L⁻ Slamf7⁺CX3CR1⁻ CD8⁺ T cells, wherein the isolated CD8⁺ T cell comprises expression of SLAMF7 and no expression of CD62L, CX3CR1, TIM3 and PD1, and wherein the isolated CD8⁺ T cell expresses an exogenous chimeric antigen receptor (CAR) or T cell receptor (TCR).

2. The isolated CD8⁺ T cell according to claim 1, wherein the CD62L⁻ Slamf7⁺CX3CR1⁻ CD8⁺ T cell comprises higher expression of one or more genes or polypeptides selected from the group consisting of Tcf7, Egr2, Zfp827, Satb1, Zfp512, Irf8, Relb, Sp140, Myb, Id3, Hes6, Fos, Ikzf2 and Myc relative to CD62L⁻ Slamf7⁺CX3CR1⁺CD8⁺ T cells.

3. The isolated CD8⁺ T cell according to claim 1, further characterized by a gene signature comprising one or more genes or polypeptides in Table 3, 4 or 5.

4. The isolated CD8⁺ T cell according to claim 1, wherein the CD8⁺ T cell is a human cell.

5. A population of CD8⁺ T cells comprising CD8⁺ T cells as defined in claim 1.

6. The population of CD8⁺ T cells according to claim 5, wherein the population of cells comprises CD8⁺ T cells autologous for a subject suffering from cancer.

7. The population of CD8⁺ T cells according to claim 5, wherein the population of cells comprises cells modified to knockout or downregulate expression of one or more genes selected from the group consisting of Bhlhe40, Klf2, Zeb2, Prdm1, Arnt1, Ets1, Junb, Id2, Hivep2, Rora, Nr1d2, Meis2, Arnt, Nr4a1, Meis3, Zmiz1, Vezf1, Nfe2l1, Mxi1, Rxra and Creb5, wherein the population of cells comprises cells modified to downregulate expression of Bhlhe40, such that the population of cells maintain at least a basal level of Bhlhe40 expression.

8. A pharmaceutical composition comprising the CD8⁺ T cell as defined in claim 1 or a population of CD8⁺ T cells comprising CD8⁺ T cells as defined in claim 1.

9. A method for treating cancer comprising administering to a subject in need thereof the pharmaceutical composition according to claim 8, wherein the method comprises:
   a) isolating from a biological sample of the subject a CD8⁺ T cell or CD8⁺ T cell population;
   b) in vitro expanding the CD8⁺ T cell or CD8⁺ T cell population of a);
   c) enriching the expanded cells for CD8⁺ T cells as defined in claim 1; and
   d) administering the in vitro expanded CD8⁺ T cell or CD8⁺ T cell population of b) or c) to the subject.

10. The method according to claim 9, wherein the pharmaceutical composition is administered after ablation therapy or before surgery; and/or
   wherein the method further comprises administering a checkpoint blockade therapy, wherein the checkpoint blockade therapy comprises anti-TIM3, anti-CTLA4, anti-PD-L1, anti-PD1, anti-TIGIT, anti-LAG3, or combinations thereof.

11. The population of CD8⁺ T cells according to claim 5, wherein the population of cells comprises greater than 5%, 10%, 20%, 30%, 40%, 50%, 60%, 70%, 80%, 90% or 95% of PD1− CD62L⁻ Slamf7⁺CX3CR1⁻ CD8⁺ T cells.

12. The population of CD8⁺ T cells according to claim 6, wherein the activated CD8⁺ T cells are activated with tumor specific antigens.

13. The population of CD8⁺ T cells according to claim 12, wherein the tumor specific antigens are subject specific antigens.

14. The isolated CD8+ T cell according to claim 1, wherein the cell is a CD8⁺ T cell autologous for a subject suffering from cancer.

15. The isolated CD8+ T cell according to claim 1, wherein said CD8⁺ T cell displays tumor specificity.

16. The population of CD8⁺ T cells according to claim 5, wherein the population of cells display tumor specificity.

17. The population of CD8⁺ T cells according to claim 5, wherein the population of cells comprise expanded cells.

18. The population of CD8⁺ T cells according to claim 5, wherein the population of cells comprise activated CD8⁺ T cells.

19. The population of CD8⁺ T cells according to claim 5, wherein the population of cells comprises cells modified to increase expression of one or more genes selected from the group consisting of Tcf7, Egr2, Zfp827, Satb1, Zfp512, Irf8, Relb, Sp140, Myb, Id3, Hes6, Fos, Ikzf2 and Myc, wherein the population of cells comprises cells modified to increase expression of Tcf7.

* * * * *